(12) United States Patent
Bonvini et al.

(10) Patent No.: US 11,685,781 B2
(45) Date of Patent: Jun. 27, 2023

(54) VARIANT CD3-BINDING DOMAINS AND THEIR USE IN COMBINATION THERAPIES FOR THE TREATMENT OF DISEASE

(71) Applicant: MacroGenics, Inc., Rockville, MD (US)

(72) Inventors: Ezio Bonvini, Potomac, MD (US); Ling Huang, Bethesda, MD (US); Chia-Ying Kao Lam, San Jose, CA (US); Gurunadh Reddy Chichili, Buffalo Grove, IL (US); Ralph Froman Alderson, North Potomac, MD (US); Paul A. Moore, North Potomac, MD (US); Leslie S. Johnson, Rockville, MD (US)

( * ) Notice: Subject to any disclaimer, the term of this patent is extended or adjusted under 35 U.S.C. 154(b) by 177 days.

(21) Appl. No.: 16/966,960

(22) PCT Filed: Feb. 13, 2019

(86) PCT No.: PCT/US2019/017772
§ 371 (c)(1),
(2) Date: Aug. 3, 2020

(87) PCT Pub. No.: WO2019/160904
PCT Pub. Date: Aug. 22, 2019

(65) Prior Publication Data
US 2021/0155694 A1 May 27, 2021

Related U.S. Application Data

(60) Provisional application No. 62/738,632, filed on Sep. 28, 2018, provisional application No. 62/631,043, filed on Feb. 15, 2018.

(51) Int. Cl.
| C07K 16/28 | (2006.01) |
| A61P 35/00 | (2006.01) |
| C07K 16/30 | (2006.01) |
| A61K 39/00 | (2006.01) |

(52) U.S. Cl.
CPC .......... *C07K 16/2809* (2013.01); *A61P 35/00* (2018.01); *C07K 16/2803* (2013.01); *C07K 16/2815* (2013.01); *C07K 16/2866* (2013.01); *C07K 16/30* (2013.01); *C07K 16/3038* (2013.01); *C07K 16/3061* (2013.01); *A61K 2039/505* (2013.01); *A61K 2039/545* (2013.01); *C07K 2317/31* (2013.01); *C07K 2317/33* (2013.01); *C07K 2317/524* (2013.01); *C07K 2317/526* (2013.01); *C07K 2317/622* (2013.01); *C07K 2317/626* (2013.01); *C07K 2317/73* (2013.01); *C07K 2317/92* (2013.01)

(58) Field of Classification Search
CPC ............ C07K 16/2809; C07K 16/2803; C07K 16/2815; C07K 16/2866; C07K 16/30; C07K 16/3038; C07K 16/3061; C07K 2317/31; C07K 2317/33; C07K 2317/524; C07K 2317/526; C07K 2317/622; A61P 35/00; A61K 2039/505; A61K 2039/545
See application file for complete search history.

(56) References Cited

U.S. PATENT DOCUMENTS

| 4,816,567 A | 3/1989 | Cabilly et al. |
| 5,565,332 A | 10/1996 | Hoogenboom et al. |
| 5,580,717 A | 12/1996 | Dower et al. |
| 5,733,743 A | 3/1998 | Johnson et al. |
| 5,807,715 A | 9/1998 | Morrison et al. |

(Continued)

FOREIGN PATENT DOCUMENTS

| EP | 0519596 | 4/1994 |
| EP | 1868650 | 12/2007 |

(Continued)

OTHER PUBLICATIONS

Abdulghani, J. et al. (2010) "*TRAIL Receptor Signaling And Therapeutics,*" Expert Opin. Ther. Targets 14(10):1091-1108.
Adenis, A. et al. (2003) "*Inhibitors Of Epidermal Growth Factor Receptor And Colorectal Cancer,*" Bull. Cancer. 90 Spec No. S228-S232 (Abstract Only).
Akcakanat, A. et al. (2006) "*Heterogeneous Expression Of GAGE, NY-ESO-1, MAGE-A and SSX Proteins In Esophageal Cancer: Implications For Immunotherapy,*" Int. J. Cancer. 118(1):123-128.
Alhussaini, M. et al. (2015) "*Targeting CD123 In AML Using A T-Cell Directed Dual-Affinity Re-Targeting (DART®) Platform,*" Blood pii: blood-2014-05-575704.
(Continued)

*Primary Examiner* — Nelson B Moseley, II
(74) *Attorney, Agent, or Firm* — Medler Ferro Woodhouse & Mills

(57) ABSTRACT

The present invention is directed to DA×CD3 Binding Molecules comprising a vCD3-Binding Domain, which comprises a CDRHI Domain, a CDRH2 Domain, a CDRH3 Domain, a CDRL I Domain, a CDRL2 Domain, and a CDRL3 Domain, at least one of which differs in amino acid sequence from the amino acid sequence of the corresponding CDR of a rCD3-Binding Domain, wherein the DA×CD3 Binding Molecule comprising such vCD3-Binding Domain exhibits an altered affinity for CD3, relative to a DA×CD3 Binding Molecule comprising such rCD3-Binding Domain. The invention particularly concerns to such DA×CD3 Binding Molecules comprising a vCD3-Binding Domain which exhibit reduced affinity for CD3 and are capable of mediating redirected killing of target cells expressing a DA and exhibit lower levels of cytokine release relative to a DA×CD3 Binding Molecule comprising a rCD3-Binding Domain. The invention particularly concerns the use of DA×CD3 Binding Molecules comprising a vCD3-Binding Domain in the treatment of cancer and pathogen-associated diseases. The present invention is also directed to pharmaceutical compositions that comprise such molecule(s).

33 Claims, 91 Drawing Sheets
Specification includes a Sequence Listing.

(56) References Cited

U.S. PATENT DOCUMENTS

| | | |
|---|---|---|
| 5,821,337 A | 10/1998 | Carter et al. |
| 5,843,749 A | 12/1998 | Maisonpierre et al. |
| 5,866,692 A | 2/1999 | Shitara et al. |
| 5,997,867 A | 12/1999 | Waldmann et al. |
| 6,054,297 A | 4/2000 | Carter et al. |
| 6,180,377 B1 | 1/2001 | Morgan et al. |
| 6,265,150 B1 | 7/2001 | Terstappen et al. |
| 6,277,375 B1 | 8/2001 | Ward |
| 6,331,415 B1 | 12/2001 | Cabilly et al. |
| 7,083,784 B2 | 8/2006 | Dall'Acqua et al. |
| 7,112,324 B1 | 9/2006 | Dorken et al. |
| 7,148,038 B2 | 12/2006 | Mather |
| 7,217,797 B2 | 5/2007 | Hinton et al. |
| 7,235,641 B2 | 6/2007 | Kufer et al. |
| 7,405,061 B2 | 7/2008 | Mather et al. |
| 7,527,969 B2 | 5/2009 | Mather et al. |
| 7,569,672 B2 | 8/2009 | Mather et al. |
| 7,572,895 B2 | 8/2009 | Mather et al. |
| 7,572,896 B2 | 8/2009 | Mather et al. |
| 7,666,424 B2 | 2/2010 | Cheung et al. |
| 7,737,258 B2 | 6/2010 | Cheung |
| 7,740,845 B2 | 6/2010 | Cheung |
| 7,892,554 B2 | 2/2011 | Marks et al. |
| 8,044,180 B2 | 10/2011 | Koenig et al. |
| 8,088,376 B2 | 1/2012 | Chamberlain et al. |
| 8,133,982 B2 | 3/2012 | Johnson et al. |
| 8,148,154 B2 | 4/2012 | Cheung et al. |
| 8,173,424 B2 | 5/2012 | Marks et al. |
| 8,187,593 B2 | 5/2012 | Koenig et al. |
| 8,193,318 B2 | 6/2012 | Koenig et al. |
| 8,350,011 B2 | 1/2013 | Cartilage et al. |
| 8,414,892 B2 | 4/2013 | Cheung |
| 8,501,471 B2 | 8/2013 | Cheung |
| 8,530,627 B2 | 9/2013 | Koenig et al. |
| 8,669,349 B2 | 3/2014 | Johnson et al. |
| 8,778,339 B2 | 7/2014 | Tuaillon et al. |
| 8,779,098 B2 | 7/2014 | Mather et al. |
| 8,784,808 B2 | 7/2014 | Johnson et al. |
| 8,795,667 B2 | 8/2014 | Johnson et al. |
| 8,802,091 B2 | 8/2014 | Johnson et al. |
| 8,802,093 B2 | 8/2014 | Johnson et al. |
| 8,858,942 B2 | 10/2014 | Cartlidge et al. |
| 8,946,387 B2 | 2/2015 | Koenig et al. |
| 8,968,730 B2 | 3/2015 | Koenig et al. |
| 8,974,792 B2 | 3/2015 | Marks et al. |
| 8,993,730 B2 | 3/2015 | Johnson et al. |
| 9,062,110 B2 | 6/2015 | Cheung |
| 2002/0147311 A1 | 10/2002 | Gillies et al. |
| 2004/0058400 A1 | 3/2004 | Holliger et al. |
| 2004/0220388 A1 | 11/2004 | Mertens et al. |
| 2006/0166291 A1 | 7/2006 | Mather et al. |
| 2006/0172349 A1 | 8/2006 | Mather et al. |
| 2006/0172350 A1 | 8/2006 | Mather et al. |
| 2007/0004909 A1 | 1/2007 | Johnson et al. |
| 2007/0148164 A1 | 6/2007 | Farrington et al. |
| 2009/0060910 A1 | 3/2009 | Johnson et al. |
| 2010/0143245 A1 | 6/2010 | Cheung |
| 2010/0174053 A1 | 7/2010 | Johnson et al. |
| 2011/0081347 A1 | 4/2011 | Gorlatov |
| 2011/0097323 A1 | 4/2011 | Johnson et al. |
| 2011/0117089 A1 | 5/2011 | Johnson et al. |
| 2011/0206672 A1 | 8/2011 | Little et al. |
| 2012/0009186 A1 | 1/2012 | Koenig et al. |
| 2012/0034221 A1 | 2/2012 | Bonvini et al. |
| 2012/0141476 A1 | 6/2012 | Johnson et al. |
| 2012/0294796 A1 | 11/2012 | Johnson et al. |
| 2013/0078234 A1 | 3/2013 | Takahashi et al. |
| 2013/0149236 A1 | 6/2013 | Johnson et al. |
| 2013/0171148 A1 | 7/2013 | De Goeij et al. |
| 2013/0295121 A1 | 11/2013 | Johnson et al. |
| 2014/0017237 A1 | 1/2014 | Johnson et al. |
| 2014/0099318 A1 | 4/2014 | Huang et al. |
| 2014/0255407 A1 | 9/2014 | Koenig |
| 2014/0328750 A1 | 11/2014 | Johnson et al. |
| 2015/0175697 A1 | 6/2015 | Bonvini et al. |
| 2015/0239961 A1 | 8/2015 | Haynes et al. |
| 2017/0081424 A1 | 3/2017 | Bernett et al. |
| 2017/0349660 A1* | 12/2017 | Saville ............... A61K 45/06 |

FOREIGN PATENT DOCUMENTS

| | | |
|---|---|---|
| EP | 2158221 | 3/2010 |
| EP | 2247304 | 11/2010 |
| EP | 2252631 | 11/2010 |
| EP | 2282770 | 2/2011 |
| EP | 2328934 | 6/2011 |
| EP | 2371866 | 10/2011 |
| EP | 2376109 | 10/2011 |
| EP | 2542256 | 1/2013 |
| EP | 2585476 | 5/2013 |
| EP | 2601216 | 6/2013 |
| EP | 2714079 | 4/2014 |
| EP | 2714733 | 4/2014 |
| EP | 2786762 | 10/2014 |
| EP | 2839842 | 2/2015 |
| EP | 2840091 | 2/2015 |
| WO | WO 1991/003493 | 3/1991 |
| WO | WO 1992/022583 | 12/1992 |
| WO | WO 1993/011161 | 6/1993 |
| WO | WO 1995/015171 | 6/1995 |
| WO | WO 1998/002463 | 1/1998 |
| WO | WO 1998/023289 | 6/1998 |
| WO | WO 1999/055367 | 11/1999 |
| WO | WO 1999/057150 | 11/1999 |
| WO | WO 2001/000245 | 1/2001 |
| WO | WO 2002/002781 | 1/2002 |
| WO | WO 2003/012069 | 2/2003 |
| WO | WO 2003/024191 | 3/2003 |
| WO | WO 2003/025018 | 3/2003 |
| WO | WO 2003/032814 | 4/2003 |
| WO | WO 2003/087340 | 10/2003 |
| WO | WO 2003/093443 | 11/2003 |
| WO | WO 2004/001381 | 12/2003 |
| WO | WO 2004/043239 | 5/2004 |
| WO | WO 2004/106381 | 12/2004 |
| WO | WO 2005/028498 | 3/2005 |
| WO | WO 2005/070966 | 8/2005 |
| WO | WO 2005/121179 | 12/2005 |
| WO | WO 2006/076584 | 7/2006 |
| WO | WO 2006/083852 | 8/2006 |
| WO | WO 2006/084075 | 8/2006 |
| WO | WO 2006/084078 | 8/2006 |
| WO | WO 2006/084092 | 8/2006 |
| WO | WO 2006/084226 | 8/2006 |
| WO | WO 2007/046893 | 4/2007 |
| WO | WO 2007/075270 | 7/2007 |
| WO | WO 2007/110205 | 10/2007 |
| WO | WO 2007/146968 | 12/2007 |
| WO | WO 2008/003103 | 1/2008 |
| WO | WO 2008/003116 | 1/2008 |
| WO | WO 2008/019290 | 2/2008 |
| WO | WO 2008/024188 | 2/2008 |
| WO | WO 2008/027236 | 3/2008 |
| WO | WO 2008/116219 | 9/2008 |
| WO | WO 2008/146911 | 12/2008 |
| WO | WO 2008/157379 | 12/2008 |
| WO | WO 2009/018386 | 2/2009 |
| WO | WO 2009/058492 | 5/2009 |
| WO | WO 2009/123894 | 10/2009 |
| WO | WO 2009/132876 | 11/2009 |
| WO | WO 2009/151717 | 12/2009 |
| WO | WO 2010/136172 | 2/2010 |
| WO | WO 2010/027797 | 3/2010 |
| WO | WO 2010/028795 | 3/2010 |
| WO | WO 2010/028796 | 3/2010 |
| WO | WO 2010/028797 | 3/2010 |
| WO | WO 2010/033279 | 3/2010 |
| WO | WO 2010/080538 | 7/2010 |
| WO | WO 2010/108127 | 9/2010 |
| WO | WO 2011/034660 | 3/2011 |
| WO | WO 2011/086091 | 7/2011 |
| WO | WO 2011/109400 | 9/2011 |
| WO | WO 2011/133886 | 10/2011 |
| WO | WO 2011/143545 | 11/2011 |

(56) References Cited

FOREIGN PATENT DOCUMENTS

| | | | |
|---|---|---|---|
| WO | WO 2011/147986 | 12/2011 | |
| WO | WO 2011/163401 | 12/2011 | |
| WO | WO 2012/009544 | 1/2012 | |
| WO | WO 2012/018687 | 2/2012 | |
| WO | WO 2012/058768 | 5/2012 | |
| WO | WO 2012/143524 | 10/2012 | |
| WO | WO 2012/147713 | 11/2012 | |
| WO | WO 2012/156430 | 11/2012 | |
| WO | WO 2012/162067 * | 11/2012 | ........... A61K 39/395 |
| WO | WO 2012/162068 | 11/2012 | |
| WO | WO 2012/162583 | 11/2012 | |
| WO | WO 2013/003652 | 1/2013 | |
| WO | WO 2013/006544 | 1/2013 | |
| WO | WO 2013/006867 | 1/2013 | |
| WO | WO 2013/012414 | 1/2013 | |
| WO | WO 2013/013700 | 1/2013 | |
| WO | WO 2013/026835 | 2/2013 | |
| WO | WO 2013/041687 | 3/2013 | |
| WO | WO 2013/070565 | 5/2013 | |
| WO | WO 2013/119903 | 8/2013 | |
| WO | WO 2013/158856 | 10/2013 | |
| WO | WO 2013/163427 | 10/2013 | |
| WO | WO 2013/174873 | 11/2013 | |
| WO | WO 2014/022540 | 2/2014 | |
| WO | WO 2014/072888 | 5/2014 | |
| WO | WO 2014/110601 | 7/2014 | |
| WO | WO 2014/159940 | 10/2014 | |
| WO | WO 2015/021089 | 2/2015 | |
| WO | WO 2015/026892 | 2/2015 | |
| WO | WO 2015/026894 | 2/2015 | |
| WO | WO 2015/184203 | 12/2015 | |
| WO | WO 2015/184207 | 12/2015 | |
| WO | WO 2016/014974 | 1/2016 | |
| WO | WO 2016/036937 | 3/2016 | |
| WO | WO 2016/048938 | 3/2016 | |
| WO | WO 2016/054053 | 4/2016 | |
| WO | WO 2016/054101 | 4/2016 | |
| WO | WO 2016/086189 | 6/2016 | |
| WO | WO 2016/105450 | 6/2016 | |
| WO | WO 2016/115274 | 7/2016 | |
| WO | WO 2016/116626 * | 7/2016 | ............ C07K 16/28 |
| WO | WO 2016/182751 | 11/2016 | |
| WO | WO 2017/011413 | 1/2017 | |
| WO | WO 2017/011414 | 1/2017 | |
| WO | WO 2017/030926 | 2/2017 | |
| WO | WO 2017/053469 | 3/2017 | |
| WO | WO 2017/106061 | 6/2017 | |
| WO | WO 2017/118675 | 7/2017 | |
| WO | WO 2017/180913 | 10/2017 | |
| WO | WO 2017/210443 A1 | 12/2017 | |
| WO | WO 2018/017786 | 1/2018 | |
| WO | WO 2018/223002 A1 | 12/2018 | |

OTHER PUBLICATIONS

Almqvist, Y. (2006) "*In vitro and in vivo Characterization of 177Lu-huA33: A Radioimmunoconjugate Against Colorectal Cancer*," Nucl. Med. Biol. 33(8):991-998.

Alt et al. (1999) "*Novel Tetravalent and Bispecific IgG-like Antibody Molecules Combining Single-Chain Diabodies with the Immunoglobulin γl Fc or CH3 Region*," FEBS Lett. 454(1-2):90-94.

Andera, L. (2009) "*Signaling Activated By The Death Receptors Of The TNFR Family*," Biomed. Pap. Med. Fac. Univ. Palacky Olomouc Czech. Repub. 153(3):173-180.

Armstrong, K.M. et al. (2008) "*Conformational Changes And Flexibility In T-Cell Receptor Recognition Of Peptide-MHC Complexes*," Biochem. J. 415(Pt 2):183-196.

Asano et al. (2004) "*A Diabody For Cancer Immunotherapy And Its Functional Enhancement By Fusion Of Human Fc Domain*," Abstract 3P-683, J. Biochem. 76(8):992.

Atwell et al. (1997) "*Stable Heterodimers From Remodeling The Domain Interface Of A Homodimer Using A Phage Display Library*," J. Mol. Biol. 270: 26-35.

Baeuerle et al. (2011) "*Bispecific T-cell Engager For Cancer Therapy*," In: Bispecific Antibodies, Kontermann, R.E. (Ed.) Springer-Verlag; 2011:273-287.

Baeuerle, P.A. et al. (2009) "*Bispecific T-Cell Engaging Antibodies For Cancer Therapy*," Cancer Res. 69(12):4941-4944.

Barderas, R. et al. (2012) "*High Expression Of IL-13 Receptor A2 In Colorectal Cancer Is Associated With Invasion, Liver Metastasis, And Poor Prognosis*," Cancer Res. 72(11):2780-2790.

Barrett, D.M. et al. (2014) "*Toxicity Management For Patients Receiving Novel T-Cell Engaging Therapies*," Curr. Opin. Pediatr. 26(1):43-49.

Bast, R.C. Jr et al. (2005) "*New Tumor Markers: CA125 And Beyond*," Int. J. Gynecol. Cancer 15(Suppl 3):274-281.

Bataille, R. (2006) "*The Phenotype Of Normal, Reactive And Malignant Plasma Cells. Identification Of "Many And Multiple Myelomas" And Of New Targets For Myeloma Therapy*," Haematologica 91(9):1234-1240.

Beier, K.C. et al. (2007) "*Master Switches Of T-Cell Activation And Differentiation*," Eur. Respir. J. 29:804-812.

Bhattacharya-Chatteijee et al. (1988) "*Idiotype Vaccines Against Human T Cell Leukemia. II. Generation And Characterization Of A Monoclonal Idiotype Cascade (Ab1, Ab2, and Ab3)*," J. Immunol. 141:1398-1403.

Blumenthal, R.D. et al. (2007) "*Expression Patterns Of CEACAM5 And CEACAM6 In Primary And Metastatic Cancers*," BMC Cancer, 7:2, pp. 1-15.

Bodey, B. (2002) "*Cancer-Testis Antigens: Promising Targets For Antigen Directed Antineoplastic Immunotherapy*," Expert Opin. Biol. Ther. 2(6):577-584.

Boghaert, E.R et al. (2008) "*The Oncofetal Protein, 5T4, Is A Suitable Target For Antibody-Guided Anti-Cancer Chemotherapy With Calicheamicin*," Int. J. Oncol. 32(1):221-234.

Bou-Assaly, W. et al. (2010) "*Cetuximab (Erbitux)*," Am. J. Neuroradiol. 31(4):626-627.

Bozinov, O. et al. (2010) "*Decreasing Expression Of The Interleukin-13 Receptor IL-13Ralpha2 In Treated Recurrent Malignant Gliomas*," Neurol. Med. Chir. (Tokyo) 50(8):617-621.

Brown et al. (1987) "*Tumor-Specific Genetically Engineered Murine/Human Chimeric Monoclonal Antibody*," Cancer Res. 47:3577-3583.

Brown, C.E. et al. (2013) "*Glioma IL13Rα2 Is Associated With Mesenchymal Signature Gene Expression And Poor Patient Prognosis*," PLoS One. 18;8(10):e77769.

Buchacher, A. et al. (1994) "*Generation Of Human Monoclonal Antibodies Against HIV-1 Proteins; Electrofusion And Epstein-Barr Virus Transformation For Peripheral Blood Lymphocyte Immortalization*," AIDS Res. Hum. Retroviruses 10(4):359-369.

Calin, G.A. et al. (2006) "*Genomics Of Chronic Lymphocytic Leukemia MicroRNAs As New Players With Clinical Significance*," Semin. Oncol. 33(2):167-173.

Cameron, S. et al. (2012) "*Focal Overexpression Of CEACAM6 Contributes To Enhanced Tumourigenesis In Head And Neck Cancer Via Suppression Of Apoptosis*," Mol. Cancer 11:74, pp. 1-11.

Carlo-Stella, C. et al. (2007) "*Targeting TRAIL Agonistic Receptors for Cancer Therapy*," Clin. Cancer 13(8):2313-2317.

Carter, P. et al. (1992) "*Humanization Of An Anti-p185her2 Antibody For Human Cancer Therapy*," Proc. Natl. Acad. Sci. (U.S.A.) 89:4285-4289.

Castelli, C. et al. (2000) "*T-Cell Recognition Of Melanoma-Associated Antigens*," J. Cell. Physiol. 182(3):323-331.

Chan, C.E. et al. (2009) "*The Use Of Antibodies In The Treatment Of Infectious Diseases*," Singapore Med. J. 50(7):663-666.

Chang, K. et al. (1996) "*Molecular Cloning Of Mesothelin, A Differentiation Antigen Present On Mesothelium, Mesotheliomas, And Ovarian Cancers*," Proc. Natl. Acad. Sci. (U.S.A.) 93:136-140.

Chapin, C. et al. (2012) "*Distribution And Surfactant Association Of Carcinoembryonic Cell Adhesion Molecule 6 In Human Lung*," Amer. J. Physiol. Lung Cell. Mol. Physiol. 302(2):L216-L25.

Chapoval, A. et al. (2001) "*B7-H3: A Costimulatory Molecule For T Cell Activation and IFN-γ Production*," Nature Immunol. 2:269-274.

Chaudhari, B.R. et al. (2006) "*Following the TRAIL to Apoptosis*," Immunologic Res. 35(3):249-262.

(56) References Cited

OTHER PUBLICATIONS

Chen, P. et al. (2014) "*EphA2 Enhances The Proliferation And Invasion Ability Of LnCap Prostate Cancer Cells,*" Oncol. Lett. 8(1):41-46.
Chetty, R. et al. (1994) "*CD3: Structure, Function, And Role Of Immuno staining In Clinical Practice,*" J. Pathol. 173(4):303-307.
Chichili, G.R. et al. (2015) "*A CD3xCD123 Bispecific DART For Redirecting Host T Cells To Myelogenous Leukemia: Preclinical Activity And Safety In Nonhuman Primates,*" Sci. Transl. Med. 7(289):289ra82.
Chothia, C. & Lesk, A. M. ((1987) "*Canonical structures for the hypervariable regions of immunoglobulins,*" J. Mol. Biol. 196:901-917.
Chu, P.G. et al. (2001) "*CD79: A Review,*" Appl. Immunohistochem. Mol. Morphol. 9(2):97-106.
Co, M. S. et al. (1991) "*Humanized Antibodies For Antiviral Therapy,*" Proc. Natl. Acad. Sci. (U.S.A.) 88:2869-2873.
Co, M.S. et al. (1992) "*Chimeric And Humanized Antibodies With Specificity For The CD33 Antigen,*" J. Immunol. 148:1149-1154.
Collins, M. et al. (2005) "*The B7 Family Of Immune-Regulatory Ligands,*" Genome Biol. 6:223.1-223.7.
Cracco, C.M. et al. (2005) "*Immune Response In Prostate Cancer,*" Minerva Urol. Nefrol. 57(4):301-311.
Dall'Acqua, W.F. et al. (2006) "*Properties of Human IgG1s Engineered for Enhanced Binding to the Neonatal Fc Receptor (FcRn),*" J. Biol. Chem. 281(33):23514-23524.
Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins,*" Nucl. Acids Res. 19:2471-2476.
Davis et al. (1999) "*Therapy of B-Cell Lymphoma With Anti-CD20 Antibodies Can Result In The Loss Of CD20 Antigen Expression.*" Clin Cancer Res, 5:611-615, 1999.
Deng, X. et al. (2014) "*Expression Profiling Of CEACAM6 Associated With The Tumorigenesis And Progression In Gastric Adenocarcinoma,*" Genet. Mol. Res. 13(3):7686-7697.
Dennis, J.W. (1999) "*Glycoprotein Glycosylation And Cancer Progression,*" Biochim. Biophys. Acta. 6;1473(1):21-34.
Di Bartolomeo, M. et al. (2015) "*Bevacizumab Treatment In The Elderly Patient With Metastatic Colorectal Cancer,*" Clin. Interv. Aging 10:127-133.
DiMaio, D. et al. (2006) "*Human Papillomaviruses And Cervical Cancer,*" Adv. Virus Res. 66:125-59.
Dong, C. et al. (2003) "*Immune Regulation by Novel Costimulatory Molecules,*" Immunolog. Res. 28(1):39-48.
Dougall et al. (1994) "*The Neu-Oncogene: Signal Transduction Pathways, Transformation Mechanisms and Evolving Therapies,*" Oncogene 9:2109-2123 (Abstract Only).
Edelson (1998) "*Cutaneous T-Cell Lymphoma: A Model For Selective Immunotherapy,*" Cancer J. Sci. Am. 4:62-71.
Egloff, A.M. et al. (2006) "*Cyclin B1 And Other Cyclins As Tumor Antigens In Immunosurveillance And Immunotherapy Of Cancer,*" Cancer Res. 66(1):6-9.
Eisen, T. et al. (2014) "*Naptumomab Estafenatox: Targeted Immunotherapy with a Novel Immunotoxin,*" Curr. Oncol. Rep. 16:370, pp. 1-6.
Eketorp, S.S. et al. (2014) "*Alemtuzumab (Anti-CD52 Monoclonal Antibody) As Single-Agent Therapy In Patients With Relapsed/Refractory Chronic Lymphocytic Leukaemia (CLL)—A Single Region Experience On Consecutive Patients,*" Ann Hematol. 93(10):1725-1733.
Estin et al. (1989) "*Transfected Mouse Melanoma Lines That Express Various Levels Of Human Melanoma-Associated Antigen p97,*" J. Natl. Cancer Instit. 81(6):445-454.
Feizi (1985) "*Demonstration By Monoclonal Antibodies That Carbohydrate Structures Of Glycoproteins And Glycolipids Are Onco-Developmental Antigens,*" Nature 314:53-57.
Ferrari, F. et al. (2015) "*Solitomab, an EpCAM/CD3 Bispecific Antibody Construct (BiTE®), is Highly Active Against Primary Uterine and Ovarian Carcinosarcoma Cell Lines in vitro,*" J. Experimental & Clinical Cancer Res. 34:123 (8 pages).
Field, K.M. (2015) "*Bevacizumab And Glioblastoma: Scientific Review, Newly Reported Updates, And Ongoing Controversies,*" Cancer 121(7):997-1007.
Fitzgerald, J.C. et al. (2017) "*Cytokine Release Syndrome After Chimeric Antigen Receptor T-Cell Therapy for Acute Lymphoblastic Leukemia,*" Crit. Care Med. 45(2):e124-e131.
Foon et al. (1995) "*Immune Response To The Carcinoembryonic Antigen In Patients Treated With An Anti-Idiotype Antibody Vaccine,*" J. Clin. Invest. 96(1):334-42.
Foon, K.A. et al. (2004) "*Preclinical And Clinical Evaluations Of ABX-EGF, A Fully Human Anti-Epidermal Growth Factor Receptor Antibody,*" Int. J. Radiat. Oncol. Biol. Phys. 58(3):984-990.
Frey, N.V. et al. (2016) "*Cytokine Release Syndrome With Novel Therapeutics For Acute Lymphoblastic Leukemia,*" Hematol. Am. Soc. Hematol. Educ Program, (1):567-572.
Fujisawa, T. et al. (2009) "*A Novel Role Of Interleukin-13 Receptor Alpha2 In Pancreatic Cancer Invasion And Metastasis,*" Cancer Res. 69(22):8678-8685.
Fukushima, A. et al. (2007) "*B7-H3 Regulates The Development Of Experimental Allergic Conjunctivitis In Mice,*" Immunol. Lett. 113:52-57.
Ganesan, A. (2006) "*Solid-Phase Synthesis In The Twenty-First Century,*" Mini Rev. Med. Chem. 6(1):3-10.
Gao, G. et al. (2000) "*Molecular Interactions Of Coreceptor CD8 And MHC Class I: The Molecular Basis For Functional Coordination With The T-Cell Receptor,*" Immunol. Today 21:630-636.
Gardnerova, M. et al. (2000) "*The Use Of TNF Family Ligands And Receptors And Agents Which Modify Their Interaction As Therapeutic Agents,*" Curr. Drug Targets 1(4):327-364.
Ge, Y. (2005) "*CD36: A Multiligand Molecule,*" Lab Hematol. 11(1):31-7 (Abstract Only).
Ghetie et al. (1994) "*Anti-CD19 Inhibits The Growth Of Human B-Cell Tumor Lines In Vitro And Of Daudi Cells In SCID Mice By Inducing Cell Cycle Arrest,*" Blood 83:1329-1336.
Gil, J. et al. (2006) "*Regulation Of The INK4b-ARF-INK4a Tumour Suppressor Locus: All For One Or One For All,*" Nat. Rev. Mol. Cell Biol. 7(9):667-677.
Goebeler, M.E. et al. (2016) "*Blinatumomab: A CD19/CD3 Bispecific T Cell Engager (Bite) With Unique Anti-Tumor Efficacy,*" Lenk. Lymphoma 57(5):1021-1032 (Abstract Only).
Gonzales, N.R. et al. (2004) "*SDR Grafting Of A Murine Antibody Using Multiple Human Germline Templates To Minimize Its Immunogenicity,*" Mol. Immunol. 41:863-872 (Abstract Only).
Gorman, S. D. et al. (1991) "*Reshaping A Therapeutic CD4 Antibody,*" Proc. Natl. Acad. Sci. (U.S.A.) 88:4181-4185.
Govindan R. (2004) "*Cetuximab In Advanced Non-Small Cell Lung Cancer,*" Clin Cancer Res. 10(12 Pt 2):4241s-4244s.
Grabowski, J.P. (2015) "*Current Management Of Ovarian Cancer,*" Minerva Med. 106(3):151-156 (Abstract Only).
Guy, C.S. et al. (2009) "*Organization of Proximal Signal Initiation at the TCR:CD3 Complex,*" Immunol Rev. 232(1):7-21.
Harris, A. et al. (2011) "*Trimeric HIV-1 Glycoprotein Gp140 Immunogens And Native HIV-1 Envelope Glycoproteins Display The Same Closed And Open Quaternary Molecular Architectures,*" Proc. Natl. Acad. Sci. (U.S.A.) 108(28):11440-11445.
Harwood, S.L., et al. (2018) "*Attack, a Novel Bispecific T Cell-Recruiting Antibody with Trivalent EGFR Binding and Monovalent CD3 Binding for Cancer Immunotherapy,*" Oncoimmunology 7(1):e1377874 (14 pages).
Heath, J.K. et al. (1997) "*The Human A33 Antigen Is A Transmembrane Glycoprotein And A Novel Member Of The Immunoglobulin Superfamily,*" Proc. Natl. Acad. Sci. (U.S.A.) 94(2):469-474.
Hellström et al. (1985) "*Monoclonal Antibodies To Cell Surface Antigens Shared By Chemically Induced Mouse Bladder Carcinomas,*" Cancer. Res. 45:2210-2188.
Hellström et al. (1986) "*Monoclonal Mouse Antibodies Raised Against Human Lung Carcinoma,*" Cancer Res. 46:3917-3923.
Henttu et al. (1989) "*cDNA Coding For The Entire Human Prostate Specific Antigen Shows High Homologies To The Human Tissue Kallikrein Genes,*" Biochem. Biophys. Res. Comm. 10(2):903-910.

(56) References Cited

OTHER PUBLICATIONS

Herlyn et al. (1982) "Monoclonal Antibody Detection Of A Circulating Tumor-Associated Antigen. I. Presence Of Antigen In Sera Of Patients With Colorectal, Gastric, And Pancreatic Carcinoma," J. Clin. Immunol. 2:135-140.
Hilkens et al. (1992) "*Cell Membrane-Associated Mucins And Their Adhesion-Modulating Property*," Trends in Biochem. Sci. 17:359-363.
Hoelzer, D. (2013) "*Targeted Therapy With Monoclonal Antibodies In Acute Lymphoblastic Leukemia*," Curr. Opin. Oncol. 25(6):701-706.
Hofmeyer, K. et al. (2008) "*The Contrasting Role Of B7-H3*," Proc. Natl. Acad. Sci. (U.S.A.) 105(30):10277-10278.
Holliger et al. (1993) "'*Diabodies': Small Bivalent And Bispecific Antibody Fragments*," Proc. Natl. Acad. Sci. (U.S.A.) 90:6444-6448.
Holliger et al. (1996) "*Specific Killing Of* Lymphoma *Cells By Cytotoxic T-Cells Mediated By A Bispecific Diabody*," Protein Eng. 9:299-305.
Holmberg, L.A. (2001) "*Theratope Vaccine (STn-KLH)*," Expert Opin. Biol. Ther. 1(5):881-91.
Hoon et al. (1993) "*Molecular Cloning Of A Human Monoclonal Antibody Reactive To Ganglioside GM3 Antigen On Human Cancers*," Cancer Res. 53:5244-5250.
Houghten, R.A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci. (U.S.A.) 82(15):5131-5135.
Hynes et al. (1994) "*The Biology of erbB-2 /neu / HER-2 and its Role in Cancer*," Biochim. Biophys. Acta 1198:165-184.
International Search Report PCT/US2019/017772 (WO 2019/160904) (dated 2019) (3 pages).
Israeli et al. (1993) "*Molecular Cloning Of A Complementary DNA Encoding A Prostate-Specific Membrane Antigen*," Cancer Res. 53:227-230.
Jennings, V.M. (1995) "*Review of Selected Adjuvants Used in Antibody Production*," ILAR J. 37(3):119-125.
Johansson, M.U. et al. (2002) "*Structure, Specificity, And Mode Of Interaction For Bacterial Albumin-Binding Modules*," J. Biol. Chem. 277(10):8114-8120.
Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449.
Jones et al. (1986) "*Replacing The Complementarity-Determining Regions In A Human Antibody With Those From A Mouse*," Nature 321:522-525.
Jurcic, J.G. (2005) "*Immunotherapy For Acute Myeloid Leukemia*," Curr. Oncol. Rep. 7(5):339-346.
Kasaian, M.T. et al. (2011) "*IL-13 Antibodies Influence IL-13 Clearance In Humans By Modulating Scavenger Activity Of IL-13Ra2*," J. Immunol. 187(1):561-569.
Kashmiri, S.V. et al. (2005) "*SDR Grafting—A New Approach To Antibody Humanization*," Methods 36(1):25-34 (Abstract Only).
Kawai, S. et al. (2008) "*Interferon-A Enhances CD317 Expression And The Antitumor Activity Of Anti-CD317 Monoclonal Antibody In Renal Cell Carcinoma Xenograft Models*," Cancer Science 99(12):2461-2466.
Kettleborough, C. A. et al. (1991) "*Humanization Of A Mouse Monoclonal Antibody By CDR-Grafting: The Importance Of Framework Residues On Loop Conformation*," Protein Engineering 4:773-3783.
Khawli, L.A. et al. (2008) "*Cytokine, Chemokine, and Co-Stimulatory Fusion Proteins for the Immunotherapy of Solid Tumors*," Exp. Pharmacol. 181:291-328.
Kim, J.H. et al. (2012) "*Humanization By CDR Grafting And Specificity-Determining Residue Grafting*," Methods Mol. Biol. 907:237-245 (Abstract Only).
Kim, K.S. et al. (2010) "*Construction Of A Humanized Antibody To Hepatitis B Surface Antigen By Specificity-Determining Residues (SDR)-Grafting And De-Immunization*," Biochem. Biophys. Res. Commun. 396(2):231-237 (Abstract Only).
Kohler, G. et al. (1975) "*Continuous Cultures Of Fused Cells Secreting Antibody Of Predefined Specificity*," Nature 256:495-497.
Korman, A. J. et al. (2007) "*Checkpoint Blockade in Cancer Immunotherapy*," Adv. Immunol. 90:297-339.
Kounalakis, N. et al. (2005) "*Tumor Cell And Circulating Markers In Melanoma: Diagnosis, Prognosis, And Management*," Curr. Oncol. Rep. 7(5):377-382.
Kreitman, R.J. (2006) "*Immunotoxins For Targeted Cancer Therapy*," AAPS J. 8(3):E532-51.
Kuhns, M.S. et al. (2006) "*Deconstructing The Form And Function Of The TCR/CD3 Complex*," Immunity, Feb. 2006;24(2):133-139.
Kuo, S.R. et al., (2012) "*Engineering a CD123xCD3 Bispecific scFv Immunofusion For The Treatment Of Leukemia And Elimination Of Leukemia Stem Cells*," Protein Eng Des Sel. 25:561-9.
Langer (1990) "*New Methods Of Drug Delivery*," Science 249:1527-1533.
Le Jeune, C. et al. (2016) "*Potential For Bispecific T-Cell Engagers: Role Of Blinatumomab In Acute Lymphoblastic Leukemia*," Drug Des. Devel. Ther. 10:757-765.
Leahy, D.J. (1995) "*A Structural View of CD4 and CD8*," FASEB J. 9:17-25.
Lee et al. (1995) "*Requirement for Neuregulin Receptor erbB2 in Neural and Cardiac Development*," Nature 378:394-398.
Lee, Y.M. et al. (2006) "*Targeting Cyclins And Cyclin-Dependent Kinases In Cancer: Lessons From Mice, Hopes For Therapeutic Applications In Human*," Cell Cycle 5(18):2110-2114.
Lefranc, G. et al. (1979) "*Gm, Am and Km Immunoglobulin Allotypes of Two Populations in Tunisia*," Hum. Genet.: 50, 199-211.
Lewis-Wambi, J.S. et al. (2008) "*Overexpression Of CEACAM6 Promotes Migration And Invasion Of Oestrogen-Deprived Breast Cancer Cells*," Eur. J. Cancer 44(12):1770-1779.
Lindley, P.S. et al. (2009) "*The Clinical Utility Of Inhibiting CD28-Mediated Costimulation*," Immunol. Rev. 229:307-321.
Liu, K.J. et al. (2015) "*Bevacizumab In Combination With Anticancer Drugs For Previously Treated Advanced Non-Small Cell Lung Cancer*," Tumour Biol. 36(3):1323-1327 (Abstract Only).
Livingston et al. (1994) "*Improved Survival In Stage III Melanoma Patients With GM2 Antibodies: A Randomized Trial Of Adjuvant Vaccination With GM2 Ganglioside*," J. Clin. Oncol. 12:1036-1044.
Livingston, P.O. et al. (2005) "*Selection Of GM2, Fucosyl GM1, Globo H And Polysialic Acid As Targets On Small Cell Lung Cancers For Antibody-Mediated Immunotherapy*," Cancer Immunol. Immunother. 54(10):1018-1025.
LoBuglio, A.F. et al. (1989) "*Mouse/Human Chimeric Monoclonal Antibody In Man: Kinetics And Immune Response*," Proc. Natl. Acad. Sci. (U.S.A.) 86:4220-4224.
Lonberg, N. et al. (1995) "*Human Antibodies From Transgenic Mice*," Int. Rev. Immunol 13:65-93.
Loo, D. et al. (2012) "*Development Of An Fc-Enhanced Anti-B7-H3 Monoclonal Antibody With Potent Antitumor Activity*," Clin. Cancer Res. 18(14):3834-3845.
Lotem, M. et al. (2006) "*Presentation Of Tumor Antigens By Dendritic Cells Genetically Modified With Viral And Nonviral Vectors*," J. Immunother. 29(6):616-27.
Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672.
Maeda, H. et al. (1991) "*Construction Of Reshaped Human Antibodies With HIV-Neutralizing Activity*," Human Antibodies Hybridoma 2:124-134.
Mallone, R. et al. (2005) "*Targeting T Lymphocytes For Immune Monitoring And Intervention In Autoimmune Diabetes*," Am. J. Ther. 12(6):534-550.
Marvin et al. (2005) "*Recombinant Approaches To IgG-Like Bispecific Antibodies*," Acta Pharmacol. Sin. 26:649-658.
Mathelin C. (2006) "*Circulating Proteinic Biomarkers And Breast Cancer*," Gynecol. Obstet. Fertil. 34(7-8):638-646.
Merrifield, B. (1986) "*Solid Phase Synthesis*," Science 232(4748):341-347.

(56) References Cited

OTHER PUBLICATIONS

Messmer, D. et al. (2005) "*CD154 Gene Therapy For Human B-Cell Malignancies,*" Ann N. Y. Acad. Sci. 1062:51-60.

Miao, B. et al. (2014) "*EphA2 is a Mediator of Vemurafenib Resistance and a Novel Therapeutic Target in Melanoma,*" Cancer Discov. pii: CD-14-0295.

Mittelman et al. (1990) "*Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies,*" J. Clin. Invest. 86:2136-2144.

Möller et al. (1991) "*Bi-specific-Monoclonal-Antibody-Directed Lysis Of Ovarian Carcinoma Cells By Activated Human T Lymphocytes,*" Cancer Immunol. Immunother. 33(4):210-216.

Moore, P.A. et al. (2011) "*Application Of Dual Affinity Retargeting Molecules To Achieve Optimal Redirected T-Cell Killing Of B-Cell Lymphoma,*" Blood 117(17):4542-4551.

Muñoz, L. et al. (2001) "*Interleukin-3 Receptor Alpha Chain (CD123) Is Widely Expressed In Hematologic Malignancies,*" Haematologica 86(12):1261-1269.

Natali et al. (1987) "*Immunohistochemical Detection Of Antigen In Human Primary And Metastatic Melanomas By The Monoclonal Antibody 140.240 And Its Possible Prognostic Significance,*" Cancer 59:55-63.

Newman, M.J. et al. (2016) "*A Review Of Blinatumomab, A Novel Immunotherapy,*" J. Oncol. Pharm. Pract. 22(4):639-645 (Abstract Only).

O'Dwyer, P.J. (2006) "*The Present And Future Of Angiogenesis-Directed Treatments Of Colorectal Cancer,*" Oncologist 11(9):992-998.

Olafsen, T. et al. (2004) "*Covalent Disulfide-Linked Anti-CEA Diabody Allows Site-Specific Conjugation And Radiolabeling For Tumor Targeting Applications,*" Protein Eng. Des. Sel. 17(1):21-27.

Pal, S.K. et al. (2006) "*Targeting HER2 Epitopes,*" Semin. Oncol. 33(4):386-391.

Peeters et al. (2001) "*Production Of Antibodies And Antibody Fragments In Plants,*" Vaccine 19:2756.

Peggs, K.S. et al. (2006) "*Principles And Use Of Anti-CTLA4 Antibody In Human Cancer Immunotherapy,*" Curr. Opin. Immunol. 18(2):206-13.

Perez et al. (1989) "*Isolation And Characterization Of A cDNA Encoding The Ks1/4 Epithelial Carcinoma Marker,*" J. Immunol. 142:3662-3667.

Pietrantonio, F. et al. (2015) "*Bevacizumab-Based Neoadjuvant Chemotherapy For Colorectal Cancer Liver Metastases: Pitfalls And Helpful Tricks In A Review For Clinicians,*" Crit. Rev. Oncol. Hematol. 95(3):272-281.

Pollock et al. (1999) "*Transgenic Milk As A Method For The Production Of Recombinant Antibodies,*" J. Immunol. Methods 231:147-157.

Portoles, P. et al. (2009) "*The TCR/CD3 Complex: Opening the Gate to Successful Vaccination,*" Current Pharmaceutical Design 15:3290-3300.

Prange W. et al. (2003) "*Beta-Catenin Accumulation In The Progression Of Human Hepatocarcinogenesis Correlates With Loss Of E-Cadherin And Accumulation Of P53, But Not With Expression Of Conventional WNT-1 Target Genes,*" J. Pathol. 201(2):250-259.

Prasad, D.V. et al. (2004) "*Murine B7-H3 Is A Negative Regulator Of T Cells,*" J. Immunol. 173:2500-2506.

Ragnhammar et al. (1993) "*Effect Of Monoclonal Antibody 17-1A And GM-CSF In Patients With Advanced Colorectal Carcinoma—Long-Lasting, Complete Remissions Can Be Induced,*" Int. J. Cancer 53:751-758.

Ragupathi, G. (2005) "*Antibody Inducing Polyvalent Cancer Vaccines,*" Cancer Treat. Res. 123:157-180.

Reff et al. (1994) "*Depletion Of B Cells In Vivo By A Chimeric Mouse Human Monoclonal Antibody To CD20,*" Blood 83:435-445.

Renders, L. et al. (2003) "*Engineered CD3 Antibodies For Immunosuppression,*" Clin. Exp. Immunol. 133(3):307-309.

Ridgway et al. (1996) "*'Knobs-Into-Holes' Engineering Of Antibody CH3 Domains For Heavy Chain Heterodimerization,*" Protein Engr. 9:617-621.

Riechmarm, L. et al. (1988) "*Reshaping Human Antibodies for Therapy,*" Nature 332:323-327.

Riley, C.J. et al. (2009) "*Design And Activity Of A Murine And Humanized Anti-CEACAM6 Single-Chain Variable Fragment In The Treatment Of Pancreatic Cancer,*" Cancer Res. 69(5):1933-1940.

Rimon, E. et al. (2004) "*Gonadotropin-Induced Gene Regulation In Human Granulosa Cells Obtained From IVF Patients: Modulation Of Genes Coding For Growth Factors And Their Receptors And Genes Involved In Cancer And Other Diseases,*" Int. J. Oncol. 24(5):1325-1338.

Ritter, G. et al. (1997) "*Characterization Of Posttranslational Modifications Of Human A33 Antigen, A Novel Palmitoylated Surface Glycoprotein Of Human Gastrointestinal Epithelium,*" Biochem. Biophys. Res. Commun. 236(3):682-686.

Rosati, S. et al. (2005) "*Chronic Lymphocytic Leukaemia: A Review Of The Immuno-Architecture,*" Curr. Top. Microbiol. Immunol. 294:91-107.

Saleh et al. (1993) "*Generation Of A Human Anti-Idiotypic Antibody That Mimics The GD2 Antigen,*" J. Immunol., 151, 3390-3398.

Sato, K. et al. (1993) "*Reshaping a Human Antibody to Inhibit the Interleukin 6-dependent Tumor Cell Growth,*" Cancer Res 53:851-856.

Sayeed, A. et al. (2013) "*Aberrant Regulation Of The BST2 (Tetherin) Promoter Enhances Cell Proliferation And Apoptosis Evasion In High Grade Breast Cancer Cells,*" PLoS One 8(6)e67191, pp. 1-10.

Sgouros et al. (1993) "*Modeling And Dosimetry Of Monoclonal Antibody M195 (Anti-CD33) In Acute Myelogenous Leukemia,*" J. Nucl. Med. 34:422-430.

Sharpe, A.H. et al. (2002) "*The B7-CD28 Superfamily,*" Nature Rev. Immunol. 2:116-126.

Shaw et al. (1987) "*Characterization Of A Mouse/Human Chimeric Monoclonal Antibody (17-1A) To A Colon Cancer Tumor-Associated Antigen,*" J. Immunol. 138:4534-4538.

Shen, R. (2010) "*GP41-Specific Antibody Blocks Cell-Free HIV Type 1 Transcytosis Through Human Rectal Mucosa And Model Colonic Epithelium,*" J. Immunol. 184(7):3648-3655.

Shitara et al. (1993) "*A Mouse/Human Chimeric Anti-(Ganglioside GD3) Antibody With Enhanced Antitumor Activities,*" Cancer Immunol. Immunother. 36:373-380.

Sloan, D.D. et al. (2015) "*Targeting HIV Reservoir in Infected CD4 T Cells by Dual-Affinity Re-targeting Molecules (DARTs) that Bind HIV Envelope and Recruit Cytotoxic T Cells,*" PLoS Pathog. 11(11):e1005233. doi: 10.1371/journal.ppat.1005233.

Smith-Garvin, J.E. et al. (2009) "*T Cell Activation,*" Annu. Rev. Immunol. 27:591-619.

St. Clair, E.W. (Epub Oct. 12, 2009) "*Novel Targeted Therapies For Autoimmunity,*" Curr. Opin. Immunol. 21(6):648-657.

Staerz et al. (1985) "*Hybrid Antibodies Can Target Sites For Attack By T Cells,*" Nature 314:628-631.

Stavenhagen, J.B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors,*" Cancer Res. 57(18):8882-8890.

Stomski, F.C. et al. (1996) "*Human Interleukin-3 (IL-3) Induces Disulfide-Linked IL-3 Receptor Alpha-And Beta-Chain Heterodimerization, Which Is Required For Receptor Activation But Not High-Affinity Binding,*" Mol. Cell. Biol. 16(6):3035-3046.

Suh, D.H. et al. (2015) "*Major Clinical Research Advances In Gynecologic Cancer In 2014,*" J. Gynecol. Oncol. 26(2):156-167.

Sun, M. et al. (2002) "*Characterization of Mouse and Human B7-H3 Genes,*" J. Immunol. 168:6294-6297.

Sun, Z. J. et al. (2001) "*Mechanisms Contributing To T Cell Receptor Signaling And Assembly Revealed By The Solution Structure Of An Ectodomain Fragment Of The CD3ε.γ Heterodimer,*" Cell 105(7):913-923.

Suresh, T. et al. (2014) "*New Antibody Approaches To Lymphoma Therapy,*" J. Hematol. Oncol. 7:58.

(56) References Cited

OTHER PUBLICATIONS

Tailor et al. (1990) "*Nucleotide Sequence Of Human Prostatic Acid Phosphatase Determined From A Full-Length cDNA Clone*," Nucl. Acids Res. 18(16):4928.
Takemura, S. et al. (2000) "*Construction Of A Diabody (Small Recombinant Bispecific Antibody) Using A Refolding System*," Protein Eng. 13(8):583-588.
Teachey, D.T. et al. (2013) "*Cytokine Release Syndrome After Blinatumomab Treatment Related To Abnormal Macrophage Activation And Ameliorated With Cytokine-Directed Therapy*," Blood 121(26):5154-5157.
Teachey, D.T. et al. (2016) "*Identification of Predictive Biomarkers for Cytokine Release Syndrome after Chimeric Antigen Receptor T-cell Therapy for Acute Lymphoblastic Leukemia*," Cancer Discov. 6(6):664-679.
Tedder (2009) "*CD19: A Promising B-Cell Target For Rheumatoid Arthritis*," Nat. Rev. Rheumatol. 5:572-577.
Tellez-Avila, F.I. et al. (2005) "*The Carcinoembryonic Antigen: Apropos Of An Old Friend*," Rev. Invest. Clin. 57(6):814-819 (Abstract Only).
Tempest, P.R. et al. (1991) "*Reshaping A Human Monoclonal Antibody To Inhibit Human Respiratory Syncytial Virus Infection in vivo*," Bio/Technology 9:266-271.
Tettamanti, M.S. et al. (2013) "*Targeting Of Acute Myeloid Leukaemia By Cytokine-Induced Killer Cells Redirected With A Novel CD123-Specific Chimeric Antigen Receptor*," Br. J. Haematol. 161:389-401.
Thomas, D.A. et al. (2006) "*Monoclonal Antibody Therapy for Hairy Cell Leukemia*," Hematol Oncol Clin North Am. 20(5):1125-1136.
Thomas, S. et al. (2010) "*Molecular Immunology Lessons From Therapeutic T-Cell Receptor Gene Transfer*," Immunology 129(2):170-177.
Thompson, J. A. et al. (1991) "*Carcinoembryonic Antigen Gene Family: Molecular Biology And Clinical Perspectives*," J. Clin. Lab. Anal. 5:344-366.
Topalian, S.L. et al. (2015) "*Immune Checkpoint Blockade: A Common Denominator Approach to Cancer Therapy*," Cancer Cell 27:450-461.
Trauth, B.C. et al. (1989) "*Monoclonal Antibody-Mediated Tumor Regression By Induction Of Apoptosis*," Science 245:301-304.
Troussard, X. et al. (1998) "*Hairy Cell Leukemia. What Is New Forty Years After The First Description?*" Hematol. Cell. Ther. 40(4):139-148.
van der Merwe, P.A. etc. (epub Dec. 3, 2010) "*Mechanisms For T Cell Receptor Triggering*," Nat. Rev. Immunol. 11:47-55.
van Horssen, R. et al. (2006) "*TNF-Alpha In Cancer Treatment: Molecular Insights, Antitumor Effects, And Clinical Utility*," Oncologist 11(4):397-408.
Verhoeyen, M. et al. (1988) "*Reshaping Human Antibodies: Grafting An Antilysozyme Activity*," Science 239:1534-1536.
Veri, M.C. et al. (2010) "*Therapeutic Control Of B-Cell Activation Via Recruitment Of Fcgamma Receptor IIb (CD32B) Inhibitory Function With A Novel Bispecific Antibody Scaffold*," Arthritis Rheum. 62(7):1933-1943.
Viglietta, V. et al. (2007) "*Modulating Co-Stimulation*," Neurotherapeutics 4:666-675.
Vijayasardahl et al. (1990) "*The Melanoma Antigen Gp75 Is The Human Homologue Of The Mouse B (Brown) Locus Gene Product*," J. Exp. Med. 171(4):1375-1380.
Wang, W. et al. (2009) "*Chimeric And Humanized Anti-HM1.24 Antibodies Mediate Antibody-Dependent Cellular Cytotoxicity Against Lung Cancer Cells*," Lung Cancer 63(1):23-31.
Wang, W. et al. (2009) *HM1.24 (CD317) Is A Novel Target Against Lung Cancer For Immunotherapy Using Anti-HM1.24 Antibody*, Cancer Immunology Immunotherapy 58(6):967-976.
Willemsen, R. (2008) "*Selection Of Human Antibody Fragments Directed Against Tumor T-Cell Epitopes For Adoptive T-Cell Therapy*," Cytometry A. 73(11):1093-1099.
Winter et al. (1991) "*Man-made Antibodies*," Nature 349:293-299;
Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989).
Winter, G. et al. (1994) "*Making Antibodies By Phage Display Technology*," Annu. Rev. Immunol. 12.433-455.
Wong, N.A. et al. (2006) "*EpCAM and gpA33 Are Markers Of Barrett's Metaplasia*," J. Clin. Pathol. 59(3):260-263.
Written Opinion of the International Searching Authority PCT/US2019/017772 (WO 2019/160904) (2019) (4 pages).
Wu, A. et al. (2001) "*Multimerization Of A Chimeric Anti-CD20 Single Chain Fv-Fv Fusion Protein Is Mediated Through Variable Domain Exchange*," Protein Engineering 14(2):1025-1033.
Wu, Z., et al. (2018) "*T Cell Engaging Bispecific Antibody (T-BsAb): From Technology to Therapeutics*," Pharmacol. Ther. 182:161-175.
Wucherpfennig, K.W. et al. (2010) "*Structural Biology Of The T-Cell Receptor: Insights into Receptor Assembly, Ligand Recognition, And Initiation of Signaling*," Cold Spring Harb. Perspect. Biol. 2(4):a005140; pp. 1-14.
Xie et al. (2005) "*A New Format Of Bispecific Antibody: Highly Efficient Heterodimerization, Expression And Tumor Cell Lysis*," J. Immunol. Methods 296:95-101.
Xu, J. et al. (2014) "*High EphA2 Protein Expression In Renal Cell Carcinoma Is Associated With A Poor Disease Outcome*," Oncol. Lett. Aug. 2014; 8(2): 687-692.
Yazdi, M.H. et al. (2015) "*A Comprehensive Review of Clinical Trials on EGFR Inhibitors Such as Cetuximab and Panitumumab as Monotherapy and in Combination for Treatment of Metastatic Colorectal Cancer*," Avicenna J. Med. Biotechnol. 7(4):134-144.
Yi, K.H. et al. (2009) "*Fine Tuning The Immune Response Through B7-H3 And B7-H4*," Immunol. Rev. 229:145-151.
Yokota et al. (1992) "*Rapid Tumor Penetration Of A Single-Chain Fv And Comparison With Other Immunoglobulin Forms*," Cancer Res. 52:3402-3408.
Yu et al. (1991) "*Coexpression Of Different Antigenic Markers On Moieties That Bear CA 125 Determinants*," Cancer Res. 51(2):468-475.
Zang, X. et al. (2007) "*The B7 Family And Cancer Therapy: Costimulation And Coinhibition*," Clin. Cancer Res. 13:5271-5279.
Zheng, C. et al. (2011) "*A Novel Anti-CEACAM5 Monoclonal Antibody, CC4, Suppresses Colorectal Tumor Growth and Enhances NK Celis-Mediated Tumor Immunity*," PLoS One 6(6):e21146, pp. 1-11.
Zhou, H. et al. (2002) "*Lung Tumorigenesis Associated With Erb-B-2 And Erb-B-3 Overexpression In Human Erb-B-3 Transgenic Mice Is Enhanced By Methylnitrosourea*," Oncogene 21(57):8732-8740.
Bonvini, E. (2018) "*Multispecific DART® and TRIDENT™ Molecules Optimized for Immune-oncology Applications*," The Next Step In Changing Treatment Paradigms In Immune-Oncology, Mar. 13-14, 2018; London UK; 59 pages.
Bonvini, E. (2018) "*Tailoring Cytolytic Activity, Proliferation and Cytokine Release via CD3 Engineering of DART® Molecules for Redirected T-cell Killing*," 2018 Keystone Symposium "Antibodies as Drugs: Translating Molecules into Treatments" Feb. 25-Mar. 1, 2018, Whistler, British Columbia, Canada; 17 pages.

\* cited by examiner

CD19-WT, 0.1 mg/kg
(Positive Control)

Pre-dose

Day 7

CD19.1-M18, 10 mg/kg

Pre-dose

Day 7

CD19.1-M18, 30 mg/kg

Pre-dose          Day 7

SEQUENCE LISTING

<160> NUMBER OF SEQ ID NOS: 209

<210> SEQ ID NO 1
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG1 CH1 Domain

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 2
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG2 CH1 Domain

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 3
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG3 CH1 Domain -continued

```
<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 4
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Exemplary Human IgG4 CH1 Domain

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 5
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Exemplary Human IgG1 Hinge Domain

<400> SEQUENCE: 5

Glu Pro Lys Ser Cys Asp Lys Thr His Thr Cys Pro Pro Cys Pro
1               5                   10                  15

<210> SEQ ID NO 6
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Exemplary Human IgG2 Hinge Domain
```

```
<400> SEQUENCE: 6

Glu Arg Lys Cys Cys Val Glu Cys Pro Pro Cys Pro
1               5                   10

<210> SEQ ID NO 7
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: Exemplary Human IgG2 Hinge Domain

<400> SEQUENCE: 7

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
        50                  55                  60

<210> SEQ ID NO 8
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Exemplary Human IgG4 Hinge Domain

<400> SEQUENCE: 8

Glu Ser Lys Tyr Gly Pro Pro Cys Pro Ser Cys Pro
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Human IgG4 Hinge Domain Comprising Stabilizing
      S228P Substitution

<400> SEQUENCE: 9

Glu Ser Lys Tyr Gly Pro Pro Cys Pro Pro Cys Pro
1               5                   10

<210> SEQ ID NO 10
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Exemplary Human IgG1
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 10

Ala Pro Glu Leu Leu Gly Gly Pro Ser Val Phe Leu Phe Pro Pro Lys
1               5                   10                  15
```

-continued

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 11
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: CH2-CH3 Domain of Exemplary Human IgG2
<220> FEATURE:
<221> NAME/KEY: MISC_FEATURE
<222> LOCATION: (216)..(216)
<223> OTHER INFORMATION: Xaa is Lysine (K) or is Absent

<400> SEQUENCE: 11

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125
```

Lys Asn Gln Val Ser Leu Thr Cys Leu Val Lys Gly Phe Tyr Pro Ser
                130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
                180                 185                 190

Ser Cys Ser Val Met His Glu Ala Leu His Asn His Tyr Thr Gln Lys
                195                 200                 205

Ser Leu Ser Leu Ser Pro Gly Xaa
                210                 215

<210> SEQ ID NO 12
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Exemplary Human IgG3
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 12

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
                35                  40                  45

Val Asp Gly Val Glu Val His Asn Ala Lys Thr Lys Pro Arg Glu Glu
                50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
                100                 105                 110

Pro Arg Glu Pro Gln Val Tyr Thr Leu Pro Pro Ser Arg Glu Glu Met
                115                 120                 125

Thr Lys Asn Gln Val Ser Leu Thr Cys Leu Val Lys Gly Phe Tyr Pro
                130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
                180                 185                 190

Phe Ser Cys Ser Val Met His Glu Ala Leu His Asn Arg Phe Thr Gln
                195                 200                 205

Lys Ser Leu Ser Leu Ser Pro Gly Xaa
                210                 215

<210> SEQ ID NO 13

```
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of Exemplary Human IgG4
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 13

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 14
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Exemplary Human CL Kappa Domain

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 15
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: Exemplary Human CL Lambda Domain

<400> SEQUENCE: 15

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Ser Ser Pro Val
         35                  40                  45

Lys Ala Gly Val Glu Thr Thr Pro Ser Lys Gln Ser Asn Asn Lys Tyr
 50                  55                  60

Ala Ala Ser Ser Tyr Leu Ser Leu Thr Pro Glu Gln Trp Lys Ser His
 65                  70                  75                  80

Arg Ser Tyr Ser Cys Gln Val Thr His Glu Gly Ser Thr Val Glu Lys
                 85                  90                  95

Thr Val Ala Pro Thr Glu Cys Ser
            100

<210> SEQ ID NO 16
<211> LENGTH: 8
<212> TYPE: PRT
<213> ORGANISM: Artificial Sequence
<220> FEATURE:
<223> OTHER INFORMATION: Preferred Intervening Spacer Peptide (Linker 1)

<400> SEQUENCE: 16

Gly Gly Gly Ser Gly Gly Gly Gly
 1               5

<210> SEQ ID NO 17
<211> LENGTH: 6
<212> TYPE: PRT
<213> ORGANISM: Artificial Sequence
<220> FEATURE:
<223> OTHER INFORMATION: Preferred Cysteine-Containing Spacer Peptide
      (Linker 2)

<400> SEQUENCE: 17

Gly Gly Cys Gly Gly Gly
 1               5

<210> SEQ ID NO 18
<211> LENGTH: 4
<212> TYPE: PRT
<213> ORGANISM: Artificial Sequence
<220> FEATURE:
<223> OTHER INFORMATION: Alternative Spacer Peptide (Linker 2) Lacking
      Cysteine Residues
```

```
<400> SEQUENCE: 18

Gly Gly Gly Ser
1

<210> SEQ ID NO 19
<211> LENGTH: 6
<212> TYPE: PRT
<213> ORGANISM: Artificial Sequence
<220> FEATURE:
<223> OTHER INFORMATION: Alternative Spacer Peptide (Linker 2) Lacking
      Cysteine Residues

<400> SEQUENCE: 19

Leu Gly Gly Gly Ser Gly
1               5

<210> SEQ ID NO 20
<211> LENGTH: 11
<212> TYPE: PRT
<213> ORGANISM: Artificial Sequence
<220> FEATURE:
<223> OTHER INFORMATION: Alternative Spacer Peptide (Linker 2) Lacking
      Cysteine Residues

<400> SEQUENCE: 20

Gly Gly Gly Ser Gly Gly Gly Ser Gly Gly Gly
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Alternative Spacer Peptide (Linker 2) Lacking
      Cysteine Residues

<400> SEQUENCE: 21

Ala Ser Thr Lys Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Alternative Spacer Peptide (Linker 2) Lacking
      Cysteine Residues

<400> SEQUENCE: 22

Leu Glu Pro Lys Ser Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Alternative Spacer Peptide (Linker 2) Lacking
      Cysteine Residues

<400> SEQUENCE: 23

Ala Pro Ser Ser Ser
1               5

<210> SEQ ID NO 24
<211> LENGTH: 7
<212> TYPE: PRT
```

```
<213> ORGANISM: Artificial Sequence
<220> FEATURE:
<223> OTHER INFORMATION: Heterodimer-Promoting Domain

<400> SEQUENCE: 24

Gly Val Glu Pro Lys Ser Cys
1               5

<210> SEQ ID NO 25
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 25

Val Glu Pro Lys Ser Cys
1               5

<210> SEQ ID NO 26
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 26

Ala Glu Pro Lys Ser Cys
1               5

<210> SEQ ID NO 27
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 27

Gly Phe Asn Arg Gly Glu Cys
1               5

<210> SEQ ID NO 28
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 28

Phe Asn Arg Gly Glu Cys
1               5

<210> SEQ ID NO 29
<211> LENGTH: 28
<212> TYPE: PRT
<213> ORGANISM: Artificial Sequence
<220> FEATURE:
<223> OTHER INFORMATION: "E-coil" Heterodimer-Promoting Domain

<400> SEQUENCE: 29

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 30
```

```
<211> LENGTH: 28
<212> TYPE: PRT
<213> ORGANISM: Artificial Sequence
<220> FEATURE:
<223> OTHER INFORMATION: "K-coil" Heterodimer-Promoting Domain

<400> SEQUENCE: 30

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 31
<211> LENGTH: 28
<212> TYPE: PRT
<213> ORGANISM: Artificial Sequence
<220> FEATURE:
<223> OTHER INFORMATION: Cysteine-Containing "E-coil" Heterodimer-
      Promoting Domain

<400> SEQUENCE: 31

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 32
<211> LENGTH: 28
<212> TYPE: PRT
<213> ORGANISM: Artificial Sequence
<220> FEATURE:
<223> OTHER INFORMATION: Cysteine-Containing "K-coil" Heterodimer-
      Promoting Domain

<400> SEQUENCE: 32

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 33
<211> LENGTH: 46
<212> TYPE: PRT
<213> ORGANISM: Streptococcus dysgalactiae
<220> FEATURE:
<221> NAME/KEY: MISC_FEATURE
<222> LOCATION: (1)..(46)
<223> OTHER INFORMATION: Albumin-Binding Domain 3 (ABD3) of Protein G of
      Streptococcus strain G148

<400> SEQUENCE: 33

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 34
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148 Comprising N66D,
      T70S and V71A Substitutions
```

```
<400> SEQUENCE: 34

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Ala Glu Ile Leu Ala Ala Leu Pro
        35                  40                  45

<210> SEQ ID NO 35
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148 Comprising L64A,
      I65A and D79A Substitutions

<400> SEQUENCE: 35

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 36
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148 Comprising N66S,
      T70S and D79A Substitutions

<400> SEQUENCE: 36

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45

<210> SEQ ID NO 37
<211> LENGTH: 8
<212> TYPE: PRT
<213> ORGANISM: Artificial Sequence
<220> FEATURE:
<223> OTHER INFORMATION: Intervening Spacer Peptide (Linker)

<400> SEQUENCE: 37

Ala Pro Ser Ser Ser Pro Met Glu
1               5

<210> SEQ ID NO 38
<211> LENGTH: 16
<212> TYPE: PRT
<213> ORGANISM: Artificial Sequence
<220> FEATURE:
<223> OTHER INFORMATION: Intervening Spacer Peptide (Linker)

<400> SEQUENCE: 38

Val Glu Pro Lys Ser Ala Asp Lys Thr His Thr Cys Pro Pro Cys Pro
1               5                   10                  15
```

<210> SEQ ID NO 39
<211> LENGTH: 16
<212> TYPE: PRT
<213> ORGANISM: Artificial Sequence
<220> FEATURE:
<223> OTHER INFORMATION: Intervening Spacer Peptide (Linker)

<400> SEQUENCE: 39

Leu Glu Pro Lys Ser Ala Asp Lys Thr His Thr Cys Pro Pro Cys Pro
1               5                   10                  15

<210> SEQ ID NO 40
<211> LENGTH: 10
<212> TYPE: PRT
<213> ORGANISM: Artificial Sequence
<220> FEATURE:
<223> OTHER INFORMATION: Intervening Spacer Peptide (Linker)

<400> SEQUENCE: 40

Asp Lys Thr His Thr Cys Pro Pro Cys Pro
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Intervening Spacer Peptide (ScFv Linker)

<400> SEQUENCE: 41

Gly Gly Gly Gly Ser Gly Gly Gly Gly Ser Gly Gly Gly Gly Ser
1               5                   10                  15

<210> SEQ ID NO 42
<211> LENGTH: 12
<212> TYPE: PRT
<213> ORGANISM: Artificial Sequence
<220> FEATURE:
<223> OTHER INFORMATION: Intervening Spacer Peptide (The "Long" Linker)

<400> SEQUENCE: 42

Gly Gly Gly Gly Ser Gly Gly Gly Ser Gly Gly Gly
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Intervening Spacer Peptide (Linker)

<400> SEQUENCE: 43

Gly Gly Gly Asp Lys Thr His Thr Cys Pro Pro Cys Pro
1               5                   10

<210> SEQ ID NO 44
<211> LENGTH: 16
<212> TYPE: PRT
<213> ORGANISM: Artificial Sequence
<220> FEATURE:
<223> OTHER INFORMATION: Intervening Spacer Peptide (Linker)

<400> SEQUENCE: 44

Leu Glu Pro Lys Ser Ser Asp Lys Thr His Thr Cys Pro Pro Cys Pro
1               5                   10                  15

```
<210> SEQ ID NO 45
<211> LENGTH: 217
<212> TYPE: PRT
<213> ORGANISM: Artificial Sequence
<220> FEATURE:
<223> OTHER INFORMATION: Human IgG1 CH2-CH3 Domain Comprising
      L234A/L235A Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 45

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 46
<211> LENGTH: 217
<212> TYPE: PRT
<213> ORGANISM: Artificial Sequence
<220> FEATURE:
<223> OTHER INFORMATION: Human IgG1 CH2-CH3 Domain Comprising
      M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 46

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30
```

```
Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Xaa
            210                 215
```

<210> SEQ ID NO 47
<211> LENGTH: 217
<212> TYPE: PRT
<213> ORGANISM: Artificial Sequence
<220> FEATURE:
<223> OTHER INFORMATION: Human IgG1 CH2-CH3 Domain Comprising
      L234A/L235A and M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 47

```
Ala Pro Glu Ala Ala Gly Gly Pro Ser Val Phe Leu Phe Pro Pro Lys
 1               5                  10                  15

Pro Lys Asp Thr Leu Tyr Ile Thr Arg Glu Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
            130                 135                 140
```

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 48
<211> LENGTH: 217
<212> TYPE: PRT
<213> ORGANISM: Artificial Sequence
<220> FEATURE:
<223> OTHER INFORMATION: Human IgG1 CH2-CH3 Domain Comprising "Knob-
      Bearing" Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 48

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 49
<211> LENGTH: 217
<212> TYPE: PRT
<213> ORGANISM: Artificial Sequence
```

-continued

```
<220> FEATURE:
<223> OTHER INFORMATION: Human IgG1 CH2-CH3 Domain Comprising "Knob-
      Bearing" Substitutions and M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 49

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 50
<211> LENGTH: 217
<212> TYPE: PRT
<213> ORGANISM: Artificial Sequence
<220> FEATURE:
<223> OTHER INFORMATION: Human IgG1 CH2-CH3 Domain Comprising "Hole-
      Bearing" Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 50

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215
```

<210> SEQ ID NO 51
<211> LENGTH: 217
<212> TYPE: PRT
<213> ORGANISM: Artificial Sequence
<220> FEATURE:
<223> OTHER INFORMATION: Human IgG1 CH2-CH3 Domain Comprising "Hole-Bearing" Substitutions and M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 51

```
Ala Pro Glu Ala Ala Gly Gly Pro Ser Val Phe Leu Phe Pro Pro Lys
  1               5                  10                  15

Pro Lys Asp Thr Leu Tyr Ile Thr Arg Glu Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175
```

```
Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
        210                 215

<210> SEQ ID NO 52
<211> LENGTH: 217
<212> TYPE: PRT
<213> ORGANISM: Artificial Sequence
<220> FEATURE:
<223> OTHER INFORMATION: Human IgG4 CH2-CH3 Domain Comprising
      Y252/T254T/E256 Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 52

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
        210                 215

<210> SEQ ID NO 53
<211> LENGTH: 217
<212> TYPE: PRT
<213> ORGANISM: Artificial Sequence
<220> FEATURE:
<223> OTHER INFORMATION: Human IgG4 CH2-CH3 Domain Comprising "Knob-
      Bearing" Substitutions and Y252/T254/E256 Substitutions
<220> FEATURE:
<221> NAME/KEY: MISC_FEATURE
<222> LOCATION: (217)..(217)
<223> OTHER INFORMATION: Xaa is Lysine (K) or is Absent
```

```
<400> SEQUENCE: 53

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
210                 215

<210> SEQ ID NO 54
<211> LENGTH: 217
<212> TYPE: PRT
<213> ORGANISM: Artificial Sequence
<220> FEATURE:
<223> OTHER INFORMATION: Human IgG4 CH2-CH3 Domain Comprising "Hole-
      Bearing" Substitutions and Y252/T254/E256 Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 54

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

-continued

```
Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Arg Leu Thr Val Asp Lys Ser Arg Trp Gln Glu Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Leu Gly Xaa
    210                 215
```

<210> SEQ ID NO 55
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 56
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: VL Domain of Anti-Human CD3 Antibody CD3 mAb 1

<400> SEQUENCE: 56

```
Gln Ala Val Val Thr Gln Glu Pro Ser Leu Thr Val Ser Pro Gly Gly
1               5                   10                  15
```

```
Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 57
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of VH Domain of Anti-Human CD3 Antibody
      CD3 mAb 1

<400> SEQUENCE: 57

Thr Tyr Ala Met Asn
1               5

<210> SEQ ID NO 58
<211> LENGTH: 19
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: CDRH2 of VH Domain of Anti-Human CD3 Antibody
      CD3 mAb 1
<220> FEATURE:
<221> NAME/KEY: MISC_FEATURE
<222> LOCATION: (19)..(19)
<223> OTHER INFORMATION: Xaa is Aspartate (D) or Glycine (G)

<400> SEQUENCE: 58

Arg Ile Arg Ser Lys Tyr Asn Asn Tyr Ala Thr Tyr Tyr Ala Asp Ser
1               5                   10                  15

Val Lys Xaa

<210> SEQ ID NO 59
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1

<400> SEQUENCE: 59

His Gly Asn Phe Gly Asn Ser Tyr Val Ser Trp Phe Ala Tyr
1               5                   10

<210> SEQ ID NO 60
<211> LENGTH: 14
<212> TYPE: PRT
<213> ORGANISM: Mus musculus
<220> FEATURE:
```

```
<221> NAME/KEY: MISC_FEATURE
<222> LOCATION: (1)..(14)
<223> OTHER INFORMATION: CDRL1 of VL Domain of Anti-Human CD3 Antibody
      CD3 mAb 1

<400> SEQUENCE: 60

Arg Ser Ser Thr Gly Ala Val Thr Thr Ser Asn Tyr Ala Asn
1               5                   10

<210> SEQ ID NO 61
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of VL Domain of Anti-Human CD3 Antibody
      CD3 mAb 1

<400> SEQUENCE: 61

Gly Thr Asn Lys Arg Ala Pro
1               5

<210> SEQ ID NO 62
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of VL Domain of Anti-Human CD3 Antibody
      CD3 mAb 1

<400> SEQUENCE: 62

Ala Leu Trp Tyr Ser Asn Leu Trp Val
1               5

<210> SEQ ID NO 63
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      Comprising D66

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 64
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M1 ("CD3 mAb 1 Low")
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Thr Trp Phe
            100                 105                 110

Ala Tyr Trp Gly Gln Gly Thr Leu Val Thr Val Ser Ser
        115                 120                 125

<210> SEQ ID NO 65
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M1 ("CD3 mAb 1 Low")

<400> SEQUENCE: 65

His Gly Asn Phe Gly Asn Ser Tyr Val Thr Trp Phe Ala Tyr
1               5                   10

<210> SEQ ID NO 66
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M2 ("CD3 mAb 1 Fast")
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

```
Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
 50                  55                  60

Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Lys Asn Phe Gly Asn Ser Tyr Val Thr Trp Phe
                100                 105                 110

Ala Tyr Trp Gly Gln Gly Thr Leu Val Thr Val Ser Ser
            115                 120                 125

<210> SEQ ID NO 67
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M2 ("CD3 mAb 1 Fast")

<400> SEQUENCE: 67

His Lys Asn Phe Gly Asn Ser Tyr Val Thr Trp Phe Ala Tyr
 1               5                  10

<210> SEQ ID NO 68
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M3
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 68

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
 50                  55                  60

Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Ile Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 69
<211> LENGTH: 14
```

```
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M3

<400> SEQUENCE: 69

His Gly Asn Phe Ile Asn Ser Tyr Val Ser Trp Phe Ala Tyr
1               5                   10

<210> SEQ ID NO 70
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M4
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Ala Val Ser Trp Phe
            100                 105                 110

Ala Tyr Trp Gly Gln Gly Thr Leu Val Thr Val Ser Ser
        115                 120                 125

<210> SEQ ID NO 71
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M4

<400> SEQUENCE: 71

His Gly Asn Phe Gly Asn Ser Ala Val Ser Trp Phe Ala Tyr
1               5                   10

<210> SEQ ID NO 72
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
```

-continued

```
<223> OTHER INFORMATION: VH Domain of Anti-Human CD3 Antibody CD3 mAb 1
      M5
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg His Gly Asn Phe Gly Asn Ser Gly Val Ser Trp Phe
        100                 105                 110

Ala Tyr Trp Gly Gln Gly Thr Leu Val Thr Val Ser Ser
    115                 120                 125

<210> SEQ ID NO 73
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M5

<400> SEQUENCE: 73

His Gly Asn Phe Gly Asn Ser Gly Val Ser Trp Phe Ala Tyr
1               5                   10

<210> SEQ ID NO 74
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M6
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60
```

```
Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Gln Val Ser Trp Phe
            100                 105                 110

Ala Tyr Trp Gly Gln Gly Thr Leu Val Thr Val Ser Ser
        115                 120                 125

<210> SEQ ID NO 75
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M6

<400> SEQUENCE: 75

His Gly Asn Phe Gly Asn Ser Gln Val Ser Trp Phe Ala Tyr
1               5                   10

<210> SEQ ID NO 76
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M7
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Asp Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 77
<211> LENGTH: 14
<212> TYPE: PRT
<213> ORGANISM: Mus musculus
<220> FEATURE:
<221> NAME/KEY: MISC_FEATURE
```

```
<222> LOCATION: (1)..(14)
<223> OTHER INFORMATION: CDRH3 of VH Domain of Anti-Human CD3 Antibody
      CD3 mAb 1 M7

<400> SEQUENCE: 77

His Asp Asn Phe Gly Asn Ser Tyr Val Ser Trp Phe Ala Tyr
1               5                   10

<210> SEQ ID NO 78
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M8
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg His Glu Asn Phe Gly Asn Ser Tyr Val Ser Trp Phe
        100                 105                 110

Ala Tyr Trp Gly Gln Gly Thr Leu Val Thr Val Ser Ser
        115                 120                 125

<210> SEQ ID NO 79
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M8

<400> SEQUENCE: 79

His Glu Asn Phe Gly Asn Ser Tyr Val Ser Trp Phe Ala Tyr
1               5                   10

<210> SEQ ID NO 80
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M9
<220> FEATURE:
<221> NAME/KEY: MISC_FEATURE
<222> LOCATION: (68)..(68)
```

<223> OTHER INFORMATION: Xaa is Aspartate (D) or Glycine (G)

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg His Lys Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 81
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M9

<400> SEQUENCE: 81

His Lys Asn Phe Gly Asn Ser Tyr Val Ser Trp Phe Ala Tyr
1               5                   10

<210> SEQ ID NO 82
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M10
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg His Gly Asn Ile Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 83
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M10

<400> SEQUENCE: 83

His Gly Asn Ile Gly Asn Ser Tyr Val Ser Trp Phe Ala Tyr
1               5                   10

<210> SEQ ID NO 84
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M11
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 84

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Phe Phe
            100                 105                 110

Ala Tyr Trp Gly Gln Gly Thr Leu Val Thr Val Ser Ser
        115                 120                 125

<210> SEQ ID NO 85
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M11

<400> SEQUENCE: 85

His Gly Asn Phe Gly Asn Ser Tyr Val Ser Phe Phe Ala Tyr
1               5                   10

```
<210> SEQ ID NO 86
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M12
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Leu Val Thr Val Ser Ser
        115                 120                 125

<210> SEQ ID NO 87
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M12

<400> SEQUENCE: 87

His Gly Asn Phe Gly Asn Ser Tyr Val Ser Tyr Phe Ala Tyr
1               5                   10

<210> SEQ ID NO 88
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M13
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Ala Met Asn Trp Val Arg Gln Ala Pro Gly Lys Gly Leu Glu Trp Val
         35                  40                  45

Gly Arg Ile Arg Ser Lys Tyr Asn Asn Tyr Ala Thr Tyr Tyr Ala Asp
 50                  55                  60

Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
                100                 105                 110

Ala Glu Trp Gly Gln Gly Thr Leu Val Thr Val Ser Ser
            115                 120                 125

<210> SEQ ID NO 89
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M13

<400> SEQUENCE: 89

His Gly Asn Phe Gly Asn Ser Tyr Val Ser Trp Phe Ala Glu
 1               5                  10

<210> SEQ ID NO 90
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M14
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 90

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Ala Met Asn Trp Val Arg Gln Ala Pro Gly Lys Gly Leu Glu Trp Val
         35                  40                  45

Gly Arg Ile Arg Ser Lys Tyr Asn Asn Tyr Ala Thr Tyr Tyr Ala Asp
 50                  55                  60

Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 91
<211> LENGTH: 5
```

```
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of VH Domain of Anti-Human CD3 Antibody
      CD3 mAb 1 M14

<400> SEQUENCE: 91

Asp Tyr Ala Met Asn
1               5

<210> SEQ ID NO 92
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M15
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 93
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of VH Domain of Anti-Human CD3 Antibody
      CD3 mAb 1 M15

<400> SEQUENCE: 93

Glu Tyr Ala Met Asn
1               5

<210> SEQ ID NO 94
<211> LENGTH: 125
<212> TYPE: PRT
<213> ORGANISM: Mus musculus
<220> FEATURE:
<221> NAME/KEY: MISC_FEATURE
```

```
<222> LOCATION: (1)..(125)
<223> OTHER INFORMATION: VH Domain of Anti-Human CD3 Antibody CD3 mAb 1
      M16
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asp
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 95
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of VH Domain of Anti-Human CD3 Antibody
      CD3 mAb 1 M16

<400> SEQUENCE: 95

Thr Asp Ala Met Asn
1               5

<210> SEQ ID NO 96
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M17
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Thr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60
```

```
Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 97
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of VH Domain of Anti-Human CD3 Antibody
      CD3 mAb 1 M17

<400> SEQUENCE: 97

Thr Thr Ala Met Asn
1               5

<210> SEQ ID NO 98
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M18
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
     50                  55                  60

Ser Val Lys Xaa Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 99
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of VH Domain of Anti-Human CD3 Antibody
      CD3 mAb 1 M18
```

<400> SEQUENCE: 99

Thr Tyr Gly Met Asn
1               5

<210> SEQ ID NO 100
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M19
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 100

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Lys Asn Ile Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 101
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M19

<400> SEQUENCE: 101

His Lys Asn Ile Gly Asn Ser Tyr Val Ser Trp Phe Ala Tyr
1               5                   10

<210> SEQ ID NO 102
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M20
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg His Lys Asn Phe Gly Asn Ser Gly Val Ser Trp Phe
        100                 105                 110

Ala Tyr Trp Gly Gln Gly Thr Leu Val Thr Val Ser Ser
        115                 120                 125

<210> SEQ ID NO 103
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M20

<400> SEQUENCE: 103

His Lys Asn Phe Gly Asn Ser Gly Val Ser Trp Phe Ala Tyr
1               5                   10

<210> SEQ ID NO 104
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M21
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

```
Tyr Cys Val Arg His Lys Asn Phe Gly Asn Ser Tyr Val Ser Phe Phe
            100                 105                 110

Ala Tyr Trp Gly Gln Gly Thr Leu Val Thr Val Ser Ser
        115                 120                 125

<210> SEQ ID NO 105
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M21

<400> SEQUENCE: 105

His Lys Asn Phe Gly Asn Ser Tyr Val Ser Phe Phe Ala Tyr
1               5                   10

<210> SEQ ID NO 106
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Anti-Human CD3 Antibody CD3 mAb 1
      M22
<220> FEATURE:
<221> NAME/KEY: MISC_FEATURE
<222> LOCATION: (68)..(68)
<223> OTHER INFORMATION: Xaa is Aspartate (D) or Glycine (G)

<400> SEQUENCE: 106

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Lys Asn Phe Gly Asn Ser Tyr Val Ser Tyr Phe
            100                 105                 110

Ala Tyr Trp Gly Gln Gly Thr Leu Val Thr Val Ser Ser
        115                 120                 125

<210> SEQ ID NO 107
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of VH Domain of Anti-Human CD3 Antibody
      CD3 mAb 1 M22

<400> SEQUENCE: 107

His Lys Asn Phe Gly Asn Ser Tyr Val Ser Tyr Phe Ala Tyr
1               5                   10
```

<210> SEQ ID NO 108
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: VL Domain of Anti-Human CD3 Antibody CD3 mAb 1
      M23

<400> SEQUENCE: 108

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Glu Trp Tyr Ser Asn
                85                  90                  95

Leu Trp Val Phe Gly Gly Gly Thr Lys Leu Thr Val Leu Gly
            100                 105                 110

<210> SEQ ID NO 109
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of VL Domain of Anti-Human CD3 Antibody
      CD3 mAb 1 M23

<400> SEQUENCE: 109

Ala Glu Trp Tyr Ser Asn Leu Trp Val
1               5

<210> SEQ ID NO 110
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: VL Domain of Anti-Human CD3 Antibody CD3 mAb 1
      M24

<400> SEQUENCE: 110

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

```
Gln Ala Glu Asp Glu Ala Asp Tyr Tyr Cys Ala Gln Trp Tyr Ser Asn
                85                  90                  95

Leu Trp Val Phe Gly Gly Gly Thr Lys Leu Thr Val Leu Gly
            100                 105                 110

<210> SEQ ID NO 111
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of VL Domain of Anti-Human CD3 Antibody
      CD3 mAb 1 M24

<400> SEQUENCE: 111

Ala Gln Trp Tyr Ser Asn Leu Trp Val
1               5

<210> SEQ ID NO 112
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: VL Domain of Anti-Human CD3 Antibody CD3 mAb 1
      M25

<400> SEQUENCE: 112

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Asp Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 113
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of VL Domain of Anti-Human CD3 Antibody
      CD3 mAb 1 M25

<400> SEQUENCE: 113

Asp Thr Asn Lys Arg Ala Pro
1               5

<210> SEQ ID NO 114
<211> LENGTH: 110
<212> TYPE: PRT
<213> ORGANISM: Mus musculus
<220> FEATURE:
<221> NAME/KEY: MISC_FEATURE
```

```
<222> LOCATION: (1)..(110)
<223> OTHER INFORMATION: VL Domain of Anti-Human CD3 Antibody CD3 mAb 1
      M26

<400> SEQUENCE: 114

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Gly Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 115
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of VL Domain of Anti-Human CD3 Antibody
      CD3 mAb 1 M26

<400> SEQUENCE: 115

Gly Thr Asn Gly Arg Ala Pro
1               5

<210> SEQ ID NO 116
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of Anti-Human CD2 Antibody CD2 mAb
      Lo-CD2a

<400> SEQUENCE: 116

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Ile Phe Thr Glu Tyr
            20                  25                  30

Tyr Met Tyr Trp Val Lys Gln Arg Pro Lys Gln Gly Leu Glu Leu Val
        35                  40                  45

Gly Arg Ile Asp Pro Glu Asp Gly Ser Ile Asp Tyr Val Glu Lys Phe
    50                  55                  60

Lys Lys Lys Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Ala Arg Gly Lys Phe Asn Tyr Arg Phe Ala Tyr Trp Gly Gln Gly Thr
            100                 105                 110

Leu Val Thr Val Ser Ser
            115
```

<210> SEQ ID NO 117
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of Anti-Human CD2 Antibody CD2 mAb
      Lo-CD2a

<400> SEQUENCE: 117

Asp Val Val Leu Thr Gln Thr Pro Pro Thr Leu Leu Ala Thr Ile Gly
1               5                   10                  15

Gln Ser Val Ser Ile Ser Cys Arg Ser Ser Gln Ser Leu Leu His Ser
            20                  25                  30

Ser Gly Asn Thr Tyr Leu Asn Trp Leu Leu Gln Arg Thr Gly Gln Ser
        35                  40                  45

Pro Gln Pro Leu Ile Tyr Leu Val Ser Lys Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Met Gln Phe
                85                  90                  95

Thr His Tyr Pro Tyr Thr Phe Gly Ala Gly Thr Lys Leu Glu Leu Lys
            100                 105                 110

<210> SEQ ID NO 118
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of Anti-Human CD8 Antibody OKT8

<400> SEQUENCE: 118

Gln Val Gln Leu Leu Glu Ser Gly Pro Glu Leu Leu Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Thr Gly Gly Thr Gly Tyr Asn Gln Lys Phe
    50                  55                  60

Lys Asn Lys Ala Thr Leu Thr Val Asp Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asn Phe Arg Tyr Thr Tyr Trp Tyr Phe Asp Val Trp Gly Gln
            100                 105                 110

Gly Thr Thr Val Thr Val Ser Ser
        115                 120

<210> SEQ ID NO 119
<211> LENGTH: 112
<212> TYPE: PRT
<213> ORGANISM: Mus musculus
<220> FEATURE:
<221> NAME/KEY: MISC_FEATURE
<222> LOCATION: (1)..(112)

<223> OTHER INFORMATION: VL Domain of Anti-Human CD8 Antibody OKT8

<400> SEQUENCE: 119

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Asp Asn Ser Leu Met His Trp Tyr Gln Gln Lys Pro Gly Gln Pro Pro
        35                  40                  45

Lys Val Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Ala Ala Thr Tyr Tyr Cys Gln Gln Asn Asn
                85                  90                  95

Glu Asp Pro Tyr Thr Phe Gly Gly Thr Lys Leu Glu Ile Lys Arg
            100                 105                 110

<210> SEQ ID NO 120
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: VH Domain of Anti-Human CD8 Antibody TRX2

<400> SEQUENCE: 120

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Gly Met Asn Trp Val Arg Gln Ala Pro Gly Lys Gly Leu Glu Trp Val
        35                  40                  45

Ala Leu Ile Tyr Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ser
        115                 120

<210> SEQ ID NO 121
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of Anti-Human CD8 Antibody TRX2

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
         35                  40                  45

Tyr Asn Thr Asp Ile Leu His Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Tyr Gln Tyr Asn Asn Gly Tyr Thr
                 85                  90                  95

Phe Gly Gln Gly Thr Lys Val Glu Ile Lys
            100                 105

<210> SEQ ID NO 122
<211> LENGTH: 120
<212> TYPE: PRT
<213> ORGANISM: Artificial Sequence
<220> FEATURE:
<223> OTHER INFORMATION: VH Domain of Humanized Anti-Human B7-H3
      Antibody B7-H3 mAb-B VH1

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Asp Gly Asp Thr Arg Tyr Thr Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
        115                 120

<210> SEQ ID NO 123
<211> LENGTH: 120
<212> TYPE: PRT
<213> ORGANISM: Artificial Sequence
<220> FEATURE:
<223> OTHER INFORMATION: VH Domain of Humanized Anti-Human B7-H3
      Antibody B7-H3 mAb-B VH2

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Gly Gly Asp Thr Arg Tyr Thr Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
        115                 120

<210> SEQ ID NO 124
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody B7-H3 mAb-B VL1

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 125
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody B7-H3 mAb-B VL2

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 126
<211> LENGTH: 117
<212> TYPE: PRT
<213> ORGANISM: Artificial Sequence
<220> FEATURE:
<223> OTHER INFORMATION: VH Domain of Humanized Anti-Human B7-H3
      Antibody B7-H3 mAb-C

<400> SEQUENCE: 126

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Ser Asn Thr Tyr Tyr Pro Asp Ser Leu
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Asp Gly Gly Ala Met Asp Tyr Trp Gly Gln Gly Thr Thr
            100                 105                 110

Val Thr Val Ser Ser
        115

<210> SEQ ID NO 127
<211> LENGTH: 108
<212> TYPE: PRT
<213> ORGANISM: Artificial Sequence
<220> FEATURE:
<223> OTHER INFORMATION: VL Domain of Humanized Anti-Human B7-H3
      Antibody B7-H3 mAb-C

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Thr Lys Thr Leu Pro Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Pro
                85                  90                  95

Trp Thr Phe Gly Gln Gly Thr Arg Leu Glu Ile Lys
            100                 105

<210> SEQ ID NO 128
<211> LENGTH: 119
<212> TYPE: PRT
<213> ORGANISM: Artificial Sequence
<220> FEATURE:
<223> OTHER INFORMATION: VH Domain of Humanized Anti-Human B7-H3
      Antibody B7-H3 mAb-D

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

```
Ala Tyr Ile Ser Ser Gly Ser Gly Thr Ile Tyr Tyr Ala Asp Thr Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Tyr Arg Tyr Glu Gly Phe Asp Tyr Trp Gly Gln Gly
            100                 105                 110

Thr Thr Val Thr Val Ser Ser
            115

<210> SEQ ID NO 129
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody B7-H3 mAb-D

<400> SEQUENCE: 129

Asp Ile Gln Met Thr Gln Ser Pro Ser Phe Leu Ser Ala Ser Val Gly
 1               5                  10                  15

Asp Arg Val Thr Ile Thr Cys Lys Ala Ser Gln Asn Val Asp Thr Asn
                 20                  25                  30

Val Ala Trp Tyr Gln Gln Lys Pro Gly Lys Ala Pro Lys Ala Leu Ile
             35                  40                  45

Tyr Ser Ala Ser Tyr Arg Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Glu Tyr Phe Cys Gln Gln Tyr Asn Asn Tyr Pro Phe
                 85                  90                  95

Thr Phe Gly Gln Gly Thr Lys Leu Glu Ile Lys
            100                 105

<210> SEQ ID NO 130
<211> LENGTH: 122
<212> TYPE: PRT
<213> ORGANISM: Artificial Sequence
<220> FEATURE:
<223> OTHER INFORMATION: VH Domain of Humanized Anti-Human B7-H3
      Antibody Enoblituzumab

<400> SEQUENCE: 130

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
                 20                  25                  30

Gly Met His Trp Val Arg Gln Ala Pro Gly Lys Gly Leu Glu Trp Val
             35                  40                  45

Ala Tyr Ile Ser Ser Asp Ser Ser Ala Ile Tyr Tyr Ala Asp Thr Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Gly Arg Gly Arg Glu Asn Ile Tyr Tyr Gly Ser Arg Leu Asp Tyr Trp
            100                 105                 110
```

```
Gly Gln Gly Thr Thr Val Thr Val Ser Ser
        115                 120

<210> SEQ ID NO 131
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody Enoblituzumab

<400> SEQUENCE: 131

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 132
<211> LENGTH: 121
<212> TYPE: PRT
<213> ORGANISM: Artificial Sequence
<220> FEATURE:
<223> OTHER INFORMATION: VH Domain of the Humanized Anti-Human CE
      ACAM5 / CEACAM6 Antibody 16C3

<400> SEQUENCE: 132

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 133
<211> LENGTH: 107
<212> TYPE: PRT
<213> ORGANISM: Artificial Sequence
<220> FEATURE:
<223> OTHER INFORMATION: VL Domain of the Humanized Anti-Human CEACAM5 /
      CEACAM6 Antibody 16C3
```

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Trp Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 134
<211> LENGTH: 121
<212> TYPE: PRT
<213> ORGANISM: Artificial Sequence
<220> FEATURE:
<223> OTHER INFORMATION: VH Domain of the Humanized Anti-Human CEACAM5 /
      CEACAM6 Antibody hMN15

<400> SEQUENCE: 134

Gln Val Gln Leu Val Glu Ser Gly Gly Gly Val Val Gln Pro Gly Arg
1               5                   10                  15

Ser Leu Arg Leu Ser Cys Ser Ser Ser Gly Phe Ala Leu Thr Asp Tyr
            20                  25                  30

Tyr Met Ser Trp Val Arg Gln Ala Pro Gly Lys Gly Leu Glu Trp Leu
        35                  40                  45

Gly Phe Ile Ala Asn Lys Ala Asn Gly His Thr Thr Asp Tyr Ser Pro
    50                  55                  60

Ser Val Lys Gly Arg Phe Thr Ile Ser Arg Asp Asn Ser Lys Asn Thr
65                  70                  75                  80

Leu Phe Leu Gln Met Asp Ser Leu Arg Pro Glu Asp Thr Gly Val Tyr
                85                  90                  95

Phe Cys Ala Arg Asp Met Gly Ile Arg Trp Asn Phe Asp Val Trp Gly
            100                 105                 110

Gln Gly Thr Pro Val Thr Val Ser Ser
        115                 120

<210> SEQ ID NO 135
<211> LENGTH: 107
<212> TYPE: PRT
<213> ORGANISM: Artificial Sequence
<220> FEATURE:
<223> OTHER INFORMATION: VL Domain of the Humanized Anti-Human CEACAM5 /
      CEACAM6 Antibody hMN15

<400> SEQUENCE: 135

Asp Ile Gln Leu Thr Gln Ser Pro Ser Ser Leu Ser Ala Ser Val Gly
1               5                   10                  15

Asp Arg Val Thr Met Thr Cys Ser Ala Ser Ser Arg Val Ser Tyr Ile
            20                  25                  30

His Trp Tyr Gln Gln Lys Pro Gly Lys Ala Pro Lys Arg Trp Ile Tyr
        35                  40                  45

```
Gly Thr Ser Thr Leu Ala Ser Gly Val Pro Ala Arg Phe Ser Gly Ser
     50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Tyr Asn Pro Pro Thr
                 85                  90                  95

Phe Gly Gln Gly Thr Lys Val Glu Ile Lys Arg
            100                 105
```

<210> SEQ ID NO 136
<211> LENGTH: 119
<212> TYPE: PRT
<213> ORGANISM: Artificial Sequence
<220> FEATURE:
<223> OTHER INFORMATION: VH Domain of the Chimeric Anti-Human EGFR
      Antibody Cetuximab

<400> SEQUENCE: 136

```
Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
             20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115
```

<210> SEQ ID NO 137
<211> LENGTH: 108
<212> TYPE: PRT
<213> ORGANISM: Artificial Sequence
<220> FEATURE:
<223> OTHER INFORMATION: VL Domain of the Chimeric Anti-Human EGFR
      Antibody Cetuximab

<400> SEQUENCE: 137

```
Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
             20                  25                  30

Ile His Trp Tyr Gln Gln Arg Thr Asn Gly Ser Pro Arg Leu Leu Ile
         35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg
            100                 105
```

<210> SEQ ID NO 138
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: VH Domain of the Anti-Human EGFR Antibody
      Panitumumab

<400> SEQUENCE: 138

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 139
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: VL Domain of the Anti-Human EGFR Antibody
      Panitumumab

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg
            100                 105

<210> SEQ ID NO 140
<211> LENGTH: 118
<212> TYPE: PRT
<213> ORGANISM: Mus musculus
<220> FEATURE:
<221> NAME/KEY: MISC_FEATURE
<222> LOCATION: (1)..(118)

<223> OTHER INFORMATION: VH Domain of the Anti-Human EphA2 Antibody mAb
      1

<400> SEQUENCE: 140

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Lys His Gly Asn Tyr Tyr Thr Met Asp Tyr Trp Gly Gln Gly Thr
            100                 105                 110

Ser Val Thr Val Ser Ser
        115

<210> SEQ ID NO 141
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of the Anti-Human EphA2 Antibody mAb
      1

<400> SEQUENCE: 141

Asp Ile Gln Met Thr Gln Thr Thr Ser Ser Leu Ser Ala Ser Leu Gly
1               5                   10                  15

Asp Arg Ile Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Tyr Thr
                85                  90                  95

Phe Gly Gly Gly Thr Lys Leu Glu Ile Lys
            100                 105

<210> SEQ ID NO 142
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of the Anti-Human EphA2 Antibody mAb
      2

<400> SEQUENCE: 142

Gln Ile Gln Leu Val Gln Ser Gly Pro Glu Leu Lys Lys Pro Gly Glu
1               5                   10                  15

```
Thr Val Lys Ile Ser Cys Lys Ala Ser Gly Phe Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ile Gly Glu Pro Thr Tyr Ala Asp Asp Phe
    50                  55                  60

Lys Gly Arg Phe Val Phe Ser Leu Glu Thr Ser Ala Ser Thr Ala Tyr
 65                  70                  75                  80

Leu Gln Ile Asn Asn Leu Lys Asn Glu Asp Met Ala Thr Tyr Phe Cys
                85                  90                  95

Ala Arg Glu Leu Gly Pro Tyr Tyr Phe Asp Tyr Trp Gly Gln Gly Thr
            100                 105                 110

Thr Leu Thr Val Ser Ser
            115

<210> SEQ ID NO 143
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of the Anti-Human EphA2 Antibody mAb
      2

<400> SEQUENCE: 143

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys
            100                 105                 110

<210> SEQ ID NO 144
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of the Anti-Human EphA2 Antibody mAb
      3

<400> SEQUENCE: 144

Glu Val Gln Leu Val Glu Ser Gly Gly Gly Ser Val Lys Pro Gly Gly
 1               5                  10                  15

Ser Leu Lys Leu Ser Cys Ala Ala Ser Gly Phe Thr Phe Thr Asp His
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Phe Thr Ser Tyr Pro Asp Ser Val
    50                  55                  60
```

```
Lys Gly Arg Phe Thr Ile Ser Arg Asp Ile Ala Lys Asn Asn Leu Tyr
 65                  70                  75                  80

Leu Gln Met Ser Ser Leu Lys Ser Glu Asp Thr Ala Met Tyr Tyr Cys
                 85                  90                  95

Thr Arg Asp Glu Ser Asp Arg Pro Phe Pro Tyr Trp Gly Gln Gly Thr
            100                 105                 110

Leu Val Thr Val Ser Ser
        115
```

<210> SEQ ID NO 145
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of the Anti-Human EphA2 Antibody mAb
      3

<400> SEQUENCE: 145

```
Asp Ile Val Leu Thr Gln Ser His Arg Ser Met Ser Thr Ser Val Gly
 1               5                  10                  15

Asp Arg Val Asn Ile Thr Cys Lys Ala Ser Gln Asp Val Thr Thr Ala
             20                  25                  30

Val Ala Trp Tyr Gln Gln Lys Pro Gly Gln Ser Pro Lys Leu Leu Ile
         35                  40                  45

Phe Trp Ala Ser Thr Arg His Ala Gly Val Pro Asp Arg Phe Thr Gly
 50                  55                  60

Ser Gly Ser Gly Thr Asp Phe Thr Leu Thr Ile Ser Ser Val Gln Ala
 65                  70                  75                  80

Gly Asp Leu Ala Leu Tyr Tyr Cys Gln Gln His Tyr Ser Thr Pro Tyr
                 85                  90                  95

Thr Phe Gly Gly Gly Thr Lys Leu Glu Ile Lys
            100                 105
```

<210> SEQ ID NO 146
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of the Anti-Human gpA33 Antibody mAb
      1

<400> SEQUENCE: 146

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Ser
             20                  25                  30

Trp Met Asn Trp Val Arg Gln Ala Pro Gly Gln Gly Leu Glu Trp Ile
         35                  40                  45

Gly Arg Ile Tyr Pro Gly Asp Gly Glu Thr Asn Tyr Asn Gly Lys Phe
 50                  55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Ile Tyr Gly Asn Asn Val Tyr Phe Asp Val Trp Gly Gln Gly
            100                 105                 110

Thr Thr Val Thr Val Ser Ser
        115

<210> SEQ ID NO 147
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of the Anti-Human gpA33 Antibody mAb
      1

<400> SEQUENCE: 147

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys
            100                 105

<210> SEQ ID NO 148
<211> LENGTH: 120
<212> TYPE: PRT
<213> ORGANISM: Artificial Sequence
<220> FEATURE:
<223> OTHER INFORMATION: VH Domain of the Humanized Anti-Human Her2/Neu
      Antibody Margetuximab

<400> SEQUENCE: 148

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
        115                 120

<210> SEQ ID NO 149
<211> LENGTH: 107
```

```
<212> TYPE: PRT
<213> ORGANISM: Artificial Sequence
<220> FEATURE:
<223> OTHER INFORMATION: VL Domain of the Humanized Anti-Human Her2/Neu
      Antibody Margetuximab

<400> SEQUENCE: 149

Asp Ile Val Met Thr Gln Ser His Lys Phe Met Ser Thr Ser Val Gly
1               5                  10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys
            100                 105

<210> SEQ ID NO 150
<211> LENGTH: 120
<212> TYPE: PRT
<213> ORGANISM: Artificial Sequence
<220> FEATURE:
<223> OTHER INFORMATION: VH Domain of the Humanized Anti-Human Her2/Neu
      Antibody Trastuzumab

<400> SEQUENCE: 150

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 151
<211> LENGTH: 107
<212> TYPE: PRT
<213> ORGANISM: Artificial Sequence
<220> FEATURE:
<223> OTHER INFORMATION: VL Domain of the Humanized Anti-Human Her2/Neu
      Antibody Trastuzumab

<400> SEQUENCE: 151

Asp Ile Gln Met Thr Gln Ser Pro Ser Ser Leu Ser Ala Ser Val Gly
1               5                  10                  15
```

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 152
<211> LENGTH: 119
<212> TYPE: PRT
<213> ORGANISM: Artificial Sequence
<220> FEATURE:
<223> OTHER INFORMATION: VH Domain of the Humanized Anti-Human Her2/Neu
      Antibody Pertuzumab

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 153
<211> LENGTH: 107
<212> TYPE: PRT
<213> ORGANISM: Artificial Sequence
<220> FEATURE:
<223> OTHER INFORMATION: VL Domain of the Humanized Anti-Human Her2/Neu
      Antibody Pertuzumab

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Tyr Ile Tyr Pro Tyr
            85                  90                  95

Thr Phe Gly Gln Gly Thr Lys Val Glu Ile Lys
            100                 105

<210> SEQ ID NO 154
<211> LENGTH: 123
<212> TYPE: PRT
<213> ORGANISM: Artificial Sequence
<220> FEATURE:
<223> OTHER INFORMATION: VH Domain of the Humanized Anti-Human VEGF
      Antibody Bevacizumab

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 155
<211> LENGTH: 108
<212> TYPE: PRT
<213> ORGANISM: Artificial Sequence
<220> FEATURE:
<223> OTHER INFORMATION: VL Domain of the Humanized Anti-Human VEGF
      Antibody Bevacizumab

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 156
<211> LENGTH: 118
<212> TYPE: PRT
<213> ORGANISM: Mus musculus

```
<220> FEATURE:
<221> NAME/KEY: MISC_FEATURE
<222> LOCATION: (1)..(118)
<223> OTHER INFORMATION: VH Domain of the Anti-Human 5T4 Antibody mAb 1

<400> SEQUENCE: 156

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Arg Ile Asp Pro Asn Arg Gly Gly Thr Glu Tyr Asn Glu Lys Ala
    50                  55                  60

Lys Ser Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Asn Pro Tyr Tyr Pro Met Asp Tyr Trp Gly Gln Gly Thr
            100                 105                 110

Thr Val Thr Val Ser Ser
        115

<210> SEQ ID NO 157
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of the Anti-Human 5T4 Antibody mAb 1

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys
            100                 105

<210> SEQ ID NO 158
<211> LENGTH: 127
<212> TYPE: PRT
<213> ORGANISM: Mus musculus
<220> FEATURE:
<221> NAME/KEY: MISC_FEATURE
<222> LOCATION: (1)..(127)
<223> OTHER INFORMATION: VH Domain of the Anti-Human 5T4 Antibody mAb 2

<400> SEQUENCE: 158

Gln Val Gln Leu Gln Gln Pro Gly Ala Glu Leu Val Lys Pro Gly Ala
1               5                   10                  15
```

```
Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Arg Ala Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Asn Cys
            85                  90                  95

Ala Arg Tyr Gly Pro Leu Phe Thr Thr Val Val Asp Pro Asn Ser Tyr
            100                 105                 110

Ala Met Asp Tyr Trp Gly Gln Gly Thr Ser Val Thr Val Ser Ser
            115                 120                 125

<210> SEQ ID NO 159
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of the Anti-Human 5T4 Antibody mAb 2

<400> SEQUENCE: 159

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Phe Thr Phe Gly Ser Gly Thr Lys Leu Glu Ile Lys
            100                 105                 110

<210> SEQ ID NO 160
<211> LENGTH: 122
<212> TYPE: PRT
<213> ORGANISM: Artificial Sequence
<220> FEATURE:
<223> OTHER INFORMATION: VH Domain of the Anti-Human IL-13R(alpha2)
      Antibody hu08

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
        115                 120

<210> SEQ ID NO 161
<211> LENGTH: 107
<212> TYPE: PRT
<213> ORGANISM: Artificial Sequence
<220> FEATURE:
<223> OTHER INFORMATION: VL Domain of the Anti-Human IL-13R(alpha2)
      Antibody hu08

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105

<210> SEQ ID NO 162
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of the Anti-Human CD123 Antibody mAb
      1

<400> SEQUENCE: 162

Glu Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 163
<211> LENGTH: 113
<212> TYPE: PRT
<213> ORGANISM: Mus musculus
<220> FEATURE:
<221> NAME/KEY: MISC_FEATURE
<222> LOCATION: (1)..(113)
<223> OTHER INFORMATION: VL Domain of the Anti-Human CD123 Antibody mAb
      1

<400> SEQUENCE: 163

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 164
<211> LENGTH: 120
<212> TYPE: PRT
<213> ORGANISM: Artificial Sequence
<220> FEATURE:
<223> OTHER INFORMATION: VH Domain of the Humanized Anti-Human CD19
      Antibody mAb 1

<400> SEQUENCE: 164

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Phe Leu Thr Met Thr Asn Met Asp Pro Val Asp Thr Ala Thr Tyr Tyr
                85                  90                  95

Cys Ala Arg Met Glu Leu Trp Ser Tyr Tyr Phe Asp Tyr Trp Gly Gln
            100                 105                 110

Gly Thr Thr Val Thr Val Ser Ser
        115                 120

<210> SEQ ID NO 165
<211> LENGTH: 106
<212> TYPE: PRT
<213> ORGANISM: Artificial Sequence
<220> FEATURE:
<223> OTHER INFORMATION: VL Domain of the Humanized Anti-Human CD19
      Antibody mAb 1

<400> SEQUENCE: 165

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys
            100                 105

<210> SEQ ID NO 166
<211> LENGTH: 126
<212> TYPE: PRT
<213> ORGANISM: Homo sapiens
<220> FEATURE:
<221> NAME/KEY: MISC_FEATURE
<222> LOCATION: (1)..(126)
<223> OTHER INFORMATION: VH Domain of the Human Anti-HIV(env) Antibody
      7B2

<400> SEQUENCE: 166

Gln Val Gln Leu Val Gln Ser Gly Gly Gly Val Phe Lys Pro Gly Gly
1               5                   10                  15

Ser Leu Arg Leu Ser Cys Glu Ala Ser Gly Phe Thr Phe Thr Glu Tyr
            20                  25                  30

Tyr Met Thr Trp Val Arg Gln Ala Pro Gly Lys Gly Leu Glu Trp Leu
        35                  40                  45

Ala Tyr Ile Ser Lys Asn Gly Glu Tyr Ser Lys Tyr Ser Pro Ser Ser
    50                  55                  60

Asn Gly Arg Phe Thr Ile Ser Arg Asp Asn Ala Lys Asn Ser Val Phe
65                  70                  75                  80

Leu Gln Leu Asp Arg Leu Ser Ala Asp Thr Ala Val Tyr Tyr Cys
                85                  90                  95

Ala Arg Ala Asp Gly Leu Thr Tyr Phe Ser Glu Leu Leu Gln Tyr Ile
            100                 105                 110

Phe Asp Leu Trp Gly Gln Gly Ala Arg Val Thr Val Ser Ser
        115                 120                 125

<210> SEQ ID NO 167
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: VL Domain of the Human Anti-HIV(env) Antibody
      7B2

<400> SEQUENCE: 167

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

```
Ser Asn Asn Arg His Ser Ile Ala Trp Tyr Gln Gln Arg Pro Gly Gln
            35                  40                  45

Pro Pro Lys Leu Leu Leu Tyr Trp Ala Ser Met Arg Leu Ser Gly Val
 50                  55                  60

Pro Asp Arg Phe Ser Gly Ser Gly Ser Gly Thr Asp Phe Thr Leu Thr
 65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys

<210> SEQ ID NO 168
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH Domain of the Human Anti-HIV(env) Antibody
      A32
<220> FEATURE:
<221> NAME/KEY: MISC_FEATURE
<222> LOCATION: (118)..(118)
<223> OTHER INFORMATION: Xaa is Leucine (L) or Methionine (M)

<400> SEQUENCE: 168

Gln Val Gln Leu Gln Glu Ser Gly Pro Gly Leu Val Lys Pro Ser Gln
 1               5                  10                  15

Thr Leu Ser Leu Ser Cys Thr Val Ser Gly Gly Ser Ser Ser Ser Gly
                20                  25                  30

Ala His Tyr Trp Ser Trp Ile Arg Gln Tyr Pro Gly Lys Gly Leu Glu
            35                  40                  45

Trp Ile Gly Tyr Ile His Tyr Ser Gly Asn Thr Tyr Tyr Asn Pro Ser
 50                  55                  60

Leu Lys Ser Arg Ile Thr Ile Ser Gln His Thr Ser Glu Asn Gln Phe
 65                  70                  75                  80

Ser Leu Lys Leu Asn Ser Val Thr Val Ala Asp Thr Ala Val Tyr Tyr
                85                  90                  95

Cys Ala Arg Gly Thr Arg Leu Arg Thr Leu Arg Asn Ala Phe Asp Ile
            100                 105                 110

Trp Gly Gln Gly Thr Xaa Val Thr Val Ser Ser
            115                 120

<210> SEQ ID NO 169
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: VL Domain of the Human Anti-HIV(env) Antibody
      A32

<400> SEQUENCE: 169

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30
```

Asn Tyr Val Ser Trp Tyr Gln His His Pro Gly Lys Ala Pro Lys Leu
            35                  40                  45

Ile Ile Ser Glu Val Asn Asn Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu
            100                 105                 110

<210> SEQ ID NO 170
<211> LENGTH: 120
<212> TYPE: PRT
<213> ORGANISM: Artificial Sequence
<220> FEATURE:
<223> OTHER INFORMATION: VH Domain of the Humanized Anti-
      RSV(glycoprotein F) Antibody palivizumab

<400> SEQUENCE: 170

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 171
<211> LENGTH: 106
<212> TYPE: PRT
<213> ORGANISM: Artificial Sequence
<220> FEATURE:
<223> OTHER INFORMATION: VL Domain of the Humanized Anti-
      RSV(glycoprotein F) Antibody palivizumab

<400> SEQUENCE: 171

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                85                  90                  95

```
Phe Gly Gly Gly Thr Lys Leu Glu Ile Lys
            100                 105

<210> SEQ ID NO 172
<211> LENGTH: 280
<212> TYPE: PRT
<213> ORGANISM: Artificial Sequence
<220> FEATURE:
<223> OTHER INFORMATION: First Polypeptide Chain of the CD123 x CD3
      DART-A-type Diabody DART-A-WT

<400> SEQUENCE: 172

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Gly Cys Gly Gly Lys Val Ala Ala
                245                 250                 255

Leu Lys Glu Lys Val Ala Ala Leu Lys Glu Lys Val Ala Ala Leu Lys
                260                 265                 270

Glu Lys Val Ala Ala Leu Lys Glu
            275                 280

<210> SEQ ID NO 173
<211> LENGTH: 272
<212> TYPE: PRT
<213> ORGANISM: Artificial Sequence
<220> FEATURE:
<223> OTHER INFORMATION: Second Polypeptide Chain of the CD123 x CD3
      DART-A-type Diabody DART-A-WT
```

<400> SEQUENCE: 173

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Leu Lys Lys Pro Gly Ala Ser Val Lys Val Ser Cys Lys Ala Ser Gly
    130                 135                 140

Tyr Thr Phe Thr Asp Tyr Tyr Met Lys Trp Val Arg Gln Ala Pro Gly
145                 150                 155                 160

Gln Gly Leu Glu Trp Ile Gly Asp Ile Ile Pro Ser Asn Gly Ala Thr
                165                 170                 175

Phe Tyr Asn Gln Lys Phe Lys Gly Arg Val Thr Ile Thr Val Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ser His Leu Leu Arg Ala Ser Trp
    210                 215                 220

Phe Ala Tyr Trp Gly Gln Gly Thr Leu Val Thr Val Ser Ser Gly Gly
225                 230                 235                 240

Cys Gly Gly Glu Val Ala Ala Leu Glu Lys Glu Val Ala Ala Leu
                245                 250                 255

Glu Lys Glu Val Ala Ala Leu Glu Lys Glu Val Ala Ala Leu Glu Lys
            260                 265                 270
```

<210> SEQ ID NO 174
<211> LENGTH: 510
<212> TYPE: PRT
<213> ORGANISM: Artificial Sequence
<220> FEATURE:
<223> OTHER INFORMATION: First Polypeptide Chain of the CD123 x CD3 DART-B-type Diabody CD123-WT

<400> SEQUENCE: 174

```
Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Cys Gly Gly Gly Glu Val Ala Ala
                245                 250                 255

Leu Glu Lys Glu Val Ala Ala Leu Glu Lys Glu Val Ala Ala Leu Glu
            260                 265                 270

Lys Glu Val Ala Ala Leu Glu Lys Gly Gly Gly Asp Lys Thr His Thr
        275                 280                 285

Cys Pro Pro Cys Pro Ala Pro Glu Ala Ala Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
                405                 410                 415

Ser Arg Glu Glu Met Thr Lys Asn Gln Val Ser Leu Trp Cys Leu Val
            420                 425                 430

Lys Gly Phe Tyr Pro Ser Asp Ile Ala Val Glu Trp Glu Ser Asn Gly
        435                 440                 445

Gln Pro Glu Asn Asn Tyr Lys Thr Thr Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495
```

Asn His Tyr Thr Gln Lys Ser Leu Ser Leu Ser Pro Gly Lys
            500                 505                 510

<210> SEQ ID NO 175
<211> LENGTH: 272
<212> TYPE: PRT
<213> ORGANISM: Artificial Sequence
<220> FEATURE:
<223> OTHER INFORMATION: Second Polypeptide Chain of the CD123 x CD3
      DART-B-type Diabody CD123-WT

<400> SEQUENCE: 175

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Leu Lys Lys Pro Gly Ala Ser Val Lys Val Ser Cys Lys Ala Ser Gly
    130                 135                 140

Tyr Thr Phe Thr Asp Tyr Tyr Met Lys Trp Val Arg Gln Ala Pro Gly
145                 150                 155                 160

Gln Gly Leu Glu Trp Ile Gly Asp Ile Ile Pro Ser Asn Gly Ala Thr
                165                 170                 175

Phe Tyr Asn Gln Lys Phe Lys Gly Arg Val Thr Ile Thr Val Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ser His Leu Leu Arg Ala Ser Trp
    210                 215                 220

Phe Ala Tyr Trp Gly Gln Gly Thr Leu Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 176
<211> LENGTH: 227
<212> TYPE: PRT
<213> ORGANISM: Artificial Sequence
<220> FEATURE:
<223> OTHER INFORMATION: Third Polypeptide Chain of the CD123 x CD3
      DART-B-type Diabody CD123-WT

<400> SEQUENCE: 176

Asp Lys Thr His Thr Cys Pro Pro Cys Pro Ala Pro Glu Ala Ala Gly
1               5                   10                  15

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225

<210> SEQ ID NO 177
<211> LENGTH: 510
<212> TYPE: PRT
<213> ORGANISM: Artificial Sequence
<220> FEATURE:
<223> OTHER INFORMATION: First Polypeptide Chain of the CD123 x CD3
      DART-B-type Diabody CD123-M1

<400> SEQUENCE: 177

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140
```

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Thr Trp Phe Ala Tyr Trp Gly Gln Gly Thr
225                 230                 235                 240

Leu Val Thr Val Ser Ser Gly Cys Gly Gly Gly Glu Val Ala Ala
                245                 250                 255

Leu Glu Lys Glu Val Ala Ala Leu Glu Lys Glu Val Ala Ala Leu Glu
            260                 265                 270

Lys Glu Val Ala Ala Leu Glu Lys Gly Gly Gly Asp Lys Thr His Thr
        275                 280                 285

Cys Pro Pro Cys Pro Ala Pro Glu Ala Ala Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
                405                 410                 415

Ser Arg Glu Glu Met Thr Lys Asn Gln Val Ser Leu Trp Cys Leu Val
            420                 425                 430

Lys Gly Phe Tyr Pro Ser Asp Ile Ala Val Glu Trp Glu Ser Asn Gly
        435                 440                 445

Gln Pro Glu Asn Asn Tyr Lys Thr Thr Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510

<210> SEQ ID NO 178
<211> LENGTH: 510
<212> TYPE: PRT
<213> ORGANISM: Artificial Sequence
<220> FEATURE:
<223> OTHER INFORMATION: First Polypeptide Chain of the CD123 x CD3
      DART-B-type Diabody CD123-M2

<400> SEQUENCE: 178

```
Asp Phe Val Met Thr Gln Ser Pro Asp Ser Leu Ala Val Ser Leu Gly
1               5                   10                  15
Glu Arg Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Asn
                85                  90                  95
Asp Tyr Ser Tyr Pro Tyr Thr Phe Gly Gln Gly Thr Lys Leu Glu Ile
            100                 105                 110
Lys Gly Gly Gly Ser Gly Gly Gly Gly Glu Val Gln Leu Val Glu Ser
        115                 120                 125
Gly Gly Gly Leu Val Gln Pro Gly Gly Ser Leu Arg Leu Ser Cys Ala
    130                 135                 140
Ala Ser Gly Phe Thr Phe Ser Thr Tyr Ala Met Asn Trp Val Arg Gln
145                 150                 155                 160
Ala Pro Gly Lys Gly Leu Glu Trp Val Gly Arg Ile Arg Ser Lys Tyr
                165                 170                 175
Asn Asn Tyr Ala Thr Tyr Tyr Ala Asp Ser Val Lys Asp Arg Phe Thr
            180                 185                 190
Ile Ser Arg Asp Asp Ser Lys Asn Ser Leu Tyr Leu Gln Met Asn Ser
        195                 200                 205
Leu Lys Thr Glu Asp Thr Ala Val Tyr Tyr Cys Val Arg His Lys Asn
    210                 215                 220
Phe Gly Asn Ser Tyr Val Thr Trp Phe Ala Tyr Trp Gly Gln Gly Thr
225                 230                 235                 240
Leu Val Thr Val Ser Ser Gly Cys Gly Gly Gly Glu Val Ala Ala
                245                 250                 255
Leu Glu Lys Glu Val Ala Ala Leu Glu Lys Glu Val Ala Ala Leu Glu
            260                 265                 270
Lys Glu Val Ala Ala Leu Glu Lys Gly Gly Gly Asp Lys Thr His Thr
        275                 280                 285
Cys Pro Pro Cys Pro Ala Pro Glu Ala Ala Gly Gly Pro Ser Val Phe
    290                 295                 300
Leu Phe Pro Pro Lys Pro Lys Asp Thr Leu Met Ile Ser Arg Thr Pro
305                 310                 315                 320
Glu Val Thr Cys Val Val Val Asp Val Ser His Glu Asp Pro Glu Val
                325                 330                 335
Lys Phe Asn Trp Tyr Val Asp Gly Val Glu Val His Asn Ala Lys Thr
            340                 345                 350
Lys Pro Arg Glu Glu Gln Tyr Asn Ser Thr Tyr Arg Val Val Ser Val
        355                 360                 365
Leu Thr Val Leu His Gln Asp Trp Leu Asn Gly Lys Glu Tyr Lys Cys
    370                 375                 380
Lys Val Ser Asn Lys Ala Leu Pro Ala Pro Ile Glu Lys Thr Ile Ser
385                 390                 395                 400
Lys Ala Lys Gly Gln Pro Arg Glu Pro Gln Val Tyr Thr Leu Pro Pro
                405                 410                 415
```

Ser Arg Glu Glu Met Thr Lys Asn Gln Val Ser Leu Trp Cys Leu Val
            420                 425                 430

Lys Gly Phe Tyr Pro Ser Asp Ile Ala Val Glu Trp Glu Ser Asn Gly
            435                 440                 445

Gln Pro Glu Asn Asn Tyr Lys Thr Thr Pro Pro Val Leu Asp Ser Asp
450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
            485                 490                 495

Asn His Tyr Thr Gln Lys Ser Leu Ser Leu Ser Pro Gly Lys
            500                 505                 510

<210> SEQ ID NO 179
<211> LENGTH: 510
<212> TYPE: PRT
<213> ORGANISM: Artificial Sequence
<220> FEATURE:
<223> OTHER INFORMATION: First Polypeptide Chain of the CD123 x CD3
      DART-B-type Diabody CD123-M18

<400> SEQUENCE: 179

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Gly Met Asn Trp Val Arg Gln
145                 150                 155                 160

Ala Pro Gly Lys Gly Leu Glu Trp Val Gly Arg Ile Arg Ser Lys Tyr
            165                 170                 175

Asn Asn Tyr Ala Thr Tyr Tyr Ala Asp Ser Val Lys Asp Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Gly Cys Gly Gly Gly Glu Val Ala Ala
            245                 250                 255

```
Leu Glu Lys Glu Val Ala Ala Leu Lys Glu Val Ala Ala Leu Glu
        260                 265                 270
Lys Glu Val Ala Ala Leu Glu Lys Gly Gly Gly Asp Lys Thr His Thr
        275                 280                 285
Cys Pro Pro Cys Pro Ala Pro Glu Ala Ala Gly Gly Pro Ser Val Phe
        290                 295                 300
Leu Phe Pro Pro Lys Pro Lys Asp Thr Leu Met Ile Ser Arg Thr Pro
305                 310                 315                 320
Glu Val Thr Cys Val Val Val Asp Val Ser His Glu Asp Pro Glu Val
                325                 330                 335
Lys Phe Asn Trp Tyr Val Asp Gly Val Glu Val His Asn Ala Lys Thr
        340                 345                 350
Lys Pro Arg Glu Glu Gln Tyr Asn Ser Thr Tyr Arg Val Val Ser Val
        355                 360                 365
Leu Thr Val Leu His Gln Asp Trp Leu Asn Gly Lys Glu Tyr Lys Cys
        370                 375                 380
Lys Val Ser Asn Lys Ala Leu Pro Ala Pro Ile Glu Lys Thr Ile Ser
385                 390                 395                 400
Lys Ala Lys Gly Gln Pro Arg Glu Pro Gln Val Tyr Thr Leu Pro Pro
                405                 410                 415
Ser Arg Glu Glu Met Thr Lys Asn Gln Val Ser Leu Trp Cys Leu Val
        420                 425                 430
Lys Gly Phe Tyr Pro Ser Asp Ile Ala Val Glu Trp Glu Ser Asn Gly
        435                 440                 445
Gln Pro Glu Asn Asn Tyr Lys Thr Thr Pro Pro Val Leu Asp Ser Asp
        450                 455                 460
Gly Ser Phe Phe Leu Tyr Ser Lys Leu Thr Val Asp Lys Ser Arg Trp
465                 470                 475                 480
Gln Gln Gly Asn Val Phe Ser Cys Ser Val Met His Glu Ala Leu His
                485                 490                 495
Asn His Tyr Thr Gln Lys Ser Leu Ser Leu Ser Pro Gly Lys
                500                 505                 510

<210> SEQ ID NO 180
<211> LENGTH: 504
<212> TYPE: PRT
<213> ORGANISM: Artificial Sequence
<220> FEATURE:
<223> OTHER INFORMATION: First Polypeptide Chain of the 5T4 x CD3
      DART-B-type Diabody 5T4-WT

<400> SEQUENCE: 180

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Tyr
                20                  25                  30
Leu Ala Trp Phe Gln Gln Lys Pro Gly Lys Ala Pro Lys Ser Leu Ile
        35                  40                  45
Tyr Arg Ala Asn Arg Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Leu Gln Tyr Asp Asp Phe Pro Trp
                85                  90                  95
```

```
Thr Phe Gly Gln Gly Thr Lys Leu Glu Ile Lys Gly Gly Ser Gly
            100                 105                 110

Gly Gly Gly Glu Val Gln Leu Val Glu Ser Gly Gly Leu Val Gln
            115                 120                 125

Pro Gly Gly Ser Leu Arg Leu Ser Cys Ala Ala Ser Gly Phe Thr Phe
130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Gly Arg Phe Thr Ile Ser Arg Asp Asp Ser
                180                 185                 190

Lys Asn Ser Leu Tyr Leu Gln Met Asn Ser Leu Lys Thr Glu Asp Thr
                195                 200                 205

Ala Val Tyr Tyr Cys Val Arg His Gly Asn Phe Gly Asn Ser Tyr Val
            210                 215                 220

Ser Trp Phe Ala Tyr Trp Gly Gln Gly Thr Leu Val Thr Val Ser Ser
225                 230                 235                 240

Gly Gly Cys Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
            275                 280                 285

Pro Glu Ala Ala Gly Gly Pro Ser Val Phe Leu Phe Pro Pro Lys Pro
            290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
                340                 345                 350

Tyr Asn Ser Thr Tyr Arg Val Val Ser Val Leu Thr Val Leu His Gln
            355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
            450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
                500
```

<210> SEQ ID NO 181
<211> LENGTH: 270
<212> TYPE: PRT
<213> ORGANISM: Artificial Sequence
<220> FEATURE:
<223> OTHER INFORMATION: Second Polypeptide Chain of the 5T4 x CD3
      DART-B-type Diabody 5T4-WT

<400> SEQUENCE: 181

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
130                 135                 140

Tyr Thr Phe Thr Ser Phe Trp Met His Trp Val Arg Gln Ala Pro Gly
145                 150                 155                 160

Gln Gly Leu Glu Trp Met Gly Arg Ile Asp Pro Asn Arg Gly Gly Thr
                165                 170                 175

Glu Tyr Asn Glu Lys Ala Lys Ser Arg Val Thr Met Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Gly Gly Asn Pro Tyr Tyr Pro Met Asp
    210                 215                 220

Tyr Trp Gly Gln Gly Thr Thr Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270
```

<210> SEQ ID NO 182
<211> LENGTH: 504
<212> TYPE: PRT
<213> ORGANISM: Artificial Sequence
<220> FEATURE:
<223> OTHER INFORMATION: First Polypeptide Chain of the 5T4 x CD3
      DART-B-type Diabody 5T4-M1

<400> SEQUENCE: 182

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30
```

-continued

```
Leu Ala Trp Phe Gln Gln Lys Pro Gly Lys Ala Pro Lys Ser Leu Ile
            35                  40                  45

Tyr Arg Ala Asn Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Tyr Asp Asp Phe Pro Trp
                 85                  90                  95

Thr Phe Gly Gln Gly Thr Lys Leu Glu Ile Lys Gly Gly Gly Ser Gly
                100                 105                 110

Gly Gly Gly Glu Val Gln Leu Val Glu Ser Gly Gly Gly Leu Val Gln
            115                 120                 125

Pro Gly Gly Ser Leu Arg Leu Ser Cys Ala Ala Ser Gly Phe Thr Phe
            130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
                180                 185                 190

Lys Asn Ser Leu Tyr Leu Gln Met Asn Ser Leu Lys Thr Glu Asp Thr
            195                 200                 205

Ala Val Tyr Tyr Cys Val Arg His Gly Asn Phe Gly Asn Ser Tyr Val
            210                 215                 220

Thr Trp Phe Ala Tyr Trp Gly Gln Gly Thr Leu Val Thr Val Ser Ser
225                 230                 235                 240

Gly Gly Cys Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
            275                 280                 285

Pro Glu Ala Ala Gly Gly Pro Ser Val Phe Leu Phe Pro Pro Lys Pro
            290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
            355                 360                 365

Asp Trp Leu Asn Gly Lys Glu Tyr Lys Cys Lys Val Ser Asn Lys Ala
            370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
            435                 440                 445
```

```
Lys Thr Thr Pro Pro Val Leu Asp Ser Asp Gly Ser Phe Phe Leu Tyr
            450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 183
<211> LENGTH: 504
<212> TYPE: PRT
<213> ORGANISM: Artificial Sequence
<220> FEATURE:
<223> OTHER INFORMATION: First Polypeptide Chain of the 5T4 x CD3
      DART-B-type Diabody 5T4-M2

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Lys Asn Phe Gly Asn Ser Tyr Val
    210                 215                 220

Thr Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
        275                 280                 285
```

Pro Glu Ala Ala Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 184
<211> LENGTH: 504
<212> TYPE: PRT
<213> ORGANISM: Artificial Sequence
<220> FEATURE:
<223> OTHER INFORMATION: First Polypeptide Chain of the 5T4 x CD3
    DART-B-type Diabody 5T4-M18

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
130                 135                 140

Ser Thr Tyr Gly Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
210                 215                 220

Ser Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
        275                 280                 285

Pro Glu Ala Ala Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 185
<211> LENGTH: 506
<212> TYPE: PRT
<213> ORGANISM: Artificial Sequence
<220> FEATURE:

<223> OTHER INFORMATION: First Polypeptide Chain of the HIV x CD3
      DART-B-type Diabody HIV-WT

<400> SEQUENCE: 185

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Ala Ser Thr Lys Gly Glu Val Ala Ala Cys Glu Lys Glu
                245                 250                 255

Val Ala Ala Leu Glu Lys Glu Val Ala Ala Leu Glu Lys Glu Val Ala
            260                 265                 270

Ala Leu Glu Lys Gly Gly Gly Asp Lys Thr His Thr Cys Pro Pro Cys
        275                 280                 285

Pro Ala Pro Glu Ala Ala Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400
```

```
Gln Pro Arg Glu Pro Gln Val Tyr Thr Leu Pro Pro Ser Arg Glu Glu
                405                 410                 415

Met Thr Lys Asn Gln Val Ser Leu Trp Cys Leu Val Lys Gly Phe Tyr
        420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
            485                 490                 495

Gln Lys Ser Leu Ser Leu Ser Pro Gly Lys
        500                 505

<210> SEQ ID NO 186
<211> LENGTH: 274
<212> TYPE: PRT
<213> ORGANISM: Artificial Sequence
<220> FEATURE:
<223> OTHER INFORMATION: Second Polypeptide Chain of the HIV x CD3
      DART-B-type Diabody HIV-WT

<400> SEQUENCE: 186

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Gln Glu Ser Gly Pro Gly
        115                 120                 125

Leu Val Lys Pro Ser Gln Thr Leu Ser Leu Ser Cys Thr Val Ser Gly
    130                 135                 140

Gly Ser Ser Ser Gly Ala His Tyr Trp Ser Trp Ile Arg Gln Tyr
145                 150                 155                 160

Pro Gly Lys Gly Leu Glu Trp Ile Gly Tyr Ile His Tyr Ser Gly Asn
                165                 170                 175

Thr Tyr Tyr Asn Pro Ser Leu Lys Ser Arg Ile Thr Ile Ser Gln His
            180                 185                 190

Thr Ser Glu Asn Gln Phe Ser Leu Lys Leu Asn Ser Val Thr Val Ala
        195                 200                 205

Asp Thr Ala Val Tyr Tyr Cys Ala Arg Gly Thr Arg Leu Arg Thr Leu
    210                 215                 220

Arg Asn Ala Phe Asp Ile Trp Gly Gln Gly Thr Leu Val Thr Val Ser
225                 230                 235                 240
```

-continued

```
Ser Ala Ser Thr Lys Gly Lys Val Ala Ala Cys Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 187
<211> LENGTH: 451
<212> TYPE: PRT
<213> ORGANISM: Artificial Sequence
<220> FEATURE:
<223> OTHER INFORMATION: Third Polypeptide Chain of Illustrative
      TRIVALENT-Type Molecules

<400> SEQUENCE: 187

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Gly Met Asn Trp Val Arg Gln Ala Pro Gly Lys Gly Leu Glu Trp Val
        35                  40                  45

Ala Leu Ile Tyr Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Tyr Thr Gln Lys Ser Leu Ser Leu Ser
        435                 440                 445

Pro Gly Lys
    450

<210> SEQ ID NO 188
<211> LENGTH: 213
<212> TYPE: PRT
<213> ORGANISM: Artificial Sequence
<220> FEATURE:
<223> OTHER INFORMATION: Fourth Polypeptide Chain of Illustrative
      TRIVALENT-Type Molecules

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Thr Asp Ile Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Tyr Gln Tyr Asn Asn Gly Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

```
Cys Glu Val Thr His Gln Gly Leu Ser Ser Pro Val Thr Lys Ser Phe
        195                 200                 205

Asn Arg Gly Glu Cys
    210

<210> SEQ ID NO 189
<211> LENGTH: 280
<212> TYPE: PRT
<213> ORGANISM: Artificial Sequence
<220> FEATURE:
<223> OTHER INFORMATION: First Polypeptide Chain of Illustrative CD123 x
      CD3 DART-A-type Diabody Having the Structure of DART-A-WT Diabody,
      but Comprising the VL and VH Domain of one of CD3 mAb 1 variants
      M1-M26
<220> FEATURE:
<221> NAME/KEY: MISC_FEATURE
<222> LOCATION: (152)..(152)
<223> OTHER INFORMATION: Xaa is Threonine (T), Aspartate (D), or
      Glutamate (E)
<220> FEATURE:
<221> NAME/KEY: MISC_FEATURE
<222> LOCATION: (153)..(153)
<223> OTHER INFORMATION: Xaa is Tyrosine (Y), Aspartate (D), or
      Threonine (T)
<220> FEATURE:
<221> NAME/KEY: MISC_FEATURE
<222> LOCATION: (154)..(154)
<223> OTHER INFORMATION: Xaa is Alanine (A) or Glycine (G)
<220> FEATURE:
<221> NAME/KEY: MISC_FEATURE
<222> LOCATION: (189)..(189)
<223> OTHER INFORMATION: Xaa is Aspartate (D) or Glycine (G)
<220> FEATURE:
<221> NAME/KEY: MISC_FEATURE
<222> LOCATION: (223)..(223)
<223> OTHER INFORMATION: Xaa is Glycine (G), Aspartate (D), Glutamate
      (E), or Lysine (K)
<220> FEATURE:
<221> NAME/KEY: MISC_FEATURE
<222> LOCATION: (225)..(225)
<223> OTHER INFORMATION: Xaa is Phenylalanine (F) or Isoleucine (I)
<220> FEATURE:
<221> NAME/KEY: MISC_FEATURE
<222> LOCATION: (226)..(226)
<223> OTHER INFORMATION: Xaa is Glycine (G) or Isoleucine (I)
<220> FEATURE:
<221> NAME/KEY: MISC_FEATURE
<222> LOCATION: (229)..(229)
<223> OTHER INFORMATION: Xaa is Tyrosine (Y), Alanine (A), Glycine (G),
      or Glutamine (Q)
<220> FEATURE:
<221> NAME/KEY: MISC_FEATURE
<222> LOCATION: (231)..(231)
<223> OTHER INFORMATION: Xaa is Serine (S) or Threonine (T)
<220> FEATURE:
<221> NAME/KEY: MISC_FEATURE
<222> LOCATION: (232)..(232)
<223> OTHER INFORMATION: Xaa is Tryptophan (W), Phenylalanine (F), or
      Tyrosine (Y)
<220> FEATURE:
<221> NAME/KEY: MISC_FEATURE
<222> LOCATION: (235)..(235)
<223> OTHER INFORMATION: Xaa is Tyrosine (Y) or Glutamate (E)

<400> SEQUENCE: 189

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45
```

```
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Ser Tyr Pro Tyr Thr Phe Gly Gln Gly Thr Lys Leu Glu Ile
                100                 105                 110

Lys Gly Gly Gly Ser Gly Gly Gly Gly Glu Val Gln Leu Val Glu Ser
                115                 120                 125

Gly Gly Gly Leu Val Gln Pro Gly Gly Ser Leu Arg Leu Ser Cys Ala
            130                 135                 140

Ala Ser Gly Phe Thr Phe Ser Xaa Xaa Xaa Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Xaa Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Xaa Asn
    210                 215                 220

Xaa Xaa Asn Ser Xaa Val Xaa Xaa Phe Ala Xaa Trp Gly Gln Gly Thr
225                 230                 235                 240

Leu Val Thr Val Ser Ser Gly Gly Cys Gly Gly Gly Lys Val Ala Ala
                245                 250                 255

Leu Lys Glu Lys Val Ala Ala Leu Lys Glu Lys Val Ala Ala Leu Lys
                260                 265                 270

Glu Lys Val Ala Ala Leu Lys Glu
                275                 280

<210> SEQ ID NO 190
<211> LENGTH: 272
<212> TYPE: PRT
<213> ORGANISM: Artificial Sequence
<220> FEATURE:
<223> OTHER INFORMATION: Second Polypeptide Chain of Illustrative
      CD123 x CD3 DART-A-type
      Diabody Having the Structure of DART-A-WT Diabody, but Comprising
      the VL and VH Domain of one of CD3 mAb 1 variants M1-M26
<220> FEATURE:
<221> NAME/KEY: MISC_FEATURE
<222> LOCATION: (52)..(52)
<223> OTHER INFORMATION: Xaa is Glycine (G) or Aspartate (D)
<220> FEATURE:
<221> NAME/KEY: MISC_FEATURE
<222> LOCATION: (55)..(55)
<223> OTHER INFORMATION: Xaa is Lysine (K) or Glycine (G)
<220> FEATURE:
<221> NAME/KEY: MISC_FEATURE
<222> LOCATION: (92)..(92)
<223> OTHER INFORMATION: Xaa is Leucine (L), Glutamate (E), or Glutamine
      (Q)

<400> SEQUENCE: 190

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                20                  25                  30
```

Asn Tyr Ala Asn Trp Val Gln Gln Lys Pro Gly Gln Ala Pro Arg Gly
            35                  40                  45

Leu Ile Gly Xaa Thr Asn Xaa Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Xaa Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Leu Lys Lys Pro Gly Ala Ser Val Lys Val Ser Cys Lys Ala Ser Gly
130                 135                 140

Tyr Thr Phe Thr Asp Tyr Tyr Met Lys Trp Val Arg Gln Ala Pro Gly
145                 150                 155                 160

Gln Gly Leu Glu Trp Ile Gly Asp Ile Ile Pro Ser Asn Gly Ala Thr
            165                 170                 175

Phe Tyr Asn Gln Lys Phe Lys Gly Arg Val Thr Ile Thr Val Asp Lys
        180                 185                 190

Ser Thr Ser Thr Ala Tyr Met Glu Leu Ser Ser Leu Arg Ser Glu Asp
    195                 200                 205

Thr Ala Val Tyr Tyr Cys Ala Arg Ser His Leu Leu Arg Ala Ser Trp
210                 215                 220

Phe Ala Tyr Trp Gly Gln Gly Thr Leu Val Thr Val Ser Ser Gly Gly
225                 230                 235                 240

Cys Gly Gly Gly Glu Val Ala Ala Leu Glu Lys Glu Val Ala Ala Leu
            245                 250                 255

Glu Lys Glu Val Ala Ala Leu Gly Lys Glu Val Ala Ala Leu Glu Lys
            260                 265                 270

<210> SEQ ID NO 191
<211> LENGTH: 502
<212> TYPE: PRT
<213> ORGANISM: Artificial Sequence
<220> FEATURE:
<223> OTHER INFORMATION: First Polypeptide Chain of the CD19 x CD3
      DART-B-type Diabody CD19-WT

<400> SEQUENCE: 191

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
            85                  90                  95

Phe Gly Gln Gly Thr Lys Leu Glu Ile Lys Gly Gly Ser Gly Gly
            100                 105                 110

-continued

Gly Gly Glu Val Gln Leu Val Glu Ser Gly Gly Leu Val Gln Pro
            115                 120                 125

Gly Gly Ser Leu Arg Leu Ser Cys Ala Ala Ser Gly Phe Thr Phe Ser
130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
210                 215                 220

Trp Phe Ala Tyr Trp Gly Gln Gly Thr Leu Val Thr Val Ser Ser Ala
225                 230                 235                 240

Ser Thr Lys Gly Glu Val Ala Ala Cys Glu Lys Val Ala Ala Leu
                245                 250                 255

Glu Lys Glu Val Ala Ala Leu Glu Lys Glu Val Ala Ala Leu Glu Lys
            260                 265                 270

Gly Gly Gly Asp Lys Thr His Thr Cys Pro Pro Cys Pro Ala Pro Glu
        275                 280                 285

Ala Ala Gly Gly Pro Ser Val Phe Leu Phe Pro Pro Lys Pro Lys Asp
290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Trp Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 192
<211> LENGTH: 271

```
<212> TYPE: PRT
<213> ORGANISM: Artificial Sequence
<220> FEATURE:
<223> OTHER INFORMATION: Second Polypeptide Chain of the CD19 x CD3
      DART-B-type Diabody CD19-WT

<400> SEQUENCE: 192
```

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Thr Leu Arg Glu Ser Gly Pro Ala
        115                 120                 125

Leu Val Lys Pro Thr Gln Thr Leu Thr Leu Thr Cys Thr Phe Ser Gly
    130                 135                 140

Phe Ser Leu Ser Thr Ser Gly Met Gly Val Gly Trp Ile Arg Gln Pro
145                 150                 155                 160

Pro Gly Lys Ala Leu Glu Trp Leu Ala His Ile Trp Trp Asp Asp Asp
                165                 170                 175

Lys Arg Tyr Asn Pro Ala Leu Lys Ser Arg Leu Thr Ile Ser Lys Asp
            180                 185                 190

Thr Ser Lys Asn Gln Val Phe Leu Thr Met Thr Asn Met Asp Pro Val
        195                 200                 205

Asp Thr Ala Thr Tyr Tyr Cys Ala Arg Met Glu Leu Trp Ser Tyr Tyr
    210                 215                 220

Phe Asp Tyr Trp Gly Gln Gly Thr Thr Val Thr Val Ser Ser Ala Ser
225                 230                 235                 240

Thr Lys Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270

```
<210> SEQ ID NO 193
<211> LENGTH: 503
<212> TYPE: PRT
<213> ORGANISM: Artificial Sequence
<220> FEATURE:
<223> OTHER INFORMATION: First Polypeptide Chain of the CD19 x CD3
      DART-B-type Diabody CD19.1-M18

<400> SEQUENCE: 193
```

Glu Asn Val Leu Thr Gln Ser Pro Ala Thr Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

-continued

```
Asp Thr Ser Lys Leu Ala Ser Gly Val Pro Ser Arg Phe Ser Gly Ser
 50                  55                  60

Gly Ser Gly Thr Asp His Phe Leu Thr Ile Ser Ser Leu Glu Ala Glu
 65                  70                  75                  80

Asp Ala Ala Thr Tyr Tyr Cys Phe Gln Gly Ser Val Tyr Pro Phe Thr
                 85                  90                  95

Phe Gly Gln Gly Thr Lys Leu Glu Ile Lys Gly Gly Gly Ser Gly Gly
                100                 105                 110

Gly Gly Glu Val Gln Leu Val Glu Ser Gly Gly Gly Leu Val Gln Pro
            115                 120                 125

Gly Gly Ser Leu Arg Leu Ser Cys Ala Ala Ser Gly Phe Thr Phe Ser
130                 135                 140

Thr Tyr Gly Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Asp Arg Phe Thr Ile Ser Arg Asp Asp Ser Lys
                180                 185                 190

Asn Ser Leu Tyr Leu Gln Met Asn Ser Leu Lys Thr Glu Asp Thr Ala
            195                 200                 205

Val Tyr Tyr Cys Val Arg His Gly Asn Phe Gly Asn Ser Tyr Val Ser
210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
                260                 265                 270

Lys Gly Gly Gly Asp Lys Thr His Thr Cys Pro Pro Cys Pro Ala Pro
            275                 280                 285

Glu Ala Ala Gly Gly Pro Ser Val Phe Leu Phe Pro Pro Lys Pro Lys
290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
                340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
                420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
450                 455                 460
```

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 194
<211> LENGTH: 272
<212> TYPE: PRT
<213> ORGANISM: Artificial Sequence
<220> FEATURE:
<223> OTHER INFORMATION: Second Polypeptide Chain of the CD19 x CD3
      DART-B-type Diabody CD19.1-M18

<400> SEQUENCE: 194

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
50                  55                  60

Ser Gly Ser Leu Leu Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Thr Leu Arg Glu Ser Gly Pro Ala
        115                 120                 125

Leu Val Lys Pro Thr Gln Thr Leu Thr Leu Thr Cys Thr Phe Ser Gly
    130                 135                 140

Phe Ser Leu Ser Thr Ser Gly Met Gly Val Gly Trp Ile Arg Gln Pro
145                 150                 155                 160

Pro Gly Lys Ala Leu Glu Trp Leu Ala His Ile Trp Trp Asp Asp Asp
                165                 170                 175

Lys Arg Tyr Asn Pro Ala Leu Lys Ser Arg Leu Thr Ile Ser Lys Asp
            180                 185                 190

Thr Ser Lys Asn Gln Val Phe Leu Thr Met Thr Asn Met Asp Pro Val
        195                 200                 205

Asp Thr Ala Thr Tyr Tyr Cys Ala Arg Met Glu Leu Trp Ser Tyr Tyr
    210                 215                 220

Phe Asp Tyr Trp Gly Gln Gly Thr Thr Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 195
<211> LENGTH: 106
<212> TYPE: PRT
<213> ORGANISM: Artificial Sequence
<220> FEATURE:

<223> OTHER INFORMATION: Alternative VL Domain of the Humanized Anti-
      Human CD19 Antibody mAb 1

<400> SEQUENCE: 195

Glu Asn Val Leu Thr Gln Ser Pro Ala Thr Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp His Phe Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys
            100                 105

<210> SEQ ID NO 196
<211> LENGTH: 506
<212> TYPE: PRT
<213> ORGANISM: Artificial Sequence
<220> FEATURE:
<223> OTHER INFORMATION: First Polypeptide Chain of the HIV x CD3
      DART-B-type Diabody HIV-M18

<400> SEQUENCE: 196

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Gly Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Ala Ser Thr Lys Gly Glu Val Ala Ala Cys Glu Lys Glu
            245                 250                 255

Val Ala Ala Leu Glu Lys Glu Val Ala Ala Leu Glu Lys Glu Val Ala
            260                 265                 270

Ala Leu Glu Lys Gly Gly Asp Lys Thr His Thr Cys Pro Pro Cys
        275                 280                 285

Pro Ala Pro Glu Ala Ala Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
            325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Glu Glu
                405                 410                 415

Met Thr Lys Asn Gln Val Ser Leu Trp Cys Leu Val Lys Gly Phe Tyr
            420                 425                 430

Pro Ser Asp Ile Ala Val Glu Trp Glu Ser Asn Gly Gln Pro Glu Asn
            435                 440                 445

Asn Tyr Lys Thr Thr Pro Pro Val Leu Asp Ser Asp Gly Ser Phe Phe
        450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
            485                 490                 495

Gln Lys Ser Leu Ser Leu Ser Pro Gly Lys
            500                 505

<210> SEQ ID NO 197
<211> LENGTH: 502
<212> TYPE: PRT
<213> ORGANISM: Artificial Sequence
<220> FEATURE:
<223> OTHER INFORMATION: First Polypeptide Chain of the CD19 x CD3
      DART-B-type Diabody CD19-M18

<400> SEQUENCE: 197

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

-continued

```
Asp Ala Ala Thr Tyr Tyr Cys Phe Gln Gly Ser Val Tyr Pro Phe Thr
                85                  90                  95
Phe Gly Gln Gly Thr Lys Leu Glu Ile Lys Gly Gly Gly Ser Gly Gly
            100                 105                 110
Gly Gly Glu Val Gln Leu Val Glu Ser Gly Gly Gly Leu Val Gln Pro
        115                 120                 125
Gly Gly Ser Leu Arg Leu Ser Cys Ala Ala Ser Gly Phe Thr Phe Ser
130                 135                 140
Thr Tyr Gly Met Asn Trp Val Arg Gln Ala Pro Gly Lys Gly Leu Glu
145                 150                 155                 160
Trp Val Gly Arg Ile Arg Ser Lys Tyr Asn Asn Tyr Ala Thr Tyr Tyr
                165                 170                 175
Ala Asp Ser Val Lys Gly Arg Phe Thr Ile Ser Arg Asp Asp Ser Lys
            180                 185                 190
Asn Ser Leu Tyr Leu Gln Met Asn Ser Leu Lys Thr Glu Asp Thr Ala
        195                 200                 205
Val Tyr Tyr Cys Val Arg His Gly Asn Phe Gly Asn Ser Tyr Val Ser
    210                 215                 220
Trp Phe Ala Tyr Trp Gly Gln Gly Thr Leu Val Thr Val Ser Ser Ala
225                 230                 235                 240
Ser Thr Lys Gly Glu Val Ala Ala Cys Glu Lys Glu Val Ala Ala Leu
                245                 250                 255
Glu Lys Glu Val Ala Ala Leu Glu Lys Glu Val Ala Ala Leu Glu Lys
            260                 265                 270
Gly Gly Gly Asp Lys Thr His Thr Cys Pro Pro Cys Pro Ala Pro Glu
        275                 280                 285
Ala Ala Gly Gly Pro Ser Val Phe Leu Phe Pro Pro Lys Pro Lys Asp
    290                 295                 300
Thr Leu Met Ile Ser Arg Thr Pro Glu Val Thr Cys Val Val Val Asp
305                 310                 315                 320
Val Ser His Glu Asp Pro Glu Val Lys Phe Asn Trp Tyr Val Asp Gly
                325                 330                 335
Val Glu Val His Asn Ala Lys Thr Lys Pro Arg Glu Glu Gln Tyr Asn
            340                 345                 350
Ser Thr Tyr Arg Val Val Ser Val Leu Thr Val Leu His Gln Asp Trp
        355                 360                 365
Leu Asn Gly Lys Glu Tyr Lys Cys Lys Val Ser Asn Lys Ala Leu Pro
    370                 375                 380
Ala Pro Ile Glu Lys Thr Ile Ser Lys Ala Lys Gly Gln Pro Arg Glu
385                 390                 395                 400
Pro Gln Val Tyr Thr Leu Pro Pro Ser Arg Glu Glu Met Thr Lys Asn
                405                 410                 415
Gln Val Ser Leu Trp Cys Leu Val Lys Gly Phe Tyr Pro Ser Asp Ile
            420                 425                 430
Ala Val Glu Trp Glu Ser Asn Gly Gln Pro Glu Asn Asn Tyr Lys Thr
        435                 440                 445
Thr Pro Pro Val Leu Asp Ser Asp Gly Ser Phe Phe Leu Tyr Ser Lys
    450                 455                 460
Leu Thr Val Asp Lys Ser Arg Trp Gln Gln Gly Asn Val Phe Ser Cys
465                 470                 475                 480
Ser Val Met His Glu Ala Leu His Asn His Tyr Thr Gln Lys Ser Leu
                485                 490                 495
```

Ser Leu Ser Pro Gly Lys
        500

<210> SEQ ID NO 198
<211> LENGTH: 510
<212> TYPE: PRT
<213> ORGANISM: Artificial Sequence
<220> FEATURE:
<223> OTHER INFORMATION: First Polypeptide Chain of the CD123 x CD3
      DART-B-type Diabody CD123-M13

<400> SEQUENCE: 198

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Glu Trp Gly Gln Gly Thr
225                 230                 235                 240

Leu Val Thr Val Ser Ser Gly Gly Cys Gly Gly Gly Glu Val Ala Ala
                245                 250                 255

Leu Glu Lys Glu Val Ala Ala Leu Glu Lys Glu Val Ala Ala Leu Glu
            260                 265                 270

Lys Glu Val Ala Ala Leu Glu Lys Gly Gly Gly Asp Lys Thr His Thr
        275                 280                 285

Cys Pro Pro Cys Pro Ala Pro Glu Ala Ala Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
            355                 360                 365

Leu Thr Val Leu His Gln Asp Trp Leu Asn Gly Lys Glu Tyr Lys Cys
        370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
                405                 410                 415

Ser Arg Glu Glu Met Thr Lys Asn Gln Val Ser Leu Trp Cys Leu Val
            420                 425                 430

Lys Gly Phe Tyr Pro Ser Asp Ile Ala Val Glu Trp Glu Ser Asn Gly
        435                 440                 445

Gln Pro Glu Asn Asn Tyr Lys Thr Thr Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510

<210> SEQ ID NO 199
<211> LENGTH: 510
<212> TYPE: PRT
<213> ORGANISM: Artificial Sequence
<220> FEATURE:
<223> OTHER INFORMATION: First Polypeptide Chain of the CD123 x CD3
      DART-B-type Diabody CD123-M17

<400> SEQUENCE: 199

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Thr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
            180                 185                 190

```
Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
        210                 215                 220

Phe Gly Asn Ser Tyr Val Ser Trp Phe Ala Tyr Trp Gly Gln Gly Thr
225                 230                 235                 240

Leu Val Thr Val Ser Ser Gly Gly Cys Gly Gly Glu Val Ala Ala
        245                 250                 255

Leu Glu Lys Glu Val Ala Ala Leu Glu Lys Glu Val Ala Ala Leu Glu
        260                 265                 270

Lys Glu Val Ala Ala Leu Glu Lys Gly Gly Asp Lys Thr His Thr
        275                 280                 285

Cys Pro Pro Cys Pro Ala Pro Glu Ala Ala Gly Gly Pro Ser Val Phe
        290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
        325                 330                 335

Lys Phe Asn Trp Tyr Val Asp Gly Val Glu Val His Asn Ala Lys Thr
        340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
        370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
        405                 410                 415

Ser Arg Glu Glu Met Thr Lys Asn Gln Val Ser Leu Trp Cys Leu Val
        420                 425                 430

Lys Gly Phe Tyr Pro Ser Asp Ile Ala Val Glu Trp Glu Ser Asn Gly
        435                 440                 445

Gln Pro Glu Asn Asn Tyr Lys Thr Thr Pro Pro Val Leu Asp Ser Asp
        450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
        485                 490                 495

Asn His Tyr Thr Gln Lys Ser Leu Ser Leu Ser Pro Gly Lys
        500                 505                 510

<210> SEQ ID NO 200
<211> LENGTH: 510
<212> TYPE: PRT
<213> ORGANISM: Artificial Sequence
<220> FEATURE:
<223> OTHER INFORMATION: First Polypeptide Chain of the CD123 x CD3
      DART-B-type Diabody CD123-M19

<400> SEQUENCE: 200

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30
```

```
Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
                100                 105                 110

Lys Gly Gly Gly Ser Gly Gly Gly Gly Glu Val Gln Leu Val Glu Ser
            115                 120                 125

Gly Gly Gly Leu Val Gln Pro Gly Gly Ser Leu Arg Leu Ser Cys Ala
            130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
                180                 185                 190

Ile Ser Arg Asp Asp Ser Lys Asn Ser Leu Tyr Leu Gln Met Asn Ser
                195                 200                 205

Leu Lys Thr Glu Asp Thr Ala Val Tyr Tyr Cys Val Arg His Lys Asn
            210                 215                 220

Ile Gly Asn Ser Tyr Val Ser Trp Phe Ala Tyr Trp Gly Gln Gly Thr
225                 230                 235                 240

Leu Val Thr Val Ser Ser Gly Gly Cys Gly Gly Gly Glu Val Ala Ala
                245                 250                 255

Leu Glu Lys Glu Val Ala Ala Leu Glu Lys Glu Val Ala Ala Leu Glu
            260                 265                 270

Lys Glu Val Ala Ala Leu Glu Lys Gly Gly Asp Lys Thr His Thr
            275                 280                 285

Cys Pro Pro Cys Pro Ala Pro Glu Ala Ala Gly Gly Pro Ser Val Phe
290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
                340                 345                 350

Lys Pro Arg Glu Glu Gln Tyr Asn Ser Thr Tyr Arg Val Val Ser Val
            355                 360                 365

Leu Thr Val Leu His Gln Asp Trp Leu Asn Gly Lys Glu Tyr Lys Cys
            370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
                405                 410                 415

Ser Arg Glu Glu Met Thr Lys Asn Gln Val Ser Leu Trp Cys Leu Val
            420                 425                 430

Lys Gly Phe Tyr Pro Ser Asp Ile Ala Val Glu Trp Glu Ser Asn Gly
            435                 440                 445
```

Gln Pro Glu Asn Asn Tyr Lys Thr Thr Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
            485                 490                 495

Asn His Tyr Thr Gln Lys Ser Leu Ser Leu Ser Pro Gly Lys
        500                 505                 510

<210> SEQ ID NO 201
<211> LENGTH: 503
<212> TYPE: PRT
<213> ORGANISM: Artificial Sequence
<220> FEATURE:
<223> OTHER INFORMATION: First Polypeptide Chain of the CD19 x CD3
      DART-B-type Diabody CD19.1-M13

<400> SEQUENCE: 201

Glu Asn Val Leu Thr Gln Ser Pro Ala Thr Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Val Pro Ser Arg Phe Ser Gly Ser
50                  55                  60

Gly Ser Gly Thr Asp His Phe Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Asp Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
210                 215                 220

Trp Phe Ala Glu Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
290                 295                 300

```
Asp Thr Leu Met Ile Ser Arg Thr Pro Glu Val Cys Val Val
305                 310                 315                 320

Asp Val Ser His Glu Asp Pro Glu Val Lys Phe Asn Trp Tyr Val Asp
            325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 202
<211> LENGTH: 503
<212> TYPE: PRT
<213> ORGANISM: Artificial Sequence
<220> FEATURE:
<223> OTHER INFORMATION: First Polypeptide Chain of the CD19 x CD3
      DART-B-type Diabody CD19.1-M17

<400> SEQUENCE: 202

Glu Asn Val Leu Thr Gln Ser Pro Ala Thr Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp His Phe Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140
```

Thr Thr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Asp Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 203
<211> LENGTH: 503
<212> TYPE: PRT
<213> ORGANISM: Artificial Sequence
<220> FEATURE:
<223> OTHER INFORMATION: First Polypeptide Chain of the CD19 x CD3
      DART-B-type Diabody CD19.1-M19

```
<400> SEQUENCE: 203

Glu Asn Val Leu Thr Gln Ser Pro Ala Thr Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp His Phe Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Asp Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Lys Asn Ile Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415
```

```
Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
            485                 490                 495

Leu Ser Leu Ser Pro Gly Lys
            500

<210> SEQ ID NO 204
<211> LENGTH: 502
<212> TYPE: PRT
<213> ORGANISM: Artificial Sequence
<220> FEATURE:
<223> OTHER INFORMATION: First Polypeptide Chain of a CD19 x CD3
      DART-B-type Diabody comprising the VL Domain of CD19 mAb 1 and the
      VH Domain of CD3 mAb 1 M13

<400> SEQUENCE: 204

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Glu Trp Gly Gln Gly Thr Leu Val Thr Val Ser Ser Ala
225                 230                 235                 240

Ser Thr Lys Gly Glu Val Ala Ala Cys Glu Lys Glu Val Ala Ala Leu
                245                 250                 255
```

-continued

Glu Lys Glu Val Ala Ala Leu Glu Lys Val Ala Ala Leu Lys
                260                 265                 270

Gly Gly Gly Asp Lys Thr His Thr Cys Pro Pro Cys Pro Ala Pro Glu
            275                 280                 285

Ala Ala Gly Gly Pro Ser Val Phe Leu Phe Pro Pro Lys Pro Lys Asp
290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Trp Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 205
<211> LENGTH: 502
<212> TYPE: PRT
<213> ORGANISM: Artificial Sequence
<220> FEATURE:
<223> OTHER INFORMATION: First Polypeptide Chain of a CD19 x CD3
      DART-B-type Diabody comprising the VL Domain of CD19 mAb 1 and the
      VH Domain of CD3 mAb 1 M17

<400> SEQUENCE: 205

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

```
Phe Gly Gln Gly Thr Lys Leu Glu Ile Lys Gly Gly Ser Gly Gly
                100                 105                 110

Gly Gly Glu Val Gln Leu Val Glu Ser Gly Gly Gly Leu Val Gln Pro
            115                 120                 125

Gly Gly Ser Leu Arg Leu Ser Cys Ala Ala Ser Gly Phe Thr Phe Ser
        130                 135                 140

Thr Thr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
210                 215                 220

Trp Phe Ala Tyr Trp Gly Gln Gly Thr Leu Val Thr Val Ser Ser Ala
225                 230                 235                 240

Ser Thr Lys Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270

Gly Gly Gly Asp Lys Thr His Thr Cys Pro Pro Cys Pro Ala Pro Glu
        275                 280                 285

Ala Ala Gly Gly Pro Ser Val Phe Leu Phe Pro Pro Lys Pro Lys Asp
        290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
        370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Trp Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
        450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500
```

<210> SEQ ID NO 206
<211> LENGTH: 502
<212> TYPE: PRT
<213> ORGANISM: Artificial Sequence
<220> FEATURE:
<223> OTHER INFORMATION: First Polypeptide Chain of a CD19 x CD3
      DART-B-type Diabody comprising the VL Domain of CD19 mAb 1 and the
      VH Domain of CD3 mAb 1 M19

<400> SEQUENCE: 206

```
Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Lys Asn Ile Gly Asn Ser Tyr Val Ser
    210                 215                 220

Trp Phe Ala Tyr Trp Gly Gln Gly Thr Leu Val Thr Val Ser Ser Ala
225                 230                 235                 240

Ser Thr Lys Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270

Gly Gly Gly Asp Lys Thr His Thr Cys Pro Pro Cys Pro Ala Pro Glu
        275                 280                 285

Ala Ala Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350
```

-continued

```
Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Trp Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 207
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of Variants of Anti-Human CD3
      Antibody CD3 mAb 1
<220> FEATURE:
<221> NAME/KEY: MISC_FEATURE
<222> LOCATION: (31)..(31)
<223> OTHER INFORMATION: Xaa is Threonine (T), Aspartate (D), or
      Glutamate (E)
<220> FEATURE:
<221> NAME/KEY: MISC_FEATURE
<222> LOCATION: (32)..(32)
<223> OTHER INFORMATION: Xaa is Tyrosine (Y), Aspartate (D) or Threonine
      (T)
<220> FEATURE:
<221> NAME/KEY: MISC_FEATURE
<222> LOCATION: (68)..(68)
<223> OTHER INFORMATION: Xaa is Aspartate (D) or Glycine (G)
<220> FEATURE:
<221> NAME/KEY: MISC_FEATURE
<222> LOCATION: (102)..(102)
<223> OTHER INFORMATION: Xaa is Glycine (G), Aspartate (D), Glutamate
      (E), or Lysine (K)
<220> FEATURE:
<221> NAME/KEY: MISC_FEATURE
<222> LOCATION: (104)..(104)
<223> OTHER INFORMATION: Xaa is Phenylalanine (F) or Isoleucine (I)
<220> FEATURE:
<221> NAME/KEY: MISC_FEATURE
<222> LOCATION: (105)..(105)
<223> OTHER INFORMATION: Xaa is Glycine (G) or Isoleucine (I)
<220> FEATURE:
<221> NAME/KEY: MISC_FEATURE
<222> LOCATION: (108)..(108)
<223> OTHER INFORMATION: Xaa is Tyrosine (Y), Alanine (A), Glycine (G),
      or Glutamine (Q)
<220> FEATURE:
<221> NAME/KEY: MISC_FEATURE
<222> LOCATION: (111)..(111)
<223> OTHER INFORMATION: Xaa is Tryptophan (W), Phenylalanine (F), or
      Tyrosine (Y)
<220> FEATURE:
```

```
<221> NAME/KEY: MISC_FEATURE
<222> LOCATION: (114)..(114)
<223> OTHER INFORMATION: Xaa is Tyrosine (Y) or Glutamate (E)

<400> SEQUENCE: 207

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Xaa Arg Phe Thr Ile Ser Arg Asp Asp Ser Lys Asn Ser
65              70                  75                  80

Leu Tyr Leu Gln Met Asn Ser Leu Lys Thr Glu Asp Thr Ala Val Tyr
            85                  90                  95

Tyr Cys Val Arg His Xaa Asn Xaa Xaa Asn Ser Xaa Ser Thr Xaa Phe
            100                 105                 110

Ala Xaa Trp Gly Gln Gly Thr Leu Val Thr Val Ser Ser
        115                 120                 125

<210> SEQ ID NO 208
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: VL Domain of Variants of Anti-Human CD3
      Antibody CD3 mAb 1
<220> FEATURE:
<221> NAME/KEY: MISC_FEATURE
<222> LOCATION: (52)..(52)
<223> OTHER INFORMATION: Xaa is is Glycine (G) or Aspartate (D)
<220> FEATURE:
<221> NAME/KEY: MISC_FEATURE
<222> LOCATION: (55)..(55)
<223> OTHER INFORMATION: Xaa is is Lysine (K) or Glycine (G)
<220> FEATURE:
<221> NAME/KEY: MISC_FEATURE
<222> LOCATION: (92)..(92)
<223> OTHER INFORMATION: Xaa is is Leucine (L), Glutamate (E) or
      Glutamine (Q)

<400> SEQUENCE: 208

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Xaa Thr Asn Xaa Arg Ala Pro Trp Thr Pro Ala Arg Phe
    50                  55                  60

Ser Gly Ser Leu Leu Gly Gly Lys Ala Ala Leu Thr Ile Thr Gly Ala
65              70                  75                  80

Gln Ala Glu Asp Glu Ala Asp Tyr Tyr Cys Ala Xaa Trp Tyr Ser Asn
            85                  90                  95

Leu Trp Val Phe Gly Gly Gly Thr Lys Leu Thr Val Leu Gly
            100                 105                 110
```

```
<210> SEQ ID NO 209
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH Domain of the Human Anti-HIV(env) Antibody
      A32, wherein residue 118 is Leucine (L)

<400> SEQUENCE: 209

Gln Val Gln Leu Gln Glu Ser Gly Pro Gly Leu Val Lys Pro Ser Gln
1               5                   10                  15

Thr Leu Ser Leu Ser Cys Thr Val Ser Gly Gly Ser Ser Ser Ser Gly
            20                  25                  30

Ala His Tyr Trp Ser Trp Ile Arg Gln Tyr Pro Gly Lys Gly Leu Glu
        35                  40                  45

Trp Ile Gly Tyr Ile His Tyr Ser Gly Asn Thr Tyr Tyr Asn Pro Ser
    50                  55                  60

Leu Lys Ser Arg Ile Thr Ile Ser Gln His Thr Ser Glu Asn Gln Phe
65                  70                  75                  80

Ser Leu Lys Leu Asn Ser Val Thr Val Ala Asp Thr Ala Val Tyr Tyr
                85                  90                  95

Cys Ala Arg Gly Thr Arg Leu Arg Thr Leu Arg Asn Ala Phe Asp Ile
            100                 105                 110

Trp Gly Gln Gly Thr Leu Val Thr Val Ser Ser
            115                 120
```

VARIANT CD3-BINDING DOMAINS AND THEIR USE IN COMBINATION THERAPIES FOR THE TREATMENT OF DISEASE

CROSS REFERENCE TO RELATED APPLICATIONS

This application claims priority to U.S. Patent Application Ser. Nos. 62/631,043 (filed on Feb. 15, 2018), and 62/738,632 (filed on Sep. 28, 2018;), each of which applications are herein incorporated by reference in their entirety.

REFERENCE TO SEQUENCE LISTING

This application includes one or more Sequence Listings pursuant to 37 C.F.R. 1.821 et seq., which are disclosed in computer-readable media (file name: 1301_0150PCT_ST25.txt, created on Jan. 30, 2019, and having a size of 295,037 bytes), which file is incorporated herein in its entirety.

FIELD OF THE INVENTION

The present invention is directed to multispecific Binding Molecules (e.g., a bispecific antibody, a diabody, a bispecific scFv, a trivalent molecule, a TandAb®, a BiTE® etc.) comprising a CD3-Binding Domain capable of binding an epitope of CD3 and also a Disease Antigen-Binding Domain capable of binding an epitope of a Disease Antigen ("DA") (e.g., a "DA×CD3 Binding Molecule"). The invention particularly concerns such DA×CD3 Binding Molecules comprising a variant CD3-Binding Domain ("vCD3-Binding Domain"), which comprises a $CDR_H1$ Domain, a $CDR_H2$ Domain, a $CDR_H3$ Domain, a $CDR_L1$ Domain, a $CDR_L2$ Domain, and a $CDR_L3$ Domain, at least one of which differs in amino acid sequence from the amino acid sequence of the corresponding CDR of a reference CD3-Binding Domain ("rCD3-Binding Domain"), and wherein the DA×CD3 Binding Molecule comprising such vCD3-Binding Domain exhibits an altered affinity for CD3, relative to a DA×CD3 Binding Molecule comprising such rCD3-Binding Domain. The invention particularly concerns to such DA×CD3 Binding Molecules comprising a vCD3-Binding Domain which exhibit reduced affinity for CD3 and are capable of mediating redirected killing of target cells expressing a DA and exhibit lower levels of cytokine release relative to a DA×CD3 Binding Molecule comprising a rCD3-Binding Domain. The invention particularly concerns the use of DA×CD3 Binding Molecules comprising a vCD3-Binding Domain in the treatment of cancer and pathogen-associated diseases. The present invention is also directed to pharmaceutical compositions that comprise such molecule(s).

BACKGROUND OF THE INVENTION

I. The Mammalian Immune System

The mammalian immune system serves as a defense against a variety of conditions, including, e.g., injury, infection and neoplasia. The efficiency with which humans and other mammals develop an immunological response to pathogens, foreign substances and cancer antigens rests on two characteristics: the exquisite specificity of the immune response for antigen recognition, and the immunological memory that allows for faster and more vigorous responses upon re-activation with the same antigen (Portolés, P. et al. (2009) "*The TCR/CD3 Complex: Opening the Gate to Successful Vaccination*," Current Pharmaceutical Design 15:3290-3300; Guy, C. S. et al. (2009) "*Organization of Proximal Signal Initiation at the TCR:CD3 Complex*," Immunol Rev. 232(1):7-21; Topalian, S. L. et al. (2015) "*Immune Checkpoint Blockade: A Common Denominator Approach to Cancer Therapy*," Cancer Cell 27:450-461).

In healthy individuals, the immune system is in a quiescent state, inhibited by a repertoire of diverse inhibitory receptors and receptor ligands. Upon recognition of a cancer antigen, microbial pathogen, or an allergen, an array of activating receptors and receptor ligands are triggered to induce the activation of the immune system. Such activation leads to the activation of macrophages, Natural Killer (NK) cells and antigen-specific, cytotoxic, T-cells, and promotes the release of various cytokines, all of which act to counter the perceived threat to the health of the subject (Dong, C. et al. (2003) "*Immune Regulation by Novel Costimulatory Molecules*," Immunolog. Res. 28(1):39-48; Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). The immune system is capable of returning to its normal quiescent state when the countervailing inhibitory immune signals outweigh the activating immune signals.

Thus, the disease state of cancer (and indeed the disease states of infectious diseases) may be considered to reflect a failure to adequately activate a subject's immune system. Such failure may reflect an inadequate presentation of activating immune signals, or it may reflect an inadequate ability to alleviate inhibitory immune signals in the subject. In some instances, researchers have determined that cancer cells can co-opt the immune system to evade being detected by the immune system (Topalian, S. L. et al. (2015) "*Immune Checkpoint Blockade: A Common Denominator Approach to Cancer Therapy*," Cancer Cell 27:450-461).

The mammalian immune system is mediated by two separate but interrelated systems: the humoral immune system and the cellular immune system. Generally speaking, the humoral system is mediated by soluble molecules (antibodies or immunoglobulins) produced by B Cells. Such molecules have the ability to combine with and neutralize antigens that have been recognized as being foreign to the body. The cellular immune system involves the mobilization of certain cells, termed "T-cells," that serve a variety of therapeutic roles. T-cells are lymphocytes that mature in the thymus and circulate between the tissues, lymphatic system and the circulatory system. In response to the presence and recognition of foreign structures (antigens), T-cells become "activated" to initiate an immune response. In many instances, these foreign antigens are expressed on host cells as a result of neoplasia or infection. Although T-cells do not themselves secrete antibodies, they are usually required for antibody secretion by the second class of lymphocytes, "B Cells" (which derive from bone marrow). Critically, T-cells exhibit extraordinary immunological specificity so as to be capable of discerning one antigen from another).

Two interactions are required for T-cell activation (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). In the first interaction, a cell must display the relevant target antigen bound to a cell's Class I or Class II Major Histocompatibility Complex ("MHC") so that it can bind the T-cell Receptor ("TCR") of a naïve T lymphocyte. Although almost all cell types can serve as antigen-presenting cells, some cells, such as macrophages, B cells, and dendritic cells, specialize in presenting foreign antigens and are "professional" "Antigen-Presenting Cells." Immunologic detection of antigen bound to an Antigen-Presenting Cell's MHC I molecules leads to the production of cytotoxic T-cells. Immunologic detection of antigen bound to an Antigen-Presenting Cell's MHC II molecules leads to the production of cytotoxic T-cells. In the second interaction, a ligand of the Antigen-Presenting Cell must bind a co-receptor of the T-cell (Dong, C. et al. (2003) "*Immune Regulation by Novel Costimulatory Molecules,*" Immunolog. Res. 28(1):39-48; Lindley, P. S. et al. (2009) "*The Clinical Utility Of Inhibiting CD28-Mediated Costimulation,*" Immunol. Rev. 229:307-321). T-cells experiencing both stimulatory signals are then capable of responding to cytokines (such as Interleukin-2 and Interleukin-12).

In the absence of both co-stimulatory signals during TCR engagement, T-cells enter a functionally unresponsive state, referred to as clonal anergy (Khawli, L. A. et al. (2008) "*Cytokine, Chemokine, and Co-Stimulatory Fusion Proteins for the Immunotherapy of Solid Tumors,*" Exp. Pharmacol. 181:291-328). In pathologic states, T-cells are the key players of various organ-specific autoimmune diseases, such as type I diabetes, rheumatoid arthritis, and multiple sclerosis (Dong, C. et al. (2003) "*Immune Regulation by Novel Costimulatory Molecules,*" Immunolog. Res. 28(1):39-48).

This immune "checkpoint" pathway is important in maintaining self-tolerance (i.e., in preventing a subject from mounting an immune system attack against his/her own cells (an "autoimmune" reaction) and in limiting collateral tissue damage during anti-microbial or anti-allergic immune responses. Where contact of a T-cell results in the generation of only one of two required signals, the T-cell does not become activated and an adaptive immune response does not occur. The "two signal" mechanism of T-cell activation thus provides a way for the immune system to avoid undesired responses, such as responses to self-antigens that would otherwise result in an immune system attack against a subject's own cells (an "autoimmune" reaction).

II. Cell Surface Molecules of the Cellular Immune System

A. CD3, CD4 and CD8

The cells of the immune system are characterized by their expression of specialized glycoprotein cell surface molecules. Interactions between such molecules and molecules of other cells triggers, maintains or dampens the immune response. In particular, all T-cells are characterized by their expression of CD3. CD3 is a T-cell co-receptor composed of four distinct chains (Wucherpfennig, K. W. et al. (2010) "*Structural Biology Of The T-Cell Receptor: Insights into Receptor Assembly, Ligand Recognition, And Initiation of Signaling,*" Cold Spring Harb. Perspect. Biol. 2(4):a005140; pages 1-14; Chetty, R. et al. (1994) "*CD3: Structure, Function, And Role Of Immunostaining In Clinical Practice,*" J. Pathol. 173(4):303-307; Guy, C. S. et al. (2009) "*Organization Of Proximal Signal Initiation At The TCR:CD3 Complex,*" Immunol. Rev. 232(1):7-21).

In mammals, the complex contains a CD3γ chain, a CD3δ chain, and two CD3ε chains. These chains associate with the TCR in order to generate an activation signal in T lymphocytes (Smith-Garvin, J. E. et al. (2009) "*T Cell Activation,*" Annu. Rev. Immunol. 27:591-619). In the absence of CD3, TCRs do not assemble properly and are degraded (Thomas, S. et al. (2010) "*Molecular Immunology Lessons From Therapeutic T-Cell Receptor Gene Transfer,*" Immunology 129(2):170-177). CD3 is found bound to the membranes of all mature T-cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer,*" Cell 105(7):913-923; Kuhns, M. S. et al. (2006) "*Deconstructing The Form And Function Of The TCR/CD3 Complex,*" Immunity. 2006 February; 24(2):133-139).

The invariant CD3ε signaling component of the TCR complex on T-cells, has been used as a target to force the formation of an immunological synapse between T-cells and cancer cells. Co-engagement of CD3 and the tumor antigen activates the T-cells, triggering lysis of cancer cells expressing the tumor antigen (Baeuerle et al. (2011) "*Bispecific T-cell Engager For Cancer Therapy,*" In: BISPECIFIC ANTIBODIES, Kontermann, R. E. (Ed.) Springer-Verlag; 2011:273-287). This approach allows bispecific antibodies to interact globally with the T-cell compartment with high specificity for cancer cells and is widely applicable to a broad array of cell surface tumor antigens and has also been implemented to target pathogen-infected cells (see, e.g., Sloan et al. (2015) "*Targeting HIV Reservoir in Infected CD4 T Cells by Dual-Affinity Re-targeting Molecules (DARTs) that Bind HIV Envelope and Recruit Cytotoxic T Cells,*" PLoS Pathog 11(11): e1005233. doi:10.1371/journal.ppat.1005233; WO 2014/159940; and WO 2016/054101).

A first subset of T-cells, known as "helper T-cells," is characterized by the expression of the CD4 (i.e., they are "CD4$^+$" as well as CD3$^+$) CD4$^+$ T-cells are the essential organizers of most mammalian immune and autoimmune responses (Dong, C. et al. (2003) "*Immune Regulation by Novel Costimulatory Molecules,*" Immunolog. Res. 28(1): 39-48). The activation of CD4$^+$ T-cells has been found to be mediated through co-stimulatory interactions between an antigen: Major histocompatibility Class II (MHC II) molecule complex that is arrayed on the surface of an Antigen-Presenting Cell (such as a B-Cell, a macrophage or a dendritic cell) and a complex of two molecules, the TCR and a CD3 cell surface receptor ligand, both of which are arrayed on the surface of a naïve CD4$^+$ T-cell. Activated T helper cells are capable of proliferating into Th1 cells that are capable of mediating an inflammatory response to the target cell.

A second subset of T-cells, known as "cytotoxic T-cells," are characterized by the expression of CD8 (i.e., they are "CD8$^+$" as well as CD3$^+$). CD8 is a T-cell co-receptor composed of two distinct chains (Leahy, D. J. (1995) "*A Structural View of CD4 and CD8,*" FASEB J. 9:17-25) that is expressed on cytotoxic T-cells. The activation of CD8$^+$ T-cells has been found to be mediated through co-stimulatory interactions between an antigen: major histocompatibility class I (MHC I) molecule complex that is arrayed on the surface of a target cell and a complex of CD8 and the T-cell Receptor, that are arrayed on surface of the CD8$^+$ T-cell ((Gao, G. et al. (2000) "*Molecular Interactions Of Coreceptor CD8 And MHC Class I: The Molecular Basis For Functional Coordination With The T-Cell Receptor,*" Immunol. Today 21:630-636). Unlike major histocompatibility class II (MHC II) molecules, which are expressed by only certain immune system cells, MHC I molecules are very widely expressed. Thus, cytotoxic T-cells are capable of binding a wide variety of cell types. Activated cytotoxic T-cells mediate cell killing through their release of the cytotoxins perforin, granzymes, and granulysin. Through the action of perforin, granzymes enter the cytoplasm of the target cell and their serine protease function triggers the caspase cascade, which is a series of cysteine proteases that eventually lead to apoptosis (programmed cell death) of targeted cells.

B. The T-Cell Receptor ("TCR")

The T-cell Receptor ("TCR") is natively expressed by CD4+ or CD8+ T-cells, and permits such cells to recognize antigenic peptides that are bound and presented by class I or class II MHC proteins of antigen-presenting cells. Recognition of a pMHC (peptide-MHC) complex by a TCR initiates the propagation of a cellular immune response that leads to the production of cytokines and the lysis of the Antigen-Presenting Cell (see, e.g., Armstrong, K. M. et al. (2008) "*Conformational Changes And Flexibility In T-Cell Receptor Recognition Of Peptide-MHC Complexes*," Biochem. J. 415(Pt 2):183-196; Willemsen, R. (2008) "*Selection Of Human Antibody Fragments Directed Against Tumor T-Cell Epitopes For Adoptive T-Cell Therapy*," Cytometry A. 73(11): 1093-1099; Beier, K. C. et al. (2007) "*Master Switches Of T-Cell Activation And Differentiation*," Eur. Respir. J. 29:804-812; Mallone, R. et al. (2005) "*Targeting T Lymphocytes For Immune Monitoring And Intervention In Autoimmune Diabetes*," Am. J. Ther. 12(6):534-550). CD3 is the receptor that binds to the TCR (Thomas, S. et al. (2010) "*Molecular Immunology Lessons From Therapeutic T-Cell Receptor Gene Transfer*," Immunology 129 (2):170-177; Guy, C. S. et al. (2009) "*Organization Of Proximal Signal Initiation At The TCR: CD3 Complex*," Immunol. Rev. 232(1):7-21; St. Clair, E. W. (Epub 2009 Oct. 12) "*Novel Targeted Therapies For Autoimmunity*," Curr. Opin. Immunol. 21(6):648-657; Baeuerle, P. A. et al. (Epub 2009 Jun. 9) "*Bispecific T-Cell Engaging Antibodies For Cancer Therapy*," Cancer Res. 69(12):4941-4944; Smith-Garvin, J. E. et al. (2009) "*T Cell Activation*," Annu. Rev. Immunol. 27:591-619; Renders, L. et al. (2003) "*Engineered CD3 Antibodies For Immunosuppression*," Clin. Exp. Immunol. 133(3):307-309).

The TCR and CD3 complex, along with the CD3ζ chain zeta chain (also known as T-Cell receptor T3 zeta chain or CD247) comprise the "TCR complex" (van der Merwe, P. A. etc. (epub Dec. 3, 2010) "*Mechanisms For T Cell Receptor Triggering*," Nat. Rev. Immunol. 11:47-55; Wucherpfennig, K. W. et al. (2010) "*Structural Biology of the T Cell Receptor: Insights into Receptor Assembly, Ligand Recognition, and Initiation of Signaling*," Cold Spring Harb. Perspect. Biol. 2:a005140). The complex is particularly significant since it contains a large number (ten) of immunoreceptor tyrosine-based activation motifs (ITAMs).

Multispecific molecules comprising a CD3 Binding Domain and a binding domain specific for a Disease Antigen ("DA") expressed on a target cell are capable of mediating redirected T-cell killing of such target cells. However, due to the affinity of such molecules for CD3, such molecules may be too potent, so as to exhibit undesirable cytokine release from the stimulated T-cells. Thus, despite prior advances in identifying the molecules involved in mammalian immune responses, a need remains for improved therapies for treating cancers and infectious diseases. The present invention provides a panel of variant CD3-Binding Domains having a range of binding kinetics, which may be used to modulate the cell killing and/or cytokine release activities of such multispecific molecules to enhance the therapeutic window. The present invention is directed to this and other goals.

SUMMARY OF THE INVENTION

The present invention is directed to multispecific Binding Molecules (e.g., a bispecific antibody, a diabody, a bispecific scFv, a trivalent molecule, a TandAb®, a BiTE® etc.) comprising a CD3-Binding Domain capable of binding an epitope of CD3 and also a Disease Antigen-Binding Domain capable of binding an epitope of a Disease Antigen ("DA") (e.g., a "DA×CD3 Binding Molecule"). The invention particularly concerns such DA×CD3 Binding Molecules comprising a variant CD3-Binding Domain ("vCD3-Binding Domain"), which comprises a $CDR_H1$ Domain, a $CDR_H2$ Domain, a $CDR_H3$ Domain, a $CDR_L1$ Domain, a $CDR_L2$ Domain, and a $CDR_L3$ Domain, at least one of which differs in amino acid sequence from the amino acid sequence of the corresponding CDR of a reference CD3-Binding Domain ("rCD3-Binding Domain"), and wherein the DA×CD3 Binding Molecule comprising such vCD3-Binding Domain exhibits an altered affinity for CD3, relative to a DA×CD3 Binding Molecule comprising such rCD3-Binding Domain. The invention particularly concerns to such DA×CD3 Binding Molecules comprising a vCD3-Binding Domain which exhibit reduced affinity for CD3 and are capable of mediating redirected killing of target cells expressing a DA and exhibit lower levels of cytokine release relative to a DA×CD3 Binding Molecule comprising a rCD3-Binding Domain. The invention particularly concerns the use of DA×CD3 Binding Molecules comprising a vCD3-Binding Domain in the treatment of cancer and pathogen-associated diseases. The present invention is also directed to pharmaceutical compositions that comprise such molecule(s).

In detail, the invention provides a DA×CD3 Binding Molecule comprising a CD3-Binding Domain capable of binding an epitope of CD3 and a Disease Antigen-Binding Domain capable of binding an epitope of a Disease Antigen, wherein the CD3-Binding Domain comprises:

(I) (A) a $CDR_H1$ Domain comprising an amino acid sequence selected from the group consisting of SEQ ID NO:99, SEQ ID NO:91, SEQ ID NO:93, SEQ ID NO:95 and SEQ ID NO:97;
(B) a $CDR_H2$ Domain comprising the amino acid sequence of SEQ ID NO:58;
(C) a $CDR_H3$ Domain comprising the amino acid sequence of SEQ ID NO:59;
(D) a $CDR_L1$ Domain comprising the amino acid sequence of SEQ ID NO:60;
(E) a $CDR_L2$ Domain comprising the amino acid sequence of SEQ ID NO:61; and
(F) a $CDR_L3$ Domain comprising the amino acid sequence of SEQ ID NO:62; or
(II) (A) a $CDR_H1$ Domain comprising the amino acid sequence of SEQ ID NO:57;
(B) a $CDR_H2$ Domain comprising the amino acid sequence of SEQ ID NO:58,
(C) a $CDR_H3$ Domain comprising an amino acid sequence selected from the group consisting of SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:101, SEQ ID NO:103, SEQ ID NO:105 and SEQ ID NO:107;
(D) a $CDR_L1$ Domain comprising the amino acid sequence of SEQ ID NO:60;
(E) a $CDR_L2$ Domain comprising the amino acid sequence of SEQ ID NO:61; and
(F) a $CDR_L3$ Domain comprising the amino acid sequence of SEQ ID NO:62; or
(III) (A) a $CDR_H1$ Domain comprising the amino acid sequence of SEQ ID NO:57;
(B) a $CDR_H2$ Domain comprising the amino acid sequence of SEQ ID NO:58;

(C) a CDR$_H$3 Domain comprising the amino acid sequence of SEQ ID NO:59;
(D) a CDR$_L$1 Domain comprising the amino acid sequence of SEQ ID NO:60;
(E) a CDR$_L$2 Domain comprising the amino acid sequence of SEQ ID NO:61; and
(F) a CDR$_L$3 Domain comprising an amino acid sequence selected from the group consisting of SEQ ID NO:109 or SEQ ID NO:111; or (IV) (A) a CDR$_H$1 Domain comprising the amino acid sequence of SEQ ID NO:57;
(B) a CDR$_H$2 Domain comprising the amino acid sequence of SEQ ID NO:58;
(C) a CDR$_H$3 Domain comprising the amino acid sequence of SEQ ID NO:59;
(D) a CDR$_L$1 Domain comprising the amino acid sequence of SEQ ID NO:60;
(E) a CDR$_L$2 Domain comprising an amino acid sequence selected from the group consisting of SEQ ID NO:113 and SEQ ID NO:115; and
(F) a CDR$_L$3 Domain comprising the amino acid sequence of SEQ ID NO:62.

The invention additionally concerns the embodiment of such DA×CD3 Binding Molecule, wherein the CD3-Binding Domain comprises:

(I) (A) a VL Domain comprising the amino acid sequence of SEQ ID NO:56;
(B) a VH Domain comprising an amino acid sequence selected from the group consisting of SEQ ID NO:98, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO: 92, SEQ ID NO:94, SEQ ID NO:96, SEQ ID NO:100, SEQ ID NO:102, SEQ ID NO:104 and SEQ ID NO:106; or (II) (A) a VL Domain comprising an amino acid sequence selected from the group consisting of SEQ ID NO:108, SEQ ID NO:110, SEQ ID NO:112; and SEQ ID NO:114;
(B) a VH Domain comprising an amino acid sequence of SEQ ID NO:55.

The invention additionally concerns the embodiment of such DA×CD3 Binding Molecule, wherein the DA×CD3 Binding Molecule is a bispecific antibody, a bispecific diabody, a bispecific scFv, a bispecific TandAb, or a trivalent binding molecule.

The invention additionally concerns the embodiment of such DA×CD3 Binding Molecule, wherein the DA×CD3 Binding Molecule is capable of binding more than one Disease Antigen and/or a different cell surface molecule of an effector cell. Particularly, wherein the different cell surface molecule of an effector cell is CD2, CD8, CD16, TCR, NKp46, or NKG2D.

The invention additionally concerns the embodiment of such DA×CD3 Binding Molecule, wherein the Disease Antigen is a Cancer Antigen, or a Pathogen-Associated Antigen.

The invention additionally concerns the embodiment of such DA×CD3 Binding Molecule, wherein the Cancer Antigen is selected from the group consisting of the Cancer Antigens: 19.9, 4.2, ADAM-9, AH6, ALCAM, B1, B7-H3, BAGE, beta-catenin, blood group ALe$^b$/Le$^y$, Burkitt's lymphoma antigen-38.13, C14, CA125, Carboxypeptidase M, CD5, CD19, CD20, CD22, CD23, CD25, CD27, CD28, CD33, CD36, CD40/CD154, CD45, CD56, CD46, CD52, CD56, CD79a/CD79b, CD103, CD123, CD317, CDK4, CEA, CEACAM5/CEACAM6, CO17-1A, CO-43, CO-514, CTA-1, CTLA-4, Cytokeratin 8, D1.1, D$_1$56-22, DR5, E$_1$ series, EGFR, an Ephrin receptor, EphA2, Erb, GAGE, a GD2/GD3/GM2 ganglioside, GICA 19-9, gp100, Gp37, gp75, gpA33, HER2/neu, HMFG, Human Papillomavirus-E6/Human Papillomavirus-E7, HMW-MAA, I antigen, IL13Rα2, Integrin β6, JAM-3, KID3, KID31, KS 1/4 pan-carcinoma antigen, L6, L20, LEA, LUCA-2, M1:22:25:8, M18, M39, MAGE, MART, mesothelin, MUC-1, MUM-1, My1, N-acetylglucosaminyltransferase, neoglycoprotein, NS-10, OFA-1, OFA-2, Oncostatin M, p15, p97, PEM, PEMA, PIPA, PSA, PSMA, prostatic acid phosphate, R$_{24}$, ROR1, a sphingolipid, SSEA-1, SSEA-3, SSEA-4, sTn, the T-cell receptor derived peptide, T$_5$A$_7$, TAG-72, TL5, TNF-receptor, TNF-γ receptor, TRA-1-85, a Transferrin Receptor, 5T4, TSTA, VEGF, a VEGF Receptor, VEP8, VEP9, VIM-D5, and Y hapten, Le$^y$.

The invention particularly concerns the embodiment of such DA×CD3 Binding Molecule, wherein the Cancer Antigen is B7-H3, CEACAM5/CEACAM6, EGRF, EphA2, gpA33, HER2/neu, VEGF, 5T4, IL13Rα2, CD123, CD19, or ROR1.

The invention additionally concerns the embodiment of such DA×CD3 Binding Molecule, wherein the Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, Human Papillomavirus E6, Human Papillomavirus E7, human T-cell leukemia virus gp64, human T-cell leukemia virus gp46, and human T-cell leukemia virus gp21.

The invention additionally concerns the embodiment of such DA×CD3 Binding Molecule, wherein the DA×CD3 Binding Molecule comprises: a first polypeptide chain and a second polypeptide chain, covalently bonded to one another, wherein:

(A) the first polypeptide chain comprises, in the N-terminal to C-terminal direction:
(i) a Domain 1, comprising:
(1) a sub-Domain (1A), which comprises a VL Domain of a monoclonal antibody capable of binding to the epitope of a Disease Antigen (VL$_{DA}$); and
(2) a sub-Domain (1B), which comprises a VH Domain of a monoclonal antibody capable of binding to the epitope of CD3 (VH$_{CD3}$);
wherein the sub-Domains 1A and 1B are separated from one another by a peptide Linker; and
(ii) a Domain 2, wherein the Domain 2 is a Heterodimer-Promoting Domain;

(B) the second polypeptide chain comprises, in the N-terminal to C-terminal direction:
(i) a Domain 1, comprising
(1) a sub-Domain (1A), which comprises a VL Domain of the monoclonal antibody capable of binding to the epitope of CD3 (VL$_{CD3}$); and
(2) a sub-Domain (1B), which comprises a VH Domain of the monoclonal antibody capable of binding to the epitope of a Disease Antigen (VH$_{DA}$);
wherein the sub-Domains 1A and 1B are separated from one another by a peptide Linker;
(ii) a Domain 2, wherein the Domain 2 is a Heterodimer-Promoting Domain, wherein the Heterodimer- Promoting Domain of the first and the second polypeptide chains are different;
and wherein:
(a) the VL Domain of the first polypeptide chain and the VH Domain of the second polypeptide chain associate to form the Disease Antigen-Binding Domain, and the VH Domain of the first polypeptide chain and the VL Domain of the second polypeptide chain associate to form the CD3-Binding Domain; or
(b) the VL Domain of the first polypeptide chain and the VH Domain of the second polypeptide chain associate to form the CD3-Binding Domain, and the VH Domain of the first polypeptide chain and the VL Domain of the second polypeptide chain associate to form the Disease Antigen-Binding Domain.

The invention additionally concerns the embodiment of such DA×CD3 Binding Molecule, wherein:
(a) said Heterodimer-Promoting Domain of said first polypeptide chain is an E-coil Domain, and said Heterodimer-Promoting Domain of said second polypeptide chain is a K-coil Domain; or
(b) said Heterodimer-Promoting Domain of said first polypeptide chain is a K-coil Domain, and said Heterodimer-Promoting Domain of said second polypeptide chain is an E-coil Domain.

The invention additionally concerns the embodiment of such DA×CD3 Binding Molecule, wherein the first or second polypeptide chain additionally comprises a Domain 3 comprising a CH2 and CH3 Domain of an immunoglobulin Fc Domain.

The invention additionally concerns the embodiment of such DA×CD3 Binding Molecule, wherein the DA×CD3 Binding Molecule further comprises a third polypeptide chain comprising a CH2 and CH3 Domain of an immunoglobulin Fc Domain.

The invention additionally concerns the embodiment of such DA×CD3 Binding Molecule, wherein the DA×CD3 Binding Molecule further comprises a CD8-Binding Domain.

The invention additionally concerns the embodiment of such DA×CD3 Binding Molecule, wherein the DA×CD3 Binding Molecule comprises:
(I) (A) a first polypeptide comprising SEQ ID NO:179;
(B) a second polypeptide comprising SEQ ID NO:175; and
(C) a third polypeptide comprising SEQ ID NO:176; or
(II) (A) a first polypeptide comprising SEQ ID NO:184;
(B) a second polypeptide comprising SEQ ID NO:181; and
(C) a third polypeptide comprising SEQ ID NO:176; or
(III) (A) a first polypeptide comprising SEQ ID NO:196;
(B) a second polypeptide comprising SEQ ID NO:186; and
(C) a third polypeptide comprising SEQ ID NO:176; or
(IV) (A) a first polypeptide comprising SEQ ID NO:197;
(B) a second polypeptide comprising SEQ ID NO:192; and
(C) a third polypeptide comprising SEQ ID NO:176; or
(V) (A) a first polypeptide comprising SEQ ID NO:193;
(B) a second polypeptide comprising SEQ ID NO:194; and
(C) a third polypeptide comprising SEQ ID NO:176; or
(VI) (A) a first polypeptide comprising SEQ ID NO:179;
(B) a second polypeptide comprising SEQ ID NO:175;
(C) a third polypeptide comprising SEQ ID NO:187; and
(D) a fourth polypeptide comprising SEQ ID NO:188; or
(VII) (A) a first polypeptide comprising SEQ ID NO:184;
(B) a second polypeptide comprising SEQ ID NO:181;
(C) a third polypeptide comprising SEQ ID NO:187; and
(D) a fourth polypeptide comprising SEQ ID NO:188; or
(VIII) (A) a first polypeptide comprising SEQ ID NO:196;
(B) a second polypeptide comprising SEQ ID NO:186;
(C) a third polypeptide comprising SEQ ID NO:187; and
(D) a fourth polypeptide comprising SEQ ID NO:188; or
(IX) (A) a first polypeptide comprising SEQ ID NO:193;
(B) a second polypeptide comprising SEQ ID NO:194;
(C) a third polypeptide comprising SEQ ID NO:187; and
(D) a fourth polypeptide comprising SEQ ID NO:188.

The invention additionally concerns a pharmaceutical composition that comprises any of the above-described DA×CD3 Binding Molecules and a pharmaceutically acceptable carrier.

The invention additionally concerns a method for the treatment of a disease, comprising administering to a subject in need thereof a therapeutically effective amount of any of the above-described DA×CD3 Binding Molecules or the above-described pharmaceutical composition.

The invention additionally concerns the embodiment of such method, wherein the disease is cancer. Including embodiments, wherein the cancer is selected from the group consisting of adrenal cancer, bladder cancer, breast cancer, colorectal cancer, gastric cancer, glioblastoma, kidney cancer, non-small-cell lung cancer, hematological cancer, multiple myeloma, melanoma, ovarian cancer, pancreatic cancer, prostate cancer, skin cancer, renal cell carcinoma, testicular cancer, and uterine cancer.

The invention additionally concerns the embodiment of such method, wherein the disease is a pathogen-associated disease; including embodiments, wherein the Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, Human Papillomavirus E6, Human Papillomavirus E7, human T-cell leukemia virus gp64, human T-cell leukemia virus gp46, and human T-cell leukemia virus gp21.

The invention additionally concerns the use of any of the above-described DA×CD3 Binding Molecules or the above-described pharmaceutical composition in the treatment of a disease.

The invention additionally concerns the embodiment of such use, wherein the disease is cancer. Including, embodiments, wherein the cancer is selected from the group consisting of adrenal cancer, bladder cancer, breast cancer, colorectal cancer, gastric cancer, glioblastoma, kidney cancer, non-small-cell lung cancer, hematological cancer, multiple myeloma, melanoma, ovarian cancer, pancreatic cancer, prostate cancer, skin cancer, renal cell carcinoma, testicular cancer, and uterine cancer.

The invention additionally concerns the embodiment of such use, wherein the disease is a pathogen-associated disease. Including embodiments, wherein the Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, Human Papillomavirus E6, Human Papillomavirus E7, human T-cell leukemia virus gp64, human T-cell leukemia virus gp46, and human T-cell leukemia virus gp21.

BRIEF DESCRIPTION OF THE DRAWINGS

FIG. 3A shows an Fc Domain-containing diabody which contains a peptide Heterodimer-Promoting Domain comprising a cysteine residue. FIG. 3B shows an Fc Domain-containing diabody, which contains E-coil and K-coil Heterodimer-Promoting Domains comprising a cysteine residue and a Linker (with an optional cysteine residue). FIG. 3C, shows an Fc Domain-Containing diabody, which contains antibody CH1 and CL Domains to promote heterodimerization.

FIGS. 6A and 6B, respectively, illustrate schematically the domains of trivalent Binding Molecules comprising two Diabody-Type Binding Domains and a Fab-Type Binding Domain having different domain orientations in which the Diabody-Type Binding Domains are N-terminal or C-terminal to an Fc Domain. The molecules in FIGS. 6A and 6B comprise four chains. FIGS. 6C and 6D, respectively, illustrate schematically the domains of trivalent Binding Molecules comprising two Diabody-Type Binding Domains N-terminal to an Fc Domain, and a Fab-Type Binding Domain in which the Light Chain and Heavy Chain are linked via a polypeptide spacer, or an scFv-Type Binding Domain. The trivalent Binding Molecules in FIGS. 6E and 6F, respectively, illustrate schematically the domains of trivalent Binding Molecules comprising two Diabody-Type Binding Domains C-terminal to an Fc Domain, and a Fab-Type Binding Domain in which the Light Chain and Heavy Chain are linked via a polypeptide spacer, or an scFv-Type Binding Domain. The trivalent Binding Molecules in FIGS. 6C-6F comprise three chains. VL and VH Domains that recognize the same epitope are shown using the same shading or fill pattern.

FIG. 7A shows the results of representative redirected cell killing (% cytotoxicity in a CTL assay) mediated by DART-A-type diabody constructs containing the VL and VH Domains of CD3 mAb 1; CD3 mAb 1 M1; CD3 mAb 1 M2; CD3 mAb 1 M15; CD3 mAb 1 M17; CD3 mAb 1 M18; CD3 mAb 1 M19; and CD3 mAb 1 M20. FIGS. 7B-7C plot the correlation between the affinity constants (FIG. 7B: KD; FIG. 7C: ka; and FIG. 7D: kd) and CTL activity ($EC_{50}$ of cytolysis at 18 hours) reported in Tables 11-12.

FIG. 8C: TNF-alpha; FIG. 8D: IL-6; FIG. 8D: IL-2); NegCtrl: negative control.

FIG. 9A shows the ability of CD123-WT, CD123-M1, CD123-M2 and CD123-M18 DART-B-type diabodies to bind to CD123-expressing MOLM-13 cells. FIG. 9B shows the ability of 5T4-WT, 5T4-M1, 5T4-M2, and 5T4-M18 DART-B-type diabodies to bind to 5T4-expressing A498 cells. Binding was detected using biotinylated antibody specific for the diabodies' E/K coils and streptavidin-phycoerythrin (PE).

FIGS. 11N-11Q: IL-2).

FIG. 12C: TNF-alpha; FIG. 12D: IL-6; FIG. 12E: IL-2).

FIGS. 13N-13Q: IL-2).

FIGS. 14C and 14H: TNF-alpha; FIGS. 14D and 14I: IL-6; FIGS. 14E and 14J: IL-2).

FIG. 17A: CD4; FIG. 17B: CD8.

FIG. 18A: CD123-WT; FIG. 18B: CD123-M2; FIG. 18C: CD123-M18; FIG. 18D: CD123-WT and CD123-M18 50 µg/kg and 500 µg/kg treatment groups.

FIG. 19A: CD123-WT; FIG. 19B: CD123-M18; FIG. 19C: CD123-M2; FIG. 19D: CD123-WT, CD123-M2 and CD123-M18 500 µg/kg treatment groups.

FIG. 20A: 5T4-WT; FIG. 20B: 5T4-M18 and 5T4-M2.

FIG. 21A: IFN-γ; FIG. 21B: TNF-α; FIG. 21C: IL-6; and FIG. 21D: IL-2.

FIG. 22A: binding to CD123-expressing MOLM-13 cells; FIG. 22B: binding to CD4$^+$ T-cells; FIG. 22C: binding to CD8$^+$ T-cells.

FIG. 23D: IFN-γ; FIG. 23E: TNF-α; FIG. 23F: IL-6; and FIG. 23G: IL-2.

FIG. 24A: IFN-γ; FIG. 24B: TNF-a; FIG. 24C: IL-6; FIG. 24D: IL-2; FIG. 24E: IL-15; FIG. 24F: Ki67 positive CD4$^+$ T-cells; FIG. 24G: Ki67 positive CD8$^+$ T-cells; FIG. 24H: platelet; FIG. 24I: C-reactive protein; FIG. 24J: blood urea nitrogen.

FIG. 25A: AML 34$^+$ blast cell count as a percent of control; FIG. 25B: CD4$^+$ cell expansion; FIG. 25C: CD8+ cell expansion; FIGS. 25D-G: Cytokine release (FIG. 25D: IFN-γ; FIG. 25E: TNF-α; FIG. 25F: IL-6; and FIG. 25G: IL-2).

FIG. 26C: TNF-alpha; FIG. 26D: IL-6; FIG. 26E: IL-2).

FIG. 28A: CD123-WT and CD123-M18. FIG. 28B: CD123-WT and CD123-M13.

FIG. 29A: CD123-WT and CD123-M18. FIG. 29B: CD123-WT and CD123-M17.

FIG. 30A: CD123-WT, CD123-M13, and CD123-M18; and FIG. 30B: CD123-WT, CD123-M17 and CD123-M18.

FIG. 31D: TNF-α; FIG. 31E: IL-6; and FIG. 31F: IL-2).

FIG. 33C: 30 mg/kg).

FIG. 35A: TNF-α, FIG. 35B: IFN-γ, FIG. 35C: IL-2, FIG. 35D: IL-6; and FIG. 35E: IL-15.

FIG. 36A: Ki67 positive T-cells CD4+ T-cells; FIG. 36B: Ki67 positive CD8+ T-cells.

DETAILED DESCRIPTION OF THE INVENTION

Figure 1A:
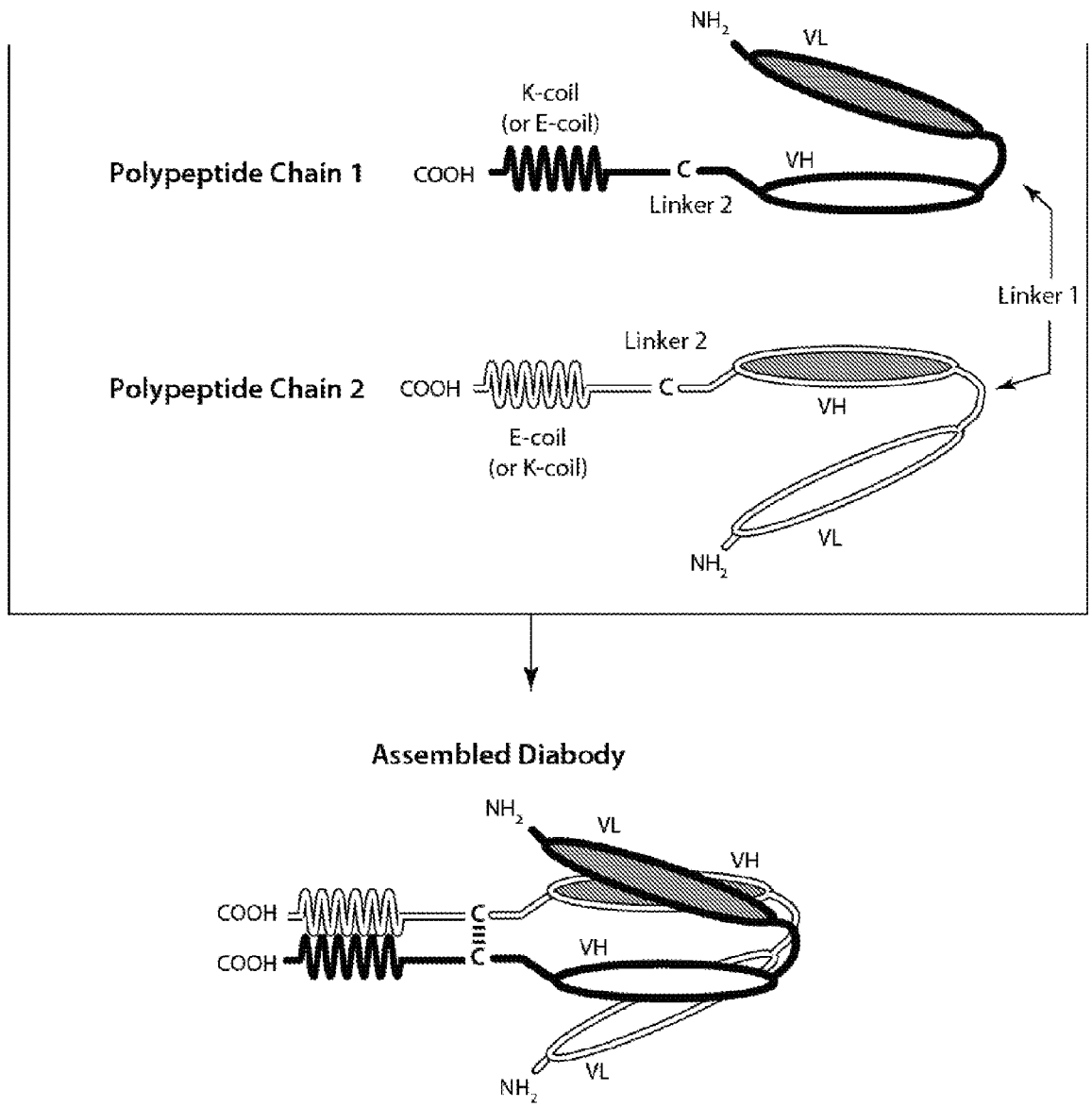
FIGS. 1A-1B provides schematics of representative covalently bonded diabodies having two Epitope-Binding Domains composed of two polypeptide chains, each having an E-coil or K-coil Heterodimer-Promoting Domain (alternative Heterodimer-Promoting Domains are provided below). A cysteine residue may be present in a Linker (FIG. 1A) and/or in the Heterodimer-Promoting Domain (FIG. 1B). VL and VH Domains that recognize the same epitope are shown using the same shading or fill pattern.

The present invention is directed to multispecific Binding Molecules (e.g., a bispecific antibody, a diabody, a bispecific scFv, a trivalent molecule, a TandAb®, a BiTE® etc.) comprising a CD3-Binding Domain capable of binding an epitope of CD3 and also a Disease Antigen-Binding Domain capable of binding an epitope of a Disease Antigen ("DA") (e.g., a "DA×CD3 Binding Molecule"). The invention particularly concerns such DA×CD3 Binding Molecules comprising a variant CD3-Binding Domain ("vCD3-Binding Domain"), which comprises a $CDR_H1$ Domain, a $CDR_H2$ Domain, a $CDR_H3$ Domain, a $CDR_L1$ Domain, a $CDR_L2$ Domain, and a $CDR_L3$ Domain, at least one of which differs in amino acid sequence from the amino acid sequence of the corresponding CDR of a reference CD3-Binding Domain ("rCD3-Binding Domain"), and wherein the DA×CD3 Binding Molecule comprising such vCD3-Binding Domain exhibits an altered affinity for CD3, relative to a DA×CD3 Binding Molecule comprising such rCD3-Binding Domain. The invention particularly concerns to such DA×CD3 Binding Molecules comprising a vCD3-Binding Domain which exhibit reduced affinity for CD3 and are capable of mediating redirected killing of target cells expressing a DA and exhibit lower levels of cytokine release relative to a DA×CD3 Binding Molecule comprising a rCD3-Binding Domain. The invention particularly concerns the use of DA×CD3 Binding Molecules comprising a vCD3-Binding Domain in the treatment of cancer and pathogen-associated diseases. The present invention is also directed to pharmaceutical compositions that comprise such molecule(s).

As indicated above, the therapeutic molecules of the present invention particularly include bispecific Binding Molecules that comprises an Epitope-Binding Domain capable of immunospecifically binding an epitope of a cell surface molecule of an effector cell and an Epitope-Binding Domain that is capable of immunospecifically binding an epitope of a target cell that expresses a Disease Antigen. As used herein, the term "Disease Antigen" (abbreviated as "DA") denotes an antigen that is expressed on the surface of an abnormal or infected cell and that is characteristic of such abnormality of infection, or that is expressed on the surface of a foreign cell and that is characteristic of such foreign origin. As used herein, a cell that expresses a Disease Antigen on its cell surface, and that may therefore become bound by the therapeutic molecules of the present invention and thereby targeted for killing by such therapeutic molecules is a "target cell." Of particular relevance to the present invention are Disease Antigens that are "Cancer Antigens" or "Pathogen-Associated Antigens."

I. Antibodies and their Binding Domains

The DA×CD3 Binding Molecules of the present invention may be antibodies or be derivable from antibodies (e.g., by fragmentation, cleavage, etc. of antibody polypeptides, or from use of the amino acid sequences of antibody molecules or of polynucleotides (or their sequences) that encode such polynucleotides, etc.).

Antibodies are immunoglobulin molecules capable of specific binding to a particular domain or moiety or conformation (an "epitope") of a molecule, such as a carbohydrate, polynucleotide, lipid, polypeptide, etc. An epitope-containing molecule may have immunogenic activity, such that it elicits an antibody production response in an animal; such molecules are termed "antigens." As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and Epitope-Binding Domains of any of the above. In particular, the term "antibody" includes immunoglobulin molecules and immunologically active fragments of immunoglobulin molecules, i.e., molecules that contain an Epitope-Binding Domain. Immunoglobulin molecules can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass. Antibodies are capable of "immunospecifically binding" to a polypeptide or protein or a non-protein molecule due to the presence on such molecule of a particular domain or moiety or conformation (an "epitope").

The term "monoclonal antibody" refers to a homogeneous antibody population wherein the monoclonal antibody is comprised of amino acids (naturally occurring or non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', F(ab')$_2$, Fv, single-chain (scFv), mutants thereof), fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3):119-125). In general, cells should be kept intact and preferably viable when used as immunogens. Intact cells may allow antigens to be better detected than ruptured cells by the immunized animal. Use of denaturing or harsh adjuvants, e.g., Freund's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced, and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody, as detailed below.

The Binding Molecules of the present invention bind epitopes via their binding domains in an "immunospecific" manner. As used herein, an antibody, diabody or other epitope-binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind a second target. As such, "immunospecific binding" does not necessarily require (although it can include) exclusive binding. Generally, but not necessarily, reference herein to binding means "immunospecific" binding.

The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Over 200 antibody-based drugs have been approved for use or are under development.

Natural antibodies (such as IgG antibodies) are composed of two "Light Chains" complexed with two "Heavy Chains." Each Light Chain contains a Variable Domain ("VL") and a Constant Domain ("CL"). Each Heavy Chain contains a Variable Domain ("VH"), three Constant Domains ("CH1," "CH2" and "CH3"), and a "Hinge" Region ("H") located between the CH1 and CH2 Domains. In contrast, scFvs are single-chain molecules made by linking Light and Heavy Chain Variable Domains together via a short linking peptide.

The basic structural unit of naturally occurring immunoglobulins (e.g., IgG) is thus a tetramer having two Light Chains and two Heavy Chains, usually expressed as a glycoprotein of about 150,000 Da. The amino-terminal ("N-terminal") portion of each chain includes a Variable Domain of about 100 to 110 or more amino acids primarily responsible for antigen recognition. The carboxy-terminal ("C-terminal") portion of each chain defines a constant region, with Light Chains having a single Constant Domain and Heavy Chains usually having three Constant Domains and a Hinge Domain. Thus, the structure of the Light Chains of an IgG molecule is n-VL-CL-c and the structure of the IgG Heavy Chains is n-VH-CH1-H-CH2-CH3-c (where n and c represent, respectively, the N-terminus and the C-terminus of the polypeptide). The ability of an intact, unmodified antibody (e.g., an IgG antibody) to bind an epitope of an antigen depends upon the presence and sequences of the Variable Domains. Unless specifically noted, the order of domains of the protein molecules described herein is in the "N-terminal to C-terminal" direction.

A. Characteristics of Antibody Variable Domains

The Variable Domains of an IgG molecule consist of three complementarity determining regions ("CDR"), which contain the amino acid residues of the antibody that will be in contact with epitope, and four intervening non-CDR segments, referred to as framework regions ("FR"), which separate the CDR segments and which in general maintain the structure and determine the positioning of the CDR residues so as to permit them to contact the epitope (although certain framework residues may also play a role in such contact). Thus, the VL and VH Domains have the structure n-FR1-CDR1-FR2-CDR2-FR3-CDR3-FR4-c, where n and c respectively denote the N-terminal end and the C-terminal end of the domains. The amino acid sequences of the CDRs determine whether an antibody will be able to bind to a particular epitope.

Amino acids from the Variable Domains of the mature Heavy and Light Chains of immunoglobulins are designated by the position of an amino acid in the chain. Kabat et al. (SEQUENCES OF PROTEINS OF IMMUNOLOGICAL INTEREST, $5^{th}$ Ed. Public Health Service, NH1, MD (1991) ("Kabat"), expressly incorporated herein by reference), described numerous amino acid sequences for antibodies, identified an amino acid consensus sequence for each subgroup, and assigned a residue number to each amino acid. The CDRs are identified as defined by Kabat (it will be understood that $CDR_H1$ as defined by Chothia, C. & Lesk, A. M. ((1987) "*Canonical structures for the hypervariable regions of immunoglobulins*," J. Mol. Biol. 196:901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody Light Chain occupies the equivalent position to an amino acid at position 50 of a mouse antibody Light Chain.

Polypeptides that are (or may serve as) the first, second and third CDR of the Light Chain of an antibody are herein respectively designated as: $CDR_L1$ Domain, $CDR_L2$ Domain, and $CDR_L3$ Domain. Similarly, polypeptides that are (or may serve as) the first, second and third CDR of the Heavy Chain of an antibody are herein respectively designated as: $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind a specific epitope regardless of whether such protein is an antibody having light and Heavy Chains or is a diabody or a single-chain binding molecule (e.g., an scFv, a BiTe, etc.), or is another type of protein. Accordingly, as used herein, the term "Epitope-Binding Domain" denotes a domain comprising a fragment or portion of a binding molecule (or a polypeptide having the amino acid sequence of such a fragment or portion) that contributes to the ability of the binding molecule to immunospecifically bind an epitope. An Epitope-Binding Domain may contain any 1, 2, 3, 4, or 5 the CDR Domains of an antibody, or may contain all 6 of the CDR Domains of an antibody and, although capable of immunospecifically binding such epitope, may exhibit an immunospecificity, affinity or selectivity towards such epitope that differs from that of such antibody. An Epitope-Binding Domain may contain only part of a CDR, namely the subset of CDR residues required for binding (termed "Specificity-Determining Residues," or "SDRs;" Kim, J. H. et al. (2012) "*Humanization By CDR Grafting And Specificity-Determining Residue Grafting*," Methods Mol. Biol. 907:237-245; Kim, K. S. et al. (2010) "*Construction Of A Humanized Antibody To Hepatitis B Surface Antigen By Specificity-Determining Residues (SDR)-Grafting And De-Immunization*," Biochem. Biophys. Res. Commun. 396(2):231-237; Kashmiri, S. V. et al. (2005) "*SDR Grafting—A New Approach To Antibody Humanization*," Methods 36(1):25-34; Gonzales, N. R. et al. (2004) "*SDR Grafting Of A Murine Antibody Using Multiple Human Germline Templates To Minimize Its Immunogenicity*," Mol. Immunol. 41:863-872). Preferably, however, an Epitope-Binding Domain will contain all 6 of the CDR Domains of such antibody. An Epitope-Binding Domain of an antibody may be a single polypeptide chain (e.g., an scFv), or may comprise two or more polypeptide chains, each having an amino terminus and a carboxy terminus (e.g., a diabody, a Fab fragment, an $Fab_2$ fragment, etc.).

The invention also particularly encompasses Binding Molecules that comprise a VL and/or VH Domain of a humanized antibody. The term "humanized antibody" refers to a chimeric molecule, generally prepared using recombinant techniques, having an Epitope-Binding Domain of an immunoglobulin from a non-human species and a remaining immunoglobulin structure of the molecule that is based upon the structure and/or sequence of a human immunoglobulin. The polynucleotide sequence of the Variable Domains of such antibodies may be used for genetic manipulation to generate such derivatives and to improve the affinity, or other characteristics of such antibodies. The general principle in humanizing an antibody involves retaining the basic sequence of the Epitope-Binding Domain of the antibody, while swapping the non-human remainder of the antibody with human antibody sequences. There are four general steps to humanize a monoclonal antibody. These are: (1) determining the nucleotide and predicted amino acid sequence of the starting antibody light and heavy Variable Domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807, 715; 5,866,692; and 6,331,415

The Epitope-Binding Domain may comprise either a complete Variable Domain fused onto Constant Domains or only the complementarity determining regions (CDRs) of such Variable Domain grafted to appropriate framework regions. Epitope-binding domains may be wild-type or modified by one or more amino acid substitutions. This eliminates the constant region as an immunogen in human individuals, but the possibility of an immune response to the foreign Variable Domain remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the Variable Domains as well so as to reshape them as closely as possible to human form. It is known that the Variable Domains of both Heavy and Light Chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the Variable Domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332: 323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

A number of humanized antibody molecules comprising an Epitope-Binding Domain derived from a non-human immunoglobulin have been described, including chimeric antibodies having rodent or modified rodent Variable Domain and their associated complementarity determining regions (CDRs) fused to human Constant Domains (see, for example, Winter et al. (1991) "*Man-made Antibodies*," Nature 349:293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-1A) To A Colon Cancer Tumor-Associated Antigen*," J. Immunol. 138: 4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321: 522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

B. Characteristics of Antibody Constant Regions

Throughout the present specification, the numbering of the residues in the constant region of an IgG is that of the EU index as in Kabat et al., SEQUENCES OF PROTEINS OF IMMUNOLOGICAL INTEREST, 5$^{th}$ Ed. Public Health Service, NH1, MD (1991) ("Kabat"), expressly incorporated herein by reference. The term "EU index as in Kabat" refers to the numbering of the Constant Domains of human IgG1 EU antibody.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Heavy Chain allotypes ("Gm allotypes") are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "*The Human IgG Subclasses: Molecular Analysis Of Structure, Function And Regulation*." Pergamon, Oxford, pp. 43-78 (1990); Lefranc, G. et al., 1979, Hum. Genet.: 50, 199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the Binding Molecules of the invention. Specifically encompassed by the instant invention are Binding Molecules lacking the C-terminal residue of the CH3 Domain. Also specifically encompassed by the instant invention are such constructs comprising the C-terminal lysine residue of the CH3 Domain.

1. Constant Regions of the Heavy Chain

The CH1 Domains of the two Heavy Chains of an antibody complex with the antibody's Light Chain's "CL" constant region, and are attached to the Heavy Chains CH2 Domains via an intervening Hinge Domain.

An exemplary CH1 Domain is a human IgG1 CH1 Domain. The amino acid sequence of an exemplary human IgG1 CH1 Domain is (SEQ ID NO:1):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV
```

An exemplary CH1 Domain is a human IgG2 CH1 Domain. The amino acid sequence of an exemplary human IgG2 CH1 Domain is (SEQ ID NO:2):

```
ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTV
```

An exemplary CH1 Domain is a human IgG3 CH1 Domain. The amino acid sequence of an exemplary human IgG3 CH1 Domain is (SEQ ID NO:3):

```
ASTKGPSVFP LAPCSRSTSG GTAALGCLVK DYFPEPVTVS

WNSGALTSGV HTFPAVLQSS GLYSLSSVVT VPSSSLGTQT

YTCNVNHKPS NTKVDKRV
```

An exemplary CH1 Domain is a human IgG4 CH1 Domain. The amino acid sequence of an exemplary human IgG4 CH1 Domain is (SEQ ID NO:4):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRV
```

One exemplary Hinge Domain is a human IgG1 Hinge Domain. The amino acid sequence of an exemplary human IgG1 Hinge Domain is (SEQ ID NO:5):

```
EPKSCDKTHTCPPCP.
```

Another exemplary Hinge Domain is a human IgG2 Hinge Domain. The amino acid sequence of an exemplary human IgG2 Hinge Domain is (SEQ ID NO:6):

```
ERKCCVECPPCP.
```

Another exemplary Hinge Domain is a human IgG3 Hinge Domain. The amino acid sequence of an exemplary human IgG2 Hinge Domain is (SEQ ID NO:7):

```
ELKTPLGDTT HTCPRCPEPK SCDTPPPCPR CPEPKSCDTP

PPCPRCPEPK SCDTPPPCPR CP
```

Another exemplary Hinge Domain is a human IgG4 Hinge Domain. The amino acid sequence of an exemplary human IgG4 Hinge Domain is (SEQ ID NO:8): ESKY-GPPCPSCP. As described herein, an IgG4 Hinge Domain may comprise a stabilizing mutation such as the S228P substitution. The amino acid sequence of an exemplary S228P-stabilized human IgG4 Hinge Domain is (SEQ ID NO:9): ESKYGPPCPPCP.

The CH2 and CH3 Domains of the two Heavy Chains of an IgG antibody interact to form an "Fc Domain," of IgG antibodies that is recognized by cellular Fc Receptors, including but not limited to Fc gamma Receptors (FcγRs). As used herein, the term "Fc Domain" is used to define a C-terminal region of an IgG Heavy Chain. An Fc Domain is said to be of a particular IgG isotype, class or subclass if its amino acid sequence is most homologous to that isotype relative to other IgG isotypes. In addition to their known uses in diagnostics, antibodies have been shown to be useful as therapeutic agents.

The amino acid sequence of the CH2-CH3 Domain of an exemplary human IgG1 is (SEQ ID NO:10):

```
          231        240        250        260        270        280
          APELLGGPSV FLFPPKPKDT LMISRTPEVT CVVVDVSHED PEVKFNWYVD 290        300        310        320        330
          GVEVHNAKTK PREEQYNSTY RVVSVLTVLH QDWLNGKEYK CKVSNKALPA 340        350        360        370        380
          PIEKTISKAK GQPREPQVYT LPPSREEMTK NQVSLTCLVK GFYPSDIAVE 390        400        410        420        430
          WESNGQPENN YKTIPPVLDS DGSFFLYSKL TVDKSRWQQG NVFSCSVMHE 440        447
          ALHNHYTQKS LSLSPGX
``` as numbered by the EU index as set forth in Kabat, wherein X is lysine (K) or is absent.

The amino acid sequence of the CH2-CH3 Domain of an exemplary human IgG2 is (SEQ ID NO:11):

```
231       240        250        260        270        280
APPVA-GPSV FLFPPKPKDT LMISRTPEVT CVVVDVSHED PEVQFNWYVD 290        300        310        320        330
GVEVHNAKTK PREEQFNSTF RVVSVLTVVH QDWLNGKEYK CKVSNKGLPA 340        350        360        370        380
PIEKTISKTK GQPREPQVYT LPPSREEMTK NQVSLTCLVK GFYPSDISVE 390        400        410        420        430
WESNGQPENN YKTTPPMLDS DGSFFLYSKL TVDKSRWQQG NVFSCSVMHE 440    447
ALHNHYTQKS LSLSPGX
``` as numbered by the EU index as set forth in Kabat, wherein X is lysine (K) or is absent.

The amino acid sequence of the CH2-CH3 Domain of an exemplary human IgG3 is (SEQ ID NO:12):

```
231       240        250        260        270        280
APFLLGGPSV FLFPPKPKDT LMISRTPEVT CVVVDVSHED PEVQFKWYVD 290        300        310        320        330
GVEVHNAKTK PREEQYNSTF RVVSVLTVLH QDWLNGKEYK CKVSNKALPA 340        350        360        370        380
PIEKTISKTK GQPREPQVYT LPPSREEMTK NQVSLTCLVK GFYPSDIAVE 390        400        410        420        430
WESSGQPENN YNTTPPMLDS DGSFFLYSKL TVDKSRWQQG NIFSCSVMHE 440    447
ALHNRFTQKS LSLSPGX
``` as numbered by the EU index as set forth in Kabat, wherein X is lysine (K) or is absent.

The amino acid sequence of the CH2-CH3 Domain of an exemplary human IgG4 is (SEQ ID NO:13):

```
231       240        250        260        270        280
APEFLGGPSV FLFPPKPKDT LMISRTPEVT CVVVDVSQED PEVQFNWYVD 290        300        310        320        330
GVEVHNAKTK PREEQFNSTY RVVSVLTVLH QDWLNGKEYK CKVSNKGLPS 340        350        360        370        380
SIEKTISKAK GQPREPQVYT LPPSQEEMTK NQVSLTCLVK GFYPSDIAVE 390        400        410        420        430
WESNGQPENN YKTIPPVLDS DGSFFLYSRL TVDKSRWQEG NVFSCSVMHE 440    447
ALHNHYTQKS LSLSLGX
``` as numbered by the EU index as set forth in Kabat, wherein X is lysine (K) or is absent.

2. Constant Regions of the Light Chain

As indicated above, each Light Chain of an antibody contains a Variable Domain ("VL") and a Constant Domain ("CL").

A preferred CL Domain is a human IgG CL Kappa Domain. The amino acid sequence of an exemplary human CL Kappa Domain is (SEQ ID NO:14):

```
RTVAAPSVFI FPPSDEQLKS GTASVVCLLN NFYPREAKVQ

WKVDNALQSG NSQESVIEQD SKDSTYSLSS TLTLSKADYE

KEKVYACEVT EQGLSSPVTK

SFNRGEC
```

Alternatively, an exemplary CL Domain is a human IgG CL Lambda Domain. The amino acid sequence of an exemplary human CL Lambda Domain is (SEQ ID NO:15):

```
QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS
```

II. Multispecific Binding Molecules

The ability of an antibody to bind an epitope of an antigen depends upon the presence and amino acid sequence of the antibody's VL and VH Domains. Interaction of an antibody's Light Chain and Heavy Chain and, in particular, interaction of its VL and VH Domains forms one of the two Epitope-Binding Domains of a natural antibody, such as an IgG. Natural antibodies are capable of binding only one epitope species (i.e., they are monospecific), although they can bind multiple copies of that species (i.e., exhibiting bivalency or multivalency).

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two Epitope-Binding Domains) for the same epitope and/or antigen.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565), most of which use Linker peptides either to fuse a further Epitope-Binding Domain (e.g., an scFv, VL, VH, etc.) to, or within the antibody core (IgA, IgD, IgE, IgG or IgM), or to fuse multiple Epitope-Binding Domains (e.g., two Fab fragments or scFvs). Alternative formats use Linker peptides to fuse Epitope-Binding Domains (e.g., an scFv, VL, VH, etc.) to a dimerization domain such as the CH2-CH3 Domain or alternative polypeptides (WO 2005/070966, WO 2006/107786 WO 2006/107617, WO 2007/046893). PCT Publication Nos. WO 2013/174873, WO 2011/133886 and WO 2010/136172 disclose a trispecific antibody in which the CL and CH1 Domains are switched from their respective natural positions and the VL and VH Domains have been diversified (WO 2008/027236; WO 2010/108127) to allow them to bind more than one antigen. PCT Publication Nos. WO 2013/163427 and WO 2013/119903 disclose modifying the CH2 Domain to contain a fusion protein adduct comprising a binding domain. PCT Publication Nos. WO 2010/028797, WO2010028796 and WO 2010/028795 disclose recombinant antibodies whose Fc Domains have been replaced with additional VL and VH Domains, so as to form trivalent Binding Molecules. PCT Publication Nos. WO 2003/025018 and WO2003012069 disclose recombinant diabodies whose individual chains contain scFv Domains. PCT Publication Nos. WO 2013/006544 discloses multivalent Fab molecules that are synthesized as a single polypeptide chain and then subjected to proteolysis to yield heterodimeric structures. PCT Publication Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional binding domains or functional groups to an antibody or an antibody portion (e.g., adding a diabody to the antibody's Light Chain, or adding additional VL and VH Domains to the antibody's light and Heavy Chains, or adding a heterologous fusion protein or chaining multiple Fab Domains to one another).

The art has additionally noted the capability to produce diabodies that differ from such natural antibodies in being capable of binding two or more different epitope species (i.e., exhibiting bispecificity or multispecificity in addition to, or in exchange of, bivalency or multivalency) (see, e.g., Holliger et al. (1993) "'*Diabodies': Small Bivalent And Bispecific Antibody Fragments*," Proc. Natl. Acad. Sci. (U.S.A.) 90:6444-6448; US 2004/0058400 (Hollinger et al.); US 2004/0220388/WO 02/02781 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng. Des. Sel. 17(1):21-27; Wu, A. et al. (2001) "*Multimerization Of A Chimeric Anti-CD20 Single Chain Fv-Fv Fusion Protein Is Mediated Through Variable Domain Exchange*," Protein Engineering 14(2): 1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

In particular, stable, covalently bonded heterodimeric non-monospecific diabodies, termed DART® diabodies have been developed; see, e.g., Sloan, D. D. et al. (2015) "*Targeting HIV Reservoir in Infected CD4 T Cells by Dual-Affinity Re-targeting Molecules (DARTs) that Bind HIV Envelope and Recruit Cytotoxic T Cells*," PLoS Pathog. 11(11):e1005233. doi: 10.1371/journal.ppat.1005233; Al Hussaini, M. et al. (2015) "*Targeting CD123 In AML Using A T-Cell Directed Dual-Affinity Re-Targeting (DART®) Platform*," Blood pii: blood-2014-05-575704; Chichili, G. R. et al. (2015) "*A CD3×CD123 Bispecific DART For Redirecting Host T Cells To Myelogenous Leukemia: Preclinical Activity And Safety In Nonhuman Primates*," Sci. Transl. Med. 7(289):289ra82; Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B-Cell Activation Via Recruitment Of Fcgamma Receptor IIb (CD32B) Inhibitory Function With A Novel Bispecific Antibody Scaffold*," Arthritis Rheum. 62(7): 1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449); U.S. Pat. Nos. 8,044,180; 8,133,982; 8,187,593; 8,193,318; 8,530, 627; 8,669,349; 8,778,339; 8,784,808; 8,795,667; 8,802, 091; 8,802,093; 8,946,387; 8,968,730; and 8,993,730; US Patent Publication Nos. 2009/0060910; 2010/0174053; 2011/0081347; 2011/0097323; 2011/0117089; 2012/ 0009186; 2012/0034221; 2012/0141476; 2012/0294796; 2013/0149236; 2013/0295121; 2014/0017237; and 2014/ 0099318; European Patent Documents No. EP 1868650; EP 2158221; EP 2247304; EP 2252631; EP 2282770; EP 2328934; EP 2376109; EP 2542256; EP 2601216; EP 2714079; EP 2714733; EP 2786762; EP 2839842; EP 2840091; and PCT Publication Nos. WO 2006/113665; WO 2008/157379; WO 2010/027797; WO 2010/033279; WO 2010/080538; WO 2011/109400; WO 2012/018687; WO 2012/162067; WO 2012/162068; WO 2014/159940; WO 2015/021089; WO 2015/026892; and WO 2015/026894). Such diabodies comprise two or more covalently complexed polypeptides and involve engineering one or more cysteine residues into each of the employed polypeptide species that permit disulfide bonds to form and thereby covalently bond one or more pairs of such polypeptide chains to one another. For example, the addition of a cysteine residue to the C-terminus of such constructs has been shown to allow disulfide bonding between the involved polypeptide chains, stabilizing the resulting diabody without interfering with the diabody's binding characteristics.

Figure 1B:
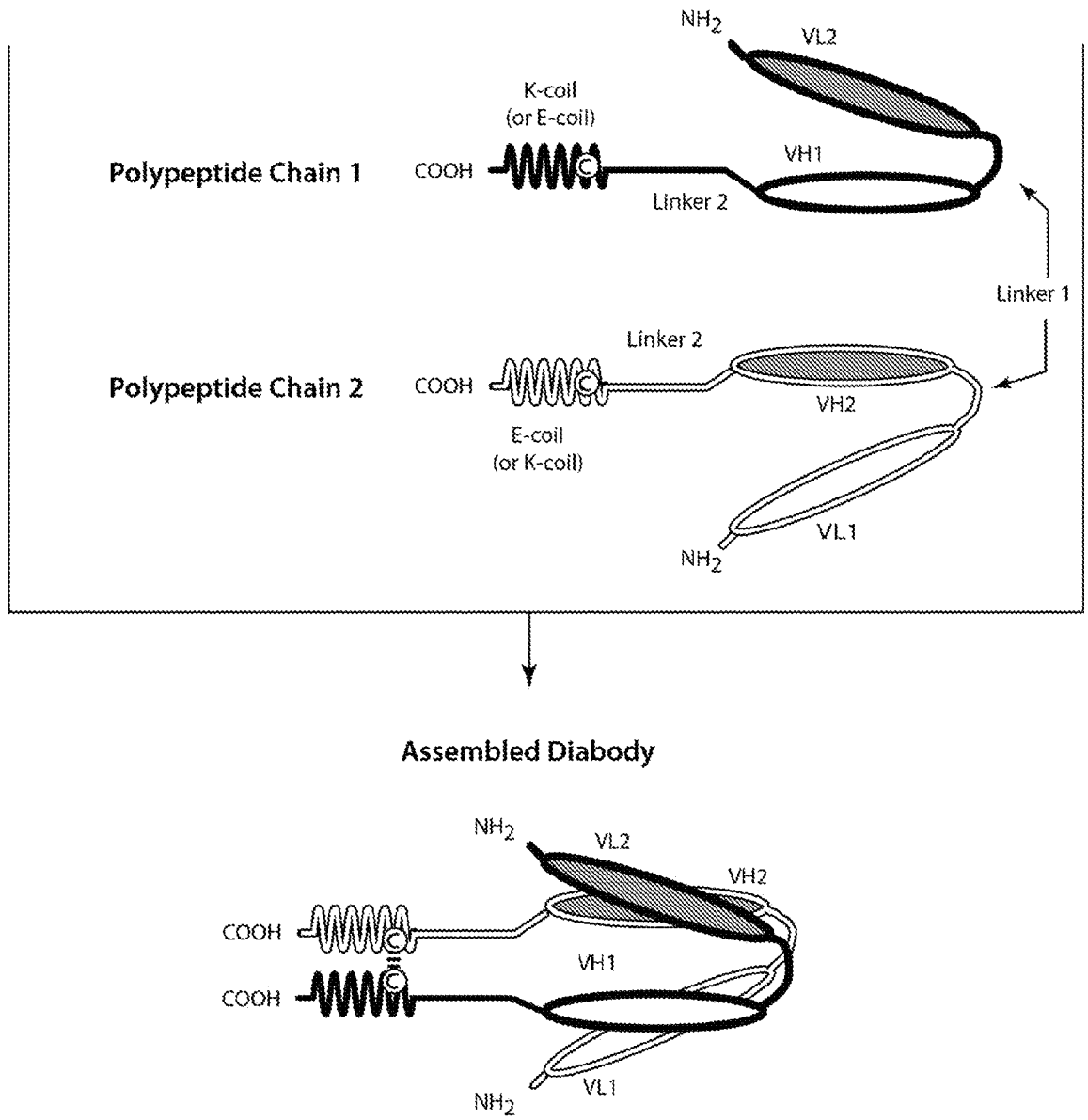

The simplest DART® diabody comprises two polypeptide chains each comprising three Domains (FIGS. 1A-1B). The first polypeptide chain comprises: (i) a Domain that comprises an Epitope-Binding Domain of a Light Chain Variable Domain of the a first immunoglobulin (VL1), (ii) a second Domain that comprises an Epitope-Binding Domain of a Heavy Chain Variable Domain of a second immunoglobulin (VH2), and (iii) a third Domain that serves to promote heterodimerization (a "Heterodimer-Promoting Domain") with the second polypeptide chain and to covalently bond the first polypeptide to the second polypeptide chain of the diabody. The second polypeptide chain contains a complementary first Domain (a VL2 Domain), a complementary second Domain (a VH1 Domain) and a third Domain that complexes with the third Domain of the first polypeptide chain in order to promote heterodimerization (a "Heterodimer-Promoting Domain") and covalent bonding with the first polypeptide chain. Such molecules are stable, potent and have the ability to simultaneously bind two or more antigens. In one embodiment, the Third Domains of the first and second polypeptide chains each contain a cysteine residue (denoted as "©" in the Figures), which serves to bind the polypeptides together via a covalent disulfide bond. The third Domain of one or both of the polypeptide chains may additionally possess the sequence of a CH2-CH3 Domain, such that complexing of one diabody polypeptide to another diabody polypeptide forms an Fc Domain. Such Fc Domains may serve to alter the biological half-life of the diabody, decrease its immunogenicity, and/or be capable of binding to an Fc Receptor of cells (such as B lymphocytes, dendritic cells, natural killer cells, macrophages, neutrophils, eosinophils, basophils and mast cells) to enhance or inhibit effector function. Many variations of such molecules have been described (see, e.g., United States Patent Publication Nos. 2015/0175697; 2014/0255407; 2014/0099318; 2013/0295121; 2010/0174053; 2009/0060910; 2007/0004909; European Patent Publication Nos. EP 2714079; EP 2601216; EP 2376109; EP 2158221; EP 1868650; and PCT Publication Nos. WO 2012/162068; WO 2012/018687; WO 2010/080538; WO 2006/113665), and are provided herein.

Recently, trivalent structures incorporating two Diabody-Type Binding Domains and one Non-Diabody-type Domain, and an Fc Domain have been described (see, e.g., PCT Publication Nos. WO 2015/184207 and WO 2015/184203). Such trivalent Binding Molecules may be utilized to generate monospecific, bispecific or trispecific molecules as provided in more detail below. The ability to bind three different epitopes provides enhanced capabilities.

Alternative constructs are known in the art for applications where a bispecific or tetravalent molecule is desirable but an Fc is not required including, but not limited to, Bispecific T-cell Engager molecules, also referred to as "BiTEs" (see, e.g., PCT Publication Nos: WO 1993/11161; and WO 2004/106381) and tetravalent tandem antibodies, also referred to as "TandAbs" (see, e.g. United States Patent Publication No: 2011-0206672; European Patent Publication No. EP 2371866, and; PCT Publication Nos. WO 1999/057150, WO 2003/025018, and WO 2013/013700). BiTEs are formed from a single polypeptide chain comprising tandem linked scFvs, while TandAbs are formed by the homo-dimerization of two identical polypeptide chains, each possessing a VH1, VL2, VH2, and VL2 Domain.

The ability to produce multispecific Binding Molecules (e.g., bispecific antibodies, bispecific diabodies, trivalent molecules, etc.) has led to their use (in "trans") to co-ligate two cells together, for example, by co-ligating receptors that are present on the surface of different cells (e.g., cross-linking cytotoxic T-cells to target cells, such as cancer cells or pathogen-infected cells, that express a Disease Antigen) (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305; Marvin et al. (2005) "*Recombinant Approaches To IgG-Like Bispecific Antibodies*," Acta Pharmacol. Sin. 26:649-658; Sloan et al. (2015) "*Targeting HIV Reservoir in Infected CD4 T Cells by Dual-Affinity Re-targeting Molecules (DARTs) that Bind HIV Envelope and Recruit Cytotoxic T Cells*," PLoS Pathog 11(11): e1005233. doi:10.1371/journal.ppat.1005233)). Alternatively (or additionally), multispecific molecules can be used (in "cis") to co-ligate molecules, such as receptors, etc., that are present on the surface of the same cell. Co-ligation of different cells and/or receptors is useful to modulate effector functions and/or immune cell signaling. Multispecific molecules (e.g., bispecific diabodies) comprising Epitope-Binding Domains may be directed to a surface determinant of any immune cell such as CD2, CD3, CD8, CD16, TCR, the Natural Killer Group 2, Member D Receptor (NKG2D), etc., which are expressed on T lymphocytes, Natural Killer (NK) cells, Antigen-Presenting Cells or other mononuclear cells. In particular, Epitope-Binding Domains directed to a cell surface receptor that is present on immune effector cells, are useful in the generation of multispecific Binding Molecules capable of mediating redirected cell killing.

The present invention provides Binding Molecules that are capable of mediating the redirected killing of a target cell (e.g., a cancer cell or a pathogen-infected cell, etc.) expressing a Disease Antigen ("DA"). Such Binding Molecules are capable of binding a "first epitope" and a "second epitope," wherein one of such epitopes is an epitope of CD3 and the other of such epitopes is an epitope of a Disease Antigen. It is irrelevant whether a particular epitope is designated as the first vs. the second epitope; such notation having relevance only with respect to the presence and orientation of the domains of the polypeptide chains of the Binding Molecules of the present invention. Thus, the bispecific molecules of the present invention comprise "$VL_{CD3}$"/"$VH_{CD3}$" Domains that are capable of binding an epitope of CD3, and "$VL_{DA}$"/"$VH_{DA}$" Domains that are capable of binding an epitope of a Disease Antigen. The instant invention particular encompasses bispecific diabodies, bispecific scFvs, BiTEs, antibodies, TandAbs, and trivalent Binding Molecules produced using any of the methods provided herein.

A. Bispecific Diabodies Lacking Fc Domains

In one embodiment, the DA×CD3 Binding Molecule of the invention are bispecific diabodies and comprises domains capable of binding both a first and a second epitope, but will lack an Fc Domain, and thus will be unable to bind FcγR molecules via an Fc-FcγR interaction. The first polypeptide chain of such an embodiment of bispecific diabodies comprises, in the N-terminal to C-terminal direction: an N-terminus, the VL Domain of a monoclonal antibody capable of binding either the first or second epitope (i.e., either $VL_{CD3}$ or $VL_{DA}$), a first intervening spacer peptide (Linker 1), a VH Domain of a monoclonal antibody capable of binding the epitope of the Disease Antigen (if such first polypeptide chain contains VL$_{CD3}$) or a VH Domain of a monoclonal antibody capable of binding CD3 (if such first polypeptide chain contains VL$_{D4}$), a second intervening spacer peptide (Linker 2) optionally containing a cysteine residue, a Heterodimer-Promoting Domain and a C-terminus (FIGS. 1A-1B).

The second polypeptide chain of this embodiment of bispecific diabodies comprises, in the N-terminal to C-terminal direction: an N-terminus, the VL Domain of a monoclonal antibody capable of binding the first or second epitope (i.e., VL$_{CD3}$ or VL$_{D4}$, and being the VL Domain not selected for inclusion in the first polypeptide chain of the diabody), an intervening spacer peptide (Linker 1), a VH Domain of a monoclonal antibody capable of binding either the first or second epitope (i.e., VH$_{CD3}$ or VH$_{D4}$, and being the VH Domain not selected for inclusion in the first polypeptide chain of the diabody), a second intervening spacer peptide (Linker 2) optionally containing a cysteine residue, a Heterodimer-Promoting Domain and a C-terminus (FIGS. 1A-1B). The employed VL and VH Domains specific for a particular epitope are preferably obtained or derived from the same monoclonal antibody. However, such domains may be derived from different monoclonal antibodies provided that they associate to form a functional binding site capable of immunospecifically binding such epitope. Such different antibodies are referred to herein as being "corresponding" antibodies.

The VL Domain of the first polypeptide chain interacts with the VH Domain of the second polypeptide chain to form a first functional Epitope-Binding Domain that is specific for one of the epitopes (e.g., the first epitope). Likewise, the VL Domain of the second polypeptide chain interacts with the VH Domain of the first polypeptide chain in order to form a second functional Epitope-Binding Domain that is specific for the other epitope (i.e., the second epitope). Thus, the selection of the VL and VH Domains of the first and second polypeptide chains is "coordinated," such that the two polypeptide chains of the diabody collectively comprise VL and VH Domains capable of binding both the first epitope and the second epitope (i.e., they collectively comprise VL$_{CD3}$/VH$_{CD3}$ and VL$_{D4}$/VH$_{D4}$).

Most preferably, the length of the intervening spacer peptide (i.e., "Linker 1," which separates such VL and VH Domains) is selected to substantially or completely prevent the VL and VH Domains of the polypeptide chain from binding one another (for example consisting of from 0, 1, 2, 3, 4, 5, 6, 7, 8 or 9 intervening Linker amino acid residues). Thus, the VL and VH Domains of the first polypeptide chain are substantially or completely incapable of binding one another. Likewise, the VL and VH Domains of the second polypeptide chain are substantially or completely incapable of binding one another. A preferred intervening spacer peptide (Linker 1) has the sequence (SEQ ID NO:16):

GGGSGGGG.

The length and composition of the second intervening spacer peptide ("Linker 2") is selected based on the choice of one or more polypeptide domains that promote such dimerization (i.e., a "Heterodimer-Promoting Domain"). Typically, the second intervening spacer peptide (Linker 2) will comprise 3-20 amino acid residues. In particular, where the employed Heterodimer-Promoting Domain(s) do/does not comprise a cysteine residue a cysteine-containing second intervening spacer peptide (Linker 2) is utilized. A cysteine-containing second intervening spacer peptide (Linker 2) will contain 1, 2, 3 or more cysteines. A preferred cysteine-containing spacer peptide (Linker 2) has the sequence GGCGGG (SEQ ID NO:17). Alternatively, Linker 2 does not comprise a cysteine (e.g., GGG, GGGS (SEQ ID NO:18), LGGGSG (SEQ ID NO:19), GGGSGGGSGGG (SEQ ID NO:20), ASTKG (SEQ ID NO:21), LEPKSS (SEQ ID NO:22), APSSS (SEQ ID NO:23), etc.) and a cysteine-containing Heterodimer-Promoting Domain, as described below is used. Optionally, both a cysteine-containing Linker 2 and a cysteine-containing Heterodimer-Promoting Domain are used.

The Heterodimer-Promoting Domains may comprise or consist of GVEPKSC (SEQ ID NO:24) or VEPKSC (SEQ ID NO:25) or AEPKSC (SEQ ID NO:26) on one polypeptide chain and GFNRGEC (SEQ ID NO:27) or FNRGEC (SEQ ID NO:28) on the other polypeptide chain (US2007/0004909).

In a preferred embodiment, the Heterodimer-Promoting Domains will comprise tandemly repeated coil domains of opposing charge for example, an "E-coil" Heterodimer-Promoting Domain (SEQ ID NO:29: EVAALEK-EVAAL EK-EVAALEK-EVAALEK), whose glutamate residues will form a negative charge at pH 7, or a "K-coil" Heterodimer-Promoting Domain (SEQ ID NO:30: KVAALKE-KVAAL KE-KVAALKE-KVAALKE), whose lysine residues will form a positive charge at pH 7. The presence of such charged domains promotes association between the first and second polypeptides, and thus fosters heterodimer formation. Heterodimer-Promoting Domains that comprise modifications of the above-described E-coil and K-coil sequences so as to include one or more cysteine residues may be utilized. The presence of such cysteine residues permits the coil present on one polypeptide chain to become covalently bonded to a complementary coil present on another polypeptide chain, thereby covalently bonding the polypeptide chains to one another and increasing the stability of the diabody. Examples of such particularly preferred are Heterodimer-Promoting Domains include a Modified E-Coil having the amino acid sequence EVAACEK-EVAALEK-EVAALEK-EVAALEK (SEQ ID NO:31), and a modified K-coil having the amino acid sequence KVAACKE-KVAALKE-KVAALKE-KVAALKE (SEQ ID NO:32).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of a polypeptide chain of the diabody. Albumin is the most abundant protein in plasma and has a half-life of 19 days in humans. Albumin possesses several small molecule binding sites that permit it to non-covalently bind other proteins and thereby extend their serum half-lives. The Albumin-Binding Domain 3 (ABD3) of protein G of Streptococcus strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules,*" J. Biol. Chem. 277(10):8114-8120). Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of Streptococcus strain G148 (SEQ ID NO:33):

```
LAEAKVLANR ELDKYGVSDY YKNLINNAKT VEGVKALIDE ILAALP.
```

As disclosed in WO 2012/162068 (herein incorporated by reference), "deimmunized" variants of SEQ ID NO:33 have the ability to attenuate or eliminate MHC class II binding. Based on combinational mutation results, the following combinations of substitutions are considered to be preferred substitutions for forming such a deimmunized ABD: 66D/70S+71A; 66S/70S+71A; 66S/70S+79A; 64A/65A/71A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

```
                                         (SEQ ID NO: 34)
LAEAKVLANR ELDKYGVSDY YKNLID₆₆NAKS₇₀ A₇₁EGVKALIDE
ILAALP,
``` or the amino acid sequence:

```
                                         (SEQ ID NO: 35)
LAEAKVLANR ELDKYGVSDY YKNA₆₄A₆₅NNAKT VEGVKALIA₇₉E
ILAALP,
``` or the amino acid sequence:

```
                                         (SEQ ID NO: 36)
LAEAKVLANR ELDKYGVSDY YKNLIS₆₆NAKS₇₀ VEGVKALIA₇₉E
ILAALP,
``` are particularly preferred as such deimmunized ABD exhibit substantially wild-type binding while providing attenuated MHC class II binding. Thus, the first polypeptide chain of such a diabody having an ABD contains a third Linker (Linker 3) preferably positioned C-terminally to the E-coil (or K-coil) Domain of such polypeptide chain so as to intervene between the E-coil (or K-coil) Domain and the ABD (which is preferably a deimmunized ABD). A preferred sequence for such Linker 3 is SEQ ID NO:18: GGGS B. Diabodies Comprising Fc Domains One embodiment of the present invention relates to multispecific diabodies (e.g., bispecific, trispecific, tetraspecific, etc.) that comprise an Fc Domain and that are capable of simultaneously binding an epitope of CD3 and an epitope of a Disease Antigen. The Fc Domain of such molecules may be of any isotype (e.g., IgG1, IgG2, IgG3, or IgG4). The molecules may further comprise a CH1 Domain and/or a Hinge Domain. When present, the CH1 Domain and/or Hinge Domain may be of any isotype (e.g., IgG1, IgG2, IgG3, or IgG4), and is preferably of the same isotype as the desired Fc Domain.

Figure 2:
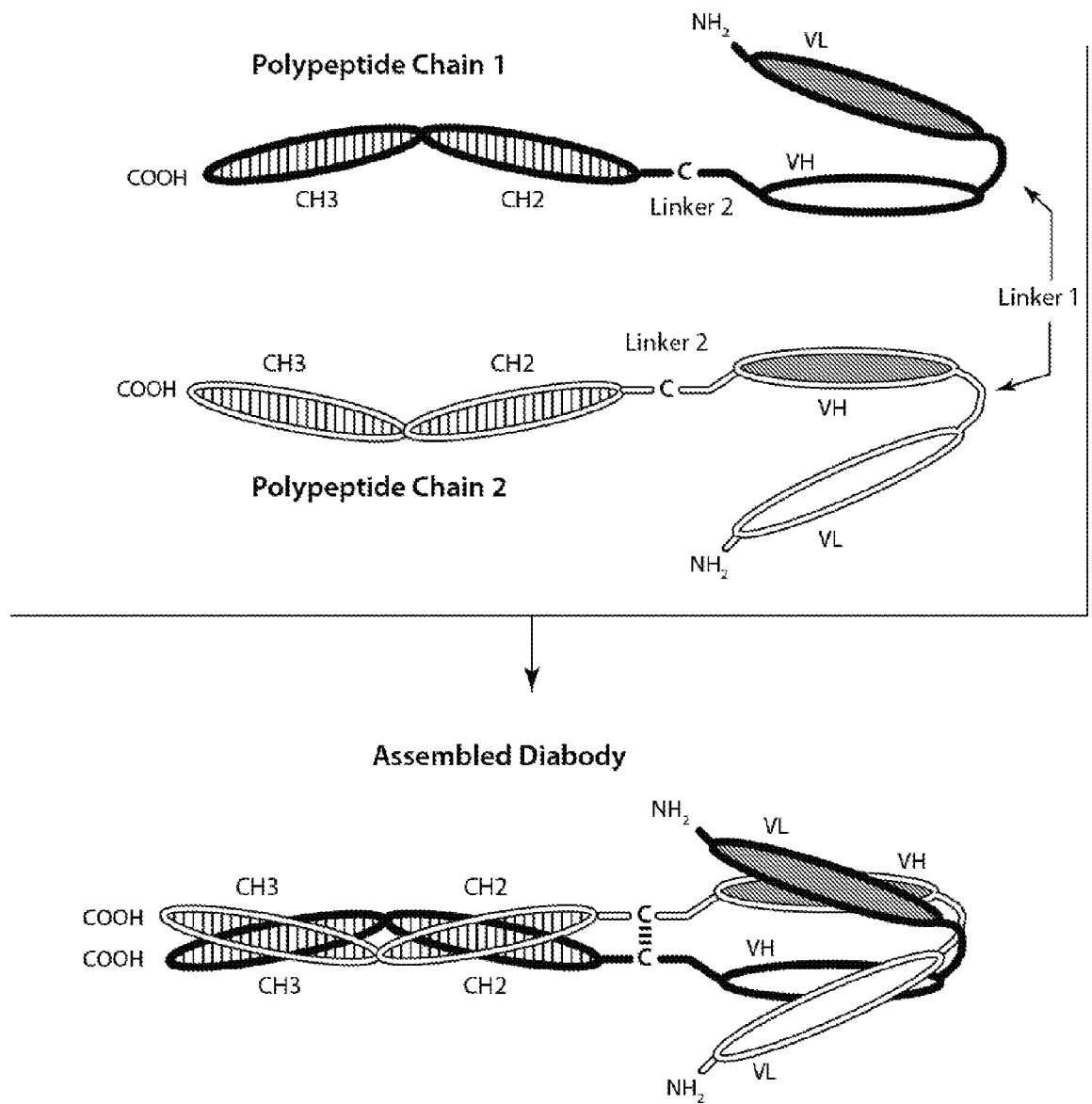
FIG. 2 provides a schematic of a representative covalently bonded diabody molecule having two Epitope-Binding Domains composed of two polypeptide chains, each having a CH2 and CH3 Domain, such that the associated chains form all or part of an Fc Domain. VL and VH Domains that recognize the same epitope are shown using the same shading or fill pattern.

The addition of an IgG CH2-CH3 Domain to one or both of the diabody polypeptide chains, such that the complexing of the diabody chains results in the formation of an Fc Domain, increases the biological half-life and/or alters the valency of the diabody. Such diabodies comprise, two or more polypeptide chains whose sequences permit the polypeptide chains to covalently bind each other to form a covalently associated diabody that is capable of simultaneously binding the first epitope and the second epitope. Incorporating an IgG CH2-CH3 Domains onto both of the diabody polypeptides will permit a two-chain bispecific Fc Domain-containing diabody to form (FIG. 2).

Figure 3A:
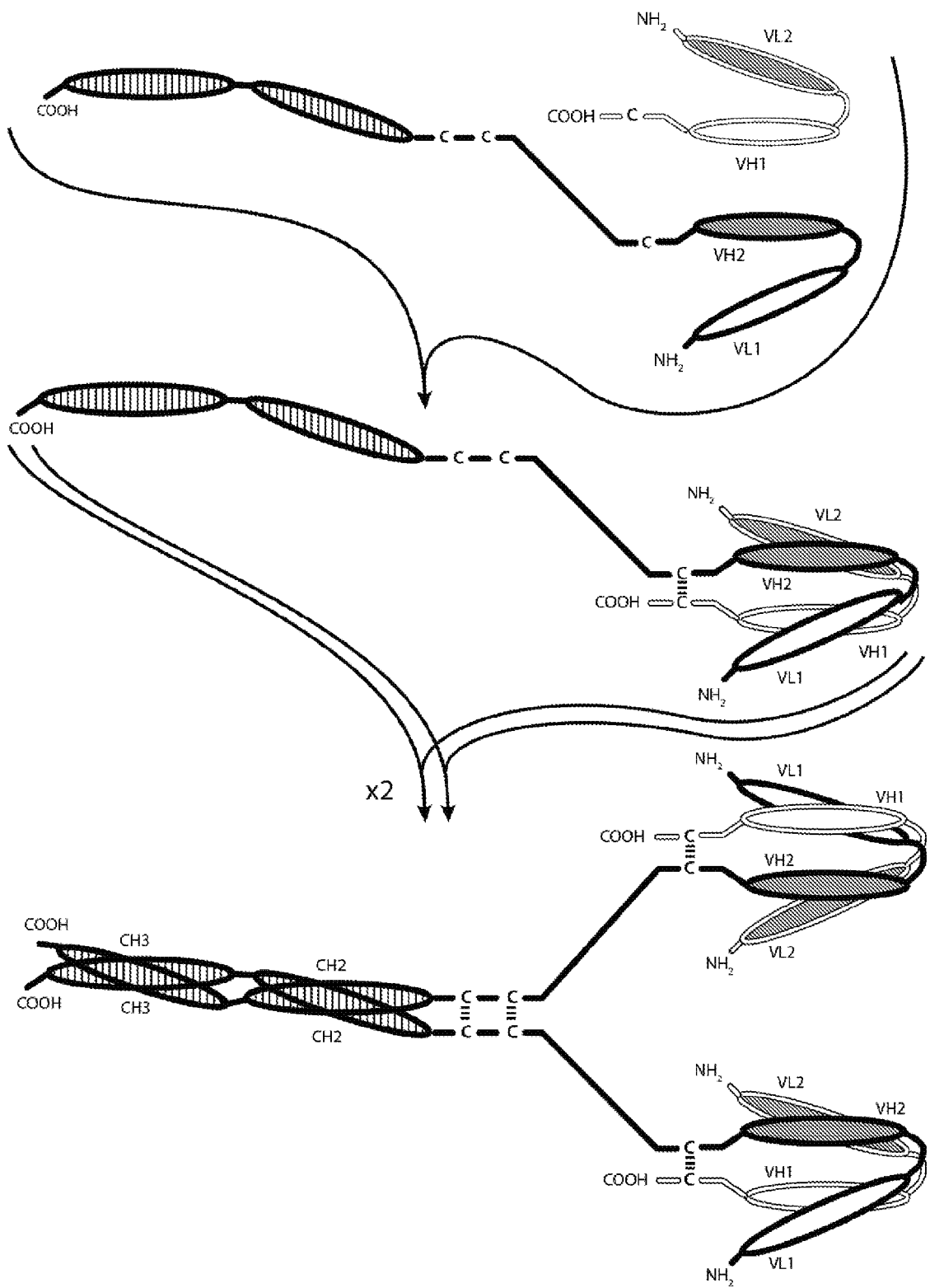
FIGS. 3A-3C provide schematics showing representative covalently bonded tetravalent diabodies having four Epitope-Binding Domains composed of two pairs of polypeptide chains (i.e., four polypeptide chains in all). One polypeptide of each pair possesses a CH2 and CH3 Domain, such that the associated chains form all or part of an Fc Domain. VL and VH Domains that recognize the same epitope are shown using the same shading or fill pattern. The two pairs of polypeptide chains may be same. In such embodiments, wherein the two pairs of polypeptide chains are the same and the VL and VH Domains recognize different epitopes (as shown in FIGS. 3A-3B), the resulting molecule possesses four Epitope-Binding Domains and is bispecific and bivalent with respect to each bound epitope. In such embodiments, wherein the VL and VH Domains recognize the same epitope (e.g., the same VL Domain CDRs and the same VH Domain CDRs are used on both chains) the resulting molecule possesses four Epitope-Binding Domains and is monospecific and tetravalent with respect to a single epitope. Alternatively, the two pairs of polypeptides may be different. In such embodiments, wherein the two pairs of polypeptide chains are different and the VL and VH Domains of each pair of polypeptides recognize different epitopes (as shown by the different shading and patterns in FIG. 3C), the resulting molecule possesses four Epitope-Binding Domains and is tetraspecific and monovalent with respect to each bound epitope.
Figure 3B:
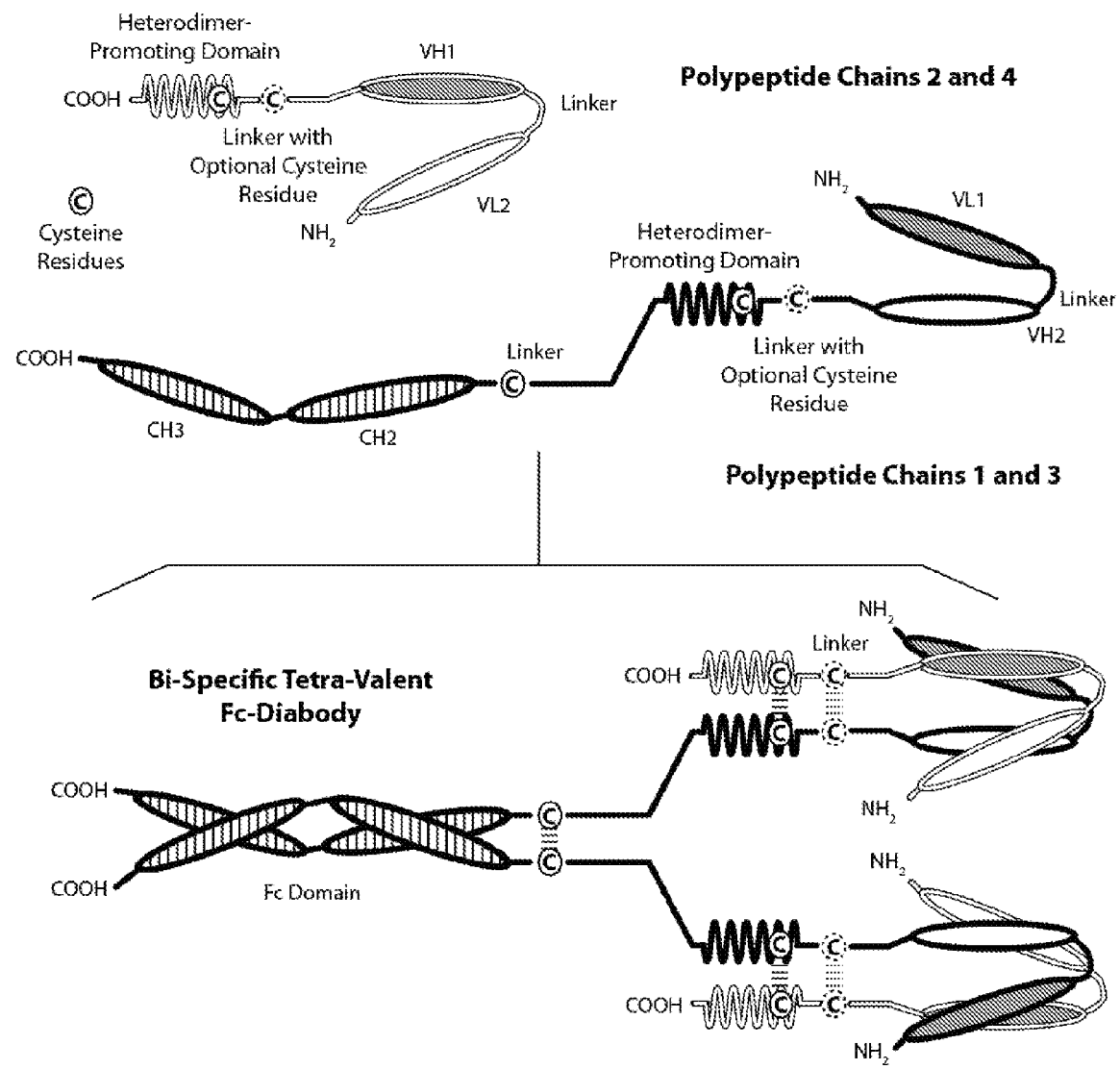
Figure 3C:
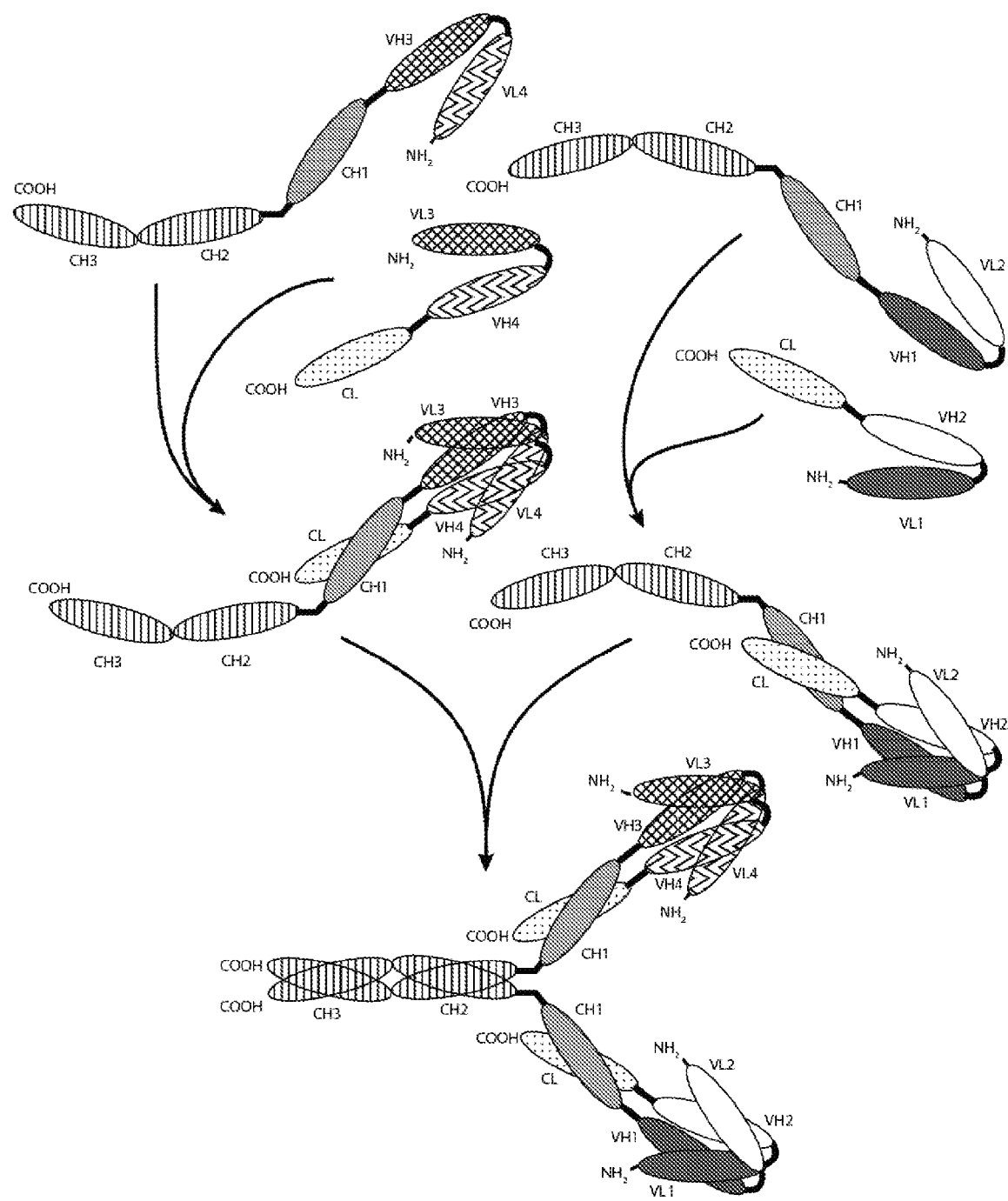

Alternatively, incorporating IgG CH2-CH3 Domains onto only one of the diabody polypeptides will permit a more complex four-chain bispecific Fc Domain-containing diabody to form (FIGS. 3A-3C). FIG. 3C shows a representative four-chain diabody possessing the Constant Light (CL) Domain and the Constant Heavy CH1 Domain, however fragments of such domains as well as other polypeptides may alternatively be employed (see, e.g., FIGS. 3A and 3B, United States Patent Publication Nos. 2013-0295121; 2010-0174053 and 2009-0060910; European Patent Publication No. EP 2714079; EP 2601216; EP 2376109; EP 2158221 and PCT Publication Nos. WO 2012/162068; WO 2012/018687; WO 2010/080538). Thus, for example, in lieu of the CH1 Domain, one may employ a peptide having the amino acid sequence GVEPKSC (SEQ ID NO:24), VEPKSC (SEQ ID NO:25), or AEPKSC (SEQ ID NO:26), derived from the Hinge Domain of a human IgG, and in lieu of the CL Domain, one may employ the C-terminal 6 amino acids of the human kappa Light Chain, GFNRGEC (SEQ ID NO:27) or FNRGEC (SEQ ID NO:28). A representative peptide containing four-chain diabody is shown in FIG. 3A. Alternatively, or in addition, one may employ a peptide comprising tandem coil domains of opposing charge such as the "E-coil" helical domains (SEQ ID NO:29: EVAALEK-EVAALEK-EVAALEK-EVAALEK or SEQ ID NO:31: EVAACEK-EVAALEK-EVAALEK-EVAALEK); and the "K-coil" domains (SEQ ID NO:30: KVAALKE-KVAALKE-KVAALKE-KVAALKE or SEQ ID NO:32: KVAACKE-KVAALKE-KVAALKE-KVAALKE). A representative coil domain containing four-chain diabody is shown in FIG. 3B.

Fc Domain-containing diabody molecules of the present invention may include additional intervening spacer peptides (Linkers), generally such Linkers will be incorporated between a Heterodimer-Promoting Domain (e.g., an E-coil or K-coil) and a CH2-CH3 Domain and/or between a CH2-CH3 Domain and a Variable Domain (i.e., VH or VL). Typically, the additional Linkers will comprise 3-20 amino acid residues and may optionally contain all or a portion of an IgG Hinge Domain (preferably a cysteine-containing portion of an IgG Hinge Domain possessing 1, 2, 3 or more cysteine residues). Linkers that may be employed in the bispecific Fc Domain-containing diabody molecules of the present invention include: GGGS (SEQ ID NO:18), LGGGSG (SEQ ID NO:19), GGGSGGGSGGG (SEQ ID NO:20), ASTKG (SEQ ID NO:21), LEPKSS (SEQ ID NO:22), APSSS (SEQ ID NO:23), APSSSPME (SEQ ID NO:37), VEPKSADKTHTCPPCP (SEQ ID NO:38), LEPKSADKTHTCPPCP (SEQ ID NO:39), DKTHTCPPCP (SEQ ID NO:40), the scFv Linker: GGGGSGGGGSGGGGS (SEQ ID NO:41); the "long" Linker: GGGGSGGGSGGG (SEQ ID NO:42), GGC, and GGG. LEPKSS (SEQ ID NO:22) may be used in lieu of GGG or GGC for ease of cloning. Additionally, the amino acids GGG, or LEPKSS (SEQ ID NO:22) may be immediately followed by DKTHTCPPCP (SEQ ID NO:40) to form the alternate Linkers: GGGDKTHTCPPCP (SEQ ID NO:43); and LEPKSSDKTHTCPPCP (SEQ ID NO:44). Bispecific Fc Domain-containing molecules of the present invention may incorporate an IgG Hinge Domain in addition to or in place of a Linker. Exemplary Hinge Domains include: EPKSCDKTHTCPPCP (SEQ ID NO:5) from IgG1, ERKCCVECPPCP (SEQ ID NO:6) from IgG2, ELKTPLGDTT HTCPRCPEPKSCDTPPPCPRC-PEPKSCDTPPPCPRCPEPKSCDTPPPCPRCP (SEQ ID NO:7) from IgG3, ESKYGPPCPSCP (SEQ ID NO:8) from IgG4, and ESKYGPPCPPCP (SEQ ID NO:9) an IgG4 Hinge variant comprising a stabilizing S228P substitution (as numbered by the EU index as set forth in Kabat) to reduce strand exchange.

As provided in FIG. 3A-3C, Fc Domain-containing diabodies of the invention may comprise four chains. The first and third polypeptide chains of such a diabody contain three domains: (i) a VL1-containing Domain, (ii) a VH2-containing Domain, (iii) a Heterodimer-Promoting Domain, and (iv) a Domain containing a CH2-CH3 sequence. The second and fourth polypeptide chains contain: (i) a VL2-containing Domain, (ii) a VH1-containing Domain, and (iii) a Heterodimer-Promoting Domain, where the Heterodimer-Promoting Domains promote the dimerization of the first/third polypeptide chains with the second/fourth polypeptide chains. The VL and/or VH Domains of the third and fourth polypeptide chains, and VL and/or VH Domains of the first and second polypeptide chains may be the same or different so as to permit tetravalent binding that is either monospecific, bispecific or tetraspecific. The notation "VL3" and "VH3" denote respectively, the Light Chain Variable Domain and Variable Heavy Chain Domain that bind a "third" epitope of such diabody. Similarly, the notation "VL4" and "VH4" denote respectively, the Light Chain Variable Domain and Variable Heavy Chain Domain that bind a "fourth" epitope of such diabody. The general structure of the polypeptide chains of a representative four-chain bispecific Fc Domain-containing diabodies of invention is provided in Table 1:

TABLE 1

| | | |
|---|---|---|
| Bispecific | 2$^{nd}$ Chain | NH$_2$—VL2—VH1—HPD—COOH |
| | 1$^{st}$ Chain | NH$_2$—VL1—VH2—HPD—CH2—CH3—COOH |
| | 1$^{st}$ Chain | NH$_2$—VL1—VH2—HPD—CH2—CH3—COOH |
| | 2$^{nd}$ Chain | NH$_2$—VL2—VH1—HPD—COOH |
| Tetraspecific | 2$^{nd}$ Chain | NH$_2$—VL2—VH1—HPD—COOH |
| | 1$^{st}$ Chain | NH$_2$—VL1—VH2—HPD—CH2—CH3—COOH |
| | 3$^{rd}$ Chain | NH$_2$—VL3—VH4—HPD—CH2—CH3—COOH |
| | 4$^{th}$ Chain | NH$_2$—VL4—VH3—HPD—COOH |

HPD = Heterodimer-Promoting Domain

In a specific embodiment, diabodies of the present invention are bispecific, tetravalent (i.e., possess four Epitope-Binding Domains), Fc-containing diabodies that are composed of four total polypeptide chains (FIGS. 3A-3C). The bispecific, tetravalent, Fc-containing diabodies of the invention comprise two first Epitope-Binding Domains and two second Epitope-Binding Domains.

Figure 4A:
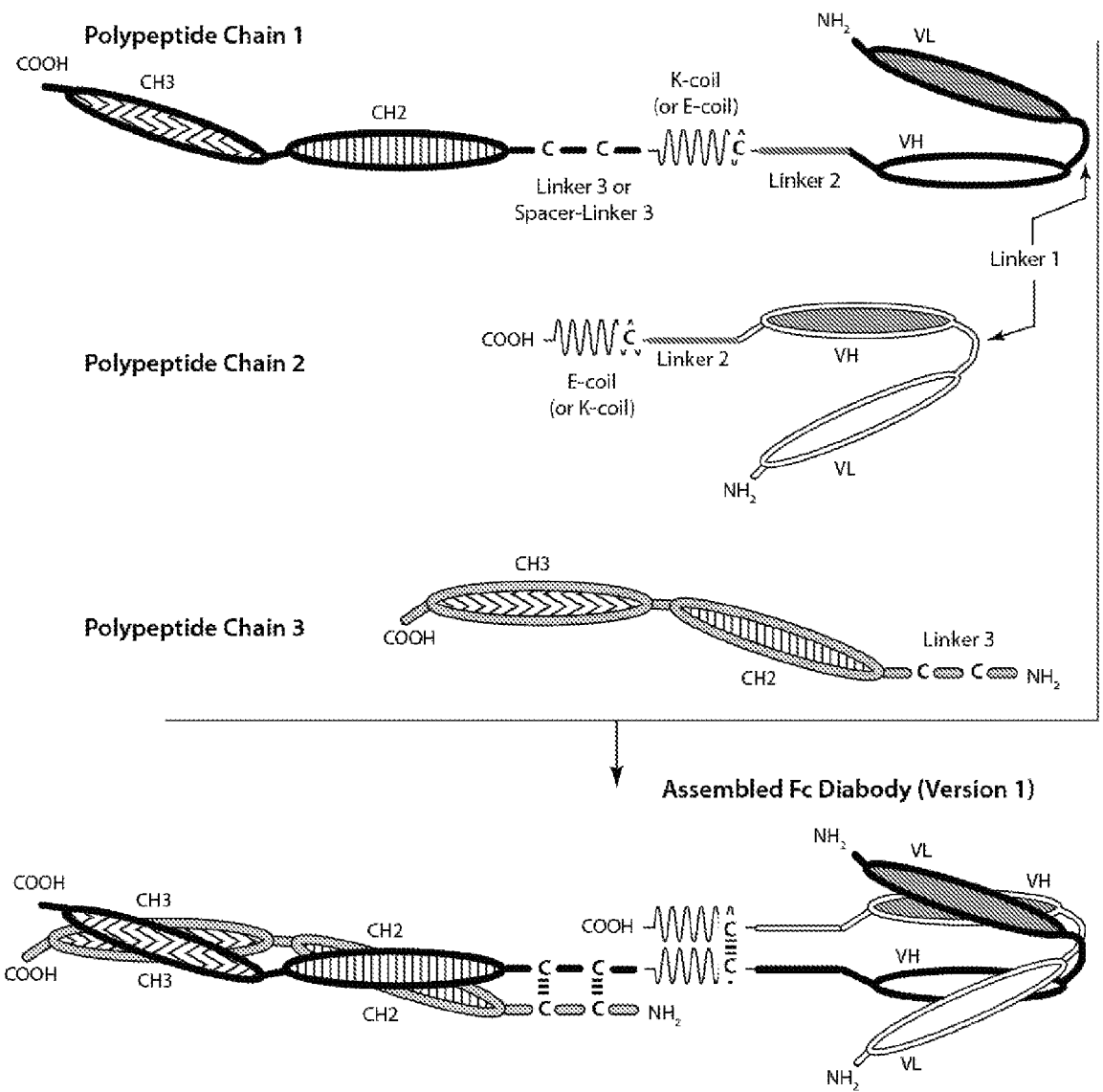
FIGS. 4A-4B provide schematics of a representative covalently bonded diabody molecule having two Epitope-Binding Domains composed of three polypeptide chains. Two of the polypeptide chains possess a CH2 and CH3 Domain, such that the associated chains form all or part of an Fc Domain. The polypeptide chains comprising the VL and VH Domain further comprise a Heterodimer-Promoting Domain. VL and VH Domains that recognize the same epitope are shown using the same shading or fill pattern.
Figure 4B:
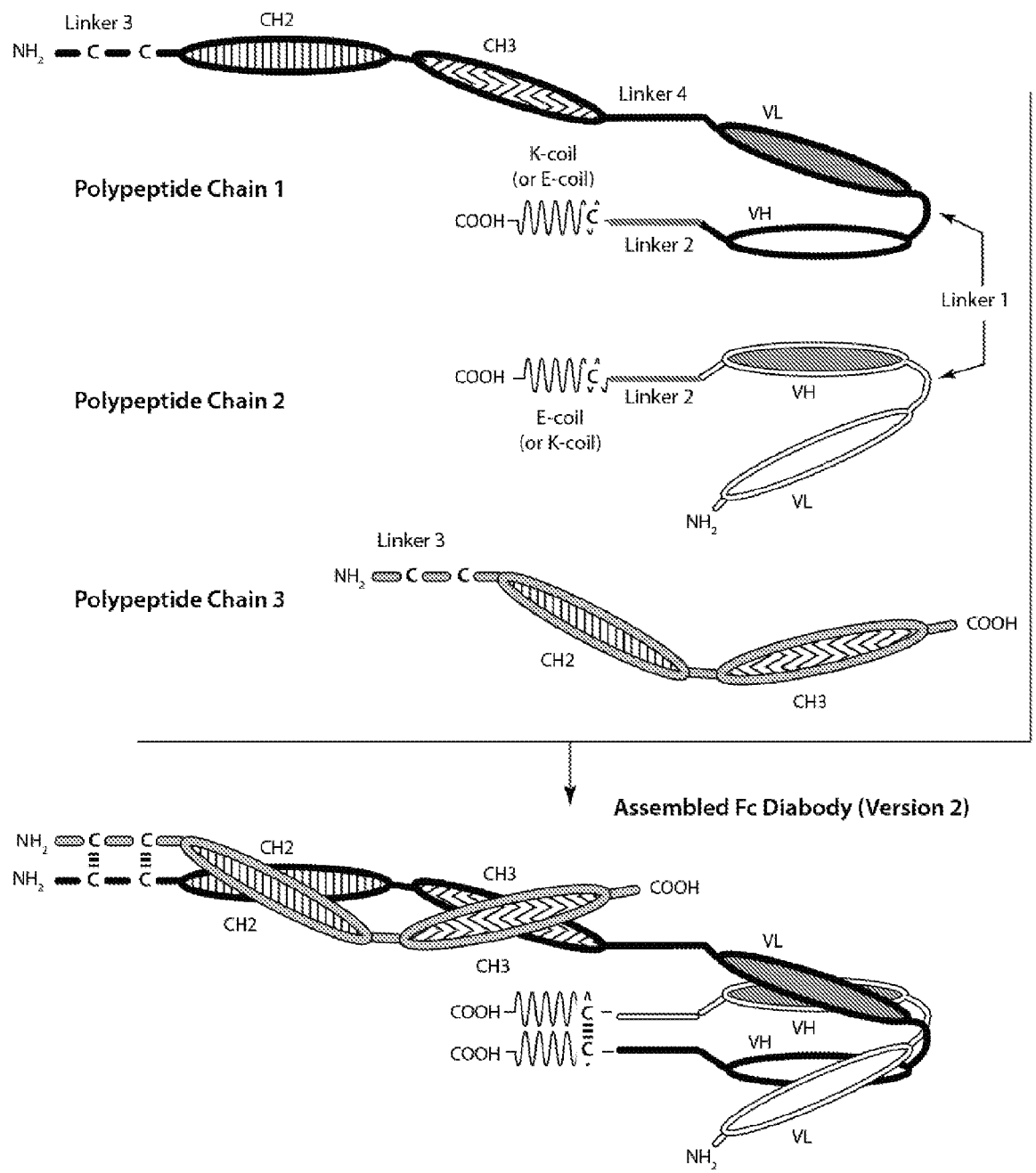

In a further embodiment, the Fc Domain-containing diabodies of the present invention may comprise three polypeptide chains. The first polypeptide of such a diabody contains three domains: (i) a VL1-containing Domain, (ii) a VH2-containing Domain and (iii) a Domain containing a CH2-CH3 sequence. The second polypeptide of such a diabody contains: (i) a VL2-containing Domain, (ii) a VH1-containing Domain and (iii) a Domain that promotes heterodimerization and covalent bonding with the diabody's first polypeptide chain. The third polypeptide of such a diabody comprises a CH2-CH3 sequence. Thus, the first and second polypeptide chains of such a diabody associate together to form a VL1/VH1 Epitope-Binding Domain that is capable of binding either the first or second epitope, as well as a VL2/VH2 Epitope-Binding Domain that is capable of binding the other of such epitopes. The first and second polypeptides are bonded to one another through a disulfide bond involving cysteine residues in their respective Third Domains. Notably, the first and third polypeptide chains complex with one another to form an Fc Domain that is stabilized via a disulfide bond. Such bispecific diabodies have enhanced potency. FIGS. 4A and 4B illustrate the structures of such diabodies. Such Fc Domain-containing diabodies may have either of two orientations (Table 2):

TABLE 2

| | | |
|---|---|---|
| First Orientation | 3$^{rd}$ Chain | NH$_2$—CH2—CH3—COOH |
| | 1$^{st}$ Chain | NH$_2$—VL1—VH2—HPD—CH2—CH3—COOH |
| | 2$^{nd}$ Chain | NH$_2$—VL2—VH1—HPD—COOH |
| Second Orientation | 3$^{rd}$ Chain | NH$_2$—CH2—CH3—COOH |
| | 1$^{st}$ Chain | NH$_2$—CH2—CH3—VL1—VH2—HPD—COOH |
| | 2$^{nd}$ Chain | NH$_2$—VL2—VH1—HPD—COOH |

HPD = Heterodimer-Promoting Domain

In a specific embodiment, diabodies of the present invention are bispecific, bivalent (i.e., possess two Epitope-Binding Domains), Fc-containing diabodies that are composed of three total polypeptide chains (FIGS. 4A-4B). The bispecific, bivalent Fc-containing diabodies of the invention comprise one Epitope-Binding Domain immunospecific for either the first or second epitope, as well as a VL2/VH2 Epitope-Binding Domain that is capable of binding the other of such epitopes.

In a further embodiment, the Fc Domain-containing diabodies may comprise a total of five polypeptide chains. In a particular embodiment, two of the five polypeptide chains have the same amino acid sequence. The first polypeptide chain of such a diabody contains: (i) a VH1-containing Domain, (ii) a CH1-containing Domain, and (iii) a Domain containing a CH2-CH3 sequence. The first polypeptide chain may be the Heavy Chain of an antibody that contains a VH1 and a Heavy Chain constant region. The second and fifth polypeptide chains of such a diabody contain: (i) a VL1-containing Domain, and (ii) a CL-containing Domain. The second and/or fifth polypeptide chains of such a diabody may be Light Chains of an antibody that contains a VL1 complementary to the VH1 of the first/third polypeptide chain. The first, second and/or fifth polypeptide chains may be isolated from a naturally occurring antibody. Alternatively, they may be constructed recombinantly. The third polypeptide chain of such a diabody contains: (i) a VH1-containing Domain, (ii) a CH1-containing Domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain.

Figure 5:
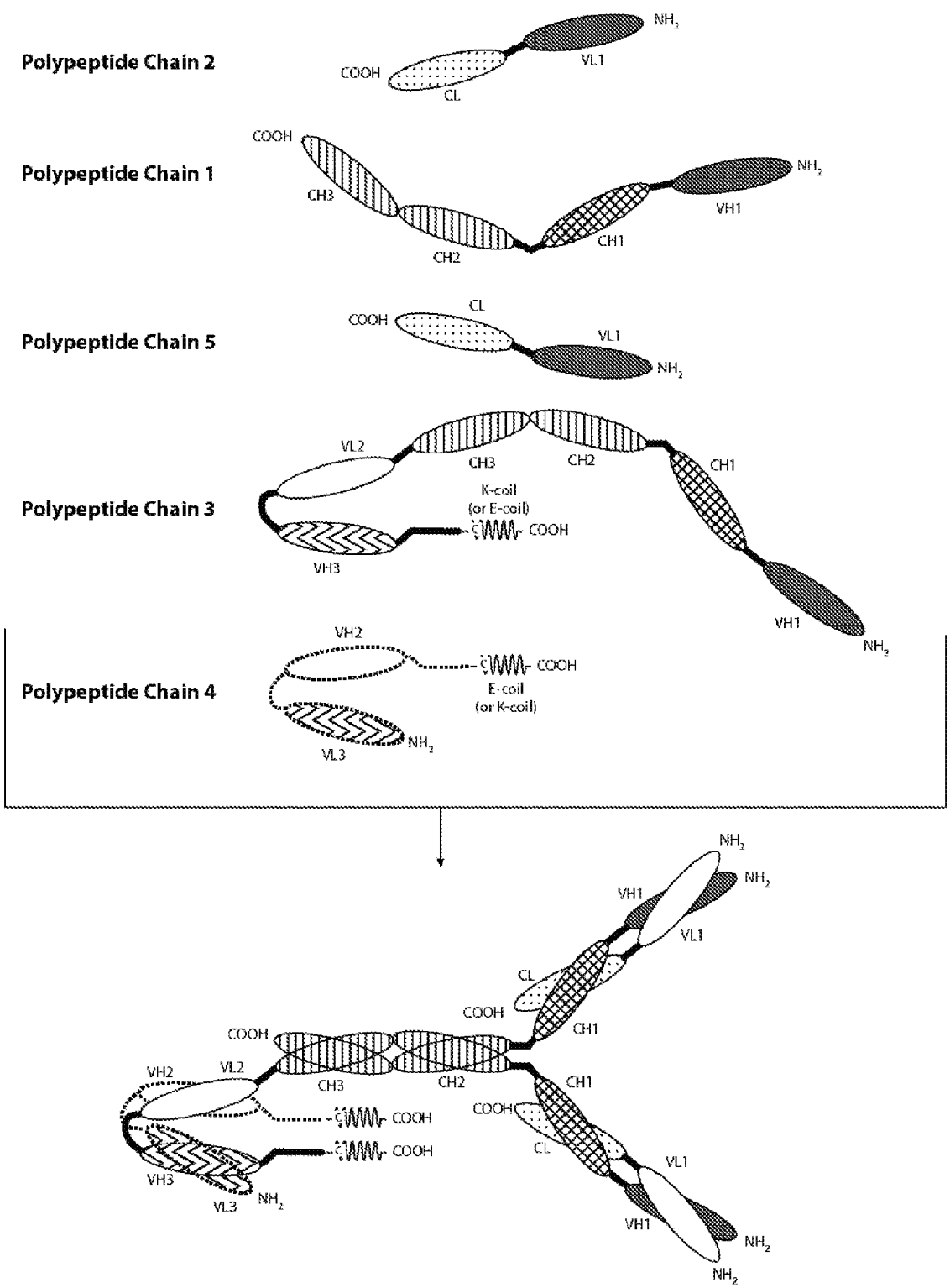
FIG. 5 provides the schematics of a representative covalently bonded diabody molecule having four Epitope-Binding Domains composed of five polypeptide chains. Two of the polypeptide chains possess a CH2 and CH3 Domain, such that the associated chains form an Fc Domain that comprises all or part of an Fc Domain. The polypeptide chains comprising the linked VL and VH Domains further comprise a Heterodimer-Promoting Domain. VL and VH Domains that recognize the same epitope are shown using the same shading or fill pattern.
Figure 6A:
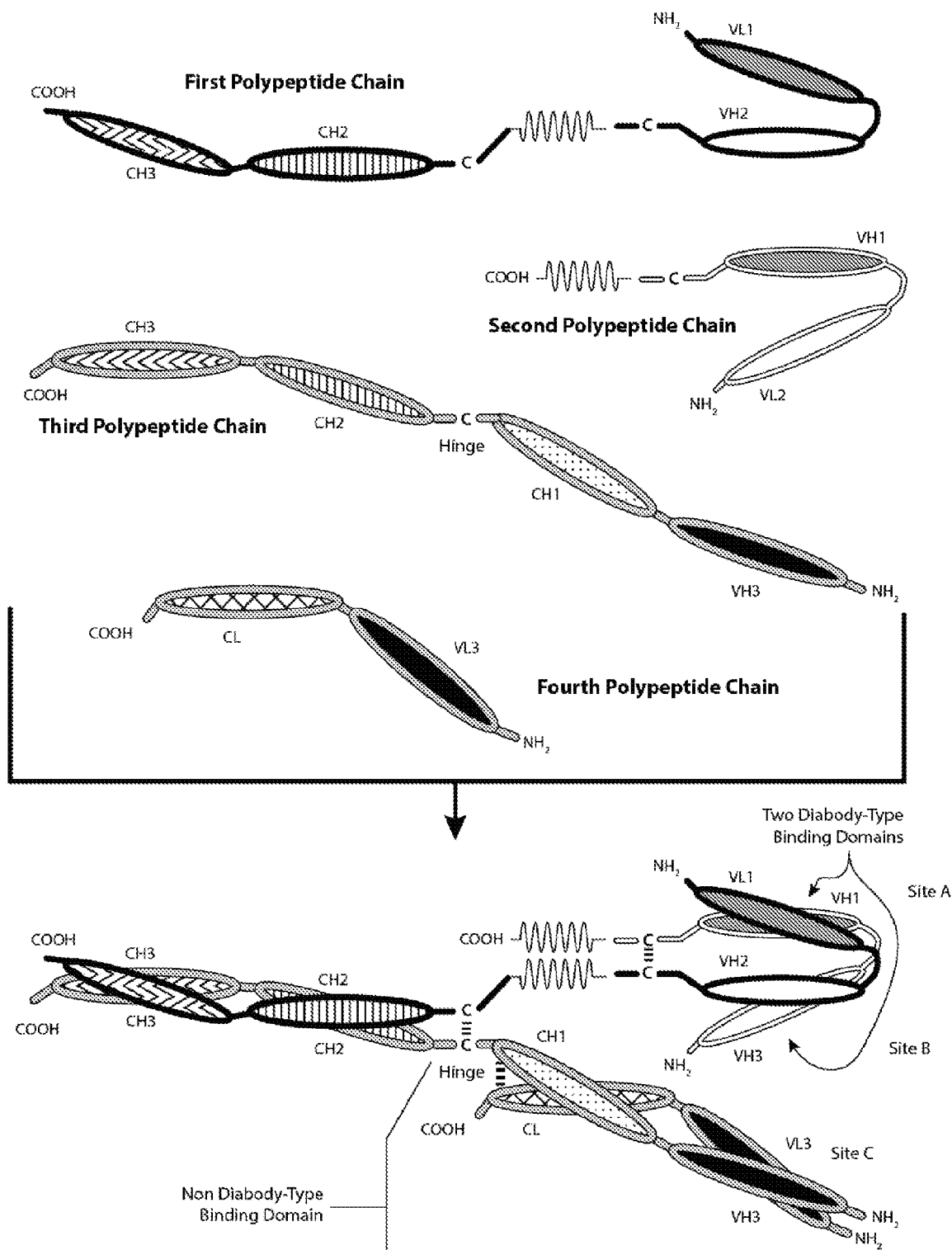
FIGS. 6A-6F provide schematics of representative Fc Domain-containing trivalent Binding Molecules having three Epitope-Binding Domains.
Figure 6B:
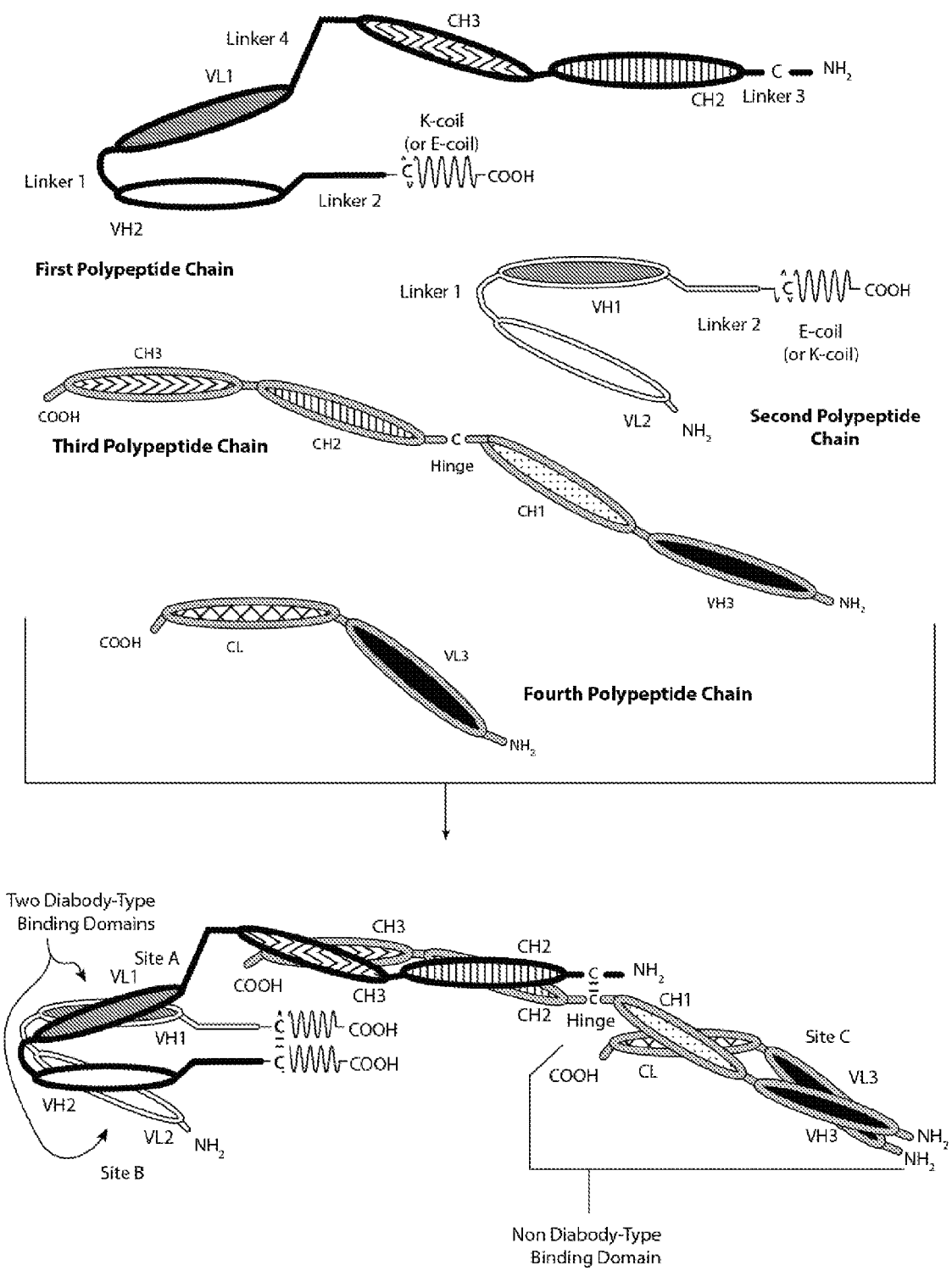
Figure 6C:
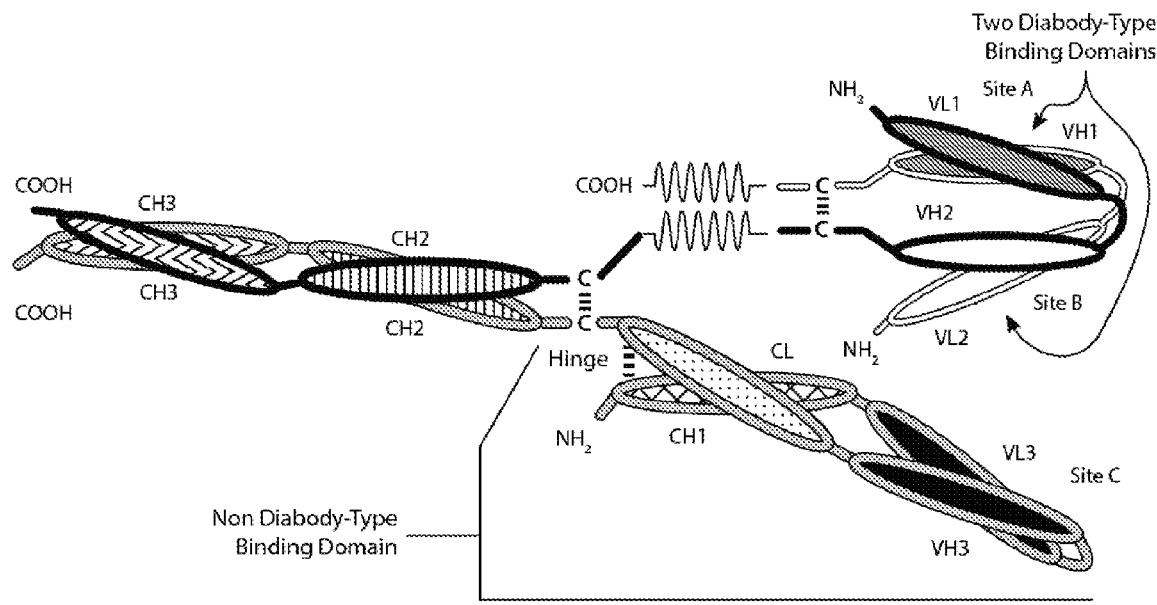
Figure 6D:
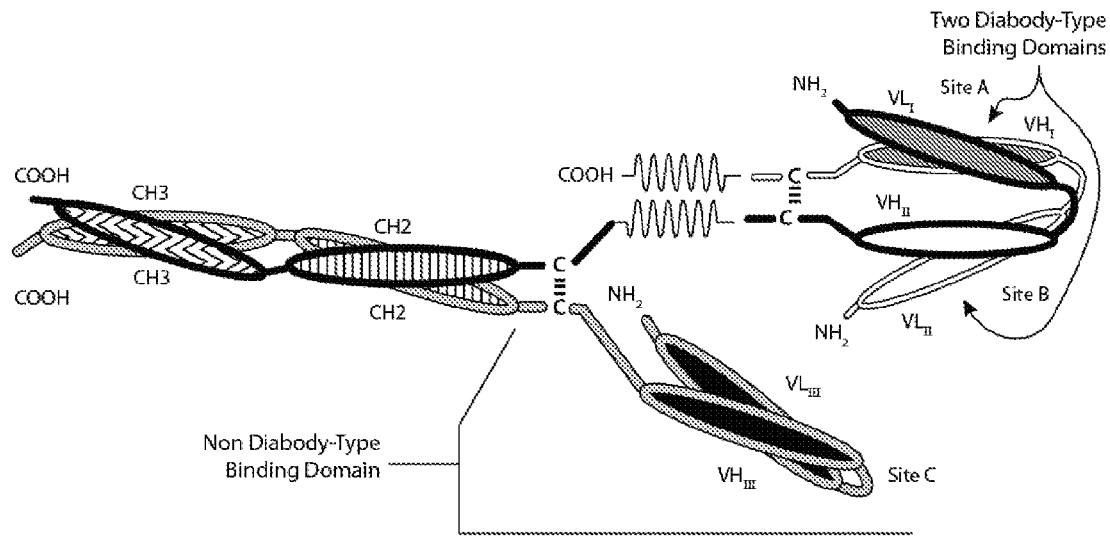
Figure 6E:
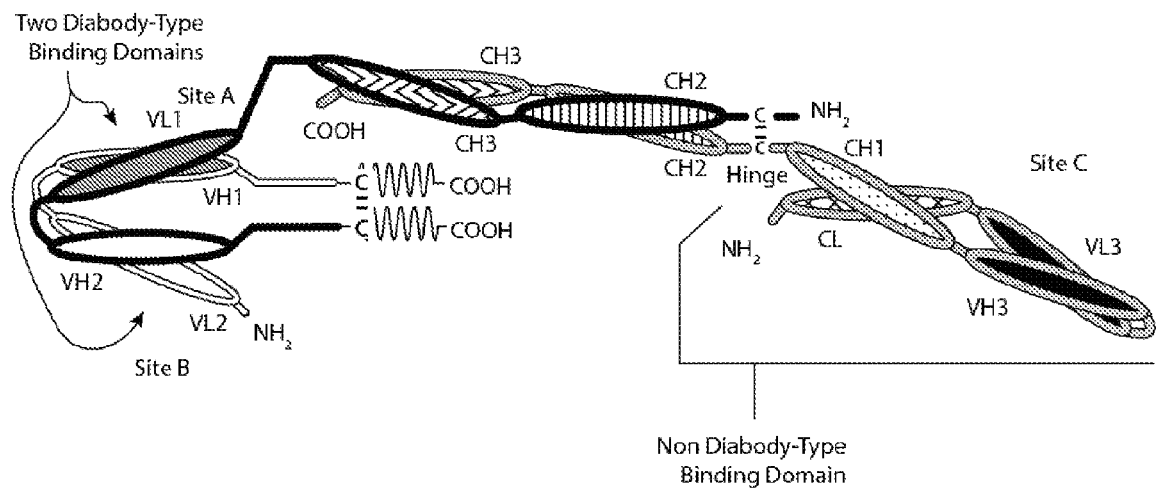
Figure 6F:
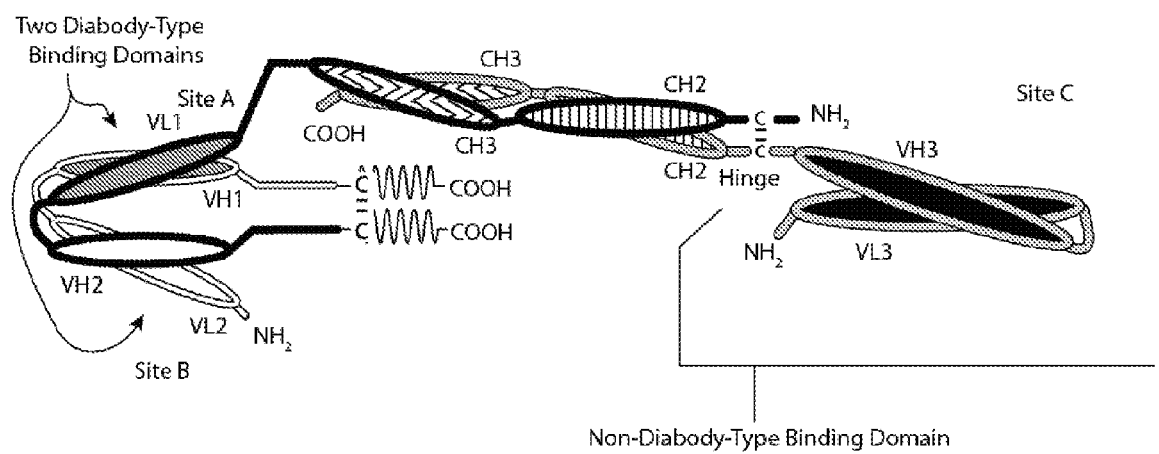

Thus, the first and second, and the third and fifth, polypeptide chains of such diabodies associate together to form two VL1/VH1 Epitope-Binding Domains capable of binding a first epitope. The third and fourth polypeptide chains of such diabodies associate together to form a VL2/VH2 Epitope-Binding Domain that is capable of binding a second epitope, as well as a VL3/VH3 binding site that is capable of binding a third epitope. The first and third polypeptides are bonded to one another through a disulfide bond involving cysteine residues in their respective constant regions. Notably, the first and third polypeptide chains complex with one another to form an Fc Domain. Such multispecific diabodies have enhanced potency. FIG. 5 illustrates the structure of such diabodies. It will be understood that the VL1/VH1, VL2/VH2, and VL3/VH3 Domains may be the same or different so as to permit binding that is monospecific, bispecific or trispecific.

The VL and VH Domains of the polypeptide chains are selected so as to form VL/VH binding sites specific for a desired epitope. The VL/VH binding sites formed by the association of the polypeptide chains may be the same or different so as to permit tetravalent binding that is monospecific, bispecific, trispecific or tetraspecific. In particular, the VL and VH Domains maybe selected such that a multivalent diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIG. 5). The general structure of the polypeptide chains of representative five-chain Fc Domain-containing diabodies of invention is provided in Table 3:

TABLE 3

| Bispecific (2 × 2) | $2^{nd}$ Chain | $NH_2$—VL1—CL—COOH |
| | $1^{st}$ Chain | $NH_2$—VH1—CH1—CH2—CH3—COOH |
| | $3^{rd}$ Chain | $NH_2$—VH1—CH1—CH2—CH3—VL2—VH2—HPD—COOH |
| | $5^{nd}$ Chain | $NH_2$—VL1—CL—COOH |
| | $4^{th}$ Cham | $NH_2$—VL2—VH2—HPD—COOH |
| Bispecific (3 × 1) | $2^{nd}$ Chain | $NH_2$—VL1—CL—COOH |
| | $1^{st}$ Chain | $NH_2$—VH1—CH1—CH2—CH3—COOH |
| | $3^{rd}$ Chain | $NH_2$—VH1—CH1—CH2—CH3—VL1—VH2—HPD—COOH |
| | $5^{nd}$ Chain | $NH_2$—VL1—CL—COOH |
| | $4^{th}$ Chain | $NH_2$—VL2—VH1—HPD—COOH |
| Trispecific (2 × 1 × 1) | $2^{nd}$ Chain | $NH_2$—VL1—CL—COOH |
| | $1^{st}$ Chain | $NH_2$—VH1—CH1—CH2—CH3—COOH |
| | $3^{rd}$ Chain | $NH_2$—VH1—CH1—CH2—CH3—VL2—VH3—HPD—COOH |
| | $5^{nd}$ Chain | $NH_2$—VL1—CL—COOH |
| | $4^{th}$ Chain | $NH_2$—VL3—VH2—HPD—COOH |

HPD = Heterodimer-Promoting Domain

In a specific embodiment, diabodies of the present invention are bispecific, tetravalent (i.e., possess four Epitope-Binding Domains), Fc-containing diabodies that are composed of five total polypeptide chains having two Epitope-Binding Domains immunospecific for the first epitope, and two Epitope-Binding Domains specific for the second epitope. In another embodiment, the bispecific, tetravalent, Fc-containing diabodies of the invention comprise three Epitope-Binding Domains immunospecific for the first epitope and one Epitope-Binding Domain specific for the second epitope. As provided above, the VL and VH Domains may be selected to permit trispecific binding. Accordingly, the invention also encompasses trispecific, tetravalent, Fc-containing diabodies. The trispecific, tetravalent, Fc-containing diabodies of the invention comprise two Epitope-Binding Domains immunospecific for the first epitope, one Epitope-Binding Domain immunospecific for the second molecule, and one Epitope-Binding Domain immunospecific for the third epitope.

In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All of these interactions are initiated through the binding of the Fc Domain of antibodies or immune complexes to specialized cell surface receptors on hematopoietic cells. The diversity of cellular responses triggered by antibodies and immune complexes results from the structural heterogeneity of the three Fc Receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. In addition, interaction with the neonatal Fc Receptor (FcRn) mediates the recycling of IgG molecules from the endosome to the cell surface and release into the blood. The amino acid sequence of exemplary wild-type IgG1 (SEQ ID NO:10), IgG2 (SEQ ID NO:11), IgG3 (SEQ ID NO:12), and IgG4 (SEQ ID NO:13) are presented above.

Modification of the Fc Domain may lead to an altered phenotype, for example altered serum half-life, altered stability, altered susceptibility to cellular enzymes or altered effector function. It may therefore be desirable to modify an Fc Domain-containing binding molecule of the present invention with respect to effector function, for example, so as to enhance the effectiveness of such molecule in treating cancer. Reduction or elimination of Fc Domain-mediated effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma). Molecules of the invention possessing such conferred or altered effector function activity are useful for the treatment and/or prevention of a disease, disorder or infection in which an enhanced efficacy of effector function activity is desired.

Accordingly, in certain embodiments, the Fc Domain of the Fc Domain-containing molecules of the present invention may be an engineered variant Fc Domain. Although the Fc Domain of the bispecific Fc Domain-containing molecules of the present invention may possess the ability to bind one or more Fc Receptors (e.g., FcγR(s)), more preferably such variant Fc Domain have altered binding FcγRIA (CD64), FcγRIIA (CD32A), FcγRIIB (CD32B), FcγRIIIA (CD16a) or FcγRIIIB (CD16b) (relative to the binding exhibited by a wild-type Fc Domain), e.g., will have enhanced binding an activating receptor and/or will have substantially reduced or no ability to bind inhibitory receptor(s). Thus, the Fc Domain of the Fc Domain-containing molecules of the present invention may include some or all of the CH2 Domain and/or some or all of the CH3 Domain of a complete Fc Domain, or may comprise a variant CH2 and/or a variant CH3 sequence (that may include, for example, one or more insertions and/or one or more deletions with respect to the CH2 or CH3 Domains of a complete Fc Domain). Such Fc Domains may comprise non-Fc polypeptide portions, or may comprise portions of non-naturally complete Fc Domains, or may comprise non-naturally occurring orientations of CH2 and/or CH3 Domains (such as, for example, two CH2 Domains or two CH3 Domains, or in the N-terminal to C-terminal direction, a CH3 Domain linked to a CH2 Domain, etc.).

Fc Domain modifications identified as altering effector function are known in the art, including modifications that increase binding activating receptors (e.g., FcγRIIA (CD16A) and reduce binding inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890). Table 4 lists exemplary single, double, triple, quadruple and quintuple substitutions (numbering (according to the EU index) and substitutions are relative to the amino acid sequence of SEQ ID NO:10 as presented above) of exemplary modification that increase binding activating receptors and/or reduce binding inhibitory receptors.

variant human IgG1 Fc Domain contains a F243L, R292P, Y300L, V305I and P396L substitution.

In certain embodiments, it is preferred for the Fc Domains of the Fc Domain-containing Binding Molecules of the present invention to exhibit decreased (or substantially no) binding FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Domain (SEQ ID NO:10)). In a specific embodiment, the Fc Domain-containing Binding Molecules of the present invention comprise an IgG Fc Domain that exhibits reduced antibody-dependent cell-mediated cytotoxicity (ADCC) effector function. In a preferred embodiment, the CH2-CH3 Domains of such Binding Molecules include any 1, 2, 3, or 4 of the substitutions: L234A, L235A, D265A, N297Q, and N297G, wherein the numbering is that of the EU index as in Kabat. In another embodiment, the CH2-CH3 Domains contain an N297Q substitution, an N297G substitution, L234A and L235A substitutions or a D265A substitution, as these mutations abolish FcR binding. Alternatively, a CH2-CH3 Domain of a naturally occurring Fc Domain that inherently exhibits decreased (or substantially no) binding FcγRIIIA (CD16a) and/or reduced effector function (relative to the binding and effector function exhibited by the wild-type IgG1 Fc Domain (SEQ ID NO:10)) is utilized. In a

TABLE 4

Variations of Preferred Activating Fc Domains†

Single-Site Variations

| | | | |
|---|---|---|---|
| F243L | R292G | D270E | R292P |
| Y300L | P396L | | |

Double-Site Variations

| | | | |
|---|---|---|---|
| F243L and R292P | F243L and Y300L | F243L and P396L | R292P and Y300L |
| D270E and P396L | R292P and V305I | P396L and Q419H | P247L and N421K |
| R292P and P396L | Y300L and P396L | R255L and P396L | R292P and P305I |
| K392T and P396L | | | |

Triple-Site Variations

| | |
|---|---|
| F243L, P247L and N421K | P247L, D270E and N421K |
| F243L, R292P and Y300L | R255L, D270E and P396L |
| F243L, R292P and V305I | D270E, G316D and R416G |
| F243L, R292P and P396L | D270E, K392T and P396L |
| F243L, Y300L and P396L | D270E, P396L and Q419H |
| V284M, R292L and K370N | R292P, Y300L and P396L |

Quadruple-Site Variations

| | |
|---|---|
| L234F, F243L, R292P and Y300L | F243L, P247L, D270E and N421K |
| L234F, F243L, R292P and Y300L | F243L, R255L, D270E and P396L |
| L235I, F243L, R292P and Y300L | F243L, D270E, G316D andR416G |
| L235Q, F243L, R292P and Y300L | F243L, D270E, K392T and P396L |
| P247L, D270E, Y300L and N421K | F243L, R292P, Y300L, and P396L |
| R255L, D270E, R292G and P396L | F243L, R292P, V305I and P396L |
| R255L, D270E, Y300L and P396L | F243L, D270E, P396L and Q419H |
| D270E, G316D, P396L and R416G | |

Quintuple-Site Variations

| | |
|---|---|
| L235V, F243L, R292P, Y300L and P396L | F243L, R292P, V305I, Y300L and P396L |
| L235P, F243L, R292P, Y300L and P396L | |

†numbering is according to the EU index as in Kabat

Exemplary variants of human IgG1 Fc Domains with reduced binding CD32B and/or increased binding CD16A contain F243L, R292P, Y300L, V305I or P396L substitutions, wherein the numbering is that of the EU index as in Kabat. These amino acid substitutions may be present in a human IgG1 Fc Domain in any combination. In one embodiment, the variant human IgG1 Fc Domain contains a F243L, R292P and Y300L substitution. In another embodiment, the specific embodiment, the Fc Domain-containing Binding Molecules of the present invention comprise an IgG2 Fc Domain (SEQ ID NO:11), an IgG3 Fc Domain (SEQ ID NO:12) or an IgG4 Fc Domain (SEQ ID NO:13). When an IgG4 Fc Domain is utilized, the instant invention also encompasses the introduction of a stabilizing mutation, such as the Hinge Region S228P substitution described above (see, e.g., SEQ ID NO:9). Since the N297G, N297Q, L234A, L235A and D265A substitutions abolish effector function, in circumstances in which effector function is desired, these substitutions would preferably not be employed.

A preferred IgG1 sequence for the CH2 and CH3 Domains of the Fc Domain-containing molecules of the present invention having reduced or abolished effector function will comprise the substitutions L234A/L235A (SEQ ID NO:45):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTIPPVLDS DGSFFLYSKL TVDKSRWQQG NVFSCSVMHE

ALHNHYTQKS LSLSPGX
wherein, X is a lysine (K) or is absent.
```

The serum half-life of proteins comprising Fc Domains may be increased by increasing the binding affinity of the Fc Domain for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's body (e.g., a human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the Fc Domain-containing Binding Molecules of the present invention comprise a variant Fc Domain that comprises at least one amino acid modification relative to a wild-type Fc Domain, such that the molecule has an increased half-life (relative to such molecule if comprising a wild-type Fc Domain). In some embodiments, the Fc Domain-containing Binding Molecules of the present invention comprise a variant IgG Fc Domain that comprises a half-life extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436, wherein the numbering is that of the EU index as in Kabat. Numerous mutations capable of increasing the half-life of an Fc Domain-containing molecule are known in the art and include, for example M252Y, S254T, T256E, and combinations thereof. For example, see the mutations described in U.S. Pat. Nos. 6,277,375, 7,083,784; 7,217,797, 8,088,376; U.S. Publication Nos. 2002/0147311; 2007/0148164; and PCT Publication Nos. WO 98/23289; WO 2009/058492; and WO 2010/033279, which are herein incorporated by reference in their entireties.

In some embodiments, the Fc Domain-containing Binding Molecules of the present invention exhibiting enhanced half-life possess a variant Fc Domain comprising substitutions at two or more of Fc Domain residues 250, 252, 254, 256, 257, 288, 307, 308, 309, 311, 378, 428, 433, 434, 435 and 436. In particular, two or more substitutions selected from: T250Q, M252Y, S254T, T256E, K288D, T307Q, V308P, A378V, M428L, N434A, H435K, and Y436I. In a specific embodiment, such molecules may possess a variant IgG Fc Domain comprising the substitution:
  (A) M252Y, S254T and T256E;
  (B) M252Y and S254T;
  (C) M252Y and T256E;
  (D) T250Q and M428L;
  (E) T307Q and N434A;
  (F) A378V and N434A;
  (G) N434A and Y436I;
  (H) V308P and N434A; or
  (I) K288D and H435K.

In a preferred embodiment, an Fc Domain-containing binding molecule of the present invention possesses a variant IgG Fc Domain comprising any 1, 2, or 3 of the substitutions: M252Y, S254T and T256E. The invention further encompasses such Binding Molecules that possess a variant Fc Domain comprising:
  (A) one or more mutations which alter effector function and/or FcγR binding; and
  (B) one or more mutations which extend serum half-life.

An IgG1 sequence for the CH2 and CH3 Domains of the Fc Domain-containing molecules of the present invention that provides an increased half-life (and that has a 10-fold increase in binding to both cynomolgus monkey and human FcRn) (Dall'Acqua, W. F. et al. (2006) "*Properties of Human IgG1s Engineered for Enhanced Binding to the Neonatal Fc Receptor (FcRn),*" J. Biol. Chem. 281(33): 23514-23524) will comprise the substitutions M252Y/S254T/T256E (SEQ ID NO:46):

```
APELLGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
wherein, X is a lysine (K) or is absent.
```

An alternative IgG1 sequence for the CH2 and CH3 Domains of the Fc Domain-containing molecules of the present invention combining the reduced or abolished effector function provided by the substitutions L234A/L235A and the increased serum half-life provided by the substitutions M252Y/S254T/T256E is provided by SEQ ID NO: 47:

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTIPPVLDS DGSFFLYSKL TVDKSRWQQG NVFSCSVMHE

ALHNHYTQKS LSLSPGX
wherein, X is a lysine (K) or is absent.
```

For certain antibodies, diabodies and trivalent Binding Molecules that are desired to have Fc-Domain-containing polypeptide chains of differing amino acid sequence (e.g., whose Fc Domain-containing polypeptide chains are desired to not be identical), it is desirable to reduce or prevent homodimerization from occurring between the CH2-CH3 Domains of identical chains (e.g., two first polypeptide chains or between the CH2-CH3 Domains of two third polypeptide chains). The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that forms an Fc Domain to foster heterodimerization. Methods of protein engineering to favor heterodimerization over homodimerization are well-known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety).

A preferred knob is created by modifying an IgG Fc Domain to contain the modification T366W. A preferred hole is created by modifying an IgG Fc Domain to contain the modification T366S, L368A and Y407V. To aid in purifying a hole-bearing polypeptide chain homodimer from the final bispecific heterodimeric Fc Domain-containing molecule, the protein A binding site of the hole-bearing CH2 and CH3 Domains a polypeptide chain is preferably mutated by amino acid substitution at position 435 (H435R). Thus, the hole-bearing polypeptide chain homodimer will not bind protein A, whereas the bispecific heterodimer will retain its ability to bind protein A via the protein A binding site on the knob-bearing polypeptide chain. In an alternative embodiment, the hole-bearing polypeptide chain may incorporate amino acid substitutions at positions 434 and 435 (N434A/N435K).

A preferred IgG1 amino acid sequence for the CH2 and CH3 Domains of one Fc Domain-containing polypeptide chain of an Fc Domain-containing molecule of the present invention will have the "knob-bearing" sequence (SEQ ID NO:48):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTIPPVLDS DGSFFLYSKL TVDKSRWQQG NVFSCSVMHE

ALHNHYTQKS LSLSPGX
wherein X is a lysine (K) or is absent.
```

An alternative IgG1 amino acid sequence for the CH2 and CH3 Domains of one Fc Domain-containing polypeptide chain of an Fc Domain-containing molecule of the present invention having a M252Y/S254T/T256E substitution and a "knob-bearing" sequence is SEQ ID NO:49:

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTIPPVLDS DGSFFLYSKL TVDKSRWQQG NVFSCSVMHE

ALHNHYTQKS LSLSPGX
wherein X is a lysine (K) or is absent.
```

A preferred IgG1 amino acid sequence for the CH2 and CH3 Domains of the other Fc Domain-containing polypeptide chain of an Fc Domain-containing molecule of the present invention will have the "hole-bearing" sequence (SEQ ID NO:50):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
wherein X is a lysine (K) or is absent.
```

An alternative IgG1 amino acid sequence for the CH2 and CH3 Domains of the other Fc Domain-containing polypeptide chain of an Fc Domain-containing molecule of the present invention having a M252Y/S254T/T256E substitution and a "hole-bearing" sequence is SEQ ID NO:51:

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFELVSKL TVDKSRWQQG NVFSCSVMHE

ALHNRYTQKS LSLSPGX
wherein X is a lysine (K) or is absent.
```

As will be noted, the CH2-CH3 Domains of SEQ ID NO:48, SEQ ID NO:49, SEQ ID NO:50 and SEQ ID NO:51 include a substitution at position 234 with alanine and 235 with alanine, and thus form an Fc Domain exhibit decreased (or substantially no) binding FcγRIA (CD64), FcγRIIA (CD32A), FcγRIIB (CD32B), FcγRIIIA (CD16a) or FcγRIIIB (CD16b) (relative to the binding exhibited by the wild-type Fc Domain (SEQ ID NO:10)). The invention also encompasses such CH2-CH3 Domains, which comprise the wild-type alanine residues, alternative and/or additional substitutions which modify effector function and/or FγR binding activity of the Fc Domain. The invention also encompasses such CH2-CH3 Domains, which further comprise one or more half-live extending amino acid substitutions. In particular, the invention encompasses such hole-bearing and such knob-bearing CH2-CH3 Domains which further comprise the M252Y/S254T/T256E.

An IgG4 amino acid sequence for the CH2 and CH3 Domains of the first polypeptide chain of an Fc Domain-containing molecule of the present invention has enhanced serum half-life (relative to IgG1 CH2 and CH3 Domains) due to its possession of Y252/T254/E256 (SEQ ID NO:52):

```
APEFLGGPSV FLFPPKPKDT LYITREPEVT CVVVDVSQED
PEVQFNWYVD GVEVHNAKTK PREEQFNSTY RVVSVLTVLH
QDWLNGKEYK CKVSNKGLPS SIEKTISKAK GQPREPQVYT
LPPSQEEMTK NQVSLTCLVK GFYPSDIAVE WESNGQPENN
YKTTPPVLDS DGSFFLYSRL TVDKSRWQEG NVFSCSVMHE
ALHNHYTQKS LSLSLGX
wherein X is a lysine (K) or is absent.
```

A "knob-bearing" variant of such an IgG4 CH2-CH3 amino acid sequence has the amino acid sequence of SEQ ID NO:53:

```
APEFLGGPSV FLFPPKPKDT LYITREPEVT CVVVDVSQED
PEVQFNWYVD GVEVHNAKTK PREEQFNSTY RVVSVLTVLH
QDWLNGKEYK CKVSNKGLPS SIEKTISKAK GQPREPQVYT
LPPSQEEMTK NQVSLWCLVK GFYPSDIAVE WESNGQPENN
YKTTPPVLDS DGSFFLYSRL TVDKSRWQEG NVFSCSVMHE
ALHNHYTQKS LSLSLGX
wherein X is a lysine (K) or is absent.
```

A "hole-bearing" variant of such an IgG4 CG2-CH3 amino acid sequence has the amino acid sequence of SEQ ID NO:54:

```
APEFLGGPSV FLFPPKPKDT LYITREPEVT CVVVDVSQED
PEVQFNWYVD GVEVHNAKTK PREEQFNSTY RVVSVLTVLH
QDWLNGKEYK CKVSNKGLPS SIEKTISKAK GQPREPQVYT
LPPSQEEMTK NQVSLSCAVK GFYPSDIAVE WESNGQPENN
YKTTPPVLDS DGSFFLVSRL TVDKSRWQEG NVFSCSVMHE
ALHNRYTQKS LSLSLGX
wherein X is a lysine (K) or is absent.
```

It is preferred that the first polypeptide chain will have a "knob-bearing" CH2-CH3 sequence, such as that of SEQ ID NO:48 or SEQ ID NO:49. However, as will be recognized, a "hole-bearing" CH2-CH3 Domain (e.g., SEQ ID NO:50 or SEQ ID NO:51) could be employed in the first polypeptide chain, in which case, a "knob-bearing" CH2-CH3 Domain (e.g., SEQ ID NO:48 or SEQ ID NO:49) would be employed in the second polypeptide chain of an Fc Domain-containing molecule of the present invention having two polypeptide chains (or in the third polypeptide chain of an Fc Domain-containing molecule having three, four, or five polypeptide chains).

In other embodiments, the invention encompasses Fc Domain-containing Binding Molecules comprising CH2 and/or CH3 Domains that have been engineered to favor heterodimerization over homodimerization using mutations known in the art, such as those disclosed in PCT Publication No. WO 2007/110205; WO 2011/143545; WO 2012/058768; WO 2013/06867, all of which are incorporated herein by reference in their entirety.

III. Trivalent Binding Molecules Containing Fc Domains

A further embodiment of the present invention relates to trivalent Binding Molecules comprising an Fc Domain capable of simultaneously binding a first epitope, a second epitope and a third epitope, wherein at least one of such epitopes is not identical to another. Such trivalent Binding Molecules comprise three Epitope-Binding Domains, two of which are Diabody-Type Binding Domains, which provide binding Site A and binding Site B, and one of which is a Fab-Type Binding Domain, or an scFv-Type Binding Domain, which provides binding Site C (see, e.g., FIGS. 6A-6F, PCT Publication Nos. WO 2015/184207 and WO 2015/184203). Such trivalent Binding Molecules thus comprise "VL1"/"VH1" domains that are capable of binding the first epitope and "VL2"/"VH2" domains that are capable of binding the second epitope and "VL3" and "VH3" domains that are capable of binding the "third" epitope of such trivalent binding molecule. A "Diabody-Type Binding Domain" is the type of Epitope-Binding Domain present in a diabody, as described above. Each of a "Fab-Type Binding Domain" and an "scFv-Type Binding Domain" are Epitope-Binding Domains that are formed by the interaction of the VL Domain of an immunoglobulin Light Chain and a complementing VH Domain of an immunoglobulin Heavy Chain. Fab-Type Binding Domains differ from Diabody-Type Binding Domains in that the two polypeptide chains that form a Fab-Type Binding Domain comprise only a single Epitope-Binding Domain, whereas the two polypeptide chains that form a Diabody-Type Binding Domain comprise at least two Epitope-Binding Domains. Similarly, scFv-Type Binding Domains also differ from Diabody-Type Binding Domains in that they comprise only a single Epitope-Binding Domain. Thus, as used herein Fab-Type, and scFv-Type Binding Domains are distinct from Diabody-Type Binding Domains.

Typically, the trivalent Binding Molecules of the present invention will comprise four different polypeptide chains (see FIGS. 6A-6B), however, the molecules may comprise fewer or greater numbers of polypeptide chains, for example by fusing such polypeptide chains to one another (e.g., via a peptide bond) or by dividing such polypeptide chains to form additional polypeptide chains, or by associating fewer or additional polypeptide chains via disulfide bonds. FIGS. 6C-6F illustrate this aspect of the present invention by schematically depicting such molecules having three polypeptide chains. As provided in FIGS. 6A-6F, the trivalent Binding Molecules of the present invention may have alternative orientations in which the Diabody-Type Binding Domains are N-terminal (FIGS. 6A, 6C and 6D) or C-terminal (FIGS. 6B, 6E and 6F) to an Fc Domain. CH2 and CH3 Domains useful for the generation of trivalent Binding Molecules are provided above and include knob-bearing and hole-bearing domains.

In certain embodiments, the first polypeptide chain of such trivalent Binding Molecules of the present invention contains: (i) a VL1-containing Domain, (ii) a VH2-containing Domain, (iii) a Heterodimer-Promoting Domain, and (iv) a Domain containing a CH2-CH3 sequence. The VL1 and VL2 Domains are located N-terminal or C-terminal to the CH2-CH3-containing domain as presented in Table 4 (also see, FIGS. 6A and 6B). The second polypeptide chain of such embodiments contains: (i) a VL2-containing Domain, (ii) a VH1-containing Domain, and (iii) a Heterodimer-Promoting Domain. The third polypeptide chain of such embodiments contains: (i) a VH3-containing Domain, (ii) a CH1-containing Domain and (iii) a Domain containing a CH2-CH3 sequence. The third polypeptide chain may be the Heavy Chain of an antibody that contains a VH3 and a Heavy Chain constant region, or a polypeptide that contains such domains. The fourth polypeptide of such embodiments contains: (i) a VL3-containing Domain and (ii) a CL-containing Domain. The fourth polypeptide chains may be a Light Chain of an antibody that contains a VL3 complementary to the VH3 of the third polypeptide chain, or a polypeptide that contains such domains. The third or fourth polypeptide chains may be isolated from naturally occurring antibodies. Alternatively, they may be constructed recombinantly, synthetically or by other means.

The Light Chain Variable Domain of the first and second polypeptide chains are separated from the Heavy Chain Variable Domains of such polypeptide chains by an intervening spacer peptide having a length that is too short to permit their VL1/VH2 (or their VL2/VH1) Domains to associate together to form Epitope-Binding Domain capable of binding either the first or second epitope. A preferred intervening spacer peptide (Linker 1) for this purpose has the sequence (SEQ ID NO:16): GGGSGGGG. Other Domains of the trivalent Binding Molecules may be separated by one or more intervening spacer peptides (Linkers), optionally comprising a cysteine residue. In particular, as provided above, such Linkers will typically be incorporated between Variable Domains (i.e., VH or VL) and peptide Heterodimer-Promoting Domains (e.g., an E-coil or K-coil) and between such peptide Heterodimer-Promoting Domains (e.g., an E-coil or K-coil) and CH2-CH3 Domains. Exemplary Linkers useful for the generation of trivalent Binding Molecules are provided above and are also provided in PCT Application Nos: PCT/US15/33081; and PCT/US15/33076. Thus, the first and second polypeptide chains of such trivalent Binding Molecules associate together to form a VL1/VH1 binding site capable of binding a first epitope, as well as a VL2/VH2 binding site that is capable of binding a second epitope. The third and fourth polypeptide chains of such trivalent Binding Molecules associate together to form a VL3/VH3 binding site that is capable of binding a third epitope.

As described above, the trivalent Binding Molecules of the present invention may comprise three polypeptides. Trivalent Binding Molecules comprising three polypeptide chains may be obtained by linking the domains of the fourth polypeptide N-terminal to the VH3-containing Domain of the third polypeptide (e.g., using an intervening spacer peptide (Linker 4)). Alternatively, a third polypeptide chain of a trivalent binding molecule of the invention containing the following domains is utilized: (i) a VL3-containing Domain, (ii) a VH3-containing Domain, and (iii) a Domain containing a CH2-CH3 sequence, wherein the VL3 and VH3 are spaced apart from one another by an intervening spacer peptide that is sufficiently long (at least 9 or more amino acid residues) so as to allow the association of these domains to form an Epitope-Binding Domain. One preferred intervening spacer peptide for this purpose has the sequence: GGGGSGGGGSGGGGS (SEQ ID NO:41).

It will be understood that the VL1/VH1, VL2/VH2, and VL3/VH3 Domains of such trivalent Binding Molecules may be different so as to permit binding that is monospecific, bispecific or trispecific. In particular, the VL and VH Domains may be selected such that a trivalent binding molecule comprises two binding sites for a first epitope and one binding sites for a second epitope, or one binding site for a first epitope and two binding sites for a second epitope, or one binding site for a first epitope, one binding site for a second epitope and one binding site for a third epitope.

The general structure of the polypeptide chains of representative trivalent Binding Molecules of invention is provided in FIGS. 6A-6F and in Table 5:

TABLE 5

| | | |
|---|---|---|
| Four | $2^{nd}$ Chain | NH$_2$—VL2—VH1—HPD—COOH |
| Chain | $1^{st}$ Chain | NH$_2$—VL1—VH2—HPD—CH2—CH3—COOH |
| $1^{st}$ Orientation | $3^{rd}$ Chain | NH$_2$—VH3—CH1—CH2—CH3—COOH |
| | $2^{nd}$ Chain | NH$_2$—VL3—CL—COOH |
| Four | $2^{nd}$ Chain | NH$_2$—VL2—VH1—HPD—COOH |
| Chain | $1^{st}$ Chain | NH$_2$—CH2—CH3—VL1—VH2—HPD—COOH |
| 2nd Orientation | $3^{rd}$ Chain | NH$_2$—VH3—CH1—CH2—CH3—COOH |
| | $2^{nd}$ Chain | NH$_2$—VL3—CL—COOH |
| Three | $2^{nd}$ Chain | NH$_2$—VL2—VH1—HPD—COOH |
| Chain | $1^{st}$ Chain | NH$_2$—VL1—VH2—HPD—CH2—CH3—COOH |
| 1st Orientation | $3^{rd}$ Chain | NH$_2$—VL3—VH3—HPD—CH2—CH3—COOH |
| Three | $2^{nd}$ Chain | NH$_2$—VL2—VH1—HPD—COOH |
| Chain | $1^{st}$ Chain | NH$_2$—CH2—CH3—VL1—VH2—HPD—COOH |
| $2^{nd}$ Orientation | $3^{rd}$ Chain | NH$_2$—VL3—VH3—HPD—CH2—CH3—COOH |

HPD = Heterodimer-Promoting Domain

As provided above, such trivalent Binding Molecules may comprise three, four, five, or more polypeptide chains.

IV. Embodiments of the Invention

As stated above, the present invention is directed to DA×CD3 Binding Molecules comprising a vCD3-Binding Domain that comprises a CDR$_H$1 Domain, a CDR$_H$2 Domain, a CDR$_H$3 Domain, a CDR$_L$1 Domain, a CDR$_L$2 Domain, and a CDR$_L$3 Domain, at least one of which differs in amino acid sequence from the amino acid sequence of the corresponding CDR of an rCD3-Binding Domain. The rCD3-Binding Domain that is to be employed in such comparison with a particular vCD3-Binding Domain is the CD3-Binding Domain of an isolated CD3-binding antibody that exhibits the greatest identity of CDR sequence with such particular vCD3-Binding Domain. The rCD3-Binding Domain preferably also exhibits at least 95% to 100% identity in the framework regions. A preferred rCD3-Binding Domain comprises the CDR$_H$1 Domain, CDR$_H$2 Domain, CDR$_H$3 Domain, CDR$_L$1 Domain, CDR$_L$2 Domain, and CDR$_L$3 Domain of CD3 mAb-1. The DA×CD3 Binding Molecules of the present invention that comprise such vCD3-Binding Domain exhibit an altered affinity for CD3, relative to a DA×CD3 Binding Molecule comprising such rCD3-Binding Domain. The invention particularly concerns to such DA×CD3 Binding Molecules comprising a vCD3-Binding Domain which exhibit reduced affinity for CD3 and are capable of mediating redirected killing of target cells expressing a Disease Antigen, and exhibit reduced levels of cytokine release relative to a DA×CD3 Binding Molecule comprising a rCD3-Binding Domain. The invention particularly concerns the use of DA×CD3 Binding Molecules comprising a vCD3-Binding Domain in the treatment of cancer and pathogen-associated diseases. The present invention is also directed to pharmaceutical compositions that comprise such molecule(s).

The invention thus encompasses DA×CD3 Binding Molecules comprising one or more of the VH and/or VL Domains of a vCD3-Binding Domain, or more preferably, the CDR$_H$1, CDR$_H$2, and CDR$_H$3, and the CDR$_L$1, CDR$_L$2 and CDR$_L$3 portions of such Domains. In a preferred embodiment of the invention, such DAxCD3 Binding Molecules Binding Molecules will additionally contain binding domains sufficient to permit such molecules to bind to epitope(s) of one, two, or more Disease Antigens. In another preferred embodiment of the invention, such DAxCD3 Binding Molecules will additional contain binding domains sufficient to permit such molecules to bind to epitope(s) of another molecule expressed on the surface of an effector cell, such as CD2, CD8, CD16, T-cell Receptor (TCR), NKp46, NKG2D, etc., which are expressed on T lymphocytes, Natural Killer (NK) cells, Antigen-Presenting Cells or other mononuclear cells).

The present invention is also directed to pharmaceutical compositions that comprise such DAxCD3 Binding Molecule(s).

By possessing binding domains sufficient to immunospecifically bind CD3 and a Disease Antigen, the molecules of the present invention have the ability to mediate the redirected killing of a target cell (e.g., a cancer cell or a pathogen-infected cell) that arrays the Disease Antigen on its surface. The combined presence of both such binding affinities serves to localize the a CD3-expressing effector cell to the site of the target cell (i.e., to "redirect" the effector cell) so that it may mediate the killing of the target cell. As discussed above, such molecules may be bispecific, or may be capable of binding more than two epitopes (e.g., trispecific).

Efforts to employ CD3 Binding Molecules have been encumbered by the high magnitude of immune activation caused by such therapies and the attendant and adverse production of high levels of cytokines in some patients. Thus, although anti-CD3 therapies have resulted in a significant degree of immune activation in recipient patients, which has correlated with greatly increased efficacy, the use of such molecules has been associated with notable toxicity (Frey, N. V. et al. (2016) "*Cytokine Release Syndrome With Novel Therapeutics For Acute Lymphoblastic Leukemia,*" Hematol. Am. Soc. Hematol. Educ Program. (1):567-572; Teachey, D. T. et al. (2013) "*Cytokine Release Syndrome After Blinatumomab Treatment Related To Abnormal Macrophage Activation And Ameliorated With Cytokine-Directed Therapy,*" Blood 121(26):5154-5157; Le Jeune, C. et al. (2016) "*Potential For Bispecific T-Cell Engagers: Role Of Blinatumomab In Acute Lymphoblastic Leukemia,*" Drug Des. Devel. Ther. 10:757-765; Newman, M. J. et al. (2016) "*A Review Of Blinatumomab, A Novel Immunotherapy,*" J. Oncol. Pharm. Pract. 22(4):639-645; Fitzgerald, J. C. et al. (2017) "*Cytokine Release Syndrome After Chimeric Antigen Receptor T-Cell Therapy for Acute Lymphoblastic Leukemia,*" Crit. Care Med. 45(2):e124-e131; Teachey, D. T. et al. (2016) "*Identification of Predictive Biomarkers for Cytokine Release Syndrome after Chimeric Antigen Receptor T-cell Therapy for Acute Lymphoblastic Leukemia,*" Cancer Discov. 6(6):664-679; Goebeler, M. E. et al. (2016) "*Blinatumomab: A CD19/CD3 Bispecific T Cell Engager (Bite) With Unique Anti-Tumor Efficacy,*" Leuk. Lymphoma 57(5): 1021-1032; Barrett, D. M. et al. (2014) "*Toxicity Management For Patients Receiving Novel T-Cell Engaging Therapies,*" Curr. Opin. Pediatr. 26(1):43-49).

The present invention addresses such encumbrance by demonstrating that parental CD3-Binding Domains rCD3-Binding Domains) that exhibit both high cytotoxicity and high cytokine release when incorporated into DAxCD3 Binding Molecules may be engineered to produce variants (i.e., vCD3-Binding Domains) having altered affinity for CD3 that are capable of mediating redirected killing and exhibit reduced levels of cytokine release relative to a DAxCD3 Binding Molecule comprising a rCD3-Binding Domain. In particular, DAxCD3 Binding Molecules comprising a vCD3-Binding Domains of the invention exhibit reduced levels of release of any one or more of: IFN-γ, TNF-α, IL-2, and/or IL-6.

The present invention stems, in part, from the recognition that cytotoxicity and cytokine release are separable properties of DAxCD3 Binding Molecules. The present invention encompasses variant CD3-Binding Domains (i.e., vCD3-Binding Domains) that retain high levels of cytotoxicity while exhibiting reduced levels of cytokine release, and the use of DAxCD3 Binding Molecules comprising such vCD3-Binding Domains in the treatment of disease. As used herein, the term "variant" with respect to such CD3-Binding Domains is intended to refer to CD3-Binding Domains having at least one $CDR_H$, and/or at least one $CDR_L$, that differs from the "corresponding" $CDR_H$ and/$CDR_L$ of a "reference" CD3-Binding Domain (i.e., rCD3-Binding Domain). As used herein the term "corresponding" $CDR_H$ and/$CDR_L$ denotes a comparison between two CDR sequences in which both such CDRs are $CD_H1$ Domains, both such CDRs are $CD_H2$ Domains, both such CDRs are $CD_H3$ Domains, both such CDRs are $CD_L1$ Domains, both such CDRs are $CD_L2$ Domains, or both such CDRs are $CD_L3$ Domains. A preferred rCD3-binding domain for the exemplary vCD3-binding domains described herein is a CD3-Binding Domain having at least 5, at least 4, at least 3, at least 2 or at least 1 of the CDRs: $CD_H1$, $CDR_H2$, $CDR_H3$ and $CD_L1$, $CDR_L2$, and $CDR_L3$ of CD3 mAb 1. Preferably, such exemplary vCD3-binding domains will possess at least 5 of the CDRs: $CD_H1$, $CDR_H2$, $CDR_H3$ and $CD_L1$, $CDR_L2$, and $CDR_L3$ of CD3 mAb 1. vCD3-binding domains may be obtained through the chemical modification of one or more CDRs of the rCD3-Binding Domain, but will more preferably be obtained by forming one or more polynucleotides that encode such one or more CDRs of the rCD3-binding Domain, except being altered to encode the desired vCD3-Binding Domain, and then expressing such polynucleotide in an appropriate protein expression system (e.g., a cell, or in vitro translation system). Cytotoxicity may be measured in any suitable manner (e.g., a CTL assay to determine the $EC_{50}$, maximum, etc.). Cytokine release may be measured by assaying for any one or more of: IFN-gamma, TNF-alpha, IL-6 or IL-2 in any suitable manner (e.g., a CTL assay to determine the $EC_{50}$, maximum, etc.).

Notably, the absolute levels of maximal cytotoxicity and cytokine release are not the only criteria used to assess whether a candidate CD3-Binding Domain is a suitable vCD3-Binding Domain encompassed by the present invention. In addition, or alternatively, $EC_{50}$ values may be employed. As provided herein, a suitable vCD3-Binding Domain is one that, when incorporated into a DAxCD3 Binding Molecule, is capable of mediating high levels of cytotoxicity (i.e., a low $EC_{50}$ concentration) while exhibiting reduced levels of cytokine release.

In certain embodiments, the instant invention provides a vCD3-Binding Domain that, when incorporated into a DAxCD3 Binding Molecule, mediates cell redirected cell killing to a maximum cytotoxicity (e.g., as measured in a CTL assay at 18-48 hours) that is at least about 60%, at least about 70%, at least about 80%, at least about 90%, at least about 100%, of that mediated by a DAxCD3 Binding Molecule comprising a rCD3-Binding Domain. Additionally, or alternatively, a DAxCD3 Binding Molecule comprising a vCD3-Binding Domains of the invention exhibits an $EC_{50}$ of cytotoxicity (e.g., a measured in a CTL assay at 18-48 hours) that is increased by less than about 10%, less than about 20%, less than about 30%, less than about 40%, less than about 50%, less than about 60%, less than about 70%, less than about 80%, less than about 90%, less than about 100%, less than about 200%, less than about 300%, less than about 400%, or less than about 500% of that exhibited by a DA×CD3 Binding Molecule comprising a rCD3-Binding Domain. Additionally, or alternatively the ratio of the $EC_{50}$ of cytotoxicity (e.g., as measured in a CTL assay at 18-24 hours) of a DA×CD3 Binding Molecule comprising a vCD3-Binding Domain of the invention to a DA×CD3 Binding Molecule comprising the rCD3-Binding Domain ($EC_{50}$ variant/$EC_{50}$ reference) is less than about 2, is less than about 5, is less than about 10, is less than about 20, is less than about 40, is less than about 60, is less than about 80, is less than about 100, or is less than about 200.

In certain embodiments, a DA×CD3 Binding Molecule comprising a vCD3-Binding Domains of the invention exhibits a maximum release of one or more cytokine (e.g., as measured in a CTL assay at 18-24 hours) that is reduced by at least about 10%, at least about 20%, at least about 30%, at least about 40%, at least about 50%, at least about 60%, at least about 70%, at least about 80%, at least about 90%, or more of that exhibited by a DA×CD3 Binding Molecule comprising a rCD3-Binding Domain. Additionally, or alternatively, DA×CD3 Binding Molecules comprising the vCD3-Binding Domains of the invention exhibit an $EC_{50}$ of release of one or more cytokine (e.g., as measured in a CTL assay at 18-48 hours) that is increased by at least about 10%, at least about 20%, at least about 30%, at least about 40%, at least about 50%, at least about 60%, at least about 70%, at least about 80, at least about 90%, or more of that exhibited by a DA×CD3 Binding Molecule comprising a rCD3-Binding Domain. In particular embodiments, the cytokine released is selected from the group consisting of: IFN-γ, TNF-α, IL-2, and IL-6. Additionally, or alternatively the ratio of the $EC_{50}$ of release of one or more cytokine (e.g., as measured in a CTL assay at 18-24 hours) of a DA×CD3 Binding Molecule comprising a vCD3-Binding Domain of the invention to a DA×CD3 Binding Molecule comprising the rCD3-Binding Domain ($EC_{50}$ variant/$EC_{50}$ reference) is more that about 1, is more than about 2, is more than about 5, is more than about 10, is more than about 20, is more than about 40, is more than about 60, is more than about 80, is more than about 100, or is more than about 200.

Additionally, DA×CD3 Binding Molecules comprising a vCD3-Binding Domain of the invention retain at least about 50%, at least about 60%, at least about 70%, at least about 80%, at least about 90%, at least about 100%, of an in vivo activity (e.g., anti-tumor, anti-pathogen activity) exhibited by a DA×CD3 Binding Molecule comprising a rCD3-Binding Domain. In view of the instant disclosure it will be understood that DA×CD3 Binding Molecules comprising a vCD3-Binding Domain may be administered at a higher dose to achieve an in vivo activity that is at least about 50% or more of that exhibited by a DA×CD3 Binding Molecule comprising a rCD3-Binding Domain, but that such higher dose will exhibit reduced levels of cytokine release as compared to the DA×CD3 Binding Molecule comprising a rCD3-Binding Domain.

In one embodiment, such DA×CD3 Binding Molecules of the present invention will be monospecific so as to possess the ability to bind to only a single epitope of CD3 and only a single epitope of the Disease Antigen.

Alternatively, such DA×CD3 Binding Molecules may be multispecific, i.e., capable of binding 1, 2, 3, 4, or more than 4 epitopes, which may be apportioned in any manner to bind 1, 2, or more epitope(s) of CD3 and 1, 2, 3, 4, or more than 4 epitope(s) of one or more Disease Antigen(s).

In certain embodiments, where such DA×CD3 Binding Molecules are capable of immunospecifically binding to only a single Disease Antigen, they may be capable of immunospecifically binding to only one CD3 epitope and to one, two epitope(s) of such Disease Antigen (which two Disease Antigen epitopes may be the same or different), or they may be capable of immunospecifically binding to only one CD3 epitope and to three epitope(s) of such Disease Antigen (which three Disease Antigen epitopes may be the same, or may be different, or may be two epitopes that are the same and one epitope that is different).

In other embodiments, where such DA×CD3 Binding Molecules are capable of immunospecifically binding to two different Disease Antigens (e.g., a First Disease Antigen and a Second Disease Antigen), they may be capable of immunospecifically binding to only one CD3 epitope and to one or two epitope(s) of the First Disease Antigen (which two First Disease Antigen epitopes may be the same or different) and two or one epitope(s) of the Second Disease Antigen (which two Second Disease Antigen epitopes may be the same or different).

In still other embodiments, such DA×CD3 Binding Molecules may be capable of immunospecifically binding to three different Disease Antigens (e.g., a First Disease Antigen, a Second Disease Antigen and a Third Disease Antigen) and only one CD3 epitope.

In still other embodiments, such DA×CD3 Binding Molecules may be capable of immunospecifically binding to one or two different Disease Antigens (e.g., a First Disease Antigen and a Second Disease Antigen), only one CD3 epitope, and one or two different cell surface molecules (which may be the same cell surface molecule or may be different surface molecules) of an effector cell (which may be the same type of effector cell or may be a different type of effector cell).

Thus, for example, such DA×CD3 Binding Molecules may bind:
(1) a single epitope of CD3 and a single epitope of a Disease Antigen that is arrayed on the surface of the target cell;
(2) a single epitope of CD3 and two epitopes of the same Disease Antigen that is arrayed on the surface of the target cell;
(3) a single epitope of CD3, an epitope of a First Disease Antigen that is arrayed on the surface of the target cell and an epitope of a Second Disease Antigen that is arrayed on the surface of the target cell;
(4) a single epitope of CD3 and three epitopes of the same Disease Antigen that is arrayed on the surface of the target cell;
(5) a single epitope of CD3, two epitopes of a First Disease Antigen that is arrayed on the surface of the target cell, and one epitope of a Second Disease Antigen that is arrayed on the surface of the target cell;
(6) a single epitope of CD3, an epitope of a First Disease Antigen that is arrayed on the surface of the target cell, and an epitope of a Second Disease Antigen that is arrayed on the surface of the target cell;
(7) a single epitope of CD3, a single epitope of a Disease Antigen that is arrayed on the surface of the target cell and a single epitope of a cell surface molecule other than CD3 that is arrayed on the surface of an effector cell (which may be the same type of effector cell as that arraying CD3 or may be a different type of effector cell);

(8) a single epitope of CD3, two epitopes of a Disease Antigen that is arrayed on the surface of the target cell and a single epitope of a cell surface molecule other than CD3 that is arrayed on the surface of an effector cell (which may be the same type of effector cell as that arraying CD3 or may be a different type of effector cell);
(9) a single epitope of CD3, an epitope of a First Disease Antigen that is arrayed on the surface of the target cell, an epitope of a Second Disease Antigen that is arrayed on the surface of the target cell and a single epitope of a cell surface molecule other than CD3 that is arrayed on the surface of an effector cell (which may be the same type of effector cell as that arraying CD3 or may be a different type of effector cell);
(10) a single epitope of CD3, an epitope of a Disease Antigen that is arrayed on the surface of the target cell, and two epitopes of a cell surface molecule other than CD3 that is arrayed on the surface of an effector cell (which may be the same type of effector cell as that arraying CD3 or may be a different type of effector cell); or
(11) a single epitope of CD3, an epitope of a Disease Antigen that is arrayed on the surface of the target cell, an epitope of a first cell surface molecule other than CD3 that is arrayed on the surface of an effector cell (which may be the same type of effector cell as that arraying CD3 or may be a different type of effector cell), and an epitope of a second cell surface molecule other than CD3 that is arrayed on the surface of an effector cell (which may be the same type of effector cell as that arraying CD3 or may be a different type of effector cell).

The invention thus contemplates DA×CD3 Binding Molecules that comprise a first Epitope-Binding Domain capable of immunospecifically binding an epitope of CD3 and a second Epitope-Binding Domain that is capable of immunospecifically binding an epitope of a Disease Antigen that is arrayed on the surface of such target cell and a third Epitope-Binding Domain capable of immunospecifically binding an epitope of a different cell surface molecule of an effector cell (which may be the same type of effector cell or may be a different type of effector cell). In a specific embodiment, the different cell surface molecule of an effector cell is CD8. Table 6 illustrates possible combination binding specificities of exemplary molecules of the invention.

TABLE 6

Number of Epitopes Recognized by Exemplary Molecules of the Invention Capable of Mediating the Redirected Killing of a Target Cell

| Total Number of Binding Domains | CD3 Epitope | Other Effector Cell Epitope | $1^{st}$ Disease Antigen Epitope | $2^{nd}$ Disease Antigen Epitope | $3^{rd}$ Disease Antigen Epitope |
|---|---|---|---|---|---|
| 2 | 1 | 0 | 1 | 0 | 0 |
| 3 | 1 | 0 | 1 | 1 | 0 |
| 3 | 1 | 1 | 1 | 0 | 0 |
| 3 | 1 | 0 | 1 | 0 | 1 |
| 3 | 2 | 0 | 1 | 0 | 0 |
| 4 | 1 | 0 | 1 | 1 | 1 |
| 4 | 1 | 0 | 1 | 2 | 0 |
| 4 | 1 | 0 | 2 | 1 | 0 |
| 4 | 1 | 1 | 2 | 0 | 0 |
| 4 | 1 | 1 | 1 | 1 | 0 |
| 4 | 1 | 2 | 1 | 0 | 0 |

TABLE 6-continued

Number of Epitopes Recognized by Exemplary Molecules of the Invention Capable of Mediating the Redirected Killing of a Target Cell

| Total Number of Binding Domains | CD3 Epitope | Other Effector Cell Epitope | $1^{st}$ Disease Antigen Epitope | $2^{nd}$ Disease Antigen Epitope | $3^{rd}$ Disease Antigen Epitope |
|---|---|---|---|---|---|
| 4 | 2 | 0 | 1 | 1 | 0 |
| 4 | 2 | 0 | 1 | 1 | 0 |
| 4 | 2 | 1 | 1 | 0 | 0 |

By forming more complex molecules, one may obtain DA×CD3 Binding Molecules that are capable of binding CD3 and one or more Disease Antigens and optionally a different cell surface molecule of an effector cell that possess more than four Epitope-Binding Domains. No limitation is placed on the nature or number of epitopes or additional epitopes that may be bound by the molecules of the present invention other than that such additional binding capability does not prevent the molecule or Binding Domain thereof that is capable of binding to an epitope of CD3 from such binding and does not prevent the molecule or Binding Domain thereof that is capable of binding to an epitope of a Disease Antigen from such binding, so that the molecule(s) may mediate the redirected killing of the target cell.

V. Exemplary Binding Molecules

The present invention is directed to DA×CD3 Binding Molecules (e.g., a diabody, a bispecific antibody, a bispecific, a trivalent molecule, a BiTe, a TandAb, etc.) capable of binding to CD3 and a Disease Antigen, such as a Cancer Antigen or a Pathogen-Associated Antigen. Such Binding Molecules can be readily produced from the CDRs of antibodies and from the VL and VH Domains of antibodies. Listed below are exemplary antibodies that may be used to produce the Binding Molecules and combination therapy of the present invention.

A. Anti-CD3 Antibody CD3 mAb 1

The present invention employs variant CD3-Binding Domains (i.e., vCD3-Binding Domains) that comprise the Light Chain Variable (VL) Domain and the Heavy Chain Variable (VH) Domain of anti-human CD3 antibodies, or CD3-binding portions thereof, and that mediate variant binding to CD3. As used herein, the term "variant binding" is intended to refer to the comparative binding exhibited by the CD3-Binding Domains of a reference antibody whose CDRs exhibit the highest sequence identity to the CDRs of the variant CD3-Binding Domain. The CD3-binding reference antibody for the illustrative vCD3-Binding Domains of the present invention is CD3 mAb 1, whose rCD3-Binding Domain is capable of binding human CD3 and CD3 of non-human primates (e.g., cynomolgus monkey).

The amino acid sequence of the VH Domain of CD3 mAb 1 (SEQ ID NO:55) is shown below (CDR$_H$ residues are shown underlined):

```
EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HGNFGNSYVS WFAYWGQGTL

VTVSS
wherein X is aspartate (D) or glycine (G)
```

The amino acid sequence of the VL Domain of CD3 mAb 1 (SEQ ID NO:56) is shown below (CDR$_L$ residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
```

| CD3 mAb 1 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

The rCD3-Binding Domain of "CD3 mAb 1" comprises a CD3 mAb 1 VH Domain having either aspartate (D) or glycine (G) at Kabat position 65, corresponding to residue 68 of SEQ ID NO:55) (i.e., X in SEQ ID NO:55 is aspartate (D) or glycine (G)) and the VL Domain of CD3 mAb 1 (SEQ ID NO:56). Thus, for example, when such CD3 mAb 1 VH Domain has a glycine (G) as its residue 68, its sequence is SEQ ID NO:63, shown below (CDR$_H$ residues are shown underlined, Kabat position 65 is shown in double underline):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVS WFAYWGQGTL

VTVSS
```

CD3-Binding Molecules that possess a vCD3-Binding Domain of the present invention may be recognized using a CTL assay in which:
(1) a bispecific Cancer Antigen×CD3 diabody (for example, a CD123×CD3 diabody or a 5T4×CD3 diabody) potentially having a vCD3-Binding Domain, and
(2) a bispecific Cancer Antigen×CD3 diabody having a corresponding rCD3-Binding Domain (e.g., the rCD3-Binding Domain of CD3 mAb 1),
are separately incubated with effector Pan-T-cells (or PBMCs) and target tumor cells (e.g., MOLM-13 or A498 cells), for example, at an effector:target cell ratio of 5:1 (or 15:1 for PBMCs) for 18, 24, or 42 hours, and the percentage cytotoxicity (i.e., cell killing) and/or EC$_{50}$ is determined (for example, by measuring the release of lactate dehydrogenase (LDH) into the media by damaged cells using the CytoTox 96® Non-Radioactive Cytotoxicity Assay Kit (Promega)). In one embodiment, the release of IFN-γ, TNF-α, IL-6, and IL-2 cytokines may be determined at the end of the CTL assay. CD4+ and CD8+ T lymphocyte populations may also be assessed for up-regulation of the activation markers CD69 and CD25 at the end of the CTL assay. A comparison of the percentage cytotoxicity and/or EC$_{50}$ for the bispecific Cancer Antigen×CD3 diabody potentially having a vCD3-Binding Domain with that of the Cancer Antigen×CD3 diabody having the rCD3-Binding Domains identifies vCD3-binding domains that exhibit the desired variant CD3 binding and/or reduced level of cytokine release.

CD3-Binding Molecules that possess a vCD3-Binding Domain of the present invention may alternatively be recognized using a binding assay in which:
(1) a bispecific Cancer Antigen×CD3 diabody potentially having a vCD3-Binding Domain, and
(2) a bispecific Cancer Antigen×CD3 diabody having an rCD3-Binding Domain (e.g., the rCD3-Binding Domain of CD3 mAb 1),
are separately evaluated for their ability to bind to the surface of cells of tumor antigen-expressing cell lines (MOLM-13 or A498 cells) by FACS analysis. Briefly, cells are incubated with the diabody molecules (in FACS buffer containing 10% human AB serum) in microtiter plates. The cells are then washed and incubated with a labeled anti-human Fc secondary antibody or with a biotin-conjugated mouse anti-EK-coil antibody that recognizes the E-coil/K-coil (EK) Heterodimer-Promoting Domain of the diabodies, mixed with streptavidin-phycoerythrin. The cells are then washed and resuspended with FACS buffer and analyzed by flow cytometry and compared.

CD3-Binding Molecules that possess a vCD3-Binding Domain of the present invention may alternatively be recognized using, for example, a Co-Mix Xenograft Model such as NOD/SCID mice. In such an assay, the mice are injected with tumor cells (e.g., KG1A (AML) cells) co-mixed with activated human CD4+ or CD8+ T-cells (E:T=1:5). The bispecific Cancer Antigen×CD3 diabody potentially having a vCD3-Binding Domain or the Cancer Antigen× CD3 diabody having the rCD3-Binding Domain is injected into the animals and the extent of tumor growth is monitored and compared.

Alternatively, any one, two, or more than two of the exemplary variants of CD3 mAb 1, designated herein as "CD3 mAb 1 M3"-"CD3 mAb 1 M26" may be employed to provide the vCD3-Binding Domain of the DA×CD3 Binding Molecules of the present invention. The invention fully contemplates anti-CD3 antibodies having the VL and VH Domains of ant of CD3 mAb 1 M3-CD3 mAb 1 M26 wherein the VH Domain possesses an aspartate (D) at Kabat position 65 or a glycine (G) at Kabat position 65. The exemplary variants of CD3 mAb 1, CD3 mAb 1 M3-CD3 mAb 1 M26 possess vCD3-Binding Domains that comprise a CDR$_H$1 Domain, a CDR$_H$2 Domain, a CDR$_H$3 Domain, a CDR$_L$1 Domain, a CDR$_L$2 Domain, and a CDR$_L$3 Domain, at least one of which differs in amino acid sequence from the amino acid sequence of the corresponding CDR of the rCD3-Binding Domain (CD3 mAb 1); and relative to a DA×CD3 Binding Domain comprising said rCD3-Binding Domain. a DA×CD3 Binding Molecule comprising said vCD3-Binding Domain binds CD3 with an altered affinity and is capable of mediating redirected killing and exhibit lower levels of cytokine release.

The amino acid sequences of preferred variant anti-CD3 VH Domains of the present invention are variants of SEQ ID NO:55 and are represented by SEQ ID NO:207 (CDR$_H$ residues are shown underlined):

```
EVQLVESGGG LVQPGGSLRL SCAASGFTFS X₁X₂X₃MNWVRQA

PGKGLEWVGR IRSKYNNYAT YYADSVKX₄RF TISRDDSKNS

LYLQMNSLKT EDTAVYYCVR HX₅NX₆X₇NSX₈ST X₉FAX₁₀WGQGTL

VTVSS
``` wherein: $X_1$ is T, D, or E; $X_2$ is Y, D or T; $X_3$ is A or G; $X_4$ is D or G; $X_5$ is G, D, E, or K; $X_6$ is F or I; $X_7$ is G or I; $X_8$ is Y, A, G, or Q; $X_9$ is W, F, or Y; and $X_{10}$ is Y or E.

The amino acid sequences of preferred variant anti-CD3 VL Domains of the present invention are variants of SEQ ID NO:56 and are represented by SEQ ID NO:208 (CDR$_L$ residues are shown underlined):

QAVVTQEPSL TVSPGGTVTL TCRSSTGAVT TSNYANWVQQ

KPGQAPRGLI GX₁TNX₂RAPWT PARFSGSLLG GKAALTITGA

QAEDEADYYC AX₃WYSNLWVF GGGTKLTVLG wherein: $X_1$ is G or D; $X_2$ is K or G; and $X_3$ is L, E or Q.

B. Variant Anti-CD3 Antibodies

1. CD3 mAb 1 M1

CD3 mAb 1 M1 is a low affinity variant of CD3 mAb 1, and is thus also referred to as "CD3 mAb 1 Low." The amino acid sequence of the VH Domain of CD3 mAb 1 M1 is shown below as SEQ ID NO:64 (CDR$_H$ residues are shown underlined). Relative to SEQ ID NO:55, SEQ ID NO:64 contains an S100dT substitution (shown in double underline, and numbered as in Kabat); additionally, position 65, numbered as in Kabat, of SEQ ID NO:64, also shown in double underline, may be aspartate (D) or glycine (G):

EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HGNFGNSYVT WFAYWGQGTL

VTVSS wherein X is aspartate (D) or glycine (G)

A preferred amino acid sequence of the VL Domain of CD3 mAb 1 M1 is SEQ ID NO:56.

| CD3 mAb 1 1 M1 | | |
| --- | --- | --- |
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVTWFAY | SEQ ID NO: 65 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

2. CD3 mAb 1 M2

CD3 mAb 1 M2 has a faster off-rate than CD3 mAb 1, and is thus also referred to as "CD3 mAb 1 Fast." The amino acid sequence of the VH Domain of CD3 mAb 1 M2 is shown below as SEQ ID NO:66 (CDR$_H$ residues are shown underlined). Relative to SEQ ID NO:55, SEQ ID NO:66 contains G96K and S100dT substitutions, numbered as in Kabat (sequence residue 110, shown in double underline); additionally, position 65, numbered as in Kabat, of SEQ ID NO:66, also shown in double underline, may be aspartate (D) or glycine (G):

EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HKNFGNSYVT WFAYWGQGTL

VTVSS wherein X is aspartate (D) or glycine (G)

A preferred amino acid sequence of the VL Domain of CD3 mAb 1 M2 is SEQ ID NO:56.

| CD3 mAb 1 M2 | | |
| --- | --- | --- |
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HKNFGNSYVTWFAY | SEQ ID NO: 67 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

3. CD3 mAb 1 M3

The amino acid sequence of the VH Domain of CD3 mAb 1 M3 (SEQ ID NO:68) is shown below (CDR$_H$ residues are shown underlined). Relative to SEQ ID NO:55, SEQ ID NO:68 contains a G99I substitution (shown in double underline, and numbered as in Kabat); additionally, position 65, numbered as in Kabat, of SEQ ID NO:68, also shown in double underline, may be aspartate (D) or glycine (G):

EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HGNFINSYVS WFAYWGQGTL

VTVSS wherein X is aspartate (D) or glycine (G)

A preferred amino acid sequence of the VL Domain of CD3 mAb 1 M3 is SEQ ID NO:56.

| CD3 mAb 1 M3 | | |
| --- | --- | --- |
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFINSYVSWFAY | SEQ ID NO: 69 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

4. CD3 mAb 1 M4

The amino acid sequence of the VH Domain of CD3 mAb 1 M4 (SEQ ID NO:70) is shown below (CDR$_H$ residues are shown underlined). Relative to SEQ ID NO:55, SEQ ID NO:70 contains a Y100bA substitution (shown in double underline, and numbered as in Kabat); additionally, position 65, numbered as in Kabat, of SEQ ID NO:70, also shown in double underline, may be aspartate (D) or glycine (G):

```
EVQLVESGGG LVQPGGSLRL SCAASGFTFS TYAMNWVRQA
PGKGLEWVGR IRSKYNNYAT YYADSVKXRF TISRDDSKNS
LYLQMNSLKT EDTAVYYCVR HGNFGNSAVS WFAYWGQGTL
VTVSS
wherein X is aspartate (D) or glycine (G)
```

A preferred amino acid sequence of the VL Domain of CD3 mAb 1 M4 is SEQ ID NO:56.

| CD3 mAb 1 M4 | | |
| --- | --- | --- |
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSAVSWFAY | SEQ ID NO: 71 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

5. CD3 mAb 1 M5

The amino acid sequence of the VH Domain of CD3 mAb 1 M5 (SEQ ID NO:72) is shown below (CDR$_H$ residues are shown underlined). Relative to SEQ ID NO:55, SEQ ID NO:72 contains a Y100bG substitution (shown in double underline, and numbered as in Kabat); additionally, position 65, numbered as in Kabat, of SEQ ID NO:72, also shown in double underline, may be aspartate (D) or glycine (G):

```
EVQLVESGGG LVQPGGSLRL SCAASGFTFS TYAMNWVRQA
PGKGLEWVGR IRSKYNNYAT YYADSVKXRF TISRDDSKNS
LYLQMNSLKT EDTAVYYCVR HGNFGNSGVS WFAYWGQGTL
VTVSS
wherein X is aspartate (D) or glycine (G)
```

A preferred amino acid sequence of the VL Domain of CD3 mAb 1 M5 is SEQ ID NO:56.

| CD3 mAb 1 M5 | | |
| --- | --- | --- |
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSGVSWFAY | SEQ ID NO: 73 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

6. CD3 mAb 1 M6

The amino acid sequence of the VH Domain of CD3 mAb 1 M6 (SEQ ID NO:74) is shown below (CDR$_H$ residues are shown underlined). Relative to SEQ ID NO:55, SEQ ID NO:74 contains a Y100bQ substitution (shown in double underline, and numbered as in Kabat); additionally, position 65, numbered as in Kabat, of SEQ ID NO:74, also shown in double underline, may be aspartate (D) or glycine (G):

```
EVQLVESGGG LVQPGGSLRL SCAASGFTFS TYAMNWVRQA
PGKGLEWVGR IRSKYNNYAT YYADSVKXRF TISRDDSKNS
LYLQMNSLKT EDTAVYYCVR HGNFGNSQVS WFAYWGQGTL
VTVSS
wherein X is aspartate (D) or glycine (G)
```

A preferred amino acid sequence of the VL Domain of CD3 mAb 1 M6 is SEQ ID NO:56.

| CD3 mAb 1 M6 | | |
| --- | --- | --- |
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSQVSWFAY | SEQ ID NO: 75 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

7. CD3 mAb 1 M7

The amino acid sequence of the VH Domain of CD3 mAb 1 M7 (SEQ ID NO:76) is shown below (CDR$_H$ residues are shown underlined). Relative to SEQ ID NO:55, SEQ ID NO:76 contains a G96D substitution (shown in double underline, and numbered as in Kabat); additionally, position 65, numbered as in Kabat, of SEQ ID NO:76, also shown in double underline, may be aspartate (D) or glycine (G):

```
EVQLVESGGG LVQPGGSLRL SCAASGFTFS TYAMNWVRQA
PGKGLEWVGR IRSKYNNYAT YYADSVKXRF TISRDDSKNS
LYLQMNSLKT EDTAVYYCVR HDNFGNSYVS WFAYWGQGTL
VTVSS
wherein X is aspartate (D) or glycine (G)
```

A preferred amino acid sequence of the VL Domain of CD3 mAb 1 M7 is SEQ ID NO:56.

| CD3 mAb 1 M7 | | |
| --- | --- | --- |
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HDNFGNSYVSWFAY | SEQ ID NO: 77 |
| CDR$_L$1 | RSSTGAVTTSNYAN | SEQ ID NO: 60 |

-continued

| CD3 mAb 1 M7 | | |
|---|---|---|
| CDR | Sequence | SEQ ID NO |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

8. CD3 mAb 1 M8

The amino acid sequence of the VH Domain of CD3 mAb 1 M8 (SEQ ID NO:78) is shown below (CDR$_H$ residues are shown underlined). Relative to SEQ ID NO:55, SEQ ID NO:78 contains a G99E substitution (shown in double underline, and numbered as in Kabat); additionally, position 65, numbered as in Kabat, of SEQ ID NO:78, also shown in double underline, may be aspartate (D) or glycine (G):

```
EVQLVESGGG LVQPGGSLRL SCAASGFTFS TYAMNWVRQA
PGKGLEWVGR IRSKYNNYAT YYADSVKXRF TISRDDSKNS
LYLQMNSLKT EDTAVYYCVR HENFGNSYVS WFAYWGQGTL
VTVSS
wherein X is aspartate (D) or glycine (G)
```

A preferred amino acid sequence of the VL Domain of CD3 mAb 1 M8 is SEQ ID NO:56.

| CD3 mAb 1 M8 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HENFGNSYVSWFAY | SEQ ID NO: 79 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

9. CD3 mAb 1 M9

The amino acid sequence of the VH Domain of CD3 mAb 1 M9 (SEQ ID NO:80) is shown below (CDR$_H$ residues are shown underlined). Relative to SEQ ID NO:55, SEQ ID NO:80 contains a G99K substitution (shown in double underline, and numbered as in Kabat); additionally, position 65, numbered as in Kabat, of SEQ ID NO:80, also shown in double underline, may be aspartate (D) or glycine (G)):

```
EVQLVESGGG LVQPGGSLRL SCAASGFTFS TYAMNWVRQA
PGKGLEWVGR IRSKYNNYAT YYADSVKXRF TISRDDSKNS
LYLQMNSLKT EDTAVYYCVR HKNFGNSYVS WFAYWGQGTL
VTVSS
wherein X is aspartate (D) or glycine (G)
```

A preferred amino acid sequence of the VL Domain of CD3 mAb 1 M9 is SEQ ID NO:56.

| CD3 mAb 1 M9 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HKNFGNSYVSWFAY | SEQ ID NO: 81 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

10. CD3 mAb 1 M10

The amino acid sequence of the VH Domain of CD3 mAb 1 M10 (SEQ ID NO:82) is shown below (CDR$_H$ residues are shown underlined). Relative to SEQ ID NO:55, SEQ ID NO:82 contains a F98I substitution (shown in double underline, and numbered as in Kabat); additionally, position 65, numbered as in Kabat, of SEQ ID NO:82, also shown in double underline, may be aspartate (D) or glycine (G):

```
EVQLVESGGG LVQPGGSLRL SCAASGFTFS TYAMNWVRQA
PGKGLEWVGR IRSKYNNYAT YYADSVKXRF TISRDDSKNS
LYLQMNSLKT EDTAVYYCVR HGNIGNSYVS WFAYWGQGTL
VTVSS
wherein X is aspartate (D) or glycine (G)
```

A preferred amino acid sequence of the VL Domain of CD3 mAb 1 M10 is SEQ ID NO:56.

| CD3 mAb 1 M10 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNIGNSYVSWFAY | SEQ ID NO: 83 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

11. CD3 mAb 1 M11

The amino acid sequence of the VH Domain of CD3 mAb 1 M11 (SEQ ID NO:84) is shown below (CDR$_H$ residues are shown underlined). Relative to SEQ ID NO:55, SEQ ID NO:84 contains a W100eF substitution (shown in double underline, and numbered as in Kabat); additionally, position 65, numbered as in Kabat, of SEQ ID NO:84, also shown in double underline, may be aspartate (D) or glycine (G):

```
EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HGNFGNSYVS FFAYWGQGTL

VTVSS
     wherein X is aspartate (D) or glycine (G)
```

A preferred amino acid sequence of the VL Domain of CD3 mAb 1 M11 is SEQ ID NO:56.

| CD3 mAb 1 M11 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSFFAY | SEQ ID NO: 85 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

12. CD3 mAb 1 M12

The amino acid sequence of the VH Domain of CD3 mAb 1 M12 (SEQ ID NO:86) is shown below (CDR$_H$ residues are shown underlined). Relative to SEQ ID NO:55, SEQ ID NO:86 contains a W100eY substitution (shown in double underline, and numbered as in Kabat); additionally, position 65, numbered as in Kabat, of SEQ ID NO:86, also shown in double underline, may be aspartate (D) or glycine (G):

```
EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HGNFGNSYVS YFAYWGQGTL

VTVSS
     wherein X is aspartate (D) or glycine (G)
```

A preferred amino acid sequence of the VL Domain of CD3 mAb 1 M12 is SEQ ID NO:56.

| CD3 mAb 1 M12 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSYFAY | SEQ ID NO: 87 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

13. CD3 mAb 1 M13

The amino acid sequence of the VH Domain of CD3 mAb 1 M13 (SEQ ID NO:88) is shown below (CDR$_H$ residues are shown underlined). Relative to SEQ ID NO:55, SEQ ID NO:88 contains a Y102E substitution (shown in double underline, and numbered as in Kabat); additionally, position 65, numbered as in Kabat, of SEQ ID NO:88, also shown in double underline, may be aspartate (D) or glycine (G):

```
EVQLVESGGG LVQPGGSLRL SCAASGFTFS TYAMNWVRQA

PGKGLEWVGR IRSKYNNYAT YYADSVK XRF TISRDDSKNS

LYLQMNSLKT EDTAVYYCVR HGNFGNSYVS WFA EWGQGTL

VTVSS
     wherein X is aspartate (D) or glycine (G)
```

A preferred amino acid sequence of the VL Domain of CD3 mAb 1 M13 is SEQ ID NO:56.

| CD3 mAb 1 M13 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSWFA E | SEQ ID NO: 89 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 |
| wherein X is aspartate (D) or glycine (G) | | |

14. CD3 mAb 1 M14

The amino acid sequence of the VH Domain of CD3 mAb 1 M14 (SEQ ID NO:90) is shown below (CDR$_H$ residues are shown underlined). Relative to SEQ ID NO:55, SEQ ID NO:90 contains a T31D substitution (shown in double underline, and numbered as in Kabat); additionally, position 65, numbered as in Kabat, of SEQ ID NO:90, also shown in double underline, may be aspartate (D) or glycine (G):

```
EVQLVESGGG LVQPGGSLRL SCAASGFTFS DYAMNWVRQA

PGKGLEWVGR IRSKYNNYAT YYADSVK XRFTISRDDSKNS

LYLQMNSLKT EDTAVYYCVR HGNFGNSYVS WFAYWGQGTL

VTVSS
     wherein X is aspartate (D) or glycine (G)
```

A preferred amino acid sequence of the VL Domain of CD3 mAb 1 M14 is SEQ ID NO:56.

| CD3 mAb 1 M14 | | |
|---|---|---|
| CDR | Sequence | SEQ ID NO |
| CDRH1 | DYAMN | SEQ ID NO: 91 |
| CDRH2 | RIRSKYNNYATYYADSVKX | SEQ ID NO: 58 |
| CDRH3 | HGNFGNSYVSWFAY | SEQ ID NO: 59 |
| CDRL1 | RSSTGAVTTSNYAN | SEQ ID NO: 60 |
| CDRL2 | GTNKRAP | SEQ ID NO: 61 |
| CDRL3 | ALWYSNLWV | SEQ ID NO: 62 | wherein X is aspartate (D) or glycine (G)

15. CD3 mAb 1 M15

The amino acid sequence of the VH Domain of CD3 mAb 1 M15 (SEQ ID NO:92) is shown below (CDR$_H$ residues are shown underlined). Relative to SEQ ID NO:55, SEQ ID NO:92 contains a T31E substitution (shown in double underline, and numbered as in Kabat); additionally, position 65, numbered as in Kabat, of SEQ ID NO:92, also shown in double underline, may be aspartate (D) or glycine (G):

```
EVQLVESGGG LVQPGGSLRL SCAASGFTFS EYAMNWVRQA

PGKGLEWVGR IRSKYNNYAT YYADSVK XRF TISRDDSKNS

LYLQMNSLKT EDTAVYYCVR HGNFGNSYVS WFAYWGQGTL

VTVSS
wherein X is aspartate (D) or glycine (G)
```

A preferred amino acid sequence of the VL Domain of CD3 mAb 1 M15 is SEQ ID NO:56.

| CD3 mAb 1 M15 | | |
|---|---|---|
| CDR | Sequence | SEQ ID NO |
| CDR$_H$1 | EYAMN | SEQ ID NO: 93 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

16. CD3 mAb 1 M16

The amino acid sequence of the VH Domain of CD3 mAb 1 M16 (SEQ ID NO:94) is shown below (CDR$_H$ residues are shown underlined). Relative to SEQ ID NO:55, SEQ ID NO:94 contains a Y32D substitution (shown in double underline, and numbered as in Kabat); additionally, position 65, numbered as in Kabat, of SEQ ID NO:94, also shown in double underline, may be aspartate (D) or glycine (G):

```
EVQLVESGGG LVQPGGSLRL SCAASGFTFS TDAMNWVRQA

PGKGLEWVGR IRSKYNNYAT YYADSVK XRFTISRDDSKNS

LYLQMNSLKT EDTAVYYCVR HGNFGNSYVS WFAYWGQGTL

VTVSS
wherein X is aspartate (D) or glycine (G)
```

A preferred amino acid sequence of the VL Domain of CD3 mAb 1 M16 is SEQ ID NO:56.

| CD3 mAb 1 M16 | | |
|---|---|---|
| CDR | Sequence | SEQ ID NO |
| CDR$_H$1 | T DAMN | SEQ ID NO: 95 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

17. CD3 mAb 1 M17

The amino acid sequence of the VH Domain of CD3 mAb 1 M17 (SEQ ID NO:96) is shown below (CDR$_H$ residues are shown underlined). Relative to SEQ ID NO:55, SEQ ID NO:96 contains a Y32T substitution (shown in double underline, and numbered as in Kabat); additionally, position 65, numbered as in Kabat, of SEQ ID NO:96, also shown in double underline, may be aspartate (D) or glycine (G):

```
EVQLVESGGG LVQPGGSLRL SCAASGFTFS TTAMN WVRQA

PGKGLEWVGR IRSKYNNYAT YYADSVK XRF TISRDDSKNS

LYLQMNSLKT EDTAVYYCVR HGNFGNSYVS WFAYWGQGTL

VTVSS
wherein X is aspartate (D) or glycine (G)
```

A preferred amino acid sequence of the VL Domain of CD3 mAb 1 M17 is SEQ ID NO:56.

| CD3 mAb 1 M17 | | |
|---|---|---|
| CDR | Sequence | SEQ ID NO |
| CDR$_H$1 | T TTAMN | SEQ ID NO: 97 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

18. CD3 mAb 1 M18

The amino acid sequence of the VH Domain of CD3 mAb 1 M18 (SEQ ID NO:98) is shown below (CDR$_H$ residues are shown underlined). Relative to SEQ ID NO:55, SEQ ID NO:98 contains a A33G substitution (shown in double underline, and numbered as in Kabat); additionally, position 65, numbered as in Kabat, of SEQ ID NO:98, also shown in double underline, may be aspartate (D) or glycine (G):

```
EVQLVESGGG LVQPGGSLRL SCAASGFTFS TYGMNWVRQA

PGKGLEWVGR IRSKYNNYAT YYADSVK XRF TISRDDSKNS

LYLQMNSLKT EDTAVYYCVR HGNFGNSYVS WFAYWGQGTL

VTVSS
wherein X is aspartate (D) or glycine (G)
```

A preferred amino acid sequence of the VL Domain of CD3 mAb 1 M18 is SEQ ID NO:56.

CD3 mAb 1 M18

| CDR | Sequence | SEQ ID NO |
|---|---|---|
| CDR$_H$1 | TYGMN | SEQ ID NO: 99 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

19. CD3 mAb 1 M19

The amino acid sequence of the VH Domain of CD3 mAb 1 M19 (SEQ ID NO:100) is shown below (CDR$_H$ residues are shown underlined). Relative to SEQ ID NO:55, SEQ ID NO:100 contains G96K and F98I substitutions (shown in double underline, and numbered as in Kabat); additionally, position 65, numbered as in Kabat, of SEQ ID NO:100, also shown in double underline, may be aspartate (D) or glycine (G):

EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HKNIGNSYVS WFAYWGQGTL

VTVSS
wherein X is aspartate (D) or glycine (G)

A preferred amino acid sequence of the VL Domain of CD3 mAb 1 M19 is SEQ ID NO:56.

CD3 mAb 1 M19

| CDR | Sequence | SEQ ID NO |
|---|---|---|
| CDR$_H$1 | TYAMN | SEQ ID NO: 57 |
| CDR$_H$2 | RIRSKYNNYATYYADSVKX | SEQ ID NO: 58 |
| CDR$_H$3 | HKNIGNSYVSWFAY | SEQ ID NO: 101 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

20. CD3 mAb 1 M20

The amino acid sequence of the VH Domain of CD3 mAb 1 M20 (SEQ ID NO:102) is shown below (CDR$_H$ residues are shown underlined). Relative to SEQ ID NO:55, SEQ ID NO:102 contains G96K and Y100bG substitutions (shown in double underline, and numbered as in Kabat); additionally, position 65, numbered as in Kabat, of SEQ ID NO:102, also shown in double underline, may be aspartate (D) or glycine (G):

EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HKFGNSGVS WFAYWGQGTL

VTVSS
wherein X is aspartate (D) or glycine (G)

A preferred amino acid sequence of the VL Domain of CD3 mAb 1 M20 is SEQ ID NO:56.

CD3 mAb 1 M20

| CDR | Sequence | SEQ ID NO |
|---|---|---|
| CDR$_H$1 | TYAMN | SEQ ID NO: 57 |
| CDR$_H$2 | RIRSKYNNYATYYADSVKX | SEQ ID NO: 58 |
| CDR$_H$3 | HKNFGNSGVSWFAY | SEQ ID NO: 103 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

21. CD3 mAb 1 M21

The amino acid sequence of the VH Domain of CD3 mAb 1 M21 (SEQ ID NO:104) is shown below (CDR$_H$ residues are shown underlined). Relative to SEQ ID NO:55, SEQ ID NO:104 contains G96K and W100eF substitutions (shown in double underline, and numbered as in Kabat); additionally, position 65, numbered as in Kabat, of SEQ ID NO:104, also shown in double underline, may be aspartate (D) or glycine (G):

EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HKNFGNSYVS FFAYWGQGTL

VTVSS
wherein X is aspartate (D) or glycine (G)

A preferred amino acid sequence of the VL Domain of CD3 mAb 1 M21 is SEQ ID NO:56.

CD3 mAb 1 M21

| CDR | Sequence | SEQ ID NO |
|---|---|---|
| CDR$_H$1 | TYAMN | SEQ ID NO: 57 |
| CDR$_H$2 | RIRSKYNNYATYYADSVKX | SEQ ID NO: 58 |
| CDR$_H$3 | HKNFGNSYVSFFAY | SEQ ID NO: 105 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

22. CD3 mAb 1 M22

The amino acid sequence of the VH Domain of CD3 mAb 1 M22 (SEQ ID NO:106) is shown below (CDR$_H$ residues are shown underlined). Relative to SEQ ID NO:55, SEQ ID NO:106 contains G96K and W100eY substitutions (shown in double underline, and numbered as in Kabat); additionally, position 65, numbered as in Kabat, of SEQ ID NO:106, also shown in double underline, may be aspartate (D) or glycine (G):

```
EVQLVESGGG LVQPGGSLRL SCAASGFTFS TYAMNWVRQA

PGKGLEWVGR IRSKYNNYAT YYADSVKXRF TISRDDSKNS

LYLQMNSLKT EDTAVYYCVR HKNFGNSYVS YFAYWGQGTL

VTVSS
wherein X is aspartate (D) or glycine (G)
```

A preferred amino acid sequence of the VL Domain of CD3 mAb 1 M22 is SEQ ID NO:56.

| CD3 mAb 1 M22 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HKNFGNSYVSYFAY | SEQ ID NO: 107 |
| CDR$_L$1 | RSSTGAVTTSNYAN | SEQ ID NO: 60 |
| CDR$_L$2 | GTNKRAP | SEQ ID NO: 61 |
| CDR$_L$3 | ALWYSNLWV | SEQ ID NO: 62 | wherein X is aspartate (D) or glycine (G)

23. CD3 mAb 1 M23

A preferred amino acid sequence of the VH Domain of CD3 mAb 1 M23 is SEQ ID NO:55 or SEQ ID NO:63.

The amino acid sequence of the VL Domain of CD3 mAb 1 M23 (SEQ ID NO:108) is shown below (CDR$_L$ residues are shown underlined). Relative to SEQ ID NO:56, SEQ ID NO:108 contains an L95E substitution (shown in double underline, and numbered as in Kabat):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC AEWYSNLWF GGGTKLTVLG
```

| CD3 mAb 1 M23 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNKRAP | SEQ ID NO: 61 |
| CDR$_L$3 | AEWYSNLWV | SEQ ID NO: 109 | wherein X is aspartate (D) or glycine (G)

24. CD3 mAb 1 M24

A preferred amino acid sequence of the VH Domain of CD3 mAb 1 M24 is SEQ ID NO:55 or SEQ ID NO:63.

The amino acid sequence of the VL Domain of CD3 mAb 1 M24 (SEQ ID NO:110) is shown below (CDR$_L$ residues are shown underlined). Relative to SEQ ID NO:56, SEQ ID NO:110 contains an L95Q substitution (shown in double underline, and numbered as in Kabat):

```
QAVVIQEPSL TVSPGGTVTL TCRSSTGAVT TSNYANWVQQ

KPGQAPRGLI GGTNKRAPWT PARFSGSLLG GKAALTITGA

QAEDEADYYC AQWYSNLWVF GGGTKLIVLG
```

| CD3 mAb 1 M24 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNKRAP | SEQ ID NO: 61 |
| CDR$_L$3 | AQWYSNLWV | SEQ ID NO: 111 | wherein X is aspartate (D) or glycine (G)

25. CD3 mAb 1 M25

A preferred amino acid sequence of the VH Domain of CD3 mAb 1 M25 is SEQ ID NO:55 or SEQ ID NO:63.

The amino acid sequence of the VL Domain of CD3 mAb 1 M25 (SEQ ID NO:112) is shown below (CDR$_L$ residues are shown underlined). Relative to SEQ ID NO:56, SEQ ID NO:112 contains a G50D substitution (shown in double underline, and numbered as in Kabat):

```
QAVVIQEPSL TVSPGGTVTL TCRSSTGAVT TSNYANWVQQ

KPGQAPRGLI GDTNKRAPWT PARFSGSLLG GKAALTITGA

QAEDEADYYC ALWYSNLWVF GGGTKLIVLG
```

| CD3 mAb 1 M25 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | DTNKRAP | SEQ ID NO: 113 |
| CDR$_L$3 | ALWYSNLWV | SEQ ID NO: 62 | wherein X is aspartate (D) or glycine (G)

26. CD3 mAb 1 M26

A preferred amino acid sequence of the VH Domain of CD3 mAb 1 M26 is SEQ ID NO:55 or SEQ ID NO:63.

The amino acid sequence of the VL Domain of CD3 mAb 1 M26 (SEQ ID NO:114) is shown below (CDR$_L$ residues are shown underlined). Relative to SEQ ID NO:56, SEQ ID NO:114 contains a K53G substitution (shown in double underline):

```
QAVVIQEPSL TVSPGGTVTL TCRSSTGAVT TSNYANWVQQ

KPGQAPRGLI GGTNGRAPWT PARFSGSLLG GKAALTITGA

QAEDEADYYC ALWYSNLWVF GGGTKLIVLG
```

| CD3 mAb 1 M26 | | |
|---|---|---|
| CDR | Sequence | SEQ ID NO |
| CDR$_H$1 | TYAMN | SEQ ID NO: 57 |
| CDR$_H$2 | RIRSKYNNYATYYADSVKX | SEQ ID NO: 58 |
| CDR$_H$3 | HGNFGNSYVSWFAY | SEQ ID NO: 59 |
| CDR$_L$1 | RSSTGAVTTSNYAN | SEQ ID NO: 60 |
| CDR$_L$2 | GTNGRAP | SEQ ID NO: 115 |
| CDR$_L$3 | ALWYSNLWV | SEQ ID NO: 62 | wherein X is aspartate (D) or glycine (G)

C. Exemplary Antibodies that Bind to Cell Surface Molecules of an Effector Cell

As used herein, the term "effector cell" denotes a cell that directly or indirectly mediates the killing of target cells (e.g., foreign cells, infected cells or cancer cells). Examples of effector cells include helper T-cells, cytotoxic T-cells, Natural Killer (NK) cells, plasma cells (antibody-secreting B cells), macrophages and granulocytes. Preferred cell surface molecules of such cells include CD2, CD3, CD8, CD16, TCR, and the NKG2D receptor. Accordingly, molecules capable of immunospecifically binding an epitope of such molecules, or to other effector cell surface molecules may be used in accordance with the principles of the present invention. Exemplary antibodies, whose VH and VL Domains may be used to construct molecules capable of mediating the redirected killing of a target cell are provided below.

1. Exemplary Anti-CD2 Antibodies

In one embodiment, the molecules of the present invention that are capable of mediating the redirected killing of a target cell will bind an effector cell by immunospecifically binding an epitope of CD2 present on the surface of such effector cell. Molecules that specifically bind CD2 include the anti-CD2 antibody "CD2 mAb Lo-CD2a."

The amino acid sequence of the VH Domain of CD2 mAb Lo-CD2a (ATCC Accession No: 11423); SEQ ID NO:116) is shown below (CDR$_H$ residues are shown underlined):

```
EVQLQQSGPE LQRPGASVKL SCKASGYIFT EYYMYWVKQR

PKQGLELVGR IDPEDGSIDY VEKFKKKATL TADTSSNTAY

MQLSSLTSED TATYFCARGK FNYRFAYWGQ GTLVTVSS
```

The amino acid sequence of the VL Domain of CD2 mAb Lo-CD2a (ATCC Accession No: 11423; SEQ ID NO:117) is shown below (CDR$_L$ residues are shown underlined):

```
DVVLTQTPPT LLATIGQSVS ISCRSSQSLL HSSGNTYLNW

LLQRTGQSPQ PLTYLVSKLE SGVPNRFSGS GSGTDFTLKI

SGVEAEDLGV YYCMQFTHYP YTFGAGTKLE LK
```

2. Exemplary Anti-CD8 Antibodies

In one embodiment, the molecules of the present invention that are capable of mediating the redirected killing of a target cell will bind an effector cell by immunospecifically binding an epitope of CD8 present on the surface of such effector cell. Antibodies that specifically bind CD8 include the anti-CD8 antibodies "OKT8" and "TRX2."

The amino acid sequence of the VH Domain of OKT8 (SEQ ID NO:118) is shown below (CDR$_H$ residues are shown underlined):

```
QVQLLESGPE LLKPGASVKM SCKASGYTFT DYNMHWVKQS

HGKSLEWIGY IYPYTGGTGY NQKFKNKATL TVDSSSTAY

MELRSLTSED SAVYYCARNF RYTYWYFDVW GQGTTVTVSS
```

The amino acid sequence of the VL Domain of OKT8 (SEQ ID NO:119) is shown below (CDR$_L$ residues are shown underlined):

```
DIVMTQSPAS LAVSLGQRAT ISCRASESVD SYDNSLMHWY

QQKPGQPPKV LIYLASNLES GVPARFSGSG SRTDFTLTID

PVEADDAATY YCQQNNEDPY TFGGGTKLEI KR
```

The amino acid sequence of the VH Domain of TRX2 (SEQ ID NO:120) is shown below (CDR$_H$ residues are shown underlined):

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS S
```

The amino acid sequence of the VL Domain of TRX2 (SEQ ID NO:121) is shown below (CDR$_L$ residues are shown underlined):

```
DIQMTQSPSS LSASVGDRVT ITCKGSQDIN NYLAWYQQKP

GKAPKLLIYN TDILHTGVPS RFSGSGSGTD FTFTISSLQP

EDIATYYCYQ YNNGYTFGQG TKVEIK
```

VI. Exemplary Cancer and Pathogen-Associated Antigens

A. Exemplary Cancer Antigens Arrayed on the Surface of Cancer Cells

As used herein, the term "Cancer Antigen" denotes an antigen that is characteristically expressed on the surface of a cancer cell, and that may thus be treated with an Antibody-Based Molecule or an Immunomodulatory Molecule. Examples of Cancer Antigens include, but are not limited to: 19.9 as found in colon cancer, gastric cancer mucins; 4.2; ADAM-9 (United States Patent Publication No. 2006/0172350; PCT Publication No. WO 06/084075); AH6 as found in gastric cancer; ALCAM (PCT Publication No. WO 03/093443); APO-1 (malignant human lymphocyte antigen) (Trauth, B. C. et al. (1989) "*Monoclonal Antibody-Mediated Tumor Regression By Induction Of Apoptosis*," Science 245:301-304); B1 (Egloff, A. M. et al. (2006) "*Cyclin B1 And Other Cyclins As Tumor Antigens In Immunosurveillance And Immunotherapy Of Cancer*," Cancer Res. 66(1): 6-9); B7-H3 (Collins, M. et al. (2005) "*The B7 Family Of Immune-Regulatory Ligands*," Genome Biol. 6:223.1-223.7). Chapoval, A. et al. (2001) "*B7-H3: A Costimulatory*

Molecule For T Cell Activation and IFN-γ Production," Nature Immunol. 2:269-274; Sun, M. et al. (2002) "Characterization of Mouse and Human B7-H3 Genes," J. Immunol. 168:6294-6297); BAGE (Bodey, B. (2002) "Cancer-Testis Antigens: Promising Targets For Antigen Directed Antineoplastic Immunotherapy," Expert Opin. Biol. Ther. 2(6):577-584); beta-catenin (Prange W. et al. (2003) "Beta-Catenin Accumulation In The Progression Of Human Hepatocarcinogenesis Correlates With Loss Of E-Cadherin And Accumulation Of P53, But Not With Expression Of Conventional WNT-1 Target Genes," J. Pathol. 201(2):250-259); blood group $ALe^b/Le^y$ as found in colonic adenocarcinoma; Burkitt's lymphoma antigen-38.13; C14 as found in colonic adenocarcinoma; CA125 (ovarian carcinoma antigen) (Bast, R. C. Jr. et al. (2005) "New Tumor Markers: CA125 And Beyond," Int. J. Gynecol. Cancer 15(Suppl 3):274-281; Yu et al. (1991) "Coexpression Of Different Antigenic Markers On Moieties That Bear CA 125 Determinants," Cancer Res. 51(2):468-475); Carboxypeptidase M (United States Patent Publication No. 2006/0166291); CD5 (Calin, G. A. et al. (2006) "Genomics Of Chronic Lymphocytic Leukemia MicroRNAs As New Players With Clinical Significance," Semin. Oncol. 33(2):167-173; CD19 (Ghetie et al. (1994) "Anti-CD19 Inhibits The Growth Of Human B-Cell Tumor Lines In Vitro And Of Daudi Cells In SCID Mice By Inducing Cell Cycle Arrest," Blood 83:1329-1336; Troussard, X. et al. 1998 Hematol Cell Ther. 40(4):139-48); CD20 (Reff et al. (1994) "Depletion Of B Cells In Vivo By A Chimeric Mouse Human Monoclonal Antibody To CD20," Blood 83:435-445; Thomas, D. A. et al. 2006 Hematol Oncol Clin North Am. 20(5).1125-36); CD22 (Kreitman, R. J. (2006) "Immunotoxins For Targeted Cancer Therapy," AAPS J. 8(3):E532-51); CD23 (Rosati, S. et al. (2005) "Chronic Lymphocytic Leukaemia: A Review Of The Immuno-Architecture," Curr. Top. Microbiol. Immunol. 294:91-107); CD25 (Troussard, X. et al. (1998) "Hairy Cell Leukemia. What Is New Forty Years After The First Description?" Hematol. Cell. Ther. 40(4): 139-148); CD27 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD28 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD33 (Sgouros et al. (1993) "Modeling And Dosimetry Of Monoclonal Antibody M195 (Anti-CD33) In Acute Myelogenous Leukemia," J. Nucl. Med. 34:422-430); CD36 (Ge, Y. (2005) "CD36: A Multiligand Molecule," Lab Hematol. 11(1):31-7); CD40/CD154 (Messmer, D. et al. (2005) "CD154 Gene Therapy For Human B-Cell Malignancies," Ann. N. Y. Acad. Sci. 1062:51-60); CD45 (Jurcic, J. G. (2005) "Immunotherapy For Acute Myeloid Leukemia," Curr. Oncol. Rep. 7(5):339-346); CD56 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD46 (U.S. Pat. No. 7,148,038; PCT Publication No. WO 03/032814); CD52 (Eketorp, S. S. et al. (2014) "Alemtuzumab (Anti-CD52 Monoclonal Antibody) As Single-Agent Therapy In Patients With Relapsed/Refractory Chronic Lymphocytic Leukaemia (CLL)—A Single Region Experience On Consecutive Patients," Ann Hematol. 93(10): 1725-1733; Suresh, T. et al. (2014) "New Antibody Approaches To Lymphoma Therapy," J. Hematol. Oncol. 7:58; Hoelzer, D. (2013) "Targeted Therapy With Monoclonal Antibodies In Acute Lymphoblastic Leukemia," Curr. Opin. Oncol. 25(6):701-706); CD56 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD79a/CD79b (Troussard, X. et al. (1998) "Hairy Cell Leukemia. What Is New Forty Years After The First Description?" Hematol. Cell. Ther. 40(4): 139-148; Chu, P. G. et al. (2001) "CD79: A Review," Appl. Immunohistochem. Mol. Morphol. 9(2):97-106); CD103 (Troussard, X. et al. (1998) "Hairy Cell Leukemia. What Is New Forty Years After The First Description?" Hematol. Cell. Ther. 40(4):139-148); CD317 (Kawai, S. et al. (2008) "Interferon-A Enhances CD317 Expression And The Antitumor Activity Of Anti-CD317 Monoclonal Antibody In Renal Cell Carcinoma Xenograft Models," Cancer Science 99(12):2461-2466; Wang, W. et al. (2009) HM1.24 (CD317) Is A Novel Target Against Lung Cancer For Immunotherapy Using Anti-HM1.24 Antibody," Cancer Immunology, Immunotherapy 58(6):967-976; Wang, W. et al. (2009) "Chimeric And Humanized Anti-HM1.24 Antibodies Mediate Antibody-Dependent Cellular Cytotoxicity Against Lung Cancer Cells. Lung Cancer," 63(1):23-31; Sayeed, A. et al. (2013) "Aberrant Regulation Of The BST2 (Tetherin) Promoter Enhances Cell Proliferation And Apoptosis Evasion In High Grade Breast Cancer Cells," PLoS ONE 8(6)e67191, pp. 1-10); CDK4 (Lee, Y. M. et al. (2006) "Targeting Cyclins And Cyclin-Dependent Kinases In Cancer: Lessons From Mice, Hopes For Therapeutic Applications In Human," Cell Cycle 5(18):2110-2114); CEA (carcinoembryonic antigen; Foon et al. (1995) "Immune Response To The Carcinoembryonic Antigen In Patients Treated With An Anti-Idiotype Antibody Vaccine," J. Clin. Invest. 96(1):334-42); Mathelin, C. (2006) "Circulating Proteinic Biomarkers And Breast Cancer," Gynecol. Obstet. Fertil. 34(7-8):638-646; Tellez-Avila, F. I. et al. (2005) "The Carcinoembryonic Antigen: Apropos Of An Old Friend," Rev. Invest. Clin. 57(6):814-819); CEACAM5/CEACAM6 (Zheng, C. et al. (2011) "A Novel Anti-CEACAM5 Monoclonal Antibody, CC4, Suppresses Colorectal Tumor Growth and Enhances NK Cells-Mediated Tumor Immunity," PLoS One 6(6):e21146, pp. 1-11); CO17-1A (Ragnhammar et al. (1993) "Effect Of Monoclonal Antibody 17-1A And GM-CSF In Patients With Advanced Colorectal Carcinoma—Long-Lasting, Complete Remissions Can Be Induced," Int. J. Cancer 53:751-758); CO-43 (blood group $Le^b$); CO-514 (blood group $Le^a$) as found in adenocarcinoma; CTA-1; CTLA-4 (Peggs, K. S. et al. (2006) "Principles And Use Of Anti-CTLA4 Antibody In Human Cancer Immunotherapy," Curr. Opin. Immunol. 18(2):206-13); Cytokeratin 8 (PCT Publication No. WO 03/024191); D1.1; $D_156$-22; DR5 (Abdulghani, J. et al. (2010) "TRAIL Receptor Signaling And Therapeutics," Expert Opin. Ther. Targets 14(10): 1091-1108; Andera, L. (2009) "Signaling Activated By The Death Receptors Of The TNFR Family," Biomed. Pap. Med. Fac. Univ. Palacky Olomouc Czech. Repub. 153(3):173-180; Carlo-Stella, C. et al. (2007) "Targeting TRAIL Agonistic Receptors for Cancer Therapy," Clin, Cancer 13(8):2313-2317; Chaudhari, B. R. et al. (2006) "Following the TRAIL to Apoptosis," Immunologic Res. 35(3):249-262); $E_1$ series (blood group B) as found in pancreatic cancer; EGFR (Epidermal Growth Factor Receptor; Adenis, A. et al. (2003) "Inhibitors Of Epidermal Growth Factor Receptor And Colorectal Cancer," Bull. Cancer. 90 Spec No: S228-S232); Ephrin receptors (and in particular EphA2 (U.S. Pat. No. 7,569,672; PCT Publication No. WO 06/084226); Erb (ErbB1; ErbB3; ErbB4; Zhou, H. et al. (2002) "Lung Tumorigenesis Associated With Erb-B-2 And Erb-B-3 Overexpression In Human Erb-B-3 Transgenic Mice Is Enhanced By Methylnitrosourea," Oncogene 21(57):8732-8740; Rimon, E. et al. (2004) "Gonadotropin-Induced Gene Regulation In Human Granulosa Cells Obtained From IVF Patients: Modulation Of Genes Coding For Growth Factors And Their Receptors And Genes Involved In Cancer And Other Diseases," Int. J. Oncol. 24(5):1325-1338); GAGE (GAGE-1; GAGE-2; Akcakanat, A. et al. (2006) "Heterogeneous Expression Of GAGE, NY-ESO-1, MAGE-A and SSX Proteins In Esophageal Cancer: Implications For Immunotherapy," Int. J. Cancer. 118(1):123-128); GD2/GD3/GM2 (Livingston, P. O. et al. (2005) "Selection Of GM2, Fucosyl GM1, Globo H And Polysialic Acid As Targets On Small Cell Lung Cancers For Antibody-Mediated Immunotherapy," Cancer Immunol. Immunother. 54(10):1018-1025); ganglioside GD2 (GD2; Saleh et al. (1993) "Generation Of A Human Anti-Idiotypic Antibody That Mimics The GD2 Antigen," J. Immunol., 151, 3390-3398); ganglioside GD3 ($G_{D3}$; Shitara et al. (1993) "A Mouse/Human Chimeric Anti-(Ganglioside GD3) Antibody With Enhanced Antitumor Activities," Cancer Immunol. Immunother. 36:373-380); ganglioside GM2 ($G_{M2}$; Livingston et al. (1994) "Improved Survival In Stage III Melanoma Patients With GM2 Antibodies: A Randomized Trial Of Adjuvant Vaccination With GM2 Ganglioside," J. Clin. Oncol. 12:1036-1044); ganglioside GM3 ($G_{M3}$; Hoon et al. (1993) "Molecular Cloning Of A Human Monoclonal Antibody Reactive To Ganglioside GM3 Antigen On Human Cancers," Cancer Res. 53:5244-5250); GICA 19-9 (Herlyn et al. (1982) "Monoclonal Antibody Detection Of A Circulating Tumor-Associated Antigen. I. Presence Of Antigen In Sera Of Patients With Colorectal, Gastric, And Pancreatic Carcinoma," J. Clin. Immunol. 2:135-140); gp100 (Lotem, M. et al. (2006) "Presentation Of Tumor Antigens By Dendritic Cells Genetically Modified With Viral And Nonviral Vectors," J. Immunother. 29(6):616-27); Gp37 (human leukemia T-cell antigen; Bhattacharya-Chatterjee et al. (1988) "Idiotype Vaccines Against Human T Cell Leukemia. II. Generation And Characterization Of A Monoclonal Idiotype Cascade (Ab1, Ab2, and Ab3)," J. Immunol. 141:1398-1403); gp75 (melanoma antigen; Vijayasardahl et al. (1990) "The Melanoma Antigen Gp75 Is The Human Homologue Of The Mouse B (Brown) Locus Gene Product," J. Exp. Med. 171(4):1375-1380); gpA33 (Heath, J. K. et al. (1997) "The Human A33 Antigen Is A Transmembrane Glycoprotein And A Novel Member Of The Immunoglobulin Superfamily," Proc. Natl. Acad. Sci. (U.S.A.) 94(2):469-474; Ritter, G. et al. (1997) "Characterization Of Posttranslational Modifications Of Human A33 Antigen, A Novel Palmitoylated Surface Glycoprotein Of Human Gastrointestinal Epithelium," Biochem. Biophys. Res. Commun. 236(3):682-686; Wong, N. A. et al. (2006) "EpCAM and gpA33 Are Markers Of Barrett's Metaplasia," J. Clin. Pathol. 59(3):260-263; Almqvist, Y. (2006) "In vitro and in vivo Characterization of 177Lu-huA33: A Radioimmunoconjugate Against Colorectal Cancer," Nucl. Med. Biol. 33(8):991-998); HER2 antigen (HER2/neu, p185$^{HER2}$; Pal, S. K. et al. (2006) "Targeting HER2 Epitopes," Semin. Oncol. 33(4):386-391); HMFG (human milk fat globule antigen; WO1995015171); Human Papillomavirus-E6/Human Papillomavirus-E7 (Di-Maio, D. et al. (2006) "Human Papillomaviruses And Cervical Cancer," Adv. Virus Res. 66:125-59; HMW-MAA (high molecular weight melanoma antigen; Natali et al. (1987) "Immunohistochemical Detection Of Antigen In Human Primary And Metastatic Melanomas By The Monoclonal Antibody 140.240 And Its Possible Prognostic Significance," Cancer 59:55-63; Mittelman et al. (1990) "Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies," J. Clin. Invest. 86:2136-2144); I antigen (differentiation antigen; Feizi (1985) "Demonstration By Monoclonal Antibodies That Carbohydrate Structures Of Glycoproteins And Glycolipids Are Onco-Developmental Antigens," Nature 314:53-57); IL13Rα2 (PCT Publication No. WO 2008/146911; Brown, C. E. et al. (2013) "Glioma IL13Rα2 Is Associated With Mesenchymal Signature Gene Expression And Poor Patient Prognosis," PLoS One. 18; 8(10):e77769; Barderas, R. et al. (2012) "High Expression Of IL-13 Receptor A2 In Colorectal Cancer Is Associated With Invasion, Liver Metastasis, And Poor Prognosis," Cancer Res. 72(11):2780-2790; Kasaian, M. T. et al. (2011) "IL-13 Antibodies Influence IL-13 Clearance In Humans By Modulating Scavenger Activity Of IL-13Rα2," J. Immunol. 187(1):561-569; Bozinov, O. et al. (2010) "Decreasing Expression Of The Interleukin-13 Receptor IL-13Ralpha2 In Treated Recurrent Malignant Gliomas," Neurol. Med. Chir. (Tokyo) 50(8):617-621; Fujisawa, T. et al. (2009) "A novel role of interleukin-13 receptor alpha2 in pancreatic cancer invasion and metastasis," Cancer Res. 69(22):8678-8685); Integrin β6 (PCT Publication No. WO 03/087340); JAM-3 (PCT Publication No. WO 06/084078); KID3 (PCT Publication No. WO 05/028498); KID31 (PCT Publication No. WO 06/076584); KS 1/4 pan-carcinoma antigen (Perez et al. (1989) "Isolation And Characterization Of A cDNA Encoding The Ks1/4 Epithelial Carcinoma Marker," J. Immunol. 142:3662-3667; Möller et al. (1991) "Bi-specific-Monoclonal-Antibody-Directed Lysis Of Ovarian Carcinoma Cells By Activated Human T Lymphocytes," Cancer Immunol. Immunother. 33(4):210-216; Ragupathi, G. 2005 Cancer Treat Res. 123:157-80); L6 and L20 (human lung carcinoma antigens; Hellström et al. (1986) "Monoclonal Mouse Antibodies Raised Against Human Lung Carcinoma," Cancer Res. 46:3917-3923); LEA; LUCA-2 (United States Patent Publication No. 2006/0172349; PCT Publication No. WO 06/083852); M1:22:25:8; M18; M39; MAGE (MAGE-1; MAGE-3; (Bodey, B. (2002) "Cancer-Testis Antigens: Promising Targets For Antigen Directed Antineoplastic Immunotherapy," Expert Opin. Biol. Ther. 2(6):577-584); MART (Kounalakis, N. et al. (2005) "Tumor Cell And Circulating Markers In Melanoma: Diagnosis, Prognosis, And Management," Curr. Oncol. Rep. 7(5):377-382; mesothelin (Chang, K. et al. (1996) "Molecular Cloning Of Mesothelin, A Differentiation Antigen Present On Mesothelium, Mesotheliomas, And Ovarian Cancers," Proc. Natl. Acad. Sci. (U.S.A.) 93:136-140); MUC-1 (Mathelin, C. (2006) "Circulating Proteinic Biomarkers And Breast Cancer," Gynecol. Obstet. Fertil. 34(7-8):638-646); MUM-1 (Castelli, C. et al. (2000) "T-Cell Recognition Of Melanoma-Associated Antigens," J. Cell. Physiol. 182(3):323-331); Myl; N-acetylglucosaminyltransferase (Dennis, J. W. (1999) "Glycoprotein Glycosylation And Cancer Progression," Biochim. Biophys. Acta. 6; 1473(1):21-34); neoglycoprotein; NS-10 as found in adenocarcinomas; OFA-1; OFA-2; Oncostatin M (Oncostatin Receptor Beta; U.S. Pat. No. 7,572,896; PCT Publication No. WO 06/084092); p15 (Gil, J. et al. (2006) "Regulation Of The INK4b-ARF-INK4a Tumour Suppressor Locus: All For One Or One For All," Nat. Rev. Mol. Cell Biol. 7(9):667-677); p97 (melanoma-associated antigen; Estin et al. (1989) "Transfected Mouse Melanoma Lines That Express Various Levels Of Human Melanoma-Associated Antigen p97," J. Natl. Cancer Instit. 81(6):445-454); PEM (polymorphic epithelial mucin; Hilkens et al. (1992) "Cell Membrane-Associated Mucins And Their Adhesion-Modulating Property," Trends in Biochem. Sci. 17:359-363); PEMA (polymorphic epithelial mucin antigen); PIPA (U.S. Pat. No. 7,405,061; PCT Publication No. WO 04/043239); PSA (prostate-specific antigen; Henttu et al. (1989) "cDNA Coding For The Entire Human Prostate Specific Antigen Shows High Homologies To The Human Tissue Kallikrein Genes," Biochem. Biophys. Res. Comm. 10(2):903-910; Israeli et al. (1993) "Molecular Cloning Of A Complementary DNA Encoding A Prostate-Specific Membrane Antigen," Cancer Res. 53:227-230; Cracco, C. M. et al. (2005) "Immune Response In Prostate Cancer," Minerva Urol. Nefrol. 57(4):301-311); PSMA (prostate-specific membrane antigen; Ragupathi, G. (2005) "Antibody Inducing Polyvalent Cancer Vaccines," Cancer Treat. Res. 123: 157-180); prostatic acid phosphate (Tailor et al. (1990) "Nucleotide Sequence Of Human Prostatic Acid Phosphatase Determined From A Full-Length cDNA Clone," Nucl. Acids Res. 18(16):4928); $R_{24}$ as found in melanoma; ROR1 (U.S. Pat. No. 5,843,749); sphingolipids; SSEA-1; SSEA-3; SSEA-4; sTn (Holmberg, L. A. (2001) "Theratope Vaccine (STn-KLH)," Expert Opin. Biol. Ther. 1(5):881-91); T-cell receptor derived peptide from a cutaneous T-cell lymphoma (see Edelson (1998) "Cutaneous T-Cell Lymphoma: A Model For Selective Immunotherapy," Cancer J. Sci. Am. 4:62-71); $T_5A_7$ found in myeloid cells; TAG-72 (Yokota et al. (1992) "Rapid Tumor Penetration Of A Single-Chain Fv And Comparison With Other Immunoglobulin Forms," Cancer Res. 52:3402-3408); TL5 (blood group A); TNF-receptor (TNF-α receptor, TNF-β receptor; TNF-γ receptor (van Horssen, R. et al. (2006) "TNF-Alpha In Cancer Treatment: Molecular Insights, Antitumor Effects, And Clinical Utility," Oncologist 11(4):397-408; Gardnerova, M. et al. (2000) "The Use Of TNF Family Ligands And Receptors And Agents Which Modify Their Interaction As Therapeutic Agents," Curr. Drug Targets 1(4):327-364); TRA-1-85 (blood group H); Transferrin Receptor (U.S. Pat. No. 7,572,895; PCT Publication No. WO 05/121179); 5T4 (TPBG, trophoblast glycoprotein; Boghaert, E. R. et al. (2008) "The Oncofetal Protein, 5T4, Is A Suitable Target For Antibody-Guided Anti-Cancer Chemotherapy With Calicheamicin," Int. J. Oncol. 32(1):221-234; Eisen, T. et al. (2014) "Naptumomab Estafenatox: Targeted Immunotherapy with a Novel Immunotoxin," Curr. Oncol. Rep. 16:370, pp. 1-6); TSTA (tumor-specific transplantation antigen) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellström et al. (1985) "Monoclonal Antibodies To Cell Surface Antigens Shared By Chemically Induced Mouse Bladder Carcinomas," Cancer. Res. 45:2210-2188); VEGF (Pietrantonio, F. et al. (2015) "Bevacizumab-Based Neoadjuvant Chemotherapy For Colorectal Cancer Liver Metastases: Pitfalls And Helpful Tricks In A Review For Clinicians," Crit. Rev. Oncol. Hematol. 95(3):272-281; Grabowski, J. P. (2015) "Current Management Of Ovarian Cancer," Minerva Med. 106(3):151-156; Field, K. M. (2015) "Bevacizumab And Glioblastoma: Scientific Review, Newly Reported Updates, And Ongoing Controversies," Cancer 121(7):997-1007; Suh, D. H. et al. (2015) "Major Clinical Research Advances In Gynecologic Cancer In 2014," J. Gynecol. Oncol. 26(2): 156-167; Liu, K. J. et al. (2015) "Bevacizumab In Combination With Anticancer Drugs For Previously Treated Advanced Non-Small Cell Lung Cancer," Tumour Biol. 36(3):1323-1327; Di Bartolomeo, M. et al. (2015) "Bevacizumab Treatment In The Elderly Patient With Metastatic Colorectal Cancer," Clin. Interv. Aging 10:127-133); VEGF Receptor (O'Dwyer. P. J. (2006) "The Present And Future Of Angiogenesis-Directed Treatments Of Colorectal Cancer," Oncologist 11(9):992-998); VEP8; VEP9; VIM-D5; and Y hapten, Le$^y$ as found in embryonal carcinoma cells. Additional Cancer Antigens, and molecules (e.g., antibodies) that bind them are disclosed in Table 7. 5T4, B7-H3, CEACAM5/CEACAM6, CD123, DR5, EGFR, an Ephrin receptor, gpA33, HER2/neu, IL13Rα2, ROR1, and VEGF are particularly preferred "Cancer Antigens" of the present invention.

TABLE 7

Antibody and Antibody-Based Molecules

| Antibody Name | Cancer Antigens | Therapeutic Target Application |
|---|---|---|
| 3F8 | Gd2 | Neuroblastoma |
| 8H9 | B7-H3 | Neuroblastoma, Sarcoma, Metastatic Brain Cancers |
| Abagovomab | CA-125 | Ovarian Cancer |
| Adecatumumab | Epcam | Prostate and Breast Cancer |
| Afutuzumab | CD20 | Lymphoma |
| Alacizumab | VEGFR2 | Cancer |
| Altumomab | CEA | Colorectal Cancer |
| Amatuximab | Mesothelin | Cancer |
| Anatumomab Mafenatox | TAG-72 | Non-Small Cell Lung Carcinoma |
| Anifrolumab | Interferon A/B Receptor | Systemic Lupus Erythematosus |
| Anrukinzumab | IL-13 | Cancer |
| Apolizumab | HLA-DR | Hematological Cancers |
| Arcitumomab | CEA | Gastrointestinal Cancer |
| Atinumab | RTN4 | Cancer |
| Bectumomab | CD22 | Non-Hodgkin's Lymphoma (Detection) |
| Belimumab | BAFF | Non-Hodgkin Lymphoma |
| Bevacizumab | VEGF-A | Metastatic Cancer, Retinopathy of Prematurity |
| Bivatuzumab | CD44 V6 | Squamous Cell Carcinoma |
| Blinatumomab | CD19 | Cancer |
| Brentuximab | CD30 (TNFRSF8) | Hematologic Cancers |
| Cantuzumab | MUC1 | Cancers |
| Cantuzumab Mertansine | Mucin Canag | Colorectal Cancer |
| Caplacizumab | VWF | Cancers |
| Capromab | Prostatic Carcinoma Cells | Prostate Cancer (Detection) |
| Carlumab | MCP-1 | Oncology/Immune Indications |
| Catumaxomab | Epcam, CD3 | Ovarian Cancer, Malignant Ascites, Gastric Cancer |
| Cc49 | Tag-72 | Tumor Detection |
| Cetuximab | EGFR | Metastatic Colorectal Cancer and Head and Neck Cancer |
| Ch.14.18 | Undetermined | Neuroblastoma |
| Citatuzumab | Epcam | Ovarian Cancer and other Solid Tumors |
| Cixutumumab | IGF-1 Receptor | Solid Tumors |
| Clivatuzumab | MUC1 | Pancreatic Cancer |
| Conatumumab | TRAIL-R2 | Cancer |
| Dacetuzumab | CD40 | Hematologic Cancers |
| Dalotuzumab | Insulin-Like Growth Factor I Receptor | Cancer |
| Daratumumab | CD38 | Cancer |
| Demcizumab | DLL4 | Cancer |
| Detumomab | B-Lymphoma Cell | Lymphoma |
| Drozitumab | DR5 | Cancer |
| Duligotumab | HER3 | Cancer |
| Dusigitumab | ILGF2 | Cancer |
| Ecromeximab | GD3 Ganglioside | Malignant Melanoma |
| Eculizumab | C5 | Paroxysmal Nocturnal Hemoglobinuria |
| Edrecolomab | Epcam | Colorectal Carcinoma |
| Elotuzumab | SLAMF7 | Multiple Myeloma |
| Elsilimomab | IL-6 | Cancer |
| Enavatuzumab | TWEAK Receptor | Cancer |
| Enlimomab | ICAM-1 (CD54) | Cancer |
| Enokizumab | IL9 | Asthma |

TABLE 7-continued

Antibody and Antibody-Based Molecules

| Antibody Name | Cancer Antigens | Therapeutic Target Application |
|---|---|---|
| Enoticumab | DLL4 | Cancer |
| Ensituximab | 5AC | Cancer |
| Epitumomab Cituxetan | Episialin | Cancer |
| Epratuzumab | CD22 | Cancer, SLE |
| Ertumaxomab | HER2/Neu, CD3 | Breast Cancer |
| Etaracizumab | Integrin A,β$_3$ | Melanoma, Prostate Cancer, Ovarian Cancer |
| Faralimomab | Interferon Receptor | Cancer |
| Farletuzumab | Folate Receptor 1 | Ovarian Cancer |
| Fasinumab | HNGF | Cancer |
| Fbta05 | CD20 | Chronic Lymphocytic Leukaemia |
| Ficlatuzumab | HGF | Cancer |
| Figitumumab | IGF-1 Receptor | Adrenocortical Carcinoma, Non-Small Cell Lung Carcinoma |
| Flanvotumab | TYRP1 (Glycoprotein 75) | Melanoma |
| Fontolizumab | IFN-γ | Crohn's Disease |
| Fresolimumab | TGF-B | Idiopathic Pulmonary Fibrosis, Focal Segmental Glomerulosclerosis, Cancer |
| Futuximab | EGFR | Cancer |
| Galiximab | CD80 | B Cell Lymphoma |
| Ganitumab | IGF-I | Cancer |
| Gemtuzumab Ozogamicin | CD33 | Acute Myelogenous Leukemia |
| Gevokizumab | IL-1β | Diabetes |
| Girentuximab | Carbonic Anhydrase 9 (CA-IX) | Clear Cell Renal Cell Carcinoma |
| Glembatumumab Vedotin | GPNMB | Melanoma, Breast Cancer |
| Golimumab | TNF-A | Rheumatoid Arthritis, Psoriatic Arthritis, Ankylosing Spondylitis |
| Ibritumomab Tiuxetan | CD20 | Non-Hodgkin's Lymphoma |
| Icrucumab | VEGFR-1 | Cancer |
| Igovomab | CA-125 | Ovarian Cancer (Diagnosis) |
| Imab362 | Cldn18.2 | Gastrointestinal Adenocarcinomas and Pancreatic Tumor |
| Imgatuzumab | EGFR | Cancer |
| Inclacumab | Selectin P | Cancer |
| Indatuximab Ravtansine | SDC1 | Cancer |
| Inotuzumab Ozogamicin | CD22 | Cancer |
| Intetumumab | CD51 | Solid Tumors (Prostate Cancer, Melanoma) |
| Ipilimumab | CD152 | Melanoma |
| Iratumumab | CD30 (TNFRSF8) | Hodgkin's Lymphoma |
| Itolizumab | CD6 | Cancer |
| Labetuzumab | CEA | Colorectal Cancer |
| Lambrolizumab | PDCD1 | Antineoplastic Agent |
| Lampalizumab | CFD | Cancer |
| Lexatumumab | TRAIL-R2 | Cancer |
| Libivirumab | Hepatitis B Surface Antigen | Hepatitis B |
| Ligelizumab | IGHE | Cancer |
| Lintuzumab | CD33 | Cancer |
| Lirilumab | KIR2D | Cancer |
| Lorvotuzumab | CD56 | Cancer |
| Lucatumumab | CD40 | Multiple Myeloma, Non-Hodgkin's Lymphoma, Hodgkin's Lymphoma |
| Lumiliximab | CD23 | Chronic Lymphocytic Leukemia |
| Mapatumumab | TRAIL-R1 | Cancer |
| Margetuximab | Ch4d5 | Cancer |
| Matuzumab | EGFR | Colorectal, Lung and Stomach Cancer |
| Milatuzumab | CD74 | Multiple Myeloma and Other Hematological Malignancies |
| Minretumomab | TAG-72 | Cancer |
| Mitumomab | GD3 Ganglioside | Small Cell Lung Carcinoma |
| Mogamulizumab | CCR4 | Cancer |
| Morolimumab | Rhesus Factor | Cancer |
| Moxetumomab Pasudotox | CD22 | Cancer |
| Nacolomab Tafenatox | C242 Antigen | Colorectal Cancer |
| Namilumab | CSF2 | Cancer |
| Naptumomab Estafenatox | 5T4 | Non-Small Cell Lung Carcinoma, Renal Cell Carcinoma |
| Narnatumab | RON | Cancer |
| Nebacumab | Endotoxin | Sepsis |
| Necitumumab | EGFR | Non-Small Cell Lung Carcinoma |
| Nerelimomab | TNF-A | Cancer |
| Nesvacumab | Angiopoietin 2 | Cancer |
| Nimotuzumab | EGFR | Squamous Cell Carcinoma, Head and Neck Cancer, Nasopharyngeal Cancer, Glioma |
| Nivolumab | PD-1 | Cancer |
| Nofetumomab Merpentan | Undetermined | Cancer |
| Ocaratuzumab | CD20 | Cancer |
| Ofatumumab | CD20 | Chronic Lymphocytic Leukemia |
| Olaratumab | PDGF-R A | Cancer |
| Olokizumab | IL6 | Cancer |
| Onartuzumab | Human Scatter Factor Receptor Kinase | Cancer |
| Ontuxizumab | TEM1 | Cancer |
| Oportuzumab Monatox | Epcam | Cancer |
| Oregovomab | CA-125 | Ovarian Cancer |
| Orticumab | Oxldl | Cancer |
| Otlertuzumab | CD37 | Cancer |
| Panitumumab | EGFR | Colorectal Cancer |
| Pankomab | Tumor Specific Glycosylation of MUC1 | Ovarian Cancer |
| Parsatuzumab | EGFL7 | Cancer |
| Patritumab | HER3 | Cancer |
| Pembrolizumab | PD-1 | Cancer |
| Pemtumomab | MUC1 | Cancer |
| Perakizumab | IL17A | Arthritis |
| Pertuzumab | HER2/Neu | Cancer |
| Pidilizumab | PD-1 | Cancer and Infectious Diseases |
| Pinatuzumab Vedotin | CD22 | Cancer |
| Pintumomab | Adenocarcinoma Antigen | Adenocarcinoma |
| Placulumab | Human TNF | Cancer |
| Polatuzumab Vedotin | CD79B | Cancer |
| Pritoxaximab | E. Coli Shiga Toxin Type-1 | Cancer |
| Pritumumab | Vimentin | Brain Cancer |
| Quilizumab | IGHE | Cancer |
| Racotumomab | N-Glycolylneuraminic Acid | Cancer |
| Radretumab | Fibronectin Extra Domain-B | Cancer |
| Ramucirumab | VEGFR2 | Solid Tumors |
| Rilotumumab | HGF | Solid Tumors |
| Rituximab | CD20 | Lymphomas, Leukemias, Some Autoimmune Disorders |
| Robatumumab | IGF-1 Receptor | Cancer |
| Roledumab | RHD | Cancer |
| Samalizumab | CD200 | Cancer |
| Satumomab Pendetide | TAG-72 | Cancer |
| Seribantumab | ERBB3 | Cancer |

TABLE 7-continued

Antibody and Antibody-Based Molecules

| Antibody Name | Cancer Antigens | Therapeutic Target Application |
|---|---|---|
| Setoxaximab | E. Coli Shiga Toxin Type-1 | Cancer |
| Sgn-CD19a | CD19 | Acute Lymphoblastic Leukemia and B Cell Non-Hodgkin Lymphoma |
| Sgn-CD33a | CD33 | Acute Myeloid Leukemia |
| Sibrotuzumab | FAP | Cancer |
| Siltuximab | IL-6 | Cancer |
| Solitomab | Epcam | Cancer |
| Sontuzumab | Episialin | Cancer |
| Tabalumab | BAFF | B Cell Cancers |
| Tacatuzumab Tetraxetan | Alpha-Fetoprotein | Cancer |
| Taplitumomab Paptox | CD19 | Cancer |
| Telimomab | Undetermined | Cancer |
| Tenatumomab | Tenascin C | Cancer |
| Teneliximab | CD40 | Cancer |
| Teprotumumab | CD221 | Hematologic Tumors |
| Ticilimumab | CTLA-4 | Cancer |
| Tigatuzumab | TRAIL-R2 | Cancer |
| Tnx-650 | Il-13 | Hodgkin's Lymphoma |
| Tositumomab | CD20 | Follicular Lymphoma |
| Tovetumab | CD140a | Cancer |
| Trastuzumab | HER2/Neu | Breast Cancer |
| Trbs07 | Gd2 | Melanoma |
| Tremelimumab | CTLA-4 | Cancer |
| Tucotuzumab Celmoleukin | Epcam | Cancer |
| Ublituximab | MS4A1 | Cancer |
| Urelumab | 4-1BB | Cancer |
| Vantictumab | Frizzled Receptor | Cancer |
| Vapaliximab | AOC3 (VAP-1) | Cancer |
| Vatelizumab | ITGA2 | Cancer |
| Veltuzumab | CD20 | Non-Hodgkin's Lymphoma |
| Vesencumab | NRP1 | Cancer |
| Volociximab | Integrin A5β1 | Solid Tumors |
| Vorsetuzumab | CD70 | Cancer |
| Votumumab | Tumor Antigen CTAA16.88 | Colorectal Tumors |
| Zalutumumab | EGFR | Squamous Cell Carcinoma of The Head And Neck |
| Zatuximab | HER1 | Cancer |
| Ziralimumab | CD147 | Cancer |

Exemplary antibodies, whose VH and VL Domains may be used to construct the Binding Molecules of the present invention that are capable of binding a Cancer Antigen arrayed on the surface of a cancer cell and mediating the redirected killing of such cancer cells are listed in Table 7 above, additional antibodies that may be used to construct molecules capable of binding a Cancer Antigen arrayed on the surface of a cancer cell and mediating the redirected killing of such cancer cells are provided below.

1. Exemplary Anti-B7-H3 Antibodies

B7-H3 is a Cancer Antigen that is overexpressed on a wide variety of solid tumor types and is a member of the B7 family of molecules that are involved in immune regulation (see, U.S. Pat. No. 8,802,091; US 2014/0328750; US 2013/0149236; Loo, D. et al. (2012) "*Development Of An Fc-Enhanced Anti-B7-H3 Monoclonal Antibody With Potent Antitumor Activity*," Clin. Cancer Res. 18(14):3834-3845). In particular, several independent studies have shown that human malignant cancer cells (e.g., cancer cells of neuroblastomas and gastric, ovarian, pancreatic, and non-small cell lung cancers) exhibit a marked increase in expression of B7-H3 protein and that this increased expression was associated with increased disease severity (Zang, X. et al. (2007) "*The B7 Family And Cancer Therapy: Costimulation And Coinhibition*," Clin. Cancer Res. 13:5271-5279), suggesting that B7-H3 is exploited by tumors as an immune evasion pathway (Hofmeyer, K. et al. (2008) "*The Contrasting Role Of B7-H3*," Proc. Natl. Acad. Sci. (U.S.A.) 105(30): 10277-10278).

B7-H3 has also been found to co-stimulate CD4+ and CD8+ T-cell proliferation. B7-H3 also stimulates IFN-γ production and CD8+ lytic activity (Chapoval, A. et al. (2001) "*B7-H3: A Costimulatory Molecule For T Cell Activation and IFN-γ Production*," Nature Immunol. 2:269-274; Sharpe, A. H. et al. (2002) "*The B7-CD28 Superfamily*," Nature Rev. Immunol. 2:116-126). However, the protein also possibly acts through NFAT (nuclear factor for activated T-cells), NF-κB (nuclear factor kappa B), and AP-1 (Activator Protein-1) factors to inhibit T-cell activation (Yi. K. H. et al. (2009) "*Fine Tuning The Immune Response Through B7-H3 And B7-H4*," Immunol. Rev. 229:145-151). B7-H3 is also believed to inhibit Th1, Th2, or Th17 in vivo (Prasad, D. V. et al. (2004) "*Murine B7-H3 Is A Negative Regulator Of T Cells*," J. Immunol. 173:2500-2506; Fukushima, A. et al. (2007) "*B7-H3 Regulates The Development Of Experimental Allergic Conjunctivitis In Mice*," Immunol. Lett. 113:52-57; Yi. K. H. et al. (2009) "*Fine Tuning The Immune Response Through B7-H3 And B7-H4*," Immunol. Rev. 229:145-151).

Preferred B7-H3-Binding Molecules possess the VL and/or VH Domains, of humanized anti-human B7-H3 monoclonal antibody "B7-H3 mAb-B," "B7-H3 mAb-C," "B7-H3 mAb-D," or any of the anti-B7-H3 antibodies provided herein; and more preferably possess 1, 2 or all 3 of the $CDR_L$s of the VL Domain and/or 1, 2 or all 3 of the $CDR_H$s of the VH Domain of such anti-B7-H3 monoclonal antibodies.

Upon humanization, antibody B7-H3 mAb-B yielded two variant VH Domains, B7-H3 mAb-B VH1 and B7-H3 mAb-B VH2; and two variant VL Domains B7-H3 mAb-B VH1 VL1 and B7-H3 mAb-B VL2, which may be used in any combination of VH/VL Domains to yield a functional B7-H3 Binding Domain.

The amino acid sequence of the VH Domain of B7-H3 mAb-B VH1 is SEQ ID NO:122 ($CDR_H$ residues are shown underlined):

```
QVQLVQSGAE VKKPGASVKV SCKASGYTFT SYWMQWVRQA

PGQGLEWMGT IYPGDGDTRY TQKFKGRVTI TADKSTSTAY

MELSSLRSED TAVYYCARRG IPRLWYFDVW GQGTTVTVSS
```

The amino acid sequence of the VH Domain of B7-H3 mAb-B VH2 is SEQ ID NO:123 ($CDR_H$ residues are shown underlined):

```
QVQLVQSGAE VKKPGASVKV SCKASGYTFT SYWMQWVRQA

PGQGLEWMGT IYPGGGDTRY TQKFQGRVTI TADKSTSTAY

MELSSLRSED TAVYYCARRG IPRLWYFDVW GQGTTVTVSS
```

The amino acid sequence of the VL Domain of B7-H3 mAb-B VL1 is SEQ ID NO:124 ($CDR_L$ residues are shown underlined).

```
DIQMTQSPSS LSASVGDRVT ITCRASQDIS NYLNWYQQKP

GKAPKLLIYY TSRLHSGVPS RFSGSGSGTD FTLTISSLQP

EDIATYYCQQ GNTLPPTFGG GTKLEIK
```

The amino acid sequence of the VL Domain of B7-H3 mAb-B VL2 is SEQ ID NO:125 (CDR$_L$ residues are shown underlined).

```
DIQMTQSPSS LSASVGDRVT ITCRASQSIS SYLNWYQQKP

GKAPKLLIYY TSRLQSGVPS RFSGSGSGTD FTLTISSLQP

EDIATYYCQQ GNTLPPTFCG GTKLEIK
```

The amino acid sequence of the VH Domain of humanized B7-H3 mAb-C is SEQ ID NO:126 (CDR$_H$ residues are shown underlined):

```
EVQLVESGGG LVKPGGSLRL SCAASGFTFS SYGMSWVRQA

PGKGLEWVAT INSGGSNTYY PDSLKGRFTI SRDNAKNSLY

LQMNSLRAED TAVYYCARHD GGAMDYWGQG TTVTVSS
```

The amino acid sequence of the VL Domain of humanized B7-H3 mAb-C is SEQ ID NO:127 (CDR$_L$ residues are shown underlined).

```
DIQMTQSPSS LSASVGDRVT ITCRASESIY SYLAWYQQKP

GKAPKLLVYN TKTLPEGVPS RFSGSGSGTD FTLTISSLQP

EDFATYYCQH HYGTPPWTFG QGTRLEIK
```

The amino acid sequence of the VH Domain of B7-H3 mAb-D (SEQ ID NO:128) is shown below (CDR$_H$ residues are shown underlined).

```
EVQLVESGGG LVQPGGSLRL SCAASGFTFS SFGMHWVRQA

PGKGLEWVAY ISSGSGTIYY ADTVKGRFTI SRDNAKNSLY

LQMNSLRAED TAVYYCARHG YRYEGFDYWG QGTTVTVSS
```

The amino acid sequence of the VL Domain of B7-H3 mAb-D (SEQ ID NO:129) is shown below (CDR$_L$ residues are shown underlined).

```
DIQMTQSPSF LSASVGDRVT ITCKASQNVD TNVAWYQQKP

GKAPKALIYS ASYRYSGVPS RFSGSGSGTD FTLTISSLQP

EDFAEYFCQQ YNNYPFTFGQ GTKLEIK
```

Particularly preferred, are B7-H3-Binding Molecules which possess a humanized VH and/or VL Domain including but not limited to "Enoblituzumab" (also known as MGA271; CAS Reg No. 1353485-38-7). Enoblituzumab is an Fc-optimized monoclonal antibody that binds to HER2/neu and mediates enhanced ADCC activity. The amino acid sequences of the complete Heavy and Light Chains of Enoblituzumab are known in the art (see, e.g., WHO Drug Information, 2017, Recommended INN: List 77, 31(1):49). The amino acid sequence of the VH Domain of Enoblituzumab is (SEQ ID NO:130) (CDR$_H$ s are underlined):

```
EVQLVESGGG LVQPGGSLRL SCAASGFTFS SFGMHWVRQA

PGKGLEWVAY ISSDSSAIYY ADTVKGRFTI SRDNAKNSLY

LQMNSLRDED TAVYYCGRGR ENIYYGSRLD YWGQGTTVTV SS
```

The amino acid sequence of the VL Domain of Enoblituzumab is (SEQ ID NO:131) (CDR$_L$s are underlined):

```
DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIK
```

In addition to the above-identified preferred anti-B7-H3 Binding Molecules, the invention contemplates the use of any of the following anti-B7-H3 Binding Molecules: LUCA1; BLAB; PA20; or SKN2 (see, U.S. Pat. Nos. 7,527,969; 8,779,098 and PCT Patent Publication WO 2004/001381); M30; cM30; M30-H1-L1; M30-H1-L2; M30-H1-L3; M30-H1-L4; M30-H1-L5; M30-H1-L6; M30-H1-L7; M30-H4-L1; M30-H4-L2; M30-H4-L3; and M30-H4-L4 (see, US Patent Publication 2013/0078234 and PCT Patent Publication WO 2012/147713); and 8H9 (see U.S. Pat. Nos. 7,666,424; 7,737,258; 7,740,845; 8,148,154; 8,414,892; 8,501,471; 9,062,110; US Patent Publication 2010/0143245 and PCT Patent Publication WO 2008/116219).

2. Exemplary Anti-CEACAM5 and Anti-CEACAM6 Antibodies

Carcinoembryonic Antigen-Related Cell Adhesion Molecules 5 (CEACAM5) and 6 (CEACAM6) have been found to be associated with various types of cancers including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Publication No. WO 2011/034660), and particularly colorectal, gastrointestinal, pancreatic, non-small cell lung cancer (NSCL), breast, thyroid, stomach, ovarian and uterine carcinomas (Zheng, C. et al. (2011) "*A Novel Anti-CEACAM5 Monoclonal Antibody, CC4, Suppresses Colorectal Tumor Growth and Enhances NK Cells-Mediated Tumor Immunity*," PLoS One 6(6):e21146, pp. 1-11).

CEACAM5 has been found to be overexpressed in 90% of gastrointestinal, colorectal and pancreatic cancers, 70% of non-small cell lung cancer cells and 50% of breast cancers (Thompson, J. A. et al. (1991) "*Carcinoembryonic Antigen Gene Family: Molecular Biology And Clinical Perspectives*," J. Clin. Lab. Anal. 5:344-366). Overexpressed carcinoembryonic antigen-related cellular adhesion molecule 6 (CEACAM6) plays important roles in the invasion and metastasis of a variety of human cancers, including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Publication No. WO 2011/034660; Deng, X. et al. (2014) "*Expression Profiling Of CEACAM6 Associated With The Tumorigenesis And Progression In Gastric Adenocarcinoma*," Genet. Mol. Res. 13(3):7686-7697; Cameron, S. et al. (2012) "*Focal Overexpression Of CEACAM6 Contributes To Enhanced Tumorigenesis In Head And Neck Cancer Via Suppression Of Apoptosis*," Mol. Cancer 11:74, pp. 1-11;

Chapin, C. et al. (2012) "*Distribution And Surfactant Association Of Carcinoembryonic Cell Adhesion Molecule 6 In Human Lung*," Amer. J. Physiol. Lung Cell. Mol. Physiol. 302(2):L216-L25; Riley, C. J. et al. (2009) "*Design And Activity Of A Murine And Humanized Anti-CEACAM6 Single-Chain Variable Fragment In The Treatment Of Pancreatic Cancer*," Cancer Res. 69(5):1933-1940; Lewis-Wambi, J. S. et al. (2008) "*Overexpression Of CEACAM6 Promotes Migration And Invasion Of Oestrogen-Deprived Breast Cancer Cells*," Eur. J. Cancer 44(12):1770-1779; Blumenthal, R. D. et al. (2007) "*Expression Patterns Of CEACAM5 And CEACAM6 In Primary And Metastatic Cancers*," BMC Cancer. 7:2, pp. 1-15). Antibodies that immunospecifically bind CEACAM5 and CEACAM6 are commercially available (Santa Cruz Biotechnology, Inc., Novus Biologicals LLC; Abnova Corporation).

The amino acid sequence of the VH Domain of the humanized anti-CEACAM5/ANTI-CEACAM6 antibody 16C3 (EP 2585476) (SEQ ID NO:132) is shown below (CDR$_H$ residues are shown underlined):

```
QVQLQQSGPE VVRPGVSVKI SCKGSGYTFT DYAMHWVKQS

MAKSLEWIGL ISTYSGDTKY NQNFKGKATM TVDKSASTAY

MELSSLRSED TAVYYCARGD YSGSRYWFAY WGQGTLVTVS S
```

The amino acid sequence of the VL Domain of the humanized anti-CEACAM5/ANTI-CEACAM6 antibody 16C3 (EP 2585476) (SEQ ID NO:133) is shown below (CDR$_L$ residues are shown underlined):

```
DIQMTQSPSS LSASVGDRVT ITCGASENIY GALNWYQRKP

GKSPKLLIWG ASNLADGMPS RFSGSGSGRQ YTLTISSLQP

EDVATYYCQN VLSSPYTFGG GTKLEIK
```

The amino acid sequence of the VH Domain of the humanized anti-CEACAM5/CEACAM6 antibody hMN15 (WO 2011/034660) (SEQ ID NO:134) is shown below (CDR$_H$ residues are shown underlined):

```
QVQLVESGGG VVQPGRSLRL SCSSSGFALT DYYMSWVRQA

PGKGLEWLGF IANKANGHTT DYSPSVKGRF TISRDNSKNT

LFLQMDSLRP EDTGVYFCAR DMGIRWNFDV WGQGTPVTVS S
```

The amino acid sequence of the VL Domain of the humanized anti-CEACAM5/CEACAM6 antibody hMN15 (WO 2011/034660) (SEQ ID NO:135) is shown below (CDR$_L$ residues are shown underlined):

```
DIQLTQSPSS LSASVGDRVT MTCSASSRVS YIHWYQQKPG

KAPKRWIYGT STLASGVPAR FSGSGSGTDF TFTISSLQPE

DIATYYCQQW SYNPPTFGQG TKVEIKR
```

The present invention specifically includes and encompasses CEACAM5/CEACAM6 Binding Molecules (e.g., CEACAM5/CEACAM6×CD3 bispecific Binding Molecules) that are capable of binding to CEACAM5 and/or CEACAM6, and particularly such Binding Molecules that comprise the VL and/or VH Domain, and/or 1, 2 or all 3 of the CDR$_L$s of the VL Domain and/or 1, 2 or all 3 of the CDR$_H$s of the VH Domain of the anti-CEACAM5/CEACAM6 monoclonal antibodies 16C3 or hMN15.

3. Exemplary Anti-EGRF Antibodies

Epidermal Growth Factor Receptor (EGFR) is a Cancer Antigen of certain metastatic colorectal cancer, metastatic non-small cell lung cancer and head and neck cancer. Exemplary antibodies that bind human EGRF are "Cetuximab" and "Panitumumab." Cetuximab is a recombinant human-mouse chimeric epidermal growth factor receptor (EGFR) IgG1 monoclonal antibody (Govindan R. (2004) "*Cetuximab In Advanced Non-Small Cell Lung Cancer*," Clin. Cancer Res. 10(12 Pt 2):4241s-4244s; Bou-Assaly, W. et al. (2010) "*Cetuximab (Erbitux)*," Am. J. Neuroradiol. 31(4):626-627). Panitumumab (Vectibix®, Amgen) is a fully humanized epidermal growth factor receptor (EGFR) IgG2 monoclonal antibody (Foon, K. A. et al. (2004) "*Preclinical And Clinical Evaluations Of ABX-EGF, A Fully Human Anti-Epidermal Growth Factor Receptor Antibody*," Int. J. Radiat. Oncol. Biol. Phys. 58(3):984-990; Yazdi, M. H. et al. (2015) "*A Comprehensive Review of Clinical Trials on EGFR Inhibitors Such as Cetuximab and Panitumumab as Monotherapy and in Combination for Treatment of Metastatic Colorectal Cancer*," Avicenna J. Med. Biotechnol. 7(4):134-144).

The amino acid sequence of the VH Domain of the chimeric anti-EGFR antibody Cetuximab (SEQ ID NO:136) is shown below (CDR$_H$ residues are shown underlined):

```
QVQLKQSGPG LVQPSQSLSI TCTVSGFSLT NYGVHWVRQS

PGKGLEWLGV IWSGGNTDYN TPFTSRLSIN KDNSKSQVFF

KMNSLQSNDT AIYYCARALT YYDYEFAYWG QGTLVIVSA
```

The amino acid sequence of the VL Domain of the chimeric anti-EGFR antibody Cetuximab (SEQ ID NO:137) is shown below (CDR$_L$ residues are shown underlined):

```
DILLTQSPVI LSVSPGERVS FSCRASQSIG TNIHWYQQRT

NGSPRLLIKY ASESISGIPS RFSGSGSGTD FTLSINSVES

EDIADYYCQQ NNNWPTTFGA GTKLELKR
```

The amino acid sequence of the VH Domain of Panitumumab (SEQ ID NO:138) is shown below (CDR$_H$ residues are shown underlined):

```
QVQLQESGPG LVKPSETLSL TCTVSGGSVS SGDYYWTWIR

QSPGKGLEWI GHIYYSGNTN YNPSLKSRLT ISIDTSKTQF

SLKLSSVTAA DTAIYYCVRD RVTGAFDIWG QGTMVTVSS
```

The amino acid sequence of the VL Domain of Panitumumab (SEQ ID NO:139) is shown below (CDR$_L$ residues are shown underlined):

```
DIQMTQSPSS LSASVGDRVT ITCQASQDIS NYLNWYQQKP

GKAPKLLIYD ASNLETGVPS RFSGSGSGTD FTFTISSLQP

EDIATYFCQH FDHLPLAFGG GTKVEIKR
```

The present application specifically includes and encompasses EGFR Binding Molecules (e.g., EGFR×CD3 bispecific Binding Molecules) that are capable of binding to EGFR, and particularly such Binding Molecules that comprise the VL and/or VH Domain, and/or 1, 2 or all 3 of the CDR$_L$s of the VL Domain and/or 1, 2 or all 3 of the CDR$_H$s of the VH Domain of the anti-EGFR monoclonal antibodies Cetuximab or Panitumumab.

4. Exemplary Anti-EphA2 Antibodies

The receptor tyrosine kinase, Ephrin type-A receptor 2 (EphA2) is normally expressed at sites of cell-to-cell contact in adult epithelial tissues, however, recent studies have shown that it is also overexpressed in various types of epithelial carcinomas, with the greatest level of EphA2 expression observed in metastatic lesions. High expression levels of EphA2 have been found in a wide range of cancers and in numerous cancer cell lines, including prostate cancer, breast cancer, non-small cell lung cancer and melanoma (Xu, J. et al. (2014) "*High EphA2 Protein Expression In Renal Cell Carcinoma Is Associated With A Poor Disease Outcome*," Oncol. Lett. August 2014; 8(2): 687-692; Miao, B. et al. (2014) "*EphA2 is a Mediator of Vemurafenib Resistance and a Novel Therapeutic Target in Melanoma*," Cancer Discov. pii: CD-14-0295). EphA2 does not appear to be merely a marker for cancer, but rather appears to be persistently overexpressed and functionally changed in numerous human cancers (Chen, P. et al. (2014) "*EphA2 Enhances The Proliferation And Invasion Ability Of LnCap Prostate Cancer Cells*," Oncol. Lett. 8(1):41-46). Exemplary antibodies that bind human EphA2 are "EphA2 mAb 1," "EphA2 mAb 2" and "EphA2 mAb 3."

The amino acid sequence of the VH Domain of EphA2 mAb 1 (SEQ ID NO:140) is shown below (CDR$_H$ residues are shown underlined):

```
QVQLKESGPG LVAPSQSLSI TCTVSGFSLS RYSVHWVRQP

PGKGLEWLGM IWGGGSTDYN SALKSRLSIS KDNSKSQVFL

KMNSLQTDDT AMYYCARKHG NYYTMDYWGQ GTSVTVSS
```

The amino acid sequence of the VL Domain of EphA2 mAb 1 (SEQ ID NO:141) is shown below (CDR$_L$ residues are shown underlined):

```
DIQMTQTTSS LSASLGDRIT ISCRASQDIS NYLNWYQQKP

DGTVKLLIYY TSRLHSGVPS RFSGSGSGTD YSLTISNLEQ

EDIATYFCQQ GYTLYTFGGG TKLEIK
```

The amino acid sequence of the VH Domain of EphA2 mAb 2 (SEQ ID NO:142) is shown below (CDR$_H$ residues are shown underlined):

```
QIQLVQSGPE LKKPGETVKI SCKASGFTFT NYGMNWVKQA

PGKGLKWMGW INTYIGEPTY ADDFKGRFVF SLETSASTAY

LQINNLKNED MATYFCAREL GPYYFDYWGQ GTTLTVSS
```

The amino acid sequence of the VL Domain of EphA2 mAb 2 (SEQ ID NO:143) is shown below (CDR$_L$ residues are shown underlined):

```
DVVMTQTPLS LPVSLGDQAS ISCRSSQSLV HSSGNTYLHW

YLQKPGQSPK LLIYKVSNRF SGVPDRFSGS GSGTDFTLKI

SRVEAEDLGV YFCSQSTHVP TFGSGTKLEI K
```

The amino acid sequence of the VH Domain of EphA2 mAb 3 (SEQ ID NO:144) is shown below (CDR$_H$ residues are shown underlined):

```
EVQLVESGGG SVKPGGSLKL SCAASGFTFT DHYMYWVRQT

PEKRLEWVAT ISDGGSFTSY PDSVKGRFTI SRDIAKNNLY

LQMSSLKSED TAMYYCTRDE SDRPFPYWGQ GTLVTVSS
```

The amino acid sequence of the VL Domain of EphA2 mAb 3 (SEQ ID NO:145) is shown below (CDR$_L$ residues are shown underlined):

```
DIVLTQSHRS MSTSVGDRVN ITCKASQDVT TAVAWYQQKP

GQSPKLLIFW ASTRHAGVPD RFTGSGSGTD FTLTISSVQA

GDLALYYCQQ HYSTPYTFGG GTKLEIK
```

The present application specifically includes and encompasses EphA2 Binding Molecules (e.g., EphA2×CD3 bispecific Binding Molecules) that are capable of binding to EphA2, and particularly such Binding Molecules that comprise the VL and/or VH Domain, and/or 1, 2 or all 3 of the CDR$_L$s of the VL Domain and/or 1, 2 or all 3 of the CDR$_H$s of the VH Domain of anti-EphA2 monoclonal antibodies EphA2 mAb 1, EphA2 mAb 2 and EphA2 mAb 3.

5. Exemplary Anti-gpA33 Antibodies

The 43 kD transmembrane glycoprotein A33 (gpA33) is expressed in >95% of all colorectal carcinomas (Heath, J. K. et al. (1997) "*The Human A33 Antigen Is A Transmembrane Glycoprotein And A Novel Member Of The Immunoglobulin Superfamily*," Proc. Natl. Acad. Sci. (U.S.A.) 94(2):469-474; Ritter, G. et al. (1997) "*Characterization Of Posttranslational Modifications Of Human A33 Antigen, A Novel Palmitoylated Surface Glycoprotein Of Human Gastrointestinal Epithelium*," Biochem. Biophys. Res. Commun. 236 (3):682-686; Wong, N. A. et al. (2006) "*EpCAM and gpA33 Are Markers Of Barrett's Metaplasia*," J. Clin. Pathol. 59(3):260-263). An exemplary antibody that binds to human gpA33 is "gpA33 mAb 1."

The amino acid sequence of the VH Domain of gpA33 mAb 1 (SEQ ID NO:146) is shown below (CDR$_H$ residues are shown underlined):

```
QVQLVQSGAE VKKPGASVKV SCKASGYTFT GSWMNWVRQA

PGQGLEWIGR IYPGDGETNY NGKFKDRVTI TADKSTSTAY

MELSSLRSED TAVYYCARIY GNNVYFDVWG QGTTVTVSS
```

The amino acid sequence of the VL Domain of gpA33 mAb 1 (SEQ ID NO:147) is shown below (CDR$_L$ residues are shown underlined):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIK
```

The present application specifically includes and encompasses gpA33 Binding Molecules (e.g., gpA33×CD3 bispecific Binding Molecules) that are capable of binding to gpA33, and particularly such Binding Molecules that comprise the VL and/or VH Domain, and/or 1, 2 or all 3 of the CDR$_L$s of the VL Domain and/or 1, 2 or all 3 of the CDR$_L$s of the VH Domain of anti-gpA33 monoclonal antibodies gpA33 mAb 1, or of any of the anti-gpA33 monoclonal antibodies provided in WO 2015/026894. The present invention additionally includes and encompasses the exemplary gpA33×CD3 bispecific Binding Molecules provided in WO 2015/026894.

6. Exemplary Anti-HER2/Neu Antibodies

HER2/neu is a 185 kDa receptor protein that was originally identified as the product of the transforming gene from neuroblastomas of chemically treated rats. HER2/neu has been extensively investigated because of its role in several human carcinomas (including breast and gastric cancers) and in mammalian development (Hynes et al. (1994) Biochim. Biophys. Acta 1198:165-184; Dougall et al. (1994) Oncogene 9:2109-2123; Lee et al. (1995) Nature 378:394-398). Exemplary antibodies that bind human HER2/neu include "Margetuximab," "Trastuzumab" and "Pertuzumab." Margetuximab (also known as MGAH22; CAS Reg No. 1350624-75-7) is an Fc-optimized monoclonal antibody that binds to HER2/neu and mediates enhanced ADCC activity. Trastuzumab (also known as rhuMAB4D5, and marketed as HERCEPTIN®; CAS Reg No 180288-69-1; see, U.S. Pat. No. 5,821,337) is the humanized version of antibody 4D5, having IgG1/kappa constant regions. Pertuzumab (also known as rhuMAB2C4, and marketed as PERJETA™; CAS Reg No 380610-27-5; see for example, WO2001/000245) is a humanized version of antibody 2C4 having IgG1/kappa constant regions.

The present application specifically includes and encompasses Her2/Neu binding molecule (e.g., Her2/Neu×CD3 bispecific Binding Molecules) that are capable of binding to Her2/Neu, and particularly such Binding Molecules that comprise the VL and/or VH Domain, and/or 1, 2 or all 3 of the CDR$_L$s of the VL Domain and/or 1, 2 or all 3 of the CDR$_H$s of the VH Domain of the anti-Her2/Neu monoclonal antibodies Margetuximab, Trastuzumab or Pertuzumab.

The amino acid sequence of the VH Domain of Margetuximab is (SEQ ID NO:148) (CDR$_H$ residues are shown underlined):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYANDYW GQGASVTVSS
```

The amino acid sequence of the VL Domain of Margetuximab is (SEQ ID NO:149) (CDR$_L$ residues are shown underlined):

```
DIVMTQSHKF MSTSVGDRVS ITCKASQDVN TAVAWYQQKP

GHSPKLLIYS ASFRYTGVPD RFTGSRSGTD FTFTISSVQA

EDLAVYYCQQ HYTTPPTFGG GTKVEIK
```

The amino acid sequences of the complete Heavy and Light Chains of Margetuximab are known in the art (see, e.g., WHO Drug Information, 2014, Recommended INN: List 71, 28(1):93-94).

The amino acid sequence of the VH Domain of Trastuzumab is (SEQ ID NO:150) (CDR$_H$ residues are shown underlined):

```
EVQLVESGGG LVQPGGSLRL SCAASGFNIK DTYIHWVRQA

PGKGLEWVAR IYPTNGYTRY ADSVKGRFTI SADTSKNTAY

LQMNSLRAED TAVYYCSRWG GDGFYANDYW GQGTLVTVSS
```

The amino acid sequence of the VL Domain of Trastuzumab is (SEQ ID NO:151) (CDR$_L$ residues are shown underlined):

```
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIK
```

The amino acid sequence of the VH Domain of Pertuzumab is (SEQ ID NO:152) (CDR$_H$ residues are shown underlined):

```
EVQLVESGGG LVQPGGSLRL SCAASGFTFT DYTMDWVRQA

PGKGLEWVAD VNPNSGGSIY NQRFKGRFTL SVDRSKNTLY

LQMNSLRAED TAVYYCARNL GPSFYFDYWG QGTLVTVSS
```

The amino acid sequence of the VL Domain of Pertuzumab is (SEQ ID NO:153) (CDR$_L$ residues are shown underlined):

```
DIQMTQSPSS LSASVGDRVT ITCKASQDVS IGVAWYQQKP

GKAPKLLIYS ASYRYTGVPS RFSGSGSGTD FTLTISSLQP

EDFATYYCQQ YYIYPYTFGQ GTKVEIK
```

In addition to the above-identified preferred anti-HER2/neu Binding Molecules, the invention contemplates Her2/Neu Binding Molecules that comprise the VL and/or VH Domain, and/or 1, 2 or all 3 of the CDR$_L$5 of the VL Domain and/or 1, 2 or all 3 of the CDR$_H$s of the VH Domain of any of the following anti-Her-2 Binding Molecules: 1.44.1; 1.140; 1.43; 1.14.1; 1.100.1; 1.96; 1.18.1; 1.20; 1.39; 1.24; and 1.71.3 (U.S. Pat. Nos. 8,350,011; 8,858,942; and PCT Patent Publication WO 2008/019290); F5 and C1 (U.S. Pat. Nos. 7,892,554; 8,173,424; 8,974,792; and PCT Patent Publication WO 99/55367); and also the anti-Her-2 Binding Molecules of US Patent Publication US2013017114 and PCT Patent Publication Nos. WO2011/147986 and WO 2012/143524). The present invention additionally includes and encompasses the exemplary Her2/Neu×CD3 bispecific Binding Molecules provided in WO 2012/143524.

7. Exemplary Anti-VEGF Antibodies

VEGF-A is a chemical signal that stimulates angiogenesis in a variety of diseases, especially in certain metastatic cancers such as metastatic colon cancer, and in certain lung cancers, renal cancers, ovarian cancers, and glioblastoma multiforme of the brain. An exemplary antibody that binds to human VEGF-A is "Bevacizumab" (Avastin®). Bevacizumab is a recombinant humanized IgG1 monoclonal antibody (Midgley, R. et al. (2005) "*Bevacizumab—Current Status And Future Directions*," Ann. Oncol. 16(7):999-1004; Hall, R. D. et al. (2015) "*Angiogenesis Inhibition As A Therapeutic Strategy In Non-Small Cell Lung Cancer (NSCLC)*," Transl. Lung Cancer Res. 4(5):515-523; Narita, Y. (2015) "*Bevacizumab For Glioblastoma*," Ther. Clin. Risk Manag. 11:1759-1765).

The amino acid sequence of the VH Domain of Bevacizumab (SEQ ID NO:154) is shown below (CDR$_H$ residues are shown underlined):

```
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS
```

The amino acid sequence of the VL Domain of Bevacizumab (SEQ ID NO:155) is shown below (CDR$_L$ residues are shown underlined):

```
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR
```

The present application specifically includes and encompasses VEGF Binding Molecules (e.g., VEGF×CD3 bispecific Binding Molecules) that are capable of binding to VEGF, and particularly such Binding Molecules that comprise the VL and/or VH Domain, and/or 1, 2 or all 3 of the CDR$_L$5 of the VL Domain and/or 1, 2 or all 3 of the CDR$_H$s of the VH Domain of the anti-VEGF monoclonal antibody Bevacizumab.

8. Exemplary Anti-5T4 Antibodies

The oncofetal protein, 5T4, is a tumor-associated protein displayed on the cell membrane of many carcinomas, including kidney, colon, prostate, lung, carcinoma and in acute lymphoblastic leukemia (see, Boghaert, E. R. et al. (2008) "*The Oncofetal Protein, 5T4, Is A Suitable Target For Antibody-Guided Anti-Cancer Chemotherapy With Calicheamicin*," Int. J. Oncol. 32(1):221-234; Eisen, T. et al. (2014) "*Naptumomab Estafenatox: Targeted Immunotherapy with a Novel Immunotoxin*," Curr. Oncol. Rep. 16:370, pp. 1-6). Exemplary antibodies that bind to human 5T4 include "5T4 mAb 1" and "5T4 mAb 2."

The amino acid sequence of the VH Domain of 5T4 mAb 1 (SEQ ID NO:156) is shown below (CDR residues are shown underlined):

```
QVQLVQSGAE VKKPGASVKV SCKASGYTFT SFWMHWVRQA

PGQGLEWMGR IDPNRGGTEY NEKAKSRVTM TADKSTSTAY

MELSSLRSED TAVYYCAGGN PYYPMDYWGQ GTTVTVSS
```

The amino acid sequence of the VL Domain of an exemplary 5T4 mAb 1 (SEQ ID NO:157) is shown below (CDR residues are shown underlined):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIK
```

The amino acid sequence of the VH Domain of 5T4 mAb 2 (SEQ ID NO:158) is shown below (CDR residues are shown underlined):

```
QVQLQQPGAE LVKPGASVKM SCKASGYTFT SYWITWVKQR

PGQGLEWIGD IYPGSGRANY NEKFKSKATL TVDTSSSTAY

MQLSSLTSED SAVYNCARYG PLFTTVVDPN SYAMDYWGQG

TSVTVSS
```

The amino acid sequence of the VL Domain of 5T4 mAb 2 (SEQ ID NO:159) is shown below (CDR residues are shown underlined):

```
DVLMTQTPLS LPVSLGDQAS ISCRSSQSIV YSNGNTYLEW

YLQKPGQSPK LLIYKVSNRF SGVPDRFSGS GSGTDFTLKI

SRVEAEDLGV YYCFQGSHVP FTFGSGTKLE IK
```

The present application specifically includes and encompasses 5T4 Binding Molecules (e.g., 5T4×CD3 bispecific Binding Molecules) that are capable of binding to 5T4 that comprise the VL and/or VH Domain, and/or 1, 2 or all 3 of the CDR$_L$5 of the VL Domain and/or 1, 2 or all 3 of the CDR$_H$s of the VH Domain of the anti-5T4 monoclonal antibodies 5T4 mAb 1 or 5T4 mAb 2, or of any of the anti-5T4 antibodies provided in WO 2013/041687 or WO 2015/184203. The present invention additional includes and encompasses the exemplary 5T4×CD3 bispecific Binding Molecules provided in WO 2015/184203.

The present application additionally specifically includes and encompasses 5T4×CD3×CD8 trispecific Binding Molecules that are capable of binding to 5T4, to CD3 and to CD8, and particularly such trispecific Binding Molecules that comprise the VL and/or VH Domain, and/or 1, 2 or all 3 of the CDR$_L$5 of the VL Domain and/or 1, 2 or all 3 of the CDR$_H$s of the VH Domain of the anti-5T4 monoclonal antibodies 5T4 mAb 1 or 5T4 mAb 2 or of any of the anti-5T4 monoclonal antibodies provided in WO 2015/184203, and/or the VL and/or VH Domain, and/or 1, 2 or all 3 of the CDR$_L$5 of the VL Domain and/or 1, 2 or all 3 of the CDR$_H$s of the VH Domain of any of the anti-CD8 monoclonal antibodies provided herein.

9. Exemplary Anti-IL13Rα2 Antibodies

Interleukin-13 Receptor a2 (IL-13Rα2) is overexpressed in a variety of cancers, including glioblastoma, colorectal cancer, cervical cancer, pancreatic cancer, multiple melanoma, osteosarcoma, leukemia, lymphoma, prostate cancer and lung cancer (PCT Publication No. WO 2008/146911; Brown, C. E. et al. (2013) "*Glioma IL13Rα2 Is Associated With Mesenchymal Signature Gene Expression And Poor Patient Prognosis*," PLoS One. 18; 8(10):e77769; Barderas, R. et al. (2012) "*High Expression Of IL-13 Receptor A2 In Colorectal Cancer Is Associated With Invasion, Liver Metastasis, And Poor Prognosis*," Cancer Res. 72(11):2780-2790; Kasaian, M. T. et al. (2011) "*IL-13 Antibodies Influence IL-13 Clearance In Humans By Modulating Scavenger Activity Of IL-13Rα2*," J. Immunol. 187(1):561-569; Bozinov, O. et al. (2010) "*Decreasing Expression Of The Interleukin-13 Receptor IL-13Ralpha2 In Treated Recurrent Malignant Gliomas*," Neurol. Med. Chir. (Tokyo) 50(8): 617-621; Fujisawa, T. et al. (2009) "*A Novel Role Of Interleukin-13 Receptor Alpha2 In Pancreatic Cancer Invasion And Metastasis*," Cancer Res. 69(22):8678-8685). Antibodies that immunospecifically bind to IL13Rα2 are commercially available and have been described in the art (Abnova Corporation, Biorbyt, LifeSpan BioSciences, United States Biologicals; see also PCT Publication No. WO 2008/146911). Exemplary antibodies that bind to human IL-13Rα2 include "hu08" (see, e.g., PCT Publication No. WO 2014/072888).

The amino acid sequence of the VH Domain of hu08 (SEQ ID NO:160) is shown below (CDR residues are shown underlined):

```
EVQLVESGGG LVQPGGSLRL SCAASGFTFS RNGMSWVRQA

PGKGLEWVAT VSSGGSYIYY ADSVKGRFTI SRDNAKNSLY

LQMNSLRAED TAVYYCARQG TTALATRFFD VWGQGTLVTV

SS
```

The amino acid sequence of the VL Domain of hu08 (SEQ ID NO:161) is shown below (CDR residues are shown underlined):

```
DIQMTQSPSS LSASVGDRVT ITCKASQDVG TAVAWYQQKP

GKAPKLLIYS ASYRSTGVPS RFSGSGSGTD FTLTISSLQP

EDFATYYCQH HYSAPWTFGG GTKVEIK
```

The present application specifically includes and encompasses IL13Rα2 Binding Molecules (e.g., IL13Rα2×CD3 bispecific Binding Molecules) that are capable of binding to IL13Rα2, and particularly such Binding Molecules that comprise the VL and/or VH Domain, and/or 1, 2 or all 3 of the CDR$_L$5 of the VL Domain and/or 1, 2 or all 3 of the CDR$_H$s of the VH Domain of the anti-IL13Rα2 monoclonal antibody hu08.

10. Exemplary Anti-CD123 Antibodies

CD123 (interleukin 3 receptor alpha, IL-3Ra) is a 40 kDa molecule and is part of the interleukin 3 receptor complex (Stomski, F. C. et al. (1996) "*Human Interleukin-3 (IL-3) Induces Disulfide-Linked IL-3 Receptor Alpha-And Beta-Chain Heterodimerization, Which Is Required For Receptor Activation But Not High-Affinity Binding*," Mol. Cell. Biol. 16(6):3035-3046). Interleukin 3 (IL-3) drives early differentiation of multipotent stem cells into cells of the erythroid, myeloid and lymphoid progenitors. CD123 has been reported to be overexpressed on malignant cells in a wide range of hematologic malignancies including acute myeloid leukemia (AML), chronic myelogenous leukemia (CML), acute B lymphoblastic leukemia (B-ALL), hairy cell leukemia (HCL), blastic plasmacytoid dendritic cell neoplasm (BPDCN), chronic myelogenous leukemia (CML), acute B lymphoblastic leukemia (B-ALL), hairy cell leukemia (HCL), blastic plasmacytoid dendritic cell neoplasm (BPDCN), and myelodysplastic syndrome (MDS) (Munoz, L. et al. (2001) "*Interleukin-3 Receptor Alpha Chain (CD123) Is Widely Expressed In Hematologic Malignancies*," Haematologica 86(12):1261-1269). Overexpression of CD123 is associated with poorer prognosis in AML (Tettamanti, M. S. et al. (2013) "*Targeting Of Acute Myeloid Leukaemia By Cytokine-Induced Killer Cells Redirected With A Novel CD123-Specific Chimeric Antigen Receptor*," Br. J. Haematol. 161:389-401).

An exemplary antibody that binds to human CD123, and that may be employed in the present invention, is "CD123 mAb 1" (see, e.g., PCT Patent Publication WO 2015/026892).

The amino acid sequence of the VH Domain of CD123 mAb 1 (SEQ ID NO:162) is shown below (CDR$_H$ residues are shown underlined):

```
EVQLVQSGAE LKKPGASVKV SCKASGYTFT DYYMKWVRQA

PGQGLEWIGD IIPSNGATFY NQKFKGRVTI TVDKSTSTAY

MELSSLRSED TAVYYCARSH LLRASWFAYW GQGTLVTVSS
```

The amino acid sequence of the VL Domain of CD123 mAb 1 (SEQ ID NO:163) is shown below (CDR$_L$ residues are shown underlined):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIK
```

The present application specifically includes and encompasses CD123 Binding Molecules (e.g., CD123×CD3 bispecific Binding Molecules) that are capable of binding to CD123, and particularly such Binding Molecules that comprise the VL and/or VH Domain, and/or 1, 2 or all 3 of the CDR$_L$s of the VL Domain and/or 1, 2 or all 3 of the CDR$_H$s of the VH Domain of the anti-CD123 monoclonal antibody CD123 mAb 1, and also any of the anti-CD123 antibodies disclosed in US 2017/081424 and WO 2016/036937. The present invention additionally includes and encompasses exemplary CD123×CD3 bispecific Binding Molecules, including: flotetuzumab (aka MGD007; CAS Registry No. 1664355-28-5), JNJ-63709178 (Johnson & Johnson, also see, WO 2016/036937) and XmAb14045 (Xencor, also see, US 2017/081424).

11. Exemplary Anti-CD19 Antibodies

CD19 (B lymphocyte surface antigen B4, Genbank accession number M28170) is a component of the B-cell-receptor (BCR) complex, and is a positive regulator of B-Cell signaling that modulates the threshold for B-Cell activation and humoral immunity. CD19 is one of the most ubiquitously expressed antigens in the B-Cell lineage and is expressed on >95% of B-Cell malignancies, including acute lymphoblastic leukemia (ALL), chronic lymphocytic leukemia (CLL), and non-Hodgkin's Lymphoma (NHL). Notably, CD19 expression is maintained on B-Cell lymphomas that become resistant to anti-CD20 therapy (Davis et al. (1999) "*Therapy of B-Cell Lymphoma With Anti-CD20 Antibodies Can Result In The Loss Of CD20 Antigen Expression*." Clin Cancer Res, 5:611-615, 1999). CD19 has also been suggested as a target to treat autoimmune diseases (Tedder (2009) "*CD19: A Promising B-Cell Target For Rheumatoid Arthritis*," Nat. Rev. Rheumatol. 5:572-577).

An exemplary humanized antibody that binds to human CD19, and that may be employed in the present invention, is the anti-CD19 antibody disclosed in WO 2016/048938 (referred to herein as "CD19 mAb 1").

The amino acid sequence of the VH Domain of CD19 mAb 1 (SEQ ID NO:164) is shown below (CDR$_H$ residues are shown underlined):

```
QVTLRESGPA LVKPTQTLTL TCTFSGFSLS TSGMGVGWIR

QPPGKALEWL AHIWWDDDKR YNPALKSRLT ISKDTSKNQV

FLTMTNMDPV DTATYYCARM ELWSYYFDYW GQGTTVTVSS
```

The amino acid sequence of the VL Domain of CD19 mAb 1 (SEQ ID NO:165) is shown below (CDR$_L$ residues are shown underlined):

```
ENVLTQSPAT LSVITGEKAT ITCRASQSVS YMHWYQQKPG

QAPRLLIYDA SNRASGVPSR FSGSGSGTDH TLTISSLEAE

DAATYYCFQG SVYPFTFGQG TKLEIK
```

The amino acid sequence of an alternative VL Domain of CD19 mAb 1 (SEQ ID NO:195) is shown below (CDR$_L$ residues are shown underlined):

```
ENVLTQSPAT LSVITGEKVT ITCSASSSVS YMHWYQQKPG

QAPRLLIYDT SKLASGVPSR FSGSGSGTDH FLTISSLEAE

DAATYYCFQG SVYPFTFGQG TKLEIK
```

The present application specifically includes and encompasses CD19 Binding Molecules (e.g., CD19×CD3 bispecific Binding Molecules) that are capable of binding to CD19, and particularly such Binding Molecules that comprise the VL and/or VH Domain, and/or 1, 2 or all 3 of the CDR$_L$s of the VL Domain and/or 1, 2 or all 3 of the CDR$_H$s of the VH Domain of the anti-CD19 monoclonal antibody CD19 mAb 1, or any of the anti-CD19 antibodies disclosed in U.S. Pat. No. 7,112,324. The present invention specifically includes and encompasses exemplary CD19×CD3 bispecific Binding Molecules that may be employed in the present invention, including: blinatumomab (BLINCYTO®; amino acid sequence found in WHO Drug Information, 2009, Recommended INN: List 62, 23(3):240-241) and duvortuxizumab (aka MGD011; amino acid sequence found in WHO Drug Information, 2016, Proposed INN: List 116, 30(4):627-629).

B. Exemplary Pathogen-Associated Antigens

As used herein, the term "Pathogen Antigen" denotes an antigen that is characteristically expressed on the surface of a pathogen-infected cell, and that may thus be treated with an Antibody-Based Molecule or an Immunomodulatory Molecule. Examples of Pathogen Antigens include, but are not limited to antigens expressed on the surface of a cell infected with: a Herpes Simplex Virus (e.g., infected cell protein (ICP)47, gD, etc.), a varicella-zoster virus, a Kaposi's sarcoma-associated herpesvirus, an Epstein-Barr Virus (e.g., LMP-1, LMP-2A, LMP-2B, etc.), a Cytomegalovirus (e.g., UL11, etc.), Human Immunodeficiency Virus (e.g., env proteins gp160, gp120, gp41, etc.), a Human Papillomavirus (e.g., E6, E7, etc.), a human T-cell leukemia virus (e.g., env proteins gp64, gp46, gp21, etc.), Hepatitis A Virus, Hepatitis B Virus, Hepatitis C Virus, Vesicular Stomatitis Virus (VSV), *Bacilli, Citrobacter, Cholera, Diphtheria, Enterobacter, Gonococci, Helicobacter pylori, Klebsiella, Legionella, Meningococci*, mycobacteria, *Pseudomonas, Pneumonococci*, rickettsia bacteria, *Salmonella, Serratia, Staphylococci, Streptococci, Tetanus, Aspergillus (fumigatus, niger*, etc.), *Blastomyces dermatitidis, Candida (albicans, krusei, glabrata, tropicalis*, etc.), *Cryptococcus neoformans*, Genus *Mucorales (mucor, absidia, rhizopus), Sporothrix schenkii, Paracoccidioides brasiliensis, Coccidioides immitis, Histoplasma capsulatum, Leptospirosis, Borrelia burgdorferi*, helminth parasite (hookworm, tapeworms, flukes, flatworms (e.g. *Schistosomia*), *Giardia lambia, trichinella, Dientamoeba Fragilis, Trypanosoma brucei, Trypanosoma cruzi*, and *Leishmania donovani*). Such antibodies are available commercially from a wide number of sources, or can be obtained by immunizing mice or other animals (including for the production of monoclonal antibodies) with such antigens.

Exemplary antibodies, whose VH and VL Domains may be used to construct molecules capable of binding a Pathogen Antigen arrayed on the surface of a pathogen-infected cell are antibodies are provided below, additional antibodies are known in the art.

1. Exemplary Anti-HIV Env Antibody

The env protein of HIV is an exemplary Pathogen-Associated Antigen, and antibodies that bind the env protein of HIV are exemplary of antibodies capable of binding a Pathogen-Associated Antigen.

The initial step in HIV-1 infection occurs with the binding of cell surface CD4 to trimeric HIV-1 envelope glycoproteins (env), a heterodimer of a transmembrane glycoprotein (gp41) and a surface glycoprotein (gp120). The gp120 and gp41 glycoproteins are initially synthesized as a single gp160 polypeptide that is subsequently cleaved to generate the non-covalently associated gp120/gp41 complex. The ectodomain of env is a heterodimer with mass of approximately 140 kDa, composed of the entire gp120 component, and approximately 20 kDa of gp41 (Harris, A. et al. (2011) "*Trimeric HIV-1 Glycoprotein Gp140 Immunogens And Native HIV-1 Envelope Glycoproteins Display The Same Closed And Open Quaternary Molecular Architectures*," Proc. Natl. Acad. Sci. (U.S.A.) 108(28):11440-11445). Antibodies that that immunospecifically bind to env proteins are commercially available and have been described in the art (see, e.g., GenBank Accession No. AFQ31503; Buchacher, A. et al. (1994) "*Generation Of Human Monoclonal Antibodies Against HIV-1 Proteins; Electrofusion And Epstein-Barr Virus Transformation For Peripheral Blood Lymphocyte Immortalization*," AIDS Res. Hum. Retroviruses 10(4): 359-369; Shen, R. (2010) "*GP41-Specific Antibody Blocks Cell-Free HIV Type 1 Transcytosis Through Human Rectal Mucosa And Model Colonic Epithelium*," J. Immunol. 184 (7):3648-3655; WO 2012/162068; and WO 2016/054101). Exemplary antibodies that bind to HIV env include "7B2" (GenBank Accession No. AFQ31503) and "A32" (PCT Publication No. WO 2014/159940). Multiple VH Domains of Antibody A32 have been reported in the art that possess minor changes in framework regions 1 and/or 4 reported (see, e.g., Protein Data Base Accession number PDB: 4YBL_H, US 2015/0239961 and WO 2006/044410). Any of these variant Antibody A32 VH Domains may be employed in accordance with the present invention.

The amino acid sequence of the VH Domain of 7B2 (SEQ ID NO:166) is shown below (CDR residues are shown underlined):

```
QVQLVQSGGG VFKPGGSLRL SCEASGFTFT EYYMTWVRQA

PGKGLEWLAY ISKNGEYSKY SPSSNGRFTI SRDNAKNSVF

LQLDRLSADD TAVYYCARAD GLTYFSELLQ YIFDLWGQGA

RVTVSS
```

The amino acid sequence of the VL Domain of 7B2 (SEQ ID NO:167) is shown below (CDR residues are shown underlined):

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIK
```

The amino acid sequence of an exemplary VH Domain of A32 (SEQ ID NO:168) is shown below (CDR residues are shown underlined):

```
QVQLQESGPG LVKPSQTLSL SCTVSGGSSS SGAHYWSWIR

QYPGKGLEWI GYIHYSGNTY YNPSLKSRIT ISQHTSENQF

SLKLNSVTVA DTAVYYCARG TRLRTLRNAF DIWGQGTXVT

VSS
``` wherein: X is L or M

The amino acid sequence of such an exemplary VH Domain of A32 (SEQ ID NO:209), wherein X is L, is shown below (CDR residues are shown underlined):

```
QVQLQESGPG LVKPSQTLSL SCTVSGGSSS SGAHYWSWIR

QYPGKGLEWI GYIHYSGNTY YNPSLKSRIT ISQHTSENQF

SLKLNSVTVA DTAVYYCARG TRLRTLRNAF DIWGQGTLVT

VSS
```

The amino acid sequence of the VL Domain of A32 (SEQ ID NO:169) is shown below (CDR residues are shown underlined):

```
QSALTQPPSA SGSPGQSVTI SCTGTSSDVG GYNYVSWYQH

HPGKAPKLII SEVNNRPSGV PDRFSGSKSG NTASLTVSGL

QAEDEAEYYC SSYTDIHNFV FGGGTKLTVL
```

The present application specifically includes and encompasses HIV Binding Molecules (e.g., HIV×CD3 bispecific Binding Molecules) that are capable of binding to HIV, and particularly such Binding Molecules that comprise the VL and/or VH Domain, and/or 1, 2 or all 3 of the CDR$_L$s of the VL Domain and/or 1, 2 or all 3 of the CDR$_H$s of the VH Domain of the anti-HIV monoclonal antibodies 7B2, A32, and also any of the anti-HIV antibodies disclosed in WO 2016/054101, WO 2017/011413, WO 2017/011414. The present invention specifically includes and encompasses the exemplary HIV×CD3 bispecific Binding Molecules provided in WO 2014/159940, WO 2015/184203, WO 2017/011413, and WO 2017/011414.

The present application additionally specifically includes and encompasses HIV×CD3×CD8 trispecific Binding Molecules that are capable of binding to HIV, to CD3 and to CD8, and particularly such trispecific Binding Molecules that comprise the VL and/or VH Domain, and/or 1, 2 or all 3 of the CDR$_L$s of the VL Domain and/or 1, 2 or all 3 of the CDR$_H$s of the VH Domain of the anti-HIV monoclonal antibodies 7B2 or A32 or of any of the anti-HIV monoclonal antibodies provided in WO 2015/184203, WO 2016/054101, WO 2017/011413, WO 2017/011414, and/or the VL and/or VH Domain, and/or 1, 2 or all 3 of the CDR$_L$s of the VL Domain and/or 1, 2 or all 3 of the CDR$_H$s of the VH Domain of any of the anti-CD8 monoclonal antibodies provided in WO 2015/184203.

2. Exemplary Anti-RSV Glycoprotein F Antibody

A further illustrative Pathogen-Associated Antigen is RSV glycoprotein F. An exemplary anti-RSV glycoprotein F antibody is palivizumab (see, e.g., Protein Data Bank (PDB) ID No. 2HWZ). Alternative anti-RSV glycoprotein F antibodies include motavizumab (see, e.g., PDB ID No. 3IXT) and a variant of palivizumab that has been engineered to remove a cysteine residue from palivizumab's CDR$_L$1. The amino acid sequence of the VH Domain of the variant of palivizumab (SEQ ID NO:170) is shown below (CDR residues are shown underlined):

```
QVTLRESGPA LVKPTQTLTL TCTFSGFSLS TSGMSVGWIR

QPPGKALEWL ADIWWDDKKD YNPSLKSRLT ISKDTSKNQV

VLKVTNMDPA DTATYYCARS MITNWYFDVW GAGTTVTSS
```

The amino acid sequence of the VL Domain of the variant of palivizumab (SEQ ID NO:171) is shown below (CDR residues are shown underlined):

```
DIQMIQSPST LSASVGDRVT ITCRASQSVG YMHWYQQKPG

KAPKLLIYDT SKLASGVPSR FSGSGSGTEF TLTISSLQPD

DFATYYCFQG SGYPFTFGGG TKLEIK
```

VII. Exemplary Binding Molecules of the Present Invention

As discussed below, the present invention is illustrated using several DA×CD3 Binding Molecules having different structures including molecules capable of mediating the redirected killing of a tumor cell (e.g., a "DART-A"-type diabody or a "DART-B"-type diabody or a TRIVALENT-type molecule, as described below).

A. DART-A-Type Diabodies

DART-A-type diabodies are bispecific diabodies capable of binding CD3 and a Disease Antigen (e.g., a Cancer Antigen) that do not comprise an Fc Domain. Provided herein are illustrative DART-A-type diabodies composed of two polypeptide chains having one binding site for CD3 and one binding site for the Cancer Antigen CD123 (see, e.g., FIG. 1).

An illustrative DART-A-type diabody (designated "DART-A-WT") has a first polypeptide chain having the amino acid sequence of SEQ ID NO:172:

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL

EIKGGGSGGG GEVQLVESGG GLVQPGGSLR LSCAASGFTF

STYAMNWVRQ APGKGLEWVG RIRSKYNNYA TYYADSVKGR

FTISRDDSKN SLYLQMNSLK TEDTAVYYCV RHGNFGNSYV

SWFAYWGQGT LVTVSSGGCG GGKVAALKEK VAALKEKVAA

LKEKVAALKE
```

Residues 1-113 of the first polypeptide chain of such illustrative DART-A-type diabody correspond to the VL Domain of CD123 mAb 1 (SEQ ID NO:162). Residues 114-121 (double underlined) of the first polypeptide chain of such illustrative DART-A-type diabody correspond to Linker 1 (GGGSGGGG; SEQ ID NO:16). Residues 122-246 of the first polypeptide chain of such illustrative DART-A-type diabody correspond to the VH Domain of CD3 mAb 1 (SEQ ID NO:55), wherein Kabat position 65 (double underlined) is aspartate (D). Residues 247-252 (underlined) of the first polypeptide chain of such illustrative DART-A-type diabody correspond to a Linker 2 (GGCGGG; SEQ ID NO:17). Residues 253-280 of the first polypeptide chain of such illustrative DART-A-type diabody correspond to the heterodimer-promoting "K-coil" (KVAALKE-KVAALKE-KVAALKE-KVAALKE; SEQ ID NO:30).

The second polypeptide chain of such illustrative DART-A-type diabody DART-A-WT has the amino acid sequence of SEQ ID NO:173:

```
QAVVIQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

QLVQSGAELK KPGASVKVSC KASGYTFTDY YMKWVRQAPG

QGLEWIGDII PSNGATFYNQ KFKGRVTITV DKSTSTAYME

LSSLRSEDTA VYYCARSHLL RASWFAYWGQ GTLVTVSSGG

CGGGEVAALE KEVAALEKEV AALEKEVAAL EK
```

Residues 1-110 of the second polypeptide chain of such illustrative DART-A-type diabody DART-A-WT correspond to the VL Domain of CD3 mAb 1 (SEQ ID NO:56). Residues 111-118 (double underlined) of the second polypeptide chain of such illustrative DART-A-type diabody correspond to Linker 1 (GGGSGGGG; SEQ ID NO:16). Residues 119-238 of the second polypeptide chain of such illustrative DART-A-type diabody correspond to the VH Domain of CD123 mAb 1 (SEQ ID NO:163). Residues 239-244 (underlined) of the second polypeptide chain of such illustrative DART-A-type diabody correspond to Linker 2 (GGCGGG; SEQ ID NO:17) Residues 245-272 of the second polypeptide chain of such illustrative DART-A-type diabody correspond to the heterodimer-promoting "E-coil" (EVAALEK-EVAALEK-EVAALEK-EVAALEK; SEQ ID NO:29).

As will be recognized in view of the instant disclosure, additional DART-A-type diabodies having a binding site for an alternative Disease Antigen and/or having the CD3 Binding Domains of a variant anti-CD3 antibody (i.e., a vCD3-Binding Domain) may likewise be constructed (by employing the VL and VH Domains of such antibodies in lieu of the VL and VH Domains of the illustrative DART-A-type diabody). Similarly, as provided herein, alternative DART-A-type molecules may likewise be constructed incorporating alternative Linkers and/or alternative Heterodimer-Promoting Domains. For example, an illustrative panel of CD123×CD3 DART-A-type diabodies were generated having the same structure as DART-A-WT diabody provided above, but comprising the VL and VH Domains of one of the CD3 mAb 1 variants (M1-M26) provided above.

Each illustrative CD123×CD3 DART-A-type diabody of the panel has a first polypeptide chain having the amino acid sequence of SEQ ID NO: SEQ ID NO:189:

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIKGGGSGGG

GEVQLVESGG GLVQPGGSLR LSCAASGFTF SX₁X₂X₃MNWVRQ

APGKGLEWVG RIRSKYNNYA TYYADSVKX₄R FTISRDDSKN
```

SLYLQMNSLK TEDTAVYYCV RHX₅NX₆X₇NSX₈V

X₉X₁₀FAX₁₁WGQGT LVTVSSGGCG GGKVAALKEK VAALKEKVAA

LKEKVAALKE wherein: X₁ is T, D, or E; X₂ is Y, D or T; X₃ is A or G; X₄ is D or G; X₅ is G, D, E, or K; X₆ is F or I; X₇ is G or I; X₈ is Y, A, G, or Q; X₉ is S or T; X₁₀ is W, F, or Y; and X₁₁ is Y or E.

Residues 1-113 of the first polypeptide chain of the panel of illustrative DART-A-type diabodies correspond to the VL Domain of CD123 mAb 1 (SEQ ID NO:162). Residues 114-121 (double underlined) of the first polypeptide chain of the panel of illustrative DART-A-type diabodies correspond to Linker 1 (GGGSGGGG; SEQ ID NO:16; double underlined). Residues 122-246 of the first polypeptide chain of the panel of illustrative DART-A-type diabodies correspond to the VH Domain of CD3 mAb 1 M1-CD3 mAb 1 M22 (SEQ ID NOs: 64, 66, 68, 70, 72, 74, 76, 78, 80, 82, 84, 86, 88, 90, 92, 94, 96, 98, 100, 102, 104 or 106). Residues 247-252 (single underlined) of the panel of illustrative DART-A-type diabodies correspond to a Linker 2 (GGCGGG; SEQ ID NO:17). Residues 253-280 of the first polypeptide chain of the panel of illustrative DART-A-type diabodies correspond to the heterodimer-promoting "K-coil" (KVAALKE-KVAALKE-KVAALKE-KVAALKE; SEQ ID NO:30).

The second polypeptide chain of such illustrative DART-A-type diabody has the amino acid sequence of SEQ ID NO:190:

```
QAVVTQEPSL TVSPGCTVTL TCRSSTGAVT TSNYANWVQQ

KPGQAPRGLI GX₁TNX₂RAPWT PARFSGSLLG GKAALTITGA

QAEDEADYYC AX₃WYSNLWVF GGGTKLTVLG GGGSGGGGEV

QLVQSGAELK KPGASVKVSC KASGYTFTDY YMKWVRQAPG

QGLEWIGDII PSNGATFYNQ KFKGRVTITV DKSTSTAYME

LSSLRSEDTA VYYCARSHLL RASWFAYWGQ GTLVTVSSGG

CGGGEVAALE KEVAALEKEV AALEKEVAAL EK
``` wherein: X₁ is G or D; X₂ is K or G; and X₃ is L, E or Q.

Residues 1-110 of the second polypeptide chain of the panel of illustrative DART-A-type diabodies correspond to the VL Domain of CD3 mAb 1 M23-CD3 mAb 1 M26 (SEQ ID NOs:108, 110, 112, and 114). Residues 111-118 (double underlined) of the second polypeptide chain of the panel of illustrative DART-A-type diabodies correspond to Linker 1 (GGGSGGGG; SEQ ID NO:16; double underlined). Residues 119-238 of the second polypeptide chain of the panel of illustrative DART-A-type diabodies correspond to the VH Domain of CD123 mAb 1 (SEQ ID NO:163). Residues 239-244 (underlined) of the second polypeptide chain of the panel of illustrative DART-A-type diabodies correspond to Linker 2 (GGCGGG; SEQ ID NO:17; single underlined). Residues 245-272 of the second polypeptide chain of the panel of illustrative DART-A-type diabodies correspond to the heterodimer-promoting "E-coil" (EVAALEK-EVAALEK-EVAALEK-EVAALEK; SEQ ID NO:29).

The amino acid sequences and designations of the panel of illustrative DART-A-type diabodies comprising the VL and VH of the CD3 mAb 1 variants are provided in Table 8 below.

TABLE 8

Illustrative DART-A-Type Diabodies

| Designation | First Polypeptide Chain SEQ ID NO: | Second Polypeptide Chain SEQ ID NO. |
|---|---|---|
| DART-A-M1 | 189 - wherein: $X_1$ is T; $X_2$ is Y; $X_3$ is A; $X_4$ is D; $X_5$ is G; $X_6$ is F; $X_7$ is G; $X_8$ is Y; $X_9$ is T; $X_{10}$ is W; and $X_{11}$ is Y | 173 |
| DART-A-M2 | 189 - wherein: $X_1$ is T; $X_2$ is Y; $X_3$ is A; $X_4$ is D; $X_5$ is K; $X_6$ is F; $X_7$ is G; $X_8$ is Y; $X_9$ is T; $X_{10}$ is W; and $X_{11}$ is Y | 173 |
| DART-A-M3 | 189 - wherein: $X_1$ is T; $X_2$ is Y; $X_3$ is A; $X_4$ is D; $X_5$ is G; $X_6$ is F; $X_7$ is I; $X_8$ is Y; $X_9$ is S; $X_{10}$ is W; and $X_{11}$ is Y | 173 |
| DART-A-M4 | 189 - wherein: $X_1$ is T; $X_2$ is Y; $X_3$ is A; $X_4$ is D; $X_5$ is G; $X_6$ is F; $X_7$ is G; $X_8$ is A; $X_9$ is S; $X_{10}$ is W; and $X_{11}$ is Y | 173 |
| DART-A-M5 | 189 - wherein: $X_1$ is T; $X_2$ is Y; $X_3$ is A; $X_4$ is D; $X_5$ is G; $X_6$ is F; $X_7$ is G; $X_8$ is G; $X_9$ is S; $X_{10}$ is W; and $X_{11}$ is Y | 173 |
| DART-A-M6 | 189 - wherein: $X_1$ is T; $X_2$ is Y; $X_3$ is A; $X_4$ is D; $X_5$ is G; $X_6$ is F; $X_7$ is G; $X_8$ is Q; $X_9$ is S; $X_{10}$ is W; and $X_{11}$ is Y | 173 |
| DART-A-M7 | 189 - wherein: $X_1$ is T; $X_2$ is Y; $X_3$ is A; $X_4$ is D; $X_5$ is D; $X_6$ is F; $X_7$ is G; $X_8$ is Y; $X_9$ is S; $X_{10}$ is W; and $X_{11}$ is Y | 173 |
| DART-A-M8 | 189 - wherein: $X_1$ is T; $X_2$ is Y; $X_3$ is A; $X_4$ is D; $X_5$ is E; $X_6$ is F; $X_7$ is G; $X_8$ is Y; $X_9$ is S; $X_{10}$ is W; and $X_{11}$ is Y | 173 |
| DART-A-M9 | 189 - wherein: $X_1$ is T; $X_2$ is Y; $X_3$ is A; $X_4$ is D; $X_5$ is K; $X_6$ is F; $X_7$ is G; $X_8$ is Y; $X_9$ is S; $X_{10}$ is W; and $X_{11}$ is Y | 173 |
| DART-A-M10 | 189 - wherein: $X_1$ is T; $X_2$ is Y; $X_3$ is A; $X_4$ is D; $X_5$ is G; $X_6$ is I; $X_7$ is G; $X_8$ is Y; $X_9$ is S; $X_{10}$ is W; and $X_{11}$ is Y | 173 |
| DART-A-M11 | 189 - wherein: $X_1$ is T; $X_2$ is Y; $X_3$ is A; $X_4$ is D; $X_5$ is G; $X_6$ is F; $X_7$ is G; $X_8$ is Y; $X_9$ is S; $X_{10}$ is F; and $X_{11}$ is Y | 173 |
| DART-A-M12 | 189 - wherein: $X_1$ is T; $X_2$ is Y; $X_3$ is A; $X_4$ is D; $X_5$ is G; $X_6$ is F; $X_7$ is G; $X_8$ is Y; $X_9$ is S; $X_{10}$ is Y; and $X_{11}$ is Y | 173 |
| DART-A-M13 | 189 - wherein: $X_1$ is T; $X_2$ is Y; $X_3$ is A; $X_4$ is D; $X_5$ is G; $X_6$ is F; $X_7$ is G; $X_8$ is Y; $X_9$ is S; $X_{10}$ is W; and $X_{11}$ is E | 173 |
| DART-A-M14 | 189 - wherein: $X_1$ is D; $X_2$ is Y; $X_3$ is A; $X_4$ is D; $X_5$ is G; $X_6$ is F; $X_7$ is G; $X_8$ is Y; $X_9$ is S; $X_{10}$ is W; and $X_{11}$ is Y | 173 |
| DART-A-M15 | 189 - wherein: $X_1$ is E; $X_2$ is Y; $X_3$ is A; $X_4$ is D; $X_5$ is G; $X_6$ is F; $X_7$ is G; $X_8$ is Y; $X_9$ is S; $X_{10}$ is W; and $X_{11}$ is Y | 173 |
| DART-A-M16 | 189 - wherein: $X_1$ is T; $X_2$ is D; $X_3$ is A; $X_4$ is D; $X_5$ is G; $X_6$ is F; $X_7$ is G; $X_8$ is Y; $X_9$ is S; $X_{10}$ is W; and $X_{11}$ is Y | 173 |
| DART-A-M17 | 189 - wherein: $X_1$ is T; $X_2$ is T; $X_3$ is A; $X_4$ is D; $X_5$ is G; $X_6$ is F; $X_7$ is G; $X_8$ is Y; $X_9$ is S; $X_{10}$ is W; and $X_{11}$ is Y | 173 |
| DART-A-M18 | 189 - wherein: $X_1$ is T; $X_2$ is Y; $X_3$ is G; $X_4$ is D; $X_5$ is G; $X_6$ is F; $X_7$ is G; $X_8$ is Y; $X_9$ is S; $X_{10}$ is W; and $X_{11}$ is Y | 173 |
| DART-A-M19 | 189 - wherein: $X_1$ is T; $X_2$ is Y; $X_3$ is A; $X_4$ is D; $X_5$ is K; $X_6$ is I; $X_7$ is G; $X_8$ is Y; $X_9$ is S; $X_{10}$ is W; and $X_{11}$ is Y | 173 |
| DART-A-M20 | 189 - wherein: $X_1$ is T; $X_2$ is Y; $X_3$ is A; $X_4$ is D; $X_5$ is K; $X_6$ is F; $X_7$ is G; $X_8$ is G; $X_9$ is S; $X_{10}$ is W; and $X_{11}$ is Y | 173 |
| DART-A-M21 | 189 - wherein: $X_1$ is T; $X_2$ is Y; $X_3$ is A; $X_4$ is D; $X_5$ is K; $X_6$ is F; $X_7$ is G; $X_8$ is Y; $X_9$ is S; $X_{10}$ is F; and $X_{11}$ is Y | 173 |
| DART-A-M22 | 189 - wherein: $X_1$ is T; $X_2$ is Y; $X_3$ is A; $X_4$ is D; $X_5$ is K; $X_6$ is F; $X_7$ is G; $X_8$ is Y; $X_9$ is S; $X_{10}$ is Y; and $X_{11}$ is Y | 173 |
| DART-A-M23 | 172 | 190 - wherein: $X_1$ is G; $X_2$ is K; and $X_3$ is E |
| DART-A-M24 | 172 | 190 - wherein: $X_1$ is G; $X_2$ is K; and $X_3$ is Q |
| DART-A-M25 | 172 | 190 - wherein: $X_1$ is D; $X_2$ is K; and $X_3$ is L |
| DART-A-M26 | 172 | 190 - wherein: $X_1$ is G; $X_2$ is G; and $X_3$ is L |

B. DART-B-Type Diabodies

DART-B-type diabodies are bispecific diabodies capable of binding CD3 and a Disease Antigen (e.g., a Cancer or Infectious Disease Antigen) that comprise an Fc Domain. Provided herein are illustrative DART-B-type diabodies (Table 9) composed of three polypeptide chains and have one binding site for CD3 and one binding site for the Cancer Antigen CD123, 5T4, or CD19 (see, e.g., FIG. 4A).

TABLE 9

| DART-B-Type No. | Disease Antigen-Binding Domain | CD3 Binding Domain | Polypeptide Chain | | | Designation |
|---|---|---|---|---|---|---|
| | | | First CD123/CD3 Binding Domains | Second CD123/CD3 Binding Domains | Third Fc Domain | |
| 1 | CD 123 mAb 1 | CD3 mAb 1 | SEQ ID NO: 174 | SEQ ID NO: 175 | SEQ ID NO: 176 | CD123-WT |
| 2 | | CD3 mAb 1 M1 | SEQ ID NO: 177 | | | CD123-M1 |
| 3 | | CD3 mAb 1 M2 | SEQ ID NO: 178 | | | CD123-M2 |
| 4 | | CD3 mAb 1 M18 | SEQ ID NO: 179 | | | CD123-M18 |
| 5 | | CD3 mAb 1 M13 | SEQ ID NO: 198 | | | CD123-M13 |
| 6 | | CD3 mAb 1 M17 | SEQ ID NO: 199 | | | CD123-M17 |
| 7 | | CD3 mAb 1 M19 | SEQ ID NO: 200 | | | CD123-M19 |
| 8 | 5T4 mAb 1 | CD3 mAb 1 | SEQ ID NO: 180 | SEQ ID NO: 181 | | 5T4-WT |
| 9 | | CD3 mAb 1 M1 | SEQ ID NO: 182 | | | 5T4-M1 |
| 10 | | CD3 mAb 1 M2 | SEQ ID NO: 183 | | | 5T4-M2 |
| 11 | | CD3 mAb 1 M18 | SEQ ID NO: 184 | | | 5T4-M18 |
| 12 | HIV mAb A32 | CD3 mAb 1 | SEQ ID NO: 185 | SEQ ID NO: 186 | | HIV-WT |
| 13 | | CD3 mAb 1 M18 | SEQ ID NO: 196 | | | HIV-M18 |
| 14 | CD19 mAb 1 | CD3 mAb 1 | SEQ ID NO: 191 | SEQ ID NO: 192 | | CD19-WT |
| 15 | (alternative VL where indicated) | CD3 mAb 1 M18 | SEQ ID NO: 197 | | | CD19-M18 |
| 16 | | CD3 mAb 1 M18 | SEQ ID NO: 193 | SEQ ID NO: 194 | | CD19.1-M18 |
| 17 | | CD3 mAb 1 M13 | SEQ ID NO: 201 | | | CD19.1-M13 |
| 18 | | CD3 mAb 1 M17 | SEQ ID NO: 202 | | | CD19.1-M17 |
| 19 | | CD3 mAb 1 M19 | SEQ ID NO: 203 | | | CD19.1-M19 |

1. First Illustrative DART-B-Type Diabody CD123-WT (CD123×CD3 mAb 1)

A first illustrative DART-B-type diabody (designated "CD123-WT") has a first polypeptide chain having the amino acid sequence of SEQ ID NO:174:

```
DFVMTQSPDS LAVSLGERVT MSCKSSQSLL NSGNQKNYLT WYQQKPGQPP KLLIYWASTR ESGVPDRFSG

SGSGTDFTLT ISSLQAEDVA VYYCQNDYSY PYTFGQGTKL EIKGGGSGGG GEVQLVESGG GLVQPGGSLR

LSCAASGFTF STYAMNWVRQ APGKGLEWVG RIRSKYNNYA TYYADSVKDR FTISRDDSKN SLYLQMNSLK

TEDTAVYYCV RHGNFGNSYV SWFAYWGQGT LVTVSSGGCG GGEVAALEKE VAALEKEVAA LEKEVAALEK

GGGDKTHTCP PCPAPEAAGG PSVFLFPPKP KDTLMISRTP EVTCVVVDVS HEDPEVKFNW YVDGVEVHNA

KTKPREEQYN STYRVVSVLT VLHQDWLNGK EYKCKVSNKA LPAPIEKTIS KAKGQPREPQ VYTLPPSREE

MTKNQVSLWC LVKGFYPSDI AVEWESNGQP ENNYKTIPPV LDSDGSFFLY SKLTVDKSRW QQGNVFSCSV

MHEALHNHYT QKSLSLSPGK
```

Residues 1-113 of the first polypeptide chain of CD123-WT correspond to the VL Domain of CD123 mAb 1 (SEQ ID NO:163). Residues 114-121 (double underlined) of the first polypeptide chain of CD123-WT correspond to Linker 1 (GGGSGGGG; SEQ ID NO:16). Residues 122-246 of the first polypeptide chain of CD123-WT correspond to the VH Domain of CD3 mAb 1 (SEQ ID NO:55), wherein Kabat position 65 (double underlined) is aspartate (D). Residues 247-252 (underlined) of the first polypeptide chain of CD123-WT correspond to a Linker 2 (GGCGGG; SEQ ID NO:17). Residues 253-280 of the first polypeptide chain of CD123-WT correspond to the heterodimer-promoting "E-coil" (EVAALEK-EVAALEK-EVAALEK-EVAALEK; SEQ ID NO:29). Residues 281-283 of the first polypeptide chain of CD123-WT correspond to a GGG Linker. Residues 284-293 (underlined) of the first polypeptide chain of CD123-WT correspond to the Linker DKTHTCPPCP (SEQ ID NO:40). Residues 294-510 of the first polypeptide chain of CD123-WT correspond to the IgG1 "knob-bearing" CH2-CH3 Domain (SEQ ID NO:48).

The second polypeptide chain of CD123-WT has the amino acid sequence of SEQ ID NO:175:

```
QAVVIQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

QLVQSGAELK KPGASVKVSC KASGYTFTDY YMKWVRQAPG

QGLEWIGDII PSNGATFYNQ KFKGRVTITV DKSTSTAYME

LSSLRSEDTA VYYCARSHLL RASWFAYWGQ GTLVTVSSGG

CGGGKVAALK EKVAALKEKV AALKEKVAAL KE
```

Residues 1-110 of the second polypeptide chain of CD123-WT correspond to the VL Domain of CD3 mAb 1 (SEQ ID NO:56). Residues 111-118 (double underlined) of the second polypeptide chain of CD123-WT correspond to Linker 1 (GGGSGGGG; SEQ ID NO:16). Residues 119-238 of the second polypeptide chain of CD123-WT correspond to the VH Domain of CD123 mAb 1 (SEQ ID NO:162). Residues 239-244 (underlined) of the second polypeptide chain correspond to Linker 2 (GGCGGG; SEQ ID NO:17). Residues 245-272 of the second polypeptide chain of CD123-WT correspond to the heterodimer-promoting "K-coil" (KVAALKE-KVAALKE-KVAALKE-KVAALKE, SEQ ID NO:30).

The third polypeptide chain of CD123-WT has the amino acid sequence of SEQ ID NO:176:

```
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSREEMTK NQVSLSCAVK GFYPSDIAVE

WESNGQPENN YKTTPPVLDS DGSFFLVSKL TVDKSRWQQG

NVFSCSVMHE ALHNRYTQKS LSLSPGK
```

Residues 1-10 of the third polypeptide chain of CD123-WT correspond to the Linker DKTHTCPPCP (SEQ ID NO:40). Residues 10-227 of the third polypeptide chain of CD123-WT correspond to the IgG1 "hole-bearing" CH2-CH3 Domain (SEQ ID NO:50).

As will be recognized, the third polypeptide chain of CD123-WT does not contain any Epitope-Binding Domains and may thus be employed in various DAxCD3 Binding Molecules having such DART-B-type structure.

2. Second Illustrative DART-B-Type Diabody CD123-M1 (CD123×CD3 mAb 1 M1)

A second illustrative DART-B-type diabody is similar to the above-described CD123-WT diabody, but contains the VH Domain of CD3 mAb 1 M1 and is designated "CD123-M1". As indicated above, CD3 mAb 1 M1 is a low affinity variant of CD3 mAb 1, (also referred to as "CD3 mAb 1 Low"). As also indicated above, the VL Domain of CD3 mAb 1 M1 has the same amino acid sequence as the VL Domain of CD3 mAb 1.

Thus, the second illustrative DART-B-type diabody (CD123-M1) has a first polypeptide chain that has the amino acid sequence (SEQ ID NO:177):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIKGGGSGGG

GEVQLVESGG GLVQPGGSLR LSCAASGFTF STYAMNWVRQ

APGKGLEWVG RIRSKYNNYA TYYADSVKDR FTISRDDSKN

SLYLQMNSLK TEDTAVYYCV RHGNFGNSYV TWFAYWGQGT

LVTVSSGGCG GGEVAALEKE VAALEKEVAA LEKEVAALEK

GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTIPPV LDSDGSFFLY SKLTVDKSRW

QQGNVFSCSV MHEALHNHYT QKSLSLSPCK
```

Residues 1-113 of the first polypeptide chain of CD123-M1 correspond to the VL Domain of CD123 mAb 1 (SEQ ID NO:163). Residues 114-121 (double underlined) of the first polypeptide chain of CD123-M1 correspond to Linker 1 (GGGSGGGG; SEQ ID NO:16). Residues 122-246 of the first polypeptide chain of CD123-M1 correspond to the VH Domain of CD3 mAb 1 M1 (SEQ ID NO:55), wherein Kabat position 65 (double underlined) is aspartate (D). Residues 247-252 (underlined) of the first polypeptide chain of CD123-M1 correspond to a Linker 2 (GGCGGG; SEQ ID NO:17). Residues 253-280 of the first polypeptide chain of CD123-M1 correspond to the heterodimer-promoting "E-coil" (EVAALEK-EVAALEK-EVAALEK-EVAALEK; SEQ ID NO:29). Residues 281-283 of the first polypeptide chain of CD123-M1 correspond to a GGG Linker. Residues 284-293 (underlined) of the first polypeptide chain of CD123-M1 correspond to the Linker DKTHTCPPCP (SEQ ID NO:40). Residues 294-510 of the first polypeptide chain of CD123-M1 correspond to the IgG1 "knob-bearing" CH2-CH3 Domain (SEQ ID NO:48).

Since the VL Domain of CD3 mAb 1 M1 is the same as that of CD3 mAb 1, the amino acid sequence of the second polypeptide chain of CD123-M1 is the same as that of the second polypeptide chain of the CD123-WT diabody (i.e., SEQ ID NO:175). Similarly, the amino acid sequence of the third polypeptide chain of CD123-M1 is the same as that of the third polypeptide chain of the CD123-WT diabody (i.e., SEQ ID NO:176).

3. Third Illustrative DART-B-Type Diabody CD123-M2 (CD123×CD3 mAb 1 M2)

A third illustrative DART-B-type diabody is similar to the above-described CD123-M1 diabody, but contains the VH Domain of CD3 mAb 1 M2 and is designated "CD123-M2". As indicated above, CD3 mAb 1 M2 has a faster off-rate than CD3 mAb 1, and is thus also referred to as "CD3 mAb 1 Fast." As also indicated above, the VL Domain of CD3 mAb 1 M2 has the same amino acid sequence as the VL Domain of CD3 mAb 1.

Thus, the third illustrative DART-B-type diabody (CD123-M2) has a first polypeptide chain that has the amino acid sequence (SEQ ID NO:178):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIKGGGSGGG

GEVQLVESGG GLVQPGGSLR LSCAASGFTF STYAMNWVRQ

APGKGLEWVG RIRSKYNNYA TYYADSVKDR FTISRDDSKN

SLYLQMNSLK TEDTAVYYCV RHKNFGNSYV TWFAYWGQGT

LVTVSSGGCG GGEVAALEKE VAALEKEVAA LEKEVAALEK

GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTTPPV LDSDGSFFLY SKLTVDKSRW

QQGNVFSCSV MHEALHNHYT QKSLSLSPGK
```

Residues 1-113 of the first polypeptide chain of CD123-M2 correspond to the VL Domain of CD123 mAb 1 (SEQ ID NO:163). Residues 114-121 (double underlined) of the first polypeptide chain of CD123-M2 correspond to Linker 1 (GGGSGGGG; SEQ ID NO:16). Residues 122-246 of the first polypeptide chain of CD123-M2 correspond to the VH Domain of CD3 mAb 1 M2 (SEQ ID NO:59), wherein Kabat position 65 (double underlined) is aspartate (D). Residues 247-252 (underlined) of the first polypeptide chain of CD123-M2 correspond to a Linker 2 (GGCGGG; SEQ ID NO:17). Residues 253-280 of the first polypeptide chain of CD123-M2 correspond to the heterodimer-promoting "E-coil" (EVAALEK-EVAALEK-EVAALEK-EVAALEK; SEQ ID NO:29). Residues 281-283 of the first polypeptide chain of CD123-M2 correspond to a GGG Linker. Residues 284-293 (underlined) of the first polypeptide chain of CD123-M2 correspond to the Linker DKTHTCPPCP (SEQ ID NO:40). Residues 294-510 of the first polypeptide chain of CD123-M2 correspond to the IgG1 "knob-bearing" CH2-CH3 Domain (SEQ ID NO:48).

Since the VL Domain of CD3 mAb 1 M2 is the same as that of CD3 mAb 1, the amino acid sequence of the second polypeptide chain of CD123-M2 is the same as that of the second polypeptide chain of the CD123-WT diabody (i.e., SEQ ID NO:175). Similarly, the amino acid sequence of the third polypeptide chain of CD123-M2 is the same as that of the third polypeptide chain of the CD123-WT diabody (i.e., SEQ ID NO:176).

4. Fourth Illustrative DART-B-Type Diabody CD123-M18 (CD123×CD3 mAb 1 M18)

A fourth illustrative DART-B-type diabody is similar to the above-described CD123-M2 diabody, but contains the VH Domain of CD3 mAb 1 M18 and is designated "CD123-M18". As indicated above, the VL Domain of CD3 mAb 1 M18 has the same amino acid sequence as the VL Domain of CD3 mAb 1.

Thus, the fourth illustrative DART-B-type diabody (CD123-M18) has a first polypeptide chain that has the amino acid sequence (SEQ ID NO:179):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIKGGGSGGG

GEVQLVESGG GLVQPGGSLR LSCAASGFTF STYGMNWVRQ

APGKGLEWVG RIRSKYNNYA TYYADSVKDR FTISRDDSKN

SLYLQMNSLK TEDTAVYYCV RHGNFGNSYV SWFAYWGQT

LVTVSSGGCG GGEVAALEKE VAALEKEVAA LEKEVAALEK

GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTTPPV LDSDGSFFLY SKLTVDKSRW

QQGNVFSCSV MHEALHNHYT QKSLSLSPGK
```

Residues 1-113 of the first polypeptide chain of CD123-M18 correspond to the VL Domain of CD123 mAb 1 (SEQ ID NO:163). Residues 114-121 (double underlined) of the first polypeptide chain of CD123-M18 correspond to Linker 1 (GGGSGGGG; SEQ ID NO:16). Residues 122-246 of the first polypeptide chain of CD123-M18 correspond to the VH Domain of CD3 mAb 1 M18 (SEQ ID NO:98), wherein Kabat position 65 (double underlined) is aspartate (D). Residues 247-252 (underlined) of the first polypeptide chain of CD123-M18 correspond to a Linker 2 (GGCGGG; SEQ ID NO:17). Residues 253-280 of the first polypeptide chain of CD123-M18 correspond to the heterodimer-promoting "E-coil" (EVAALEK-EVAALEK-EVAALEK-EVAALEK; SEQ ID NO:29). Residues 281-283 of the first polypeptide chain of CD123-M18 correspond to a GGG Linker. Residues 284-293 (underlined) of the first polypeptide chain of CD123-M18 correspond to the Linker DKTHTCPPCP (SEQ ID NO:40). Residues 294-510 of the first polypeptide chain of CD123-M18 correspond to the IgG1 "knob-bearing" CH2-CH3 Domain (SEQ ID NO:48).

Since the VL Domain of CD3 mAb 1 M18 is the same as that of CD3 mAb 1, the amino acid sequence of the second polypeptide chain of CD123-M18 is the same as that of the second polypeptide chain of the CD123-WT diabody SEQ ID NO:175). Similarly, the amino acid sequence of the third polypeptide chain of CD123-M18 is the same as that of the third polypeptide chain of the CD123-WT diabody (i.e., SEQ ID NO:176).

5. Fifth Illustrative DART-B-Type Diabody CD123-M13 (CD123×CD3 mAb 1 M13)

A fifth illustrative DART-B-type diabody is similar to the above-described CD123-WT diabody, but contains the VH Domain of CD3 mAb 1 M13 and is designated "CD123-

M13". As indicated above, the VL Domain of CD3 mAb 1 M13 has the same amino acid sequence as the VL Domain of CD3 mAb 1.

Thus, the fifth illustrative DART-B-type diabody (CD123-M13) has a first polypeptide chain that has the amino acid sequence (SEQ ID NO:198):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFQQGTKL EIKGGGSGGG

GEVQLVESGG GLVQPGGSLR LSCAASGFTF STYAMNWVRQ

APGKGLEWVG RIRSKYNNYA TYYADSVKDR FTISRDDSKN

SLYLQMNSLK TEDTAVYYCV RHGNFGNSYV SWFAEWGQGT

LVTVSSGGCG GGEVAALEKE VAALEKEVAA LEKEVAALEK

GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTTPPV LDSDGSFFLY SKLTVDKSRW

QQGNVFSCSV MHEALHNHYT QKSLSLSPGK
```

Residues 1-113 of the first polypeptide chain of CD123-M13 correspond to the VL Domain of CD123 mAb 1 (SEQ ID NO:163). Residues 114-121 (double underlined) of the first polypeptide chain of CD123-M13 correspond to Linker 1 (GGGSGGGG; SEQ ID NO:16). Residues 122-246 of the first polypeptide chain of CD123-M13 correspond to the VH Domain of CD3 mAb 1 M13 (SEQ ID NO:88), wherein Kabat position 65 (double underlined) is aspartate (D). Residues 247-252 (underlined) of the first polypeptide chain of CD123-M1 correspond to a Linker 2 (GGCGGG; SEQ ID NO:17). Residues 253-280 of the first polypeptide chain of CD123-M13 correspond to the heterodimer-promoting "E-coil" (EVAALEK-EVAALEK-EVAALEK-EVAALEK; SEQ ID NO:29). Residues 281-283 of the first polypeptide chain of CD123-M13 correspond to a GGG Linker. Residues 284-293 (underlined) of the first polypeptide chain of CD123-M13 correspond to the Linker DKTHTCPPCP (SEQ ID NO:40). Residues 294-510 of the first polypeptide chain of CD123-M13 correspond to the IgG1 "knob-bearing" CH2-CH3 Domain (SEQ ID NO:48).

Since the VL Domain of CD3 mAb 1 M13 is the same as that of CD3 mAb 1, the amino acid sequence of the second polypeptide chain of CD123-M13 is the same as that of the second polypeptide chain of the CD123-WT diabody (i.e., SEQ ID NO:175). Similarly, the amino acid sequence of the third polypeptide chain of CD123-M1 is the same as that of the third polypeptide chain of the CD123-WT diabody (i.e., SEQ ID NO:176).

6. Sixth Illustrative DART-B-Type Diabody CD123-M17 (CD123×CD3 mAb 1 M17)

A sixth illustrative DART-B-type diabody is similar to the above-described CD123-WT diabody, but contains the VH Domain of CD3 mAb 1 M17 and is designated "CD123-M17". As indicated above, the VL Domain of CD3 mAb 1 M17 has the same amino acid sequence as the VL Domain of CD3 mAb 1.

Thus, the sixth illustrative DART-B-type diabody (CD123-M17) has a first polypeptide chain that has the amino acid sequence (SEQ ID NO:199):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTEGQGTKL EIKGGGSGGG

GEVQLVESGG GLVQPGGSLR LSCAASGFTF STTAMNWVRQ

APGKGLEWVG RIRSKYNNYA TYYADSVKDR FTISRDDSKN

SLYLQMNSLK TEDTAVYYCV RHGNFGNSYV SWFAYWGQGT

LVTVSSGGCG GGEVAALEKE VAALEKEVAA LEKEVAALEK

GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTTPPV LDSDGSFFLY SKLTVDKSRW

QQGNVFSCSV MHEALHNHYT QKSLSLSPGK
```

Residues 1-113 of the first polypeptide chain of CD123-M17 correspond to the VL Domain of CD123 mAb 1 (SEQ ID NO:163). Residues 114-121 (double underlined) of the first polypeptide chain of CD123-M17 correspond to Linker 1 (GGGSGGGG; SEQ ID NO:16). Residues 122-246 of the first polypeptide chain of CD123-M17 correspond to the VH Domain of CD3 mAb 1 M17 (SEQ ID NO:96), wherein Kabat position 65 (double underlined) is aspartate (D). Residues 247-252 (underlined) of the first polypeptide chain of CD123-M17 correspond to a Linker 2 (GGCGGG; SEQ ID NO:17). Residues 253-280 of the first polypeptide chain of CD123-M17 correspond to the heterodimer-promoting "E-coil" (EVAALEK-EVAALEK-EVAALEK-EVAALEK; SEQ ID NO:29). Residues 281-283 of the first polypeptide chain of CD123-M17 correspond to a GGG Linker. Residues 284-293 (underlined) of the first polypeptide chain of CD123-M17 correspond to the Linker DKTHTCPPCP (SEQ ID NO:40). Residues 294-510 of the first polypeptide chain of CD123-M17 correspond to the IgG1 "knob-bearing" CH2-CH3 Domain (SEQ ID NO:48).

Since the VL Domain of CD3 mAb 1 M17 is the same as that of CD3 mAb 1, the amino acid sequence of the second polypeptide chain of CD123-M17 is the same as that of the second polypeptide chain of the CD123-WT diabody (i.e., SEQ ID NO:175). Similarly, the amino acid sequence of the third polypeptide chain of CD123-M17 is the same as that of the third polypeptide chain of the CD123-WT diabody (i.e., SEQ ID NO:176).

7. Seventh Illustrative DART-B-Type Diabody CD123-M19 (CD123×CD3 mAb 1 M19)

A seventh illustrative DART-B-type diabody is similar to the above-described CD123-WT diabody, but contains the VH Domain of CD3 mAb 1 M19 and is designated "CD123-M19". As indicated above, the VL Domain of CD3 mAb 1 M19 has the same amino acid sequence as the VL Domain of CD3 mAb 1.

Thus, the seventh illustrative DART-B-type diabody (CD123-M19) has a first polypeptide chain that has the amino acid sequence (SEQ ID NO:200):

```
DFVMTQSPDS LAVSLGERVT MSCKSSQSLL NSGNQKNYLT

WYQQKPGQPP KLLIYWASTR ESGVPDRFSG SGSGTDFTLT
```

```
ISSLQAEDVA VYYCQNDYSY PYTFGQGTKL EIKGGGSGGG

GEVQLVESGG GLVQPGGSLR LSCAASGFTF STYAMNWVRQ

APGKGLEWVG RIRSKYNNYA TYYADSVKDR FTISRDDSKN

SLYLQMNSLK TEDTAVYYCV RHKNIGNSYV SWFAYWGQGT

LVTVSSGGCG GGEVAALEKE VAALEKEVAA LEKEVAALEK

GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTTPPV LDSDGSFFLY SKLTVDKSRW

QQGNVFSCSV MHEALHNHYT QKSLSLSPGK
```

Residues 1-113 of the first polypeptide chain of CD123-M19 correspond to the VL Domain of CD123 mAb 1 (SEQ ID NO:163). Residues 114-121 (double underlined) of the first polypeptide chain of CD123-M19 correspond to Linker 1 (GGGSGGGG; SEQ ID NO:16). Residues 122-246 of the first polypeptide chain of CD123-M19 correspond to the VH Domain of CD3 mAb 1 M19 (SEQ ID NO:100), wherein Kabat position 65 (double underlined) is aspartate (D). Residues 247-252 (underlined) of the first polypeptide chain of CD123-M19 correspond to a Linker 2 (GGCGGG; SEQ ID NO:17). Residues 253-280 of the first polypeptide chain of CD123-M19 correspond to the heterodimer-promoting "E-coil" (EVAALEK-EVAALEK-EVAALEK-EVAALEK; SEQ ID NO:29). Residues 281-283 of the first polypeptide chain of CD123-M19 correspond to a GGG Linker. Residues 284-293 (underlined) of the first polypeptide chain of CD123-M1 correspond to the Linker DKTHTCPPCP (SEQ ID NO:40). Residues 294-510 of the first polypeptide chain of CD123-M19 correspond to the IgG1 "knob-bearing" CH2-CH3 Domain (SEQ ID NO:48).

Since the VL Domain of CD3 mAb 1 M19 is the same as that of CD3 mAb 1, the amino acid sequence of the second polypeptide chain of CD123-M19 is the same as that of the second polypeptide chain of the CD123-WT diabody (i.e., SEQ ID NO:175). Similarly, the amino acid sequence of the third polypeptide chain of CD123-M1 is the same as that of the third polypeptide chain of the CD123-WT diabody (i.e., SEQ ID NO:176).

8. Eighth Illustrative DART-B-Type Diabody 5T4-WT (5T4×CD3 mAb 1)

An eighth illustrative DART-B-type diabody is similar to the above-described CD123-M18 diabody, but comprises a 5T4 Binding Domain in lieu of the CD123 Binding Domain of the CD123-M18 diabody. Additionally, the eighth illustrative DART-B-type diabody contains the VH Domain of CD3 mAb 1. This eighth illustrative DART-B-type diabody is designated "5T4-WT".

Thus, the eighth illustrative DART-B-type diabody (5T4-WT) has a first polypeptide chain that has the amino acid sequence (SEQ ID NO:180):

```
DIQMIQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHGNFG NSYVSWFAYW GQGTLVTVSS

GGCGGGEVAA LEKEVAALEK EVAALEKEVA ALEKGGGDKT

HTCPPCPAPE AAGGPSVFLF PPKPKDILMI SRTPEVTCVV

VDVSEEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLWCLVKGFY PSDIAVEWES

NGQPENNYKT TPPVLDSDGS FFLYSKLTVD KSRWQQGNVF

SCSVMHEALE NHYTQKSLSL SPGK
```

Residues 1-107 of the first polypeptide chain of 5T4-WT correspond to the VL Domain of 5T4 mAb 1 (SEQ ID NO:157). Residues 108-115 (double underlined) of the first polypeptide chain of 5T4-WT correspond to Linker 1 (GGGSGGGG; SEQ ID NO:16). Residues 116-240 of the first polypeptide chain of 5T4-WT correspond to the VH Domain of CD3 mAb 1 (SEQ ID NO:55), wherein Kabat position 65 (double underlined) is glycine (G). Residues 241-246 (underlined) of the first polypeptide chain of 5T4-WT correspond to a Linker 2 (GGCGGG; SEQ ID NO:17). Residues 247-274 of the first polypeptide chain of 5T4-WT correspond to the heterodimer-promoting "E-coil" (EVAALEK-EVAALEK-EVAALEK-EVAALEK; SEQ ID NO:29). Residues 275-277 of the first polypeptide chain of 5T4-WT correspond to a GGG Linker. Residues 278-287 (underlined) of the first polypeptide chain of 5T4-WT correspond to the Linker DKTHTCPPCP (SEQ ID NO:40). Residues 288-504 of the first polypeptide chain of 5T4-WT correspond to the IgG1 "knob-bearing" CH2-CH3 Domain (SEQ ID NO:48).

The second polypeptide chain of 5T4-WT has the amino acid sequence (SEQ ID NO:181):

```
QAVVTQEPSL TVSPGGTVTL TGRSSTGAVT TSNYANWVQQ

KPGQAPRGLI GGINKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTSF WMHWVRQAPG

QGLEWMGRID PNRGGTEYNE KAKSRVTMTA DKSTSTAYME

LSSLRSEDTA VYYCAGGNPY YPMDYWGQGT TVTVSSGGCG

GGKVAALKEK VAALKEKVAA LKEKVAALKE
```

Residues 1-110 of the second polypeptide chain of 5T4-WT correspond to the VL Domain of CD3 mAb 1 (SEQ ID NO:56). Residues 111-118 (double underlined) of the second polypeptide chain of 5T4-WT correspond to Linker 1 (GGGSGGGG; SEQ ID NO:16). Residues 119-236 of the second polypeptide chain of 5T4-WT correspond to the VH Domain of 5T4 mAb 1 (SEQ ID NO:156). Residues 237-242 (underlined) of the second polypeptide chain of 5T4-WT correspond to a Linker 2 (GGCGGG; SEQ ID NO:17). Residues 243-280 of the second polypeptide chain of 5T4-WT correspond to the heterodimer-promoting "K-coil" (KVAALKE-KVAALKE-KVAALKE-KVAALKE; SEQ ID NO:30).

The third polypeptide chain of 5T4-WT has the same amino acid sequence as the third polypeptide chain of the CD123-WT diabody (i.e., SEQ ID NO:176).

9. Ninth Illustrative DART-B-Type Diabody 5T4-M1 (5T4×CD3 mAb 1 M1)

A ninth illustrative DART-B-type diabody is similar to the above-described 5T4-WT diabody, but comprises the VH Domain of CD3 mAb 1 M1 and is designated "5T4-M1."

Thus, the ninth illustrative DART-B-type diabody (5T4-M1) has a first polypeptide chain that has the amino acid sequence (SEQ ID NO:182):

```
DIQMTQSPSS LSASVGDRVT ITCRASQGIS NYLAWFQQKP
GKAPKSLIYR ANRLQSGVPS RFSGSGSGTD FTLTISSLQP
EDVATYYCLQ YDDFPWTFGQ GTKLEIKGGG SGGGGEVQLV
ESGGGLVQPG GSLRLSCAAS GFTFSTYAMN WVRQAPGKGL
EWVGRIRSKY NNYATYYADS VKDRFTISRD DSKNSLYLQM
NSLKTEDTAV YYCVRHGNFG NSYVTWFAYW GQGTLVTVSS
GGCGGGEVAA LEKEVAALEK EVAALEKEVA ALEKGGGDKT
HTCPPCPAPE AAGGPSVFLF PPKPKDILMI SRTPEVTCVV
VDVSHEDPEV KFNWYVDGVE VHNAKTKPRE EQYNSTYRVV
SVLTVLHQDW LNGKEYKCKV SNKALPAPIE KTISKAKGQP
REPQVYTLPP SREEMTKNQV SLWCLVKGFY PSDIAVEWES
NGQPENNYKT TPPVLDSDGS FFLYSKLTVD KSRWQQGNVF
SCSVMHEALH NHYTQKSLSL SPGK
```

Residues 1-107 of the first polypeptide chain of 5T4-M1 correspond to the VL Domain of 5T4 mAb 1 (SEQ ID NO:157). Residues 108-115 (double underlined) of the first polypeptide chain of 5T4-M1 correspond to Linker 1 (GGGSGGGG; SEQ ID NO:16). Residues 116-240 of the first polypeptide chain of 5T4-M1 correspond to the VH Domain of CD3 mAb 1 M1 (SEQ ID NO:64), wherein Kabat position 65 (double underlined) is aspartate (D). Residues 241-246 (underlined) of the first polypeptide chain of 5T4-M1 correspond to a Linker 2 (GGCGGG; SEQ ID NO:17). Residues 247-274 of the first polypeptide chain of 5T4-M1 correspond to the heterodimer-promoting "E-coil" (EVAALEK-EVAALEK-EVAALEK-EVAALEK; SEQ ID NO:29). Residues 275-277 of the first polypeptide chain of 5T4-M1 correspond to a GGG Linker. Residues 278-287 (underlined) of the first polypeptide chain of 5T4-M1 correspond to the Linker DKTHTCPPCP (SEQ ID NO:40). Residues 288-504 of the first polypeptide chain of 5T4-M1 correspond to the IgG1 "knob-bearing" CH2-CH3 Domain (SEQ ID NO:48).

Since the VL Domain of CD3 mAb 1 M1 is the same as that of CD3 mAb 1, the amino acid sequence of the second polypeptide chain of 5T4-M1 is the same as that of the second polypeptide chain of the 5T4-WT diabody (i.e., SEQ ID NO:181). Similarly, the amino acid sequence of the third polypeptide chain of 5T4-M1 is the same as that of the third polypeptide chain of the CD123-WT diabody (i.e., SEQ ID NO:176).

10. Tenth Illustrative DART-B-Type Diabody 5T4-M2 (5T4×CD3 mAb 1 M2)

A tenth illustrative DART-B-type diabody is similar to the above-described 5T4-M1 diabody, but comprises the VH Domain of CD3 mAb 1 M2 and is designated "5T4-M2".

Thus, the tenth illustrative DART-B-type diabody (5T4-M2) has a first polypeptide chain that has the amino acid sequence (SEQ ID NO:183):

```
DIQMTQSPSS LSASVGDRVT ITCRASQGIS NYLAWFQQKP
GKAPKSLIYR ANRLQSGVPS RFSGSGSGTD FTLTISSLQP
EDVATYYCLQ YDDFPWTFGQ GTKLEIKGGG SGGGGEVQLV
ESGGGLVQPG GSLRLSCAAS GFTFSTYAMN WVRQAPGKGL
EWVGRIRSKY NNYATYYADS VKDRFTISRD DSKNSLYLQM
NSLKTEDTAV YYCVRHKNFG NSYVTWFAYW GQGTLVTVSS
GGCGGGEVAA LEKEVAALEK EVAALEKEVA ALEKGGGDKT
HTCPPCPAPE AAGGPSVFLF PPKPKDILMI SRTPEVTCVV
VDVSHEDPEV KFNWYVDGVE VHNAKTKPRE EQYNSTYRVV
SVLTVLHQDW LNGKEYKCKV SNKALPAPIE KTISKAKGQP
REPQVYTLPP SREEMTKNQV SLWCLVKGFY PSDIAVEWES
NGQPENNYKT TPPVLDSDGS FFLYSKLTVD KSRWQQGNVF
SCSVMHEALH NHYTQKSLSL SPGK
```

Residues 1-107 of the first polypeptide chain of 5T4-M2 correspond to the VL Domain of 5T4 mAb 1 (SEQ ID NO:157). Residues 108-115 (double underlined) of the first polypeptide chain of 5T4-M2 correspond to Linker 1 (GGGSGGGG; SEQ ID NO:16). Residues 116-240 of the first polypeptide chain of 5T4-M2 correspond to the VH Domain of CD3 mAb 1 M2 (SEQ ID NO:66), wherein Kabat position 65 (double underlined) is aspartate (D). Residues 241-246 (underlined) of the first polypeptide chain of 5T4-M2 correspond to a Linker 2 (GGCGGG; SEQ ID NO:17). Residues 247-274 of the first polypeptide chain of 5T4-M2 correspond to the heterodimer-promoting "E-coil" (EVAALEK-EVAALEK-EVAALEK-EVAALEK; SEQ ID NO:29). Residues 275-277 of the first polypeptide chain of 5T4-M2 correspond to a GGG Linker. Residues 278-287 (underlined) of the first polypeptide chain of 5T4-M2 correspond to the Linker DKTHTCPPCP (SEQ ID NO:40). Residues 288-504 of the first polypeptide chain of 5T4-M2 correspond to the IgG1 "knob-bearing" CH2-CH3 Domain (SEQ ID NO:48).

Since the VL Domain of CD3 mAb 1 M2 is the same as that of CD3 mAb 1, the amino acid sequence of the second polypeptide chain of 5T4-M2 is the same as that of the second polypeptide chain of the 5T4-WT diabody (i.e., SEQ ID NO:181). Similarly, the amino acid sequence of the third polypeptide chain of 5T4-M2 is the same as that of the third polypeptide chain of the CD123-WT diabody (i.e., SEQ ID NO:176).

11. Eleventh Illustrative DART-B-Type Diabody 5T4-M18 (5T4×CD3 mAb 1 M18)

An eleventh illustrative DART-B-type diabody is similar to the above-described 5T4-WT diabody, but comprises the VH Domain of CD3 mAb 1 M18 and is designated "5T4-M18".

Thus, the eleventh illustrative DART-B-type diabody (5T4-M18) has a first polypeptide chain that has the amino acid sequence (SEQ ID NO:184):

```
DIQMTQSPSS LSASVGDRVT ITCRASQGIS NYLAWFQQKP
GKAPKSLTYR ANRLQSGVPS RFSGSGSGTD FTLTISSLQP
EDVATYYCLQ YDDFPWTFGQ GTKLEIKGGG SGGGGEVQLV
```

```
ESGGGLVQPG GSLRLSCAAS GFTFSTYGMN WVRQAPGKGL

EWVGRIRSKY NNYATYYADS VKDRFTISRD DSKNSLYLQM

NSLKTEDTAV YYCVRHGNFG NSYVSWFAYW GQGTLVTVSS

GGCGGGEVAA LEKEVAALEK EVAALEKEVA ALEKGGGDKT

HTCPPCPAPE AAGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLWCLVKGFY PSDIAVEWES

NGQPENNYKT TPPVLDSDGS FFLYSKLTVD KSRWQQGNVF

SCSVMHEALH NHYTQKSLSL SPGK
```

Residues 1-107 of the first polypeptide chain of 5T4-M18 correspond to the VL Domain of 5T4 mAb 1 (SEQ ID NO:157). Residues 108-115 (double underlined) of the first polypeptide chain of 5T4-M18 correspond to Linker 1 (GGGSGGGG; SEQ ID NO:16). Residues 116-240 of the first polypeptide chain of 5T4-M18 correspond to the VH Domain of CD3 mAb 1 M18 (SEQ ID NO:98), wherein Kabat position 65 (double underlined) is aspartate (D). Residues 241-246 (underlined) of the first polypeptide chain of 5T4-M18 correspond to a Linker 2 (GGCGGG; SEQ ID NO:17). Residues 247-274 of the first polypeptide chain of 5T4-M18 correspond to the heterodimer-promoting "E-coil" (EVAALEK-EVAALEK-EVAALEK-EVAALEK; SEQ ID NO:29). Residues 275-277 of the first polypeptide chain of 5T4-M18 correspond to a GGG Linker. Residues 278-287 (underlined) of the first polypeptide chain of 5T4-M18 correspond to the Linker DKTHTCPPCP (SEQ ID NO:40). Residues 288-504 of the first polypeptide chain of 5T4-M18 correspond to the IgG1 "knob-bearing" CH2-CH3 Domain (SEQ ID NO:48).

Since the VL Domain of CD3 mAb 1 M18 is the same as that of CD3 mAb 1, the amino acid sequence of the second polypeptide chain of 5T4-M18 is the same as that of the second polypeptide chain of the 5T4-WT diabody (i.e., SEQ ID NO:181). Similarly, the amino acid sequence of the third polypeptide chain of 5T4-M18 is the same as that of the third polypeptide chain of the CD123-WT diabody (i.e., SEQ ID NO:176).

12. Twelfth Illustrative DART-B-Type Diabody HIV-WT (HIV×CD3 mAb 1)

A twelfth illustrative DART-B-type diabody is similar to the above-described CD123-WT diabody, but comprises the HIV Binding Domain of the anti-HIV antibody A32 in lieu of the CD123 Binding Domain of the CD123-WT diabody. This twelfth illustrative DART-B-type diabody is designated "HIV-WT".

Thus, the twelfth illustrative DART-B-type diabody (HIV-WT) has a first polypeptide chain that has the amino acid sequence (SEQ ID NO:185):

```
QSALTQPPSA SGSPGQSVTI SCTGTSSDVG GYNYVSWYQH

HPGKAPKLII SEVNNRPSGV PDRFSGSKSG NTASLTVSGL

QAEDEAEYYC SSYTDIHNFV FGGGTKLTVL GGGSGGGGEV

QLVESGGGLV QPGGSLRLSC AASGFTFSTY AMNWVRQAPG

KCLEWVGRIR SKYNNYATYY ADSVKGRFTI SRDDSKNSLY

LQMNSLKTED TAVYYCVRHG NFGNSYVSWF AYWGQGTLVT

VSSASTKGEV AACEKEVAAL EKEVAALEKE VAALEKGGGD

KTHTCPPCPA PEAAGGPSVF LFPPKPKDTL MISRTPEVTC

VVVDVSEEDP EVKFNWYVDG VEVHNAKTKP REEQYNSTYR

VVSVLTVLHQ DWLNGKEYKG KVSNKALPAP IEKTISKAKG

QPREPQVYTL PPSREEMTKN QVSLWCLVKG FYPSDIAVEW

ESNGQPENNY KTTPPVLDSD GSFFLYSKLT VDKSRWQQGN

VFSCSVMHEA LHNHYTQKSL SLSPGK
```

Residues 1-110 of the first polypeptide chain of HIV-WT correspond to the VL Domain of A32 (SEQ ID NO:169). Residues 111-118 (double underlined) of the first polypeptide chain of HIV-WT correspond to Linker 1 (GGGSGGGG; SEQ ID NO:16). Residues 119-243 of the first polypeptide chain of HIV-WT correspond to the VH Domain of CD3 mAb 1 (SEQ ID NO:55), wherein Kabat position 65 (double underlined) is glycine (G). Residues 244-248 (underlined) of the first polypeptide chain of HIV-WT correspond to a Linker 2 (ASTKG; SEQ ID NO:21; single underlined). Residues 249-276 of the first polypeptide chain of HIV-WT correspond to the heterodimer-promoting "E-coil" (EVAACEK-EVAALEK-EVAALEK-EVAALEK; SEQ ID NO:31). Residues 277-279 of the first polypeptide chain of HIV-WT correspond to a GGG Linker. Residues 280-289 (underlined) of the first polypeptide chain of HIV-WT correspond to the Linker DKTHTCPPCP (SEQ ID NO:40; single underlined). Residues 290-506 of the first polypeptide chain of HIV-WT correspond to the IgG1 "knob-bearing" CH2-CH3 Domain (SEQ ID NO:48).

The second polypeptide chain of HIV-WT has the amino acid sequence (SEQ ID NO:186):

```
QAVVIQEPSL TVSPGGTVTL TCRSSTGAVT TSNYANWVQQ

KPGQAPRGLI GGINKRAPWT PARFSGSLLG GKAALTITGA

QAEDEADYYC ALWYSNLWVF GGGTKLIVLG GGGSGGGGQV

QLQESGPGLV KPSQTLSLSC TVSGGSSSSG AHYWSWIRQY

PGKGLEWIGY IHYSGNTYYN PSLKSRITIS QHTSENQFSL

KLNSVTVADT AVYYCARGTR LRTLRNAFDI WGQGTLVTVS

SASTKGKVAA CKEKVAALKE KVAALKEKVA ALKE
```

Residues 1-110 of the second polypeptide chain of HIV-WT correspond to the VL Domain of CD3 mAb 1 (SEQ ID NO:56). Residues 111-118 (double underlined) of the second polypeptide chain of HIV-WT correspond to Linker 1 (GGGSGGGG; SEQ ID NO:16). Residues 119-241 of the second polypeptide chain of HIV-WT correspond to the VH Domain of A32 (SEQ ID NO:209 (i.e., SEQ ID NO:168, wherein X is L)). Residues 242-246 (underlined) of the second polypeptide chain of HIV-WT correspond to a Linker 2 (ASTKG; SEQ ID NO:21). Residues 247-274 of the second polypeptide chain of HIV-WT correspond to the heterodimer-promoting "K-coil" (KVAACKE-KVAALKE-KVAALKE-KVAALKE; SEQ ID NO:32).

The third polypeptide chain of HIV-WT has the same amino acid sequence as the third polypeptide chain of the CD123-WT diabody SEQ ID NO:176).

13. Thirteenth Illustrative DART-B-Type Diabody HIV-M18 (HIV×CD3 mAb 18)

A thirteenth illustrative DART-B-type diabody is similar to the above-described HIV-WT diabody, but contains the VH Domain of CD3 mAb 1 M18. This illustrative DART-B-type diabody is designated "HIV-M18".

Thus, the thirteenth illustrative DART-B-type diabody (HIV-M18) has a first polypeptide chain that has the amino acid sequence (SEQ ID NO:196):

```
QSALTQPPSA SGSPGQSVTI SCTGTSSDVG
GYNYVSWYQH HPGKAPKLII SEVNNRPSGV
PDRFSGSKSG NTASLTVSGL QAEDEAEYYC
SSYTDIHNFV FGGGTKLTVL GGGSGGGGEV
QLVESGGGLV QPGGSLRLSC AASGFTFSTY
GMNWVRQAPG KGLEWVGRIR SKYNNYATYY
ADSVKGRFTI SRDDSKNSLY LQMNSLKTED
TAVYYCVRHG NFGNSYVSWF AYWGQGTLVT
VSSASTKGEV AACEKEVAAL EKEVAALEKE
VAALEKGGGD KTHTCPPCPA PEAAGGPSVF
LFPPKPKDTL MISRTPEVTC VVVDVSHEDP
EVKFNWYVDG VEVHNAKTKP REEQYNSTYR
VVSVLTVLHQ DWLNGKEYKC KVSNKALPAP
IEKTISKAKG QPREPQVYTL PPSREEMTKN
QVSLWCLVKG FYPSDIAVEW ESNGQPENNY
KTTPPVLDSD GSFFLYSKLT VDKSRWQQGN
VFSCSVMHEA LHNHYTQKSL SLSPGK
```

Residues 1-110 of the first polypeptide chain of HIV-M18 correspond to the VL Domain of A32 (SEQ ID NO:169). Residues 111-118 (double underlined) of the first polypeptide chain of HIV-M18 correspond to Linker 1 (GGGSGGGG; SEQ ID NO:16). Residues 119-243 of the first polypeptide chain of HIV-M18 correspond to the VH Domain of CD3 mAb 1 M18 (SEQ ID NO:55), wherein Kabat position 65 (double underlined) is glycine (G). Residues 244-248 (underlined) of the first polypeptide chain of HIV-M18 correspond to a Linker 2 (ASTKG; SEQ ID NO:21; single underlined). Residues 249-276 of the first polypeptide chain of HIV-M18 correspond to the heterodimer-promoting "E-coil" (EVAACEK-EVAALEK-EVAALEK-EVAALEK; SEQ ID NO:31). Residues 277-279 of the first polypeptide chain of HIV-M18 correspond to a GGG Linker. Residues 280-289 (underlined) of the first polypeptide chain of HIV-M18 correspond to the Linker DKTHTCPPCP (SEQ ID NO:40; single underlined). Residues 290-506 of the first polypeptide chain of HIV-M18 correspond to the IgG1 "knob-bearing" CH2-CH3 Domain (SEQ ID NO:48).

Since the VL Domain of CD3 mAb 1 M18 is the same as that of CD3 mAb 1, the amino acid sequence of the second polypeptide chain of HIV-M18 is the same as that of the second polypeptide chain of the HIV-WT diabody (i.e., SEQ ID NO:186). Similarly, the amino acid sequence of the third polypeptide chain of HIV-M18 is the same as that of the third polypeptide chain of the CD123-WT diabody (i.e., SEQ ID NO:176).

14. Fourteenth Illustrative DART-B-Type Diabody CD19-WT (CD19×CD3 mAb 1)

An fourteenth illustrative DART-B-type diabody is similar to the above-described HIV-WT diabody, but comprises CD19 mAb 1 in lieu of the A32 Binding Domain. This fourteenth illustrative DART-B-type diabody is designated "CD19-WT".

Thus, the fourteenth illustrative DART-B-type diabody (CD19-WT) has a first polypeptide chain that has the amino acid sequence (SEQ ID NO:191):

```
ENVLTQSPAT LSVTPGEKAT ITCRASQSVS YMHWYQQKPG
QAPRLLIYDA SNRASGVPSR FSGSGSGIDE TLTISSLEAE
DAATYYCFQG SVYPFTFGQG TKLEIKGGGS GGGGEVQLVE
SCGCLVQPGC SLRLSCAASG FTFSTYAMNW VRQAPGKGLE
WVGRIRSKYN NYATYYADSV KGRFTISRDD SKNSLYLQMN
SLKTEDTAVY YCVRHGNFGN SYVSWFAYWG QGTLVTVSSA
STKGEVAACE KEVAALEKEV AALEKEVAAL EKGGGDKTHT
CPPCPAPEAA GGPSVFLFPP KPKDILMISR TPEVTCVVVD
VSHEDPEVKF NWYVDGVEVE NAKTKPREEQ YNSTYRVVSV
LTVLHQDWLN GKEYKCKVSN KALPAPIEKT ISKAKGQPRE
PQVYTLPPSR EEMTKNQVSL WCLVKGFYPS DIAVEWESNG
QPENNYKTTP PVLDSDGSFF LYSKLIVDKS RWQQGNVFSC
SVMHEALHNH YTQKSLSLSP GK
```

Residues 1-106 of the first polypeptide chain of CD19-WT correspond to the VL Domain of CD19 mAb 1 (SEQ ID NO:165). Residues 107-114 (double underlined) of the first polypeptide chain of CD19-WT correspond to Linker 1 (GGGSGGGG, SEQ ID NO:16). Residues 115-239 of the first polypeptide chain of CD19-WT correspond to the VH Domain of CD3 mAb 1 (SEQ ID NO:55), wherein Kabat position 65 (double underlined) is glycine (G). Residues 240-244 (underlined) of the first polypeptide chain of CD19-WT correspond to a Linker 2 (ASTKG; SEQ ID NO:21; single underlined). Residues 245-272 of the first polypeptide chain of CD19-WT correspond to the heterodimer-promoting "E-coil" (EVAACEK-EVAALEK-EVAALEK-EVAALEK; SEQ ID NO:31). Residues 273-275 of the first polypeptide chain of CD19-WT correspond to a GGG Linker (double underlined). Residues 276-285 (single underlined) of the first polypeptide chain of CD19-WT correspond to the Linker DKTHTCPPCP (SEQ ID NO:40). Residues 286-502 of the first polypeptide chain of CD19-WT correspond to the IgG1 "knob-bearing" CH2-CH3 Domain (SEQ ID NO:48).

The second polypeptide chain of CD19-WT has the amino acid sequence (SEQ ID NO:192):

```
QAVVIQEPSL TVSPGGTVTL TCRSSTGAVT TSNYANWVQQ
KPGQAPRGLI GGINKRAPWT PARFSGSLLG GKAALTITGA
QAEDEADYYC ALWYSNLWVF GGGTKLTVLG GGGSGGGGQV
TLRESGPALV KPTQTLTLTC TFSGFSLSTS GMGVGWIRQP
```

-continued

```
PGKALEWLAH IWWDDDKRYN PALKSRLTIS KDTSKNQVFL

TMTNMDPVDT ATYYCARMEL WSYYFDYWGQ GTTVTVSSAS

TKGKVAACKE KVAALKEKVA ALKEKVAALK E
```

Residues 1-110 of the second polypeptide chain of CD19-WT correspond to the VL Domain of CD3 mAb 1 (SEQ ID NO:56). Residues 111-118 (double underlined) of the second polypeptide chain of CD19-WT correspond to Linker 1 (GGGSGGGG; SEQ ID NO:16). Residues 119-238 of the second polypeptide chain of CD19-WT correspond to the VH Domain of CD19 mAb 1 (SEQ ID NO:164). Residues 239-243 (underlined) of the second polypeptide chain of CD19-WT correspond to a Linker 2 (ASTKG; SEQ ID NO:21). Residues 244-271 of the second polypeptide chain of CD19-WT correspond to the heterodimer-promoting "K-coil" (KVAACKE-KVAALKE-KVAALKE-KVAALKE; SEQ ID NO:32).

The third polypeptide chain of CD19-WT has the same amino acid sequence as the third polypeptide chain of the CD123-WT diabody (i.e., SEQ ID NO:176).

15. Fifteenth Illustrative DART-B-Type Diabody CD19-M18 (CD19×CD3 mAb 1 M18)

A fifteenth illustrative DART-B-type diabody is similar to the above-described CD19-WT diabody, but contains the VH Domain of CD3 mAb 1 M18. This fifteenth illustrative DART-B-type diabody is designated "CD19-M18".

Thus, the fifteenth illustrative DART-B-type diabody (CD19-M18) has a first polypeptide chain that has the amino acid sequence (SEQ ID NO:197):

```
ENVLIQSPAT LSVTPGEKAT ITCRASQSVS

YMHWYQQKPG QAPRLLIYDA SNRASGVPSR

FSGSGSGTDH TLTISSLEAE DAATYYCFQG

SVYPFTFGQG TKLEIKGGGS GGGGEVQLVE

SGGGLVQPGG SLRLSCAASG FTFSTYGMNW

VRQAPGKGLE WVGRIRSKYN NYATYYADSV

KGRFTISRDD SKNSLYLQMN SLKTEDTAVY

YCVRHGNFGN SYVSWFAYWG QGTLVTVSSA

STKGEVAACE KEVAALEKEV AALEKEVAAL

EKGGGDKTHT CPPCPAPEAA GGPSVFLFPP

KPKDILMISR TPEVTCVVVD VSHEDPEVKF

NWYVDGVEVE NAKTKPREEQ YNSTYRVVSV

LTVLHQDWLN GKEYKCKVSN KALPAPIEKT

ISKAKGQPRE PQVYTLPPSR EEMTKNQVSL

WCLVKGFYPS DIAVEWESNG QPENNYKTTP

PVLDSDSFF LYSKLTVDKS RWQQGNVFSC

SVMHEALENE YTQKSLSLSP GK
```

Residues 1-106 of the first polypeptide chain of CD19-M18 correspond to the VL Domain of CD19 mAb 1 (SEQ ID NO:165). Residues 107-114 (double underlined) of the first polypeptide chain of CD19-M18 correspond to Linker 1 (GGGSGGGG; SEQ ID NO:16). Residues 115-239 of the first polypeptide chain of CD19-M18 correspond to the VH Domain of CD3 mAb 1 M18 (SEQ ID NO:98), wherein Kabat position 65 (double underlined) is glycine (G). Residues 240-244 (underlined) of the first polypeptide chain of CD19-M18 correspond to a Linker 2 (ASTKG; SEQ ID NO:21; single underlined). Residues 245-272 of the first polypeptide chain of CD19-M18 correspond to the heterodimer-promoting "E-coil" (EVAACEK-EVAALEK-EVAALEK-EVAALEK; SEQ ID NO:31). Residues 273-275 of the first polypeptide chain of CD19-M18 correspond to a GGG Linker. Residues 276-285 (single underlined) of the first polypeptide chain of CD19-M18 correspond to the Linker DKTHTCPPCP (SEQ ID NO:40). Residues 286-502 of the first polypeptide chain of CD19-M18 correspond to the IgG1 "knob-bearing" CH2-CH3 Domain (SEQ ID NO:48).

Since the VL Domain of CD3 mAb 1 M18 is the same as that of CD3 mAb 1, the amino acid sequence of the second polypeptide chain of CD19-M18 is the same as that of the second polypeptide chain of the CD19-WT diabody (i.e., SEQ ID NO:192). Similarly, third polypeptide chain of CD19-M18 has the same amino acid sequence as the third polypeptide chain of the CD123-WT diabody (i.e., SEQ ID NO:176).

16. Sixteenth Illustrative DART-B-Type Diabody CD19.1-M18 (CD19.1×CD3 mAb 1 M18)

A sixteenth illustrative DART-B-type diabody is similar to the above-described CD123-M18 diabody, but comprising a CD19 Binding Domain, containing the alternative VL Domain of CD19 mAb 1, in lieu of the CD123 Binding Domain of CD123-M18. This illustrative DART-B-type diabody is designated "CD19.1-M18". As indicated above, the VL Domain of CD3 mAb 1 M18 has the same amino acid sequence as the VL Domain of CD3 mAb 1.

Thus, the sixteenth illustrative DART-B-type diabody (CD19.1-M18) has a first polypeptide chain that has the amino acid sequence (SEQ ID NO:193):

```
ENVLIQSPAT LSVITGEKVT ITCSASSSVS YMHWYQQKPG

QAPRLLIYDT SKLASGVPSR FSGSGSGTDH FLTISSLEAE

DAATYYCFQG SVYPFTFGQG TKLEIKGGGS GGGGEVQLVE

SGGGLVQPGG SLRLSCAASG FTFSTYGMNW VRQAPGKGLE

WVGRIRSKYN NYATYYADSV KDRFTISRDD SKNSLYLQMN

SLKTEDTAVY YCVRHGNFGN SYVSWFAYWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

Residues 1-106 of the first polypeptide chain of CD19.1-M18 correspond to the alternative VL Domain of CD19 mAb 1 (SEQ ID NO:195). Residues 107-114 (double underlined) of the first polypeptide chain of CD19.1-M18 correspond to Linker 1 (GGGSGGGG; SEQ ID NO:16). Residues 115-239 of the first polypeptide chain of CD19.1-M18 correspond to the VH Domain of CD3 mAb 1 M18 (SEQ ID NO:98), wherein Kabat position 65 (double underlined) is aspartate (D). Residues 240-245 (single underlined) of the first polypeptide chain of CD19.1-M18 correspond to a Linker 2 (GGCGGG; SEQ ID NO:17). Residues 246-273 of the first polypeptide chain of CD19.1-M18 correspond to the heterodimer-promoting "E-coil" (<u>E</u>VAAL<u>E</u>K-<u>E</u>VAAL<u>E</u>K-<u>E</u>VAAL<u>E</u>K-<u>E</u>VAAL<u>E</u>K; SEQ ID NO:29). Residues 274-276 of the first polypeptide chain of CD19-M18 correspond to a GGG Linker. Residues 277-286 (single underlined) of the first polypeptide chain of CD19.1-M18 correspond to the Linker DKTHTCPPCP (SEQ ID NO:40). Residues 287-503 of the first polypeptide chain of CD19.1-M18 correspond to the IgG1 "knob-bearing" CH2-CH3 Domain (SEQ ID NO:48).

The second polypeptide chain of CD19.1-M18 has the amino acid sequence (SEQ ID NO:194):

```
QAVVTQEPSL TVSPGGTVTL TCRSSTGAVT TSNYANWVQQ

KPGQAPRGLI GGINKRAPWT PARFSGSLLG GKAALTITGA

QAEDEADYYC ALWYSNLWVF GGGTKLIVLG GGGSGGGGQV

TLRESGPALV KPTQTLTLTC TFSGFSLSTS CMCVCWIRQP

PCKALEWLAH IWWDDDKRYN PALKSRLTIS KDTSKNQVFL

TMTNMDPVDT ATYYCARMEL WSYYFDYWGQ GTTVTVSSGG

CGGGKVAALK EKVAALKEKV AALKEKVAAL KE
```

Residues 1-110 of the second polypeptide chain of CD19.1-M18 correspond to the VL Domain of CD3 mAb 1 (SEQ ID NO:56). Residues 111-118 (double underlined) of the second polypeptide chain of CD19.1-M18 correspond to Linker 1 (GGGSGGGG; SEQ ID NO:16). Residues 119-238 of the second polypeptide chain of CD19.1-M18 correspond to the VH Domain of CD19 mAb 1 (SEQ ID NO:164). Residues 239-244 (single underlined) of the second polypeptide chain of CD19.1-M18 correspond to a Linker 2 (GGCGGG; SEQ ID NO:17). Residues 245-272 of the second polypeptide chain of CD19.1-M18 correspond to the heterodimer-promoting "K-coil" (<u>K</u>VAAL<u>K</u>E-<u>K</u>VAAL<u>K</u>E-<u>K</u>VAAL<u>K</u>E-<u>K</u>VAAL<u>K</u>E; SEQ ID NO:30).

The amino acid sequence of the third polypeptide chain of CD19.1-M18 is the same as that of the third polypeptide chain of the CD123-WT diabody (i.e., SEQ ID NO:176).

17. Seventeenth Illustrative DART-B-Type Diabody CD19.1-M13 (CD19.1×CD3 mAb 1 M13)

A seventeenth illustrative DART-B-type diabody is similar to the above-described CD19.1-M18 diabody, but contains the VH Domain of CD3 mAb 1 M13 and is designated "CD19.1-M13". As indicated above, the VL Domain of CD3 mAb 1 M13 has the same amino acid sequence as the VL Domain of CD3 mAb 1.

Thus, the seventeenth illustrative DART-B-type diabody (CD19.1-M13) has a first polypeptide chain that has the amino acid sequence (SEQ ID NO:201):

```
ENVLIQSPAT LSVITGEKVT ITCSASSSVS YMHWYQQKPG

QAPRLLIYDT SKLASGVPSR FSGSGSGTDH FLTISSLEAE

DAATYYCFQG SVYPFTFGQG TKLEIKGGGS GGGGEVQLVE

SGGGLVQPGG SLRLSCAASG FTFSTYAMNW VRQAPGKGLE

WVGRIRSKYN NYATYYADSV KDRFTISRDD SKNSLYLQMN

SLKTEDTAVY YCVRHGNFGN SYVSWFAEWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV ENAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVES

CSVMHEALHN HYTQKSLSLS PGK
```

Residues 1-106 of the first polypeptide chain of CD19.1-M13 correspond to the alternative VL Domain of CD19 mAb 1 (SEQ ID NO:195). Residues 107-114 (double underlined) of the first polypeptide chain of CD19.1-M13 correspond to Linker 1 (GGGSGGGG; SEQ ID NO:16). Residues 115-239 of the first polypeptide chain of CD19.1-M18 correspond to the VH Domain of CD3 mAb 1 M13 (SEQ ID NO:88), wherein Kabat position 65 (double underlined) is aspartate (D). Residues 240-245 (single underlined) of the first polypeptide chain of CD19.1-M13 correspond to a Linker 2 (GGCGGG; SEQ ID NO:17). Residues 246-273 of the first polypeptide chain of CD19.1-M13 correspond to the heterodimer-promoting "E-coil" (<u>E</u>VAAL<u>E</u>K-<u>E</u>VAAL<u>E</u>K-<u>E</u>VAAL<u>E</u>K-<u>E</u>VAAL<u>E</u>K; SEQ ID NO:29). Residues 274-276 of the first polypeptide chain of CD19-M13 correspond to a GGG Linker. Residues 277-286 (single underlined) of the first polypeptide chain of CD19.1-M13 correspond to the Linker DKTHTCPPCP (SEQ ID NO:40). Residues 287-503 of the first polypeptide chain of CD19.1-M13 correspond to the IgG1 "knob-bearing" CH2-CH3 Domain (SEQ ID NO:48).

Since the VL Domain of CD3 mAb 1 M13 is the same as that of CD3 mAb 1 the amino acid sequence of the second polypeptide chain of CD19.1-M13 is the same as that of the second polypeptide chain of the CD19.1-M18 diabody (i.e., SEQ ID NO:194). The amino acid sequence of the third polypeptide chain of CD19.1-M13 is the same as that of the third polypeptide chain of the CD123-WT diabody (i.e., SEQ ID NO:176).

18. Eighteenth Illustrative DART-B-Type Diabody CD19.1-M17 (CD19.1×CD3 mAb 1 M17)

An eighteenth illustrative DART-B-type diabody is similar to the above-described CD19.1-M18 diabody, but contains the VH Domain of CD3 mAb 1 M17 and is designated "CD19.1-M17". As indicated above, the VL Domain of CD3 mAb 1 M17 has the same amino acid sequence as the VL Domain of CD3 mAb 1.

Thus, the eighteenth illustrative DART-B-type diabody (CD19.1-M17) has a first polypeptide chain that has the amino acid sequence (SEQ ID NO:202):

```
ENVLTQSPAT LSVITGEKVT ITCSASSSVS YMHWYQQKPG

QAPRLLIYDT SKLASGVPSR FSGSGSGIDE FLTISSLEAE

DAATYYCFQG SVYPFTFGQG TKLEIKGGGS GGGGEVQLVE

SGGGLVQPGG SLRLSCAASC FTFSTTAMNW VRQAPGKGLE

WVGRIRSKYN NYATYYADSV KDRFTISRDD SKNSLYLQMN

SLKTEDTAVY YCVRHGNFGN SYVSWFAYWG QGTLVTVSSG

GCGGGEVAAL EKEVAALEKE VAALEKEVAA LEKGGGDKTH
```

-continued

```
TCPPCPAPEA AGGPSVFLFP PKPKDTLMIS RTPEVTCVVV

DVSHEDPEVK FNWYVDGVEV ENAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

Residues 1-106 of the first polypeptide chain of CD19.1-M17 correspond to the alternative VL Domain of CD19 mAb 1 (SEQ ID NO:195). Residues 107-114 (double underlined) of the first polypeptide chain of CD19.1-M17 correspond to Linker 1 (GGGSGGGG; SEQ ID NO:16). Residues 115-239 of the first polypeptide chain of CD19.1-M17 correspond to the VH Domain of CD3 mAb 1 M17 (SEQ ID NO:96), wherein Kabat position 65 (double underlined) is aspartate (D). Residues 240-245 (single underlined) of the first polypeptide chain of CD19.1-M17 correspond to a Linker 2 (GGCGGG; SEQ ID NO:17). Residues 246-273 of the first polypeptide chain of CD19.1-M17 correspond to the heterodimer-promoting "E-coil" (EVAALEK-EVAALEK-EVAALEK-EVAALEK; SEQ ID NO:29). Residues 274-276 of the first polypeptide chain of CD19-M17 correspond to a GGG Linker. Residues 277-286 (single underlined) of the first polypeptide chain of CD19.1-M17 correspond to the Linker DKTHTCPPCP (SEQ ID NO:40). Residues 287-503 of the first polypeptide chain of CD19.1-M17 correspond to the IgG1 "knob-bearing" CH2-CH3 Domain (SEQ ID NO:48).

Since the VL Domain of CD3 mAb 1 M17 is the same as that of CD3 mAb 1 the amino acid sequence of the second polypeptide chain of CD19.1-M17 is the same as that of the second polypeptide chain of the CD19.1-M18 diabody (i.e., SEQ ID NO:194). The amino acid sequence of the third polypeptide chain of CD19.1-M17 is the same as that of the third polypeptide chain of the CD123-WT diabody (i.e., SEQ ID NO:176).

19. Nineteenth Illustrative DART-B-Type Diabody CD19.1-M19 (CD19.1×CD3 mAb 1 M19)

A nineteenth illustrative DART-B-type diabody is similar to the above-described CD19.1-M18 diabody, but contains the VH Domain of CD3 mAb 1 M19 and is designated "CD19.1-M19". As indicated above, the VL Domain of CD3 mAb 1 M19 has the same amino acid sequence as the VL Domain of CD3 mAb 1.

Thus, the nineteenth illustrative DART-B-type diabody (CD19.1-M19) has a first polypeptide chain that has the amino acid sequence (SEQ ID NO:203):

```
ENVLTQSPAT LSVTPGEKVT ITCSASSSVS YMHWYQQKPG

QAPRLLIYDT SKLASGVPSR FSGSGSGTDH FLTISSLEAE

DAATYYCFQG SVYPFTFGQG TKLEIKGGGS GGGGEVQLVE

SGGGLVQPGG SLRLSCAASG FTFSTYAMNW VRQAPGKGLE

WVGRIRSKYN NYATYYADSV KDRFTISRDD SKNSLYLQMN

SLKTEDTAVY YCVRHKNIGN SYVSWFAYWG QGTLVTVSSG

GCGGGEVAAL EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

Residues 1-106 of the first polypeptide chain of CD19.1-M19 correspond to the alternative VL Domain of CD19 mAb 1 (SEQ ID NO:195). Residues 107-114 (double underlined) of the first polypeptide chain of CD19.1-M19 correspond to Linker 1 (GGGSGGGG; SEQ ID NO:16). Residues 115-239 of the first polypeptide chain of CD19.1-M19 correspond to the VH Domain of CD3 mAb 1 M9 (SEQ ID NO:100), wherein Kabat position 65 (double underlined) is aspartate (D). Residues 240-245 (single underlined) of the first polypeptide chain of CD19.1-M19 correspond to a Linker 2 (GGCGGG; SEQ ID NO:17). Residues 246-273 of the first polypeptide chain of CD19.1-M19 correspond to the heterodimer-promoting "E-coil" (EVAALEK-EVAALEK-EVAALEK-EVAALEK; SEQ ID NO:29). Residues 274-276 of the first polypeptide chain of CD19-M19 correspond to a GGG Linker. Residues 277-286 (single underlined) of the first polypeptide chain of CD19.1-M19 correspond to the Linker DKTHTCPPCP (SEQ ID NO:40). Residues 287-503 of the first polypeptide chain of CD19.1-M19 correspond to the IgG1 "knob-bearing" CH2-CH3 Domain (SEQ ID NO:48).

Since the VL Domain of CD3 mAb 1 M19 is the same as that of CD3 mAb 1 the amino acid sequence of the second polypeptide chain of CD19.1-M19 is the same as that of the second polypeptide chain of the CD19.1-M18 diabody (i.e., SEQ ID NO:194). The amino acid sequence of the third polypeptide chain of CD19.1-M13 is the same as that of the third polypeptide chain of the CD123-WT diabody (i.e., SEQ ID NO:176).

Additional CD19×CD3 DART-B-Type Diabodies specifically contemplated are similar to the above-described CD19-WT (see, the fourteenth illustrative DART-B-Type Diabody) but will comprise the VH Domain of CD3 mAb 1 M13, M17, or M19. Such diabodies will comprise a first polypeptide chain having one of the following amino acid sequences:

SEQ ID NO:204 for such diabody comprising the VH Domain of CD3 mAb 1 M13:

```
ENVLTQSPAT LSVTPGEKAT ITCRASQSVS YMHWYQQKPG

QAPRLLIYDA SNRASGVPSR FSGSGSGTDH TLTISSLEAE

DAATYYCFQG SVYPFTFGQG TKLEIKGGGS GGGGEVQLVE

SGGGLVQPGG SLRLSCAASG FTFSTYAMNW VRQAPGKGLE

WVGRIRSKYN NYATYYADSV KGRFTISRDD SKNSLYLQMN

SLKTEDTAVY YCVRHGNFGN SYVSWFAEWG QGTLVTVSSA

STKGEVAACE KEVAALEKEV AALEKEVAAL EKGGGDKTHT

CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL WCLVKGFYPS DIAVEWESNG
```

-continued

```
QPENNYKTTP PVLDSDGSFF LYSKLIVDKS RWQQGNVFSC

SVMHEALENE YTQKSLSLSP GK
```

SEQ ID NO:205 for such diabody comprising the VH Domain of CD3 mAb 1 M17:

```
ENVLTQSPAT LSVTPGEKAT ITCRASQSVS YMHWYQQKPG

QAPRLLIYDA SNRASGVPSR FSGSGSGTDH TLTISSLEAE

DAATYYCFQG SVYPFTFGQG TKLEIKGGGS GGGGEVQLVE

SGGGLVQPGG SLRLSCAASG FTFSTTAMNW VRQAPGKGLE

WVGRIRSKYN NYATYYADSV KGRFTISRDD SKNSLYLQMN

SLKTEDTAVY YCVRHGNFGN SYVSWFAYWG QGTLVTVSSA

STKGEVAACE KEVAALEKEV AALEKEVAAL EKGGGDKTHT

CPPCPAPEAA GGPSVFLFPP KPKDILMISR TPEVTCVVVD

VSHEDPEVKF NWYVDGVEVE NAKTKPREEQ YNSTYRVVSV

LTVLHQDWLN GKEYKCKVSN KALPAPIEKT ISKAKGQPRE

PQVYTLPPSR EEMTKNQVSL WCLVKGFYPS DIAVEWESNG

QPENNYKTTP PVLDSDGSFF LYSKLTVDKS RWQQGNVFSC

SVMHEALENE YTQKSLSLSP GK
```

SEQ ID NO:206 for such diabody comprising the VH Domain of CD3 mAb 1 M19:

```
ENVLIQSPAT LSVTPGEKAT ITCRASQSVS YMHWYQQKPG

QAPRLLIYDA SNRASGVPSR FSGSGSGTDH TLTISSLEAE

DAATYYCFQG SVYPFTFGQG TKLEIKGGGS GGGGEVQLVE

SGGGLVQPGG SLRLSCAASG FTFSTYAMNW VRQAPGKGLE

WVGRIRSKYN NYATYYADSV KGRFTISRDD SKNSLYLQMN

SLKTEDTAVY YCVRHKNIGN SYVSWFAYWG QGTLVTVSSA

STKGEVAACE KEVAALEKEV AALEKEVAAL EKGGGDKTHT

CPPCPAPEAA GGPSVFLFPP KPKDILMISR TPEVTCVVVD

VSHEDPEVKF NWYVDGVEVE NAKTKPREEQ YNSTYRVVSV

LTVLHQDWLN GKEYKCKVSN KALPAPIEKT ISKAKGQPRE

PQVYTLPPSR EEMTKNQVSL WCLVKGFYPS DIAVEWESNG

QPENNYKTTP PVLDSDGSFF LYSKLTVDKS RWQQGNVFSC

SVMHEALHNH YTQKSLSLSP GK
```

The second polypeptide chains of such diabodies will have the same amino acid sequence of CD19-WT (i.e., SEQ ID NO:192) and the third polypeptide chain of such diabodies will have the same amino acid sequence as the third polypeptide chain of CD123-WT (i.e., SEQ ID NO:176).

As will be recognized in view of the instant disclosure, additional DART-B-type diabodies having a binding site for an alternative Disease Antigens and/or having the CD3 Binding Domains of alternative variant anti-CD3 antibodies (i.e., vCD3-Binding Domains) may likewise be constructed (by employing the VL and VH Domains of such antibodies). Similarly, as provided herein, alternative DART-B-type molecules may likewise be constructed incorporating alternative Linkers and/or alternative Heterodimer-Promoting Domains.

Additional, exemplary molecules capable of mediating the redirected killing of a cell expressing a Disease Antigen (e.g., a tumor cell) which may be used in the methods of the present invention include bispecific molecules capable of binding: CD19 and CD3 (see, e.g., U.S. Pat. No. 7,235,641 and WO 2016/048938); CD123 and CD3 (see, e.g., Kuo, S. R. et al., (2012) "*Engineering a CD123×CD3 Bispecific scFv Immunofusion For The Treatment Of Leukemia And Elimination Of Leukemia Stem Cells*," Protein Eng Des Sel. 25:561-9; WO 2015/026892; WO 2016/086189); gpA33 and CD3 (e.g., WO 2015/026894); CEA and CD3 (e.g., WO 2013/012414; WO 2017/118675); B7-H3 and CD3 (e.g., WO 2017/030926); HER2 and CD3 (e.g., WO 2012/143524); 5T4 and CD3 (e.g., WO 2015/184203 and WO 2013/041687), and other molecules having a CD3 Binding Domain (see, e.g., etc., WO 2013/026835, WO 2013/158856, WO 2014/110601, WO 2016/182751, WO 2017/053469). As will be recognized in view of the instant disclosure, the vCD3-Binding Domains of the instant invention may be incorporated into such molecules.

C. TRIVALENT-Type Molecules

TRIVALENT-type molecules are trivalent molecules capable of binding up to three different epitopes. In particular, the TRIVALENT-type molecules of the instant invention are capable of binding CD3 and a Disease Antigen (e.g., a Cancer or Infectious Disease Antigen) and may further bind an addition antigen such as an additional Disease Antigen (e.g., a Cancer or Infectious Disease Antigen) or an additional antigen expressed on the surface of an effector cell (e.g., CD8), or may bind to a second epitope of CD3 or a second epitope of the Disease Antigen. TRIVALENT-type molecules comprise an Fc Domain. Provided herein are illustrative TRIVALENT-type diabodies composed of four polypeptide chains and have one binding site for CD3, one binding site for the Cancer Antigen CD123 or for the Cancer Antigen 5T4, and one binding site for CD8 (see, e.g., FIG. 6A). The illustrative TRIVALENT-type molecules of the invention are generated using the first and second polypeptide chains of the DART-B-type diabodies provided above in combination with the illustrative third and fourth polypeptide chains provided below, which provide the CD8 Binding Domain. The first and second polypeptide chains form the CD3 and DA Binding Domains while the third and fourth polypeptide chains form the CD8 Binding Domain. The first and third polypeptide chains form an Fc Domain.

The illustrative TRIVALENT-type molecules provide below each incorporate a third polypeptide chain having the amino acid sequence of SEQ ID NO:187:

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS

SASTKGPSVF PLAPSSKSTS GGTAALGCLV KDYFPEPVTV

SWNSGALTSG VHTFPAVLQS SGLYSLSSVV TVPSSSLGTQ

TYICNVNHKP SNTKVDKRVE PKSCDKTHTC PPCPAPEAAG

GPSVFLFPPK PKDTLMISRT PEVTCVVVDV SHEDPEVKFN

WYVDGVEVHN AKTKPREEQY NSTYRVVSVL TVLHQDWLNG
```

-continued
```
KEYKCKVSNK ALPAPIEKTI SKAKGQPREP QVYTLPPSRE

EMTKNQVSLS CAVKGFYPSD IAVEWESNGQ PENNYKTTPP

VLDSDGSFFL VSKLTVDKSR WQQGNVFSCS VMHEALHNRY

TQKSLSLSPG K
```

Residues 1-121 of the third polypeptide chain of such illustrative TRIVALENT-type molecules correspond to the VH Domain of the anti-CD8 antibody TRX2 (SEQ ID NO:120). Residues 121-219 of the third polypeptide chain of such illustrative TRIVALENT-type molecule correspond to an IgG1 CH1 Domain (SEQ ID NO:1). Residues 220-234 of the third polypeptide chain of such illustrative TRIVALENT-type molecule correspond to an IgG1 Hinge Domain (SEQ ID NO:5). Residues 235-451 correspond to the IgG1 "hole-bearing" CH2-CH3 Domain (SEQ ID NO:50)

The illustrative TRIVALENT-type molecules described below each incorporate a fourth polypeptide chain having the amino acid sequence of SEQ ID NO:188:

```
DIQMTQSPSS LSASVGDRVT ITCKGSQDIN NYLAWYQQKP

GKAPKLLIYN TDILHTGVPS RFSGSGSGTD FTFTISSLQP

EDIATYYCYQ YNNGYTFGQG TKVEIKRTVA APSVFIFPPS

DEQLKSGTAS VVCLLNNFYP REAKVQWKVD NALQSGNSQE

SVTEQDSKDS TYSLSSTLTL SKADYEKEKV YACEVTEQGL

SSPVTKSFNR GEC
```

Residues 1-106 of the fourth polypeptide chain of such illustrative TRIVALENT-type molecules correspond to the VL Domain of the anti-CD8 antibody TRX2 (SEQ ID NO:121). Residues 107-213 correspond to a CL Kappa Domain (SEQ ID NO:14).

The SEQ ID NOs. of the polypeptide chains of Illustrative TRIVALENT-type molecules are summarized in Table 10.

(SEQ ID NO:175). Also indicated above, the amino acid sequences of the third and fourth polypeptide chains of all the illustrative TRIVALENT-type molecules are SEQ ID NO:187 and SEQ ID NO:188, respectively.

2. Second Illustrative TRIVALENT-Type Molecule T-CD123-M1 (CD123 mAb 1×CD3 mAb 1 M1×TRX2)

A second illustrative TRIVALENT-type molecule (designated "T-CD123-M1") contains the VH and VL Domains of CD123 mAb 1, the VH and VL Domains of CD3 mAb 1 M1, and the VH and VL Domains of TRX2. As indicated above, the amino acid sequence of the first polypeptide chain is the same as that of the above-described CD123-M1 diabody (SEQ ID NO:177). Similarly, the amino acid sequence of the second polypeptide chain is the same as that of the above-described CD123-WT diabody (SEQ ID NO:175). Also as indicated above, the amino acid sequences of the third and fourth polypeptide chains of all the illustrative TRIVALENT-type molecules are SEQ ID NO:187 and SEQ ID NO:188, respectively.

3. Third Illustrative TRIVALENT-Type Molecule T-CD123-M2 (CD123 mAb 1×CD3 mAb 1 M2×TRX2)

A third illustrative TRIVALENT-type molecule designated T-CD123-M2 binds contains the VH and VL Domains of CD123 mAb 1, the VH and VL Domains of CD3 mAb 1 M2, and the VH and VL Domains of TRX2. As indicated above, the amino acid sequence of the first polypeptide chain is the same as that of the above-described CD123-M2 diabody (SEQ ID NO:178). Similarly, the amino acid sequence of the second polypeptide chain is the same as that of the above-described CD123-WT diabody (SEQ ID NO:175). Also indicated above, the amino acid sequences of the third and fourth polypeptide chains of all the illustrative TRIVALENT-type molecules are SEQ ID NO:187 and SEQ ID NO:188 respectively.

4. Fourth Illustrative TRIVALENT-Type Molecule T-CD123-M18 (CD123 mAb 1×CD3 mAb 1 M18×TRX2)

A fourth illustrative TRIVALENT-type molecule designated T-CD123-M18 binds contains the VH and VL

TABLE 10

CD123 × CD3 × CD8 TRIDENT Molecules

| TRIDENT-Type No. | Disease Antigen-Binding Domain | CD3 Binding Domain | Polypeptide Chain | | | | Designation |
|---|---|---|---|---|---|---|---|
| | | | First CD123/CD3 Binding Domains | Second | Third CD8 Binding Domains | Fourth | |
| 1 | CD123 mAb 1 | CD3 mAb 1 | SEQ ID NO: 174 | SEQ ID NO: 175 | SEQ ID NO: 187 | SEQ ID NO: 188 | T-CD123-WT |
| 2 | | CD3 mAb 1 M1 | SEQ ID NO: 177 | | | | T-CD123-M1 |
| 3 | | CD3 mAb 1 M2 | SEQ ID NO: 178 | | | | T-CD123-M2 |
| 4 | | CD3 mAb 1 M18 | SEQ ID NO: 179 | | | | T-CD123-M18 |

1. First Illustrative TRIVALENT-Type Molecule T-CD123-WT (CD123 mAb 1×CD3 mAb 1×TRX2)

A first illustrative TRIVALENT-type molecule (designated "T-CD123-WT") contains the VH and VL Domains of CD123 mAb 1, the VH and VL Domains of CD3 mAb 1, and the VH and VL Domains of the anti-CD8 antibody TRX2. As indicated above, the amino acid sequence of the first polypeptide chain is the same as that of the above-described CD123-WT diabody (SEQ ID NO:174). Similarly, the amino acid sequence of the second polypeptide chain is the same as that of the above-described CD123-WT diabody Domains of CD123 mAb 1, the VH and VL Domains of CD3 mAb 1 M18, and the VH and VL Domains of TRX2. As indicated above, the amino acid sequence of the first polypeptide chain is the same as that of the above-described CD123-M18 diabody (SEQ ID NO:179). Similarly, the amino acid sequence of the second polypeptide chain is the same as that of the above-described CD123-WT diabody (SEQ ID NO:175). Also indicated above, the amino acid sequences of the third and fourth polypeptide chains of all the illustrative TRIVALENT-type molecules are SEQ ID NO:187 and SEQ ID NO:188, respectively.

As will be recognized in view of the instant disclosure, additional TRIVALENT-type diabodies having a binding site for an alternative Disease Antigens and/or having the CD3 Binding Domains of alternative variant anti-CD3 antibodies (i.e., vCD3-Binding Domains) may likewise be constructed (by employing the VL and VH Domains of such antibodies). Similarly, as provided herein, alternative TRIVALENT-type molecules may likewise be constructed incorporating alternative Linkers and/or alternative Heterodimer-Promoting Domains.

Additional, exemplary molecules capable of mediating the redirected killing of a cell expressing a Disease Antigen (e.g., a tumor cell) which may be used in the methods of the present invention include trivalent molecules capable of binding: B7-H3, CD3 and CD8 (see, e.g., WO 2015/184203); 5T4, CD3 and CD8 (see, e.g., WO 2015/184203); ROR1, CD3 and CD8 (see, e.g., WO 2015/184203 and WO 2017/106061); HIV, CD3 and CD8 (see, e.g., WO 2015/184203; WO2017/011413; and WO2017/011414); gpA33, CD3 and DR5 (see, e.g., WO 2015/184207); EphA2, CD3 and DR5 (see, e.g., WO 2015/184207); gpA33, CD3 and EphA2 (see, e.g., WO 2015/184207); and other trivalent molecules (see, e.g., WO 2016/105450; WO 2016/115274; WO 2017/180913). As will be recognized in view of the instant disclosure, the vCD3-Binding Domains of the instant invention may be incorporated into such molecules.

VIII. Methods of Production

The molecules of the present invention are most preferably produced through the recombinant expression of nucleic acid molecules that encode such polypeptides, as is well-known in the art.

Polypeptides of the invention may be conveniently prepared using solid-phase peptide synthesis (Merrifield, B. (1986) "*Solid Phase Synthesis,*" Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids,*" Proc. Natl. Acad. Sci. (U.S.A.) 82(15):5131-5135; Ganesan, A. (2006) "*Solid-Phase Synthesis In The Twenty-First Century,*" Mini Rev. Med. Chem. 6(1):3-10).

Antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "*Production Of Antibodies And Antibody Fragments In Plants,*" Vaccine 19:2756; Lonberg, N. et al. (1995) "*Human Antibodies From Transgenic Mice,*" Int. Rev. Immunol 13:65-93; and Pollock et al. (1999) "*Transgenic Milk As A Method For The Production Of Recombinant Antibodies,*" J. Immunol. Methods 231:147-157). Suitable methods for making derivatives of antibodies, e.g., humanized, single-chain, etc. are known in the art, and have been described above. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology,*" Annu. Rev. Immunol. 12.433-455).

Vectors containing polynucleotides of interest (e.g., polynucleotides encoding the polypeptide chains of the Binding Molecules of the present invention) can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of expressing a polypeptide or protein of interest. Non-limiting examples of suitable mammalian host cells include but are not limited to COS, HeLa, and CHO cells.

The invention includes polypeptides comprising an amino acid sequence of a binding molecule of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available.

The invention includes variants of the disclosed Binding Molecules, including functionally equivalent polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

In one embodiment, a fusion polypeptide is provided that comprises a Light Chain, a Heavy Chain or both a Light and Heavy Chain. In another embodiment, the fusion polypeptide contains a heterologous immunoglobulin constant region. In another embodiment, the fusion polypeptide contains a VH and a VL Domain of an antibody produced from a publicly-deposited hybridoma. For purposes of this invention, an antibody fusion protein contains one or more polypeptide domains that specifically bind CD3, or to both CD3 and to a Disease Antigen, and which contains another amino acid sequence to which it is not attached in the native molecule, for example, a heterologous sequence or a homologous sequence from another region.

The present invention particularly encompasses such Binding Molecules (e.g., antibodies, diabodies, trivalent Binding Molecules, etc.) conjugated to a diagnostic or therapeutic moiety. For diagnostic purposes, the Binding Molecules of the invention may be coupled to a detectable substance. Such Binding Molecules are useful for monitoring and/or prognosing the development or progression of a disease as part of a clinical testing procedure, such as determining the efficacy of a particular therapy. Examples of detectable substances include various enzymes (e.g., horseradish peroxidase, beta-galactosidase, etc.), prosthetic groups (e.g., avidin/biotin), fluorescent materials (e.g., umbelliferone, fluorescein, or phycoerythrin), luminescent materials (e.g., luminol), bioluminescent materials (e.g., luciferase or aequorin), radioactive materials (e.g., carbon-14, manganese-54, strontium-85 or zinc-65), positron emitting metals, and nonradioactive paramagnetic metal ions. The detectable substance may be coupled or conjugated either directly to the binding molecule or indirectly, through an intermediate (e.g., a Linker) using techniques known in the art.

For therapeutic purposes, the Binding Molecules of the invention may be conjugated to a therapeutic moiety such as a cytotoxin, (e.g., a cytostatic or cytocidal agent), a therapeutic agent or a radioactive metal ion, e.g., alpha-emitters. A cytotoxin or cytotoxic agent includes any agent that is detrimental to cells such as, for example, Pseudomonas exotoxin, Diptheria toxin, a botulinum toxin A through F, ricin abrin, saporin, and cytotoxic fragments of such agents. A therapeutic agent includes any agent having a therapeutic effect to prophylactically or therapeutically treat a disorder. Such therapeutic agents may be may be chemical therapeutic agents, protein or polypeptide therapeutic agents, and include therapeutic agents that possess a desired biological activity and/or modify a given biological response. Examples of therapeutic agents include alkylating agents, angiogenesis inhibitors, anti-mitotic agents, hormone therapy agents, and antibodies useful for the treatment of cell proliferative disorders. The therapeutic moiety may be coupled or conjugated either directly to the binding molecule or indirectly, through an intermediate (e.g., a Linker) using techniques known in the art.

IX. Uses of the Binding Molecules of the Present Invention

As discussed above, molecules capable of binding CD3 and a Disease Antigen are capable of mediating the redirected cell killing of a target cell (i.e., a cancer cell, or a pathogen-infected cell) that expresses such Disease Antigen on its cell surface. Such molecules may be used for therapeutic purposes, for example in subjects with cancer or an infection. Thus, Binding Molecules of the present invention have the ability to treat any disease or condition associated with or characterized by the expression of a Disease Antigen, particularly a Cancer Antigen or a Pathogen-Associated Antigen, on the surface of such target cell. Thus, without limitation, the Binding Molecules of the present invention may be employed in the treatment of cancer, particularly a cancer characterized by the expression of a Cancer Antigen. The Binding Molecules of the present invention may be employed in the treatment of infection, particularly an infection characterized by the expression of a Pathogen-Associated Antigen.

In particular, the present invention encompasses such methods wherein the molecule capable of binding CD3 comprises an Epitope-Binding Domain of an antibody that is capable of binding CD3 and also comprises an Epitope-Binding Domain capable of binding a Disease Antigen (in particular a Cancer Antigen or a Pathogen-Associated Antigen) on the surface of a target cell so as to mediate the redirected killing of the target cell (for example, by mediating redirected cell killing (e.g., redirected T-cell cytotoxicity)).

In a specific embodiment, the molecule capable of binding CD3 and the Disease Antigen is a bispecific antibody, or a molecule comprising the Epitope-Binding Domains thereof, (including a bispecific scFv a BiTe, a TandAb).

In a specific embodiment, the molecule capable of binding CD3 and the Disease Antigen is a bispecific diabody.

In a specific embodiment, the molecule capable of binding CD3 and the Disease Antigen is a trivalent binding molecule.

"Providing a therapy" or "treating" refers to any administration of a composition that is associated with any indicia of beneficial or desired result, including, without limitation, any clinical result such as decreasing symptoms resulting from the disease, attenuating a symptom of infection (e.g., viral load, fever, pain, sepsis, etc.) a shrinking of the size of a tumor (in the cancer context, for example, a tumor of breast, gastric or prostate cancer), a retardation of cancer cell growth, a delaying of the onset, development or progression of metastasis, a decreasing of a symptom resulting from the disease, an increasing of the quality of life of the recipient subject, a decreasing of the dose of other medications being provided to treat a subject's disease, an enhancing of the effect of another medication such as via targeting and/or internalization, a delaying of the progression of the disease, and/or a prolonging of the survival of recipient subject.

Subjects for treatment include animals, most preferably mammalian species such as non-primate (e.g., bovine, equine, feline, canine, rodent, etc.) or a primate (e.g., monkey such as, a cynomolgus monkey, human, etc.). In a preferred embodiment, the subject is a human.

Exemplary disorders that may be treated by various embodiments of the present invention include, but are not limited to, proliferative disorders, cell proliferative disorders, and cancer (especially a cancer expressing a Cancer Antigen bound by a molecule capable of mediating redirected cell killing), pathogen-associated diseases (especially a chronic viral infection associated with expression of a Pathogen-Associated Antigen bound by a molecule capable of mediating redirected cell killing). In various embodiments, the invention encompasses methods and compositions for treatment, prevention or management of a disease or disorder in a subject, comprising administering to the subject a therapeutically effective amount the Binding Molecules of the present invention. Such molecules are particularly useful for the prevention, inhibition, reduction of growth, or regression of primary tumors, and metastasis of tumors, and for reducing pathogen load, or eliminating pathogen-infected cells. Although not intending to be bound by a particular mechanism of action, such molecules may mediate effector function against target cells, promote the activation of the immune system against target cells, cross-link cell surface antigens and/or receptors on target cells and enhance apoptosis or negative growth regulatory signaling, or a combination thereof, resulting in clearance and/or reduction in the number of target cells.

The cancers that may be treated by molecules of the present invention, and by the methods of the present invention, include, but are not limited to: adrenal cancer, bladder cancer, breast cancer, colorectal cancer, gastric cancer, glioblastoma, kidney cancer, non-small-cell lung cancer, hematological cancer, multiple myeloma, melanoma, ovarian cancer, pancreatic cancer, prostate cancer, skin cancer, renal cell carcinoma, testicular cancer, and uterine cancer.

In particular, the CD19×CD3 Binding Molecules, CD19×CD3×CD8 Binding Molecules, CD123×CD3 Binding Molecules and CD123×CD3×CD8 Binding Molecules of the present invention may be used in the treatment of a hematological cancer including but not limited to: acute myeloid leukemia (AML), chronic myelogenous leukemia (CML), myelodysplastic syndrome (MDS), acute B lymphoblastic leukemia (B-ALL), chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin's lymphoma (NHL), including mantle cell lymphoma (MCL) and small lymphocytic lymphoma (SLL), Hodgkin's lymphoma, systemic mastocytosis, and Burkitt's lymphoma.

Pathogen-associated diseases that may be treated by the LAG-3-Binding Molecules of the present invention include chronic viral, bacterial, fungal and parasitic infections. Chronic infections that may be treated by the LAG-3-Binding Molecules of the present invention include Epstein-Barr Virus, Hepatitis A Virus (HAV); Hepatitis B Virus (HBV); Hepatitis C Virus (HCV); herpes viruses (e.g. HSV-1, HSV-2, HHV-6, CMV), Human Immunodeficiency Virus (HIV), Vesicular Stomatitis Virus (VSV), *Bacilli, Citrobacter, Cholera, Diphtheria, Enterobacter, Gonococci, Helicobacter pylori, Klebsiella, Legionella, Meningococci*, mycobacteria, *Pseudomonas, Pneumonococci*, rickettsia bacteria, *Salmonella, Serratia, Staphylococci, Streptococci, Tetanus, Aspergillus (fumigatus, niger*, etc.), *Blastomyces dermatitidis, Candida (albicans, krusei, glabrata, tropicalis*, etc.), *Cryptococcus neoformans*, Genus *Mucorales (mucor, absidia, rhizopus), Sporothrix schenkii, Paracoccidioides brasiliensis, Coccidioides immitis, Histoplasma capsulatum, Leptospirosis, Borrelia burgdorferi*, helminth parasite (hookworm, tapeworms, flukes, flatworms (e.g. *Schistosomia), Giardia lambia, trichinella, Dientamoeba Fragilis, Trypanosoma brucei, Trypanosoma cruzi*, and *Leishmania donovani*).

X. Pharmaceutical Compositions

The present invention encompasses compositions comprising a molecule capable of binding CD3 and also capable of binding to a Disease Antigen (e.g., a DA×CD3 Binding Molecule, including, for example, a DA×CD3×CD8 Binding Molecule, a DA×CD3×DA Binding Molecule, etc.). The compositions of the invention include bulk drug compositions useful in the manufacture of pharmaceutical compositions (e.g., impure or non-sterile compositions) and pharmaceutical compositions (i.e., compositions that are suitable for administration to a subject or patient) that can be used in the preparation of unit dosage forms. Such compositions comprise a prophylactically or therapeutically effective amount of a molecule capable of binding CD3 and also capable of binding to a Disease Antigen so as to be capable of mediating the redirected killing of a target cell (e.g., a cancer cell, a pathogen-infected cell, etc.), or a combination of such agents and a pharmaceutically acceptable carrier. Preferably, compositions of the invention comprise a prophylactically or therapeutically effective amount of the Binding Molecules of the present invention and a pharmaceutically acceptable carrier. In a preferred aspect, such compositions are substantially purified (i.e., substantially free from substances that limit its effect or produce undesired side effects).

Various formulations of such compositions may be used for administration. In addition to the pharmacologically active agent(s), the compositions of the present invention may contain suitable pharmaceutically acceptable carriers comprising excipients and auxiliaries that are well-known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with a binding molecule of the present invention, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the Binding Molecules of the present invention. The kit can further comprise one or more other prophylactic and/or therapeutic agents useful for the treatment of cancer, in one or more containers.

XI. Methods of Administration

The compositions of the present invention may be provided for the treatment, prophylaxis, and amelioration of one or more symptoms associated with a disease, disorder or infection by administering to a subject an effective amount of the pharmaceutical compositions of the present invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Methods of administering a molecule or composition of the invention include, but are not limited to, parenteral administration (e.g., intradermal, intramuscular, intraperitoneal, intravenous and subcutaneous), epidural, and mucosal (e.g., intranasal and oral routes). In a specific embodiment, the Binding Molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

The invention also provides that preparations of the Binding Molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the Binding Molecules of the present invention are supplied as a dry sterile lyophilized powder in a hermetically sealed container.

The lyophilized preparations of the Binding Molecules of the present invention should be stored at between 2° C. and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such Binding Molecules, when provided in liquid form, are supplied in a hermetically sealed container.

The amount of such preparations of the invention that will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition is an amount sufficient to effect beneficial or desired results including, without limitation, clinical results such as decreasing symptoms resulting from the disease, attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals. When applied to an individual active ingredient, administered alone, the term refers to that ingredient alone. When applied to a combination, the term refers to combined amounts of the active ingredients that result in the therapeutic effect, whether administered in combination, serially, or simultaneously.

An effective amount can be administered in one or more administrations. For purposes of this invention, an effective amount of drug, compound, or pharmaceutical composition is an amount sufficient: to kill and/or reduce the proliferation of cancer cells, and/or to eliminate, reduce and/or delay the development of metastasis from a primary site of cancer; or to reduce the proliferation of (or the effect of) an infectious pathogen and to reduce and/or delay the development of the pathogen-mediated disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art.

For the Binding Molecules encompassed by the invention, the dosage administered to a patient is preferably determined based upon the body weight (kg) of the recipient subject. For the Binding Molecules encompassed by the invention, the dosage administered to a patient is typically from about 0.01 µg/kg to about 30 mg/kg or more of the subject's body weight.

The dosage and frequency of administration of a binding molecule of the present invention may be reduced or altered by enhancing uptake and tissue penetration of the molecule by modifications such as, for example, lipidation.

The dosage of a binding molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as silastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327).

Treatment of a subject with a therapeutically or prophylactically effective amount of a binding molecule of the present invention can include a single treatment or, preferably, can include a series of treatments. In a preferred example, a subject is treated with a pharmaceutical composition of the invention for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day with such administration occurring once a week, twice a week, once every two weeks, once a month, once every six weeks, once every two months, twice a year or once per year, etc. Alternatively, the pharmaceutical compositions of the invention can be administered twice a day with such administration occurring once a week, twice a week, once every two weeks, once a month, once every six weeks, once every two months, twice a year or once per year, etc. Alternatively, the pharmaceutical compositions of the invention can be administered three times a day with such administration occurring once a week, twice a week, once every two weeks, once a month, once every six weeks, once every two months, twice a year or once per year, etc. It will also be appreciated that the effective dosage of the molecules used for treatment may increase or decrease over the course of a particular treatment.

XII. Specific Embodiments of the Invention

Specific embodiments of the of the invention include Embodiments E1-E27:

E1. A DAxCD3 Binding Molecule comprising a CD3-Binding Domain capable of binding an epitope of CD3 and a Disease Antigen-Binding Domain capable of binding an epitope of a Disease Antigen, wherein said CD3-Binding Domain comprises:
 (I) (A) a $CDR_H1$ Domain comprising an amino acid sequence selected from the group consisting of SEQ ID NO:99, SEQ ID NO:91, SEQ ID NO:93, SEQ ID NO:95 and SEQ ID NO:97;
   (B) a $CDR_H2$ Domain comprising the amino acid sequence of SEQ ID NO:58;
   (C) a $CDR_H3$ Domain comprising the amino acid sequence of SEQ ID NO:59;
   (D) a $CDR_L1$ Domain comprising the amino acid sequence of SEQ ID NO:60;
   (E) a $CDR_L2$ Domain comprising the amino acid sequence of SEQ ID NO:61; and
   (F) a $CDR_L3$ Domain comprising the amino acid sequence of SEQ ID NO:62; or
 (II) (A) a $CDR_H1$ Domain comprising the amino acid sequence of SEQ ID NO:57;
   (B) a $CDR_H2$ Domain comprising the amino acid sequence of SEQ ID NO:58;
   (C) a $CDR_H3$ Domain comprising an amino acid sequence selected from the group consisting of SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:101, SEQ ID NO:103, SEQ ID NO:105 and SEQ ID NO:107;
   (D) a $CDR_L1$ Domain comprising the amino acid sequence of SEQ ID NO:60;
   (E) a $CDR_L2$ Domain comprising the amino acid sequence of SEQ ID NO:61; and
   (F) a $CDR_L3$ Domain comprising the amino acid sequence of SEQ ID NO:62; or
 (III) (A) a $CDR_H1$ Domain comprising the amino acid sequence of SEQ ID NO:57;
   (B) a $CDR_H2$ Domain comprising the amino acid sequence of SEQ ID NO:58;
   (C) a $CDR_H3$ Domain comprising the amino acid sequence of SEQ ID NO:59;
   (D) a $CDR_L1$ Domain comprising the amino acid sequence of SEQ ID NO:60;
   (E) a $CDR_L2$ Domain comprising the amino acid sequence of SEQ ID NO:61; and
   (F) a $CDR_L3$ Domain comprising an amino acid sequence selected from the group consisting of SEQ ID NO:109 or SEQ ID NO:111; or
 (IV) (A) a $CDR_H1$ Domain comprising the amino acid sequence of SEQ ID NO:57;
   (B) a $CDR_H2$ Domain comprising the amino acid sequence of SEQ ID NO:58;
   (C) a $CDR_H3$ Domain comprising the amino acid sequence of SEQ ID NO:59;
   (D) a $CDR_L1$ Domain comprising the amino acid sequence of SEQ ID NO:60;
   (E) a $CDR_L2$ Domain comprising an amino acid sequence selected from the group consisting of SEQ ID NO:113 and SEQ ID NO:115; and
   (F) a $CDR_L3$ Domain comprising the amino acid sequence of SEQ ID NO:62.

E2. The DAxCD3 Binding Molecule of E1, wherein said CD3-Binding Domain comprises:
 (I) (A) a VL Domain comprising the amino acid sequence of SEQ ID NO:56;
   (B) a VH Domain comprising an amino acid sequence selected from the group consisting of SEQ ID NO:98, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO: 92, SEQ ID NO:94, SEQ ID NO:96, SEQ ID NO:100, SEQ ID NO:102, SEQ ID NO:104 and SEQ ID NO:106; or
 (II) (A) a VL Domain comprising an amino acid sequence selected from the group consisting of SEQ ID NO:108, SEQ ID NO:110, SEQ ID NO:112; and SEQ ID NO:114;
   (B) a VH Domain comprising an amino acid sequence of SEQ ID NO:55.

E3. The DAxCD3 Binding Molecule of E1 or E2, wherein said DAxCD3 Binding Molecule is a bispecific antibody, a bispecific diabody, a bispecific scFv, a bispecific TandAb, or a trivalent binding molecule.

E4. The DAxCD3 Binding Molecule of any one of E1-E3, wherein said DAxCD3 Binding Molecule is capable of binding more than one Disease Antigen and/or a different cell surface molecule of an effector cell.

E5. The DAxCD3 Binding Molecule of any one of E1-E4, wherein said Disease Antigen is a Cancer Antigen.

E6. The DAxCD3 Binding Molecule of any one of E1-E4, wherein said Disease Antigen is a Pathogen-Associated Antigen.

E7. The DAxCD3 Binding Molecule, of any one of E4-E6, wherein said different cell surface molecule of an effector cell is CD2, CD8, CD16, TCR, NKp46, or NKG2D.

E8. The DAxCD3 Binding Molecule of E5 or E7, wherein said Cancer Antigen is selected from the group consisting of the Cancer Antigens: 19.9, 4.2, ADAM-9, AH6, ALCAM, B1, B7-H3, BAGE, beta-catenin, blood group $ALe^b/Le^y$, Burkitt's lymphoma antigen-38.13, C14, CA125, Carboxypeptidase M, CD5, CD19, CD20, CD22, CD23, CD25, CD27, CD28, CD33, CD36, CD40/CD154, CD45, CD56, CD46, CD52, CD56, CD79a/CD79b, CD103, CD123, CD317, CDK4, CEA, CEACAM5/CEACAM6, C017-1A, CO-43, CO-514, CTA-1, CTLA-4, Cytokeratin 8, D1.1, $D_1$56-22, DR5, $E_1$ series, EGFR, an Ephrin receptor, EphA2, Erb, GAGE, a GD2/GD3/GM2 ganglioside, GICA 19-9, gp100, Gp37, gp75, gpA33, HER2/neu, HMFG, Human Papillomavirus-E6/

Human Papillomavirus-E7, HMW-MAA, I antigen, IL13Rα2, Integrin β6, JAM-3, KID3, KID31, KS 1/4 pan-carcinoma antigen, L6, L20, LEA, LUCA-2, M1:22:25:8, M18, M39, MAGE, MART, mesothelin, MUC-1, MUM-1, Myl, N-acetylglucosaminyltransferase, neoglycoprotein, NS-10, OFA-1, OFA-2, Oncostatin M, p15, p97, PEM, PEMA, PIPA, PSA, PSMA, prostatic acid phosphate, R24, ROR1, a sphingolipid, SSEA-1, SSEA-3, SSEA-4, sTn, the T-cell receptor derived peptide, $T_5A_7$, TAG-72, TL5, TNF-receptor, TNF-γ receptor, TRA-1-85, a Transferrin Receptor, 5T4, TSTA, VEGF, a VEGF Receptor, VEP8, VEP9, VIM-D5, and Y hapten, Le$^y$.

E9. The DAxCD3 Binding Molecule of E8, wherein said Disease Antigen is B7-H3, CEACAM5/CEACAM6, EGRF, EphA2, gpA33, HER2/neu, VEGF, 5T4, IL13Rα2, CD123, CD19, or ROR1.

E10. The DAxCD3 Binding Molecule of E6 or E7, wherein said Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, Human Papillomavirus E6, Human Papillomavirus E7, human T-cell leukemia virus gp64, human T-cell leukemia virus gp46, and human T-cell leukemia virus gp21.

E11. The DAxCD3 Binding Molecule of any one of E1-E10, wherein said DAxCD3 Binding Molecule comprises: a first polypeptide chain and a second polypeptide chain, covalently bonded to one another, wherein:
(A) the first polypeptide chain comprises, in the N-terminal to C-terminal direction:
  (i) a Domain 1, comprising:
    (1) a sub-Domain (1A), which comprises a VL Domain of a monoclonal antibody capable of binding to said epitope of a Disease Antigen (VL$_{DA}$); and
    (2) a sub-Domain (1B), which comprises a VH Domain of a monoclonal antibody capable of binding to said epitope of CD3 (VH$_{CD3}$);
    wherein said sub-Domains 1A and 1B are separated from one another by a peptide Linker; and
  (ii) a Domain 2, wherein said Domain 2 is a Heterodimer-Promoting Domain;
(B) the second polypeptide chain comprises, in the N-terminal to C-terminal direction:
  (i) a Domain 1, comprising:
    (1) a sub-Domain (1A), which comprises a VL Domain of said monoclonal antibody capable of binding to said epitope of CD3 (VL$_{CD3}$); and
    (2) a sub-Domain (1B), which comprises a VH Domain of said monoclonal antibody capable of binding to said epitope of a Disease Antigen (VH$_{DA}$);
    wherein said sub-Domains 1A and 1B are separated from one another by a peptide Linker;
  (ii) a Domain 2, wherein said Domain 2 is a Heterodimer-Promoting Domain, wherein said Heterodimer-Promoting Domain of said first and said second polypeptide chains are different;
and wherein:
(a) the VL Domain of the first polypeptide chain and the VH Domain of the second polypeptide chain associate to form the Disease Antigen-Binding Domain, and the VH Domain of the first polypeptide chain and the VL Domain of the second polypeptide chain associate to form the CD3-Binding Domain; or
(b) the VL Domain of the first polypeptide chain and the VH Domain of the second polypeptide chain associate to form the CD3-Binding Domain, and the VH Domain of the first polypeptide chain and the VL Domain of the second polypeptide chain associate to form the Disease Antigen-Binding Domain.

E12. The DAxCD3 Binding Molecule of E11, wherein:
(a) said Heterodimer-Promoting Domain of said first polypeptide chain is an E-coil Domain, and said Heterodimer-Promoting Domain of said second polypeptide chain is a K-coil Domain; or
(b) said Heterodimer-Promoting Domain of said first polypeptide chain is a K-coil Domain, and said Heterodimer-Promoting Domain of said second polypeptide chain is an E-coil Domain.

E13. The DAxCD3 Binding Molecule of E11 or E12, wherein the first or second polypeptide chain additionally comprises a Domain 3 comprising a CH2 and CH3 Domain of an immunoglobulin Fc Domain.

E14. The DAxCD3 Binding Molecule of E13, wherein said DAxCD3 Binding Molecule further comprises a third polypeptide chain comprising a CH2 and CH3 Domain of an immunoglobulin Fc Domain.

E15. The DAxCD3 Binding Molecule of any one of E11-E14, wherein said DAxCD3 Binding Molecule further comprises a CD8-Binding Domain.

E16. The DAxCD3 Binding Molecule of any one of E11-E15, wherein said DAxCD3 Binding Molecule comprises:
(I) (A) a first polypeptide comprising SEQ ID NO:179;
(B) a second polypeptide comprising SEQ ID NO:175; and
(C) a third polypeptide comprising SEQ ID NO:176; or
(II) (A) a first polypeptide comprising SEQ ID NO:184;
(B) a second polypeptide comprising SEQ ID NO:181; and
(C) a third polypeptide comprising SEQ ID NO:176; or
(III) (A) a first polypeptide comprising SEQ ID NO:196;
(B) a second polypeptide comprising SEQ ID NO:186; and
(C) a third polypeptide comprising SEQ ID NO:176; or
(IV) (A) a first polypeptide comprising SEQ ID NO:197;
(B) a second polypeptide comprising SEQ ID NO:192; and
(C) a third polypeptide comprising SEQ ID NO:176; or
(V) (A) a first polypeptide comprising SEQ ID NO:193;
(B) a second polypeptide comprising SEQ ID NO:194; and
(C) a third polypeptide comprising SEQ ID NO:176; or
(VI) (A) a first polypeptide comprising SEQ ID NO:179;
(B) a second polypeptide comprising SEQ ID NO:175;
(C) a third polypeptide comprising SEQ ID NO:187; and
(D) a fourth polypeptide comprising SEQ ID NO:188; or
(VII) (A) a first polypeptide comprising SEQ ID NO:184;
(B) a second polypeptide comprising SEQ ID NO:181;
(C) a third polypeptide comprising SEQ ID NO:187; and
(D) a fourth polypeptide comprising SEQ ID NO:188; or
(VIII) (A) a first polypeptide comprising SEQ ID NO:196;
(B) a second polypeptide comprising SEQ ID NO:186;
(C) a third polypeptide comprising SEQ ID NO:187; and
(D) a fourth polypeptide comprising SEQ ID NO:188; or
(IX) (A) a first polypeptide comprising SEQ ID NO:193;
(B) a second polypeptide comprising SEQ ID NO:194;
(C) a third polypeptide comprising SEQ ID NO:187; and (D) a fourth polypeptide comprising SEQ ID NO:188.

E17. A pharmaceutical composition that comprises the DA×CD3 Binding Molecule of any of E1-E16 and a pharmaceutically acceptable carrier.

E18. A method for the treatment of a disease, comprising administering to a subject in need thereof a therapeutically effective amount of the DA×CD3 Binding Molecule of any of E1-E16 or the pharmaceutical composition of E17.

E19. The method of E18, wherein said disease is cancer.

E20. The method of E19, wherein said cancer is selected from the group consisting of adrenal cancer, bladder cancer, breast cancer, colorectal cancer, gastric cancer, glioblastoma, kidney cancer, non-small-cell lung cancer, hematological cancer, multiple myeloma, melanoma, ovarian cancer, pancreatic cancer, prostate cancer, skin cancer, renal cell carcinoma, testicular cancer, and uterine cancer.

E21. The method of E18, wherein said disease is a pathogen-associated disease.

E22. The method of E21, wherein said Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, Human Papillomavirus E6, Human Papillomavirus E7, human T-cell leukemia virus gp64, human T-cell leukemia virus gp46, and human T-cell leukemia virus gp21.

E23. The DA×CD3 Binding Molecule of any of E1-E16 or the pharmaceutical composition of E16 for use in the treatment of a disease.

E24. The DA×CD3 Binding Molecule or pharmaceutical composition of E23, wherein said disease is cancer.

E25. The DA×CD3 Binding Molecule or pharmaceutical composition of E24, wherein said cancer is selected from the group consisting of adrenal cancer, bladder cancer, breast cancer, colorectal cancer, gastric cancer, glioblastoma, kidney cancer, non-small-cell lung cancer, hematological cancer, multiple myeloma, melanoma, ovarian cancer, pancreatic cancer, prostate cancer, skin cancer, renal cell carcinoma, testicular cancer, and uterine cancer.

E26. The DA×CD3 Binding Molecule or pharmaceutical composition of E23, wherein said disease is a pathogen-associated disease.

E27. The DA×CD3 Binding Molecule or pharmaceutical composition of E26, wherein said Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, Human Papillomavirus E6, Human Papillomavirus E7, human T-cell leukemia virus gp64, human T-cell leukemia virus gp46, and human T-cell leukemia virus gp21.

EXAMPLES

Having now generally described the invention, the same will be more readily understood through reference to the following examples, which are provided by way of illustration and are not intended to be limiting of the present invention unless specified.

Example 1

Evaluation of CD3 mAb 1 M3-CD3 mAb 1 M26

A CD3 mAb 1 scFv saturation-mutant library at 29 CDR positions was constructed and expressed in *E. coli* (XL-1 Blue). A multi-well format was used to produce soluble scFv. scFv-containing supernatants were captured on anti-His surface and screened for binding to recombinant CD3 (Ely chain Fos/Jun heterodimer) using an Attana biosensor to identify vCD3-Binding Domains.

Variants of the CD123×CD3 DART-A-type diabody (designated DART-A-WT; amino acid sequences provided above) were generated comprising the VH and VL Domains of the identified scFvs. Thus, a panel of DART-A-type diabodies, designated DART-A-M1-DART-A-M26, comprising vCD3-Binding Domains (such vCD3-Binding Domains being respectively designated "CD3 mAb 1 M1-CD3 mAb 1 M26") were generated. The CD3-binding kinetics of DART-A-M1-DART-A-M26 were measured by BIACORE® and compared to DART-A-WT. Table 11 summarizes the CD3-binding kinetics of DART-A-WT and the DART-A-type diabodies comprising the vCD3-Binding Domains of CD3 mAb 1 M1-CD3 mAb 1 M26, ranked by $k_a$ (R denotes $k_a$, $k_d$, or $k_D$ ratio of variant DART-A-type diabody (comprising a vCD3-Binding Domain) to DART-A-WT (comprising the rCD3-Binding Domain of CD3 mAb 1)).

TABLE 11

CD3-Binding Kinetics of CD123 × CD3 DART-A-Type Diabodies CD3 mAb 1 M1 -- CD3 mAb 1 M26

| CD3 mAb1 Variant | Substitution (Relative to CD3 Mab-1) | ka ($M^{-1}s^{-1}$) | R | kd ($s^{-1}$) | R | KD (M) | R |
|---|---|---|---|---|---|---|---|
| M25 | G50D/VL | $1.54 \times 10^5$ | 0.3 | $1.92 \times 10^{-2}$ | 4.7 | $1.25 \times 10^{-7}$ | 15 |
| M18 | A33G/VH | $2.87 \times 10^5$ | 0.6 | $5.88 \times 10^{-2}$ | 14 | $2.05 \times 10^{-7}$ | 25 |
| M14 | T31D/VH | $3.08 \times 10^5$ | 0.6 | $1.43 \times 10^{-2}$ | 3.5 | $4.66 \times 10^{-8}$ | 5.7 |
| M26 | K53G/VL | $3.19 \times 10^5$ | 0.6 | $1.74 \times 10^{-2}$ | 4.3 | $5.44 \times 10^{-8}$ | 6.7 |
| M13 | Y102E/VH | $3.21 \times 10^5$ | 0.6 | $2.20 \times 10^{-2}$ | 5.4 | $6.86 \times 10^{-8}$ | 8.4 |
| M16 | Y32D/VH | $3.47 \times 10^5$ | 0.7 | $1.04 \times 10^{-1}$ | 25 | $3.01 \times 10^{-7}$ | 37 |
| M15 | T31E/VH | $3.52 \times 10^5$ | 0.7 | $3.75 \times 10^{-2}$ | 9.2 | $1.07 \times 10^{-7}$ | 13 |
| M1 | S100dT/VH | $4.08 \times 10^5$ | 0.8 | $6.50 \times 10^{-2}$ | 16 | $1.59 \times 10^{-7}$ | 19 |
| M3 | G99I/VH | $4.49 \times 10^5$ | 0.9 | $8.30 \times 10^{-3}$ | 2 | $1.85 \times 10^{-8}$ | 2.3 |
| M23 | L95E/VL | $4.59 \times 10^5$ | 0.9 | $1.24 \times 10^{-2}$ | 3 | $2.69 \times 10^{-8}$ | 3.3 |
| CD3 Mab-1 | Wild-Type | $5.00 \times 10^5$ | 1 | $4.09 \times 10^{-3}$ | 1 | $8.17 \times 10^{-9}$ | 1 |
| M24 | L95Q/VL | $5.94 \times 10^5$ | 1.2 | $8.61 \times 10^{-3}$ | 2.1 | $1.45 \times 10^{-8}$ | 1.8 |
| M6 | Y100bQ/VH | $6.99 \times 10^5$ | 1.4 | $2.01 \times 10^{-2}$ | 4.9 | $2.88 \times 10^{-8}$ | 3.5 |

TABLE 11-continued

CD3-Binding Kinetics of CD123 × CD3 DART-
A-Type Diabodies CD3 mAb 1 M1 -- CD3 mAb 1 M26

| CD3 mAb1 Variant | Substitution (Relative to CD3 Mab-1) | ka $(M^{-1}s^{-1})$ | R | kd $(s^{-1})$ | R | KD (M) | R |
|---|---|---|---|---|---|---|---|
| M10 | F98I/VH | $7.17 \times 10^5$ | 1.4 | $3.10 \times 10^{-2}$ | 7.6 | $4.33 \times 10^{-8}$ | 5.3 |
| M19 | G96K/F98I/VH | $7.53 \times 10^5$ | 1.5 | $4.11 \times 10^{-2}$ | 10 | $5.46 \times 10^{-8}$ | 6.7 |
| M4 | Y100bA/VH | $7.90 \times 10^5$ | 1.6 | $2.03 \times 10^{-2}$ | 5 | $2.57 \times 10^{-8}$ | 3.1 |
| M17 | Y32T/VH | $8.37 \times 10^5$ | 1.7 | $4.78 \times 10^{-2}$ | 12 | $5.72 \times 10^{-8}$ | 7 |
| M12 | W100eY/VH | $8.66 \times 10^5$ | 1.7 | $1.11 \times 10^{-2}$ | 2.7 | $1.28 \times 10^{-8}$ | 1.6 |
| M7 | G96D/VH | $1.02 \times 10^6$ | 2 | $2.29 \times 10^{-2}$ | 5.6 | $2.25 \times 10^{-8}$ | 2.8 |
| M8 | G96E/VH | $1.13 \times 10^6$ | 2.3 | $7.84 \times 10^{-3}$ | 1.9 | $6.91 \times 10^{-9}$ | 0.8 |
| M5 | Y100bG/VH | $1.31 \times 10^6$ | 2.6 | $2.80 \times 10^{-2}$ | 6.8 | $2.14 \times 10^{-8}$ | 2.6 |
| M11 | W100eF/VH | $1.39 \times 10^6$ | 2.8 | $2.67 \times 10^{-2}$ | 6.5 | $1.92 \times 10^{-8}$ | 2.4 |
| M9 | G96K/VH | $2.15 \times 10^6$ | 4.3 | $7.16 \times 10^{-3}$ | 1.8 | $3.33 \times 10^{-9}$ | 0.4 |
| M22 | G96K/W100eY/VH | $2.37 \times 10^6$ | 4.7 | $1.56 \times 10^{-2}$ | 3.8 | $6.60 \times 10^{-9}$ | 0.8 |
| M21 | G96K/W100eF/VH | $2.45 \times 10^6$ | 4.9 | $1.03 \times 10^{-2}$ | 2.5 | $4.18 \times 10^{-9}$ | 0.5 |
| M2 | G96K/S100dT/VH | $3.07 \times 10^6$ | 6.1 | $3.91 \times 10^{-2}$ | 9.6 | $1.27 \times 10^{-8}$ | 1.6 |
| M20 | G96K/Y100bG/VH | $3.87 \times 10^6$ | 7.7 | $7.32 \times 10^{-2}$ | 18 | $1.89 \times 10^{-8}$ | 2.3 |

Figure 7A:
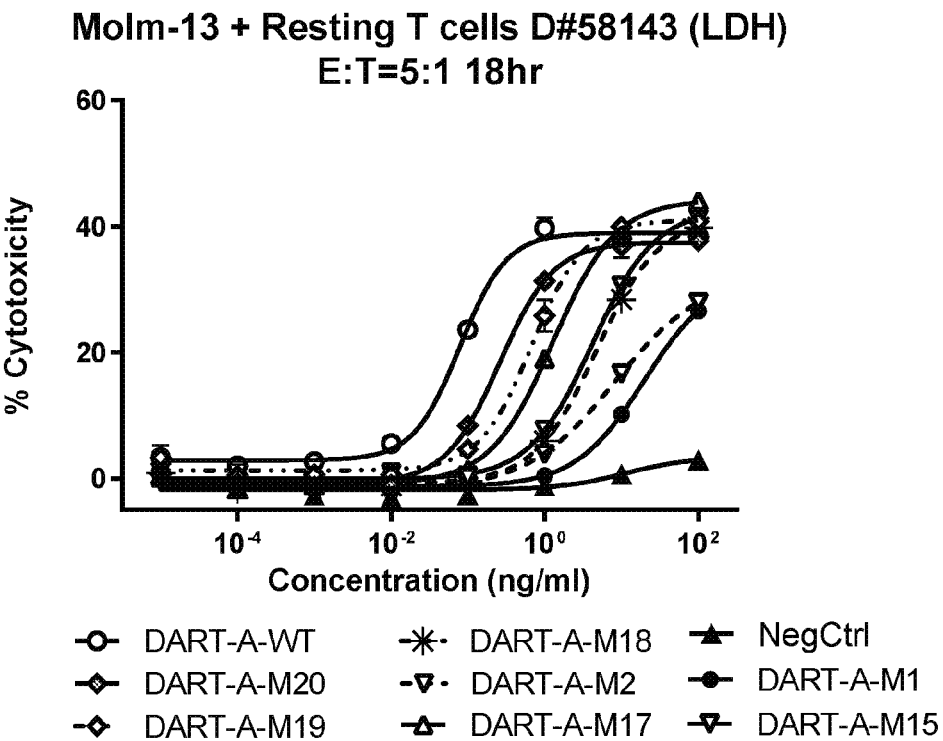
FIG. 7A-7D show the results of CTL and binding assays.
Figure 7B:
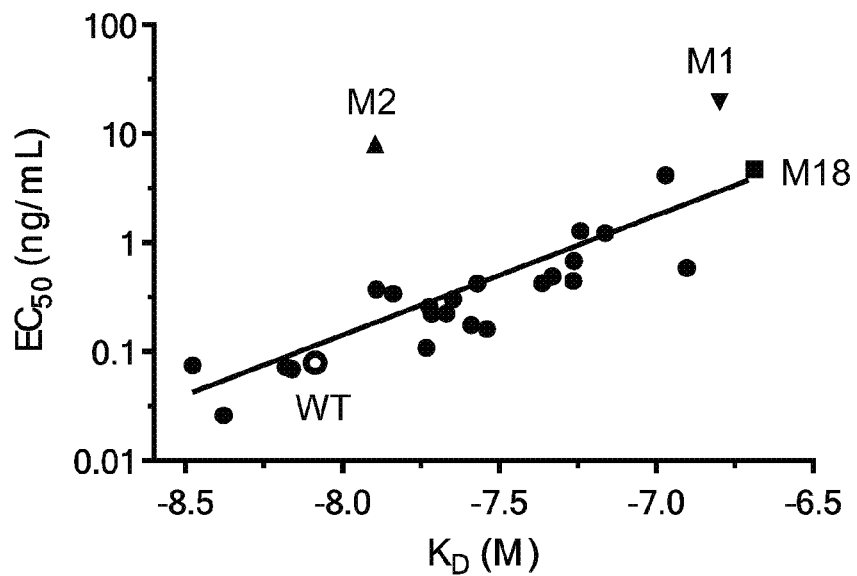
Figure 7C:
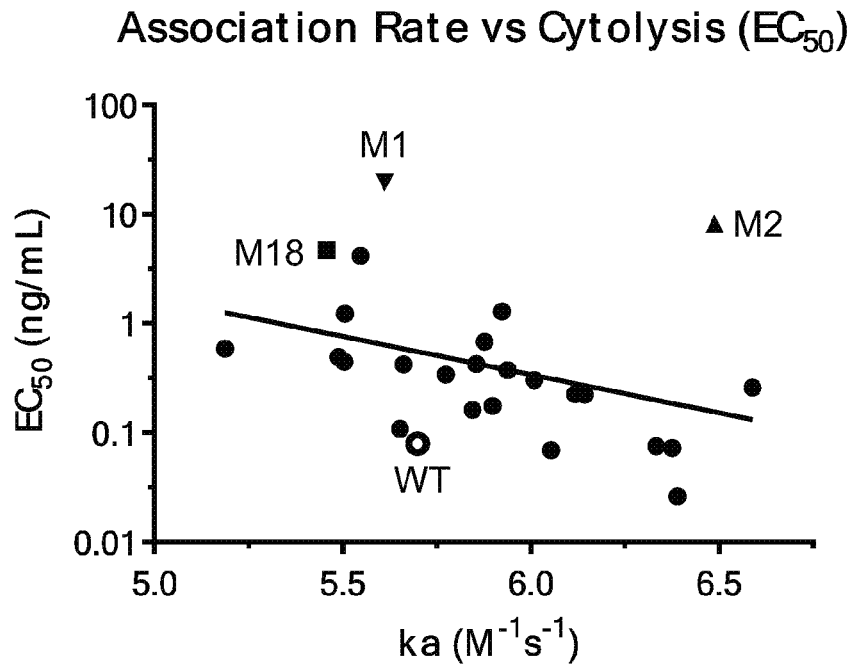
Figure 7D:
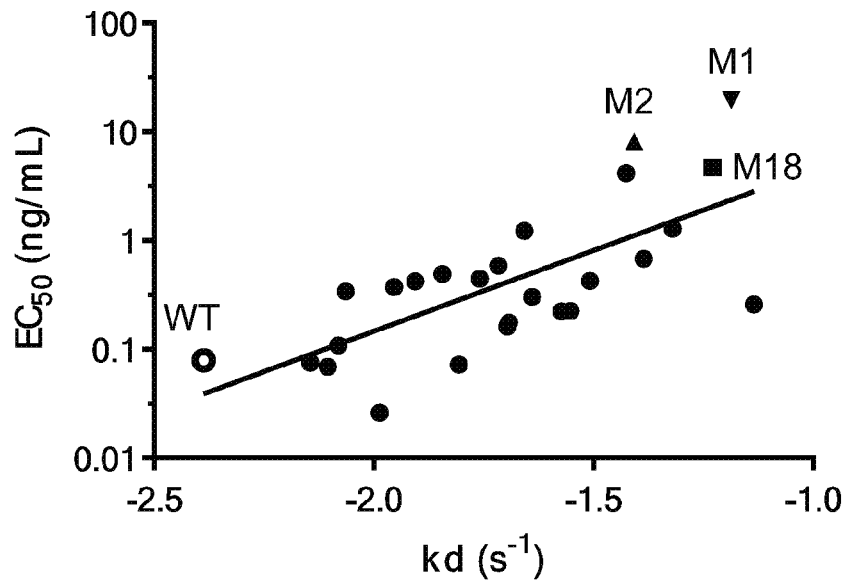

The ability of DART-A-M1-DART-A-M26 (comprising vCD3-Binding Domains) to mediate T-cell redirected cell killing was measured in CTL assay and compared to DART-A-WT (comprising the rCD3-Binding Domain). Briefly, the DART-A-type diabodies were incubated with effector Pan-T-cells and MOLM-13 target tumor cells, at an effector:target cell ratio of 5:1 for 18 and 42 hours and the $EC_{50}$ was determined by measuring the release of lactate dehydrogenase (LDH) into the media by damaged cells (e.g., by using the CytoTox 96® Non-Radioactive Cytotoxicity Assay Kit (Promega) that quantitatively measures LDH release, or similar). A 4420×CD3 fluorescein-binding DART-A-type diabody having the CD3 Binding Domain of CD3 mAb 1 was employed as a negative control. In addition, the stability of the DART-A-type diabodies was evaluated by measuring the Tm using DSF. Representative cytotoxicity curves for DART-A-WT; DART-A-M1; DART-A-M2; DART-A-M15; DART-A-M17; DART-A-M18; DART-A-M19; and DART-A-M20 are presented in FIG. 7A. Table 12 summarizes the cytotoxicity (i.e., T-cell redirected killing activity) of DART-A-M1-DART-A-M26, ranked by 18-hour $EC_{50}$ (R denotes ratio of variant DART-A-type diabody (comprising a vCD3-Binding domain) to DART-A-WT (comprising the rCD3-Binding Domain of CD3 mAb 1); ΔTm denotes change in Tm as compared to WT (Tm=63° C.). The relationship of the kinetic parameters and cytolytic potency is plotted in FIGS. 7B-7D (FIG. 7B: affinity vs cytolysis (18 hour EC50), FIG. 7C: association rate vs cytolysis (EC50). FIG. 7C: dissociation rate vs cytolysis (EC50)). The CD3 mAb1 (○), M18 (■), M2 (▲) and M1 (▼) variants are indicated.

TABLE 12

Cytotoxicity Of Antibodies CD3 mAb 1 M1 - CD3 mAb 1 M26

| | | MOLM-13 (E:T = 5:1) | | | | | | |
|---|---|---|---|---|---|---|---|---|
| CD3 mAb 1 Variant | Substitution (Relative to CD3 Mab-1) | $EC_{50}$ (ng/mL) 18 Hour | R | max % CytoTox | $EC_{50}$ (ng/mL) 42 Hour | R | max % CytoTox | R ΔTm (° C.) |
| M21 | G96K/W100eF/VH | 0.026 | 0.3 | 36.54 | 0 | 0 | 29.92 | -1 |
| M8 | G96E/VH | 0.069 | 0.9 | 38.43 | 0.005 | 1.7 | 29.35 | 1 |
| M22 | G96K/W100eY/VH | 0.072 | 0.9 | 38.26 | 0.01 | 3.5 | 31.58 | -0.5 |
| M9 | G96K/VH | 0.075 | 1 | 38.25 | 0.001 | 0.4 | 30.46 | 0 |
| CD3 Mab-1 | Wild-Type | 0.079 | 1 | 38.97 | 0.003 | 1 | 29.13 | — |
| M3 | G99I/VH | 0.108 | 1.4 | 39.69 | 0.006 | 2.3 | 28.58 | 0 |
| M6 | Y100bQ/VH | 0.162 | 2.1 | 41.86 | 0.011 | 3.9 | 29.46 | 1 |
| M4 | Y100bA/VH | 0.176 | 2.2 | 41.69 | 0.011 | 3.9 | 29.8 | 1 |
| M11 | W100eF/VH | 0.223 | 2.8 | 48.55 | 0.016 | 5.8 | 32.43 | 0.5 |
| M5 | Y100bG/VH | 0.225 | 2.9 | 40.75 | 0.011 | 3.8 | 28.41 | 1 |
| M20 | G96K/Y100bG/VH | 0.259 | 3.3 | 37.48 | 0.038 | 13.5 | 30.89 | -0.5 |
| M7 | G96D/VH | 0.304 | 3.8 | 41.38 | 0.03 | 10.8 | 32.54 | 1 |
| M24 | L95Q/VL | 0.34 | 4.3 | 49.41 | 0.031 | 11.1 | 31.12 | 0.5 |
| M12 | W100eY/VH | 0.372 | 4.7 | 49.72 | 0.067 | 24 | 31.54 | 0.5 |
| M23 | L95E/VL | 0.421 | 5.3 | 49.29 | 0.061 | 21.6 | 31.37 | -0.5 |
| M10 | F98I/VH | 0.426 | 5.4 | 39.26 | 0.095 | 33.7 | 29.87 | 0 |
| M26 | K53G/VL | 0.444 | 5.6 | 44.23 | 0.078 | 27.9 | 28.19 | 0 |
| M14 | T31D/VH | 0.492 | 6.2 | 44.69 | 0.11 | 39.3 | 31.36 | 1.5 |
| M25 | G50D/VL | 0.585 | 7.4 | 46.56 | 0.1 | 35.7 | 30.41 | 0 |
| M19 | G96K/F98I/VH | 0.68 | 8.6 | 41.01 | 0.11 | 39.1 | 32.83 | -0.5 |
| M13 | Y102E/VH | 1.223 | 15.5 | 45.08 | 0.203 | 72.3 | 31.48 | -0.5 |
| M17 | Y32T/VH | 1.283 | 16.2 | 44.23 | 0.126 | 44.9 | 30.69 | -0.5 |
| M15 | T31E/VH | 4.164 | 52.7 | 42.74 | 0.975 | 347.2 | 32.05 | 1.5 |
| M18 | A33G/VH | 4.687 | 59.3 | 41.3 | 0.91 | 324 | 30.58 | 0.5 |
| M2 | G96K/S100dT/VH | 8.113 | 102.7 | 32.33 | 0.693 | 246.9 | 32.77 | -1 |
| M1 | S100dT/VH | 19.64 | 248.6 | 32.32 | 2.336 | 831.9 | 32.37 | 0 |
| M16 | Y32D/VH | NA | NA | NA | NA | NA | NA | -0.5 |

As indicated in Tables 11-12, the DART-A-M1-DART-A-M26 variants displayed a range of binding kinetics and CTL activity, while retaining their thermal stability. Such DA×CD3 Binding Molecules, and their vCD3-Binding Domains, are useful for modulating CD3 binding, redirected T-cell killing activity, and/or T-cell stimulation activity.

Example 2

CTL Activity and Cytokine Release of Representative Variants

Figure 8A:
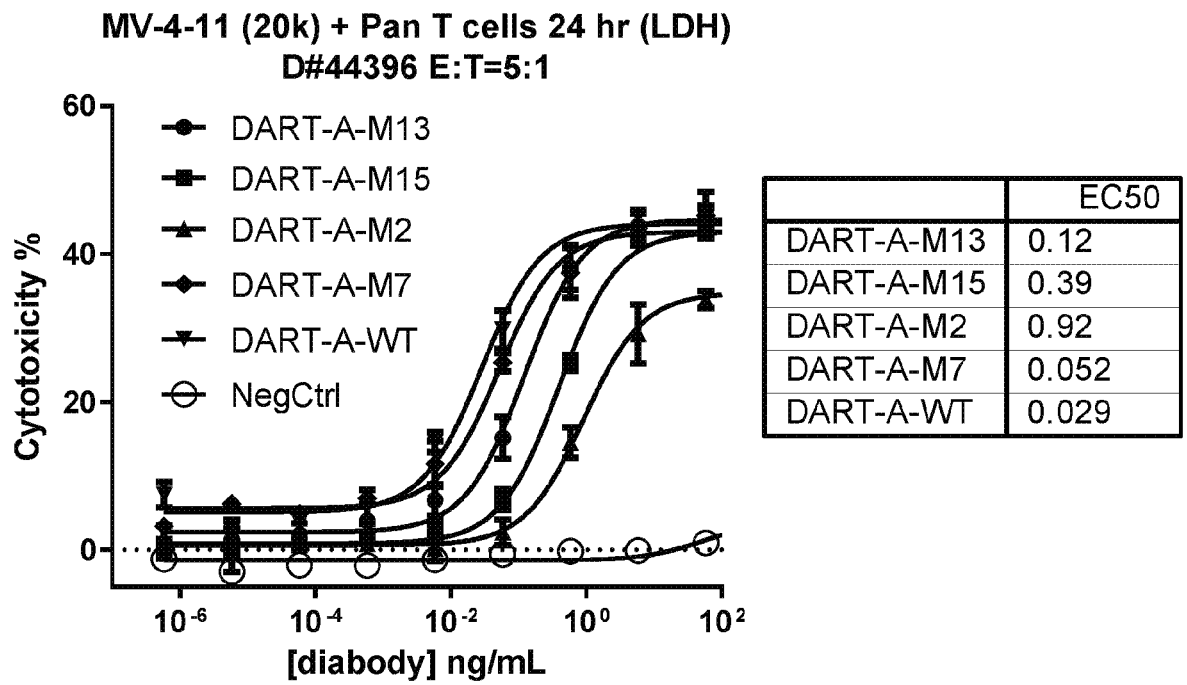
FIG. 8A-8E show the results of representative studies of redirected cell killing (CTL assay) mediated DART A-type diabody constructs containing the VL and VH Domains of CD3 mAb 1; CD3 mAb 1 M2; CD3 mAb 1 M7; CD3 mAb 1 M13; and CD3 mAb 1 M15; using Pan-T effector cells and MV-4-11 leukemia target cells. Percent cytotoxicity is plotted in FIG. 8A. Cytokine responses are plotted in FIGS. 8B-8E (FIG. 8B: IFN-gamma.
Figure 8B:
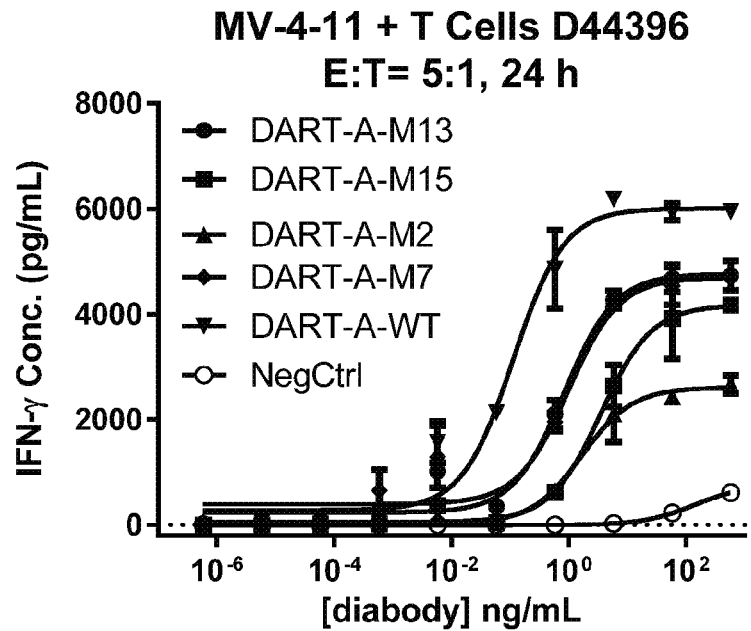
Figure 8C:
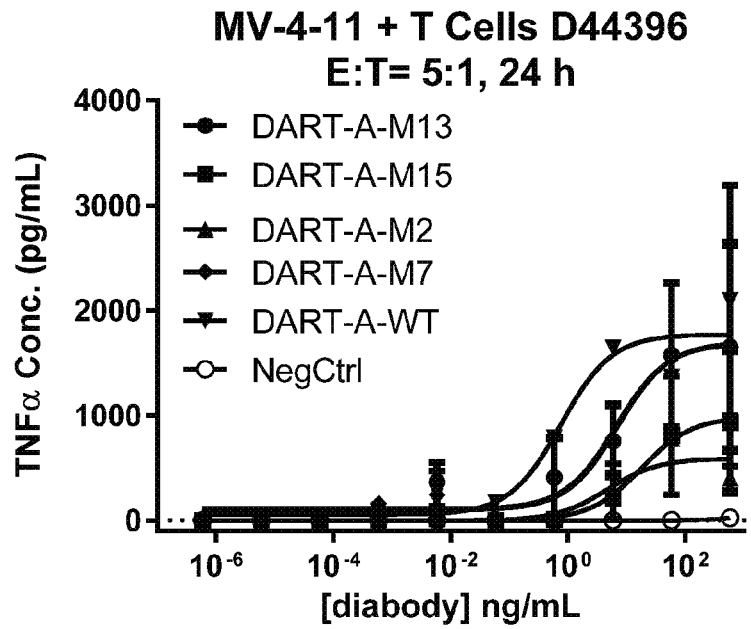
Figure 8D:
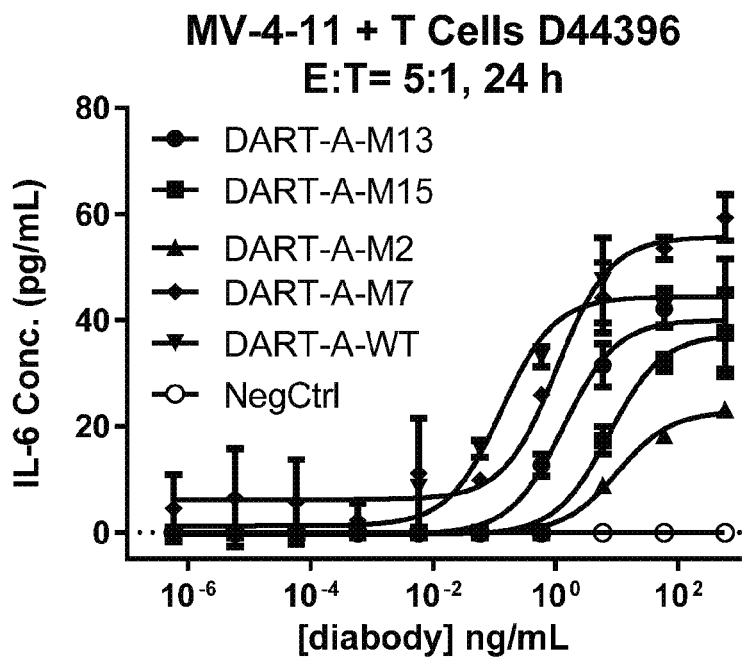
Figure 8E:
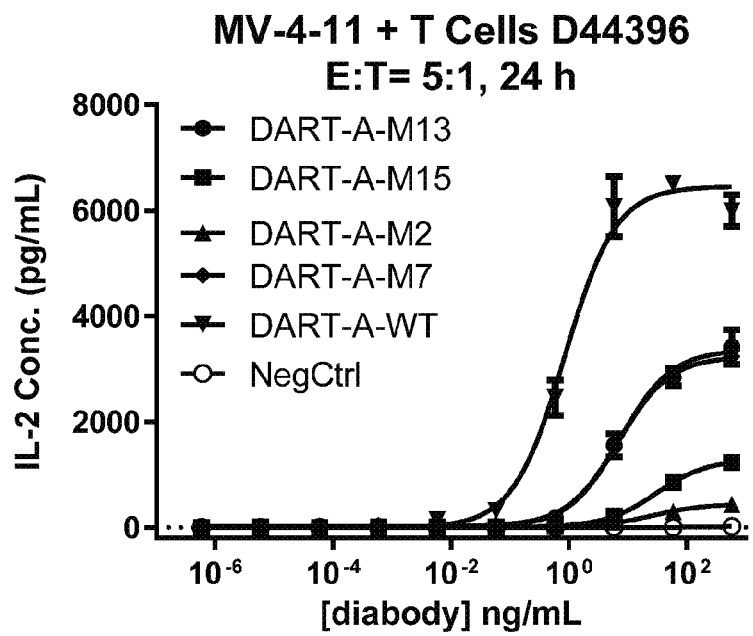

The cytotoxic (CTL) activity and cytokine release profile of a representative set of DART-A-type diabodies comprising variant CD3 mAb 1 VL or VH Domains was assessed by incubating DART-A-WT; DART-A-M2; DART-A-M7; DART-A-M13; and DART-A-M15 in the presence of Pan-T-cells effector cells and MV-4-11 leukemia target tumor cells at an effector:target cell ratio of 5:1 24 hours. The percentage cytotoxicity (i.e., cell killing) and/or $EC_{50}$ was determined by measuring the release of lactate dehydrogenase (LDH) into the media by damaged cells (e.g., by using the CytoTox 96® Non-Radioactive Cytotoxicity Assay Kit (Promega) that quantitatively measures LDH release, or similar) and is plotted in FIG. 8A. Cytokines released into the supernatant during the CTL was measured (e.g., using Enzyme-Linked ImmunoSpot (ELISPOT) assay or milliplex cytokine assay). Cytokine release is plotted in FIGS. 8B-8E (FIG. 8B: INF-γ, FIG. 8C: TNF-α, FIG. 8D: IL-6, and FIG. 8E: IL-2). The $EC_{50}$ Values for cytotoxicity and cytokine release are provided in Table 13. A 4420×CD3 fluorescein-binding DART-A-type diabody having the CD3 Binding Domain of CD3 mAb 1 was employed as a negative control (NegCtrl).

TABLE 13

| DART-A-Type | $EC_{50}$CTL | $EC_{50}$INF-γ | $EC_{50}$TNFα | $EC_{50}$IL-6 | EC50-IL2 |
|---|---|---|---|---|---|
| WT | 0.029 | 0.11 | 0.76 | 0.13 | 0.85 |
| M2 | 0.92 | 1.7 | 4.7 | 10 | 27 |
| M7 | 0.052 | 0.98 | 6.6 | 1.1 | 7.0 |
| M13 | 0.12 | 0.83 | 0.12 | 1.3 | 7.5 |
| M15 | 0.39 | 3.5 | 18 | 7.5 | 30 |

The results from these studies show that DA×CD3 Binding Molecules comprising vCD3-Binding Domains displaying having altered affinity retain cytolytic activity and exhibit one or more reduced cytokine responses (max response and/or EC50) as compared to a DA×CD3 Binding Molecule comprising the rCD3-Binding Domain.

Example 3

Generation of DART-B-Type Diabodies

Diabodies possessing the VH Domain of CD3 mAb 1 M18 were selected for further characterization and comparison to diabodies possessing the VH Domain of CD3 mAb 1, CD3 mAb 1 M1 and CD3 mAb 1 M2. Thus, the DART-B-type diabodies of Table 9 were prepared comprising a Disease Antigen (DA) Binding Domain binding the Cancer Antigen CD123, 5T4, or CD19. The amino acid sequences of each chain are provided in detail herein (see First-Nineteenth Illustrative DART-B-type Diabodies, supra). Briefly, the diabodies were expressed in CHO cells (transient or stably transfected) and purified over a Protein A affinity resin (e.g., MabSelect) followed by HPLC size exclusion chromatography.

Example 4

Ability of DART-B-Type Diabodies to Bind to Disease Antigens

Figure 9A:
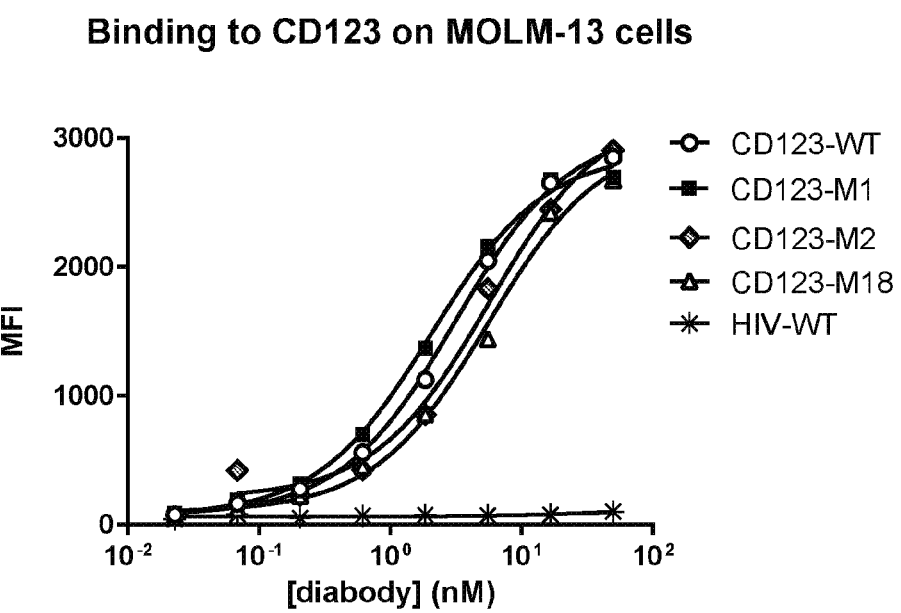
FIG. 9A-9B show the ability of DART-B-type diabodies to bind to Disease Antigens.
Figure 9B:
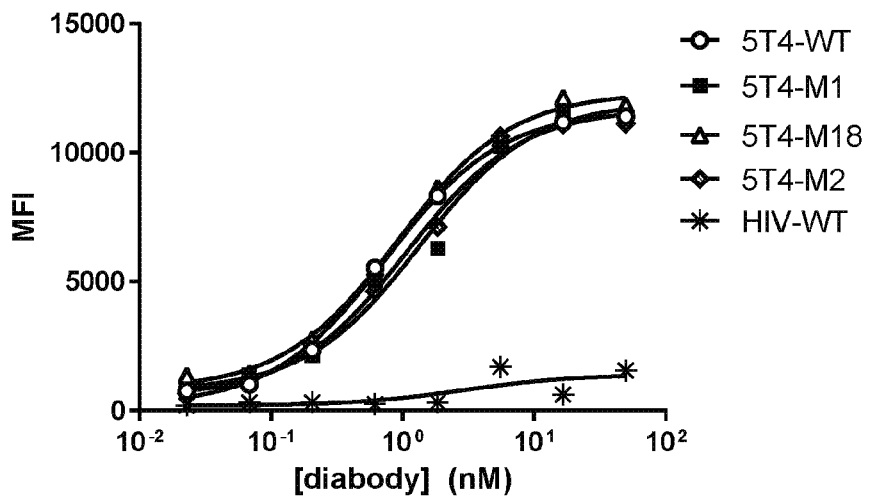

The ability of such diabodies to bind to their respective Disease Antigen (i.e., CD123 or 5T4) on the surface of MOLM-13 leukemia (CD123) or A-498 kidney carcinoma (5T4) target cancer cells was assessed using FACS. Briefly, cells were incubated with the diabody molecules (in FACS buffer containing 10% human AB serum) in microtiter plates. The cells were washed and incubated with biotin-conjugated mouse anti-EK-coil antibody that recognizes the E-coil/K-coil (EK) Heterodimer-Promoting Domain of the diabodies mixed with streptavidin-phycoerythrin. Representative data of such assays are shown in FIGS. 9A-9B. The data shows that the representative diabodies were capable of binding to their respective Disease Antigens.

Example 5

Ability of DART-B-Type Diabodies to Bind to $CD4^+$ and $CD8^+$ T-Cells

Figure 10A:
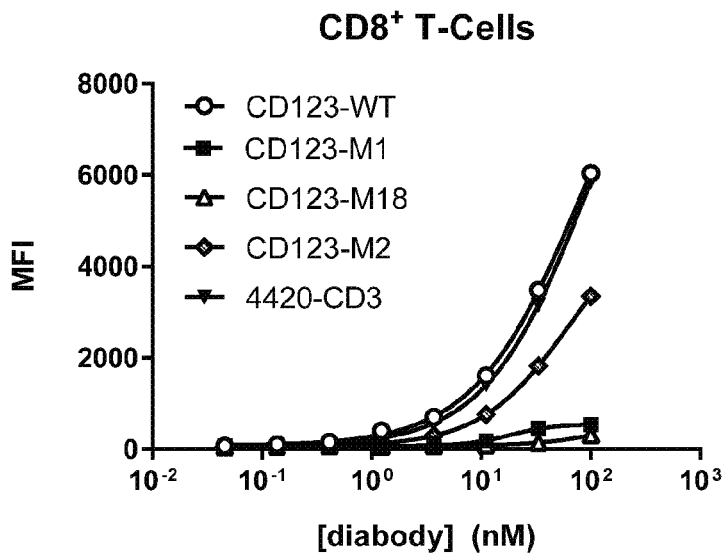
FIGS. 10A-10B show the ability of CD123-WT, CD123-M1, CD123-M2 and CD123-M18 DART-B-type diabodies to bind to CD8+ T-cells (FIG. 10A) and CD4+ T-cells (FIG. 10B).
Figure 10B:
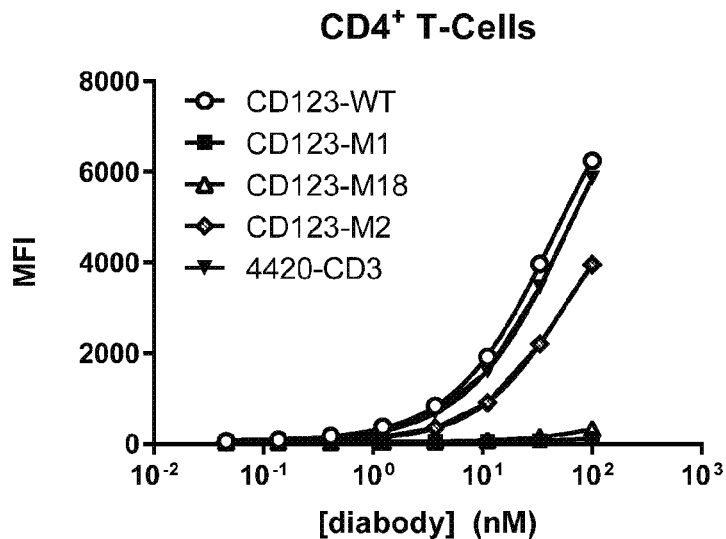

The ability of the CD123-binding diabodies: CD123-WT, CD123-M1, CD123-M2 and CD123-M18 to bind to $CD4^+$ and $CD8^+$ T-cells was also assessed using FACS. A 4420× CD3 fluorescein-binding DART-A-type diabody having the CD3 Binding Domain of CD3 mAb 1 was employed as a control for CD3 binding ("4420-CD3"). Briefly, CD4+ and CD8+ T-cells were incubated with the diabody molecules (in FACS buffer containing 10% human AB serum) in microtiter plates. The cells were washed and incubated with a labeled anti-human Fc secondary antibody. The cells were then washed and resuspended with FACS buffer, and analyzed by flow cytometry. Representative data of such assays are shown in FIG. 10A (binding to $CD8^+$ T-cells) and FIG. 10B (binding to $CD4^+$ T-cells). T-CD123-M1 and T-CD123-M18 exhibit reduced binding to CD3 expressing $CD4^+$ and $CD8^+$ T-cells.

The ability of the CD123-binding diabodies: CD123-WT, CD123-M1, CD123-M2 and CD123-M18 to bind to human CD3 and CD123 was also evaluated using BIAcore®. Briefly, diabodies at concentrations of 62.5-1000 nM were passed over soluble human CD3 that had been immobilized to a surface (normalized; 1:1 Binding Fit). The high analyte concentrations (62.5-1000 nM) were used in order to allow evaluation of parameters for weak CD3 interactions, however, high concentrations of analyte can be associated with a contribution of non-specific binding. In separate studies diabodies at concentrations of 62.5-100 nM were passed over soluble CD123 that had been His-tagged and captured to an anti-PentaHis surface (normalized; 1:1 Binding Fit). Table 14 presents the calculated $k_a$, $k_d$ and KD from these studies.

TABLE 14

| | Binding to human CD3 | | | Binding to human CD123 | | |
|---|---|---|---|---|---|---|
| CD3 Variant | $k_a$ (×10$^4$) | $k_d$ (×10$^{-3}$) | KD (nM) | $k_a$ (×10$^5$) | $k_d$ (×10$^{-4}$) | KD (nM) |
| CD123-WT | 9.1 | 6.1 | 67 | 2.7 | 5.3 | 2.0 |
| CD123-M1 | 9.5 | 80 | 842 | 3.2 | 3.9 | 1.2 |

TABLE 14-continued

|  | Binding to human CD3 | | | Binding to human CD123 | | |
|---|---|---|---|---|---|---|
| CD3 Variant | $k_a$ (×10⁴) | $k_d$ (×10⁻³) | KD (nM) | $k_a$ (×10⁵) | $k_d$ (×10⁻⁴) | KD (nM) |
| CD123-M2 | 3.8 | 41 | 108 | 4.2 | 4.5 | 1.1 |
| CD123-M18 | 8.6 | 51 | 593 | 2.4 | 5.4 | 2.3 |

The ability of the 5T4-binding diabodies: 5T4-WT, 5T4-M1, 5T4-M2 and 5T4-M18 to bind to CD3 was also evaluated using BIAcore®, as described above. Table 15A presents the calculated $k_a$, $k_d$ and KD.

TABLE 15A

|  | Binding to human CD3 | | |
|---|---|---|---|
| CD3 Variant | $k_a$ (×10⁵) ($M^{-1}s^{-1}$) | $k_d$ (×10⁻³) ($s^{-1}$) | KD (nM) |
| 5T4-WT | 1.5 | 5.4 | 36 |
| 5T4-M1 | 0.95 | 31 | 326 |
| 5T4-M2 | 3.5 | 41 | 118 |
| 5T4-M18 | 0.75 | 34 | 453 |

In additional studies the ability of CD123-binding diabodies: CD123-WT, CD123-M13, CD123-M17 and CD123-M19 to bind to human CD3 and cynomolgus CD3 was also evaluated using BIAcore®. Briefly, diabodies at concentrations of 6.25-400 nM were passed over immobilized human CD3 or cyno CD3 (1:1 Langmuir Binding Fit). Table 15B presents the calculated $k_a$, $k_d$ and KD.

TABLE 15B

|  | Binding to human CD3 | | | Binding to cyno CD3 | | |
|---|---|---|---|---|---|---|
| CD3 Variant | $k_a$ (×10⁴) | $k_d$ (×10⁻³) | KD (nM) | $k_a$ (×10⁴) | $k_d$ (×10⁻³) | KD (nM) |
| CD123-WT | 9.3 | 4.8 | 52 | 11 | 4.3 | 39 |
| CD123-M13 | 5.9 | 27 | 458 | 5 | 29 | 580 |
| CD123-M17 | 19 | 55 | 290 | 17 | 56 | 329 |
| CD123-M19 | 22 | 48 | 218 | 22 | 50 | 227 |

Example 6

Ability of Exemplary DART-B-Type Diabodies to Mediate Redirected Cell Killing

Exemplary DART-B-type diabodies were evaluated for their ability to mediate redirected cell killing. Where indicated, HIV-WT or HIV-M18 (described above) are used here as a negative control as they do not bind a Cancer Antigen. It will be understood that the HIV-WT and HIV-M18 diabodies will bind cells expressing the epitope bound by the A32 antibody (HIV env) on their cell surface (e.g., HIV infected cells), see for example: WO 2014/1599401 and WO 2016/054101, and are capable of mediating redirected cell killing of such cells.

The results of representative studies of redirected cell killing mediated by exemplary CD123×CD3 DART B-type diabody constructs are presented in FIGS. 11A-11Q, FIGS. 12A-12E, and FIGS. 26A-26E. The results of representative studies of redirected cell killing mediated by exemplary 5T4×CD3 DART B-type diabody constructs are presented in FIGS. 13A-13Q. The results of representative studies of redirected cell killing mediated by exemplary CD19×CD3 DART B-type diabody constructs are presented in FIGS. 14A-14J. These assays were performed essentially as described above using the indicated effector and target cells, effector:target cell ratios, and incubation times described below (also see, FIGS. 11A, 12A, 13A and 14A). Where indicated, the release of IFN-γ, TNF-α, IL-6, and IL-2 cytokines was determined at the end of the CTL assay using standard commercial reagents.

Figure 11A:
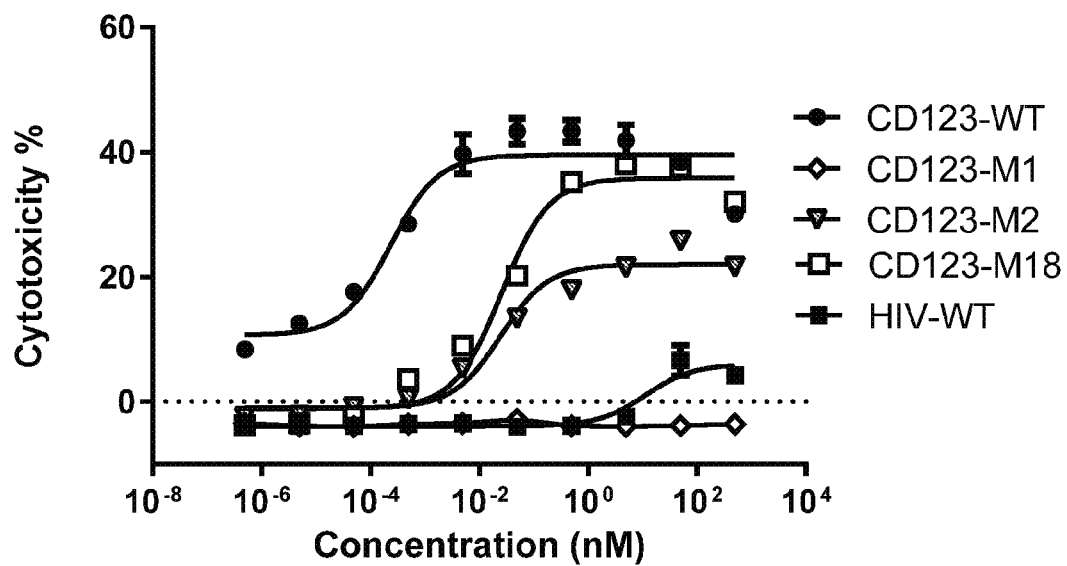
FIGS. 11A-11Q show the results of representative studies of redirected cell killing (CTL assay) mediated by CD123× CD3 DART B-type diabody constructs (possessing Fc Domains): CD123-WT (FIGS. 11B, 11F, 11J and 11N), CD123-M2 (FIGS. 11C, 11G, 11K and 11O), CD123-M18 (FIGS. 11D, 11H, 11L and 11P), HIV-WT (FIGS. 11E, 11I, 11M and 11Q), using Pan-T effector cells and MOLM-13 acute monocytic leukemia (AML) target cells. Percent cytotoxicity is plotted in FIG. 11A. Cytokine responses and percent cytotoxicity are plotted in FIGS. 11B-11Q (FIGS. 11B-11E: IFN-gamma.
Figure 11B:
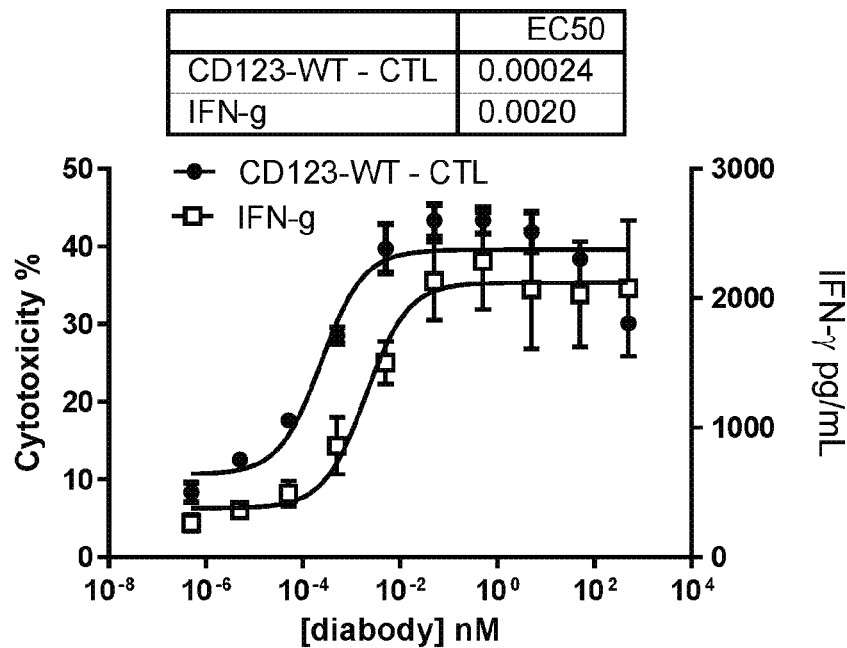
Figure 11C:
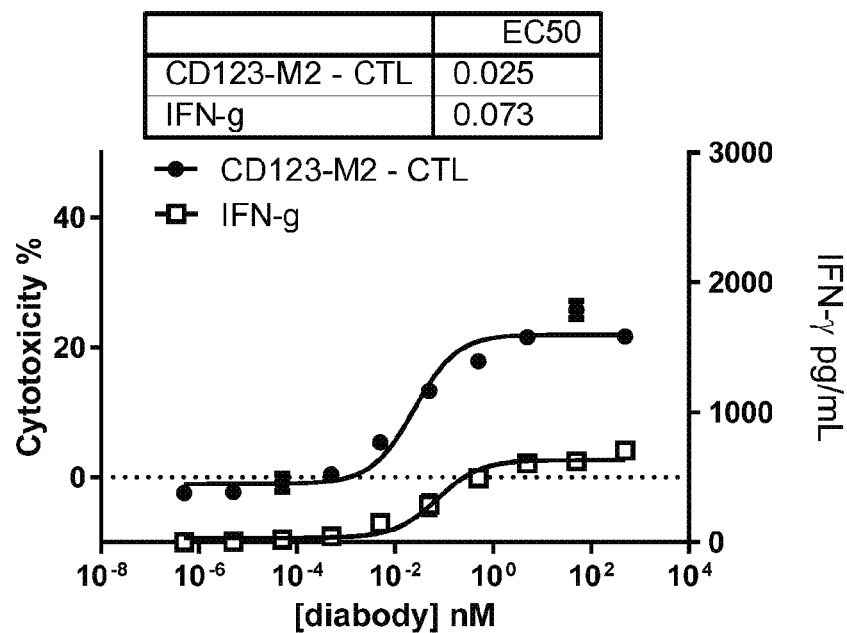
Figure 11D:
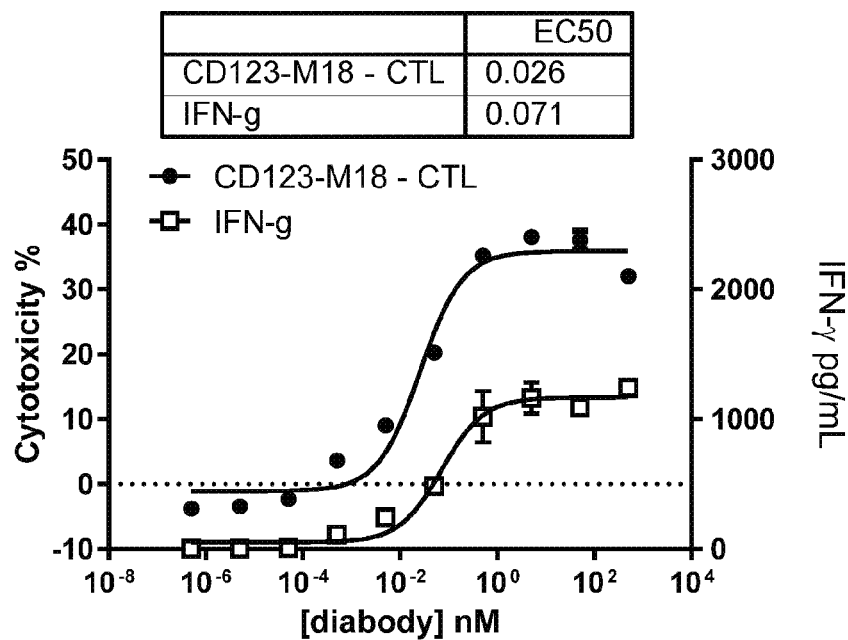
Figure 11E:
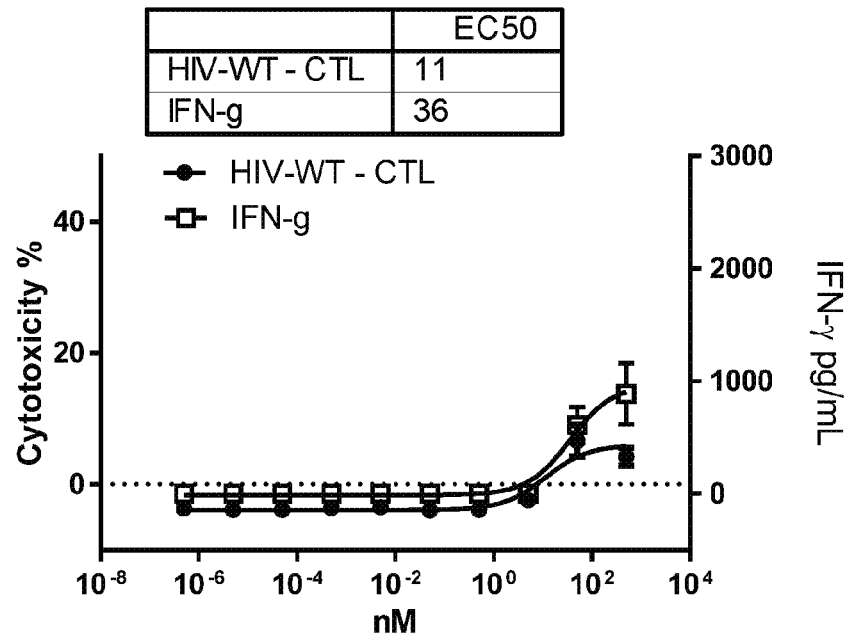
Figure 11F:
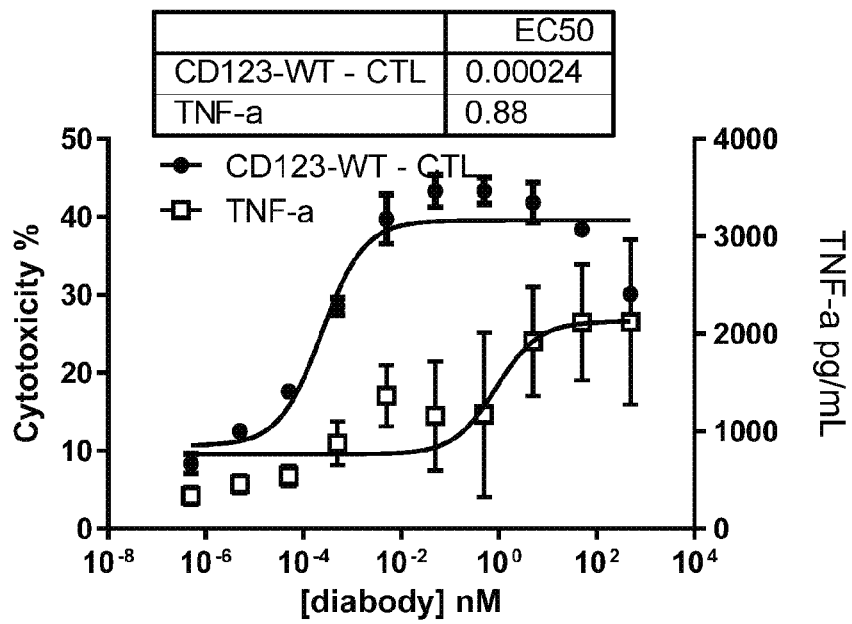
FIGS. 11F-11I: TNF-alpha.
Figure 11G:
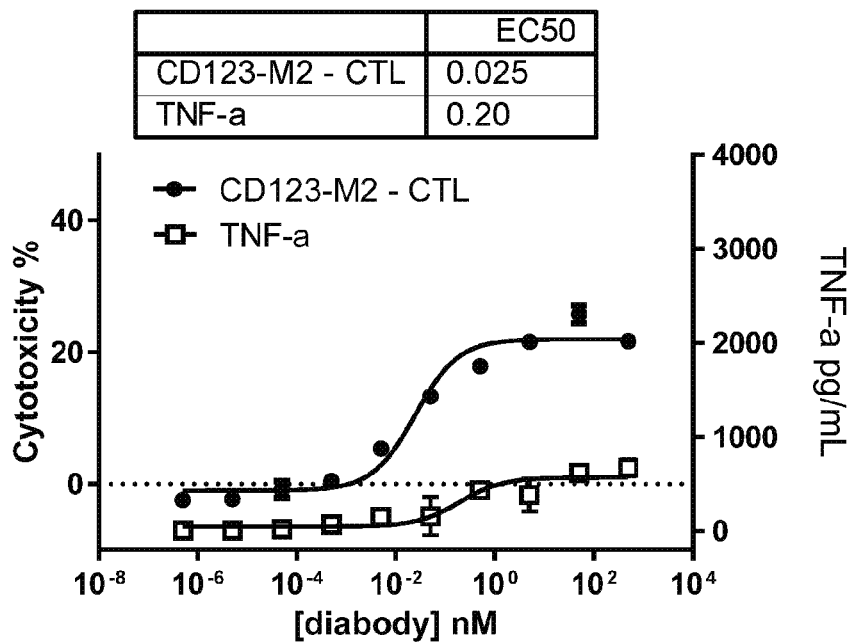
Figure 11H:
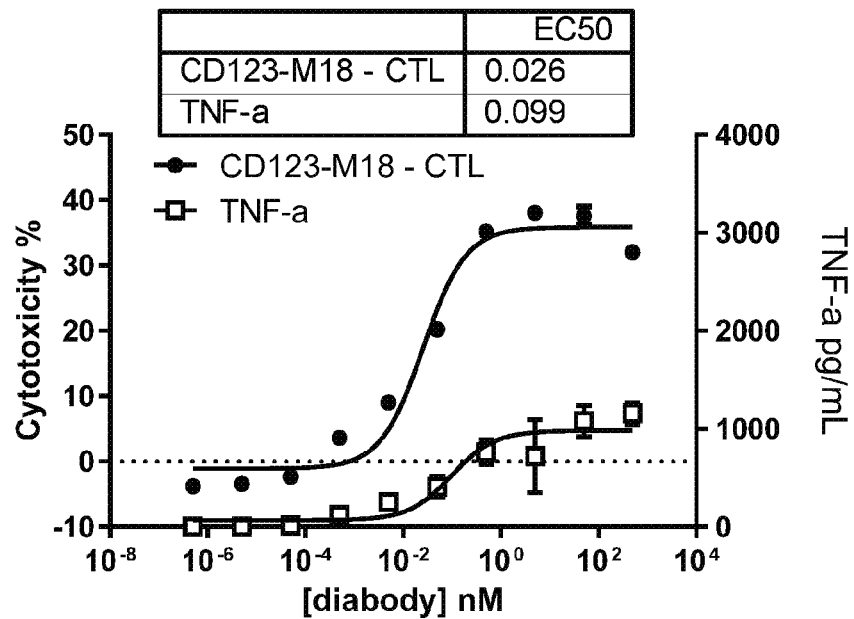
Figure 11I:
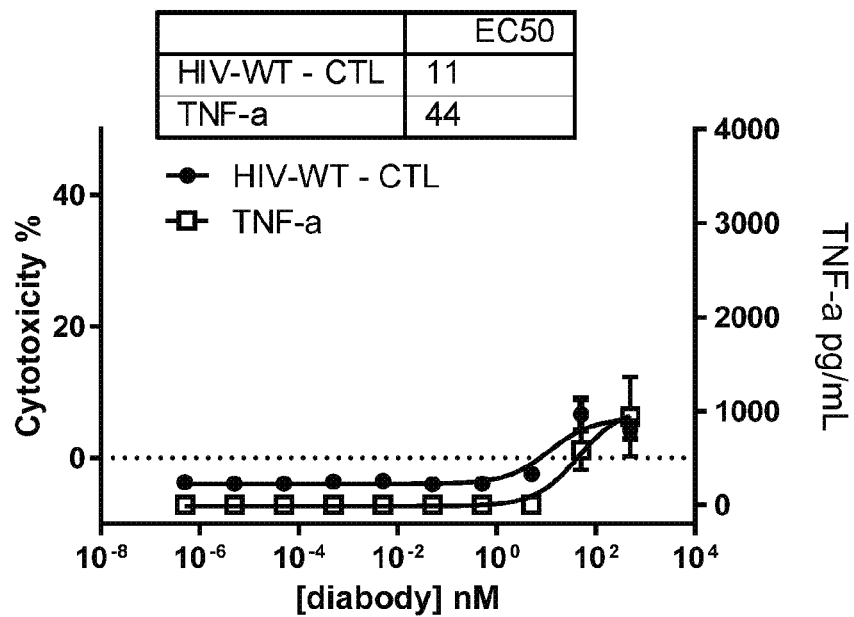
Figure 11J:
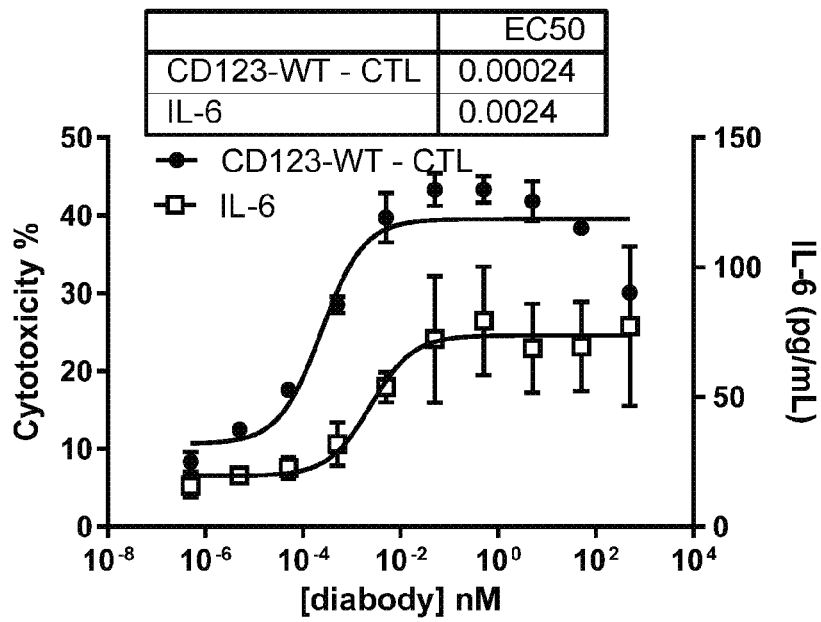
FIGS. 11J-11M: IL-6.
Figure 11K:
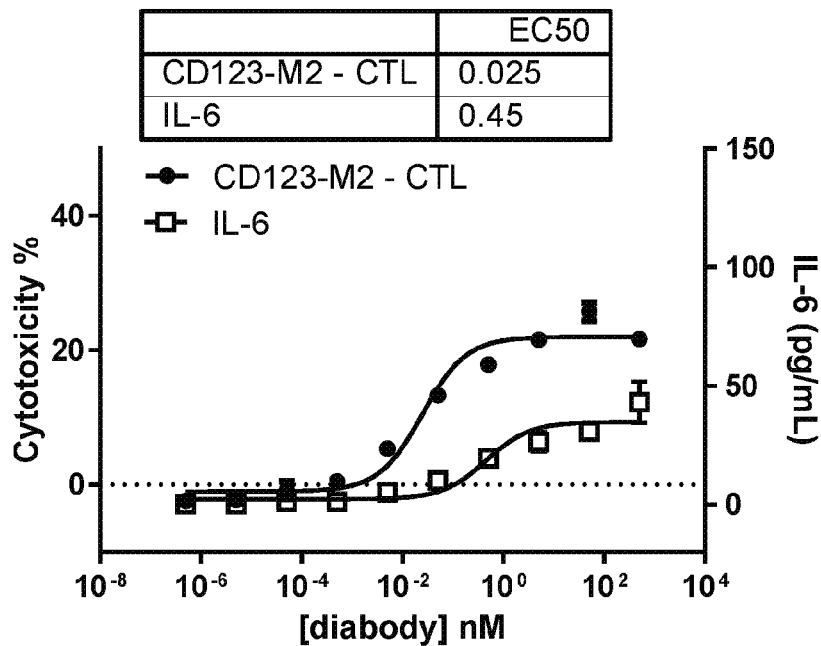
Figure 11L:
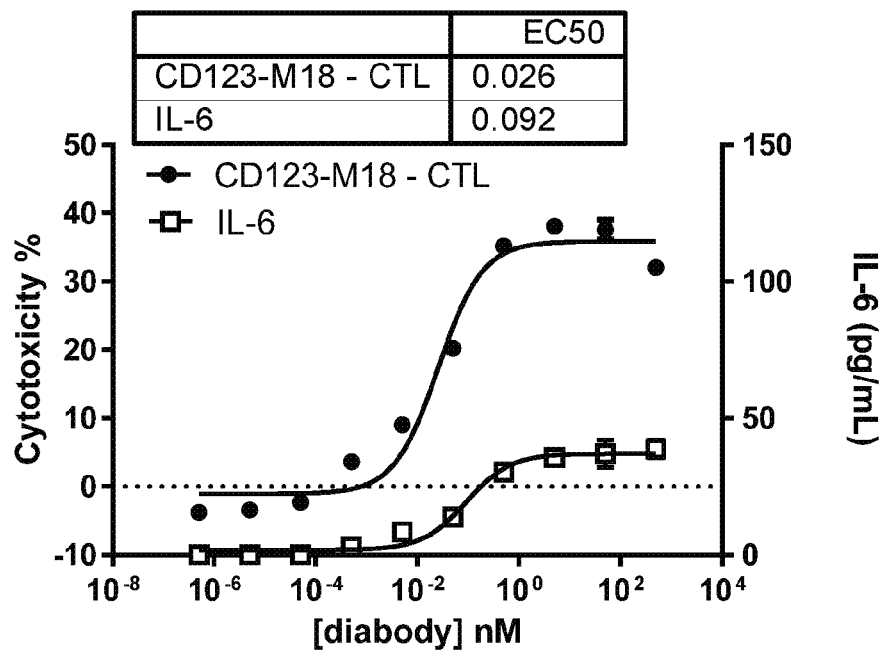
Figure 11M:
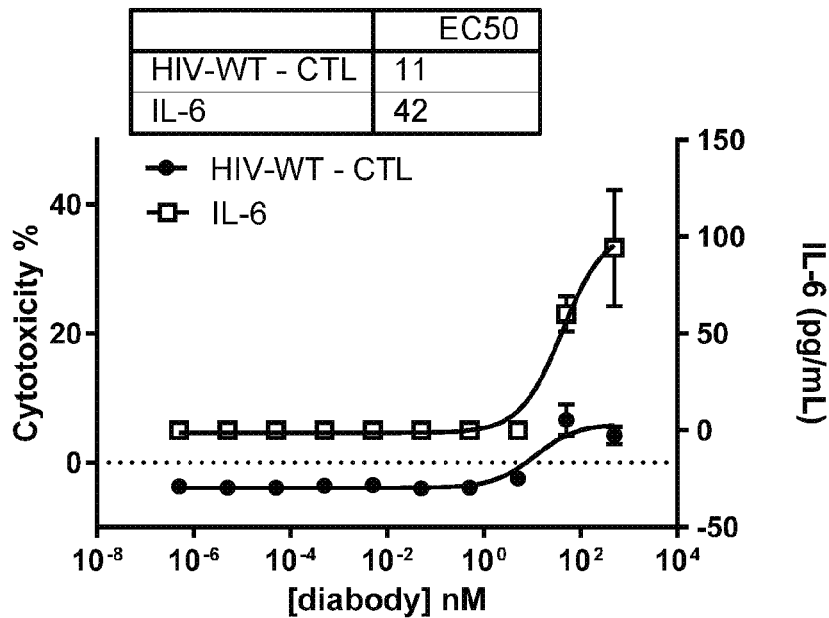
Figure 11N:
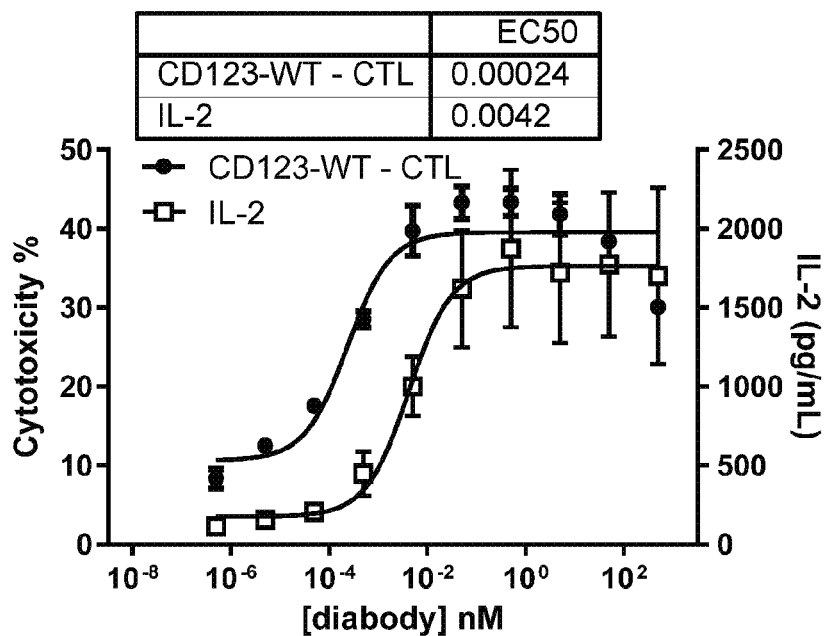
Figure 11O:
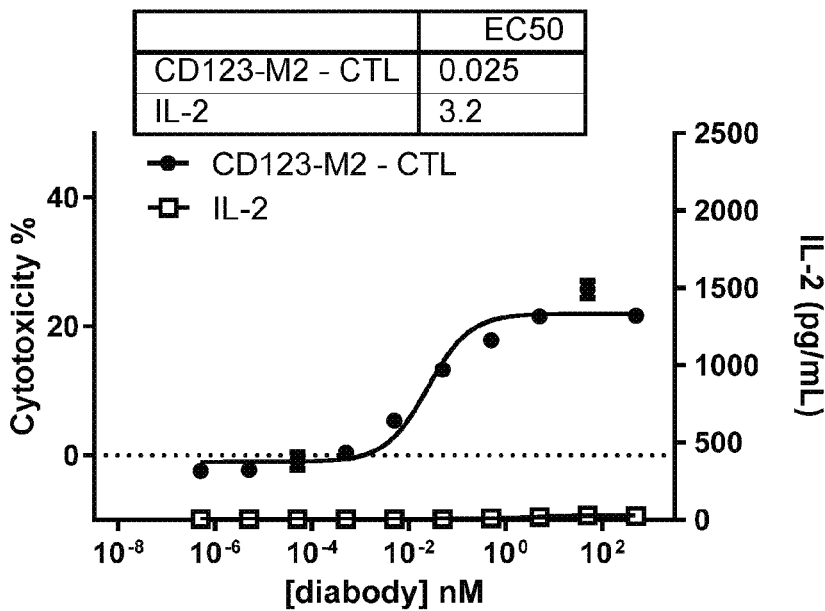
Figure 11P:
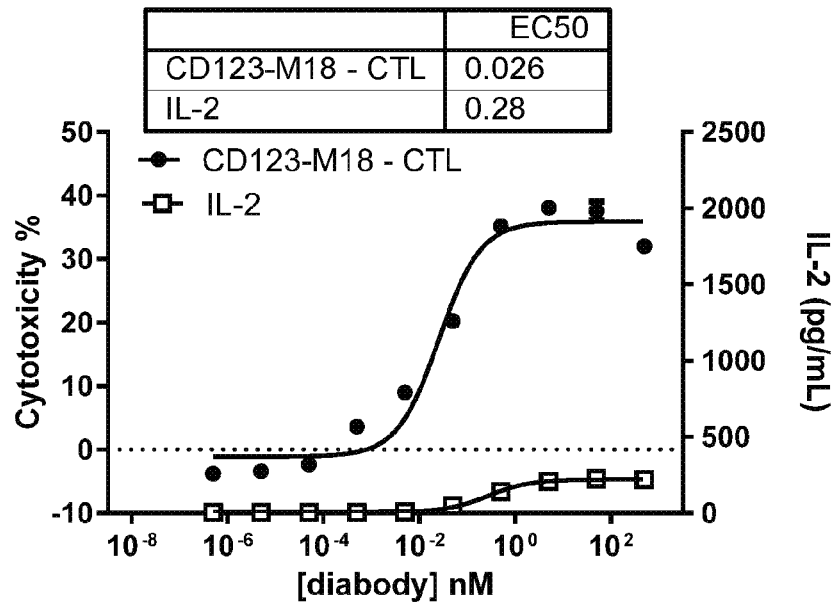
Figure 11Q:
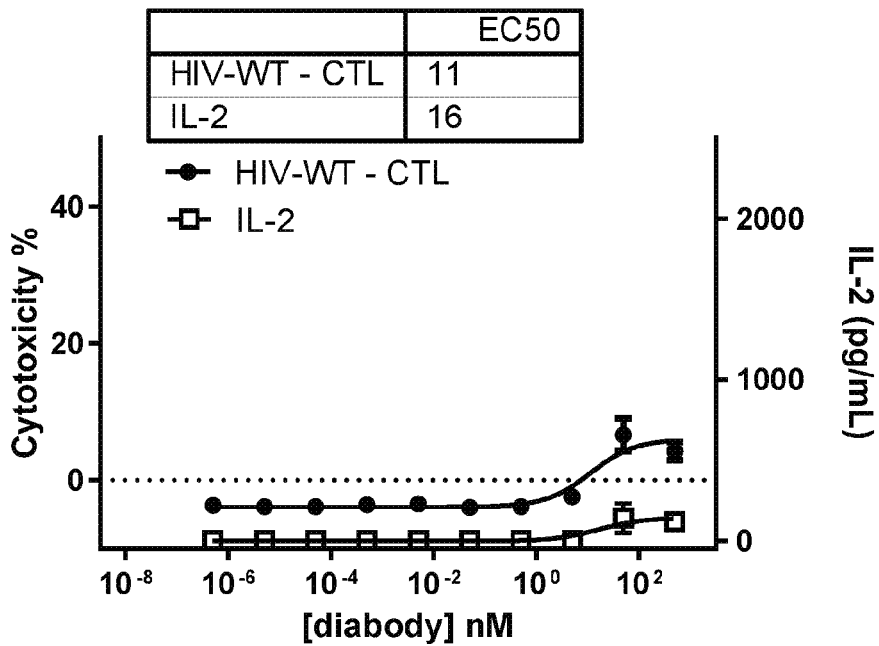

FIGS. 11A-11Q show the results of representative studies of redirected cell killing mediated by CD123×CD3 DART B-type diabody constructs (possessing Fc Domains) CD123-WT, CD123-M2 and CD123-M18 using Pan-T effector cells and MOLM-13 acute monocytic leukemia (AML) target cells (E:T=5:1, 24 h). Percent cytotoxicity is plotted in FIG. 11A. Cytokine responses and cytotoxicity are plotted in FIGS. 11B-11Q (FIGS. 11B-11E: IFN-gamma; FIGS. 11F-11I: TNF-alpha; FIGS. 11J-11M: IL-6; FIGS. 11N-11Q: IL-2). FIGS. 11B, 11F, 11J and 11N: CD123-WT; FIGS. 11C, 11G, 11K and 11O: CD123-M2; FIGS. 11D, 11H, 11L and 11P: CD123-M18; FIGS. 11E, 11I, 11M and 11Q: HIV-WT (Negative Control). Similar cytotoxicity was observed against another AML cell line, MV-4-11.

FIG. 11A shows that CD123×CD3 Binding Molecules comprising different CD3 mAb 1 variants exhibited markedly differing abilities to mediate cytotoxicity particularly as measured by comparing $EC_{50}$, but reaching a similar maximum cytotoxicity. In addition, these molecules exhibited differing abilities to mediate cytokine responses. For example, as seen in FIGS. 11B-11Q, although CD123-M18 exhibited levels of maximal cytotoxicity that were similar to those exhibited by CD123-WT, the levels of cytokines IFN-α, TNF-α and IL-6 released by treatment with CD123-M18 were approximately 50% of the levels released by treatment with CD123-WT, and the level of IL-2 observed with CD123-M18 was significantly less than the IL-2 level observed with CD123-WT. Thus, CD123-M18 was found to be able to provide a therapeutic value that was comparable to that of CD123-WT, but with less attending side effects than CD123-WT.

Figure 12A:
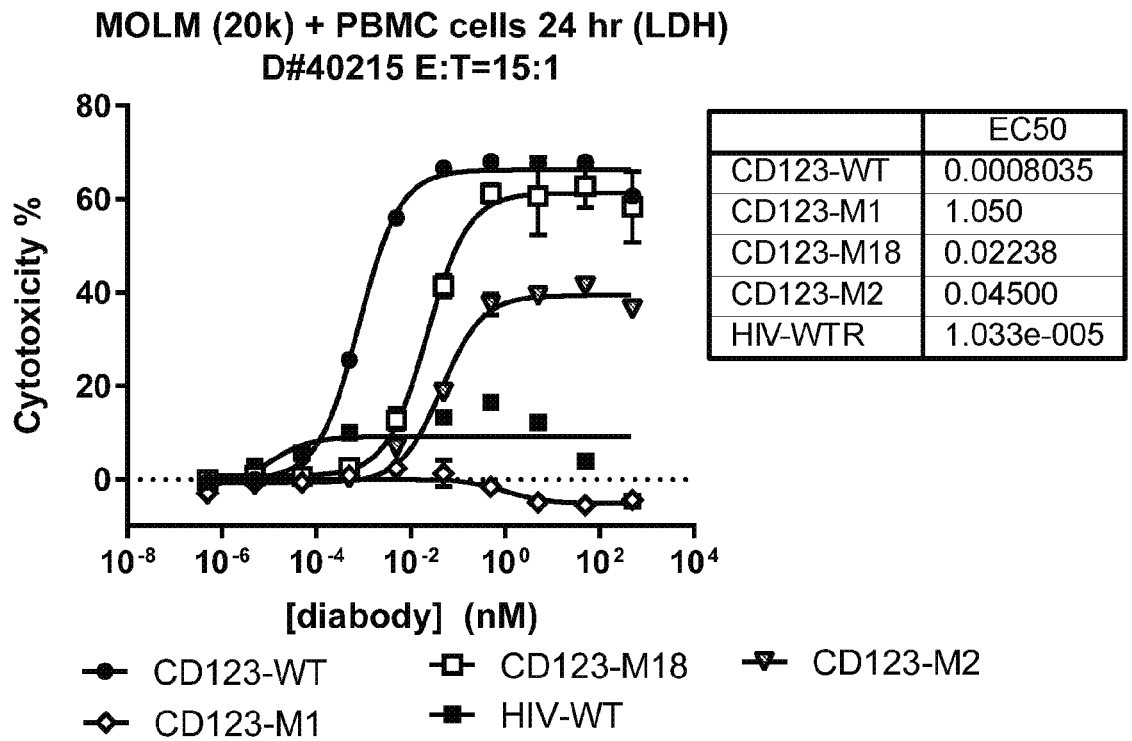
FIGS. 12A-12E show the results of representative studies of redirected cell killing (CTL assay) mediated by CD123× CD3 DART B-type diabody constructs (possessing Fc Domains) using PBMC effector cells and MOLM-13 AML target cells. Percent cytotoxicity is plotted in FIG. 12A (E:T=15:1, 24 h). Cytokine responses are plotted in FIGS. 12B-12E (FIG. 12B: IFN-gamma.
Figure 12B:
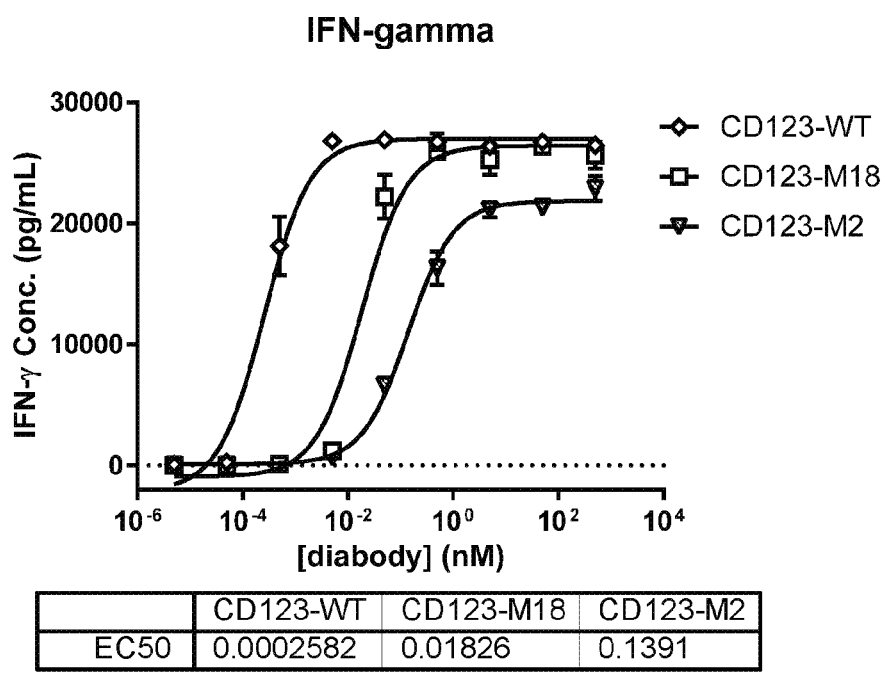
Figure 12C:
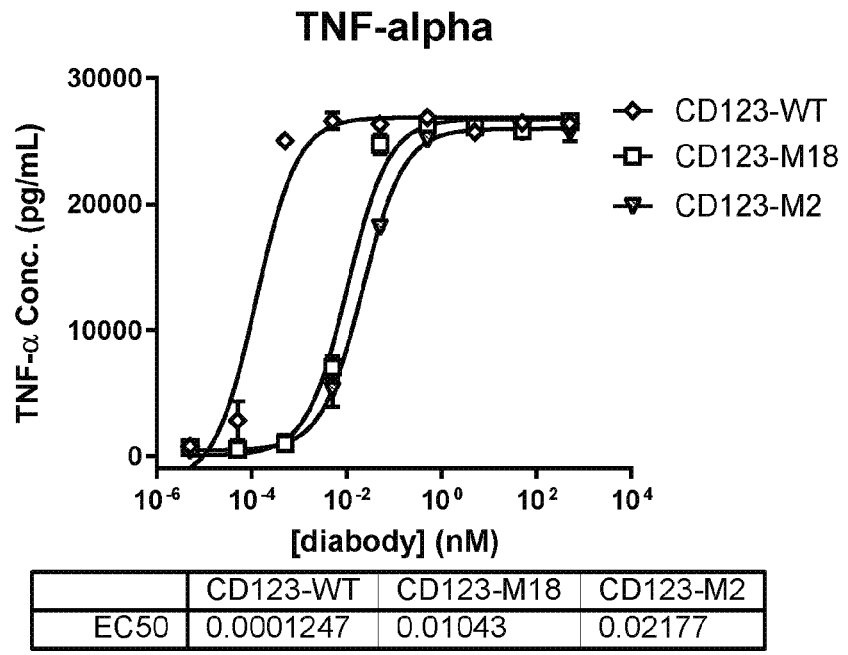
Figure 12D:
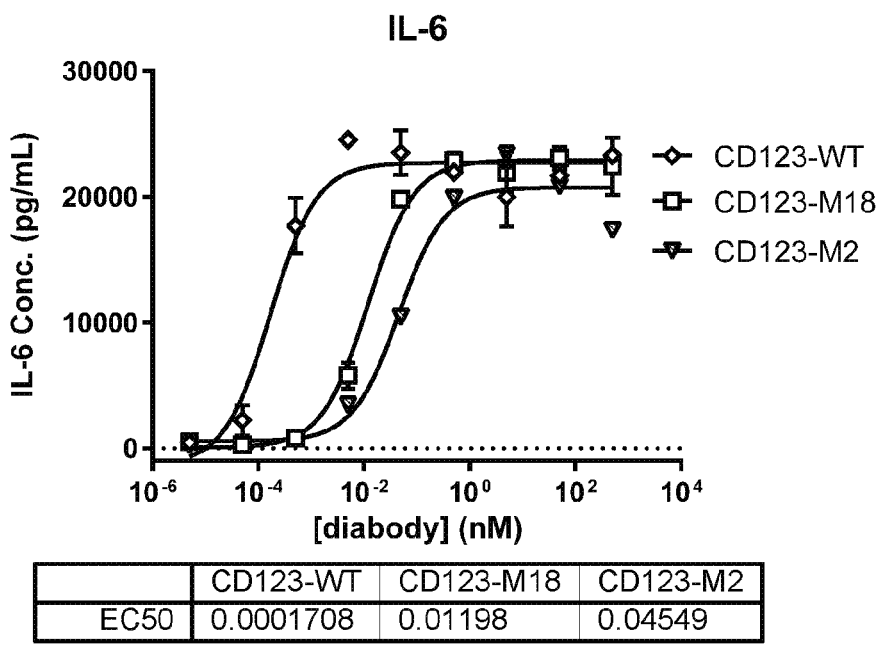
Figure 12E:
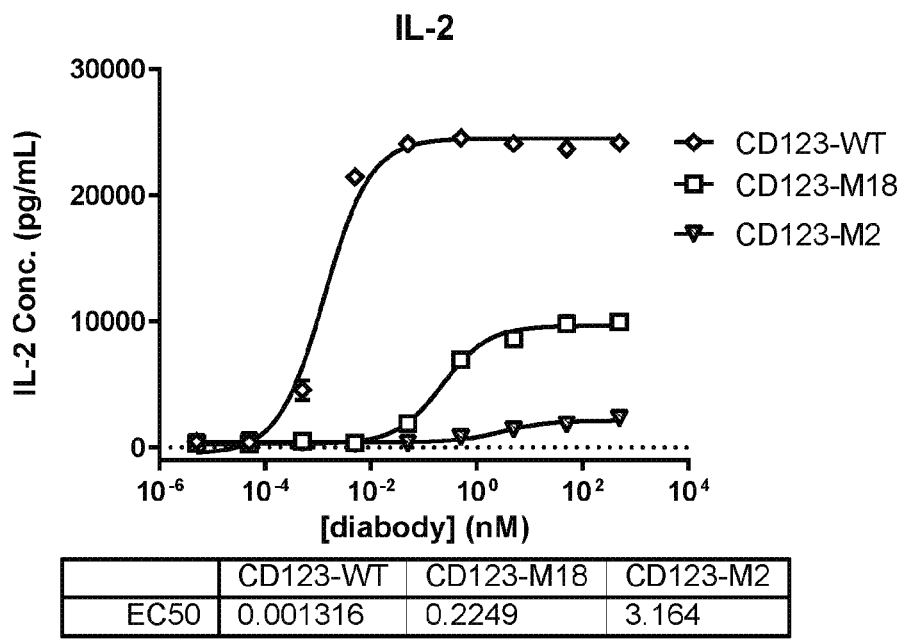

FIGS. 12A-12E show the results of representative studies of redirected cell killing mediated by CD123×CD3 DART B-type diabody constructs (possessing Fc Domains) using PBMC effector cells and MOLM-13 AML target cells. Percent cytotoxicity is plotted in FIG. 12A (E:T=15:1, 24 h). Cytokine responses (measured in a milliplex cytokine assay) are plotted in FIGS. 12B-12E (FIG. 12B: IFN-gamma; FIG. 12C: TNF-alpha; FIG. 12D: IL-6; FIG. 12E: IL-2).

The results again demonstrate that CD123-WT and CD123-M18 exhibit similar levels of maximal cytotoxicity, but CD123-M18 exhibited markedly reduced cytokine responses. Additionally, the $EC_{50}$ values of CD123-M18 for release of IFN-γ, TNF-α or IL-6 were substantially more those of CD123-WT indicating that treatment with CD123-M18 resulted in significantly less cytokine release as compared to treatment with CD123-WT.

Figure 26A:
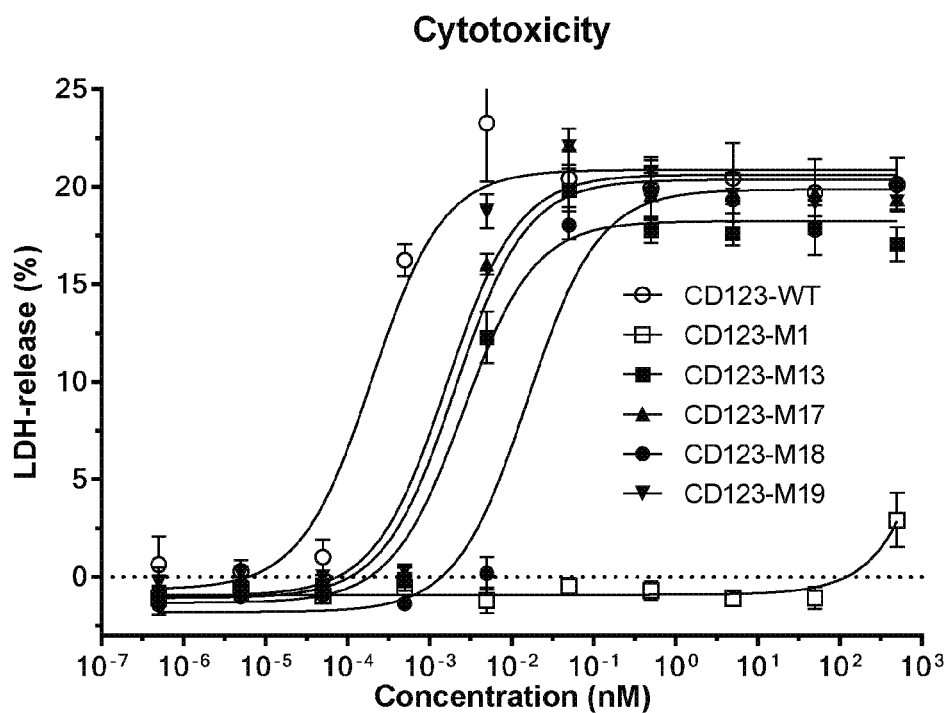
FIGS. 26A-26E show the results of representative studies of redirected cell killing (CTL assay) mediated by CD123× CD3 diabody constructs CD123-WT, CD123-M1, CD123-M13, CD123-M17, CD123-M18, and CD123-M19 using Pan-T effector cells and MOLM-13 AML target cells (E:T=15:1, 48-96 hr). Cytotoxicity as a function of % LDH released is plotted in FIG. 26A. Cytokine responses are plotted in FIGS. 26B-26E (FIG. 26B: IFN-gamma.

FIGS. 26A-26D and FIGS. 27A-27D show the results of studies of redirected cell killing mediated by CD123×CD3 DART B-type diabody constructs (possessing Fc Domains) CD123-WT, CD123-M1, CD123-M13, CD123-M17, CD123-M18 and CD123-M19 using Pan-T effector cells and MOLM-13 acute monocytic leukemia (AML) target cells (E:T=5:1, 48 to 96 hours). As noted below, DART-A-WT was included as a comparator in some studies. FIGS. 26A-26D show the results of a representative study performed for 48 hours. In FIG. 26A cytotoxicity is plotted, as a function of % LDH released. Cytokine responses and cytotoxicity are plotted in FIGS. 26B-26E (FIG. 26B: IFN-gamma; FIG.

Figure 26B:
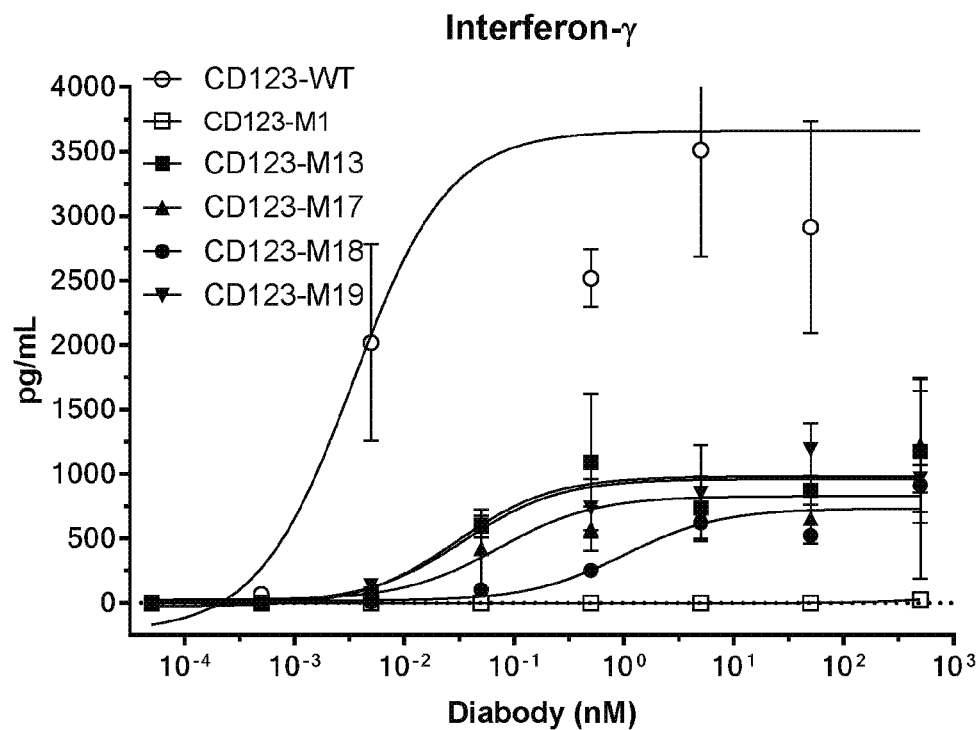
Figure 26C:
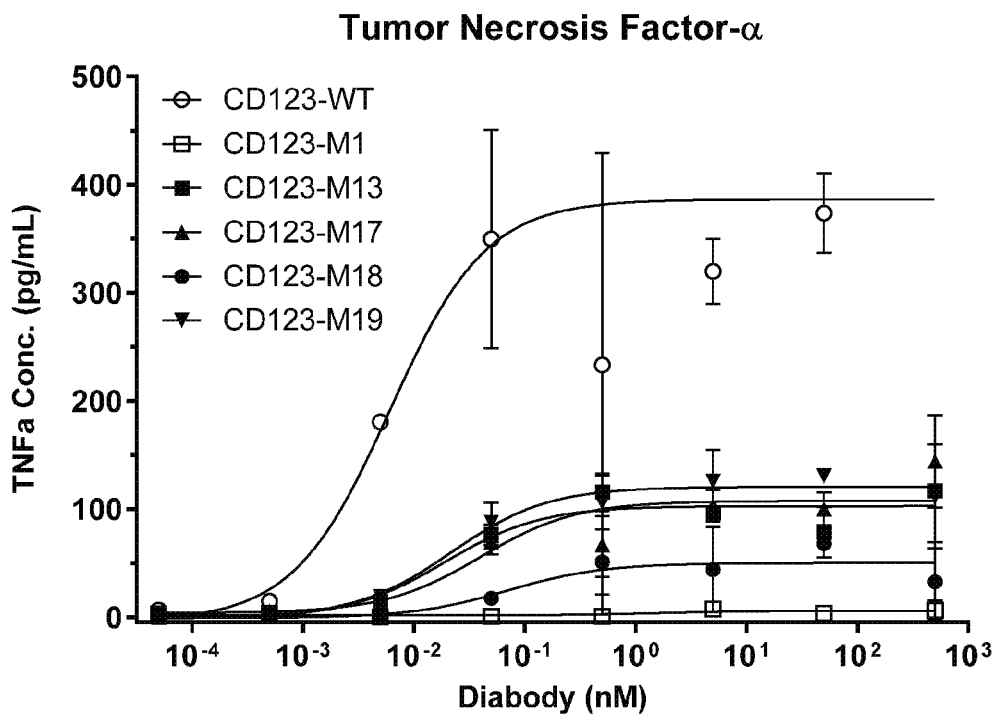
Figure 26D:
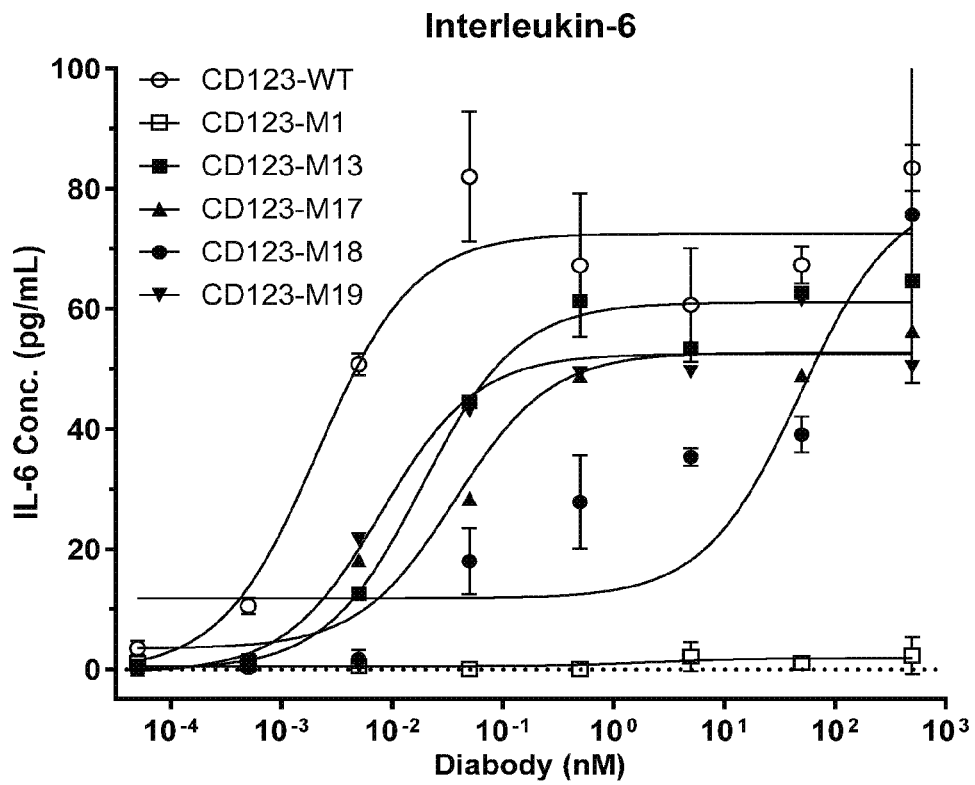
Figure 26E:
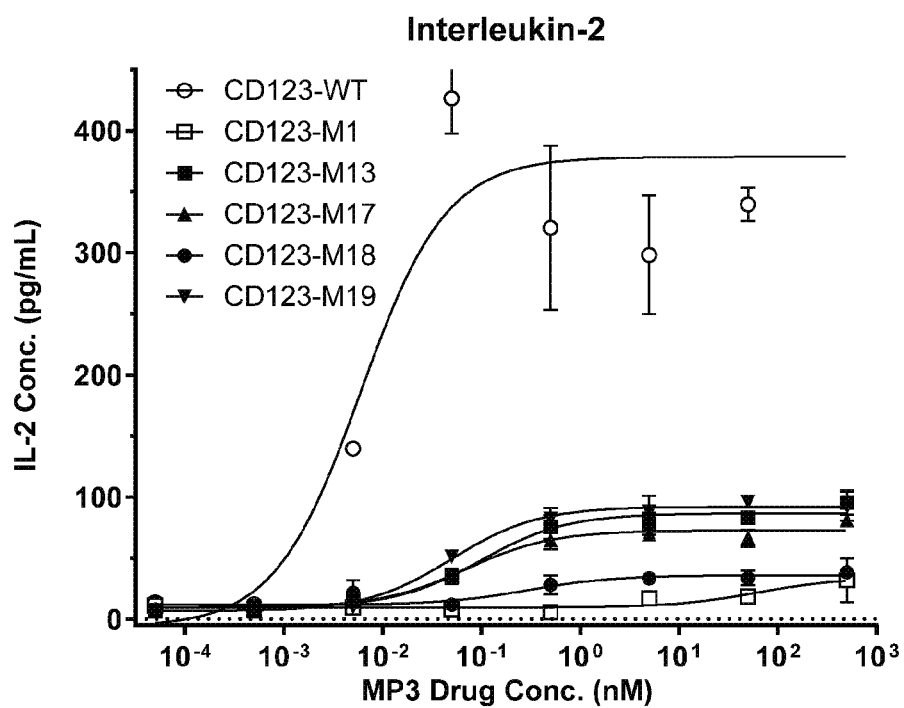
Figure 27A:
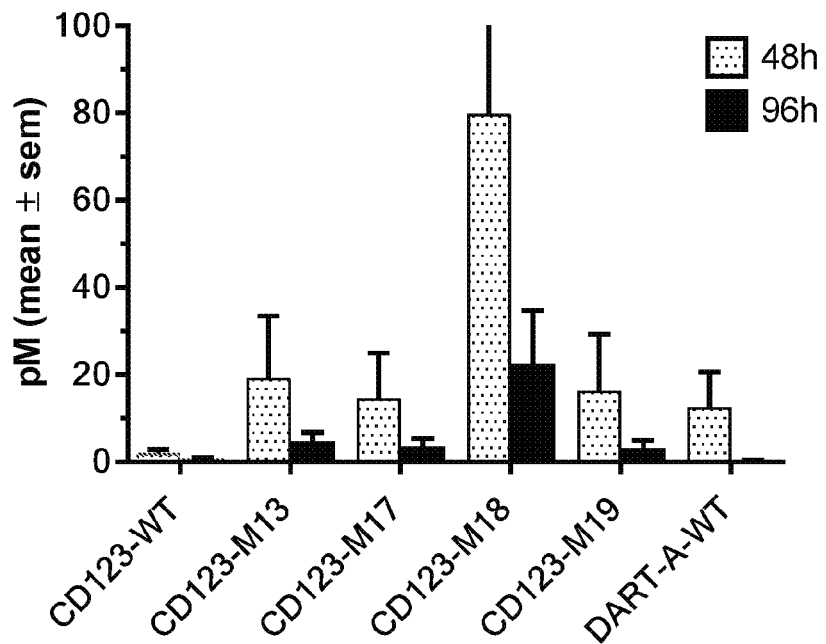
FIGS. 27A-27D present the cumulative results from 4-7 redirected cell killing assays (CTL assay) and cytokine release studies mediated by CD123×CD3 diabody constructs CD123-WT, CD123-M1, CD123-M13, CD123-M17, CD123-M18, CD123-M19, and DART-A-WT using Pan-T effector cells and MOLM-13 AML target cells (E:T=15:1, 48-96 hr). CTL activity $EC_{50}$ values in pM are plotted in FIG. 27A. CTL activity as a multiple of the $EC_{50}$ value of CD123-WT is plotted in FIG. 27B. CTL activity Emax as a percent of CD123-WT) is plotted in FIG. 27C. The calculated Therapeutic Index (TI=$E_{max}$ (CTL):$E_{max}$ (cytokine)) normalized to CD123-WT is plotted in FIG. 27D.
Figure 27B:
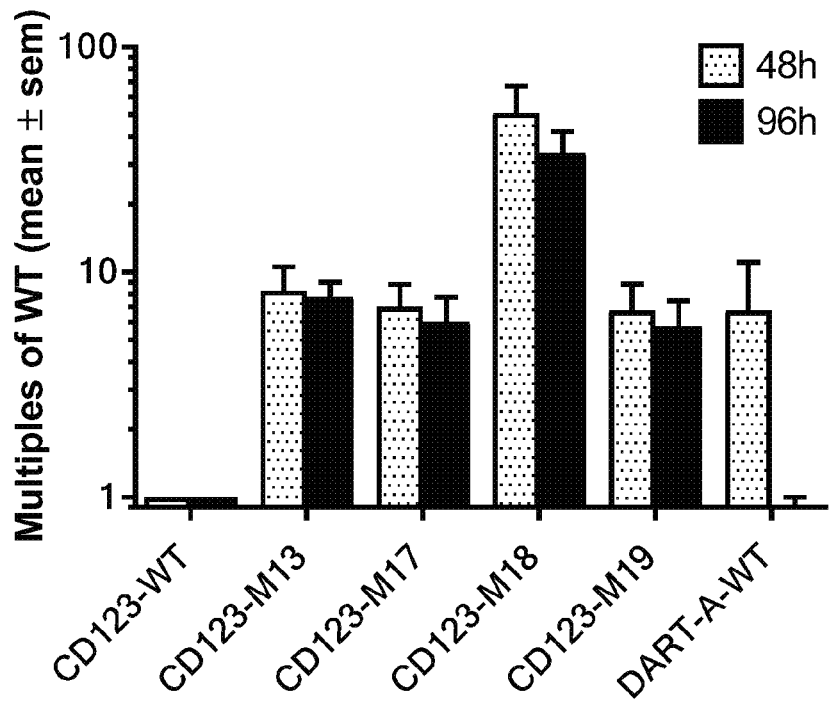
Figure 27C:
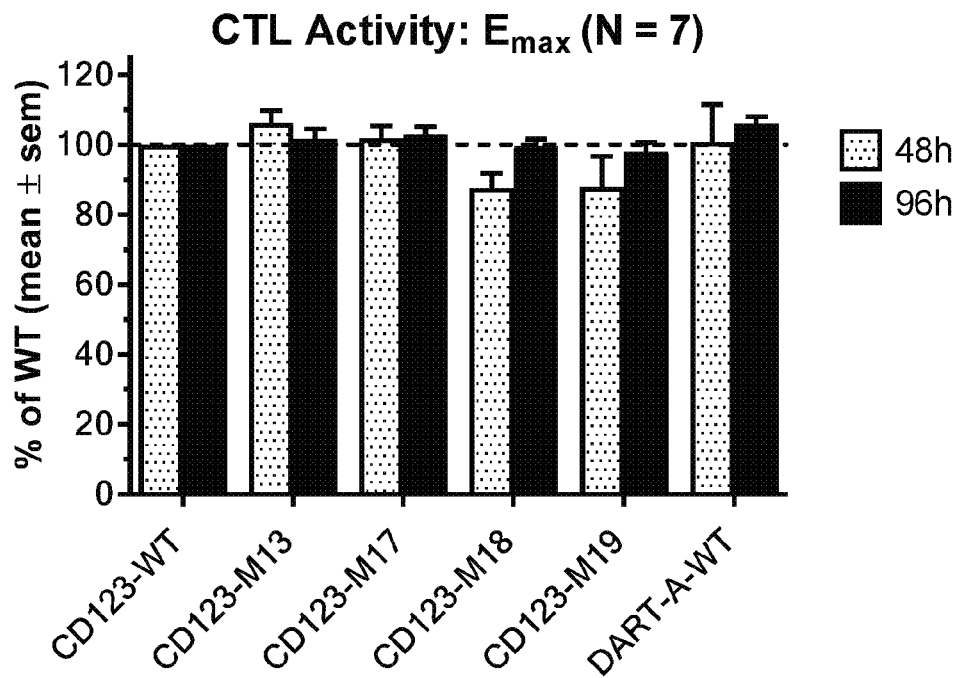
Figure 27D:
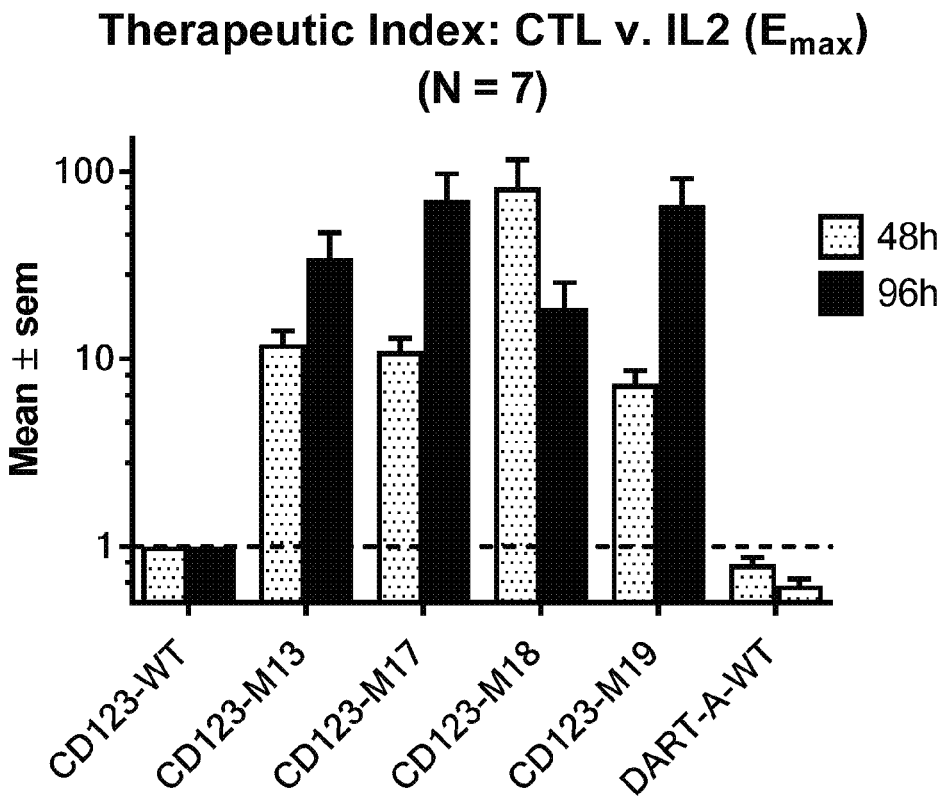

26C: TNF-alpha; FIG. 26D: IL-6; FIG. 26E: IL-2). FIGS. 27A-27D summarize the results from 4-7 such studies performed for 48 and 96 hours that included DART-A-WT. FIGS. 27A-27C provide comparative plots of the cytotoxicity (CTL) activity at 48 and 96 hours from four such studies (FIG. 27A: CTL activity $EC_{50}$ values in pM; FIG. 27B: CTL activity as a multiple of the $EC_{50}$ value of CD123-WT, FIG. 27C: CTL activity Emax as a percent of CD123-WT). FIG. 27D plots the Therapeutic Index for CTL Activity against the cytokine IL-2.

FIG. 26A shows that while CD123×CD3 Binding Molecules comprising different CD3 mAb 1 variants exhibited markedly different cytotoxicity curves with CD123-M13, CD123-M17, CD123-M18 and CD123-M19, they are able to reach a similar maximum cytotoxicity. As was seen above, each of the variants mediated lower cytokine responses. For example, as seen in FIGS. 26B-26D, although CD123-M13, CD123-M17, CD123-M18 and CD123-M19 exhibited levels of maximal cytotoxicity that were similar to those exhibited by CD123-WT, the levels of cytokines IFN-α, TNF-α, IL-6 and IL-2 released were significantly less than the level observed with CD123-WT treatment. Thus, each of the diabody molecules comprising the CD3 mAb 1 variants M13, M17, M18 and M19 were found to be able to provide a therapeutic value that was comparable to that of diabody constructs comprising wild-type CD3 mAb 1, but with less attending side effects.

The results shown in FIG. 27A-27C further demonstrate that CD123-M13, CD123-M17, CD123-M18 and CD123-M19 exhibit marked different cytotoxicity $EC_{50}$ values but reach a maximum CTL activity that is comparable to CD123-WT and DART-A-WT. Using IL-2 as a representative cytokine, a Therapeutic Index (TI) was determined as follows:

$$TI = E_{max}(CTL) : E_{max}(cytokine)$$

The calculated TI values normalized to the values for CD123-WT are plotted in FIG. 27D and further demonstrate that DA×CD3 Binding Molecules comprising the CD3 mAb 1 variants M13, M17, M18 and M19 exhibit an enhanced TI over those comprising wild-type CD3 mAb 1.

Figure 13A:
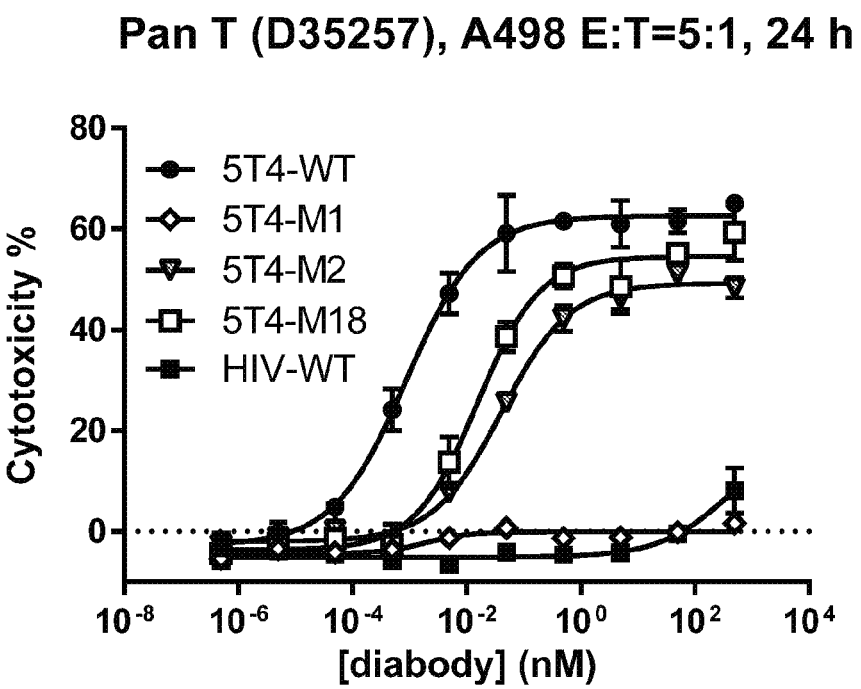
FIGS. 13A-13Q show the results of representative studies of redirected cell killing (CTL assay) mediated by 5T4×CD3 DART B-type diabody constructs (possessing Fc Domains) 5T4-WT (FIGS. 13B, 13F, 13J and 13N), 5T4-M2 (FIGS. 13C, 13G, 13K and 13O), 5T4-M18 (FIGS. 13D, 13H, 13L and 13P), HIV-WT (FIGS. 13E, 13I, 13M and 13Q), using Pan-T effector cells and A498 renal cell carcinoma target cells (E:T=5:1, 24 h). Cytotoxicity is plotted in FIG. 13A. Cytokine responses and percent cytotoxicity are plotted in FIGS. 13B-13Q (FIGS. 13B-13E: IFN-gamma.
Figure 13B:
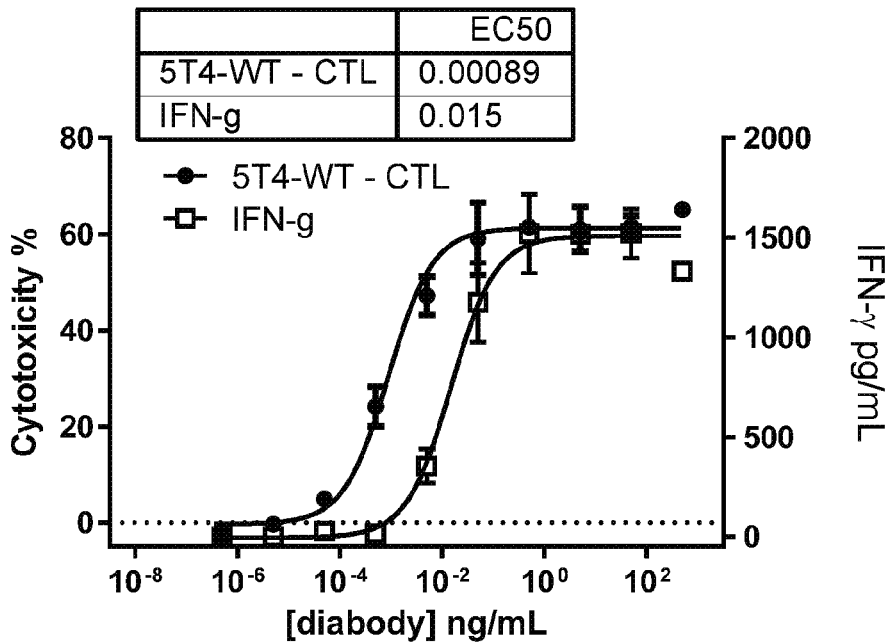
Figure 13C:
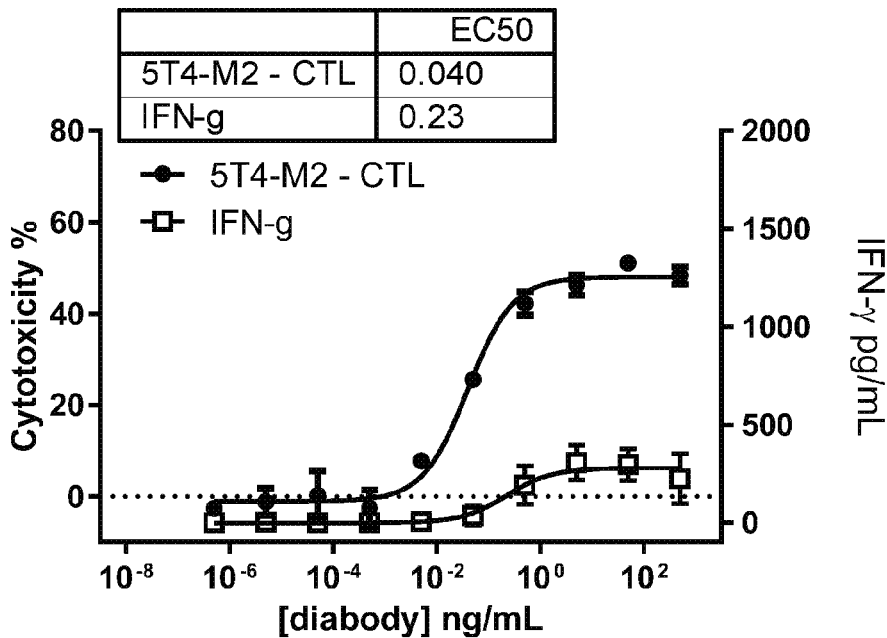
Figure 13D:
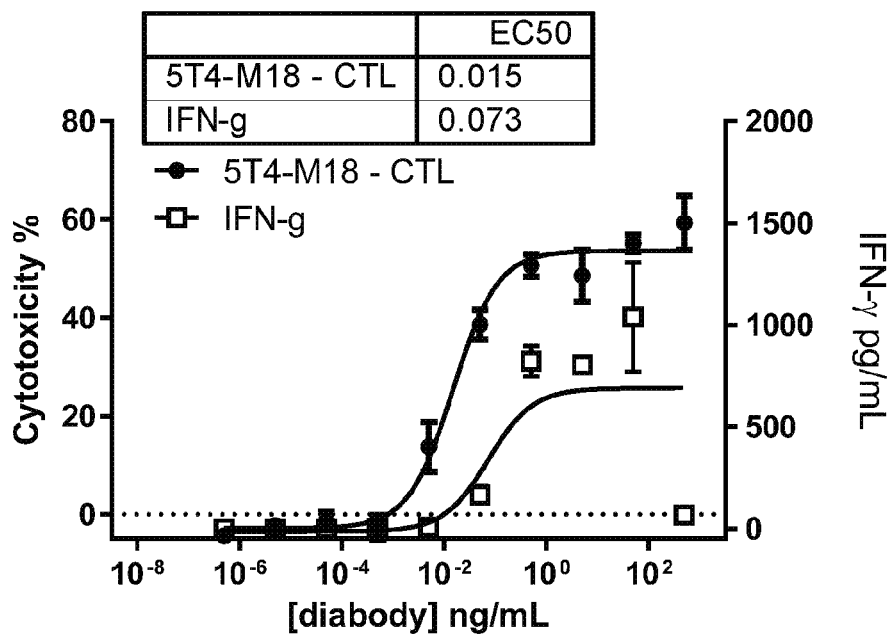
Figure 13E:
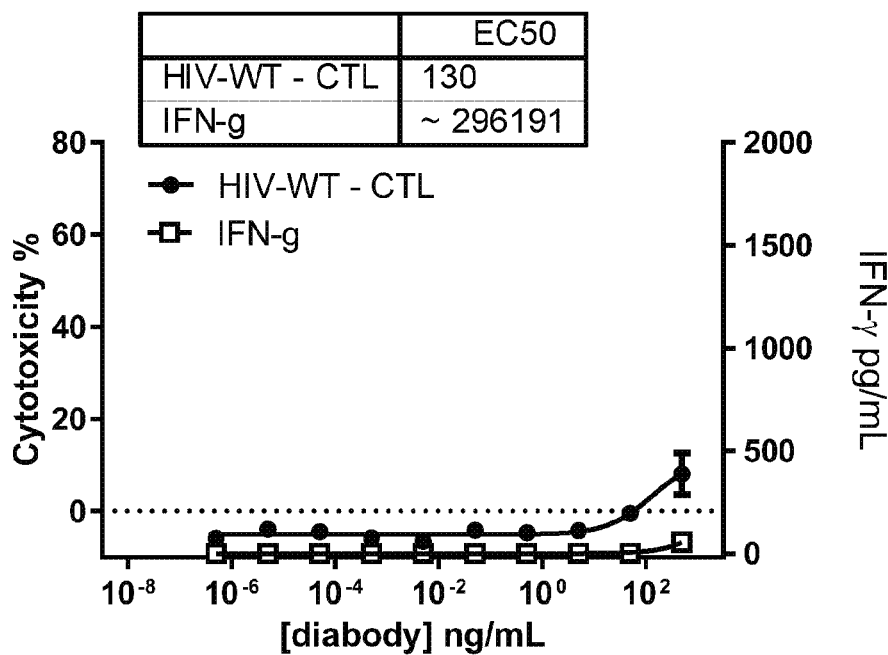
Figure 13F:
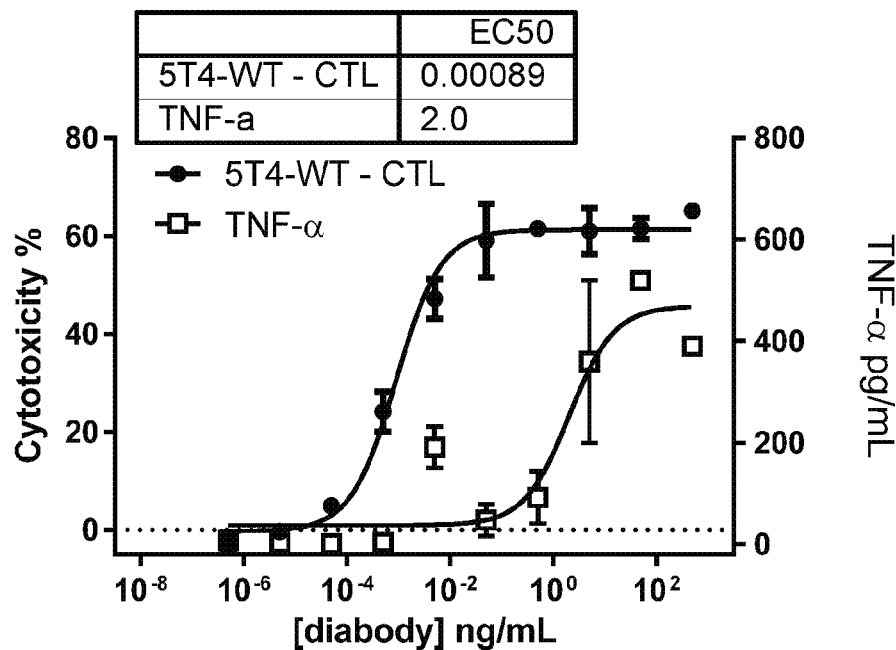
FIGS. 13F-13I: TNF-alpha.
Figure 13G:
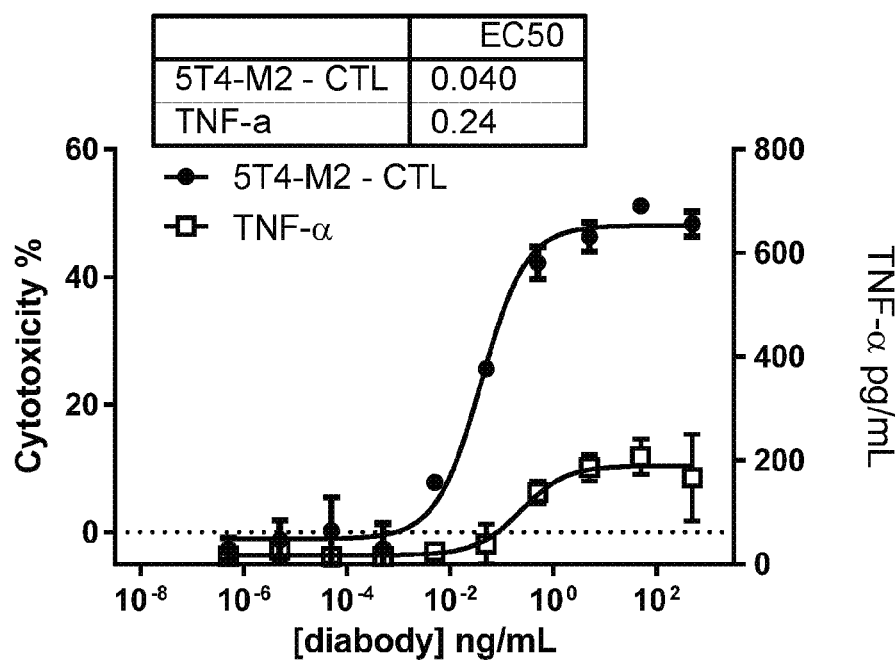
Figure 13H:
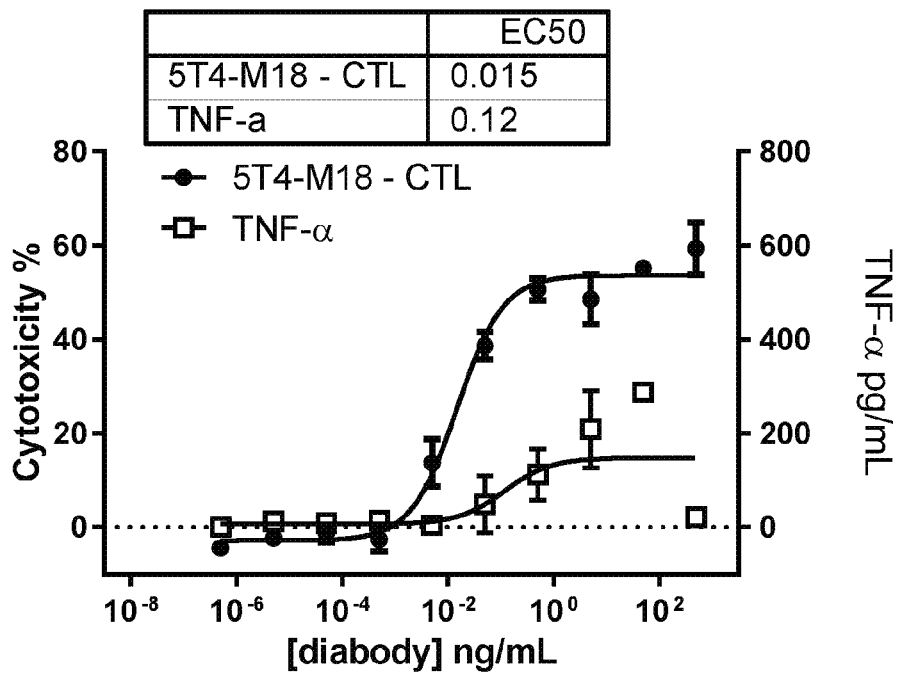
Figure 13I:
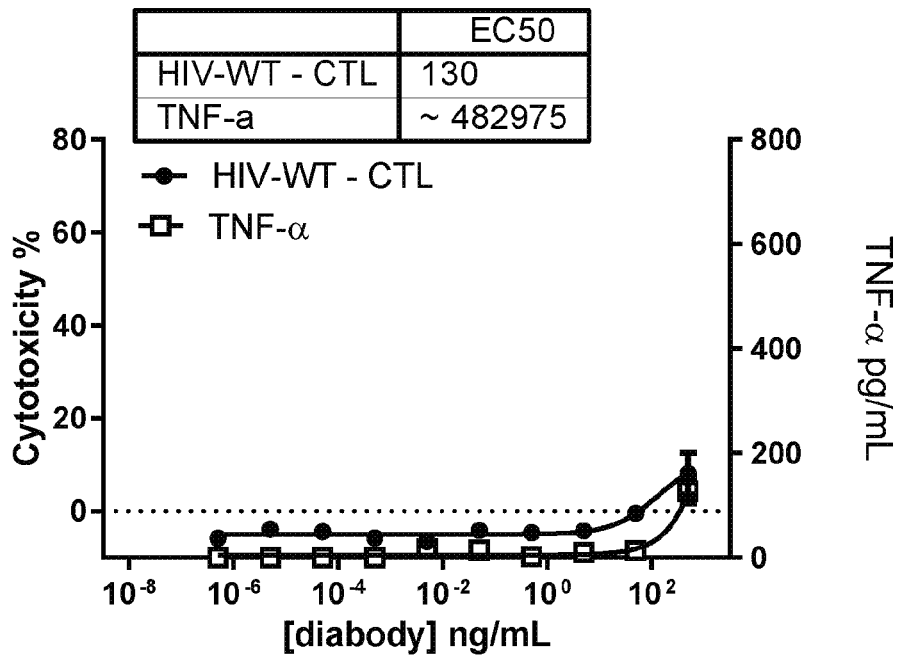
Figure 13J:
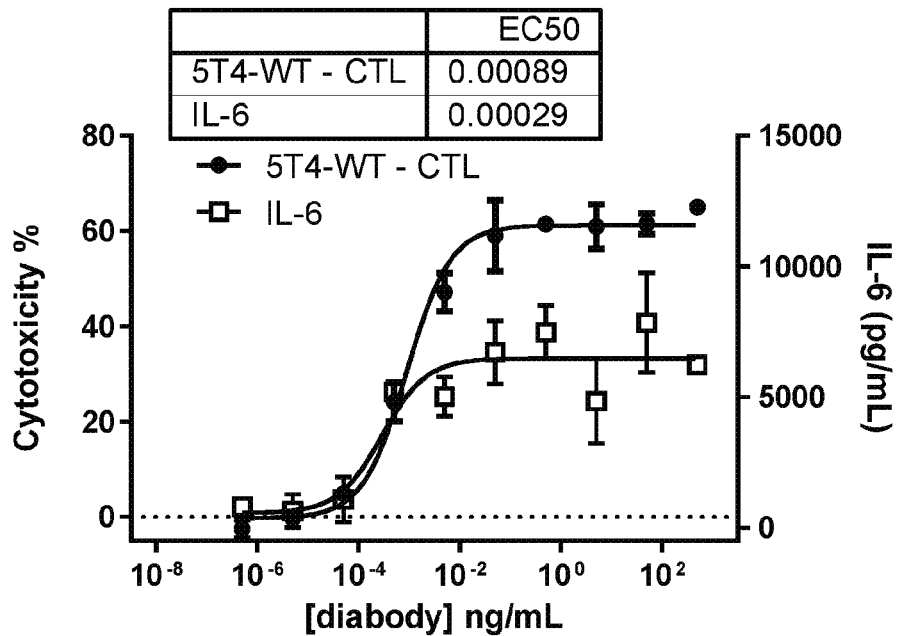
FIGS. 13J-13M: IL-6.
Figure 13K:
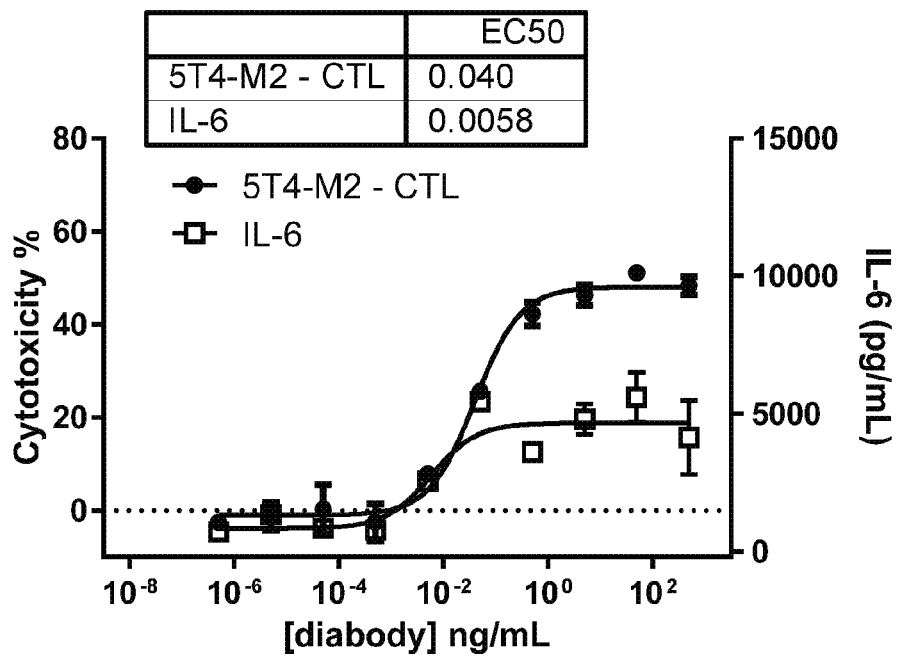
Figure 13L:
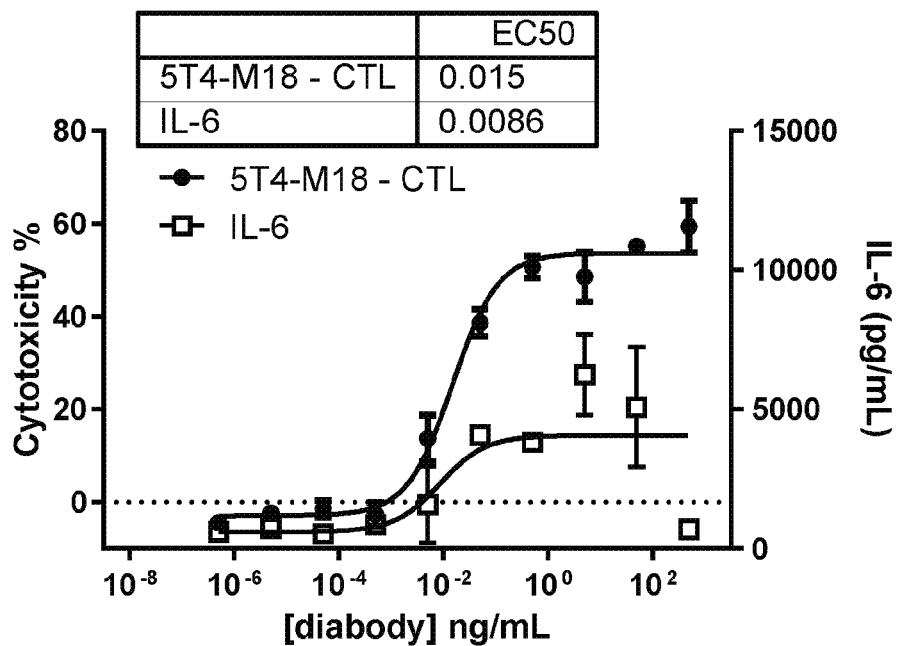
Figure 13M:
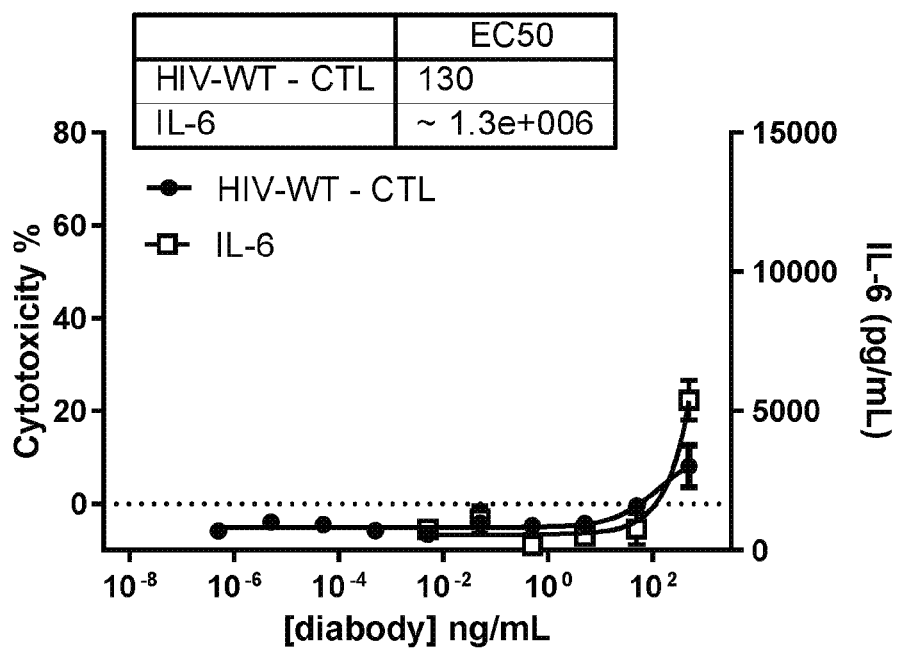
Figure 13N:
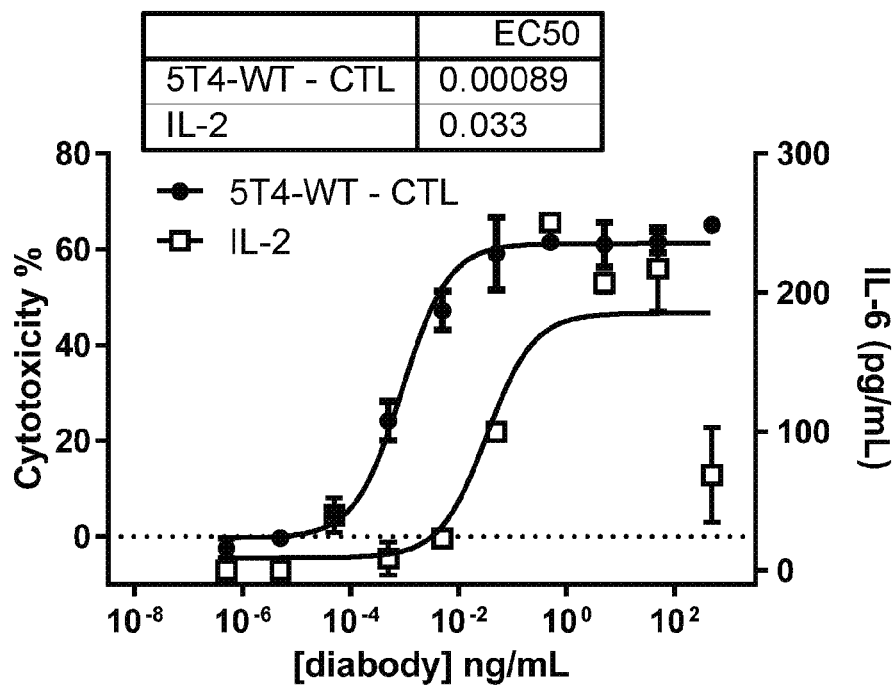
Figure 13O:
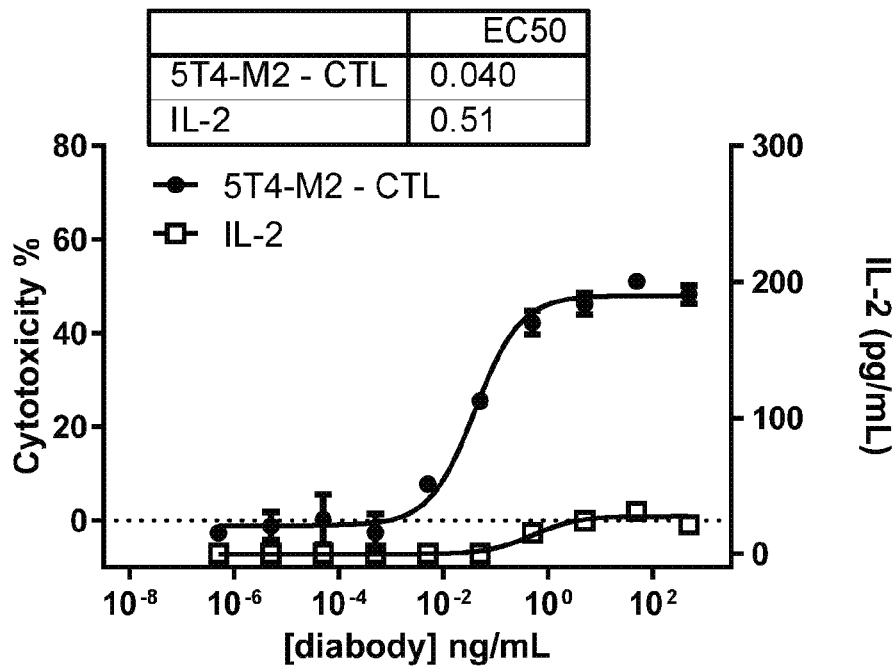
Figure 13P:
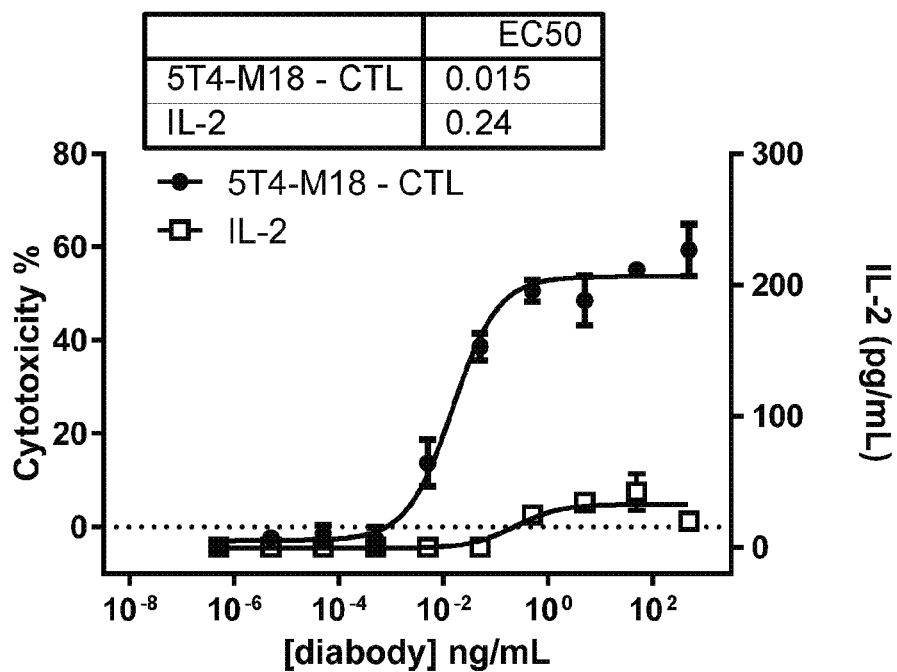
Figure 13Q:
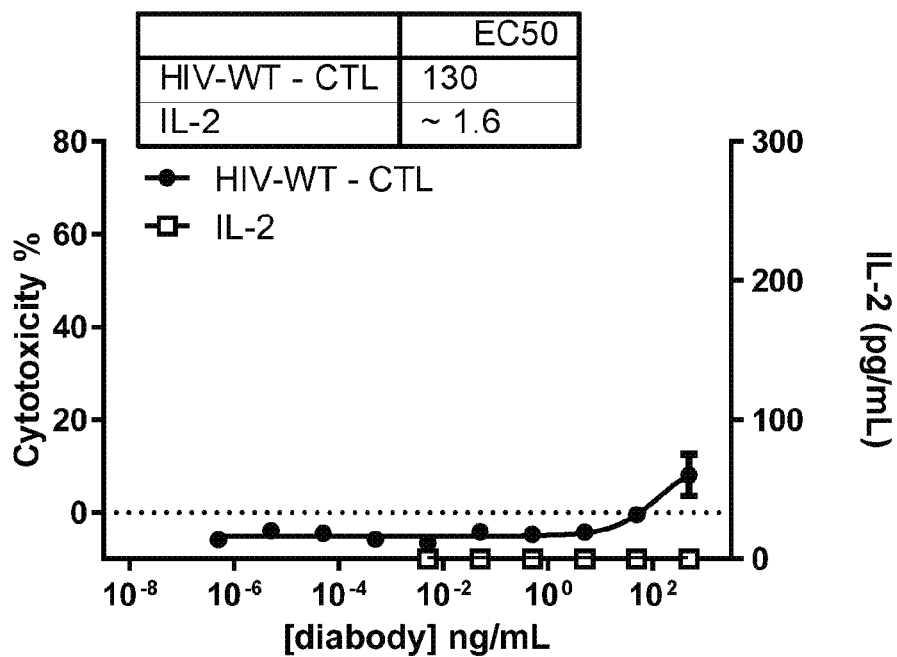

FIGS. 13A-13Q show the results of representative studies of redirected cell killing mediated by 5T4×CD3 DART B-type diabody constructs (possessing Fc Domains,) 5T4-WT, 5T4-M1, 5T4-M2, and 5T4-M18, using Pan-T effector cells and A498 renal cell carcinoma target cells (E:T=5:1, 24 h). Percent cytotoxicity is plotted in FIG. 13A. Cytokine responses and cytotoxicity are plotted in FIGS. 13B-13Q (FIGS. 13B-13E: IFN-gamma; FIGS. 13F-13I: TNF-alpha; FIGS. 13J-13M: IL-6; FIGS. 13N-13Q: IL-2). FIGS. 13B, 13F, 13J and 13N: 5T4-WT; FIGS. 13C, 13G, 13K and 13O: 5T4-M2; FIGS. 13D, 13H, 13L and 13P: 5T4-M18; FIGS. 13E, 13I, 13M and 13Q: HIV-WT (Negative Control). Cytotoxicity was also observed against JIMT-1 breast carcinoma cells. These results demonstrate that 5T4-WT and 5T4-M18 exhibit similar levels of maximal cytotoxicity, but markedly different cytokine responses, with 5T4-M18 exhibiting significantly reduced levels of cytokine release as compared to 5T4-WT.

Figure 14A:
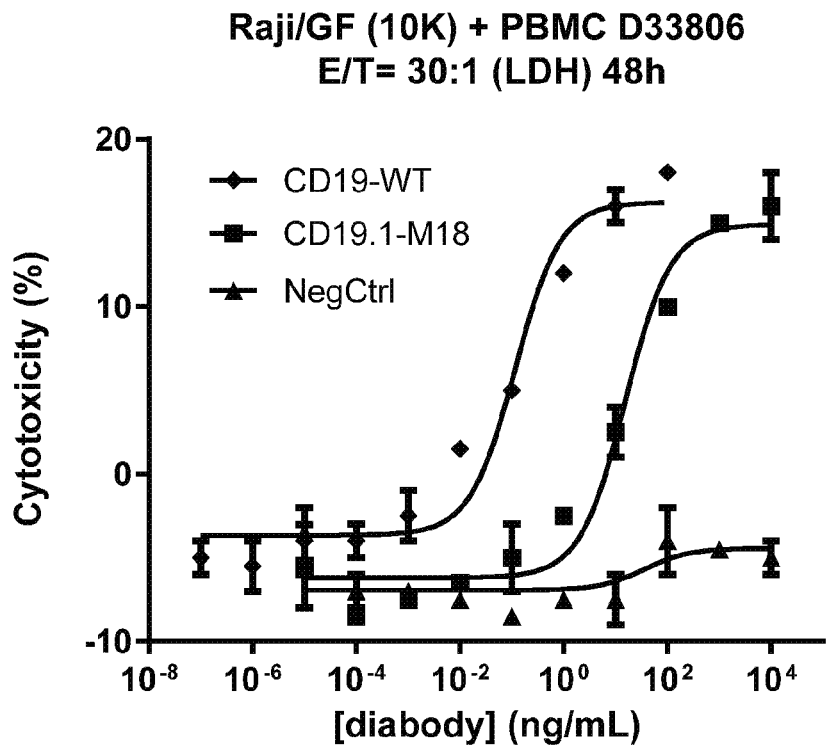
FIGS. 14A-14J show the results of representative studies of redirected cell killing (CTL assay) mediated by CD19× CD3 DART B-type diabody constructs (possessing Fc Domains) using PBMCs (FIGS. 14A-14E) or Pan-T effector cells (FIGS. 14F-14J) (E:T=30:1 for PBMCs and 10:1 for Pan-T-cells, 24-48 h). Percent cytotoxicity (48 hrs) is plotted in FIG. 14A (PBMCs) and FIG. 14F (Pan-T-cells). Cytokine responses at 48 hours using PBMCs are plotted in FIGS. 14B-14E (PBMCs) and FIGS. 14G-14J (Pan T-cells) (FIGS. 14B and 14G: IFN-gamma.
Figure 14B:
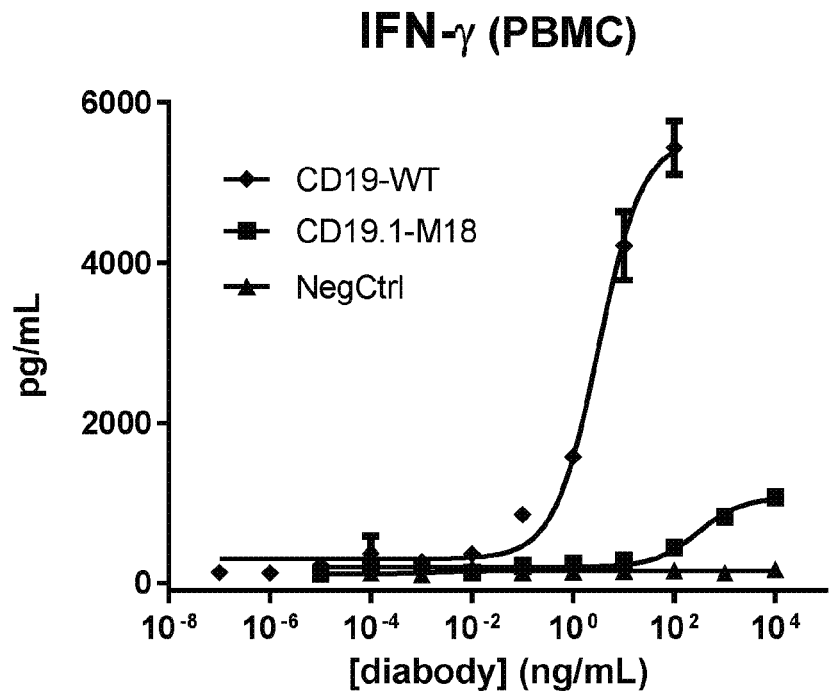
Figure 14C:
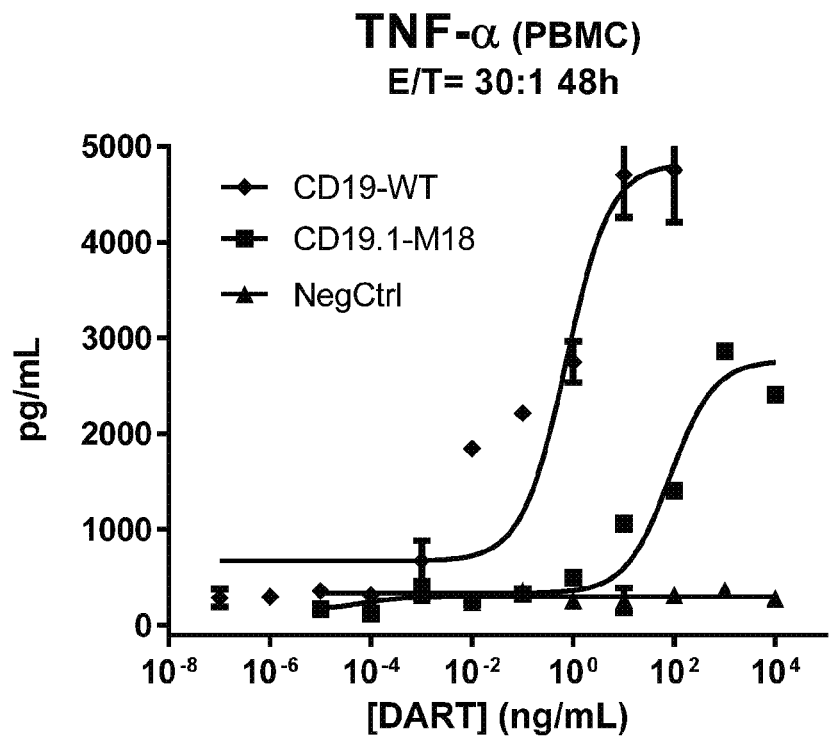
Figure 14D:
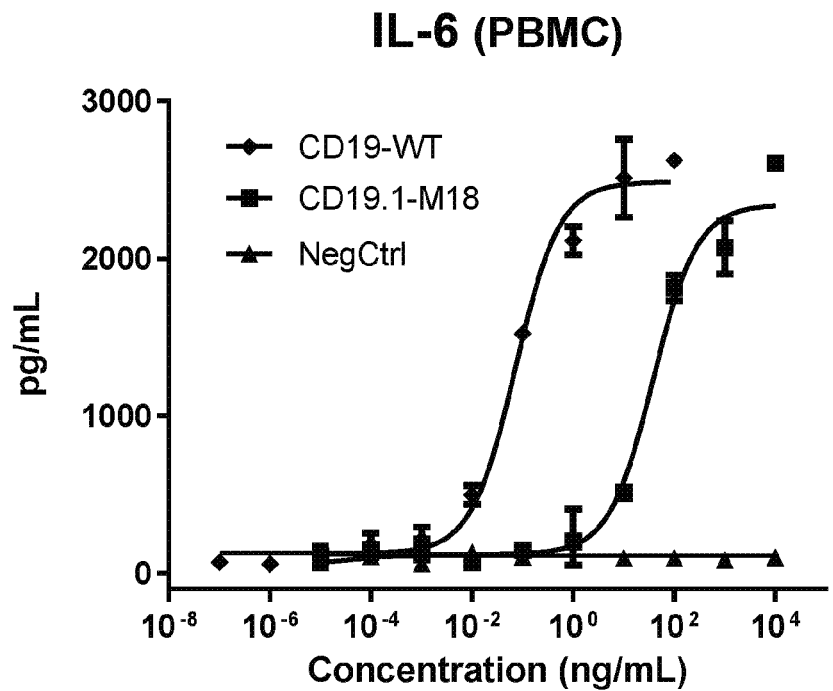
Figure 14E:
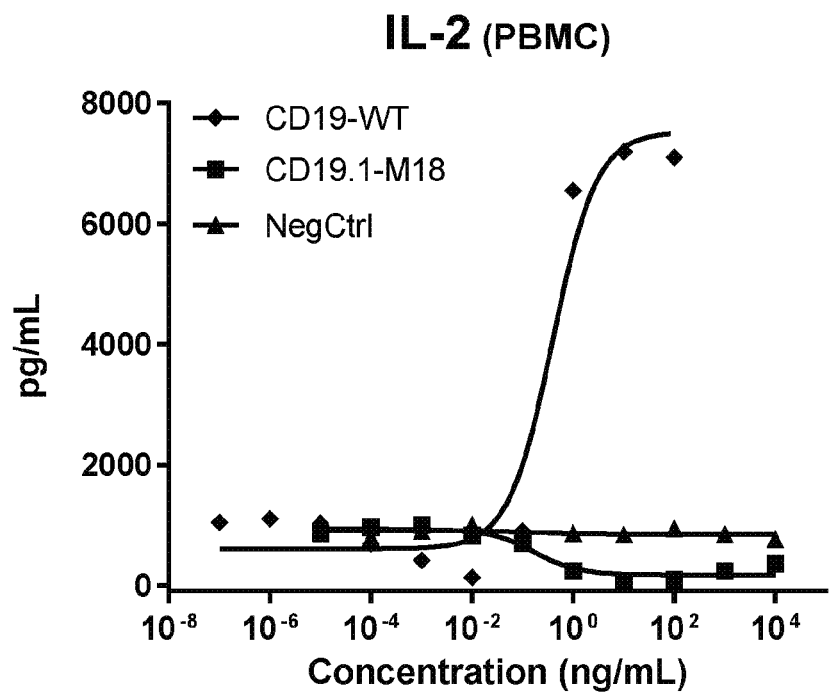
Figure 14F:
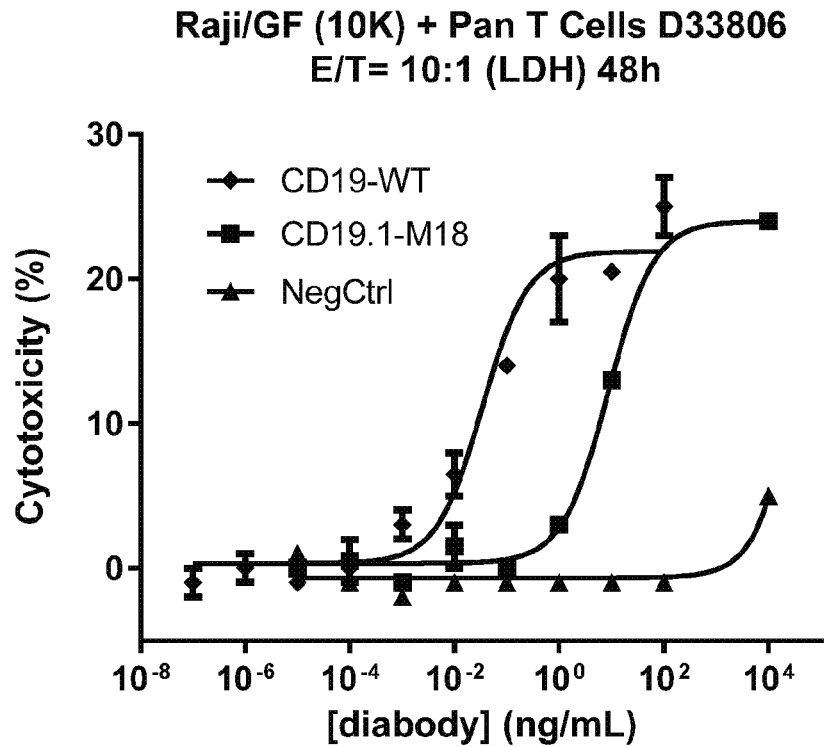
Figure 14G:
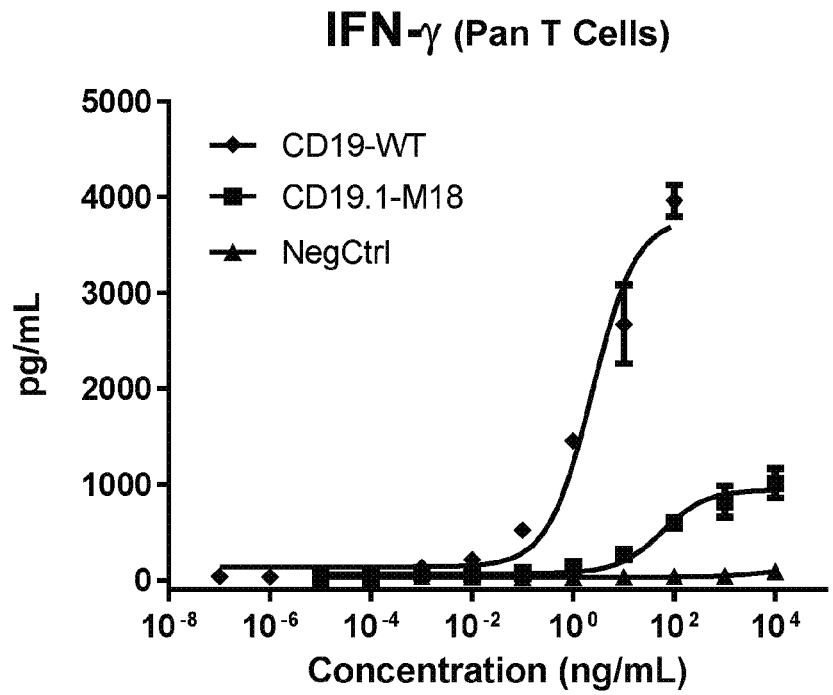
Figure 14H:
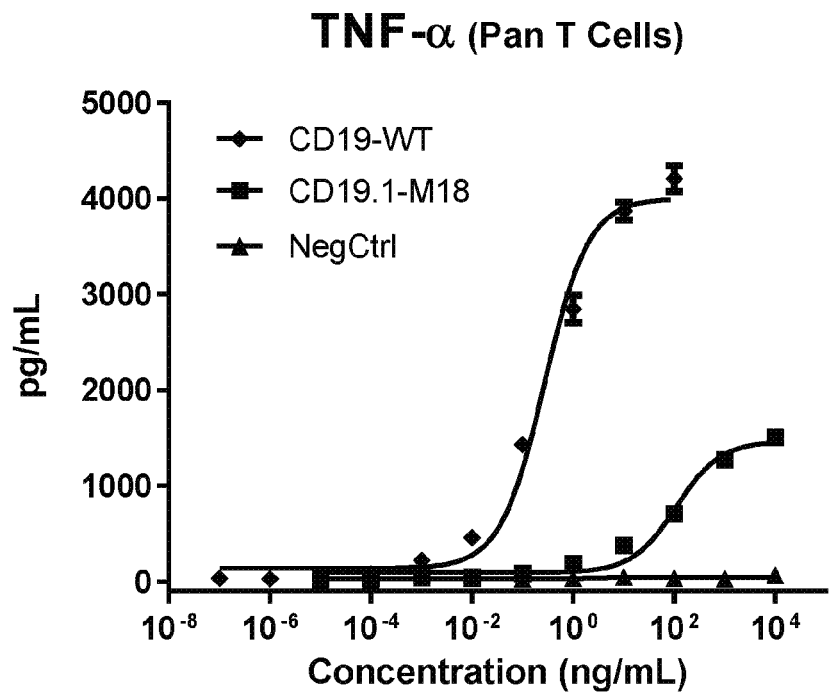
Figure 14I:
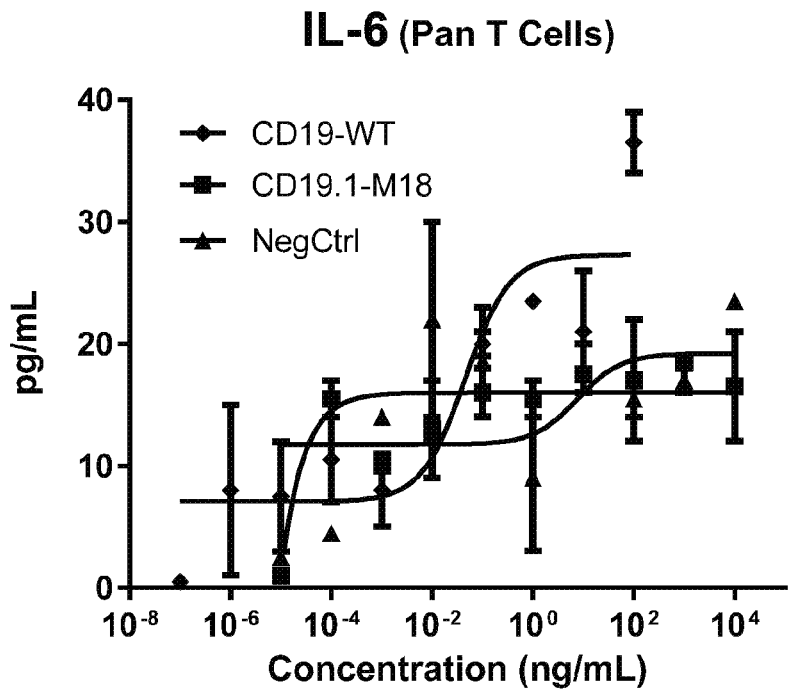
Figure 14J:
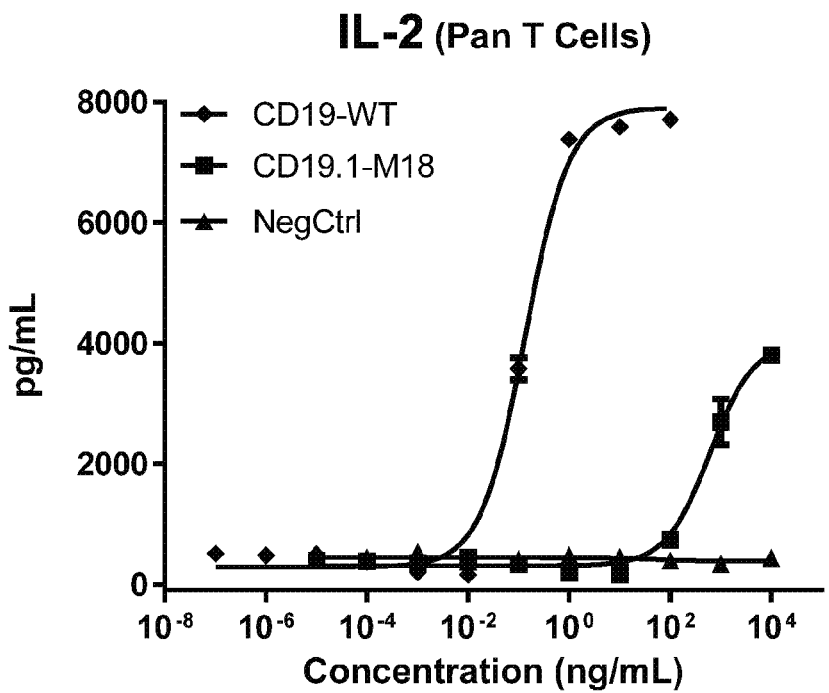
Figure 15A:
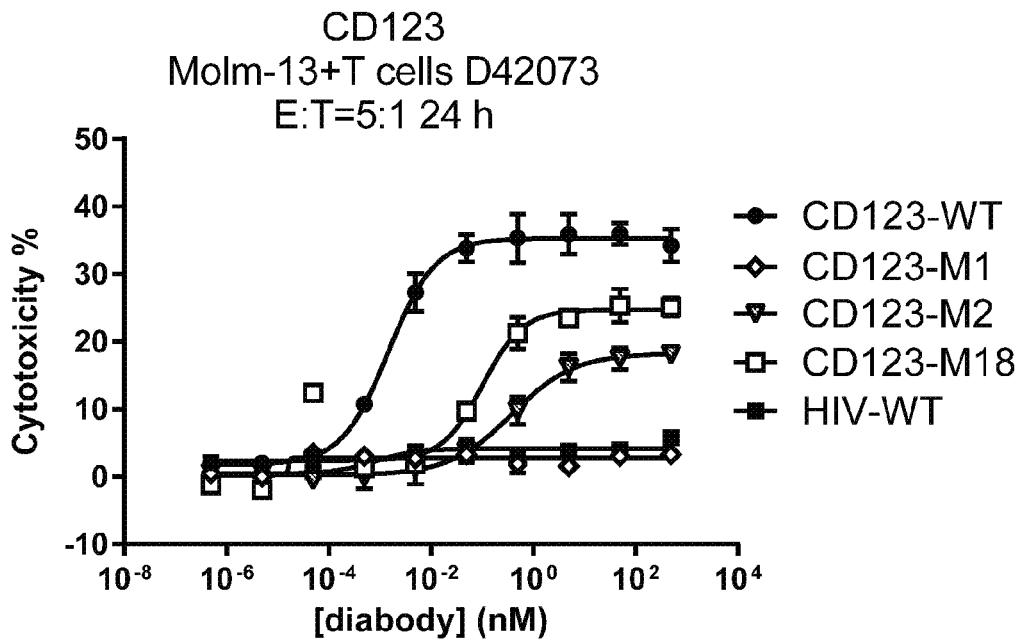
FIGS. 15A-15E show the ability of representative CD123×CD3 DART-B-type diabodies to mediate T-cell activation. T-cell activation was measured by evaluating the ability of the diabodies to affect expression of CD25 and CD69. Percent cytotoxicity is plotted in FIG. 15A. Activation of CD4$^+$ T-cells as determined by measuring CD25 is plotted in FIG. 15B. Activation of CD4$^+$ T-cells as determined by measuring CD69 is plotted in FIG. 15C Activation of CD8$^+$ T-cells as determined by measuring CD25 is plotted in FIG. 15D. Activation of CD8$^+$ T-cells as determined by measuring CD69 is plotted in FIG. 15E.
Figure 15B:
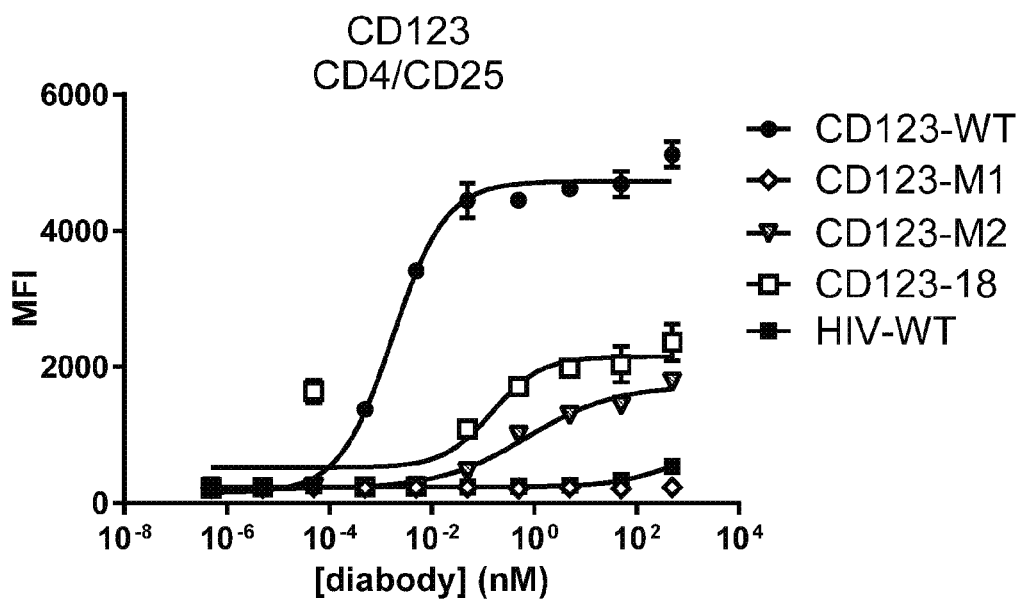
Figure 15C:
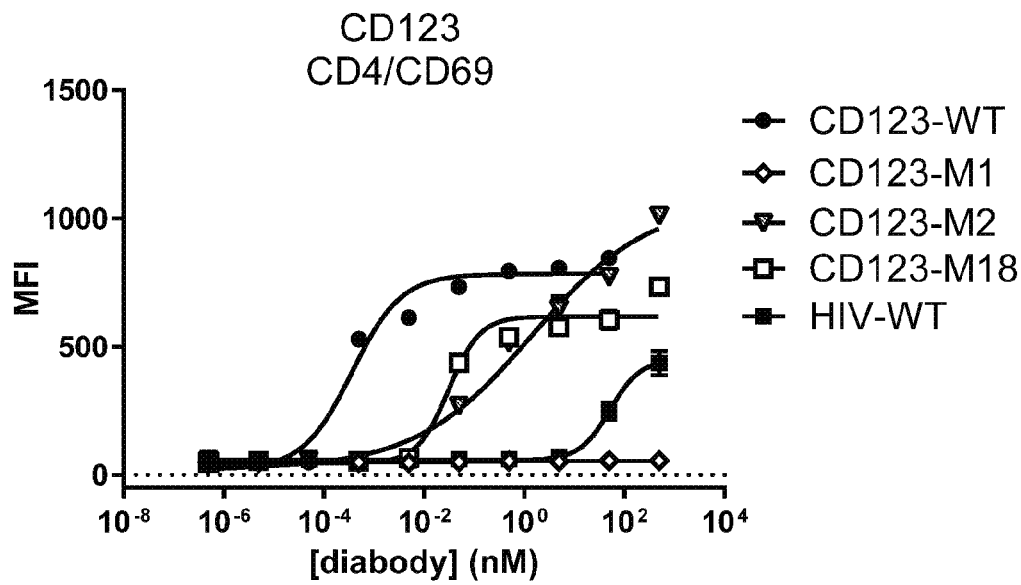
Figure 15D:
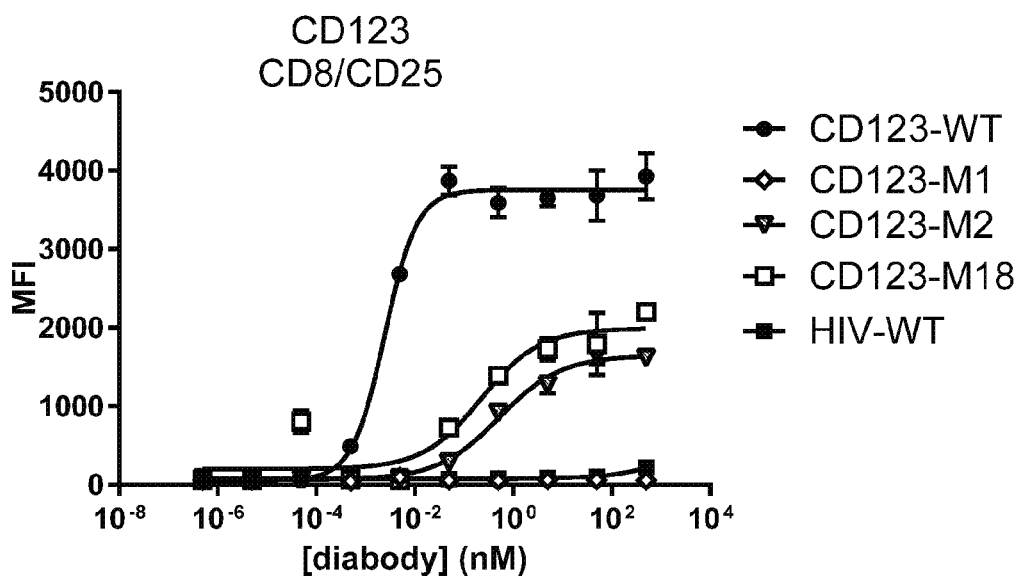
Figure 15E:
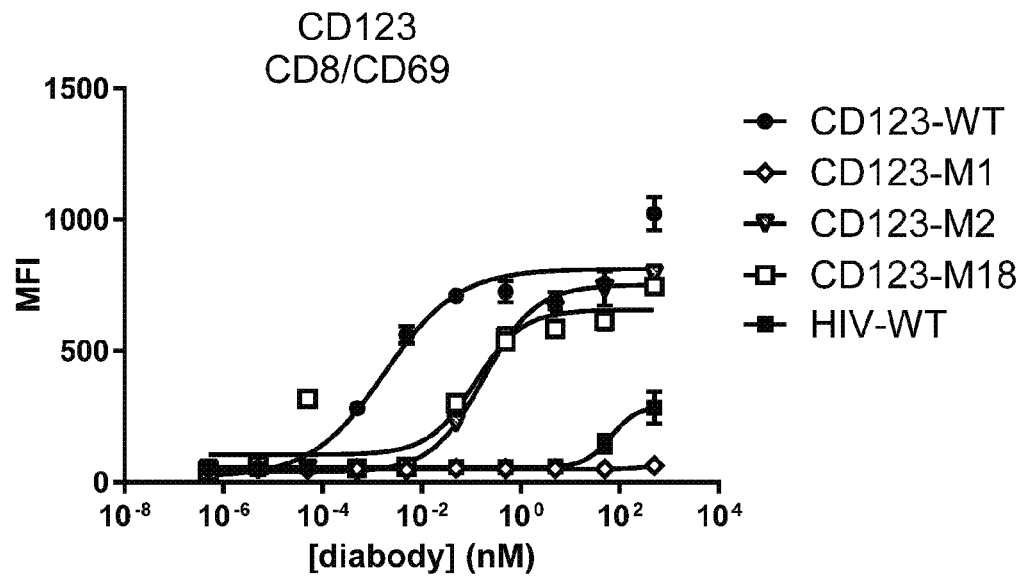
Figure 16A:
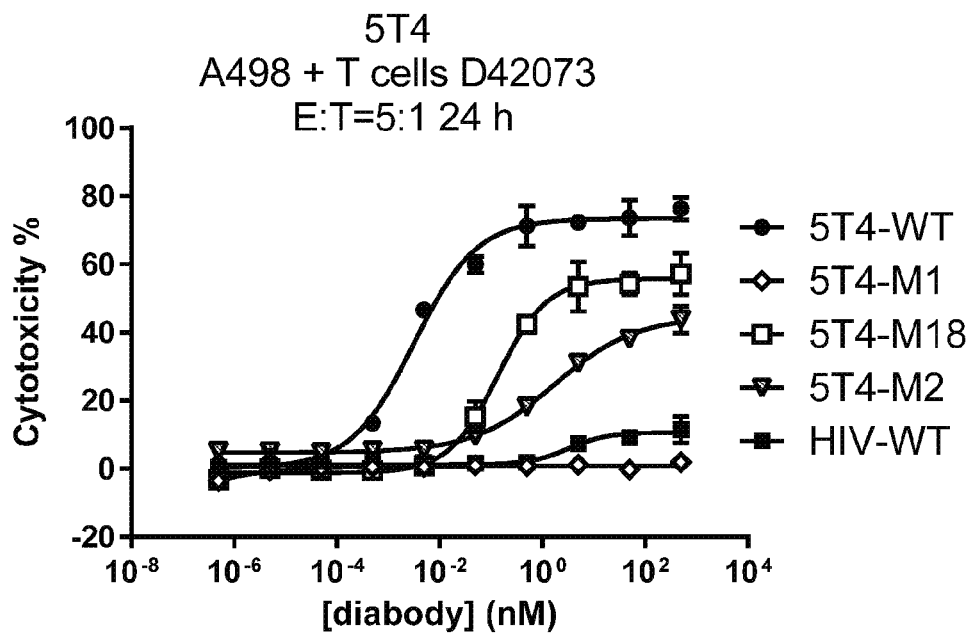
FIGS. 16A-16E show the ability of representative 5T4× CD3 DART-B-type diabodies to mediate T-cell activation. T-cell activation was measured by evaluating the ability of the diabodies to affect expression of CD25 and CD69. Percent cytotoxicity is plotted in FIG. 16A. Activation of CD4$^+$ T-cells as determined by measuring CD25 is plotted in FIG. 16B. Activation of CD4$^+$ T-cells as determined by measuring CD69 is plotted in FIG. 16C. Activation of CD8$^+$ T-cells as determined by measuring CD25 is plotted in FIG. 16D. Activation of CD8$^+$ T-cells as determined by measuring CD69 is plotted in FIG. 16E.
Figure 16B:
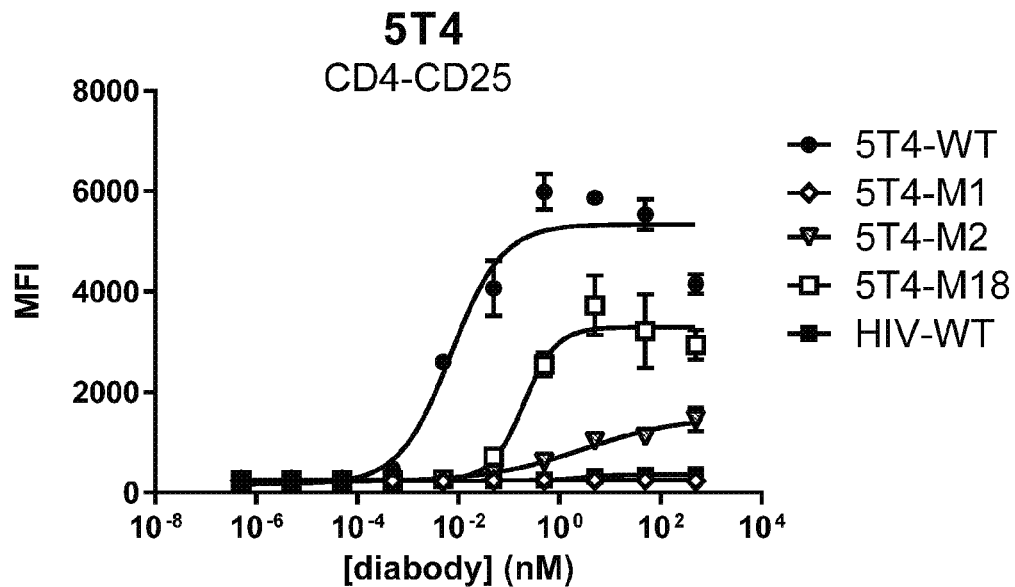
Figure 16C:
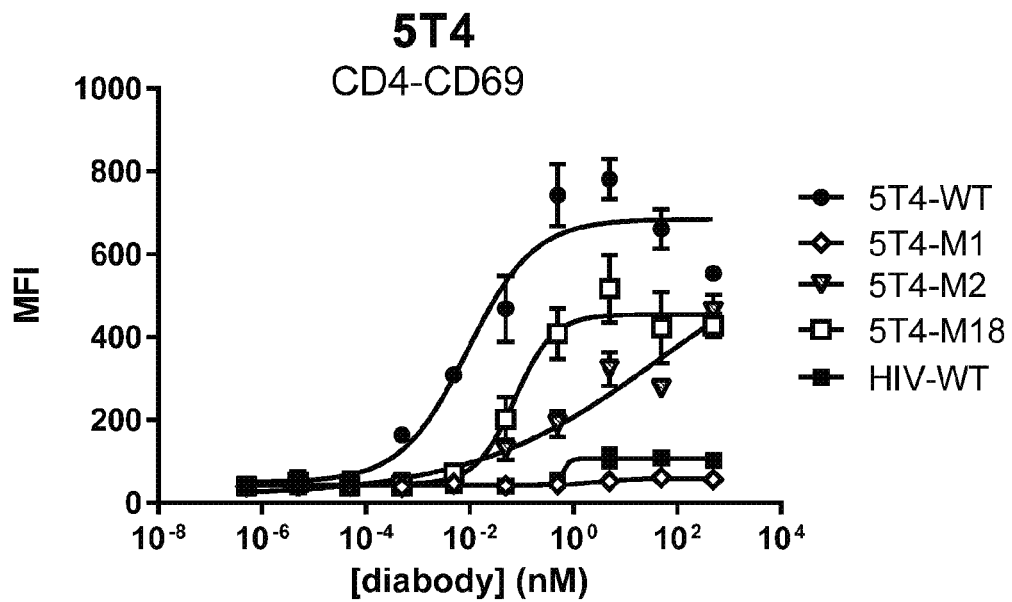
Figure 16D:
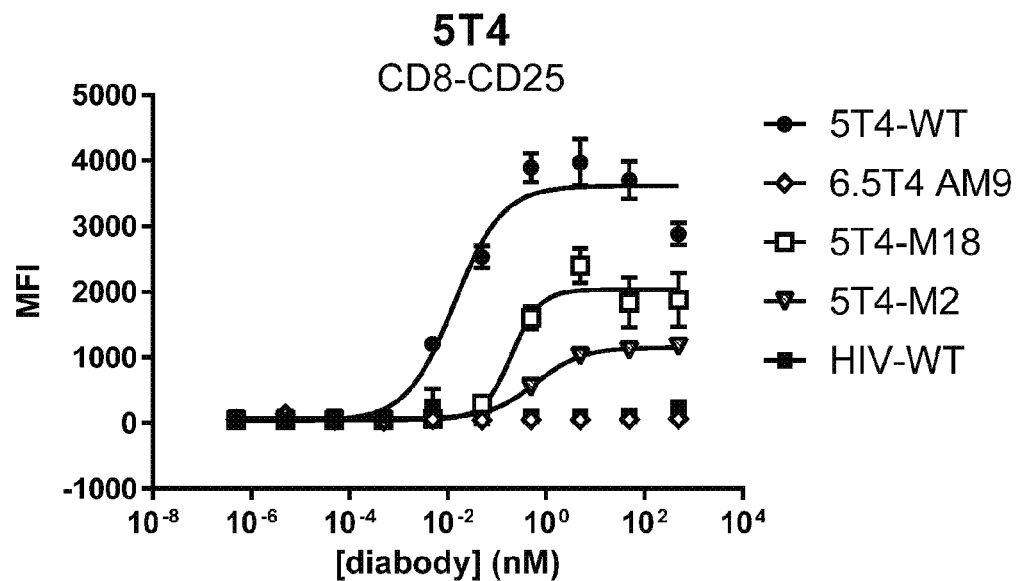
Figure 16E:
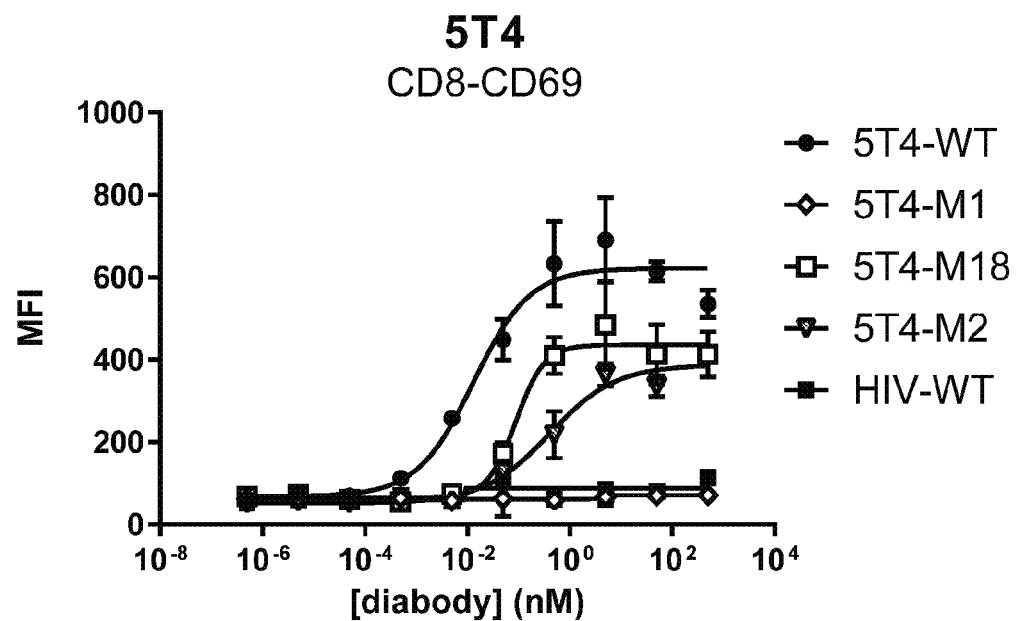

FIGS. 14A-14J show the results of representative studies of redirected cell killing mediated by CD19×CD3 DART B-type diabody constructs (possessing Fc Domains), CD19-WT, and CD19.1-M18, using Pan-T, or PBMC effector cells and Raji lymphoblastoid target cells (E:T=30:1 for PBMCs and 10:1 for Pan-T-cells, 24-48 h). Percent cytotoxicity (48 hrs) is plotted in FIG. 14A (PBMCs) and FIG. 14F (Pan-T-cells). Cytokine responses at 48 hours using PBMCs are plotted in FIGS. 14B-14E (PBMCs) and FIGS. 14G-14J (Pan T-cells) (FIGS. 14B and 14G: IFN-gamma; FIGS. 14C and 14H: TNF-alpha; FIGS. 14D and 14I: IL-6; FIGS. 14E and 14J: IL-2; HIV-M18 (Negative control)). CD19.1-M18 exhibited similar cytotoxicity and reduced cytokine release against Daudi target cells. These results demonstrate that CD19-WT and CD19.1-M18 exhibit similar levels of maximal cytotoxicity, but markedly different cytokine responses with CD19.1-M18 exhibiting significantly reduced levels of cytokine release as compared to CD19-WT.

The results of the above studies confirm that constructs comprising the CD3 mAb 1 M18 variant exhibited higher cytotoxic (CTL) activity in CTL assays than those comprising the M1 and M2 variants. The CTL studies also indicate that constructs comprising the M18 variant exhibited lower cytokine responses as compared to WT, and similar to or only slightly above those exhibited by the less active M2 variant. Thus, the M18 variant appears to have a larger window for CTL active vs cytokine release.

Example 7

Ability of Exemplary DART-B-Type Diabodies to Mediate T-Cell Activation

The ability to mediate T-cell activation measured by evaluating the ability of the diabodies to affect expression of CD25 and CD69, which are markers of T-cell activation, on CD4$^+$ and CD8$^+$ T-cell populations. The T-cell populations were obtained from CTL assays, which were performed essentially as described above. Where indicated, CD4+ and CD8+ T lymphocyte populations were assessed for up-regulation of the activation markers CD69 and CD25 by flow cytometry at the end of the CTL assay.

Representative data for CD123×CD3 DART-B-type diabody constructs is shown in FIGS. 15A-15E. Cytotoxicity is plotted in FIG. 15A. Activation of CD4$^+$ T-cells as determined by measuring CD25 is plotted in FIG. 15B. Activation of CD4$^+$ T-cells as determined by measuring CD69 is plotted in FIG. 15C. Activation of CD8$^+$ T-cells as determined by measuring CD25 is plotted in FIG. 15D. Activation of CD8$^+$ T-cells as determined by measuring CD69 is plotted in FIG. 15E.

Representative data for 5T4×CD3 DART-B-type diabody constructs is shown in FIGS. 16A-16E. Cytotoxicity is plotted in FIG. 16A. Activation of CD4$^+$ T-cells as determined by measuring CD25 is plotted in FIG. 16B. Activation of CD4+ T-cells as determined by measuring CD69 is plotted in FIG. 16C. Activation of CD8$^+$ T-cells as determined by measuring CD25 is plotted in FIG. 16D. Activation of CD8$^+$ T-cells as determined by measuring CD69 is plotted in FIG. 16E.

The results of these studies show that constructs comprising the CD3-M18 variant exhibited enhanced T-cell activation activity relative to constructs comprising the M1 and M2 variants.

Example 8

In Vivo Activity of Exemplary DART-B-Type Diabodies in Murine Models

The in vivo activity of the CD123×CD3 DART-B-type diabodies CD123-WT and CD123-M18 were evaluated in a co-mix KG1A cell AML model (E:T=1:5). Briefly, NOD/SCID mice (6 per group) were injected with KG1A (AML) cells co-mixed with activated human CD4+ or CD8+ T-cells (E:T=1:5) on Day 0. Vehicle control, CD123-WT (50 µg/kg), or CD123-M18 (5 µg/kg or 50 µg/kg) were subsequently administered. Tumor volume was monitored over the course of the study.

Figure 17A:
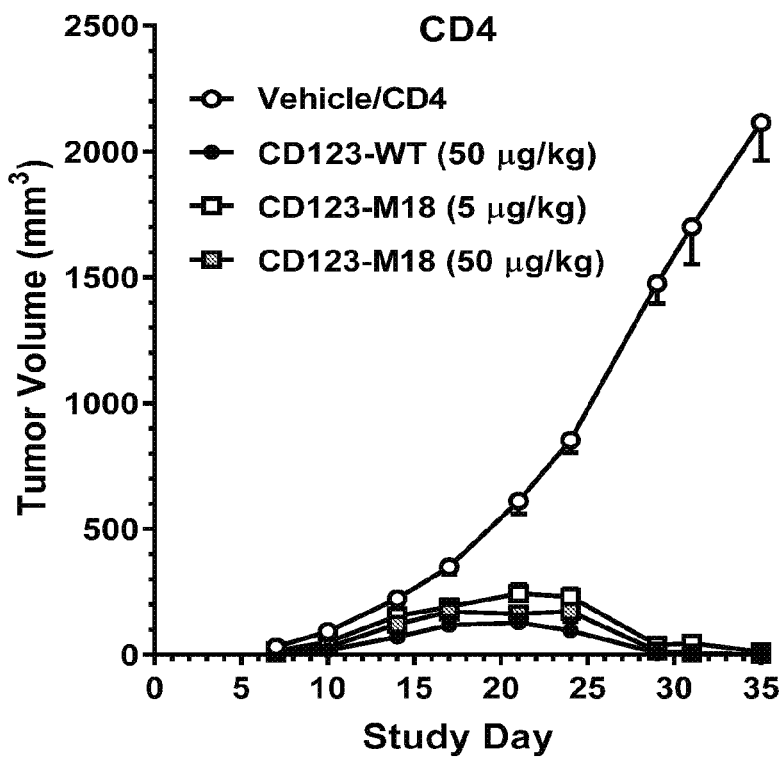
FIGS. 17A-17B show the results of in vivo studies on the ability of exemplary CD123×CD3 DART B-type diabody constructs to mediate the reduction of tumors in vivo. CD123-WT (50 µg/kg) or CD123-M18 (at 5 µg/kg or 50 µg/kg) were provided to mice that had received the KG1A cells, and tumor volume was assessed over 35 days.
Figure 17B:
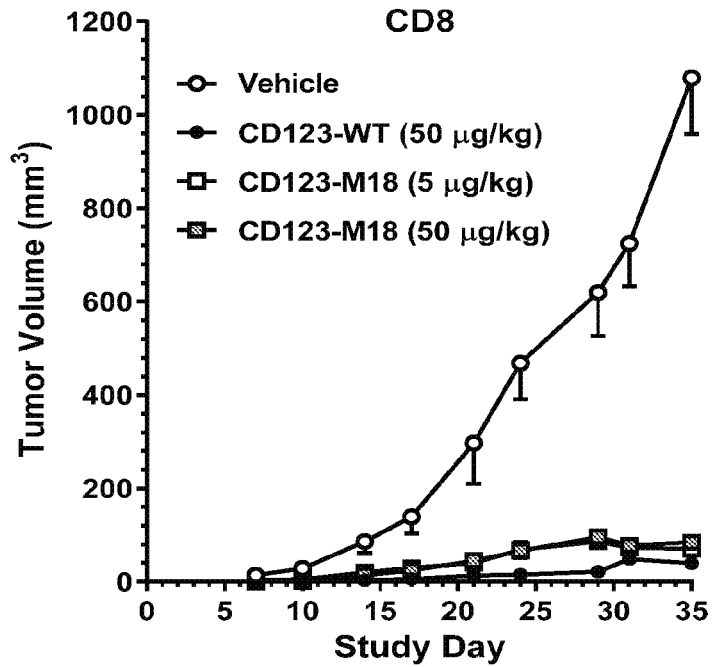

The results of this study are provided in FIG. 17A (CD4$^+$ T-cells) and FIG. 17B (CD8$^+$ T-cells). The results show that constructs comprising the M18 variant exhibited anti-tumor activity comparable to that of constructs comprising the WT CD3 Binding Domains.

A further study to evaluate the in vivo activity of the CD123×CD3 DART-B-type diabodies was performed using a reconstituted tumor model in which 5×10$^6$ KG1A (AML) cells were subcutaneously (SC) injected into MHCI$^{-/-}$ mice (5 female per group) on Day 0. On Day 9 1×10$^7$ PBMC cell were injected intraperitoneal (IP). Vehicle control, CD123-WT, CD123-M2 or CD123-M18 (each at 0.5, 5, 50, or 500 µg/kg) were administered intravenously (IV) twice a week (2QW) starting on Day 15. Tumor volume was monitored over the course of the study.

Figure 18A:
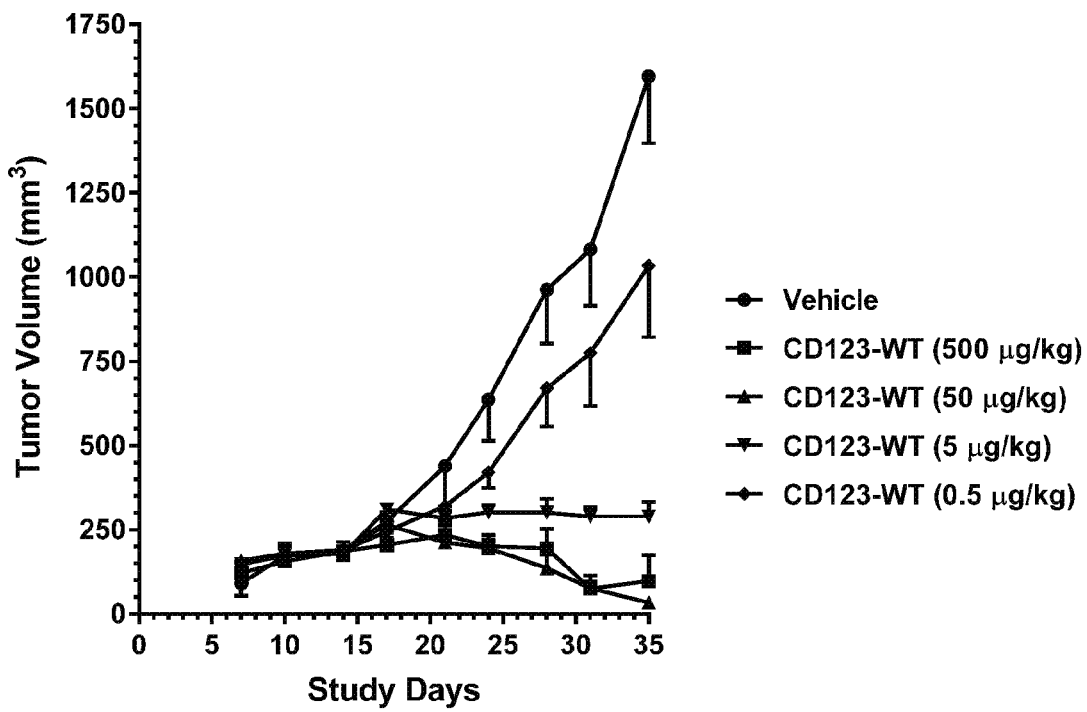
FIGS. 18A-18D show the results of in vivo studies on the ability of CD123×CD3 DART B-type diabody constructs to mediate the reduction of tumors in vivo. CD123-WT, CD123-M2 or CD123-M18 (at 0.5, 5 50, or 500 µg/kg) were provided to mice that had received the KG1A cells, and tumor volume was assessed over 35 days.
Figure 18B:
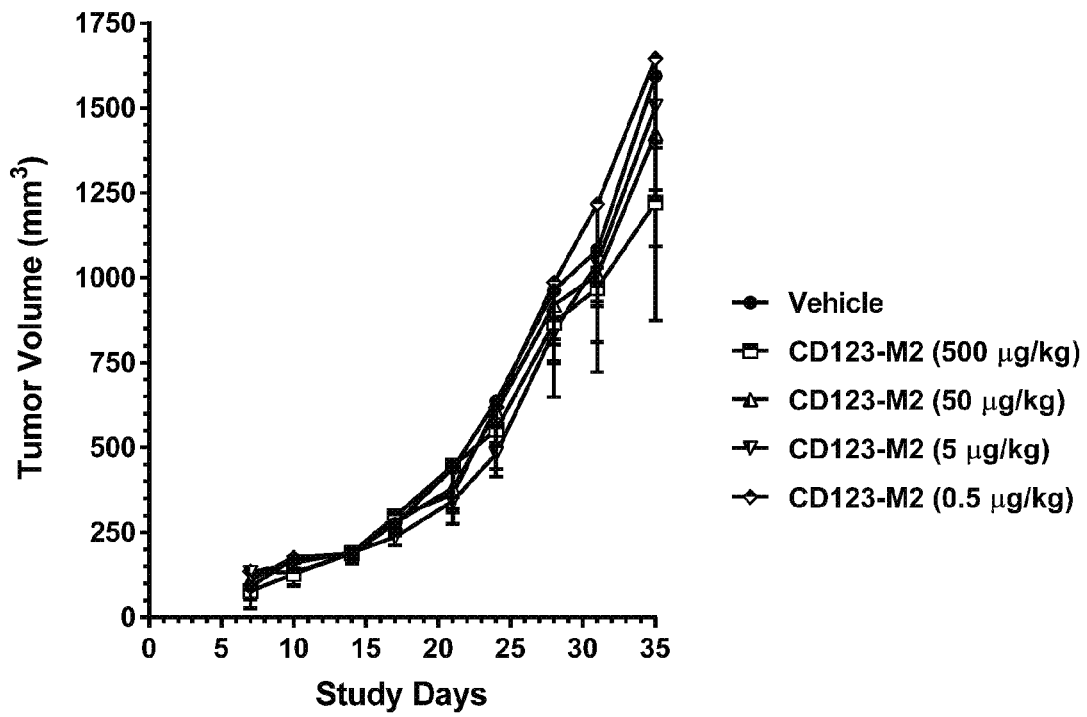
Figure 18C:
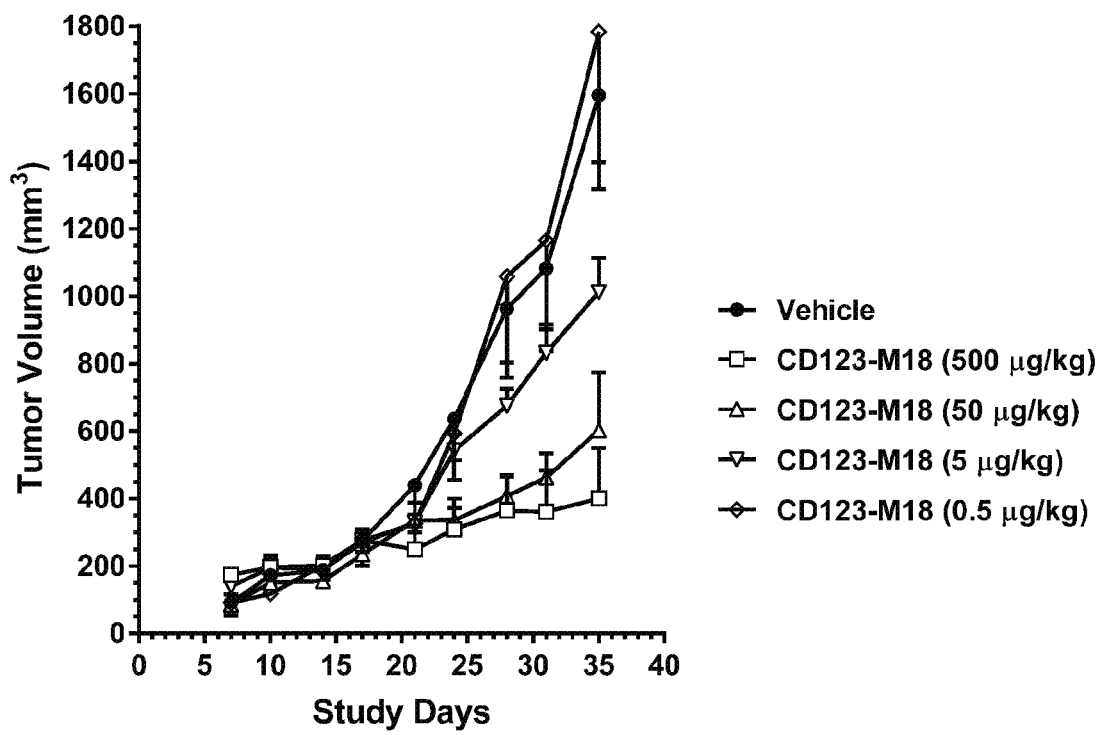
Figure 18D:
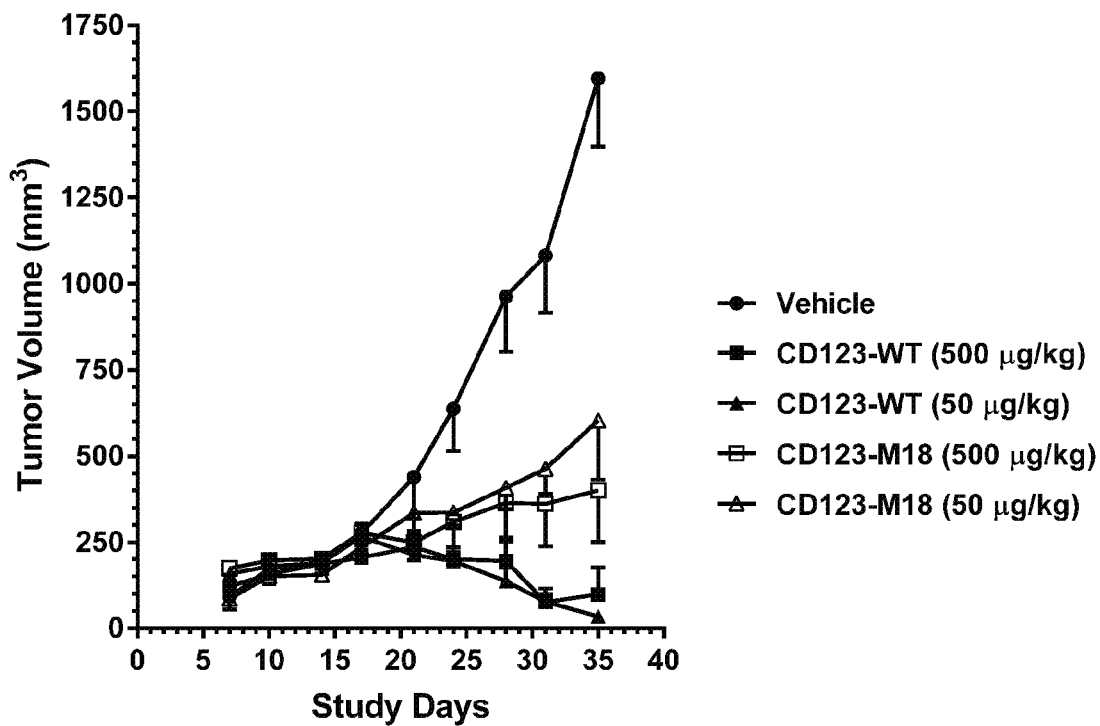

The results of this study are provided in FIGS. 18A-18D. The results show that CD123-M2 exhibited no activity in this model (FIG. 18B). In contrast, CD123-M18 (FIG. 18C) exhibited anti-tumor activity comparable to that of CD123-WT (FIG. 18A) particularly at 50 µg/kg and 500 µg/kg doses (FIG. 18D).

Another study to evaluate the in vivo activity of the CD123×CD3 DART-B-type diabodies was performed using a PBMC engraftment model in which 5×10$^6$ MV4-11 (leukemia) cells were injected SC and 1×10$^7$ PBMC cell were injected retro-orbitally (RO) into MHCI$^{-/-}$ mice (6 males per group) on Day 0. Vehicle control, CD123-WT (at 0.5, 5, 50, or 500 µg/kg), CD123-M18 or CD123-M2 (each at 5, 50, 500 or 1000 µg/kg) were administered intravenously (IV) twice a week (2QW) starting on Day 14. Tumor volume was monitored over the course of the study.

Figure 19A:
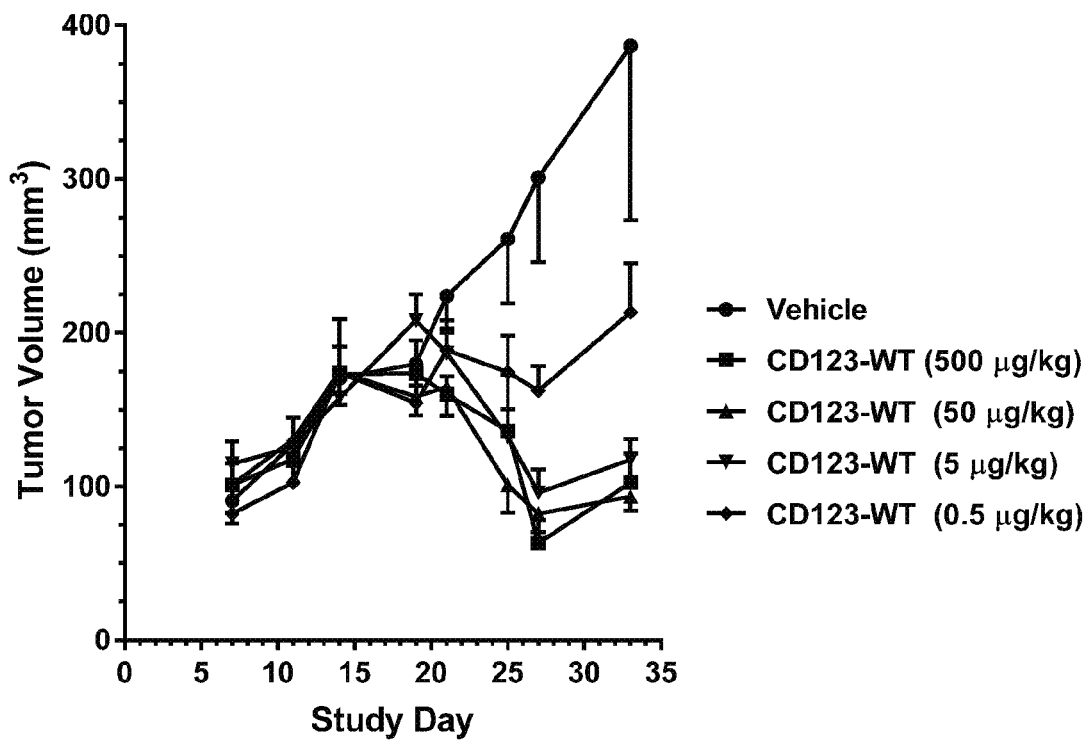
FIGS. 19A-19D show the results of in vivo studies on the ability of CD123×CD3 DART B-type diabody constructs to mediate the reduction of tumors in vivo. CD123-WT, CD123-M2 or CD123-M18 (at 0.5, 5 50, or 500 µg/kg) were provided to mice that had received the MV4-11 cells, and tumor volume was assessed over 35 days.
Figure 19B:
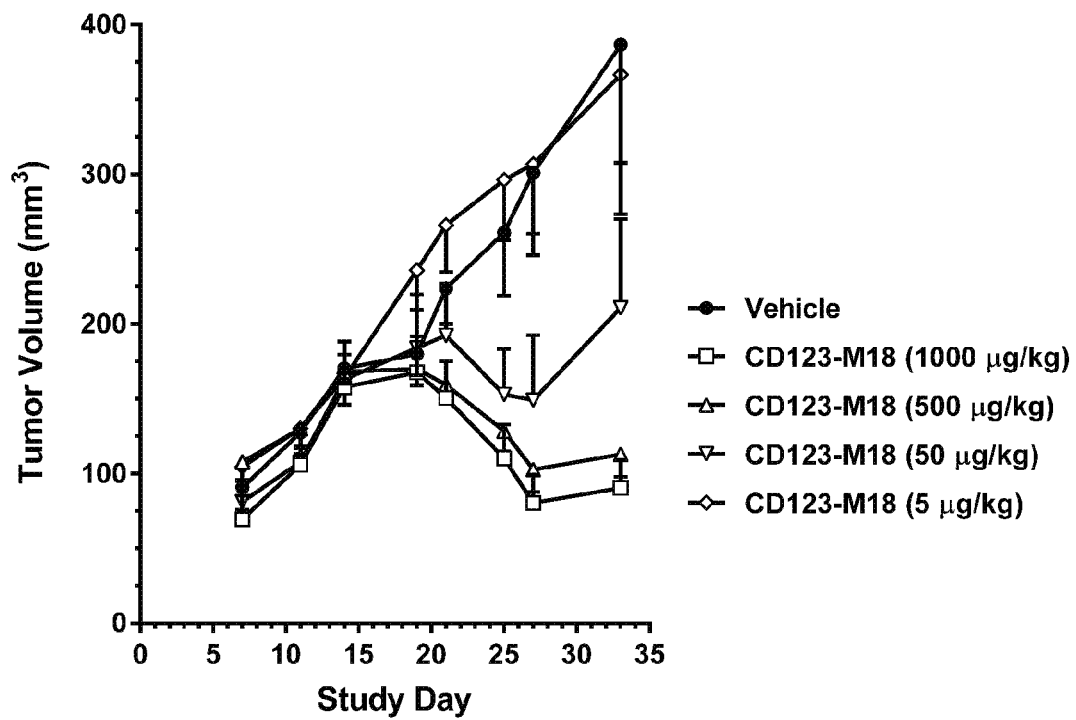
Figure 19C:
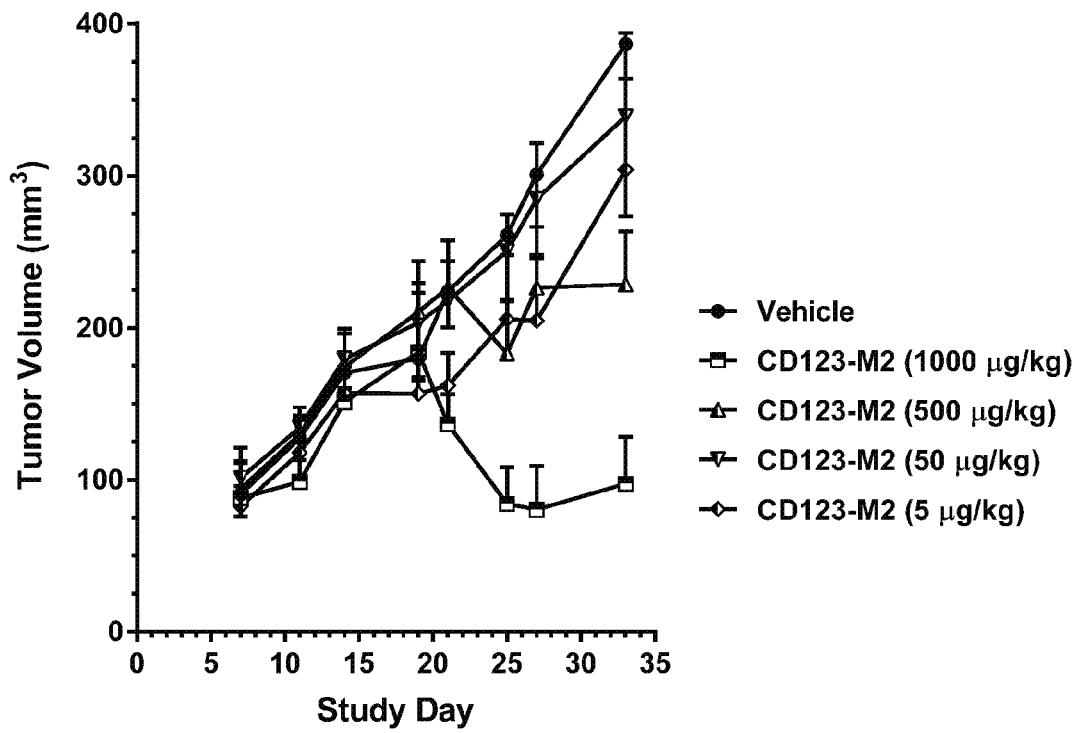
Figure 19D:
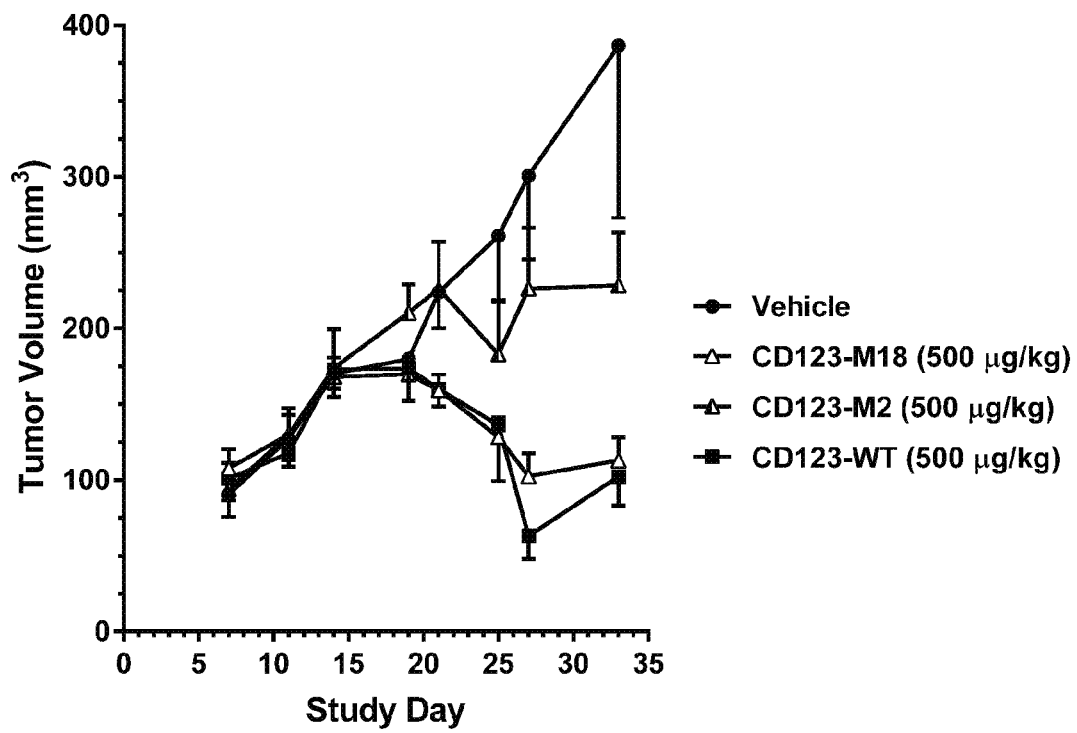

The results of this study are provided in FIGS. 19A-19D. The results show that CD123-WT exhibited anti-tumor activity at 0.5 µg/kg and above (FIG. 19A). CD123-M18 exhibited anti-tumor activity at 50 µg/kg and above (FIG. 19B). In contrast, CD123-M2 only exhibited anti-tumor activity at 1000 µg/kg (FIG. 19C). As shown in FIG. 19D, CD123-M18 anti-tumor activity is comparable to that of CD123-WT at 500 µg/kg, while CD123-M2 exhibited little or no anti-tumor activity at this concentration.

The in vivo activity of the 5T4×CD3 DART-B-type diabodies, 5T4-WT, 5T4-M1 and 5T4-M18, were evaluated in a in PBMC engraftment model in which 5×10$^6$ SKOV3 (ovarian carcinoma) cells were injected SC and 1×10$^7$ PBMC cell were injected RO into MHCI$^{-/-}$ mice (8 females per group) on Day 0. Vehicle control, 5T4-WT (10, 50, 100, or 500 µg/kg), 5T4-M18 (10, 50, 100, or 500 µg/kg), or 5T4-M2 (500 µg/kg) were administered intravenously (IV) twice a week (2QW) starting on Day 7. Tumor volume was monitored over the course of the study.

Figure 20A:
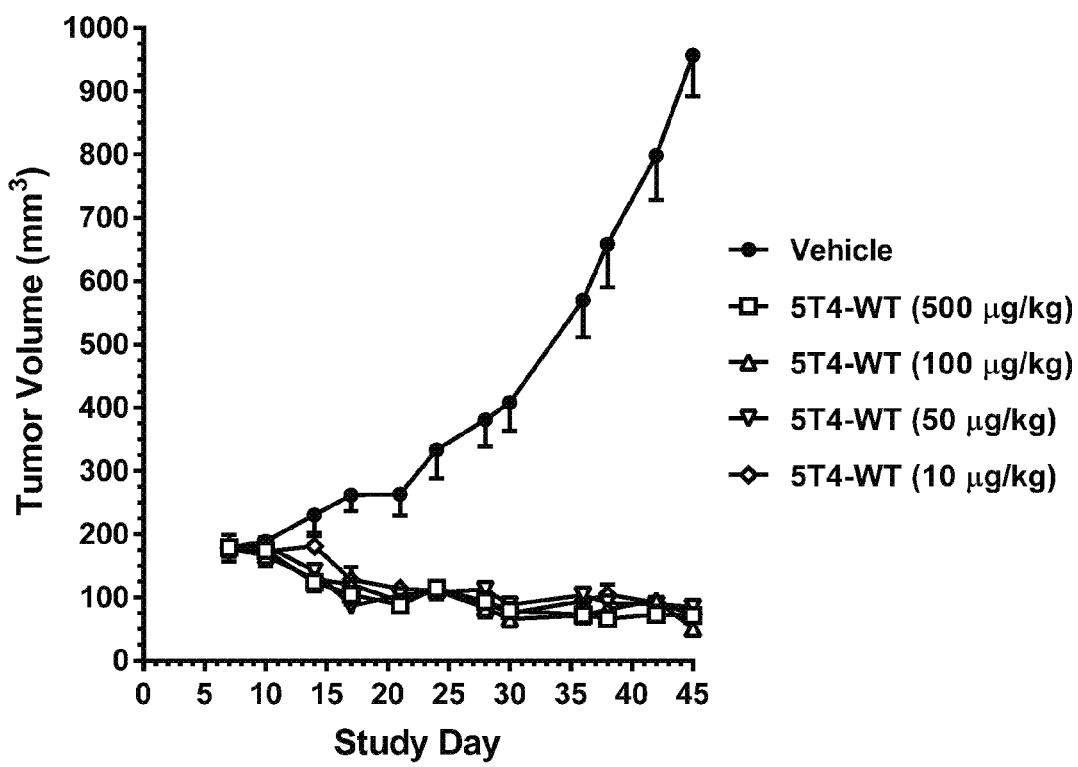
FIGS. 20A-20B show the results of in vivo studies on the ability of 5T4×CD3 DART B-type diabody constructs to mediate the reduction of tumors in vivo. 5T4-WT (at 10, 50, 100, or 500 µg/kg), 5T4-M18 (at 10, 50, 100, or 500 µg/kg) or 5T4-M2 (at 500 µg/kg) were provided to mice that had received the SKOV3 cells, and tumor volume was assessed over 45 days.
Figure 20B:
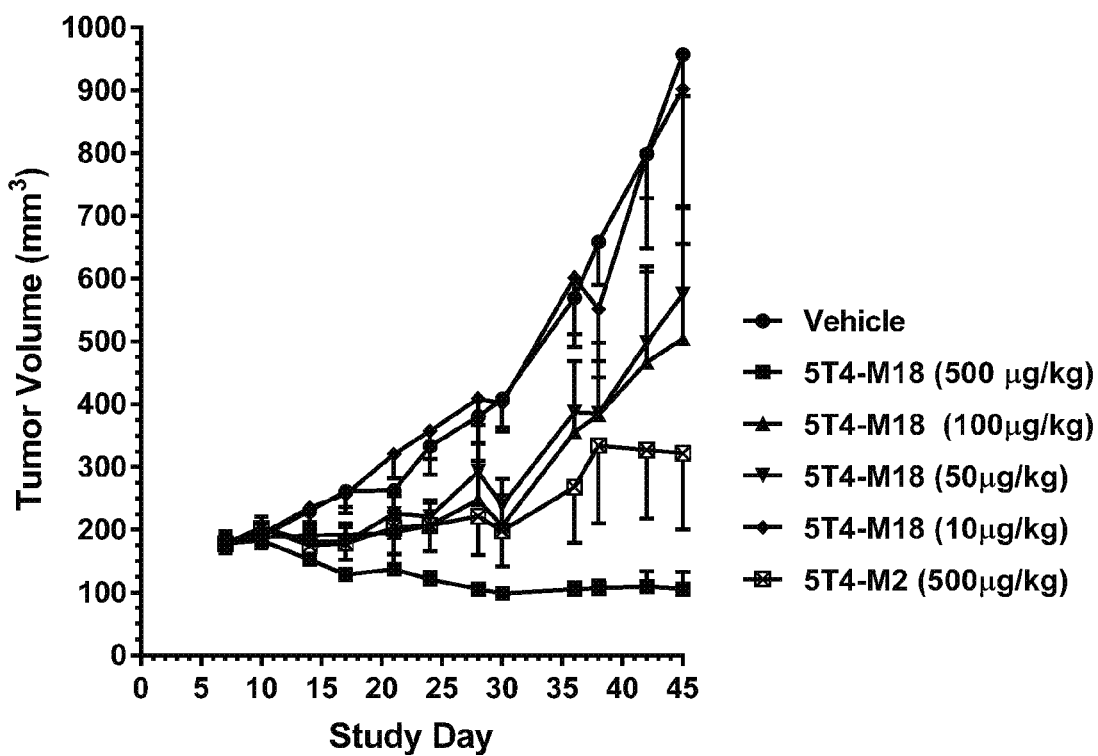

The results of this study are provided in FIGS. 20A-20B. The results show that 5T4-WT exhibited potent anti-tumor activity at all doses tested (FIG. 20A). 5T4-M18 exhibited dose dependent anti-tumor activity that was comparable to 5T4-WT at 500 µg/kg, while 5T4-M2 exhibited significantly lower activity at 500 µg/kg (FIG. 20B).

Figure 21A:
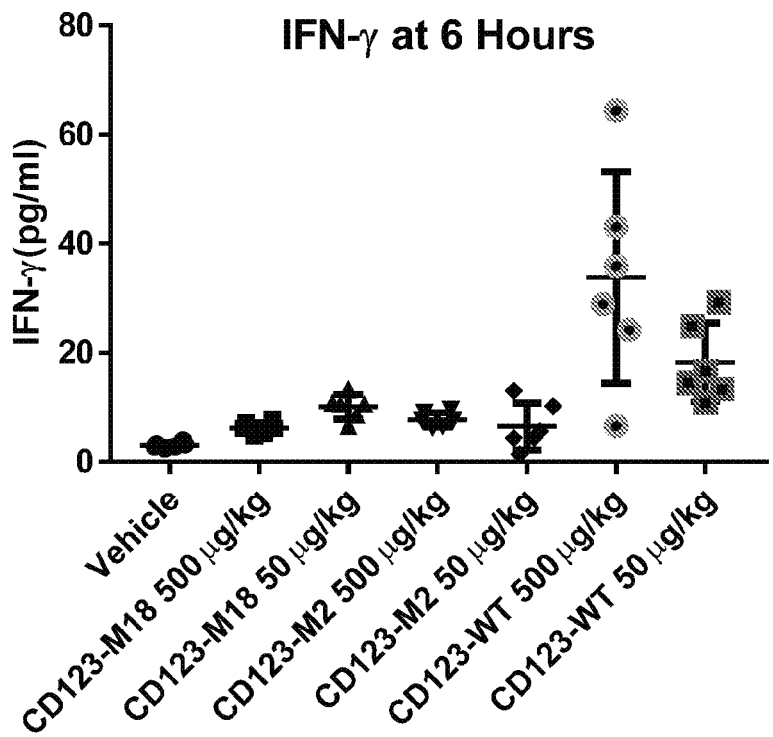
FIGS. 21A-21D show the results of in vivo studies on the cytokine release profile induced by CD123×CD3 DART-B-type diabodies. Serum cytokine levels (pg/ml) were evaluated six hours after administration of CD123-WT, CD123-M2 or CD123-M18 (at 50, or 500 µg/kg) to mice that had received the KG1A cells.
Figure 21B:
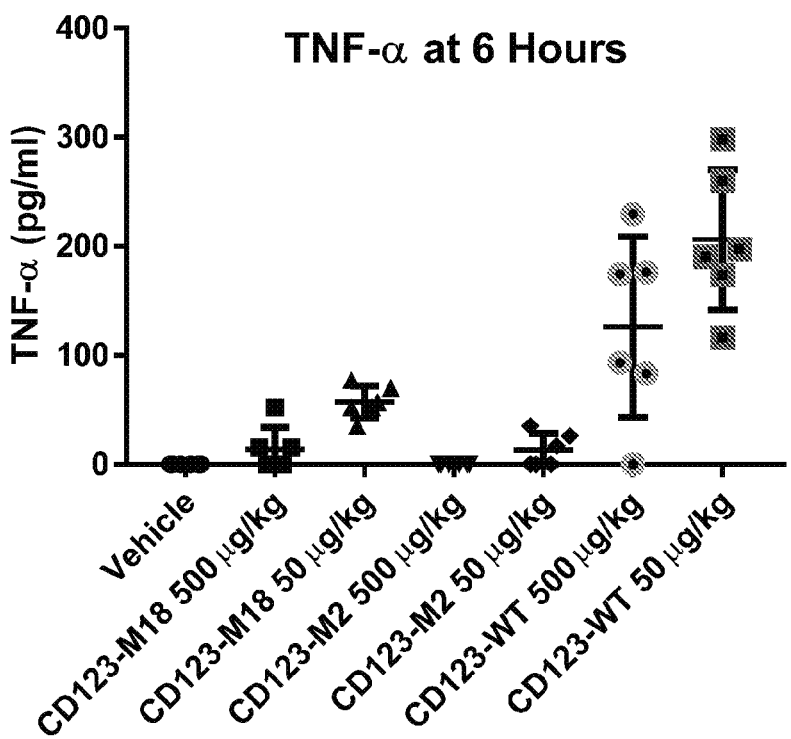
Figure 21C:
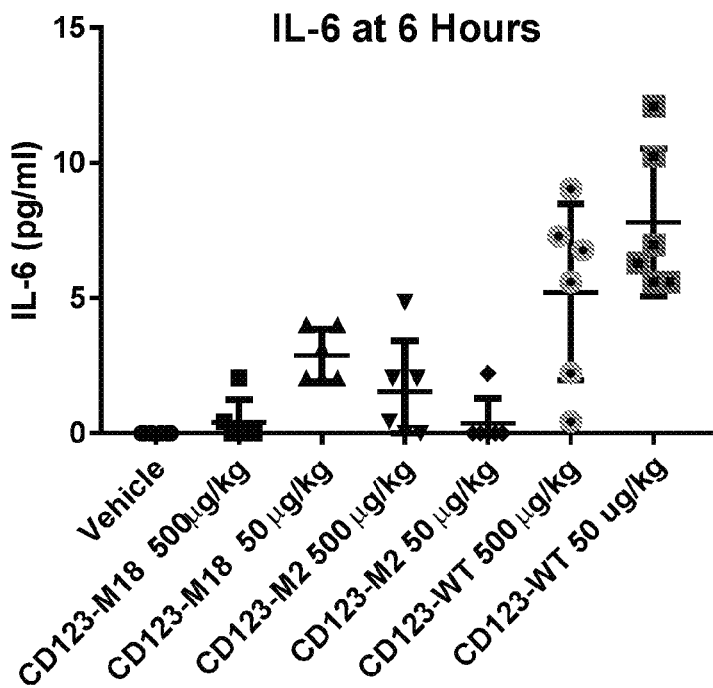
Figure 21D:
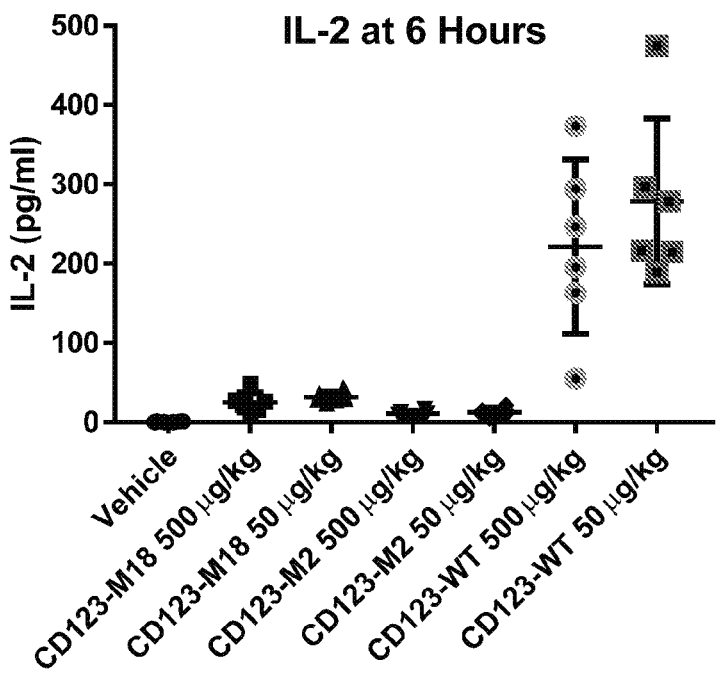

The in vivo cytokine release profile induced by CD123× CD3 DART-B-type diabodies was examined in a PBMC co-mix model. Briefly, 5×10$^6$ KG1A (AML) and 1×10$^7$ PBMC cells were mixed and incubated overnight, the next day the mixed cells were injected SC into NSG mice (6 males per group) and a single dose of vehicle control, CD123-WT, CD123-M18 or CD123-M2 (each at 50, or 500 µg/kg) was administered intravenously (IV). Six hours post administration serum cytokine levels were evaluated. The cytokine release profiles are plotted in FIGS. 20A-20D (FIG. 21A: IFN-γ; FIG. 21B: TNF-α; FIG. 21C: IL-6; and FIG. 21D: IL-2). The results of these studies show that treatment with DA×CD3 Binding Molecules comprising the variant VL and VH Domains of CD3 mAb 1 M2, and CD3 mAb 1 M18 exhibit lower levels of cytokine release Two further studies to evaluate the in vivo activity of the CD123×CD3 DART-B-type diabodies were performed using a reconstituted tumor model in which PBMC reconstituted (8×10$^6$ PBMC injected retro-orbitally on Day 0) NSG/MHCI$^{-/-}$ mice (7-8 mice per group), were subcutaneously (SC) injected with 5×10$^6$ KG1A (AML) cells on day 7. In one study, CD123-WT (0.5 mg/kg), CD123-M18 and CD123-M13 (at 0.005, 0.05, 0.5 and 1 mg/kg) or vehicle were administered intravenously (IV) twice a week (2QW) starting on Day 28. In the other study CD123-WT (0.05 mg/kg), CD123-M18 and CD123-M17 (at 0.005, 0.05, 0.5 and 1 mg/kg) or vehicle were administered intravenously (IV) twice a week (2QW) starting on Day 28. Tumor volume was monitored over the course of the study.

Figure 28A:
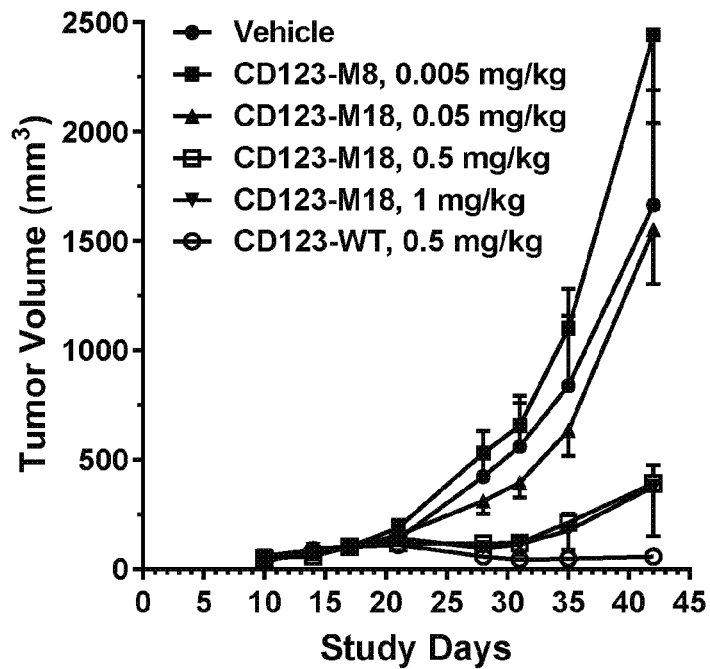
FIGS. 28A-28B show the results of in vivo studies on the ability of CD123×CD3 diabody constructs to mediate the reduction of tumors in vivo. CD123-WT (0.5 mg/kg), CD123-M18 or CD123-M13 (at 0.005, 0.05, 0.5 and 1 mg/kg) were provided to mice that had received KG1A cells, and tumor volume was assessed over 42 days.
Figure 28B:
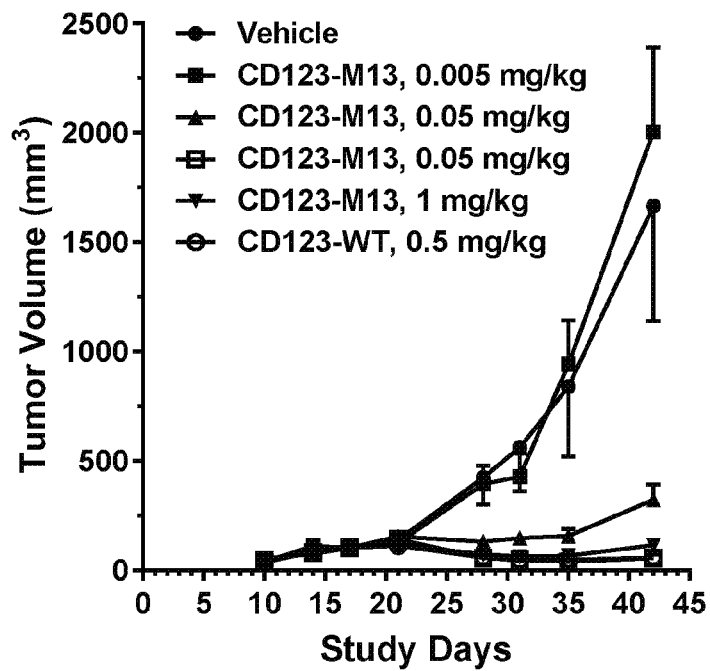
Figure 29A:
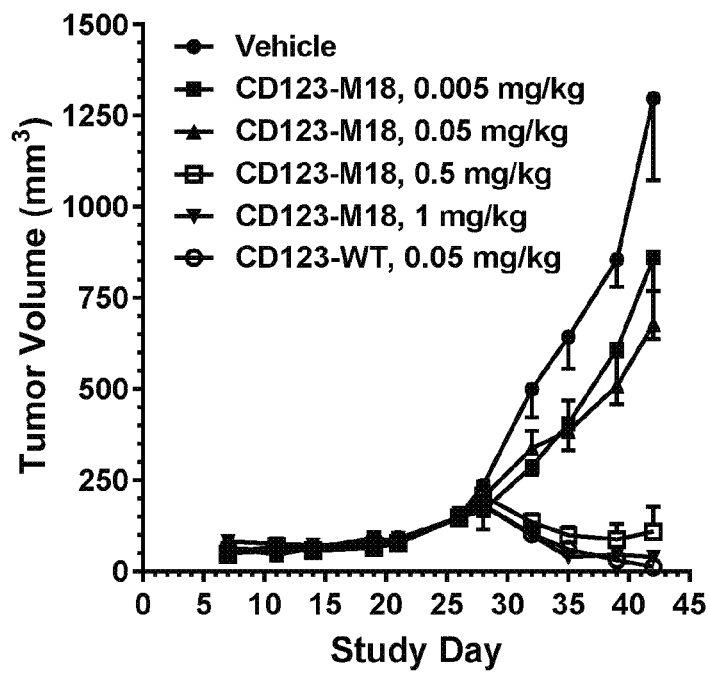
FIGS. 29A-29B show the results of in vivo studies on the ability of CD123×CD3 diabody constructs to mediate the reduction of tumors in vivo. CD123-WT (0.05 mg/kg), CD123-M18 or CD123-M17 (at 0.005, 0.05, 0.5 and 1 mg/kg) were provided to mice that had received KG1A cells, and tumor volume was assessed over 42 days.
Figure 29B:
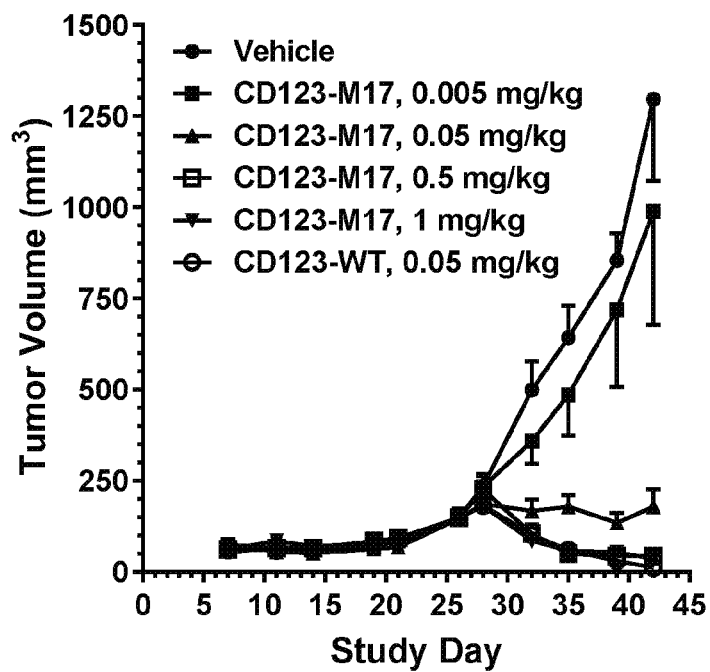

The results of these studies are provided in FIGS. 28A-28B (treatment with CD123-WT, CD123-M18 and CD123-M13) and FIGS. 29A-29B (treatment with CD123-WT, CD123-M18 and CD123-M17) The results show that CD123-M18 anti-tumor activity was similar to that of CD123-WT at doses of 0.5 mg/kg and above (FIGS. 28A and 29A) and that CD123-M13 and CD123-M17 exhibited anti-tumor activity similar to that of CD123-WT starting at just 0.05 mg/kg, a 10 fold lower dose that for CD123-M18 (FIGS. 28B and 29B).

Figure 30A:
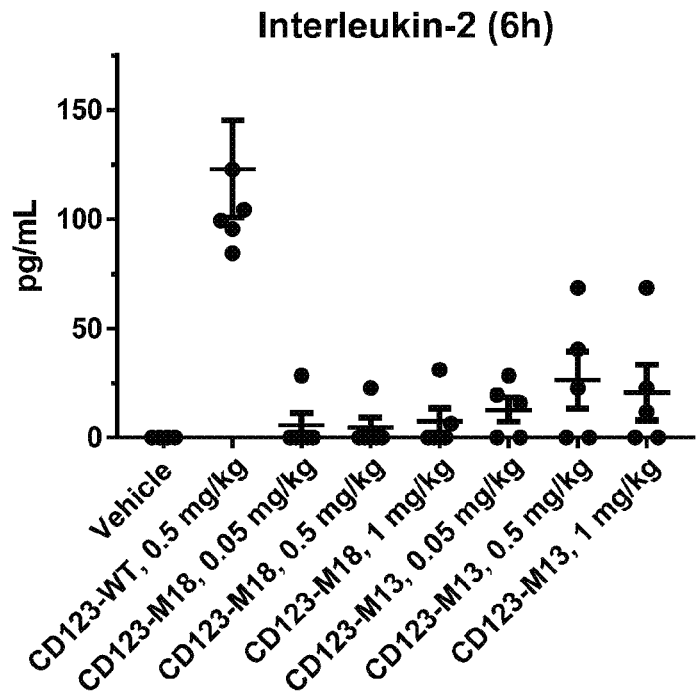
FIGS. 30A-30B show the results of in vivo studies on the interleukin-2 cytokine release profile induced by CD123× CD3 DART-B-type diabodies. Serum cytokine levels (pg/ml) were evaluated six hours after administration of CD123-WT (0.5 mg/kg), CD123-M13, CD123-M17 or CD123-M18 (at 0.05, 0.5 and 1 mg/kg) to mice that had received the KG1A cells.
Figure 30B:
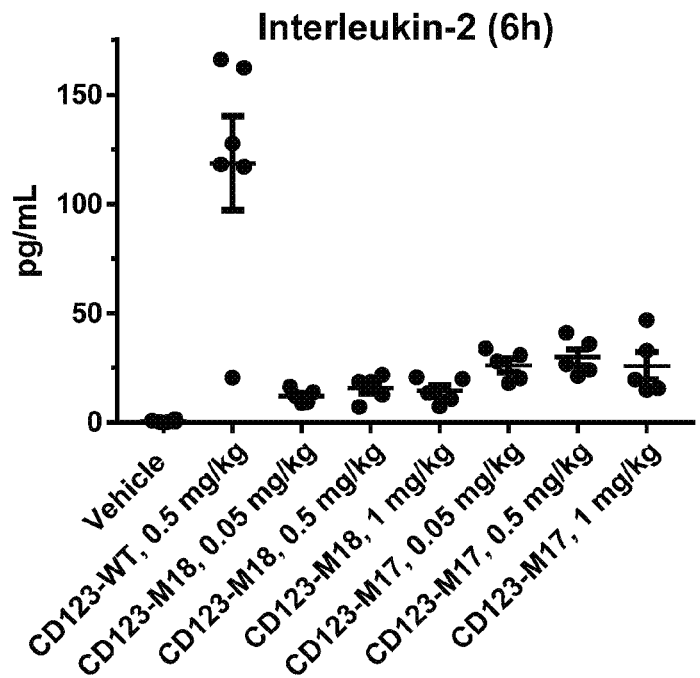

The in vivo cytokine release profiles induced by CD123× CD3 DART-B-type diabodies CD123-WT, CD123-M13, CD123-M17 and CD123-M18 were examined in a PBMC co-mix model. Briefly, 5×10$^6$ KG1A (AML) and 1×10$^7$ PBMC cells were mixed and incubated overnight, the next day the mixed cells were injected SC into NSG mice (7-8 per group) and a single dose of CD123-WT (0.5 mg/kg), CD123-M13, CD123-M17 and CD123-M18 (at 0.05, 0.5 and 1 mg/kg), or vehicle was administered intravenously (IV). Six hours post administration serum cytokine levels were evaluated. In one study animals were treated with CD123-WT, CD123-M18 and CD123-M13, and in a separate study, animals were treated with CD123-WT, CD123-M18 and CD123-M17. The IL-2 cytokine release profiles are plotted in FIGS. 30A-30B (FIG. 30A: CD123-WT, CD123-M18 and CD123-M13); FIG. 30B: CD123-WT, CD123-M18 and CD123-M17) and show that treatment with DA×CD3 Binding Molecules comprising the variant CD3 mAb 1 VL and VH Domains results in reduced levels of cytokine release as compared to the DA×CD3 Binding Molecule comprising the wild type VL and VH domains.

The results of these animal studies show that administration of the DA×CD3 Binding Molecules comprising the variant VL and VH Domains of CD3 mAb 1, particularly the VL and VH Domains of CD3 mAb 1 M2, CD3 mAb 1 M13, CD3 mAb M17, and CD3 mAb 1 M18 (i.e., vCD3-Binding Domains) results in reduced levels of cytokine release as compared to DA×CD3 Binding Molecules comprising the VL and VH Domains of CD3 mAb 1 (i.e., rCD3-Binding Domain). In particular, the results of these studies demonstrate that DA×CD3 Binding Molecules comprising the variant VL and VH Domains of CD3 mAb 1 M13, CD3 mAb M17, and CD3 mAb 1 M18 exhibit lower levels of cytokine release while retaining anti-tumor activity in vivo.

Example 9

Generation of TRIVALENT-Type Molecules

The VH and VL Domains of CD3 mAb 1, CD3 mAb 1 M1, CD3 mAb 1 M2, or CD3 mAb 1 M18 were used to generate TRIVALENT-type molecules comprising a Disease Antigen (DA) Binding Domain binding the Cancer Antigen CD123 and a Binding Domain binding the effector cell antigen CD8 ("DA×CD3×CD8 TRIVALENT-type molecule"). Table 10 summarizes the CD3 Binding Domains and SEQ ID NOs. for each polypeptide chain. The amino acid sequences of each chain are provided in detail herein (see First-Fourth Illustrative TRIVALENT-type molecules, supra).

Example 10

Characterization of DA×CD3×CD8 TRIVALENT-Type Molecules

Figure 22A:
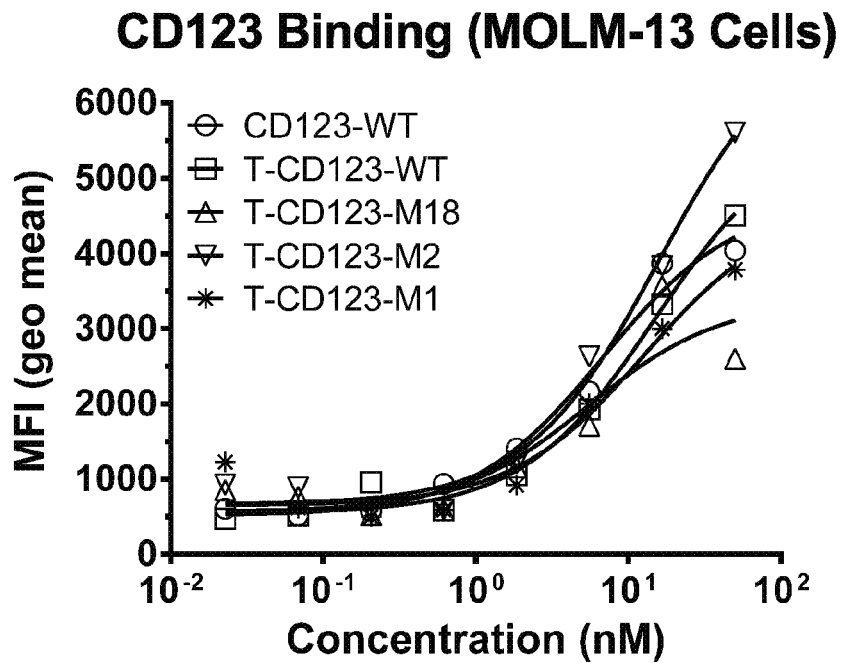
FIGS. 22A-22C show the ability of CD123×CD3×CD8 TRIVALENT-type molecules, T-CD123-WT, T-CD123-M1, T-CD123-M2 and T-CD123-M18, to bind to cell surface antigens.
Figure 22B:
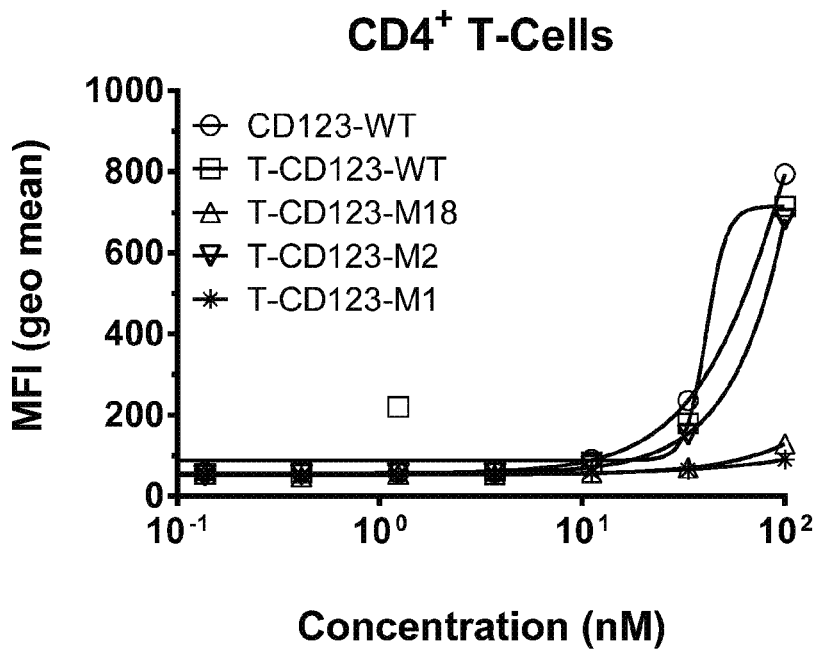
Figure 22C:
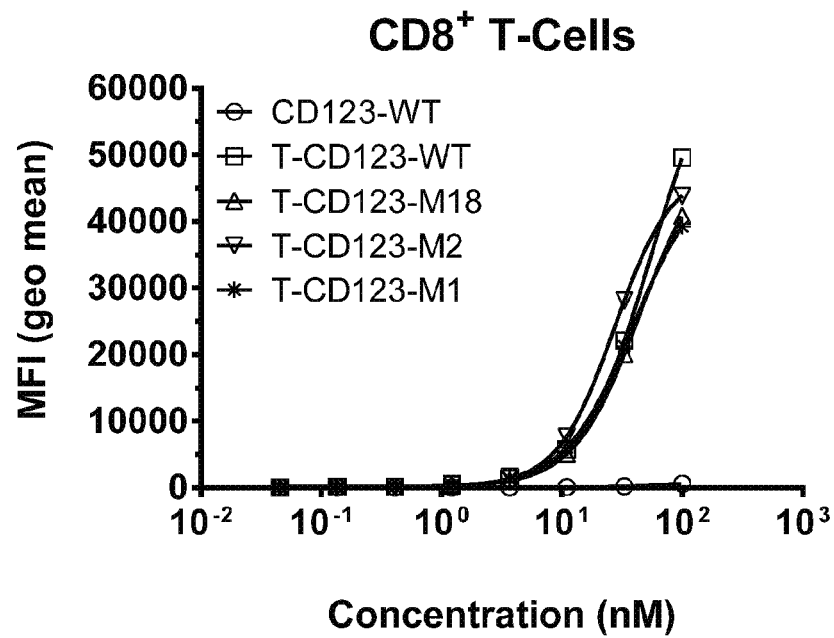

The ability of T-CD123-WT, T-CD123-M1, T-CD123-M2 and T-CD123-M18 to bind CD123 expressed on MOLM-13 cells was evaluated essentially as described above. In addition, the ability of these molecules to bind CD4$^+$ T-cells and CD8$^+$ T-cells was evaluated essentially as described above. The DART-B-type diabody CD123-WT is included in these studies for comparison. Representative data from these studies is provided in FIG. 22A (binding to MOLM-13 cells), FIG. 22B (binding to CD4$^+$ T-cells) and FIG. 22C (binding to CD8$^+$ T-cells). All of the tested molecules exhibit comparable binding to CD123 expressing MOLM-13 cells and CD8 expressing CD8$^+$ T-cells. T-CD123-M1 and T-CD123-M18 exhibit significantly reduced binding to CD3 expressing CD4$^+$ T-cells as measured by MFI (geo mean). Binding to CD8$^+$ T-cells is mediated by both the CD3- and CD8-Binding Domains present in the TRIVALENT-type molecules.

Figure 23A:
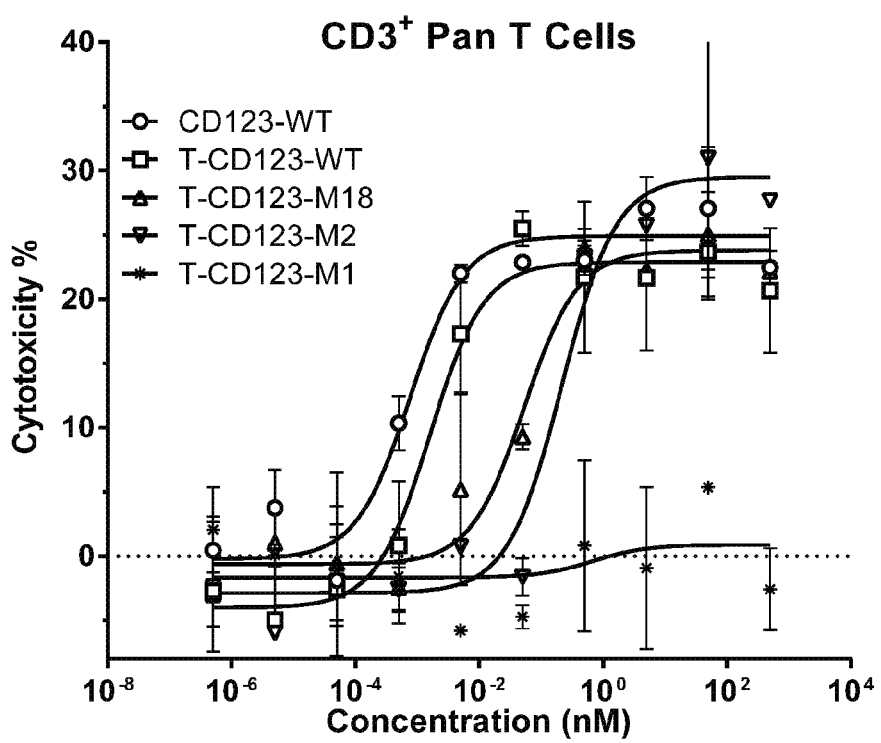
FIGS. 23A-23G show the results of representative studies of redirected cell killing (CTL assay) mediated by T-CD123-WT, T-CD123-M1, T-CD123-M2 and T-CD123-M18 CD123×CD3×CD8 TRIVALENT-type molecules using different T-cell populations. Percent cytotoxicity using CD3$^+$ Pan-T-cells (FIG. 23A); CD4$^+$ T-cells (FIG. 23B) and CD8$^+$ T-cells (FIG. 23C). Cytokine responses using CD3$^+$ Pan-T-cells are plotted in FIGS. 23D-23G.
Figure 23B:
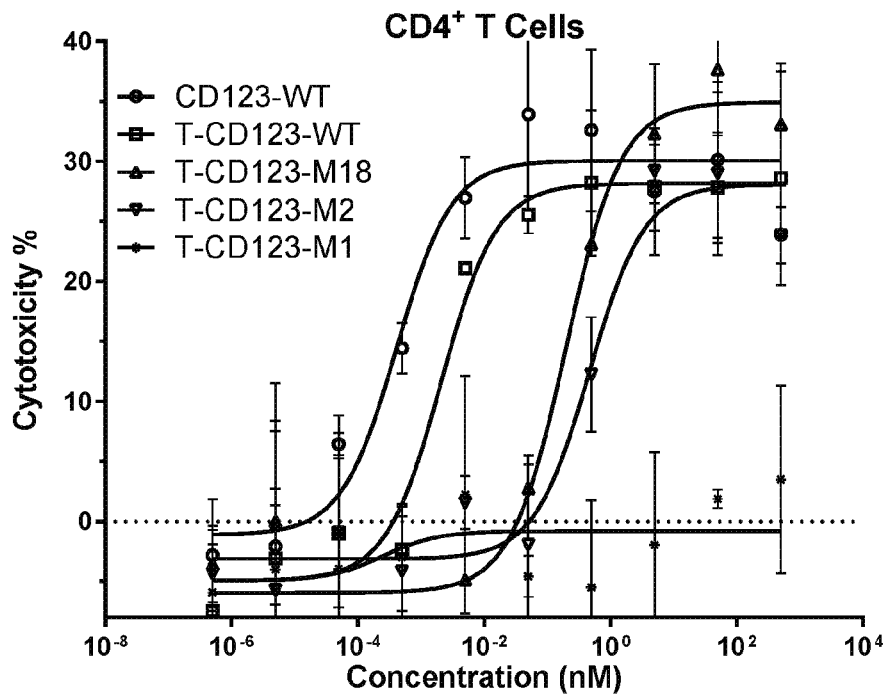
Figure 23C:
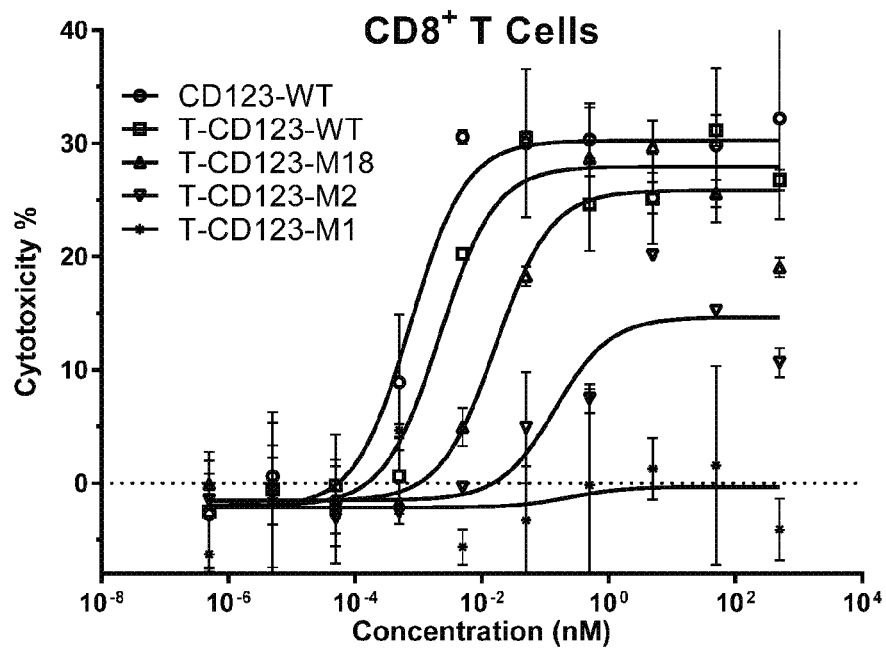
Figure 23D:
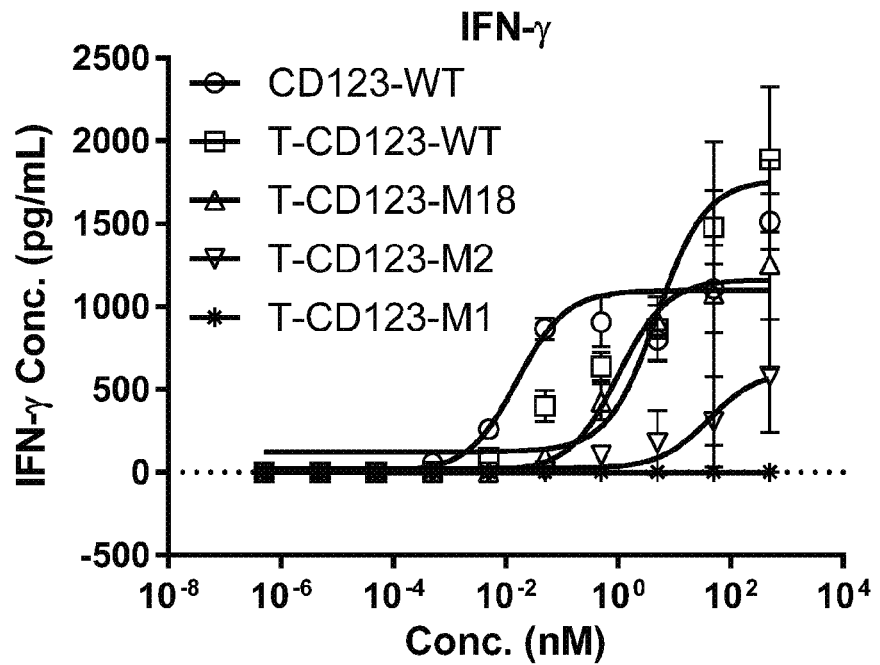
Figure 23E:
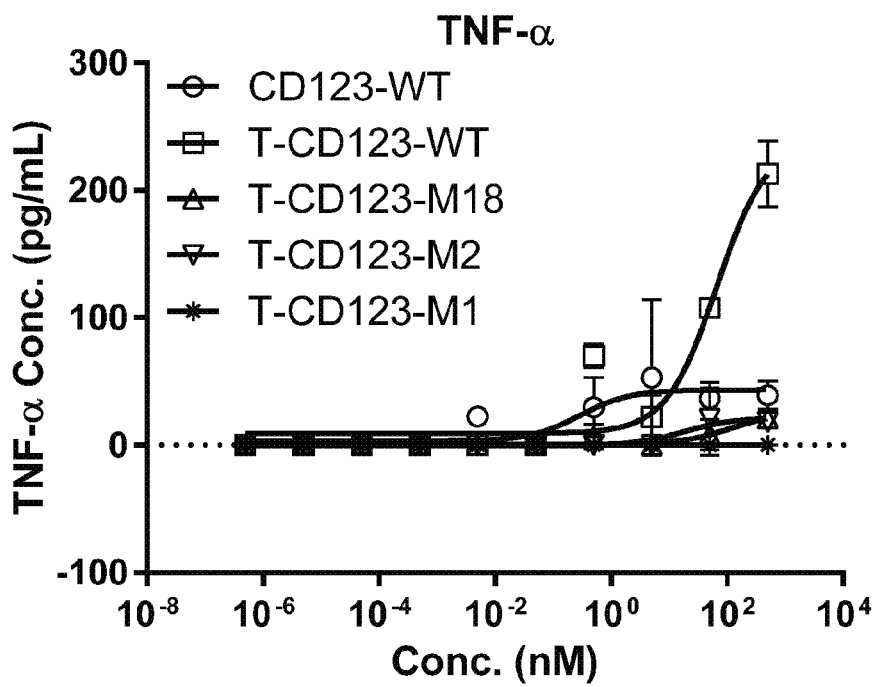
Figure 23F:
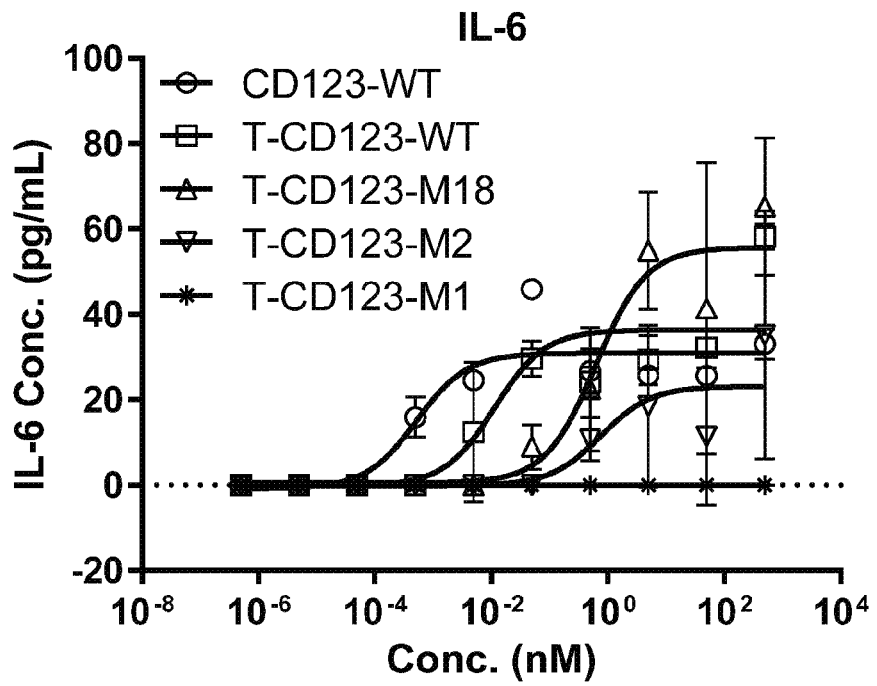
Figure 23G:
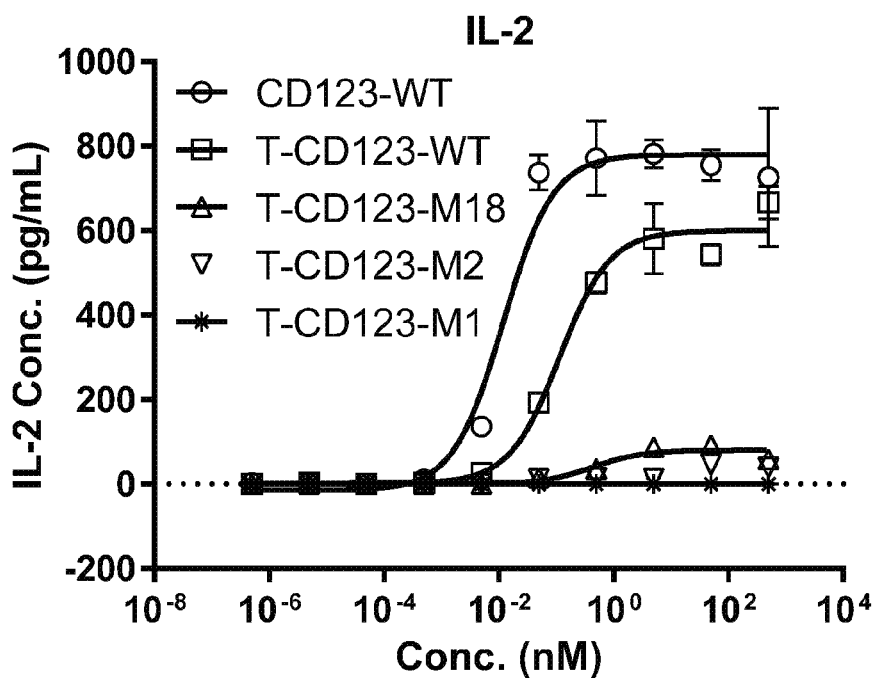

The ability of T-CD123-WT, T-CD123-M1, T-CD123-M2 and T-CD123-M18 to mediate redirected cell killing was evaluated. Briefly, the TRIVALENT-type molecules were incubated in the presence of Pan-T-cell or purified CD4$^+$ or CD8$^+$ T-cell effector cells and MOLM-13 target tumor cells at an effector:target cell ratio of 1:1 for 48 hours. The cytotoxicity was determined by measuring the release of lactate dehydrogenase (LDH) into the media by damaged cells (e.g., using the CytoTox 96® Non-Radioactive Cytotoxicity Assay Kit (Promega) that quantitatively measures LDH release, or similar). Cytokine response was examined in the Pan-T-cell samples. The DART-B-type diabody CD123-WT is included in these studies for comparison. Percent cytotoxicity is plotted in in FIG. 23A-23C (FIG. 23A: Pan-T-cells; FIG. 23B: CD4$^+$ T-cells; and FIG. 23C: CD8$^+$ T-cells). Cytokine responses are plotted in FIGS. 23D-23G (FIG. 23D: IFN-gamma; FIG. 23E: TNF-alpha; FIG. 23F: IL-6; FIG. 23G: IL-2).

Example 11

Toxicology Studies

The safety and cytokine release profiles of representative CD123×CD3 Binding Molecules was assessed in a dosing study in cynomolgus monkeys. In this study the potential toxicity and cytokine release profiles of CD123-M18 (comprising the vCD3-Binding Domain of CD3 mAb 1 M18) and CD123-WT (comprising the rCD3-Binding Domain of CD3 mAb 1), when administered by repeated intravenous infusions was evaluated. Cell killing activity is not readily accessed in this model. The study design is presented in Table 16.

TABLE 16

| Group No. | Test Material | Dose Level (mg/kg) | Dosing Days | No. of Animals (male) |
|---|---|---|---|---|
| 1 | Control | 0 | 0 | 2 |
| 2 | CD123-WT | 0.003 | 0, 7 | 3 |
| 3 | CD123-M18 | 10 | 0, 7 | 3 |
| 4 | CD123-M18 | 20 | 0, 7 | 2 |

Figure 24A:
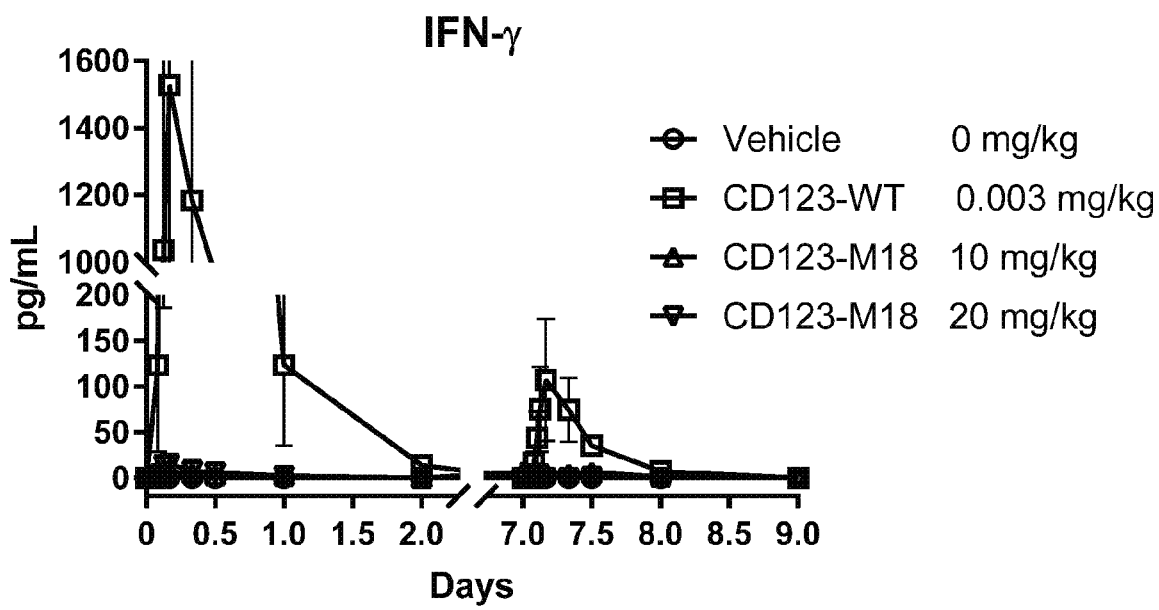
FIGS. 24A-24J show the serum cytokine levels, Ki67 expression, and clinical pathology marker levels observed in cynomolgus monkeys treated with CD123-M18 (10 mg/kg and 20 mg/kg) or CD123-WT (0.003 mg/kg).
Figure 24B:
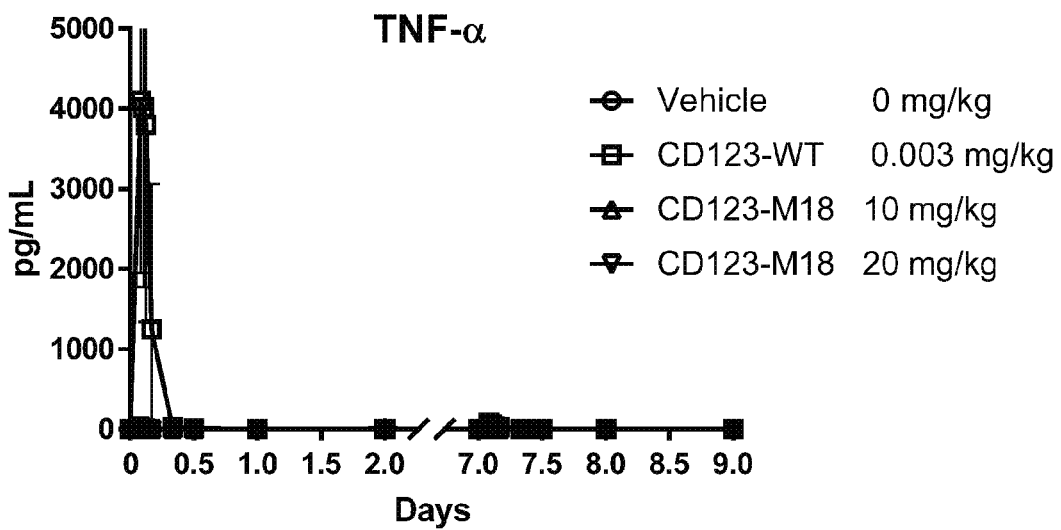
Figure 24C:
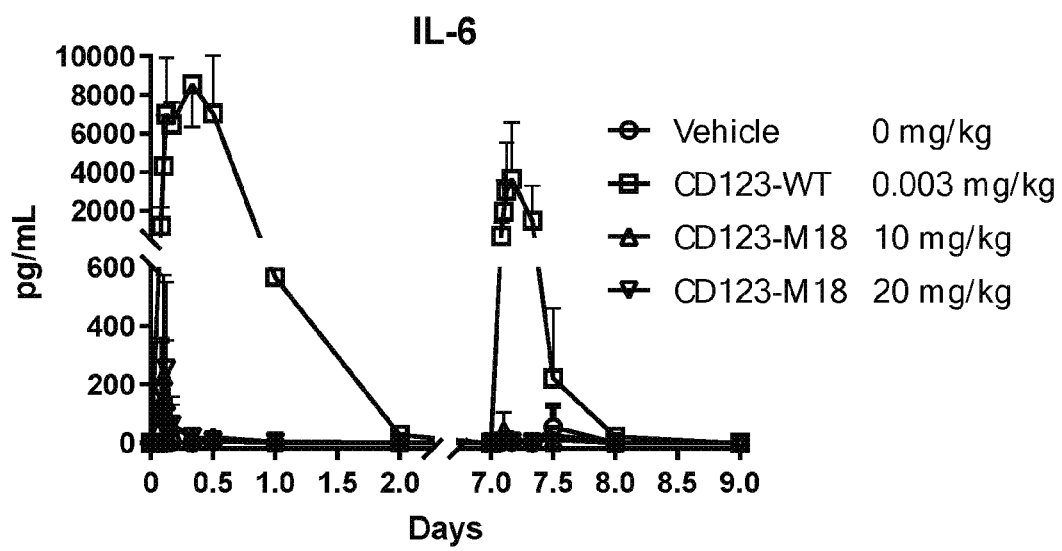
Figure 24D:
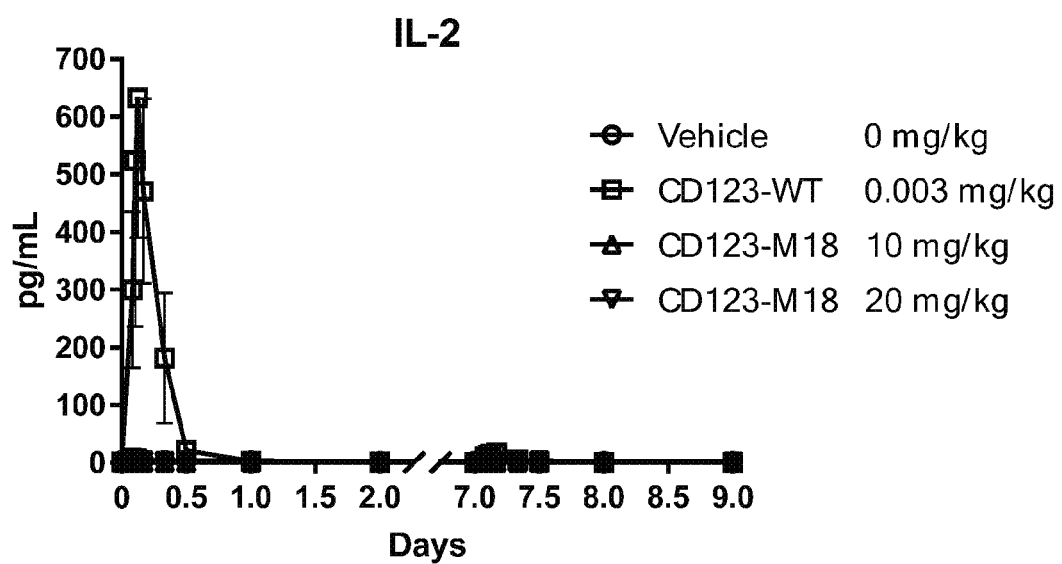
Figure 24E:
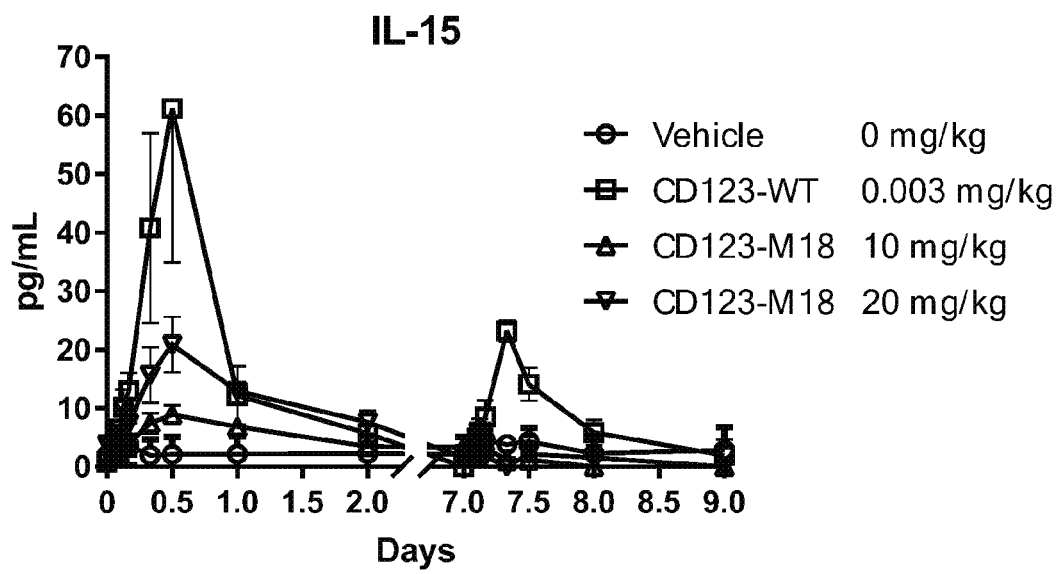
Figure 24F:
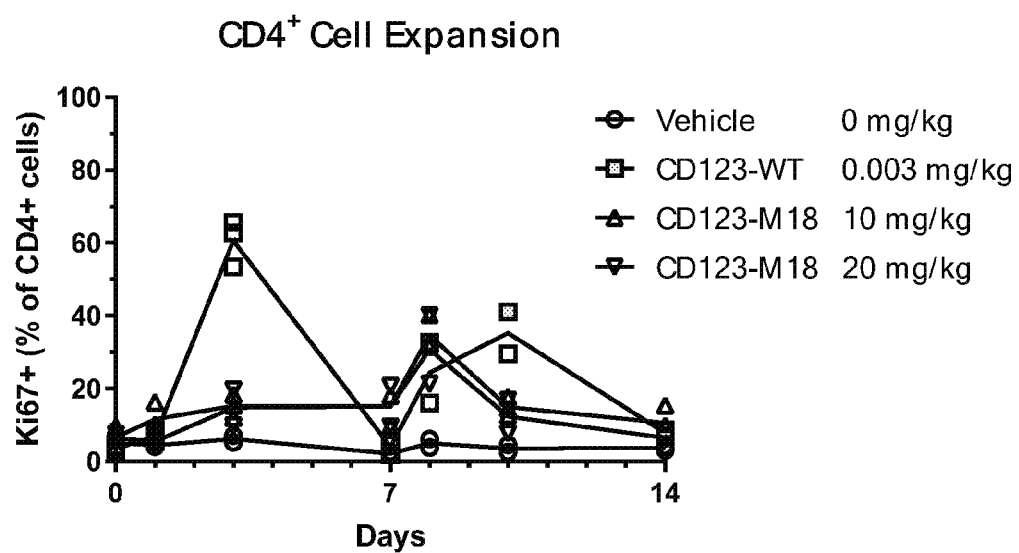
Figure 24G:
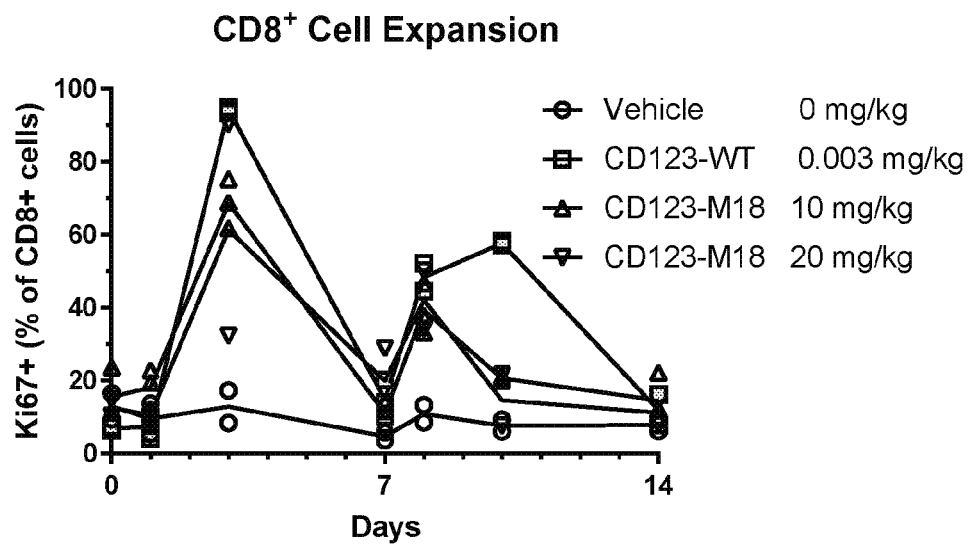
Figure 24H:
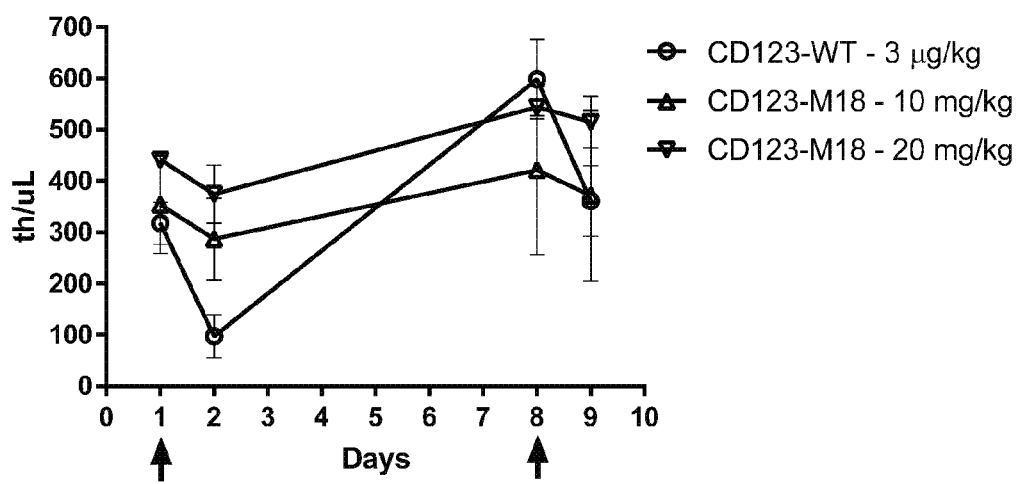
Figure 24I:
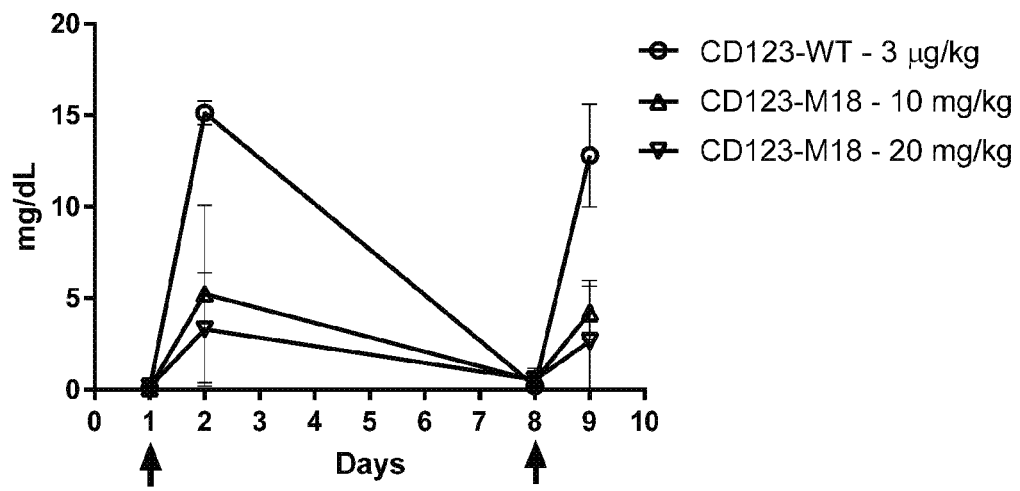
Figure 24J:
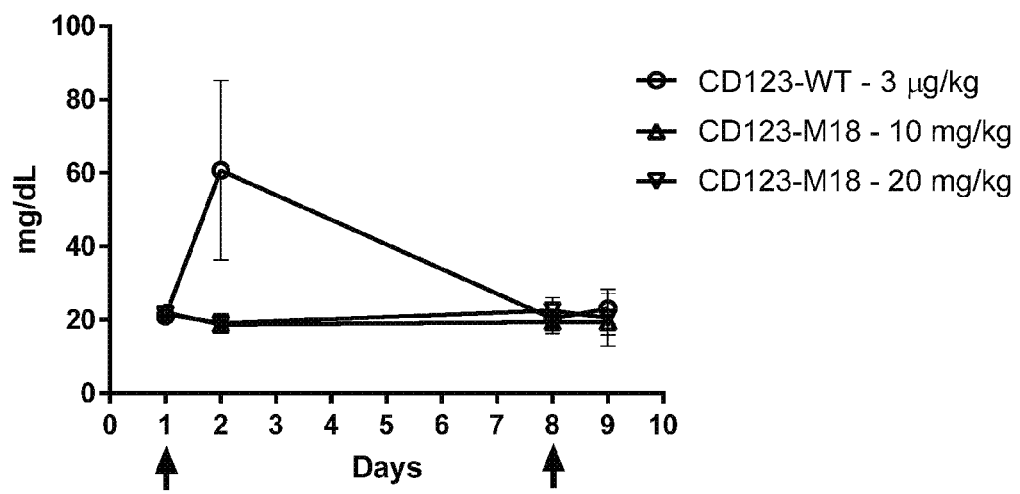

No mortality, body weight loss or other adverse observations were observed in the CD123-M18 treatment groups (10 and 20 mg/kg). In addition, no significant hematology or clinical chemistry changes were observed for in these groups. In contrast, the CD123-WT molecule (0.003 mg/kg) was not well tolerated. Cytokine release syndrome and mortality (⅓) was observed in this group. The serum cytokine levels (Days 0-9) are plotted in FIGS. 24A-24E (FIG. 24A: IFN-γ, FIG. 24B: TNF-α, FIG. 24C: IL-6, FIG. 24D: IL-2, and FIG. 24E: IL-15). In addition, T-cell proliferation was examined by FACS using expression of Ki67 as a marker of proliferating cells. FIG. 24F plots CD4$^+$ T-cell expansion, and FIG. 24G plots CD8$^+$ T-cells expansion as a percent of CD4$^+$ or CD8$^+$ cells positive for Ki67 (Days 0-14). FIGS. 24H-24I present plots of several hematology and clinical chemistry markers of significance for the animals in the treatment groups (FIG. 24H: Platelet counts; FIG. 24I: C-reactive protein; FIG. 24J: Urea Nitrogen). The results of this study show that DA×CD3 Binding Molecules comprising the vCD3-Binding Domain CD3 mAb 1 M18 are well tolerated in cynomolgus monkeys and exhibit minimal, transient increases in release of TNF-α, IFN-γ, IL-2 and IL-6 even at doses exceeding projected therapeutic levels, and exhibit smaller changes in multiple clinical chemistry markers. In addition, DA×CD3 Binding Molecules comprising the vCD3-Binding Domain CD3 mAb 1 M18 were seen to preferentially stimulate proliferation of CD8$^+$ T-cells.

A further toxicology study was performed with CD123-M13 (comprising the vCD3-Binding Domain of CD3 mAb 1 M13) dosed at 1 mg/kg and 10 mg/kg, CD123-M17 (comprising the vCD3-Binding Domain of CD3 mAb 1 M17) dosed at 1 mg/kg and 10 mg/kg, and CD123-M19 (comprising the vCD3-Binding Domain of CD3 mAb 1 M19) dosed at 10 mg/kg. In these studies, CD123-M13 was observed to exhibited higher cytokine release than CD123-M17 or CD123-M19, particularly in the 10 mg/kg group. Some mortality was observed in this study, particularly in the CD123-M13 high dose group and transient hematological and clinical chemistry changes were observed. Table 17 provides a summary of observed mortality from this study and previous toxicology studies with CD123-WT and CD123-M19.

TABLE 17

| CD3 Variant | Dose | # Dosed | # Died | |
|---|---|---|---|---|
| CD123-WT | 10 µg/kg | 1 | 1 | Euthanasia on Day 3 |
| | 3 → 3 µg/kg (Day 1 → 8) | 3 | 1 | Euthanasia on Day 8 |

TABLE 17-continued

| CD3 Variant | Dose | # Dosed | # Died | |
|---|---|---|---|---|
| | 3 → 10 µg/kg (Day 1 → 8) | 2 | 1 | Euthanasia on Day 8 |
| | 3 → 30 µg/kg (Day 1 → 8) | 2 | 2 | Euthanasia on Day 8 or 9 |
| CD123-M13 | 1 mg/kg | 2 | 1 | Euthanasia on Day 3 |
| | 10 mg/kg | 2 | 2 | Death or euthanasia on Day 3 |
| CD123-M17 | 1 mg/kg | 2 | 0 | No mortality |
| | 10 mg/kg | 5 | 1 | Euthanasia on Day 4 |
| CD123-M18 | No mortality at 10 (n = 3) or 20 mg/kg (n = 2) | | | |
| CD123-M19 | No mortality at 10 mg/kg (n = 2) (higher doses not tested) | | | |

As shown in Table 17 mortality is observed in animals treated with as little as 3 µg/kg (0.003 mg/kg) CD123-M13 (comprising the rCD3-Binding Domain of CD3 mAb 1) while CD123×CD3 Binding Molecules comprising the vCD3-Binding Domain of CD3 mAb 1 M13, M17, M18, and M19 are tolerable at much higher doses and exhibit reduced cytokine release profiles as compared to CD123-M13 comprising the rCD3-Binding Domain of CD3 mAb 1. The tolerated dose ranking from these studies is CD123-M18≥CD123-M19>CD123-M17>CD123-M13>CD123-WT. These findings track with the Therapeutic Index evaluation provided above.

Example 12

Ability of Exemplary CD123×CD3 Molecules to Mediate AML Blast Depletion

Figure 25A:
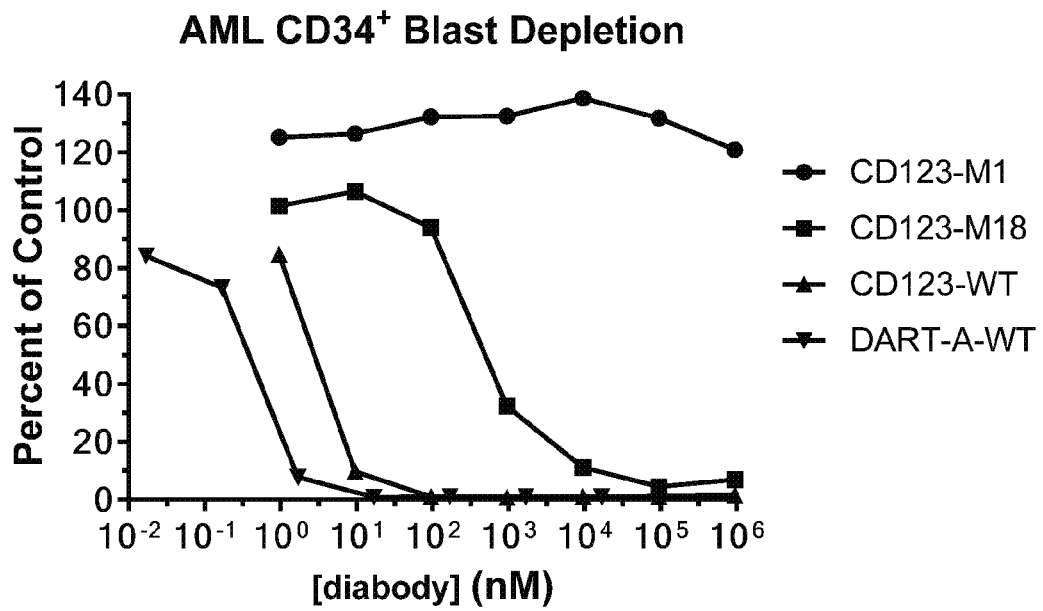
FIGS. 25A-25G show the results of a representative study of AML, blast depletion mediated by DART-A-WT, CD123-WT, CD123-M1 and CD123-M18 in peripheral blood samples from an AML patient.
Figure 25B:
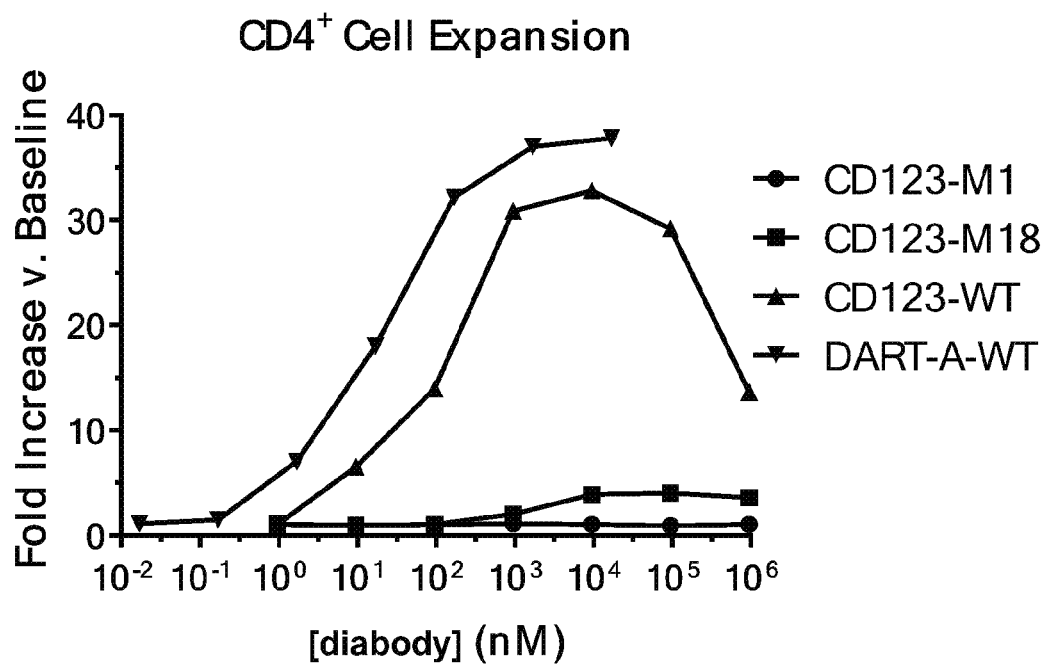
Figure 25C:
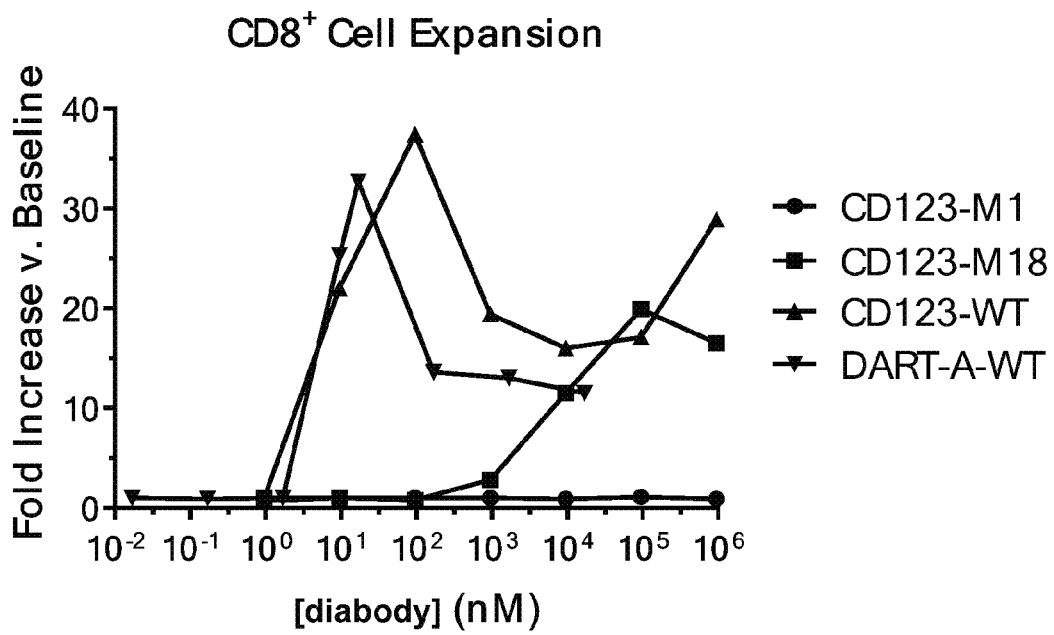
Figure 25D:
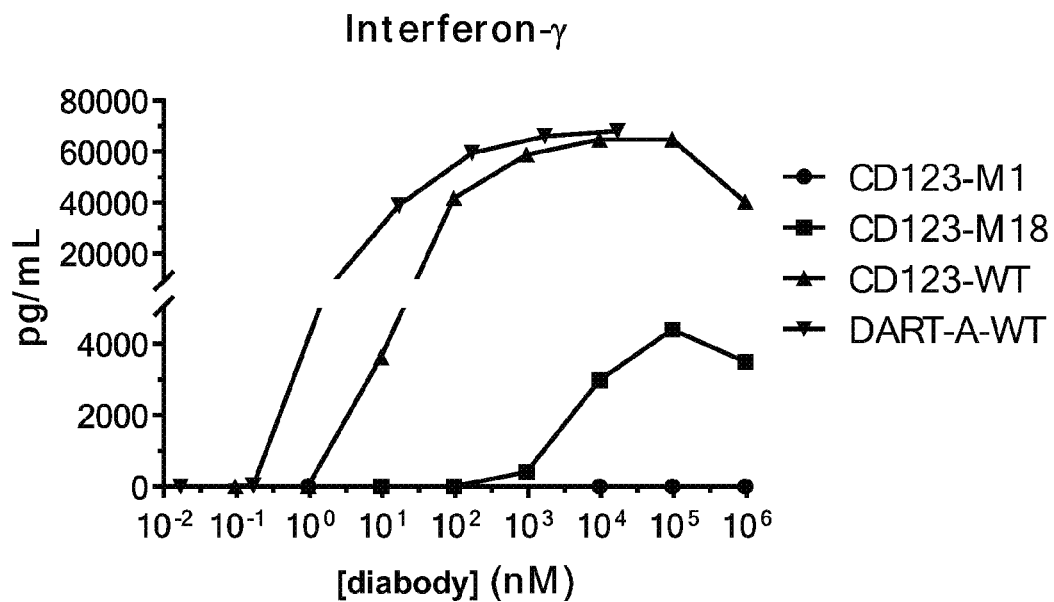
Figure 25E:
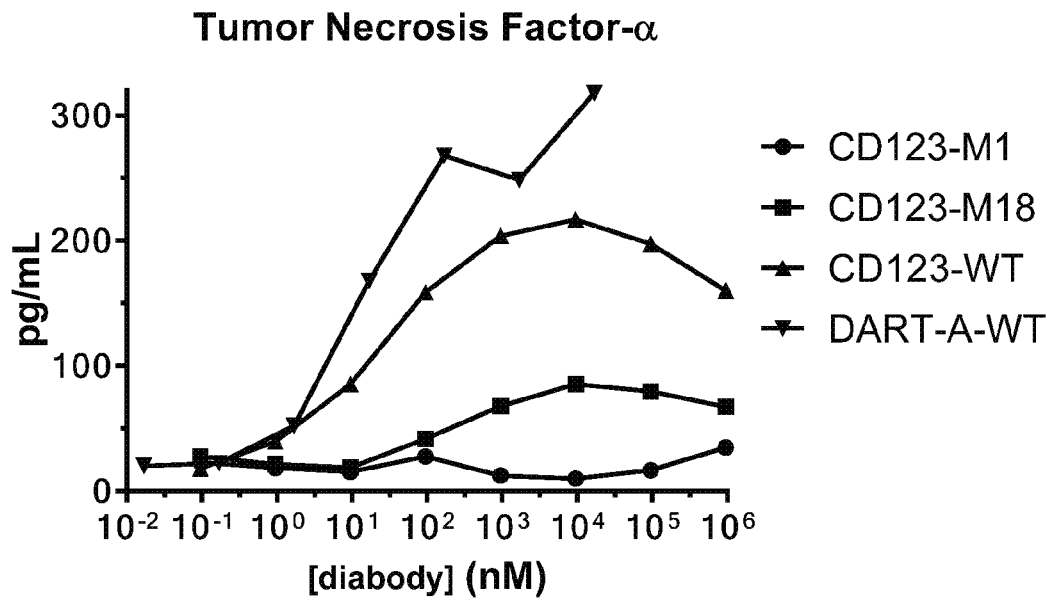
Figure 25F:
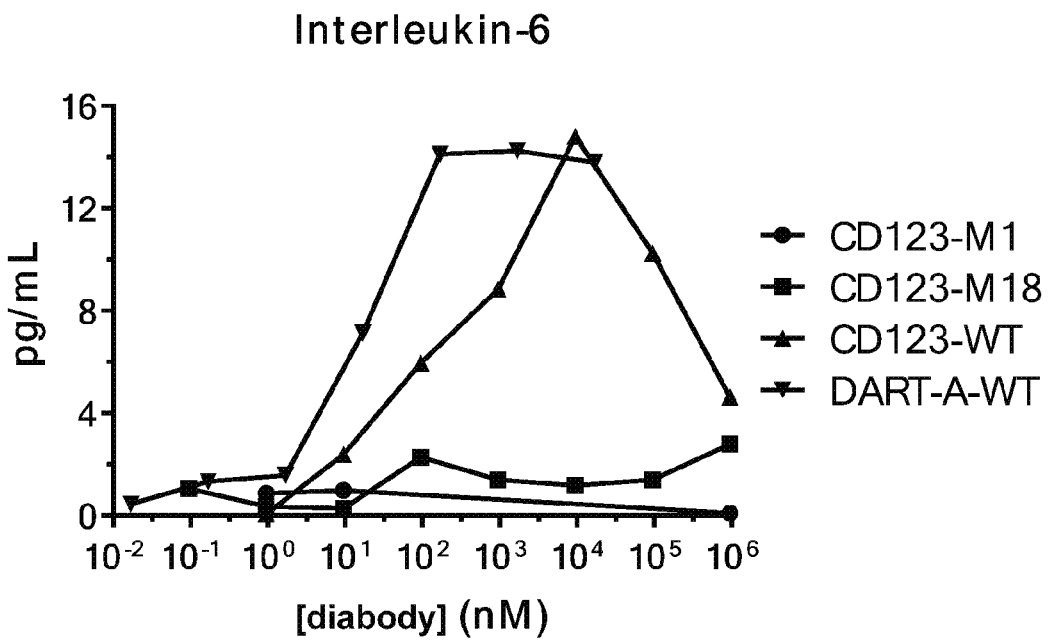
Figure 25G:
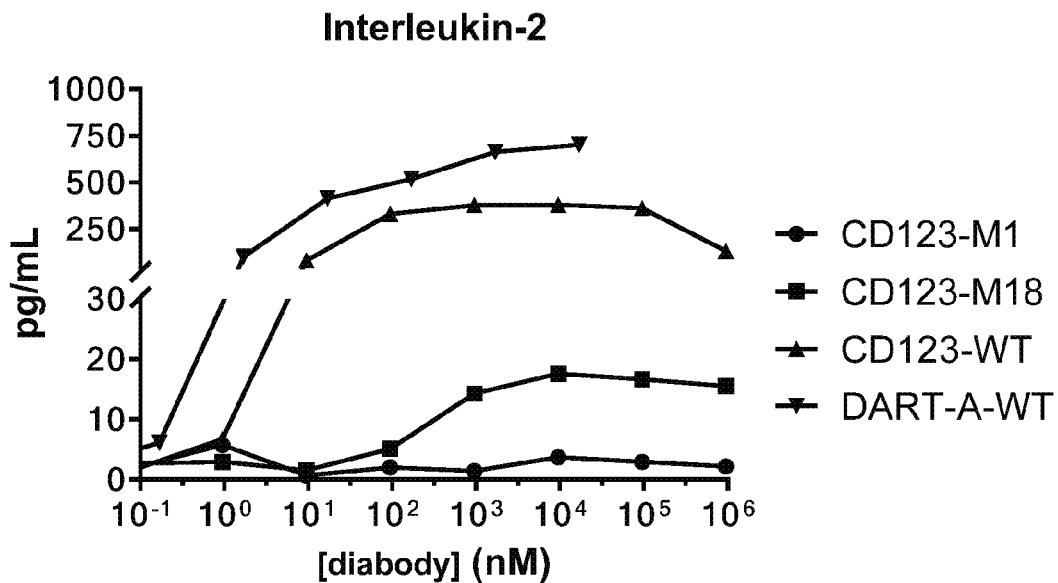

Exemplary CD123×CD3 diabodies were evaluated for their ability to mediate AML blast cell depletion from peripheral blood samples from an AML, patient. Briefly, peripheral blood cells from an AML patient were incubated in supplemented medium in the presence of increasing concentrations of DART-A-WT, CD123-WT, CD123-M1 and CD123-M18. Cellularity (CD34$^+$ blasts, CD3$^+$ and CD8$^+$ T-cells) were analyzed by flow cytometry at time 0 and on day 6 and is plotted as a percent of untreated control or as fold increase of baseline. Cytokine levels were analyzed by cytokine-bead array (BD) on supernatants harvested on day 4 of incubation. The results of this study are presented in FIGS. 25A-25G. As shown in FIG. 25A, CD123-M18 was able to mediate depletion AML blast cells to the same extent as DART-A-WT and CD123-WT. However, CD123-M18 exhibited significantly reduced expansion of T-cell population (FIG. 25B: CD4+ T-cells; FIG. 25C: CD8$^+$ T-cells). Furthermore, CD123-M18 exhibited significantly lower levels of cytokine release (FIG. 25D: IFN-γ; FIG. 25E: TNF-α; FIG. 25F: IL-6; and FIG. 25G: IL-2).

These results further demonstrate that DA×CD3 Binding Molecules comprising the vCD3-Binding Domains of CD3 mAb 1 M18 retained maximum killing potential with slightly reduced potency, but commensurably greater reduction in target-induced cytokine release in vitro and in vivo. Incorporating such vCD3-Binding Domains into DA×CD3 Binding Molecules may expand the therapeutic index in redirected T-cell killing applications.

Example 13

Ability of Exemplary CD19×CD3 Molecules to Mediate Autologous B-Cell Depletion

Figure 31A:
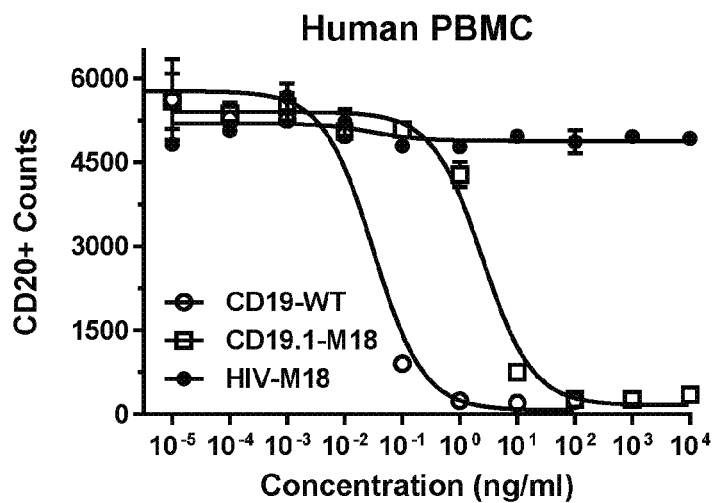
FIGS. 31A-31F show the results of a representative study of autologous B-cell depletion by CD19-WT, CD19.1-M18, and HIV-M18 from human and cynomolgus monkey PBMCs. Depletion of CD20+ B-cells is plotted in FIG. 31A (human PBMCs) and FIG. 31B (cyno PBMCs). Cytokine release from the treated human PBMCs is plotted in FIGS. 31C-F (FIG. 31C: IFN-γ.
Figure 31B:
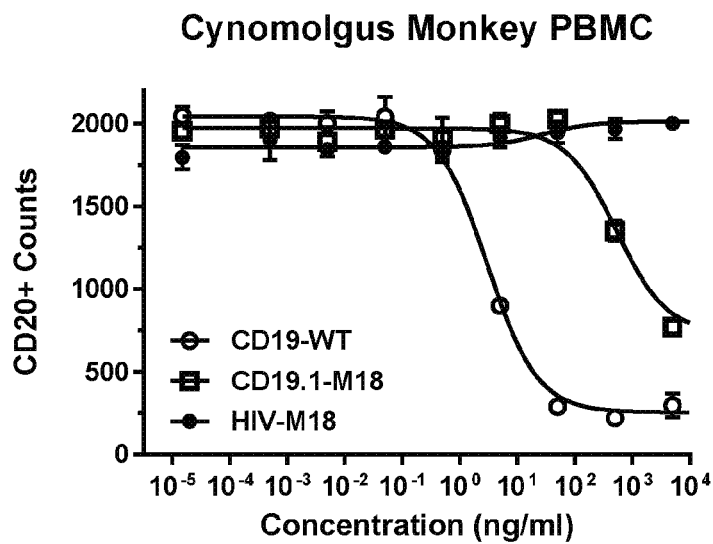
Figure 31C:
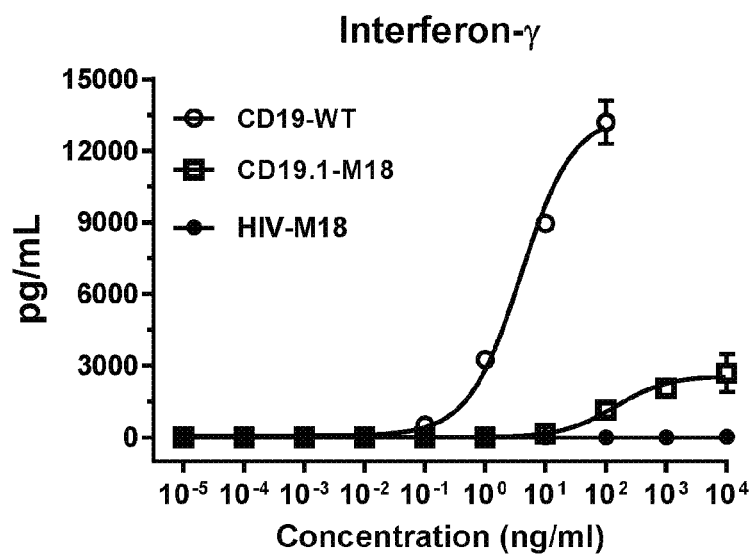
Figure 31D:
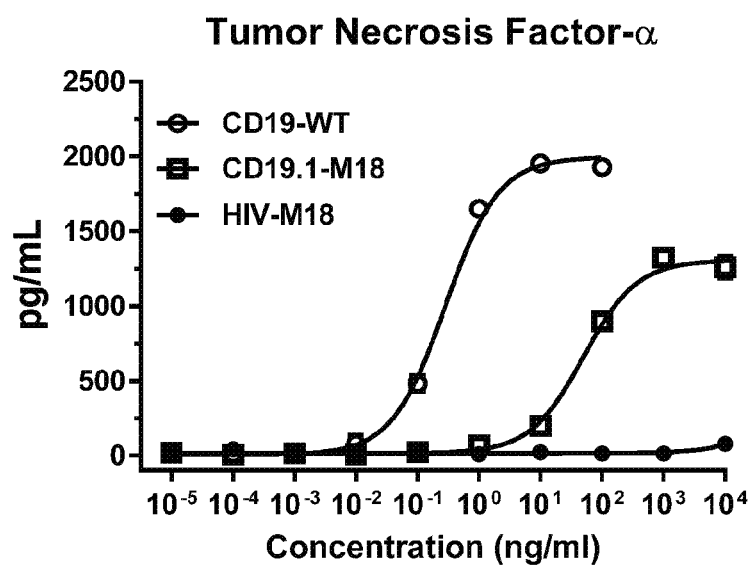
Figure 31E:
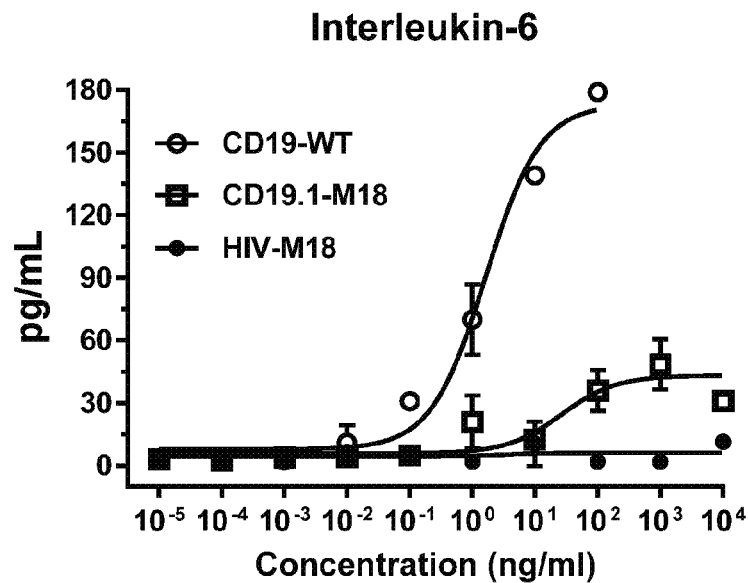
Figure 31F:
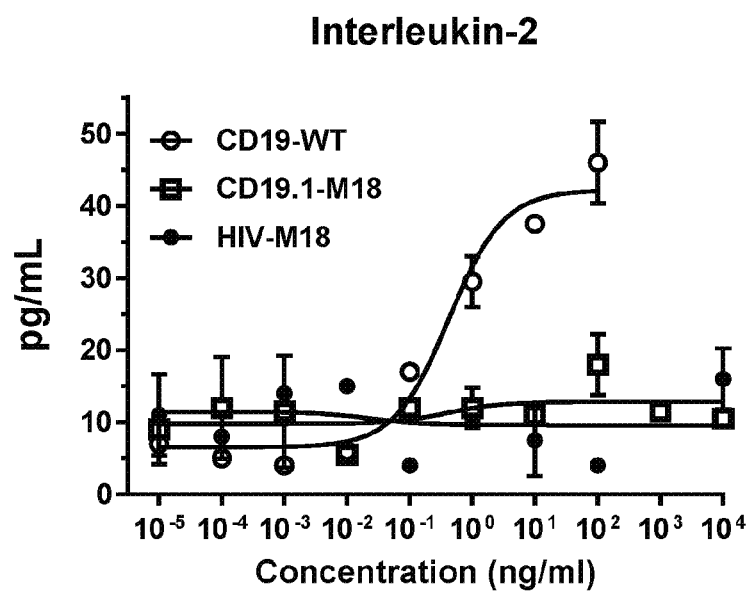

In one set of studies, the exemplary CD19×CD3 diabodies CD19-WT (a positive control comprising the rCD3-Binding Domain of CD3 mAb 1) and CD19.1-M18 (comprising the vCD3-Binding Domain of CD3 mAb 1 M18), were evaluated for their ability to mediate autologous B-cell depletion in vitro and in vivo. For the in vitro studies PMBCs from human and cynomolgus monkey were utilized. Briefly, PMBCs isolated from human or cynomolgus monkey were incubated in supplemented medium in the presence of increasing concentrations of CD19-WT (a positive control) or CD19.1-M18 or the negative control HIV-M18. B-cell levels were analyzed by flow cytometry (using CD20 as a B-cell marker) at 48 hours post incubation. Cytokine levels in the supernatants from the human samples were analyzed by cytokine-bead array (BD). The results of this study are presented in FIGS. 31A-31F. As shown in FIGS. 31A-31B, CD19.1-M18 was able to deplete autologous B-cells from both human and cynomolgus monkey PMBCs to the same extent as CD19-WT. Furthermore, CD19.1-M18 exhibited significantly lower levels of cytokine release (FIG. 31C: IFN-γ; FIG. 31D: TNF-α; FIG. 31E: IL-6; and FIG. 31F: IL-2).

The ability of the positive control, CD19-WT and CD19.1-M18 (comprising the vCD3-Binding Domain of CD3 mAb 1 M18), to mediate autologous B-cell depletion in vivo was assessed in a dosing study in cynomolgus monkeys. The study design is presented in Table 18.

TABLE 18

| Group No. | Test Material | Dose Level (mg/kg) | No. of Animals (male) |
|---|---|---|---|
| 1 | CD19-WT | 0.1 | 2 |
| 2 | CD19.1-M18 | 1 | 2 |
| 3 | CD19.1-M18 | 10 | 2 |
| 4 | CD19.1-M18 | 30 | 2 |

Figure 32A:
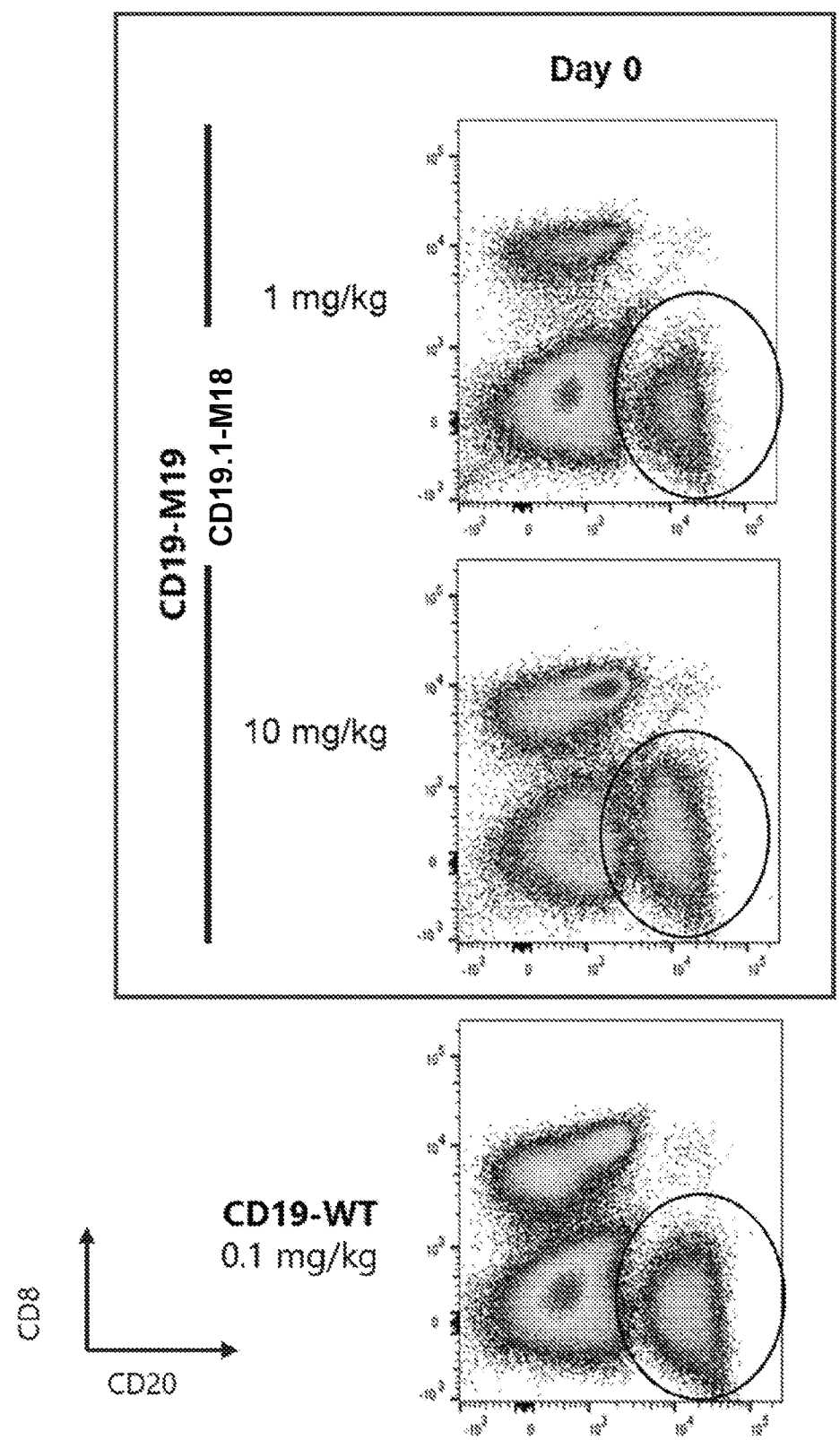
FIGS. 32A-32D show the reduction in B-cells levels observed in the peripheral blood of cynomolgus monkeys treated with CD19.1-M18 (1 mg/kg and 10 mg/kg) or CD123-WT (0.1 mg/kg). The predose B-cell levels are show in FIG. 32A (the B-cell population is indicated with an oval). The levels at Day 1, Day 8 and Day 15 are shown in FIGS. 32B-32C, respectively.
Figure 32B:
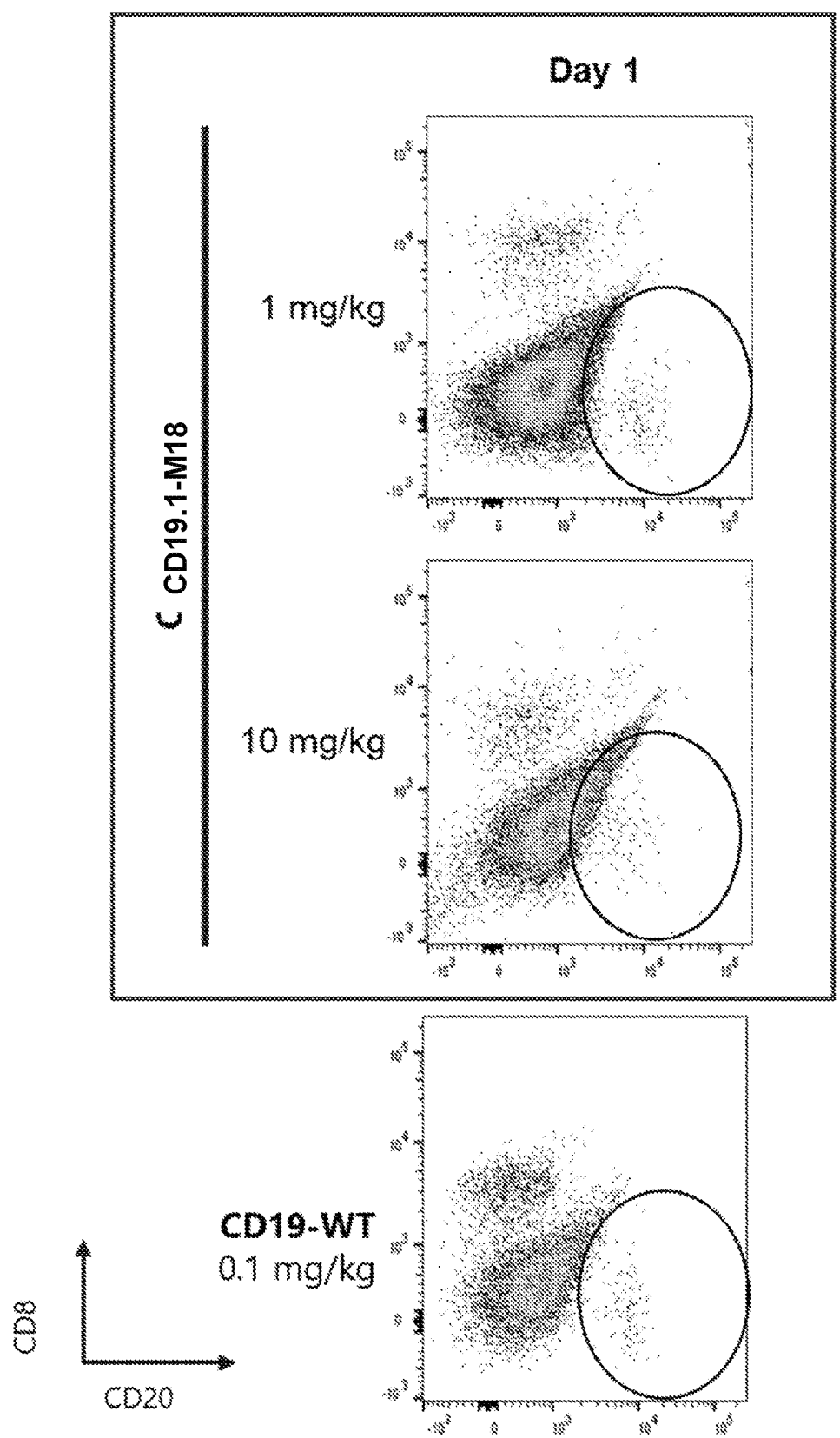
Figure 32C:
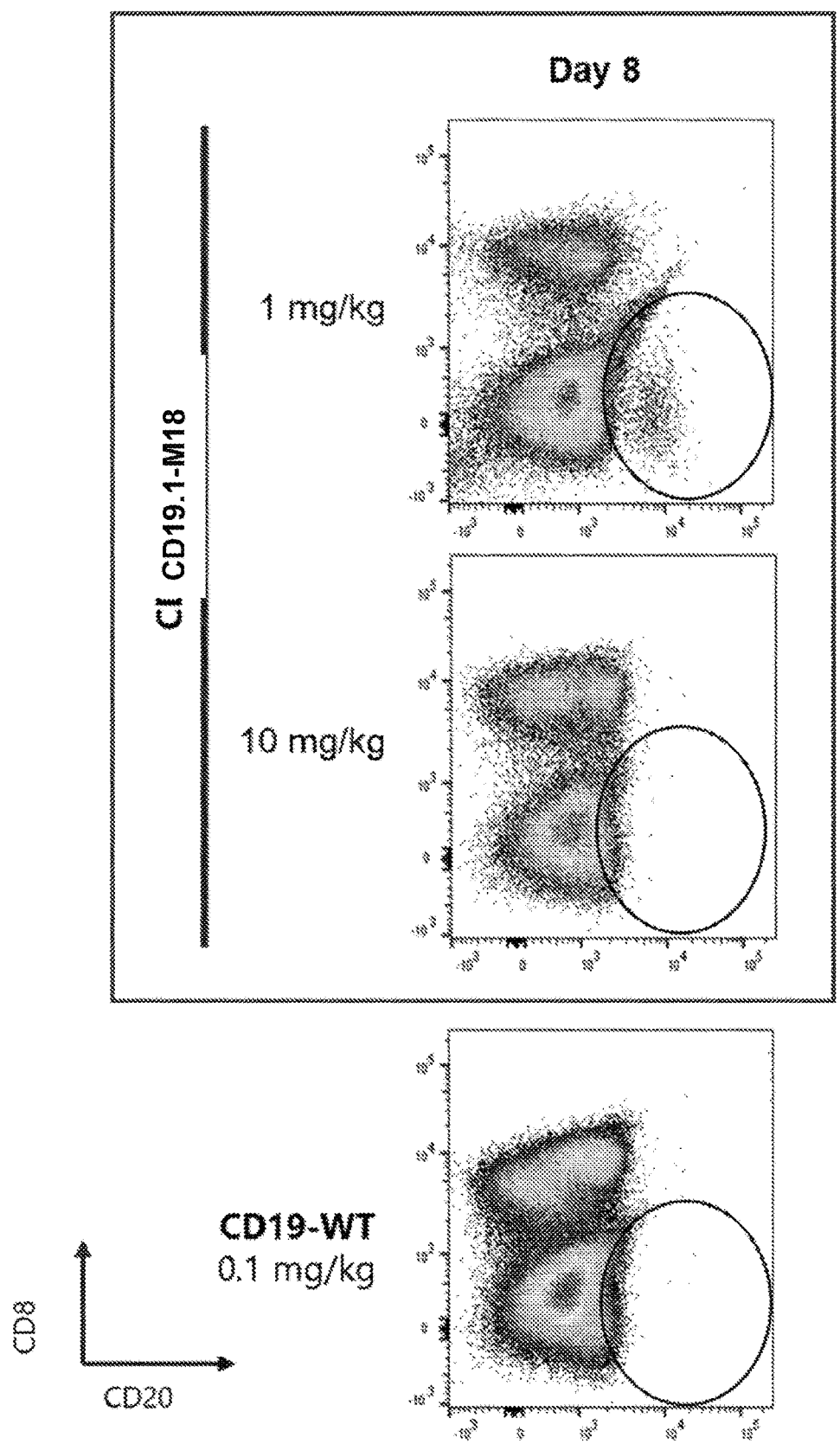
Figure 32D:
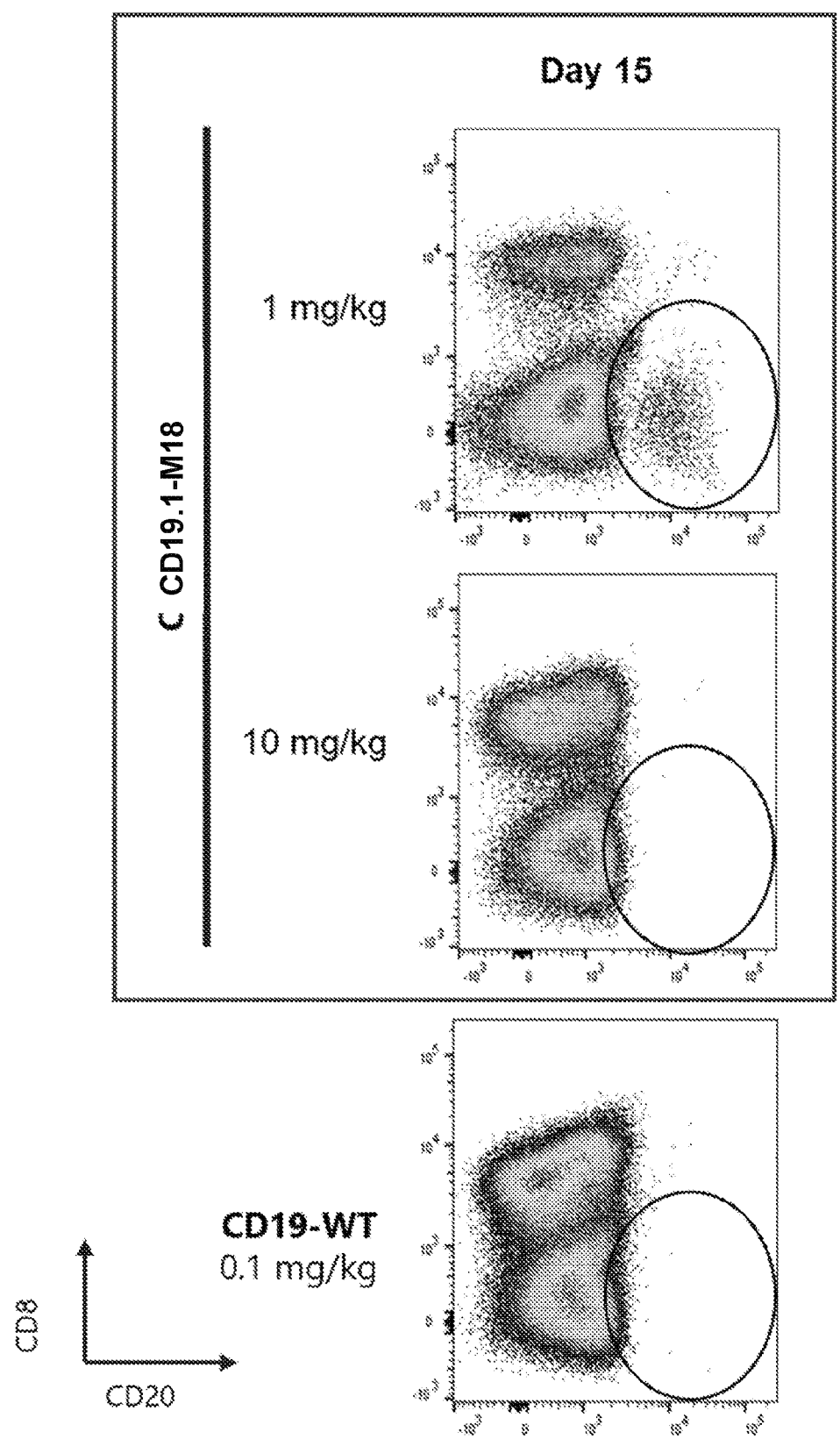
Figure 33A:
FIGS. 33A-33C show the immunohistochemistry staining of B-cells in lymph nodes from cynomolgus monkeys pretreatment and at Day 7 post treatment with the positive control CD19-WT (FIG. 33A: 0.1 mg/kg) or the CD3 variant CD19.1-M18 (FIG. 33B: 10 mg/kg.
Figure 33A:
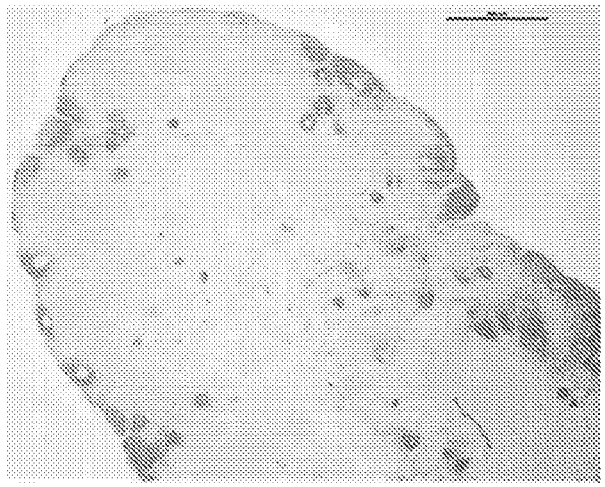
Figure 33B:
Figure 33B:
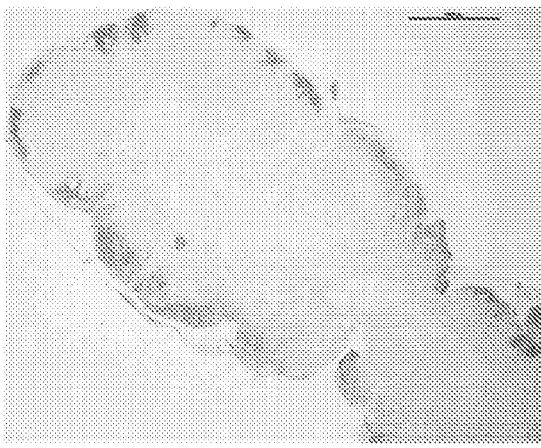
Figure 33C:
Figure 33C:
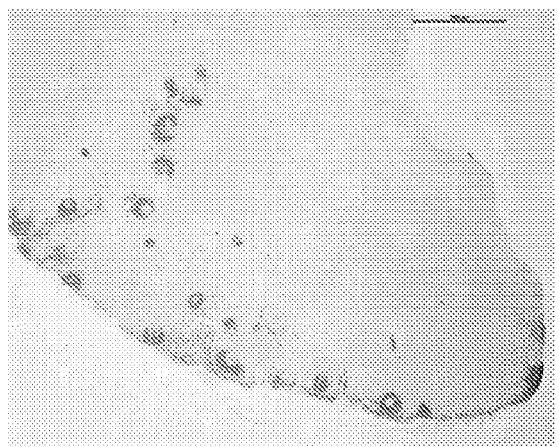

The CD19×CD3 diabodies were administered by a single 2-hr intravenous infusion on Day 0. Peripheral blood samples were taken predose and periodically postdose. B-cell levels in peripheral blood samples were analyzed by flow cytometry (using CD20 as a B-cell marker). Representative data from 1 of 2 monkeys treated in groups 1-3 are shown in FIGS. 32A-32D (FIG. 32A: predose Day 0; FIG. 32B: Day 1; FIG. 32C: Day 8; FIG. 32D: Day 15; B-cell populations are indicated with an oval). In addition, inguinal lymph nodes collected predose, at Day 7, and at Day 15 were stained for B-cells (using CD20 as a B-cell marker). Representative immunohistochemistry images from pre-dose and Day 7 samples from 1 of 2 monkeys treated in groups 1, 3 and 4 are shown in FIG. 33A-33C (FIG. 33A: group 1; FIG. 33B: group 3; FIG. 33C: group 4; predose on the left and Day 7 on the right; stained B-cells appear dark). The results of this in vivo study show that B-cells were efficiently depleted in peripheral blood within one day and that the depletion persisted for up to 15 days after administration (see FIGS. 32A-32D) of a single dose of exemplary CD19×CD3 diabody CD19.1-M18. Similarly, B-cells were efficiently depleted in lymph nodes within 7 days (the earliest time point examined after administration) demonstrating that CD19.1-M18 at doses of as little as 1 mg/kg is capable of mediating autologous B-cell depletion via T-cell redirected killing in vivo to a similar degree as the CD19-WT positive control.

The ability of additional CD19×CD3 Binding Molecules to mediate autologous B-cell depletion was assessed in cynomolgus monkeys. In this study the activity of CD19-WT (a positive control comprising the rCD3-Binding Domain of CD3 mAb 1); CD19.1-M13 (comprising the vCD3-Binding Domain of CD3 mAb 1 M13); and CD19.1-M17 (comprising the vCD3-Binding Domain of CD3 mAb 1 M17) were evaluated for their ability to mediate autologous B-cell depletion when administered by repeated intravenous infusions. The study design is presented in Table 19.

TABLE 19

| Group No. | Test Material | Dose Level (mg/kg) | Dosing Days | No. of Animals |
|---|---|---|---|---|
| 1 | CD19-WT | 0.1 | 1, 8 | 2M |
| 2 | CD19.1-M13 | 1 | 1, 8 | 3M |
| 3 | CD19.1-M17 | 1 | 1, 8 | 3M |

Figure 34:
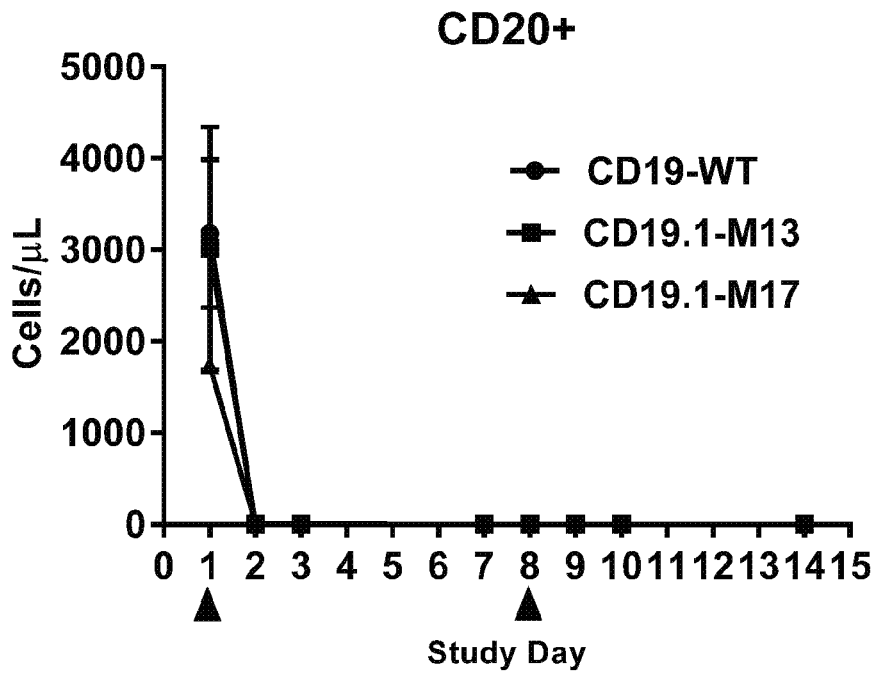
FIG. 34 shows the reduction in B-cells levels observed in the peripheral blood of cynomolgus monkeys treated with CD19.1-M13 (1 mg/kg), CD19.1-M17 (1 mg/kg) or CD19-WT (0.1 mg/kg).
Figure 35A:
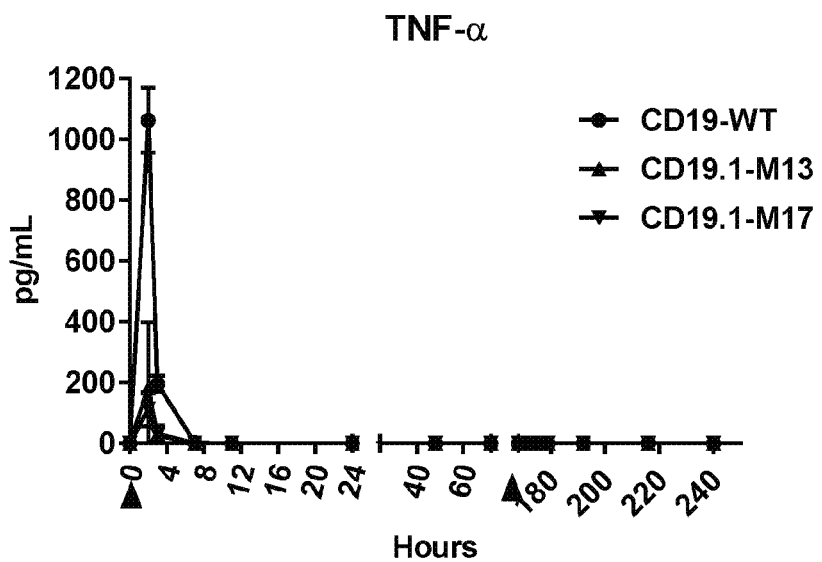
FIGS. 35A-35E show the serum cytokine levels observed in cynomolgus monkeys treated with CD19.1-M13 (1 mg/kg), CD19.1-M17 (1 mg/kg), or CD19-WT (0.1 mg/kg).
Figure 35B:
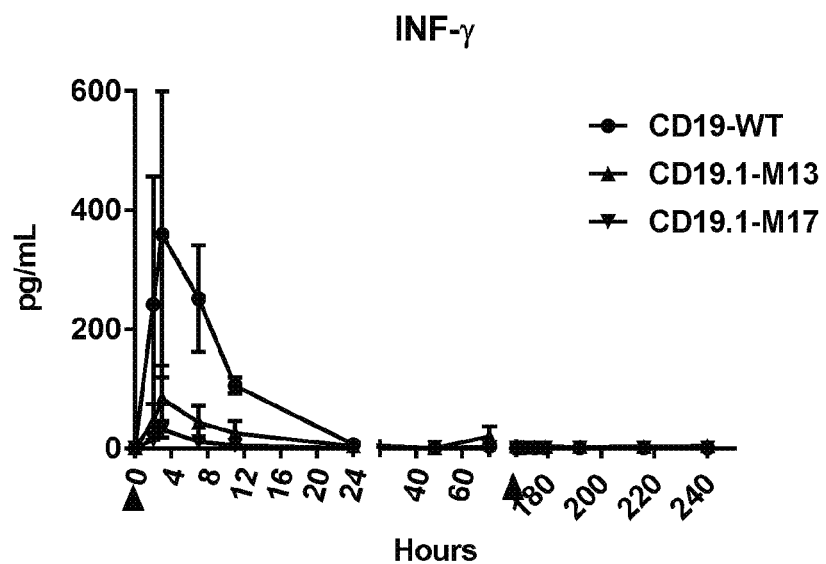
Figure 35C:
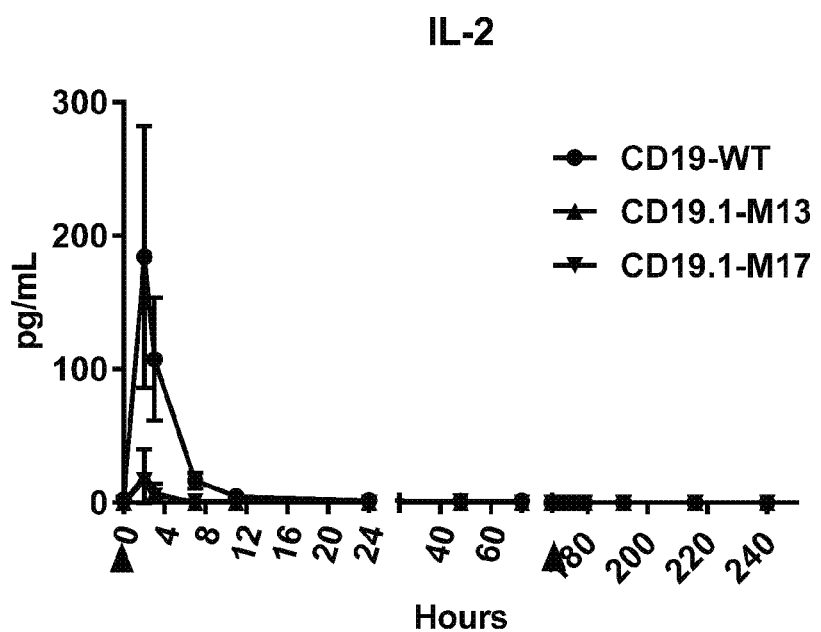
Figure 35D:
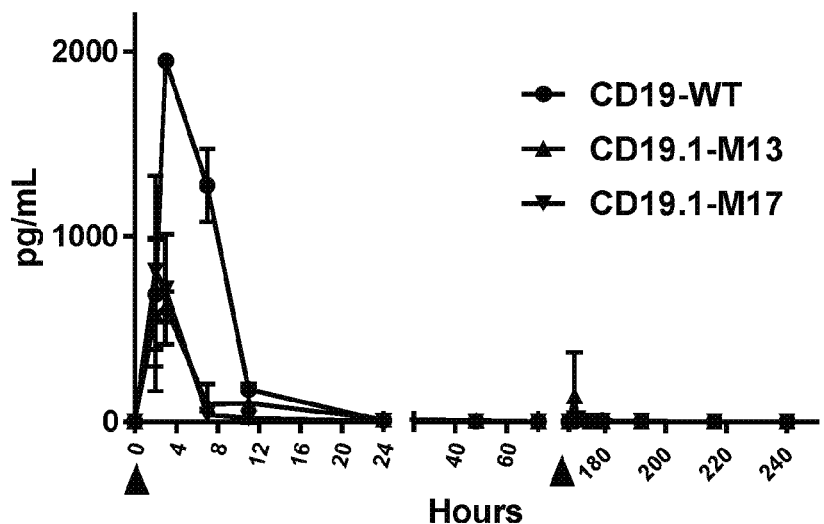
Figure 35E:
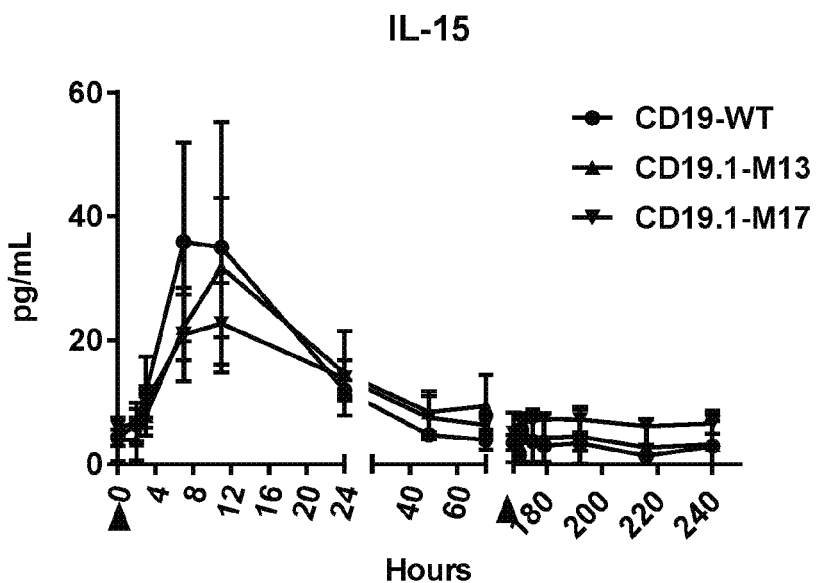
Figure 36A:
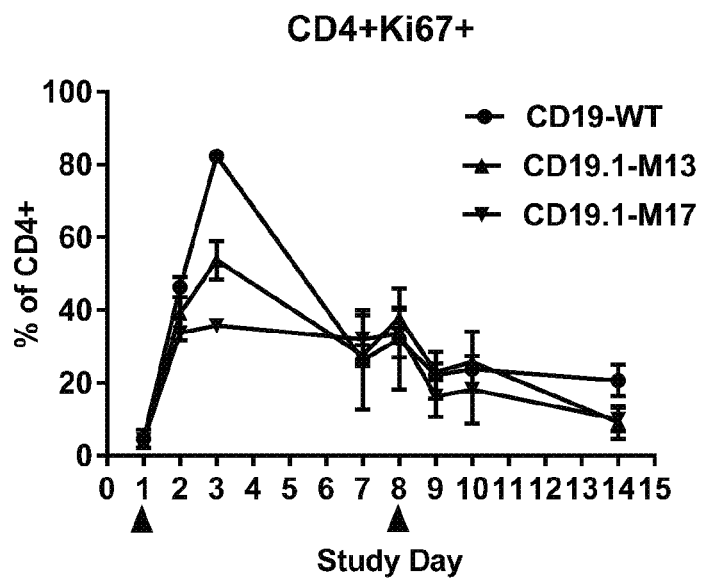
FIGS. 36A-36B show the proliferation of T-cells observed in cynomolgus monkeys treated with CD19.1-M13 (1 mg/kg), CD19.1-M17 (1 mg/kg), or CD19-WT (0.1 mg/kg).
Figure 36B:
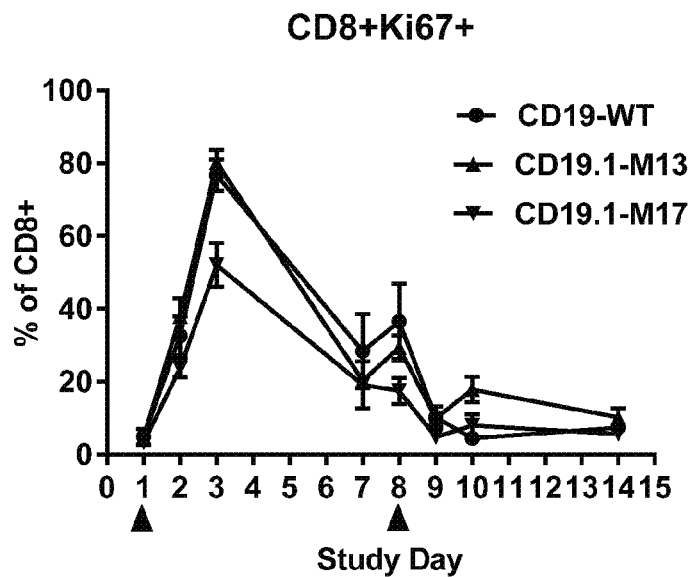

No mortality, body weight loss or other significant adverse observations were observed, cold limbs were observed after dosing in one animal in group 3 on Day 1 and in one animal in group 2 on Day 8, both resolved by the next day. B-cell levels in peripheral blood samples (taken predose and periodically postdose) were analyzed by flow cytometry (using CD20 as a B-cell marker). In addition, tissue samples (spleen, bone marrow and lymph nodes (LN)) were evaluated by immunohistochemistry for CD20 staining. Flow cytometry data from groups 1-3 are shown in FIG. 34 and tissue staining data from each animal (and an untreated negative control animal) are summarized in Table 20. Serum cytokine levels were evaluated over the course of the study (predose and periodically postdose). Serum levels of TNF-α, IFN-γ, IL-2, IL-6, and IL-15 for each treatment group are plotted in FIGS. 35A-35E, respectively. In addition, T-cell populations in peripheral blood were examined by FACS using expression of Ki67 as a marker of proliferating cells. FIG. 36A plots CD4$^+$ T-cell expansion, and FIG. 36B plots CD8$^+$ T-cells expansion as a percent of CD4$^+$ or CD8$^+$ cells positive for Ki67 (taken predose and periodically postdose).

TABLE 20

CD20 Tissue Staining

| | Neg Control‡ | CD19-WT Animal Number | |
|---|---|---|---|
| | 5001 | 1001 | 1002 |
| Spleen | X | 2+ | 1+ |
| Bone marrow | 2+ | 0 | 0 |
| LN, axillary | 3+ | 1+ | 1+ |
| LN, mandibular | 3+ | 1+ | 1+ |
| LN, mesenteric | 3+ | 1+ | 1+ |
| LN, inguinal | 3+ | 1+ | 1+ |

| | CD19.1-M13 Animal Number | | |
|---|---|---|---|
| | 2001 | 2002 | 2003 |
| Spleen | 1+ | 2+ | 1+ |
| Bone marrow | 0 | 0 | 0 |
| LN, axillary | 1+ | 2+ | 1+ |
| LN, mandibular | 1+ | 1+ | 1+ |
| LN, mesenteric | 0 | 1+ | 1+ |
| LN, inguinal | 1+ | 1+ | 1+ |

TABLE 20-continued

CD20 Tissue Staining

| | CD19.1-M17 Animal Number | | |
|---|---|---|---|
| | 3001 | 3002 | 3003 |
| Spleen | 1+ | 1+ | 1+ |
| Bone marrow | 0 | 1+ | 1+ |
| LN, axillary | 1+ | 2+ | 2+ |
| LN, mandibular | 1+ | 2+ | 2+ |
| LN, mesenteric | 1+ | 1+ | 2+ |
| LN, inguinal | 1+ | 2+ | 2+ |

‡one animal in negative control group
X—Not examined
0—No staining observed
1+—Weak staining observed
2+—Moderate staining observed
3+—Strong staining observed The results of this study show that CD19×CD3 Binding Molecules comprising the vCD3-Binding Domain CD3 mAb 1 M13 or CD3 mAb 1 M17 were active with animals treated with 1 mg/kg CD19.1-M13 exhibiting autologous B-cell depletion to a similar degree as the CD19-WT positive control. Animals treated with 1 mg/kg CD19.1-M17 also exhibited autologous B-cell depletion, but to a slightly lesser extent than the positive control. It is expected that CD19.1-M17 would achieve comparable depletion as higher dosages. The variants mediated much lower increases in the release of INF-γ, TNF-α, IL-2, and IL-6 and slight reductions in the release of IL-15. In addition, binding molecules comprising CD3 mAb 1 M13 and CD3 mAb 1 M17 were seen to stimulate proliferation of T-cells, with molecules comprising CD3 mAb 1 M13 exhibiting higher levels of proliferation. In addition, both molecules exhibited preferential stimulation of proliferation of CD8$^+$ T-cells.

Together the studies provided in the above examples show that DA×CD3 Binding Molecules comprising the vCD3-Binding Domain of CD3 mAb 1 (e.g., M13, M17, M18, M19), exhibit a range of binding affinities, a range of cytotoxicity EC$_{50}$ values but all reach a maximum CTL activity that is comparable to molecules comprising the rCD3-Binding Domain of CD3 mAb 1, thus exhibit an enhanced Therapeutic Index. These studies further show that such molecules are tolerated and active at mediating T-cell redirected cell killing, and at stimulating T-cell activation and proliferation in vivo.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A Disease Antigen×CD3 (DA×CD3) Binding Molecule comprising a CD3-Binding Domain capable of binding an epitope of CD3 and a Disease Antigen-Binding Domain capable of binding an epitope of CD123, wherein said CD3-Binding Domain comprises:
   (A) a $CDR_H1$ Domain comprising the amino acid sequence of SEQ ID NO:99;
   (B) a $CDR_H2$ Domain comprising the amino acid sequence of SEQ ID NO:58;
   (C) a $CDR_H3$ Domain comprising the amino acid sequence of SEQ ID NO:59;
   (D) a $CDR_L1$ Domain comprising the amino acid sequence of SEQ ID NO:60;
   (E) a $CDR_L2$ Domain comprising the amino acid sequence of SEQ ID NO:61; and
   (F) a $CDR_L3$ Domain comprising the amino acid sequence of SEQ ID NO:62.

2. The DA×CD3 Binding Molecule of claim 1, wherein said CD3-Binding Domain comprises:
   (A) a VL Domain comprising the amino acid sequence of SEQ ID NO:56; and
   (B) a VH Domain comprising the amino acid sequence of SEQ ID NO:98.

3. The DA×CD3 Binding Molecule of claim 1, wherein said DA×CD3 Binding Molecule is a bispecific antibody, a bispecific diabody, a bispecific scFv, a bispecific tetravalent tandem antibody, or a trivalent binding molecule.

4. The DA×CD3 Binding Molecule of claim 1, wherein said DA×CD3 Binding Molecule comprises: a first polypeptide chain and a second polypeptide chain, covalently bonded to one another, wherein:

(A) the first polypeptide chain comprises, in the N-terminal to C-terminal direction:
   (i) a Domain 1, comprising:
      (1) a sub-Domain (1A), which comprises a VL Domain of a monoclonal antibody capable of binding to said epitope of CD123 ($VL_{CD123}$); and
      (2) a sub-Domain (1B), which comprises a VH Domain of a monoclonal antibody capable of binding to said epitope of CD3 ($VH_{CD3}$);
      wherein said sub-Domains 1A and 1B are separated from one another by a peptide Linker; and
   (ii) a Domain 2, wherein said Domain 2 is a Heterodimer-Promoting Domain;
(B) the second polypeptide chain comprises, in the N-terminal to C-terminal direction:
   (i) a Domain 1, comprising:
      (1) a sub-Domain (1A), which comprises a VL Domain of said monoclonal antibody capable of binding to said epitope of CD3 ($VL_{CD3}$); and
      (2) a sub-Domain (1B), which comprises a VH Domain of said monoclonal antibody capable of binding to said epitope of CD123 ($VH_{CD123}$);
      wherein said sub-Domains 1A and 1B are separated from one another by a peptide Linker;
   (ii) a Domain 2, wherein said Domain 2 is a Heterodimer-Promoting Domain, wherein said Heterodimer-Promoting Domain of said first and said second polypeptide chains are different;
and wherein:
the VL Domain of the first polypeptide chain and the VH Domain of the second polypeptide chain associate to form the Disease Antigen-Binding Domain, and the VH Domain of the first polypeptide chain and the VL Domain of the second polypeptide chain associate to form the CD3-Binding Domain.

5. The DA×CD3 Binding Molecule of claim 4, wherein:
(a) said Heterodimer-Promoting Domain of said first polypeptide chain is an E-coil Domain, and said Heterodimer-Promoting Domain of said second polypeptide chain is a K-coil Domain; or
(b) said Heterodimer-Promoting Domain of said first polypeptide chain is a K-coil Domain, and said Heterodimer-Promoting Domain of said second polypeptide chain is an E-coil Domain.

6. The DA×CD3 Binding Molecule of claim 4, wherein the first or second polypeptide chain additionally comprises a Domain 3 comprising a CH2 and CH3 Domain of an immunoglobulin Fc Domain.

7. The DA×CD3 Binding Molecule of claim 6, wherein said DA×CD3 Binding Molecule further comprises a third polypeptide chain comprising a CH2 and CH3 Domain of an immunoglobulin Fc Domain.

8. A pharmaceutical composition that comprises the DA×CD3 Binding Molecule of claim 1 and a pharmaceutically acceptable carrier.

9. A method for the treatment of a hematological cancer, comprising administering to a subject in need thereof a therapeutically effective amount of the pharmaceutical composition of claim 8.

10. The DA×CD3 Binding Molecule of claim 1, wherein said Disease Antigen-Binding Domain comprises:
(A) the $CDR_H1$ Domain, the $CDR_H2$ Domain, and the $CDR_H3$ Domain of SEQ ID NO:162; and
(B) the $CDR_L1$ Domain, the $CDR_L2$ Domain, and the $CDR_L3$ Domain of SEQ ID NO:163.

11. The DA×CD3 Binding Molecule of claim 1, wherein said Disease Antigen-Binding Domain comprises:
(A) a VH Domain comprising the amino acid sequence of SEQ ID NO:162; and
(B) a VL Domain comprising the amino acid sequence of SEQ ID NO:163.

12. The DA×CD3 Binding Molecule of claim 2, wherein said Disease Antigen-Binding Domain comprises:
(A) a VH Domain comprising the amino acid sequence of SEQ ID NO:162; and
(B) a VL Domain comprising the amino acid sequence of SEQ ID NO:163.

13. The DA×CD3 Binding Molecule of claim 4, wherein:
(A) said $VH_{CD123}$ comprises the amino acid sequence of SEQ ID NO:162;
(B) said $VL_{CD123}$ comprises the amino acid sequence of SEQ ID NO:163;
(C) said $VH_{CD3}$ comprises the amino acid sequence of SEQ ID NO:98; and
(D) said $VL_{CD3}$ comprises the amino acid sequence of SEQ ID NO:56.

14. The DA×CD3 Binding Molecule of claim 5, wherein:
(A) said $VH_{CD123}$ comprises the amino acid sequence of SEQ ID NO:162;
(B) said $VL_{CD123}$ comprises the amino acid sequence of SEQ ID NO:163;
(C) said $VH_{CD3}$ comprises the amino acid sequence of SEQ ID NO:98; and
(D) said $VL_{CD3}$ comprises the amino acid sequence of SEQ ID NO:56.

15. The DA×CD3 Binding Molecule of claim 6, wherein:
(A) said $VH_{CD123}$ comprises the amino acid sequence of SEQ ID NO:162;
(B) said $VL_{CD123}$ comprises the amino acid sequence of SEQ ID NO:163;
(C) said $VH_{CD3}$ comprises the amino acid sequence of SEQ ID NO:98; and
(D) said $VL_{CD3}$ comprises the amino acid sequence of SEQ ID NO:56.

16. The DA×CD3 Binding Molecule of claim 7, wherein:
(A) said $VH_{CD123}$ comprises the amino acid sequence of SEQ ID NO:162;
(B) said $VL_{CD123}$ comprises the amino acid sequence of SEQ ID NO:163;
(C) said $VH_{CD3}$ comprises the amino acid sequence of SEQ ID NO:98; and
(D) said $VL_{CD3}$ comprises the amino acid sequence of SEQ ID NO:56.

17. A CD123×CD3 Binding Molecule, wherein said CD123×CD3 Binding Molecule comprises:
(A) a first polypeptide chain comprising the amino acid sequence of SEQ ID NO:179;
(B) a second polypeptide chain comprising the amino acid sequence of SEQ ID NO:175; and
(C) a third polypeptide chain comprising the amino acid sequence of SEQ ID NO:176.

18. A pharmaceutical composition that comprises the CD123×CD3 Binding Molecule of claim 17 and a pharmaceutically acceptable carrier.

19. A method for the treatment of a hematological cancer, comprising administering to a subject in need thereof a therapeutically effective amount of the pharmaceutical composition of claim 18.

20. The method of claim 19, wherein said hematological cancer is selected from the group consisting of: acute myeloid leukemia (AML), chronic myelogenous leukemia (CML), myelodysplastic syndrome (MDS), acute B lymphoblastic leukemia (B-ALL), chronic lymphocytic leukemia (CLL), Richter's syndrome, hairy cell leukemia (HCL), blastic plasmacytoid dendritic cell neoplasm (BPDCN), non-Hodgkin's lymphoma (NHL), including mantle cell lymphoma (MCL) and small lymphocytic lymphoma (SLL), Hodgkin's lymphoma, systemic mastocytosis, and Burkitt's lymphoma.

21. The method of claim 20, wherein said hematologic cancer is AML.

22. The method of claim 20, wherein said hematologic cancer is Hodgkin's lymphoma.

23. The method of claim 20, wherein said hematologic cancer is CML.

24. The method of claim 20, wherein said hematologic cancer is B-ALL.

25. The method of claim 20, wherein said hematologic cancer is HCL.

26. The method of claim 20, wherein said hematologic cancer is BPDCN.

27. The method of claim 20, wherein said hematologic cancer is MDS.

28. The method of claim 20, wherein said hematologic cancer is systemic mastocytosis.

29. The method of claim 20, wherein the pharmaceutical composition is administered intravenously.

30. The method of claim 29, wherein said intravenous administration is by infusion.

31. The method of 30, wherein the CD123×CD3 Binding Molecule of the pharmaceutical composition is administered at a dosage of about 0.01 µg/kg to about 30 mg/kg of said subject's body weight.

32. The method of 30, wherein the pharmaceutical composition is administered once a week, once every two weeks, or once a month.

33. A host cell comprising:
(a) a polynucleotide encoding a polypeptide chain comprising the amino acid sequence of SEQ ID NO: 179;
(b) a polynucleotide encoding a polypeptide chain the amino acid sequence of SEQ ID NO: 175; and
(c) a polynucleotide encoding a polypeptide chain the amino acid sequence of SEQ ID NO: 176.

* * * * *